United States Patent
Haketa et al.

(10) Patent No.: US 10,629,821 B2
(45) Date of Patent: Apr. 21, 2020

(54) COMPOUND, MATERIAL FOR ORGANIC ELECTROLUMINESCENT ELEMENTS USING SAME, AND ORGANIC ELECTROLUMINESCENT ELEMENT AND ELECTRONIC DEVICE EACH USING SAME

(71) Applicant: IDEMITSU KOSAN CO., LTD., Chiyoda-ku (JP)

(72) Inventors: Tasuku Haketa, Chiba (JP); Masahiro Kawamura, Chiba (JP); Yumiko Mizuki, Basel (CH); Yoichi Ikeda, Itabashi-ku (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 392 days.

(21) Appl. No.: 15/502,398

(22) PCT Filed: Apr. 5, 2016

(86) PCT No.: PCT/JP2016/061176
§ 371 (c)(1),
(2) Date: Feb. 7, 2017

(87) PCT Pub. No.: WO2016/163372
PCT Pub. Date: Oct. 13, 2016

(65) Prior Publication Data
US 2017/0237016 A1    Aug. 17, 2017

(30) Foreign Application Priority Data

Apr. 8, 2015    (JP) ................ 2015-079639

(51) Int. Cl.
| | | |
|---|---|---|
| *H01L 51/00* | (2006.01) | |
| *C07D 401/14* | (2006.01) | |
| *C07D 405/14* | (2006.01) | |
| *C09K 11/06* | (2006.01) | |
| *H01L 51/50* | (2006.01) | |
| *C09K 11/02* | (2006.01) | |
| *H05B 33/20* | (2006.01) | |

(52) U.S. Cl.
CPC ........ *H01L 51/0072* (2013.01); *C07D 401/14* (2013.01); *C07D 405/14* (2013.01); *C09K 11/025* (2013.01); *C09K 11/06* (2013.01); *H01L 51/0052* (2013.01); *H01L 51/0073* (2013.01); *H01L 51/0085* (2013.01); *H01L 51/50* (2013.01); *H05B 33/20* (2013.01); *C09K 2211/1007* (2013.01); *C09K 2211/1029* (2013.01); *C09K 2211/185* (2013.01); *H01L 51/5012* (2013.01); *H01L 51/5016* (2013.01); *H01L 51/5056* (2013.01); *H01L 51/5072* (2013.01)

(58) Field of Classification Search
CPC .. C07D 401/14; C07D 405/14; C09K 11/025; C09K 11/06; C09K 2211/1007; C09K 2211/1029; C09K 2211/185; H01L 51/0052; H01L 51/0072; H01L 51/0073; H01L 51/0085; H01L 51/50; H01L 51/5012; H01L 51/5016; H01L 51/5056; H01L 51/5072; H05B 33/20
See application file for complete search history.

(56) References Cited

U.S. PATENT DOCUMENTS

| | | |
|---|---|---|
| 9,190,618 B2 | 11/2015 | Bae et al. |
| 2009/0121625 A1 | 5/2009 | Ohrui et al. |
| 2009/0243476 A1 | 10/2009 | Nomura et al. |
| 2009/0247753 A1 | 10/2009 | Takasu et al. |
| 2009/0278118 A1 | 11/2009 | Ohrui et al. |
| 2010/0117526 A1 | 5/2010 | Ohrui et al. |
| 2012/0223295 A1 | 9/2012 | Inoue et al. |
| 2013/0119353 A1 | 5/2013 | Zeng et al. |
| 2015/0228904 A1 | 8/2015 | Kawamura et al. |
| 2015/0364692 A1 | 12/2015 | Kawamura et al. |
| 2016/0218299 A1* | 7/2016 | Haketa ................ C07D 401/04 |
| 2018/0226601 A1* | 8/2018 | Ikeda ................ H01L 51/5206 |

FOREIGN PATENT DOCUMENTS

| | | |
|---|---|---|
| CN | 104342126 A | 2/2015 |
| EP | 2 158 290 B1 | 11/2015 |
| JP | 2002-69044 A | 3/2002 |
| JP | 2003-212875 A | 7/2003 |
| JP | 2003-238534 A | 8/2003 |
| JP | 2005-68367 A | 3/2005 |
| JP | 2008-56658 A | 3/2008 |

(Continued)

OTHER PUBLICATIONS

Machine translation of JP 2013-103937 A ( publication date: May 2013). (Year: 2013).*
Machine translation of WO 2013/146942 (publication date Oct. 2013). (Year: 2013).*
Machine translation of KR 10-2012-0044523 (publication date: May 2012). (Year: 2012).*
Machine translation KR 10-2015-0111106 (publication date Oct. 2015). (Year: 2015).*
International Search Report dated Jun. 7, 2016 in PCT/JP2016/061176 filed Apr. 5, 2016.

(Continued)

*Primary Examiner* — Dawn L Garrett
(74) *Attorney, Agent, or Firm* — Oblon, McClelland, Maier & Neustadt, L.L.P.

(57) ABSTRACT

The present invention provides a material useful as an organic electroluminescence device material, and particularly provides: a compound having, as a substituent, a substituted aromatic heterocyclic group having a specific structure wherein any of the 1-position to 6-position or the 7-position to 10-position of fluoranthene is substituted with a nitrogen atom; a material for low-voltage organic electroluminescence devices using the compound; and an organic electroluminescence device and an electronic equipment using the material.

35 Claims, 1 Drawing Sheet

(56) References Cited

FOREIGN PATENT DOCUMENTS

| | | |
|---|---|---|
| JP | 2008-156315 A | 7/2008 |
| JP | 2009-256343 A | 11/2009 |
| JP | 2009-256348 A | 11/2009 |
| JP | 2010-111635 A | 5/2010 |
| JP | 2013-103937 A | 5/2013 |
| JP | 2014-531419 A | 11/2014 |
| KR | 10-2012-0044523 A | 5/2012 |
| KR | 10-2014-0083189 A | 7/2014 |
| KR | 10-2015-0111106 * | 10/2015 |
| WO | 2012/108388 A1 | 8/2012 |
| WO | 2013/094921 A1 | 6/2013 |
| WO | 2013/146942 A1 | 10/2013 |
| WO | 2013/187258 A1 | 12/2013 |
| WO | 2014/007287 A1 | 1/2014 |
| WO | 2014/157574 A1 | 10/2014 |
| WO | 2014/178434 A1 | 11/2014 |
| WO | 2015/020217 A1 | 2/2015 |
| WO | 2015/033894 A1 | 3/2015 |
| WO | 2015/050140 A1 | 4/2015 |
| WO | 2015/050173 A1 | 4/2015 |
| WO | 2015/156587 A1 | 10/2015 |

OTHER PUBLICATIONS

Tokito et al, "Confinement of triplet energy on phosphorescent molecules for highly-efficient organic blue-light-emitting devices", *Applied Physics Letters*, 2003, vol. 83, No. 3, pp. 569-571.

\* cited by examiner

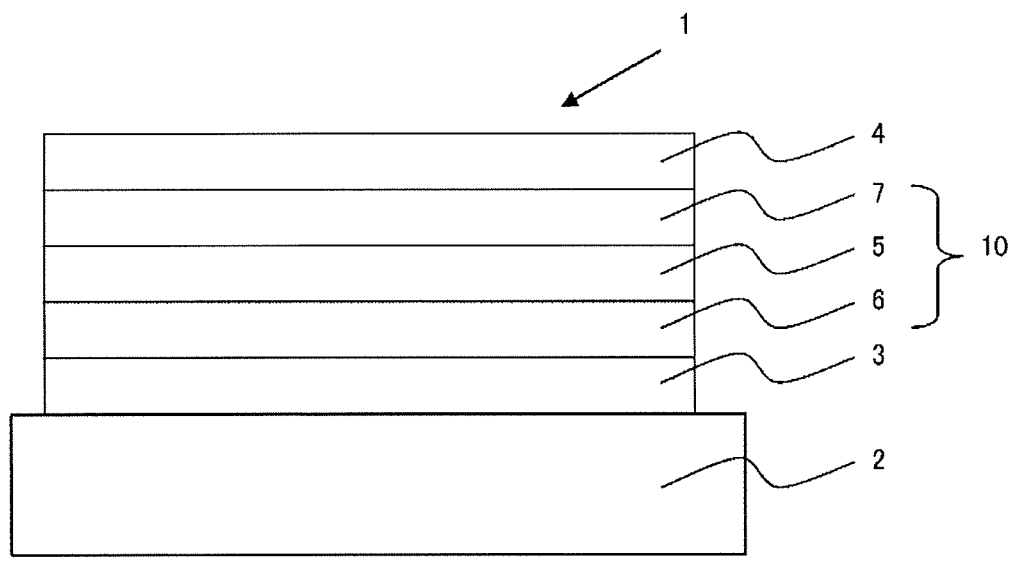

COMPOUND, MATERIAL FOR ORGANIC ELECTROLUMINESCENT ELEMENTS USING SAME, AND ORGANIC ELECTROLUMINESCENT ELEMENT AND ELECTRONIC DEVICE EACH USING SAME

TECHNICAL FIELD

The present invention relates to a compound, a material for an organic electroluminescence device using the compound, and an organic electroluminescence device and an electronic equipment using the material.

BACKGROUND ART

An electroluminescence device (hereinafter this may be abbreviated as an organic EL device) using an organic substance is expected to be hopeful for use for solid light emission-type, inexpensive large-area full-color display device, and many developments for the device are under way. In general, an organic EL device is composed of a light emitting layer and pair of opposite electrodes that sandwich the light emitting layer. When voltage is applied across the electrodes, electrons are injected from the cathode side and holes are injected from the anode side. Further, the electrons recombine with the holes in the light emitting layer to form an excited state, and light is emitted when the excited state returns to the ground state.

In addition, an organic EL device can provide a wide variety of light emitting colors, using various light emitting materials in the light emitting layer, and therefore intensive studies for practical use of the device in displays and others are conducted. In particular, studies on light emitting materials for the three primary colors, red, green and blue, are most extensively conducted, and the materials are studied intensively for the improvement of the properties.

As materials for such organic EL devices, a compound having an unsubstituted carbazolyl group via an unsubstituted benzene ring in a fluoranthene skeleton and the like are disclosed in PTL 1; use of a compound, in which the 7-positioned and/or the 10-positioned carbon atoms constituting a fluoranthene skeleton are substituted with nitrogen atoms, in an organic EL device is disclosed in PTL 2; an acenaphthopyridine derivative having a pyridyl group or a quinolyl group in a fluoranthene skeleton is disclosed in PTL 3; and an azaindenoglycerin derivative having a fluoranthene skeleton is disclosed in PTL 4.

CITATION LIST

Patent Literature

PTL 1: Korean Published Patent No. 2012-044523
PTL 2: JP 2005-68367 A
PTL 3: JP 2009-256348 A
PTL 4: JP 2010-111635 A

SUMMARY OF INVENTION

Technical Problem

However, in the field of organic EL devices, development of materials useful for the devices is required to further improve the performance thereof.

The present invention has been made for solving the above-described problems, and an object thereof is to provide a compound useful as a material for organic EL devices, and a low-voltage organic EL device using the compound.

Solution to Problem

The present inventors have assiduously studied to attain the above-described object and, as a result, have found that a compound, in which any of the 1-position to 6-position, or any of the 7-position to 10-position of a fluoranthene is substituted with a nitrogen atom and which has, as a substituent, an aromatic heterocyclic group having a substituent and having a specific structure, is effective for improvement of device performance as a material for organic EL devices.

Specifically, according to an aspect of the present invention, the following compound is provided.

[1] A compound represented by the following formula (1):

[Chem. 1]

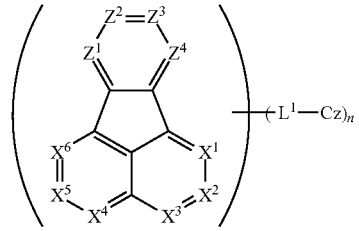

(1)

In the formula (1), any "n" number of $X^1$ to $X^6$ and $Z^1$ to $Z^4$ each represent a carbon atom bonding to $L^1$, and when $X^1$ to $X^6$ and $Z^1$ to $Z^4$ do not represent a carbon atom bonding to $L^1$, $X^1$ to $X^6$ and $Z^1$ to $Z^4$ each independently represent $CR^1$ or a nitrogen atom, with the proviso that at least one of $X^1$ to $X^6$ is a nitrogen atom.

n indicates an integer of 1 to 3.

$R^1$ each independently represent a hydrogen atom or a substituent.

$L^1$ represents a single bond, a substituted or unsubstituted arylene group having 6 to 50 ring carbon atoms, or a substituted or unsubstituted heteroarylene group having 5 to 50 ring atoms.

Cz represents a group represented by the following formula (2):

[Chem. 2]

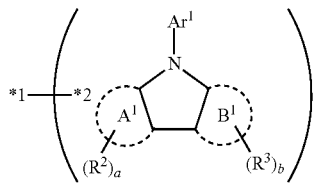

(2)

In the formula (2), $Ar^1$ represents a single bond bonding to *2 or a monovalent substituent.

The ring $A^1$ and the ring $B^1$ each independently represent an aromatic hydrocarbon ring having 5 to 50 ring carbon atoms, or an aromatic hetero ring having 5 to 50 ring atoms.

$R^2$ and $R^3$ each independently represent a substituent.

a and b each independently indicate an integer of 0 or more, provided that in the case where $Ar^1$ represents a single bond bonding to *2, the total of a and b is 1 or more.

*1 represents the bonding position to $L^1$.

*2 bonds to any one of one ring carbon atom of the ring $A^1$, one ring carbon atom of the ring $B^1$, and $Ar^1$.

At least one of $Ar^1$, $R^2$ and $R^3$ is a substituted or unsubstituted aryl group having 6 to 50 ring carbon atoms, or a substituted or unsubstituted heteroaryl group having 5 to 50 ring atoms.

[2] A material for organic electroluminescence devices, containing the compound described in [1].

[3] A material for organic electroluminescence devices, containing a compound represented by the following formula (13):

[Chem. 3]

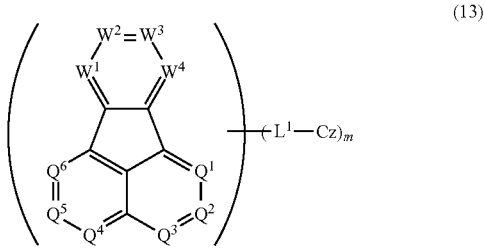

(13)

In the formula (13), any "m" number of $Q^1$ to $Q^6$ and $W^1$ to $W^4$ each represent a carbon atom bonding to $L^1$, and when $Q^1$ to $Q^6$ and $W^1$ to $W^4$ do not represent a carbon atom bonding to $L^1$, $W^2$ and $W^3$ each independently represent $CR^{11}$, and $W^1$ and $W^4$ each independently represent $CR^{11}$ or a nitrogen atom, $Q^1$ to $Q^6$ each independently represent $CR^{11}$ or a nitrogen atom, with the proviso that at least one of $W^1$ and $W^4$ is a nitrogen atom.

m indicates an integer of 1 to 3.

$R^{11}$ each independently represent a hydrogen atom or a substituent.

$L^1$ represents a single bond, a substituted or unsubstituted arylene group having 6 to 50 ring carbon atoms, or a substituted or unsubstituted heteroarylene group having 5 to 50 ring atoms.

Cz represents a group represented by the following formula (2):

[Chem. 4]

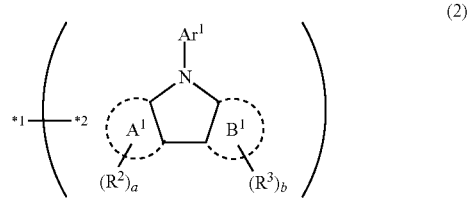

(2)

In the formula (2), $Ar^1$ represents a single bond bonding to *2 or a monovalent substituent.

The ring $A^1$ and the ring $B^1$ each independently represent an aromatic hydrocarbon ring having 5 to 50 ring carbon atoms, or an aromatic hetero ring having 5 to 50 ring atoms.

$R^2$ and $R^3$ each independently represent a substituent.

a and b each independently indicate an integer of 0 or more, provided that in the case where $Ar^1$ represents a single bond bonding to *2, the total of a and b is 1 or more.

*1 represents the bonding position to $L^1$.

*2 bonds to any one of one ring carbon atom of the ring $A^1$, one ring carbon atom of the ring $B^1$, and $Ar^1$.

At least one of $Ar^1$, $R^2$ and $R^3$ is a substituted or unsubstituted aryl group having 6 to 50 ring carbon atoms, or a substituted or unsubstituted heteroaryl group having 5 to 50 ring atoms.

[4] An organic electroluminescence device including a cathode, an anode and an organic thin-film layer formed of one layer or plural layers sandwiched between the cathode and the anode, wherein the organic thin-film layer contains a light emitting layer and at least one layer of the organic thin-film layer contains the compound described in [1].

[5] An organic electroluminescence device including a cathode, an anode and an organic thin-film layer formed of one layer or plural layers sandwiched between the cathode and the anode, wherein the organic thin-film layer contains a light emitting layer and at least one layer of the organic thin-film layer contains the compound described in [3].

[6] An electronic equipment provided with the organic electroluminescence device described in [4] or [5].

Advantageous Effects of Invention

The present invention provides a novel material useful for organic EL devices, and a low-voltage organic EL device using the material.

BRIEF DESCRIPTION OF DRAWING

FIGURE shows a view showing an example of a schematic configuration of an organic EL device according to an aspect of the present invention.

DESCRIPTION OF EMBODIMENTS

[Material for Organic Electroluminescence Device]

The material for an organic EL device according to an aspect of the present invention contains a compound of an aspect of the present invention to be described below [a compound represented by the formula (1) or a compound represented by the formula (2)].

The content of the compound of an aspect of the present invention is, for example, may be 1% by mass or more, and is preferably 10% by mass or more, more preferably 50% by mass or more, even more preferably 80% by mass or more, and especially preferably 90% by mass or more.

The compound and the material for organic EL devices of aspects of the present invention are useful as a material in organic EL devices, and, for example, can be used as a host material and a dopant material in a light emitting layer of a fluorescent light emitting unit, or a host material in a light emitting layer in a phosphorescent light emitting unit. In this case, the light emitting layer contains the material for organic EL devices of an aspect of the present invention and a fluorescent light emitting material or a phosphorescent light emitting material. In any of the fluorescent light emitting unit and the phosphorescent light emitting unit, the compound and the material are useful as a material for the anode-side organic thin-film layer to be provided between the anode and the light emitting layer in an organic EL device, or as a material for the cathode-side organic thin-film layer to be provided between the cathode and the light emitting layer in an organic EL device, that is, they are useful as a material for a hole transporting layer, a hole injection layer, an electron transporting layer, an electron injection layer, a hole blocking layer, an electron blocking layer, etc.

The "light emitting unit" here is the smallest unit which includes one or more organic layers, where one of the layers is a light emitting layer, and which can emit light through the recombination of the injected holes and electrons.

The compound represented by the formula (1) and the compound represented by the formula (2) that are compounds of aspects of the present invention are described in detail hereinunder.

In this description, the "XX to YY carbon atoms" in an expression "a substituted or unsubstituted ZZ group having XX to YY carbon atoms" refer to the number of the carbon atoms of the unsubstituted ZZ group, and when the ZZ group has a substituent, the carbon atoms of the substituent are not included.

Also in this description, the "XX to YY atoms" in an expression "a substituted or unsubstituted ZZ group having XX to YY atoms" refer to the number of the atoms of the unsubstituted ZZ group, and when the ZZ group has a substituent, the atoms of the substituent are not included.

In this description, the number of the ring carbon atoms refers to the number of the carbon atoms of the atoms constituting the ring itself of a compound having a structure in which the atoms combine and form a ring (for example, a monocyclic compound, a condensed ring compound, a cross-linked compound, a carbocyclic compound or a heterocyclic compound). When the ring has a substituent, the carbon atoms contained in the substituent are not counted as the ring carbon atoms. The term "the number of the ring carbon atoms" used below is the same unless otherwise noted. For example, a benzene ring has six ring carbon atoms, and a naphthalene ring has 10 ring carbon atoms. A pyridinyl group has five ring carbon atoms, and a furanyl group has four ring carbon atoms. When a benzene ring or a naphthalene ring has an alkyl group as a substituent for example, the carbon atoms of the alkyl group are not counted as the ring carbon atoms. Also, when a fluorene ring is bonded to another fluorene ring as a substituent for example (including a spirofluorene ring), the carbon atoms of the fluorene ring as the substituent are not counted as the ring carbon atoms.

In this description, the number of the ring atoms refers to the number of the atoms constituting the ring itself of a compound having a structure in which the atoms combine and form a ring (for example a monocycle, a condensed ring or a ring assembly) (for example, the compound is a monocyclic compound, a condensed ring compound, a cross-linked compound, a carbocyclic compound or a heterocyclic compound). The atoms which do not constitute the ring (for example, a hydrogen atom which terminates a binding site of an atom constituting the ring) and the atoms contained in a substituent which the ring has, if any, are not counted as the ring atoms. The term "the number of the ring atoms" used below is the same unless otherwise noted. For example, a pyridine ring has six ring atoms, and a quinazoline ring has 10 ring atoms. A furan ring has five ring atoms. The hydrogen atoms bonded to the carbon atoms of a pyridine ring or a quinazoline ring and the atoms constituting a substituent are not counted as the ring atoms. When a fluorene ring is bonded to another fluorene ring as a substituent for example (including a spirofluorene ring), the atoms of the fluorene ring as the substituent are not counted as the ring atoms.

In this description, the term "hydrogen atom" includes isotopes with a different number of neutrons, namely protium, deuterium and tritium.

In this description, the "heteroaryl group" and the "heteroarylene group" each are a group containing at least one hetero atom as a ring atom, and the hetero atom is preferably one or more selected from a nitrogen atom, an oxygen atom, a sulfur atom and a selenium atom.

The substituent referred to by the term "substituted or unsubstituted" and the substituent referred to by the simple term "substituent" are preferably at least one selected from the group consisting of; an alkyl group having 1 to 50 (preferably 1 to 18, and more preferably 1 to 8) carbon atoms; a cycloalkyl group having 3 to 50 (preferably 3 to 10, more preferably 3 to 8, and still more preferably 5 or 6) ring carbon atoms; an aryl group having 6 to 50 (preferably 6 to 25, and more preferably 6 to 18) ring carbon atoms; an aralkyl group having 7 to 51 (preferably 7 to 30, and more preferably 7 to 20) carbon atoms which has an aryl group having 6 to 50 (preferably 6 to 25, and more preferably 6 to 18) ring carbon atoms; an alkoxy group which has an alkyl group having 1 to 50 (preferably 1 to 18, and more preferably 1 to 8) carbon atoms; an aryloxy group which has an aryl group having 6 to 50 (preferably 6 to 25, and more preferably 6 to 18) ring carbon atoms; a di-substituted amino group having a substituent selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; a mono-substituted, di-substituted or tri-substituted silyl group having a substituent selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; a heteroaryl group having 5 to 50 (preferably 5 to 24, and more preferably 5 to 13) ring atoms; a haloalkyl group having 1 to 50 (preferably 1 to 18, and more preferably 1 to 8) carbon atoms; a halogen atom (a fluorine atom, a chlorine atom, a bromine atom or an iodine atom); a cyano group; a nitro group; a sulfonyl group having a substituent selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; a di-substituted phosphoryl group having substituents selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxy group; an alkyl-substituted or aryl-substituted carbonyl group; a carboxyl group; a vinyl group; a (meth)acryloyl group; an epoxy group; and an oxetanyl group.

These substituents may further have any of the optional substituents above. Also, a plurality of these substituents may combine to form a ring.

"Unsubstituted" in the expression of "substituted or unsubstituted" means that the group is not substituted with any such substituents and a hydrogen atom bonds thereto.

Among the above substituents, more preferable substituents are a substituted or unsubstituted alkyl group having 1 to 50 (preferably 1 to 18, and more preferably 1 to 8) carbon atoms, a substituted or unsubstituted aryl group having 6 to 50 (preferably 6 to 25, and more preferably 6 to 18) ring carbon atoms, a substituted or unsubstituted heteroaryl group having 5 to 50 (preferably 5 to 24, and more preferably 5 to 13) ring atoms, a halogen atom, a cyano group, a substituted or unsubstituted fluoroalkyl group having 1 to 50 (preferably 1 to 20, more preferably 1 to 10, even more preferably 1 to 5) carbon atoms, a substituted or unsubstituted alkoxy group having 1 to 50 (preferably 1 to 20, more preferably 1 to 10, even more preferably 1 to 5) carbon atoms, a substituted or unsubstituted fluoroalkoxy group having 1 to 50 (preferably 1 to 20, more preferably 1 to 10, even more preferably 1 to 5) carbon atoms, a substituted or unsubstituted aryloxy group having 6 to 50 (preferably 6 to 25, more preferably 6 to 18, even more preferably 6 to 12) ring carbon atoms, a di-substituted amino group having substituents selected from an alkyl group having 1 to 50 (preferably 1 to 18, more preferably 1 to 8) carbon atoms and an aryl group having 6 to 50 (preferably 6 to 25, more preferably 6 to 18) ring carbon atoms, and a tri-substituted silyl group having substituents selected from an alkyl group having 1 to 50 (preferably 1 to 18, more preferably 1 to 8) carbon atoms and an aryl group having 6 to 50 (preferably 6 to 25, more preferably 6 to 18) ring carbon atoms.

Among the above substituents, even more preferable substituents are a substituted or unsubstituted aryl group having 6 to 50 (preferably 6 to 25, and more preferably 6 to 18) ring carbon atoms, a substituted or unsubstituted heteroaryl group having 5 to 50 (preferably 5 to 24, and more preferably 5 to 13) ring atoms, a halogen atom, a cyano group, a substituted or unsubstituted fluoroalkyl group having 1 to 50 (preferably 1 to 20, more preferably 1 to 10, even more preferably 1 to 5) carbon atoms, a substituted or unsubstituted alkoxy group having 1 to 50 (preferably 1 to 20, more preferably 1 to 10, even more preferably 1 to 5) carbon atoms, a substituted or unsubstituted fluoroalkoxy group having 1 to 50 (preferably 1 to 20, more preferably 1 to 10, even more preferably 1 to 5) carbon atoms, and a substituted or unsubstituted aryloxy group having 6 to 50 (preferably 6 to 25, more preferably 6 to 18, even more preferably 6 to 12) ring carbon atoms.

<Examples of Above-Described Substituents>

Examples of the alkyl group having 1 to 50 carbon atoms include a methyl group, an ethyl group, an n-propyl group, an isopropyl group, an n-butyl group, an isobutyl group, an s-butyl group, a t-butyl group, a pentyl group (including isomer groups), a hexyl group (including isomer groups), a heptyl group (including isomer groups), an octyl group (including isomer groups), a nonyl group (including isomer groups), a decyl group (including isomer groups), an undecyl group (including isomer groups), a dodecyl group (including isomer groups), etc.

Examples of the aryl group having 6 to 50 ring carbon atoms include a phenyl group, a naphthylphenyl group, a biphenylyl group, a terphenylyl group, a biphenylenyl group, a naphthyl group, a phenylnaphthyl group, an acenaphthylenyl group, an anthryl group, a benzoanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a pentacenyl group, a picenyl group, a pentaphenyl group, a pyrenyl group, a chrysenyl group, a benzochrysenyl group, an s-indacenyl group, an as-indacenyl group, a fluoranthenyl group, a perylenyl group, etc.

The heteroaryl group having 5 to 50 ring atoms contains at least one, preferably 1 to 3 same or different hetero atoms (for example, a nitrogen atom, a sulfur atom, and an oxygen atom).

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolidinyl group, a quinolidinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, a xanthenyl group, etc.

Examples of the fluoroalkyl group having 1 to 50 carbon atoms include groups obtained by substituting at least one hydrogen atom, preferably 1 to 7 hydrogen atoms or all hydrogen atoms in the above-described alkyl group having 1 to 50 carbon atoms, with fluorine atoms.

Specific examples of the fluoroalkyl group include a pentafloropropyl group, a pentafluoroethyl group, a 2,2,2-trifluoroethyl group, and a trifluoromethyl group.

The above alkoxy group having 1 to 50 carbon atoms is a group represented by $-OR^X$, wherein $R^X$ represents the above-described alkyl group having 1 to 50 carbon atoms.

Specific examples of the alkoxy group include a t-butoxy group, a propoxy group, an ethoxy group and a methoxy group.

The above fluoroalkoxy group having 1 to 50 carbon atoms is a group represented by $-OR^Y$, wherein $R^Y$ represents the above-described fluoroalkyl group having 1 to 50 carbon atoms.

Specific examples of the fluoroalkoxy group include a heptafluoropropoxy group, a pentafluoroethoxy group, a 2,2,2-trifluoroethoxy group, and a trifluoromethoxy group.

The above aryloxy group having 6 to 50 ring carbon atoms is a group represented by $-OR^Z$, wherein $R^Z$ represents the above-described aryl group having 6 to 50 ring carbon atoms.

Specific examples of the aryloxy group include a phenyloxy group, a 1-naphthyloxy group, a 2-naphthyloxy group, a 4-biphenylyloxy group, a p-terphenyl-4-yloxy group, a p-tolyloxy group.

The alkyl group and the aryl group in the di-substituted amino group having substituents selected from an alkyl group having 1 to 50 carbon atoms and an aryl group having 6 to 50 ring carbon atoms include the above-described alkyl group having 1 to 50 carbon atoms and the aryl group having 6 to 50 ring carbon atoms.

Examples of the di-substituted amino group include a dialkylamino group such as a dimethylamino group, a diethylamino group, a diisopropylamino group, a di-t-butylamino group, etc.; a diphenylamino group, a di(methylphenyl) amino group, a dinaphthylamino group, a dibiphenylylamino group, etc.

The alkyl group and the aryl group in the tri-substituted silyl group having substituents selected from an alkyl group having 1 to 50 carbon atoms and an aryl group having 6 to 50 ring carbon atoms include the above-described alkyl group having 1 to 50 carbon atoms and the aryl group having 6 to 50 ring carbon atoms.

The tri-substituted silyl group is preferably a trialkylsilyl group (where the alkyl group is as described above), or a triarylsilyl group (where the aryl group is as described above). Examples of the trialkylsilyl group include a trimethylsilyl group, a triethylsilyl group, a triisopropylsilyl group, a tri-t-butylsilyl group, a tri-n-butylsilyl group. Examples of the triarylsilyl group include a trip henylsilyl group, a tri(methylphenyl)silyl group.

These substituents may be further substituted with the above-described optional substituents. A plurality of these substituents may bond to form a ring, or may bond not to form a ring.

In this description, preferred definitions may be selected in any arbitrary manner, and a combination of preferred definitions can be said to be more preferred.

[Compounds]
[Compound Represented by Formula (1)]

The organic EL device material of an aspect of the present invention may contain a compound represented by the following formula (1).

[Chem. 5]

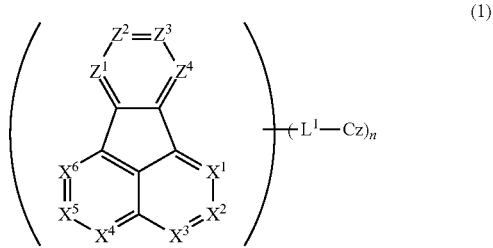

(1)

In the formula (1), any "n" number of $X^1$ to $X^6$ and $Z^1$ to $Z^4$ each represent a carbon atom bonding to $L^1$, and when $X^1$ to $X^6$ and $Z^1$ to $Z^4$ do not represent a carbon atom bonding to $L^1$, $X^1$ to $X^6$ and $Z^1$ to $Z^4$ each independently represent $CR^1$ or a nitrogen atom, with the proviso that at least one of $X^1$ to $X^6$ is a nitrogen atom.

n indicates an integer of 1 to 3.

$R^1$ each independently represent a hydrogen atom or a substituent.

$L^1$ represents a single bond, a substituted or unsubstituted arylene group having 6 to 50 ring carbon atoms, or a substituted or unsubstituted heteroarylene group having 5 to 50 ring atoms.

Cz is described hereinunder.

In the formula (1), plural $R^1$'s bonding to the adjacent carbon atom of the carbon atoms to which $R^1$'s bond may bond to each other to form a saturated or unsaturated ring structure, or may not form a ring structure.

In the formula (1), the substituent of $R^1$ that represents a substituent is preferably selected from the following.

There are described a substituted or unsubstituted alkyl group having 1 to 50 (more preferably 1 to 18, even more preferably 1 to 8) carbon atoms, a substituted or unsubstituted cycloalkyl group having 3 to 50 (more preferably 3 to 10, even more preferably 3 to 8) ring carbon atoms, a substituted or unsubstituted aryl group (this has the same meaning as that of "aromatic hydrocarbon group", and the same shall apply hereinunder) having 6 to 60 (more preferably 6 to 25, even more preferably 6 to 18) ring carbon atoms, a substituted or unsubstituted aralkyl group having 7 to 61 (more preferably 7 to 25, eve more preferably 7 to 18) carbon atoms, an amino group, a mono-substituted or di-substituted amino group having substituents selected from a substituted or unsubstituted alkyl group having 1 to 50 (more preferably 1 to 18, even more preferably 1 to 8) carbon atoms and a substituted or unsubstituted aryl group having 6 to 60 (more preferably 6 to 25, even more preferably 6 to 18) ring carbon atoms, a substituted or unsubstituted alkoxy group having 1 to 50 (more preferably 1 to 18, even more preferably 1 to 8) carbon atoms, a substituted or unsubstituted cycloalkoxy group having 3 to 50 (more preferably 3 to 10, even more preferably 3 to 8) ring carbon atoms, a substituted or unsubstituted aryloxy group having 6 to 60 (more preferably 6 to 25, even more preferably 6 to 18) ring carbon atoms, a substituted or unsubstituted alkylthio group having 1 to 50 (more preferably 1 to 18, even more preferably 1 to 8) carbon atoms, a substituted or unsubstituted arylthio group having 6 to 60 (more preferably 6 to 25, even more preferably 6 to 18) ring carbon atoms, a mono-substituted, a di-substituted or tri-substituted silyl group having a substituent selected from a substituted or unsubstituted alkyl group having 1 to 50 (more preferably 1 to 18, even more preferably 1 to 8) carbon atoms and a substituted or unsubstituted aryl group having 6 to 60 (more preferably 6 to 25, even more preferably 6 to 18) ring carbon atoms, a substituted or unsubstituted heteroaryl group (this has the same meaning as that of "heterocyclic group", and the same shall apply hereinunder) having 5 to 60 (more preferably 5 to 30, even more preferably 5 to 26) ring atoms, a substituted or unsubstituted haloalkyl group having 1 to 50 (more preferably 1 to 18, even more preferably 1 to 8) carbon atoms, a halogen atom, a cyano group, a nitro group, a sulfonyl group having a substituent selected from a substituted or unsubstituted alkyl group having 1 to 50 (more preferably 1 to 18, even more preferably 1 to 8) carbon atoms and a substituted or unsubstituted aryl group having 6 to 60 (more preferably 6 to 25, even more preferably 6 to 18) ring carbon atoms, a di-substituted phosphoryl group having substituents selected from a substituted or unsubstituted alkyl group having 1 to 50 (more preferably 1 to 18, even more preferably 1 to 8) carbon atoms and a substituted or unsubstituted aryl group having 6 to 60 (more preferably 6 to 25, even more preferably 6 to 18) ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, an alkyl-substituted or aryl-substituted carbonyl group, a carboxyl group, a vinyl group, a (meth)acryloyl group, an epoxy group, and an oxetanyl group.

Examples of the alkyl group in this aspect include a methyl group, an ethyl group, an n-propyl group, an isopropyl group, an n-butyl group, an isobutyl group, an s-butyl group, a t-butyl group, a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group, a tetradecyl group, an octadecyl group, a tetracosanyl group, a tetracontanyl group, etc. These may be substituted.

More preferably, there are mentioned a methyl group, an ethyl group, an n-propyl group, an isopropyl group, an n-butyl group, an isobutyl group, an s-butyl group, a t-butyl group, a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group, a tetradecyl group and an octadecyl group. These may be substituted.

Even more preferably, there are mentioned a methyl group, an ethyl group, an n-propyl group, an isopropyl group, an n-butyl group, an isobutyl group, an s-butyl group, a t-butyl group, a pentyl group (including isomers), a hexyl group (including isomers), a heptyl group (including isomers) and an octyl group (including isomers). These may be substituted.

The cycloalkyl group in this aspect includes a cyclopropyl group, a cyclobutyl group, a cyclopentyl group, a cyclohexyl group, a cycloheptyl group, a cyclooctyl group, an adamantyl group, etc. These may be substituted.

More preferably, there are mentioned a cyclopentyl group and a cyclohexyl group. These may be substituted.

Examples of the aryl group in this aspect include a phenyl group, a naphthyl group, a naphthylphenyl group, a biphenylyl group, a terphenylyl group, a quaterphenylyl group, a quinquephenylyl group, an acenaphthylenyl group, an anthryl group, a benzoanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, an s-indanyl group, an as-indanyl group, a fluoranthenyl group, a benzofluoranthenyl group, a tetracenyl group, a triphenylenyl group, a benzotriphenylenyl group, a perylenyl group, a coronyl group, a dibenzoanthryl group, a 9,9-dimethylfluorenyl group, a 9,9-diphenylfluorenyl group, etc. These may be substituted.

More preferably, there are mentioned a phenyl group, a naphthyl group, a biphenylyl group, a terphenylyl group, a phenanthryl group, a benzophenanthryl group, a fluorenyl group, a 9,9'-spirobifluorenyl group, a benzofluorenyl group, a dibenzofluorenyl group, a chrysenyl group, a benzochrysenyl group, an s-indanyl group, an as-indanyl group, a triphenylenyl group, a benzotriphenylenyl group, an anthryl group, a 9,9-dimethylfluorenyl group, a 9,9-diphenylfluorenyl group. These may be substituted.

More preferably, there are mentioned a phenyl group, a biphenylyl group, a terphenylyl group, a naphthyl group, a phenanthryl group, a fluorenyl group, a 9,9'-spirobifluorenyl group, a chrysenyl group, a triphenylenyl group, a 9,9-dimethylfluorenyl group, a 9,9-diphenylfluorenyl group. These may be substituted.

The heteroaryl group in this aspect contains at least one, preferably 1 to 5 (more preferably 1 to 3, even more preferably 1 to 2) hetero atoms, for example, a nitrogen atom, a sulfur atom, an oxygen atom and a phosphorus atom. Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolidinyl group, a quinolidinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a bicarbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, a dinaphthothienothiophenyl group, a dinaphtho-<2',3':2,3:2',3':6,7>-carbazolyl group, etc. These may be substituted.

More preferably, there are mentioned a pyridyl group, a pyridazinyl group, a pyrimidinyl group, a pyrazyl group, a triazinyl group, an imidazolyl group, an indolyl group, an isoindolyl group, a benzofuranyl group, an isobenzofuranyl group, a benzothiophenyl group, an isobenzothiophenyl group, an indolidinyl group, a qinolidinyl group, a quinolyl group, an isoquinolyl group, a quinazolinyl group, a quinoxalinyl group, a benzimidazolyl group, a benzoxazolyl group, a benzothiazolyl group, a benzisoxazolyl group, a benzisothiazolyl group, a dibenzofuranyl group, a dibenzothiophenyl group, a carbazolyl group, a bicarbazolyl group, a phenanthridinyl group, an acridinyl group, a phenanthrolinyl group, an azatriphenylenyl group, a diazatriphenylenyl group, a xanthenyl group, an azacarbazolyl group, an azadibenzofuranyl group, an azadibenzothiophenyl group. These may be substituted.

Even more preferably, there are mentioned a pyridyl group, a pyrimidinyl group, a triazinyl group, a benzofuranyl group, an isobenzofuranyl group, a quinolyl group, an isoquinolyl group, a quinazolyl group, a benzothiophenyl group, an isobenzothiophenyl group, an indolidinyl group, a dibenzofuranyl group, a dibenzothiophenyl group, a carbazolyl group, a bicarbazolyl group, an azatriphenylenyl group, a diazatriphenylenyl group, a xanthenyl group, an azacarbazolyl group, an azadibenzofuranyl group, an azadibenzothiophenyl group. These may be substituted.

The aralkyl group in this aspect includes an aralkyl group having the above-described aryl group having 6 to 60 ring carbon atoms. These may be substituted. More preferably, it is an aralkyl group having the above-described aryl group having 6 to 25 ring carbon atoms, and even more preferably an aralkyl group having the above-described aryl group having 6 to 18 ring carbon atoms. These may be further substituted.

The mono-substituted or di-substituted amino group in this aspect includes a mono-substituted or di-substituted amino group having a substituent selected from the above-described alkyl group having 1 to 50 carbon atoms and the above-described aryl group having 6 to 60 ring carbon atoms. The di-substituted amino group is preferred, and the di-substituted amino group having substituents selected from the above-described aryl group are more preferred. These may be further substituted. More preferably, there is mentioned a mono-substituted or di-substituted amino group having a substituent selected from the above-described alkyl group having 1 to 18 carbon atoms and the above-described aryl group having 6 to 25 ring carbon atoms. These may be further substituted. Even more preferably, there is mentioned a mono-substituted or di-substituted amino group having a substituent selected from the above-described alkyl group having 1 to 8 carbon atoms and the above-described aryl group having 6 to 18 ring carbon atoms. These may be further substituted.

The alkoxy group in this aspect includes an alkoxy group having the above-described alkyl group having 1 to 50 carbon atoms. These may be further substituted. More preferably, there is mentioned an alkoxy group having the above-described alkyl group having 1 to 18 carbon atoms. These may be further substituted. Even more preferably, there is mentioned an alkoxy group having the above-described alkyl group having 1 to 8 carbon atoms. For example, a methoxy group and an ethoxy group are preferred. These may be further substituted.

The cycloalkoxy group in this aspect includes a cycloalkoxy group having the above-described cycloalkyl group having 3 to 50 carbon atoms. These may be further substituted.

The aryloxy group in this aspect includes an aryloxy group having the above-described aryl group having 6 to 60 ring carbon atoms. These may be further substituted. More preferably, there is mentioned an aryloxy group having the above-described aryl group having 6 to 25 ring carbon atoms. These may be further substituted. Even preferably, there is mentioned an aryloxy group having the above-described aryl group having 6 to 18 ring carbon atoms. For example, a phenoxy group and the like are preferred. These may be further substituted.

The alkylthio group in this aspect includes an alkylthio group having the above-described alkyl group having 1 to 50 carbon atoms. These may be further substituted. More preferably, there is mentioned an alkylthio group having the above-described alkyl group having 1 to 18 carbon atoms. These may be further substituted. Even more preferably, there is mentioned an alkylthio group having the above-described alkyl group having 1 to 8 carbon atoms. These may be further substituted.

The arylthio group in this aspect includes an arylthio group having the above-described aryl group having 6 to 60 ring carbon atoms. These may be further substituted. More preferably, there is mentioned an arylthio group having the above-described aryl group having 6 to 25 ring carbon atoms. These may be further substituted. Even more preferably, there is mentioned an arylthio group having the above-described aryl group having 6 to 18 ring carbon atoms. These may be further substituted.

The mono-substituted, di-substituted or tri-substituted silyl group in this aspect includes a mono-substituted, di-substituted or tri-substituted silyl group having substituents selected from the above-described alkyl group having 1 to 50 carbon atoms and the above-described aryl group having 6 to 60 ring carbon atoms. These may be further substituted. More preferably, there is mentioned a mono-substituted, di-substituted or tri-substituted silyl group having substituents selected from the above-described alkyl group having 1 to 18 carbon atoms and the above-described aryl group having 6 to 25 ring carbon atoms. These may be further substituted. Even more preferably, there is mentioned a mono-substituted, di-substituted or tri-substituted silyl group having substituents selected from the above-described alkyl group having 1 to 8 carbon atoms and the above-described aryl group having 6 to 18 ring carbon atoms. These may be further substituted. For example, there are mentioned a trimethylsilyl group, a triethylsilyl group, a t-butyldimethylsilyl group, a vinyldimethylsilyl group, a propyldimethylsilyl group, an isopropyldimethylsilyl group, a triphenylsilyl group, a phenyldimethylsilyl group, a t-butyldiphenylsilyl group, a tritolylsilyl group, etc. These may be further substituted.

The haloalkyl group in this aspect includes the above-described alkyl group having 1 to 50 carbon atoms in which one or more hydrogen atoms are substituted with a halogen atom (fluorine atom, chlorine atom, bromine atom, iodine atom). These may be further substituted. More preferably, there is mentioned the above-described alkyl group having 1 to 18 carbon atoms in which one or more hydrogen atoms are substituted with the above-described halogen atom. These may be further substituted. Even more preferably, there is mentioned the above-described alkyl group having 1 to 8 carbon atoms in which one or more hydrogen atoms are substituted with the above-described halogen atom. These may be further substituted. Specifically, there are mentioned a trifluoromethyl group, a pentafluoromethyl group, a heptafluoromethyl group.

The sulfonyl group in this aspect includes a sulfonyl group having a substituent selected from the above-described alkyl group having 1 to 50 carbon atoms and the above-described aryl group having 6 to 60 ring carbon atoms. These may be further substituted. More preferably, there is mentioned a sulfonyl group having a substituent selected from the above-described alkyl group having 1 to 18 carbon atoms and the above-described aryl group having 6 to 25 ring carbon atoms. These may be further substituted. Even more preferably, there is mentioned a sulfonyl group having a substituent selected from the above-described alkyl group having 1 to 8 carbon atoms and the above-described aryl group having 6 to 18 carbon atoms. These may be further substituted.

The di-substituted phosphoryl group in this aspect includes a di-substituted phosphoryl group having substituents selected from the above-described alkyl group having 1 to 50 carbon atoms and the above-described aryl group having 6 to 60 ring carbon atoms. These may be further substituted. More preferably, there is mentioned a di-substituted phosphoryl group having substituents selected from the above-described alkyl group having 1 to 18 carbon atoms and the above-described aryl group having 6 to 25 ring carbon atoms. These may be further substituted. Even more preferably, there is mentioned a di-substituted phosphoryl group having substituents selected from the above-described alkyl group having 1 to 8 carbon atoms and the above-described aryl group having 6 to 18 ring carbon atoms. These may be further substituted.

The above-described alkylsulfonyloxy group, arylsulfonyloxy group, alkylcarbonyloxy group, arylcarbonyloxy group and alkyl-substituted or aryl-substituted carbonyl group include those having a substituent selected from the above-described alkyl group and the above-described aryl group.

Among the above substituents, in particular, a fluorine atom, a cyano group, an alkyl group, an aryl group, a heteroaryl group, a di-substituted amino group, a trifluoromethyl group, a pentafluoromethyl group and a heptafluoropropyl group are preferred.

In this aspect, preferably, the substituent represented by $R^1$ in the formula (1) each independently represent a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aryl group having 6 to 60 ring carbon atoms, a substituted or unsubstituted heteroaryl group having 5 to 60 ring atoms, a substituted or unsubstituted amino group, a substituted or unsubstituted aryloxy group having 6 to 60 ring carbon atoms, a substituted silyl group, a substituted or unsubstituted haloalkyl group having 1 to 50 carbon atoms, a halogen atom, a cyano group or a nitro group. Specific examples of these groups include the same ones as those described hereinabove.

In this aspect, the substituent represented by $R^1$ in the formula (1) is each independently preferably a substituted or unsubstituted aryl group having 6 to 60 ring carbon atoms, or a substituted or unsubstituted heteroaryl group having 5 to 60 ring atoms, and is more preferably any of a substituted or unsubstituted phenyl group, a substituted or unsubstituted naphthyl group, a substituted or unsubstituted anthracenyl group, a substituted or unsubstituted phenanthryl group, a substituted or unsubstituted fluorenyl group, a substituted or unsubstituted dibenzofuranyl group, a substituted or unsubstituted dibenzothiophenyl group, a substituted or unsubstituted carbazolyl group, or an aza form thereof.

In $R^1$ in the formula (1), the ring that may be formed by the adjacent substituents bonding to each other includes a substituted or unsubstituted aromatic hydrocarbon ring having 6 to 60 ring carbon atoms, or a substituted or unsubstituted hetero ring having 5 to 60 ring atoms.

The substituted or unsubstituted aromatic hydrocarbon ring having 6 to 60 ring carbon atoms includes the ring corresponding to the aryl group that is a substituent represented by the above $R^1$.

The substituted or unsubstituted hetero ring having 5 to 60 ring atoms includes the ring corresponding to the heteroaryl group that is a substituent represented by the above $R^1$.

In the formula (1), $L^1$ represents a single bond, a substituted or unsubstituted arylene group having 6 to 50 ring carbon atoms, or a substituted or unsubstituted heteroarylene group having 5 to 50 ring atoms.

Examples of the substituted or unsubstituted aryl group having 6 to 60 ring carbon atoms include the same ones as those of the aryl group that is a substituent represented by the above-described $R^1$.

Examples of the substituted or unsubstituted heteroaryl group having 5 to 60 ring atoms include the same ones as those of the heteroaryl group that is a substituent represented by the above-described $R^1$.

In the formula (1), $L^1$ represents a single bond, or a substituted or unsubstituted arylene group having 6 to 50 ring carbon atoms.

In the formula (1), $L^1$ preferably bonds to the carbon atom adjacent to $X^1$ to $X^6$ or $Z^1$ to $Z^4$ representing a nitrogen atom, and more preferably bonds to the carbon atom adjacent to $X^1$ to $X^6$ representing a nitrogen atom.

At least one $L^1$ preferably bonds to the carbon atom represented by $X^2$.

In the formula (1), $X^3$ is preferably a nitrogen atom.

Here, the "carbon atom adjacent to $X^1$ to $X^6$ or $Z^1$ to $Z^4$ representing a nitrogen atom" is considered as follows. For example, in the case where $X^1$ is a nitrogen atom as shown in the following formula (NL1), "$X^2$ is adjacent thereto". In the case where $X^2$ is a nitrogen atom as shown in the following formulae (NL2-1) to (NL2-3), "$X^1$ and $X^3$ are adjacent thereto". In the case where $X^3$ is a nitrogen atom as shown in the following formulae (NL3-1) to (NL3-3), "$X^2$ or $X^4$ is adjacent thereto". In the case where $X^1$ and $X^3$ are nitrogen atoms as shown in the following formula (NL4), "$X^2$ is adjacent thereto". Only the cases where $X^1$ to $X^3$ each are a nitrogen atom are described, but the same shall apply to other cases where $X^4$ to $X^6$ and $Z^1$ to $Z^4$ each are a nitrogen atom. $X^1$ to $X^6$, $Z^1$ to $Z^4$ and $L^1$ in the formulae (NL1) to (NL4) are the same as $X^1$ to $X^6$, $Z^1$ to $Z^4$ and $L^1$ in the formula (1).

[Chem. 6]

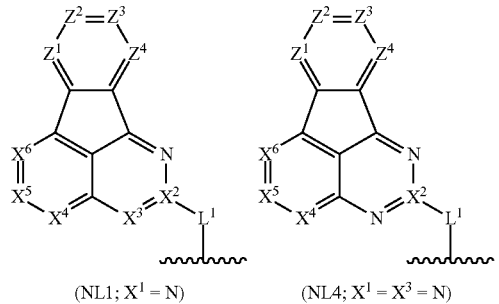

(NL1; $X^1$ = N)            (NL4; $X^1$ = $X^3$ = N)

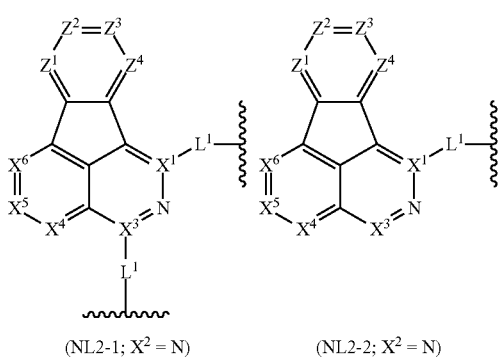

(NL2-1; $X^2$ = N)          (NL2-2; $X^2$ = N)

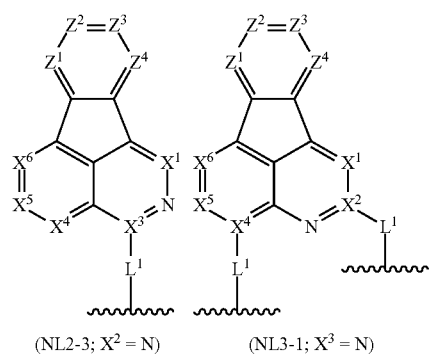

(NL2-3; $X^2$ = N)          (NL3-1; $X^3$ = N)

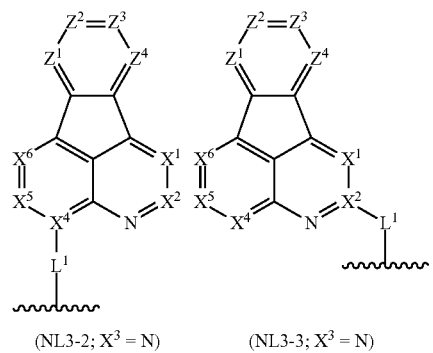

(NL3-2; $X^3$ = N)          (NL3-3; $X^3$ = N)

In the formula (1), n indicates an integer of 1 to 3. Preferably, n is an integer of 1 to 2, and is more preferably 1. Specifically, the compound represented by the formula (1) is preferably represented by the formula (3).

[Chem. 7]

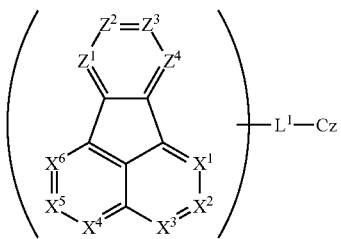

(3)

In the formula (3), $X^1$ to $X^6$ and $Z^1$ to $Z^4$, $L^1$ and Cz are the same as those described above.

In the formula (3), $L^1$ preferably bonds to the carbon atom adjacent to $X^1$, $X^2$ or $X^3$, or preferably bonds to the carbon atom represented by $X^2$.

In the formula (3), $X^3$ is preferably a nitrogen atom.

Cz represents a group represented by the following formula (2).

[Chem. 8]

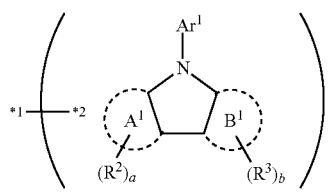

(2)

In the formula (2), $Ar^1$ represents a single bond bonding to *2 or a monovalent substituent.

The ring $A^1$ and the ring $B^1$ each independently represent an aromatic hydrocarbon ring having 5 to 50 ring carbon atoms, or an aromatic hetero ring having 5 to 50 ring atoms.

$R^2$ and $R^3$ each independently represent a substituent.

a and b each independently indicate an integer of 0 or more, provided that in the case where $Ar^1$ represents a single bond bonding to *2, the total of a and b is 1 or more.

*1 represents the bonding position to $L^1$.

*2 bonds to any one of one ring carbon atom of the ring $A^1$, one ring carbon atom of the ring $B^1$, and $Ar^1$.

At least one of $Ar^1$, $R^2$ and $R^3$ is a substituted or unsubstituted aryl group having 6 to 50 ring carbon atoms, or a substituted or unsubstituted heteroaryl group having 5 to 50 ring atoms.

In the formula (2), $Ar^1$ represents a single bond when bonding to *2. Specifically, the nitrogen atom of the ring $C^1$ in the following formula (2') bonds to $L^1$. When $Ar^1$ bonds to *2, the total of a and b in the formula (2) is 1 or more. When $Ar^1$ bonds to *2, the total of a and b in the formula (2) is preferably 1 to 3, more preferably 1 to 2, and even more preferably 1.

[Chem. 9]

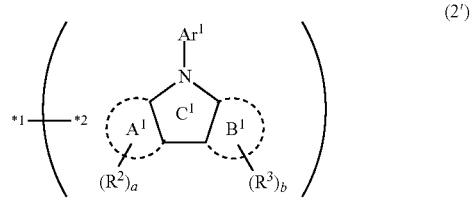

(2')

$Ar^1$, $R^2$, $R^3$, a, b, *1 and *2 in the formula (2') are the same as $Ar^1$, $R^2$, $R^3$, a, b, *1 and *2, respectively, in the formula (2).

In the formula (2) where $Ar^1$ does not bond to *2, $Ar^1$ represents a monovalent substituent. Examples of the substituent represented by $Ar^1$ include the same as those of the substituent represented by the above-described $R^1$. However, at least one of $Ar^1$, $R^2$ and $R^3$ is a substituted or unsubstituted aryl group having 6 to 50 ring carbon atoms or a substituted or unsubstituted heteroaryl group having 5 to 50 ring atoms. Accordingly, when both $R^2$ and $R^3$ are not a substituted or unsubstituted aryl group having 6 to 50 ring carbon atoms and are not a substituted or unsubstituted heteroaryl group having 5 to 50 ring atoms, $Ar^1$ is a substituted or unsubstituted aryl group having 6 to 50 ring carbon atoms or a substituted or unsubstituted heteroaryl group having 5 to 50 ring atoms.

Examples of the substituted or unsubstituted aryl group having 6 to 60 ring carbon atoms include the same ones as those of the aryl group that is a substituent represented by the above-described $R^1$.

Examples of the substituted or unsubstituted heteroaryl group having 5 to 60 ring atoms include the same ones as those of the heteroaryl group that is a substituent represented by the above-described $R^1$.

The ring $A^1$ and the ring $B^1$ each independently represent an aromatic hydrocarbon ring having 5 to 50 (more preferably 6 to 25, even more preferably 6 to 18) ring carbon atoms, or an aromatic hetero ring having 5 to 50 (more preferably 5 to 30, even more preferably 5 to 26) ring atoms.

In the formula (2), specific examples of the condensed ring formed by the ring $A^1$, the ring $B^1$ and the ring $C^1$ include, though not limited thereto, the following structures (abc-1) to (abc-17) and (abc-h1) to (abc-h26).

In the structures (abc-1) to (abc-17) and (abc-h1) to (abc-h26), ** represents the bonding position to $Ar^1$. In the structures (abc-h1) to (abc-h26), X and Y each independently represent NR, an oxygen atom or a sulfur atom, and R represents a hydrogen atom or a substituent. Examples of the substituent represented by R include the same ones as those of the substituent represented by the above-described $R^1$.

[Chem. 10]

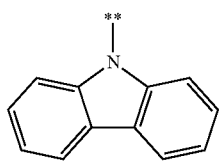

(abc-1)

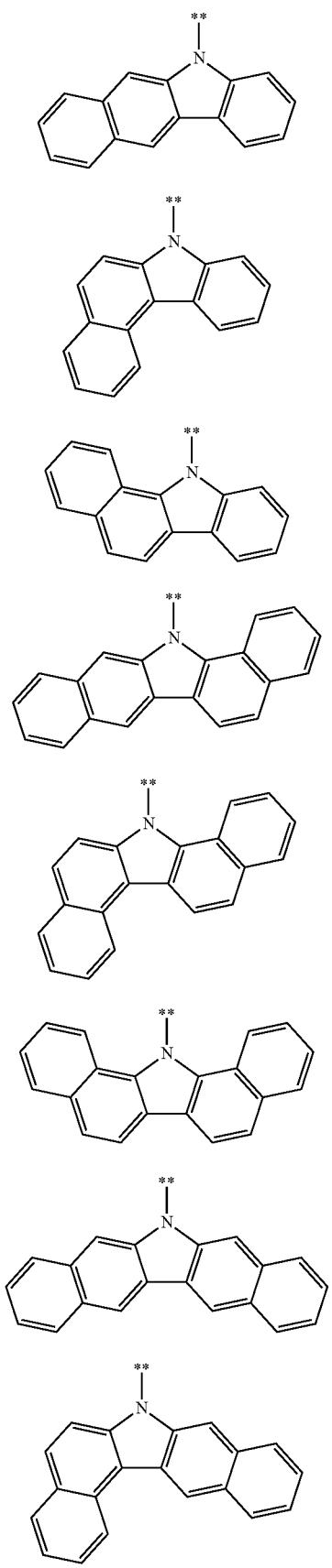
(abc-2)
(abc-3)
(abc-4)
(abc-5)
(abc-6)
(abc-7)
(abc-8)
(abc-9)
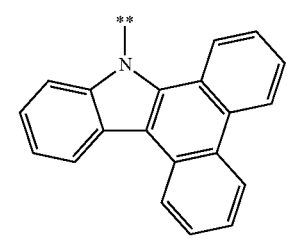
(abc-10)
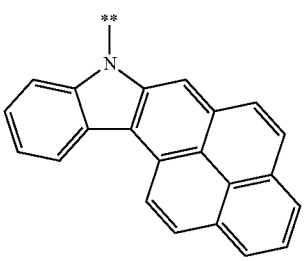
(abc-11)
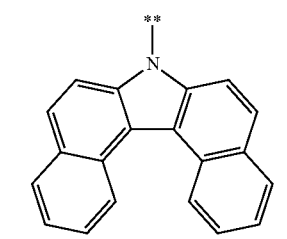
(abc-12)
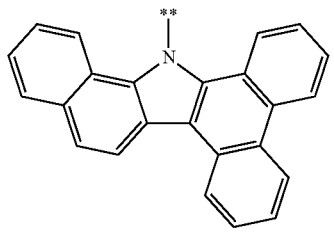
(abc-13)
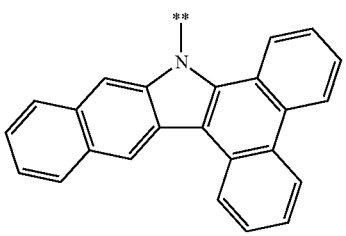
(abc-14)
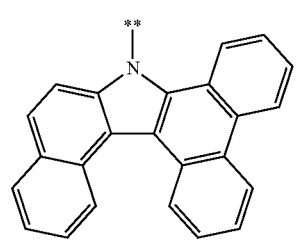
(abc-15)

-continued
(abc-16)
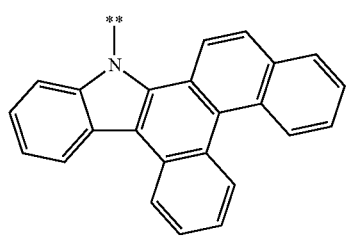
(abc-17)
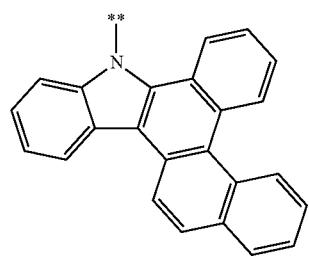
[Chem. 11]
(abc-h1)
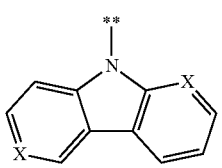
(abc-h2)
(abc-h3)
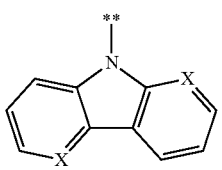
(abc-h4)
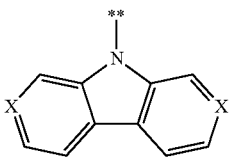
(abc-h5)
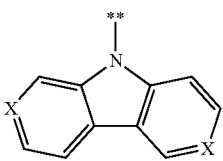
(abc-h6)
-continued
(abc-h7)
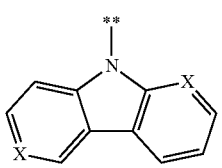
(abc-h8)
(abc-h9)
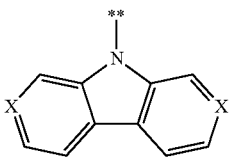
(abc-h10)
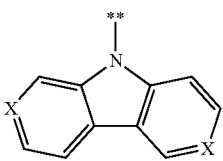
(abc-h11)
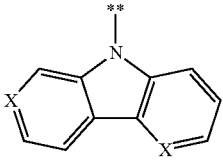
(abc-h12)
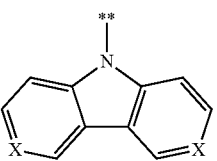
(abc-h13)
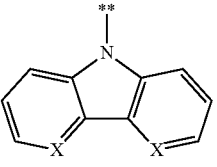
(abc-h14)
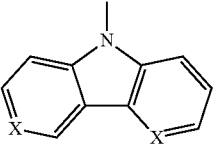
(abc-h15)
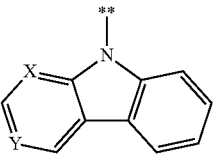

(abc-h16) 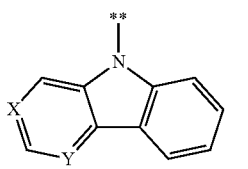

(abc-h17) 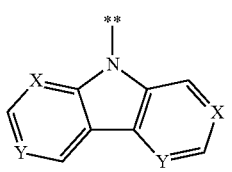

(abc-h18) 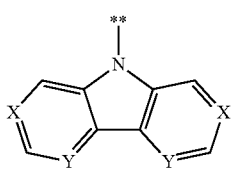

(abc-h19) 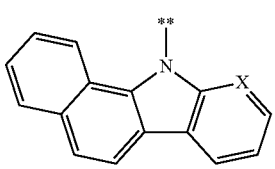

(abc-h20) 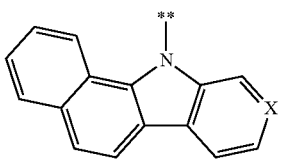

(abc-h21) 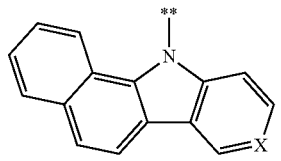

(abc-h22) 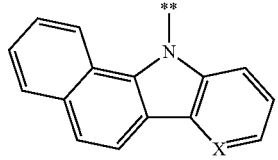

(abc-h23) 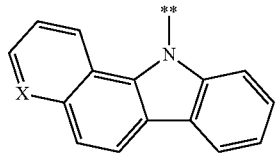

(abc-h24) 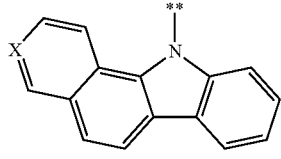

(abc-h25) 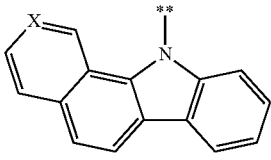

(abc-h26) 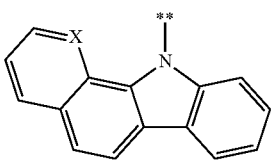

In the formula (2), $R^2$ and $R^3$ each independently represent a substituent. Examples of the substituent represented by $R^2$ and $R^3$ each independently include the same ones as those described hereinabove for the above-described $R^1$.

However, when $Ar^1$ bonds to *2, at least one of $R^2$ and $R^3$ is a substituted or unsubstituted aryl group having 6 to 50 ring carbon atoms or a substituted or unsubstituted heteroaryl group having 5 to 50 ring atoms.

Examples of the substituted or unsubstituted aryl group having 6 to 60 ring carbon atoms include the same ones as those of the aryl group that is a substituent represented by the above-described $R^1$.

Examples of the substituted or unsubstituted heteroaryl group having 5 to 60 ring atoms include the same ones as those of the heteroaryl group that is a substituent represented by the above-described $R^1$.

At least one of $R^2$ and $R^3$ is preferably represented by the following formula (5).

[Chem. 12]

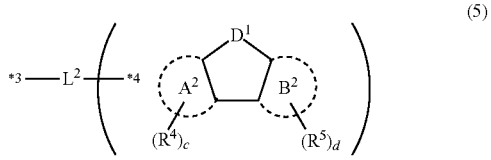

(5)

In the formula (5), the ring $A^2$ and the ring $B^2$ each independently represent an aromatic hydrocarbon ring having 5 to 50 ring carbon atoms, or an aromatic hetero ring having 5 to 50 ring atoms.

$R^4$ and $R^5$ each independently represent a substituent, c and d each indicate an integer of 0 or more.

$D^1$ represents an oxygen atom, a sulfur atom, $CR^6R^7$ or $NR^8$.

$R^6$ to $R^8$ each independently represent a hydrogen atom, a substituent or a single bond bonding to *4.

$L^2$ represents a single bond, a substituted or unsubstituted arylene group having 6 to 50 ring carbon atoms, or a substituted or unsubstituted heteroarylene group having 5 to 50 ring atoms.

*3 bonds to the ring carbon atom of the ring $A^1$ or the ring $B^1$.

*4 bonds to any one of one ring carbon atom of the ring $A^2$, one ring carbon atom of the ring $B^2$, and $R^6$ to $R^8$.

The $A^2$ and the ring $B^2$ in the formula (5) are the same as the ring $A^1$ and the ring $B^1$ in the formula (2), and specific examples of the condensed ring to be formed by the $A^2$ and the ring $B^2$ in the formula (5) and the 5-membered ring formed including $D^1$ in the formula (5) include the aforementioned structures (abc-1) to (abc-17) and (abc-h1) to (abc-h26).

In the formula (5), $R^4$ and $R^5$ each represent a substituent, and c and d each indicate an integer of 0 or more. Examples of the substituent represented by $R^4$ and $R^5$ each independently include the same ones as those described hereinabove as the substituent represented by the above-described $R^1$.

Preferably, c and d are both 0 to 2, more preferably 0 to 1.

In the formula (5), $D^1$ represents an oxygen atom, a sulfur atom, $CR^6R^7$ or $NR^8$. $R^6$ to $R^8$ each independently represent a hydrogen atom, a substituent or a single bond bonding to *4. Examples of the substituent represented by $R^6$ to $R^8$ each are independently the same ones as those of the substituent represented by the above-described $R^1$.

$D^1$ is preferably $NR^8$, an oxygen atom or a sulfur atom, more preferably $NR^8$, and even more preferably NH.

In the formula (5), $L^2$ represents a single bond, a substituted or unsubstituted arylene group having 6 to 50 ring carbon atoms, or a substituted or unsubstituted heteroarylene group having 5 to 50 ring atoms.

Examples of the substituted or unsubstituted aryl group having 6 to 60 ring carbon atoms include the same ones as those of the aryl group that is a substituent represented by the above-described $R^1$.

Examples of the substituted or unsubstituted heteroaryl group having 5 to 60 ring atoms include the same ones as those of the heteroaryl group that is a substituent represented by the above-described $R^1$.

In the formula (5), $L^2$ is preferably a single bond, or a substituted or unsubstituted arylene group having 6 to 50 ring carbon atoms.

Cz is preferably represented by the following formula (6).

[Chem. 13]

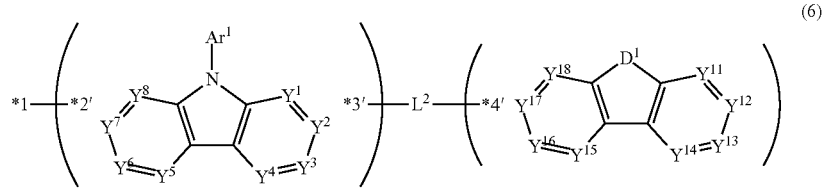

(6)

In the formula (6), $Y^1$ to $Y^8$ each independently represent $CR^9$ or a nitrogen atom, $Y^{11}$ to $Y^{18}$ each independently represent $CR^{10}$ or a nitrogen atom, $R^9$ each independently represent a hydrogen atom, a substituent or a single bond bonding to *2'.

$R^{10}$ each independently represent a hydrogen atom, a substituent or a single bond bonding to *4'.

*1, $Ar^1$, $D^1$ and $L^2$ are the same as above.

*2' bonds to the carbon atom that any one of $Ar^1$ or $R^9$ represents.

*3' bonds to any one of plural $R^9$'s.

*4' bonds to any one of $R^6$ to $R^8$ or plural $R^{10}$'s.

In the formula (6), preferably, $L^2$ bonds to the two carbon atoms that $Y^2$ and $Y^{13}$ represent, the two carbon atoms that $Y^3$ and $Y^{12}$ represent, or the two carbon atoms that $Y^3$ and $Y^{13}$ represent.

In the formula (2) where $Ar^1$ is a single bond bonding to *2, Cz is preferably represented by the following formula (7), more preferably by the following formula (8).

[Chem. 14]

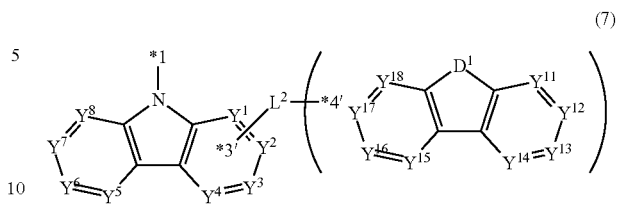

(7)

[Chem. 15]

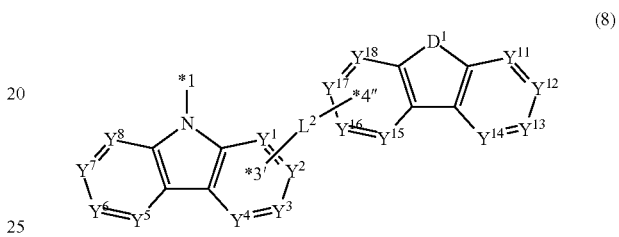

(8)

In the formula (7), *1, *3', *4', $Y^1$ to $Y^8$, $Y^{11}$ to $Y^{18}$, $L^2$, and $D^1$ are the same as described above.

In the formula (8), *1, *3', $Y^1$ to $Y^8$, $Y^{11}$ to $Y^{18}$, $L^2$, and $D^1$ are the same as described above.

*4" bonds to the carbon atom that any one of $Y^{15}$ to $Y^{18}$ represents, and the other $Y^{15}$ to $Y^{18}$ each independently represent $CR^{10}$ or a nitrogen atom.

$R^{10}$ is the same as described above.

In the formula (2) where $Ar^1$ represents a monovalent substituent, Cz is preferably represented by the following formula (9), more preferably by the following formula (10).

[Chem. 16]

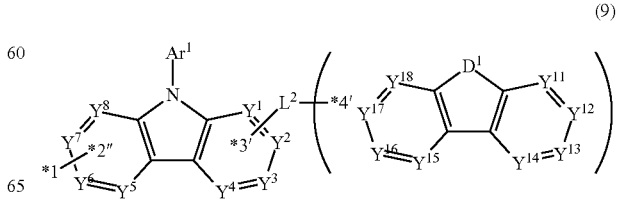

(9)

-continued

[Chem. 17]

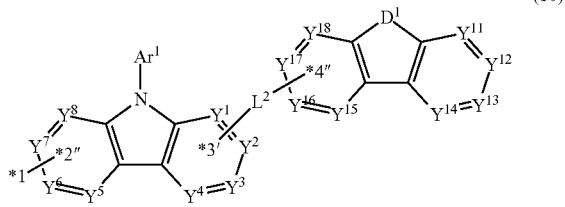
(10)

In the formula (9), *1, *3', *4', $Y^1$ to $Y^8$, $Y^{11}$ to $Y^{18}$, $L^2$, and $D^1$ are the same as described above.

In the formula (9), *2" bonds to the carbon atom that any one of $Y^5$ to $Y^8$ represents, and the other $Y^5$ to $Y^8$ each independently represent $CR^{10}$ or a nitrogen atom. $R^{10}$ is the same as described above.

In the formula (10), *1, *2", *3', *4", $Y^1$ to $Y^8$, $Y^{11}$ to $Y^{18}$, $L^2$, and $D^1$ are the same as described above.

Among the above-described structures, the compound represented by the formula (1) is preferably represented by the formula (1) having Cz represented by the formula (7), more preferably represented by the formula (1) having Cz represented by the formula (8), even more preferably by the formula (3) having Cz represented by the formula (7), and further more preferably by the formula (3) having Cz represented by the formula (8).

Specifically, the compound represented by the formula (1) is further preferably represented by the following formula (11), and further more preferably represented by the following formula (12).

[Chem. 18]

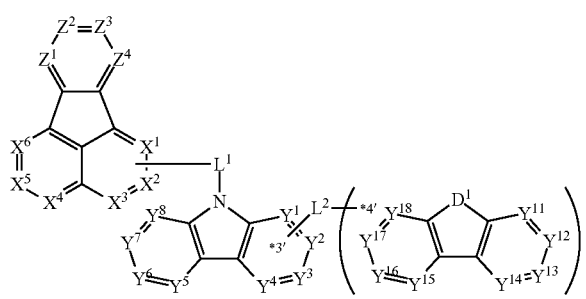
(11)

[Chem. 19]

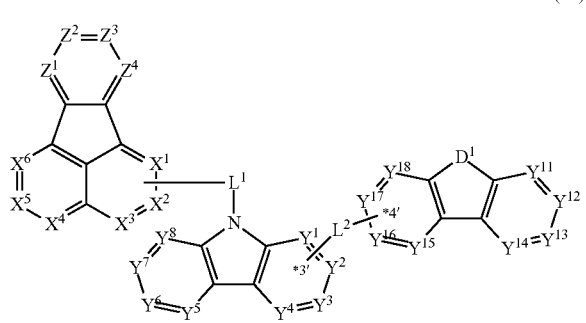
(12)

In the formula (11), $X^1$ to $X^6$, $Z^1$ to $Z^4$, $L^1$, $Y^1$ to $Y^8$, *3', $L^2$, *4', $Y^{11}$ to $Y^{18}$, and $D^1$ are the same as described above.

In the formula (12), $X^1$ to $X^6$, $Z^1$ to $Z^4$, $L^1$, $Y^1$ to $Y^8$, *3', $L^2$, *4", $Y^{11}$ to $Y^{18}$, and $D^1$ are the same as described above.

[Compound Represented by Formula (13)]

The organic EL device material of an aspect of the present invention may contain a compound represented by the following formula (13).

[Chem. 20]

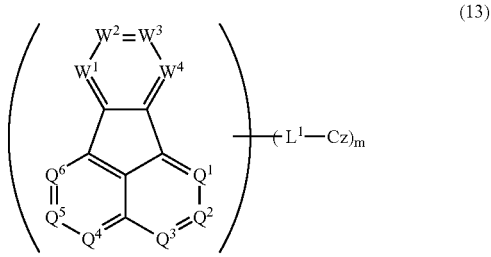
(13)

In the formula (13),
any "m" number of $Q^1$ to $Q^6$ and $W^1$ to $W^4$ each represent a carbon atom bonding to $L^1$, and when $Q^1$ to $Q^6$ and $W^1$ to $W^4$ do not represent a carbon atom bonding to $L^1$, $W^2$ and $W^3$ each independently represent $CR^{11}$, $W^1$ and $W^4$ each independently represent $CR^{11}$ or a nitrogen atom, and $Q^1$ to $Q^6$ each independently represent $CR^{11}$ or a nitrogen atom, with the proviso that at least one of $W^1$ and $W^4$ is a nitrogen atom.

m indicates an integer of 1 to 3.

$R^{11}$ each independently represent a hydrogen atom or a substituent.

$L^1$ represents a single bond, a substituted or unsubstituted arylene group having 6 to 50 ring carbon atoms, or a substituted or unsubstituted heteroarylene group having 5 to 50 ring atoms.

Cz represents a group represented by the above-described formula (2).

The formula (2) is the same as the formula (2) described hereinabove for the compound represented by the formula (1).

In the formula (13), examples of the substituent represented by $R^{11}$ each are independently the same ones as those described hereinabove for $R^1$.

In the formula (13), plural $R^{11}$'s bonding to the adjacent carbon atom of the carbon atoms to which $R^{11}$'s bond may bond to each other to form a saturated or unsaturated ring structure, or may not form a ring structure.

Regarding $R^{11}$ in the formula (13), the ring that may be formed by the adjacent substituents bonding to each other includes a substituted or unsubstituted aromatic hydrocarbon ring having 6 to 60 ring carbon atoms or a substituted or unsubstituted hetero ring having 5 to 60 ring atoms.

The substituted or unsubstituted aromatic hydrocarbon ring having 6 to 60 ring carbon atoms includes the ring corresponding to the aryl group that is a substituent represented by the above-described $R^1$.

The substituted or unsubstituted hetero ring having 5 to 60 ring atoms includes the ring corresponding to the heteroaryl group that is a substituent represented by the above-described $R^1$.

In the formula (13), m indicates an integer of 1 to 3, and is preferably an integer of 2 to 3.

In the formula (13), $L^1$ and Cz are the same as $L^1$ and Cz in the formula (1) described for the compound represented by the formula (1).

In the formula (13), $L^1$ preferably bonds to any one to three carbon atoms that $Q^1$ to $Q^6$ and $W^2$ to $W^4$ represent, more preferably bonds to any one to three carbon atoms that $Q^1$ to $Q^6$, $W^2$ and $W^3$ represent.

In the formula (13), $Q^1$ to $Q^6$, $W^2$ and $W^3$ are preferably $CR^{11}$, and $W^1$ is preferably a nitrogen atom.

In the compound represented by the formula (13), at least one of $R^2$ and $R^3$ in the formula (2) is preferably represented by the above-described formula (5). The formula (5) is the same as the formula (5) described hereinabove for the compound represented by the formula (1).

Cz in the formula (13) is preferably represented by any of the formula (6) to the formula (10), more preferably by the formula (9), and even more preferably by the formula (10). The formula (6) to the formula (10) are the same as the formula (6) to the formula (10), respectively, described hereinabove for the compound represented by the formula (1).

Specific examples of the compound represented by the formula (1) and those of the compound represented by the formula (13) in an aspect of the present invention are shown below, but the present invention is not limited to these.

[Chem. 21]

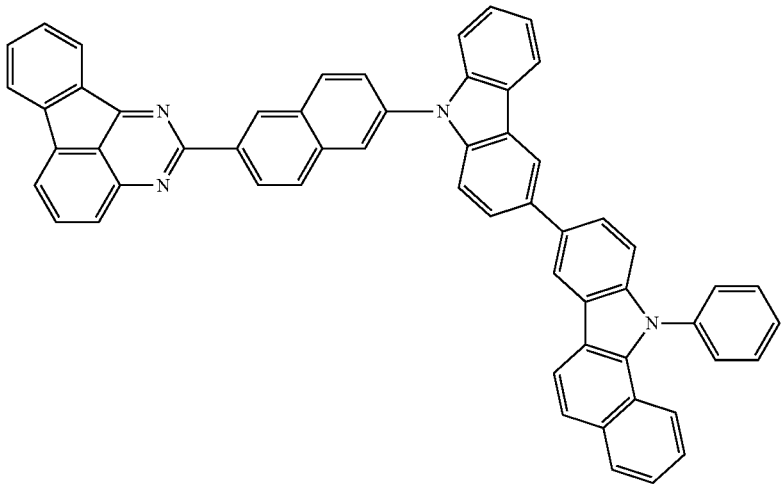

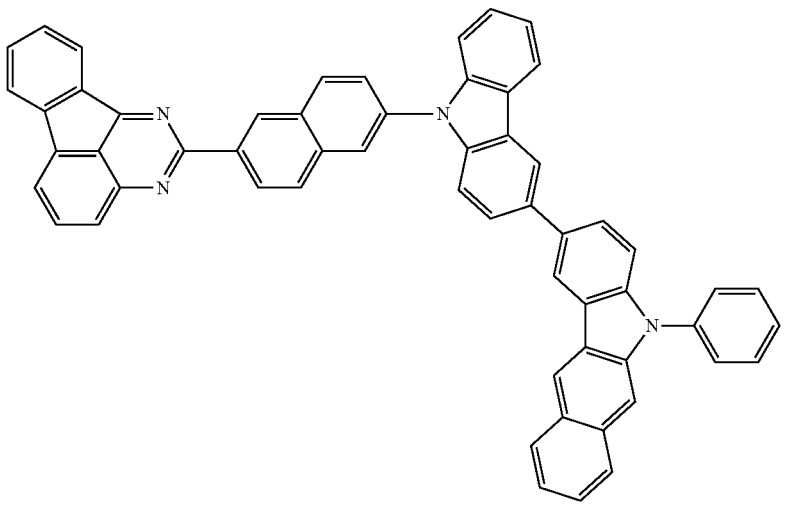

-continued
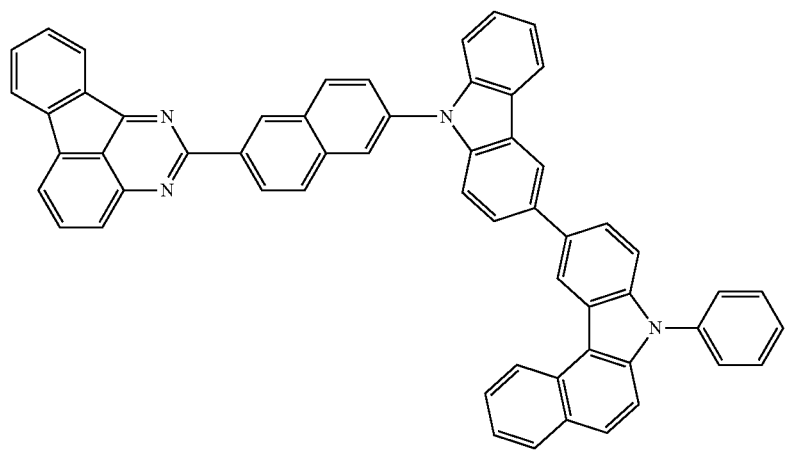
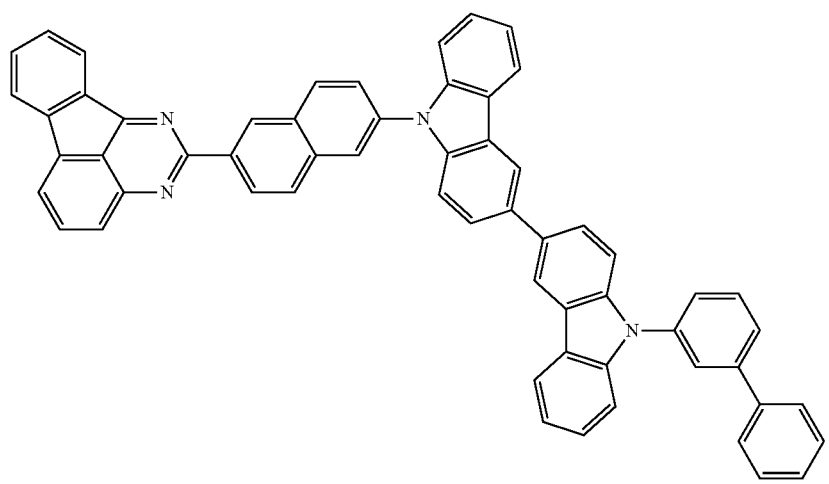
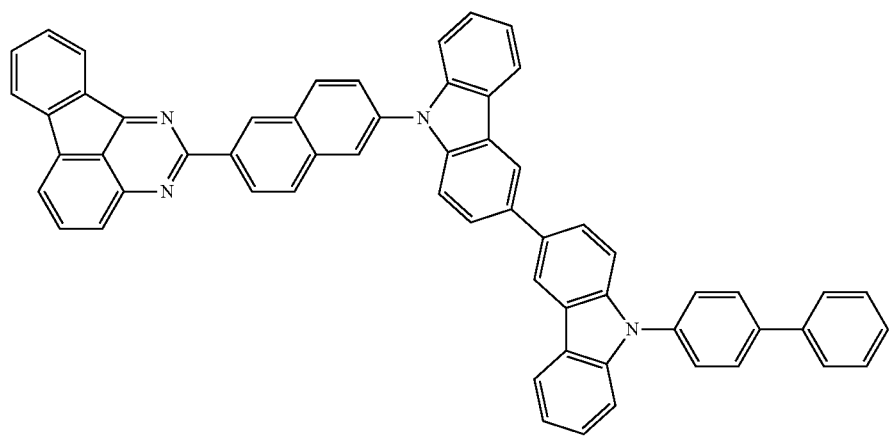

-continued
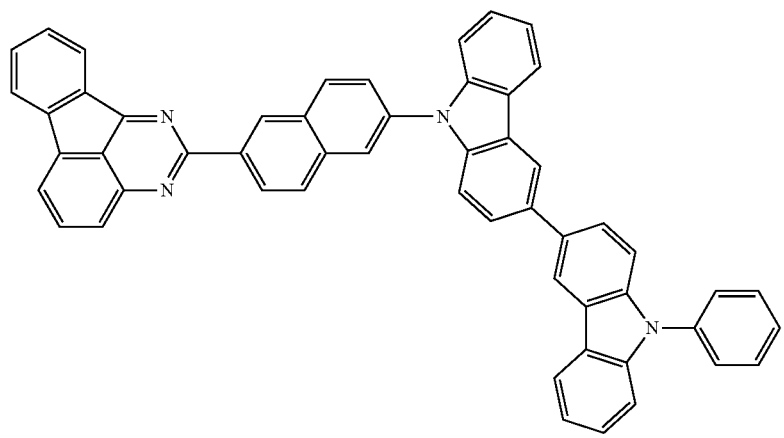
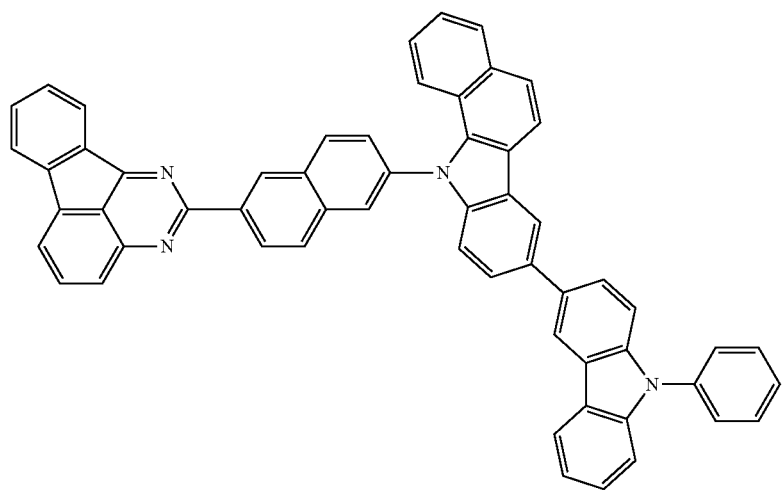
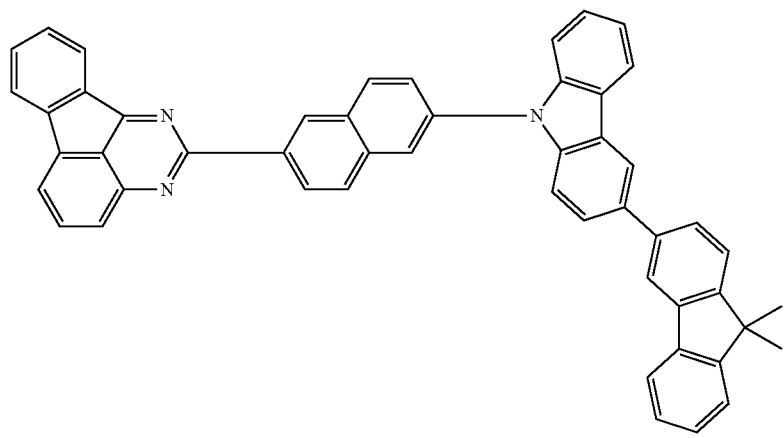

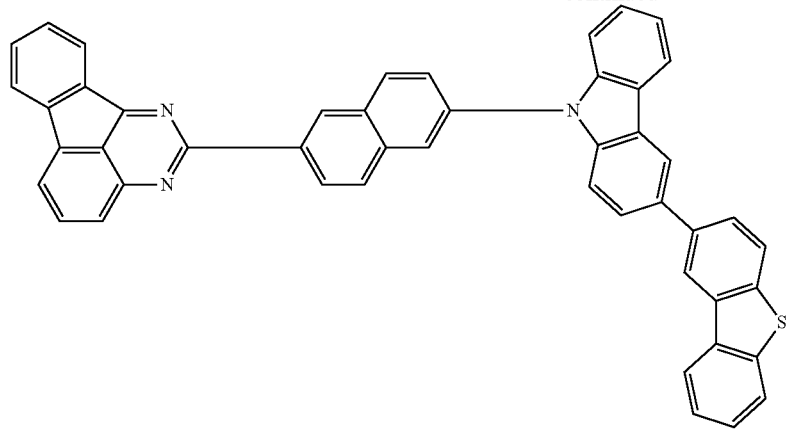
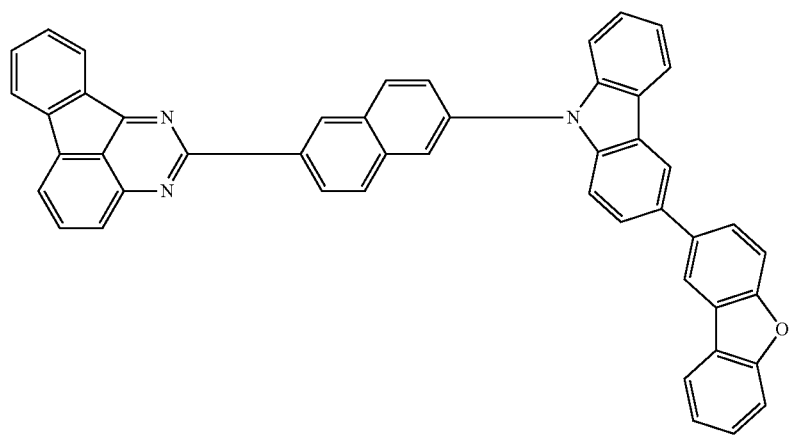
[Chem. 22]
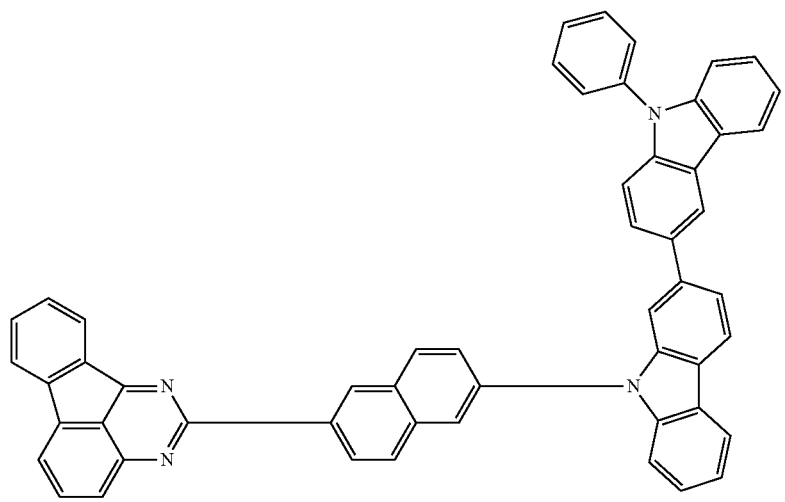

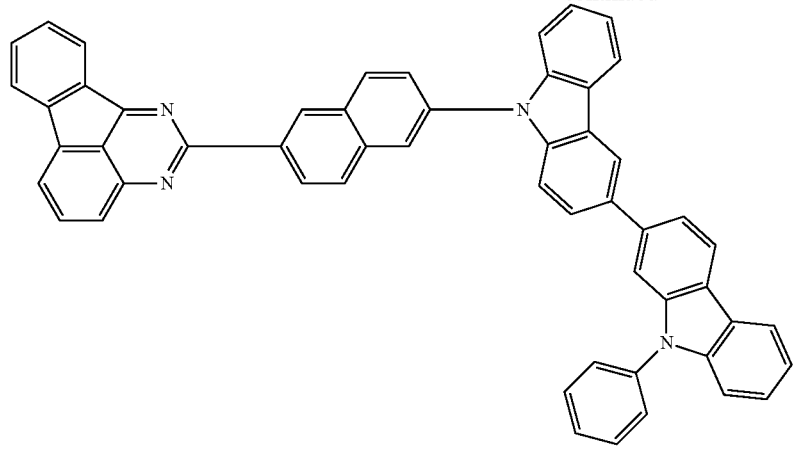
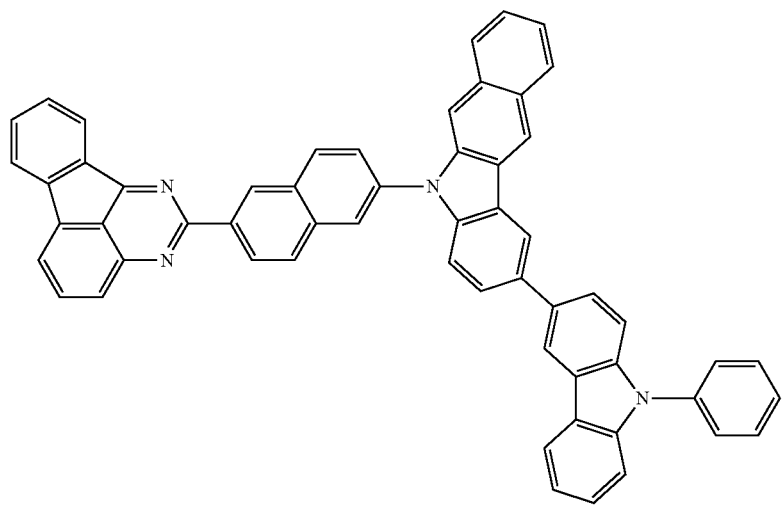
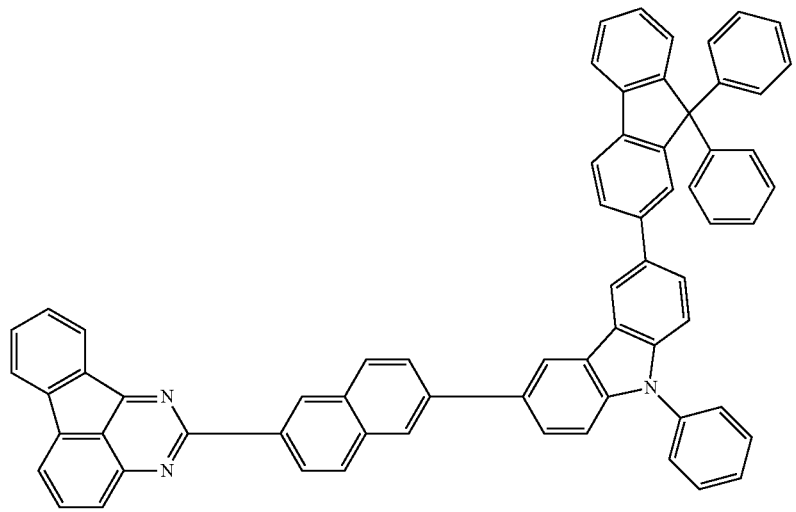

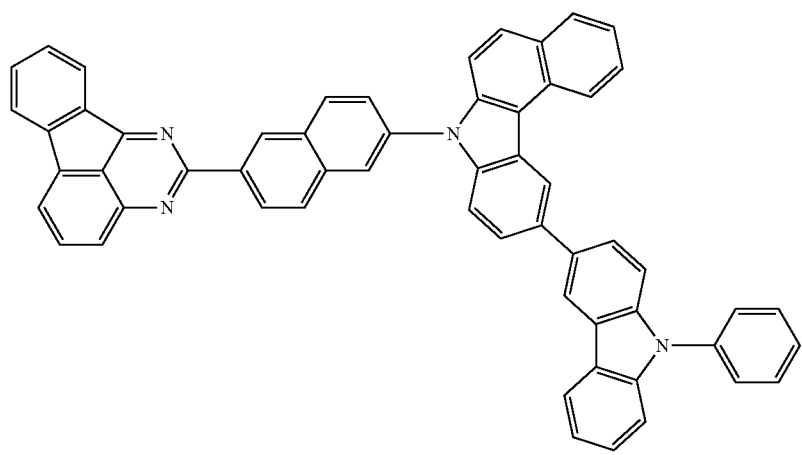
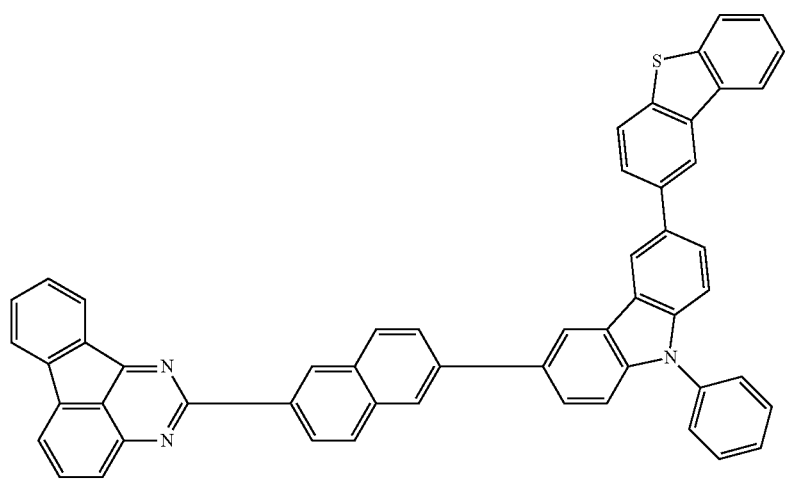
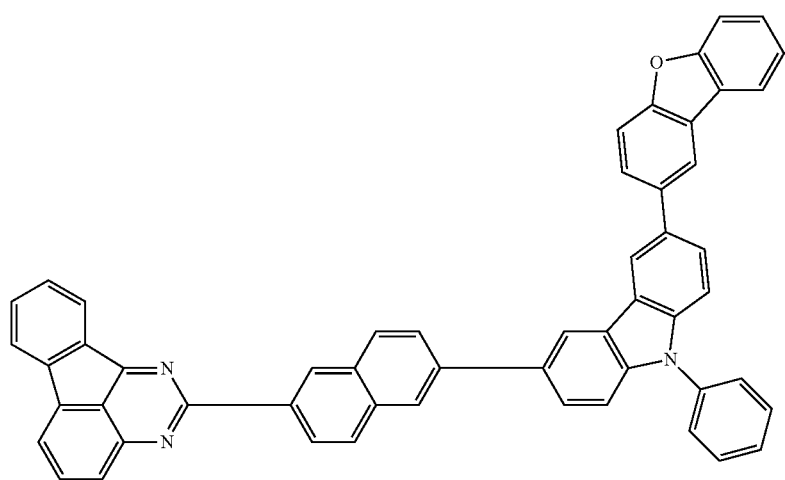

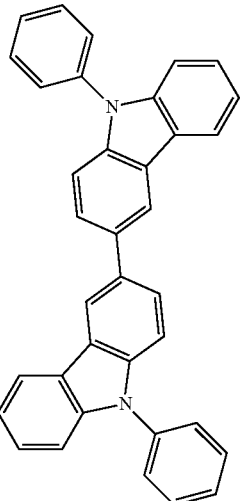
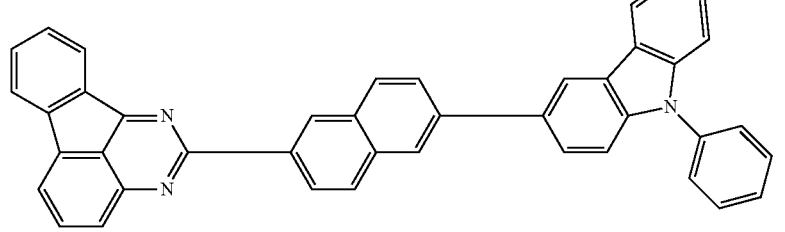
[Chem. 23]
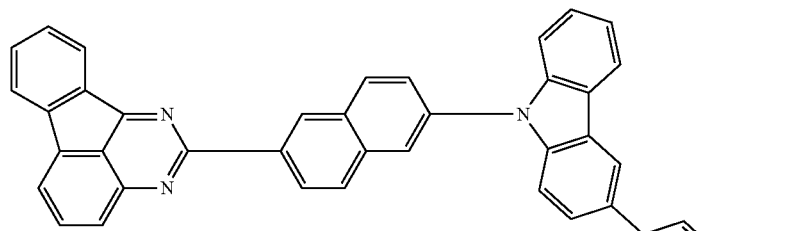
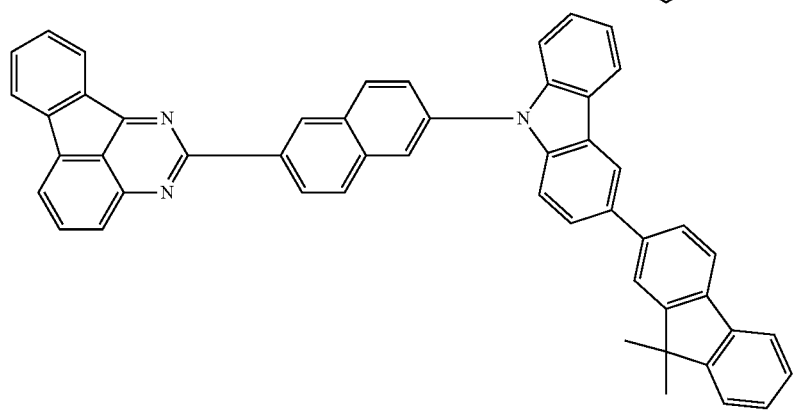

-continued
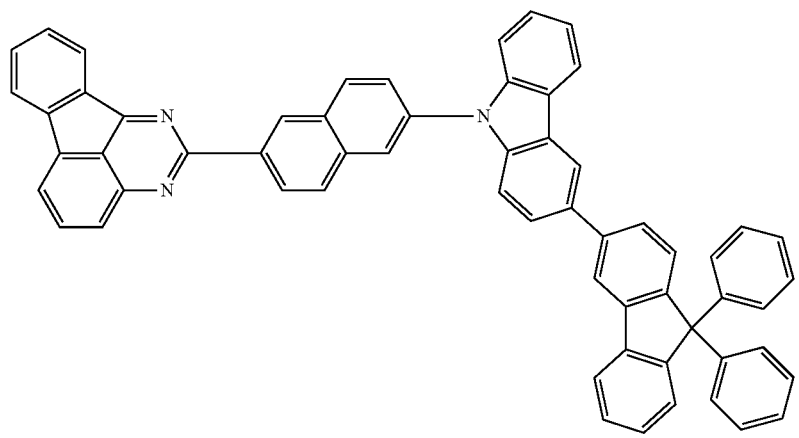
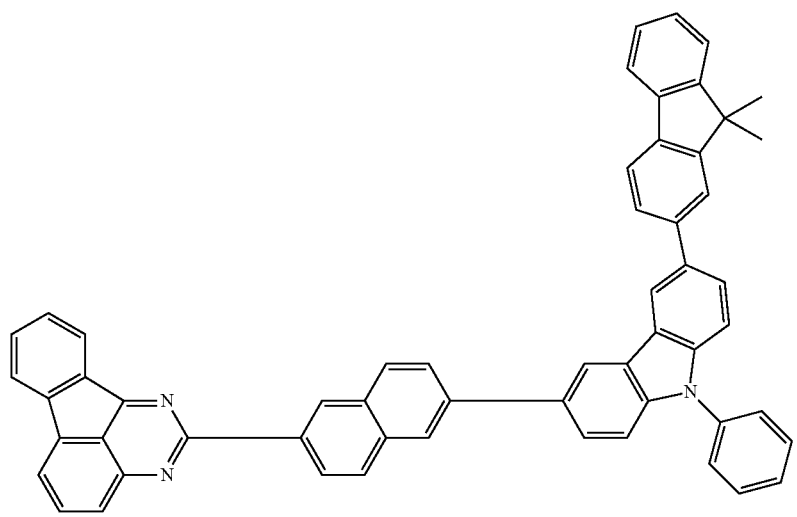
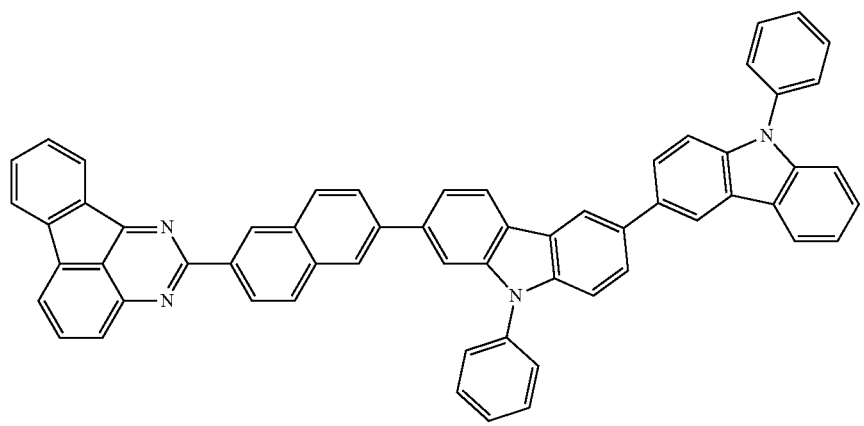

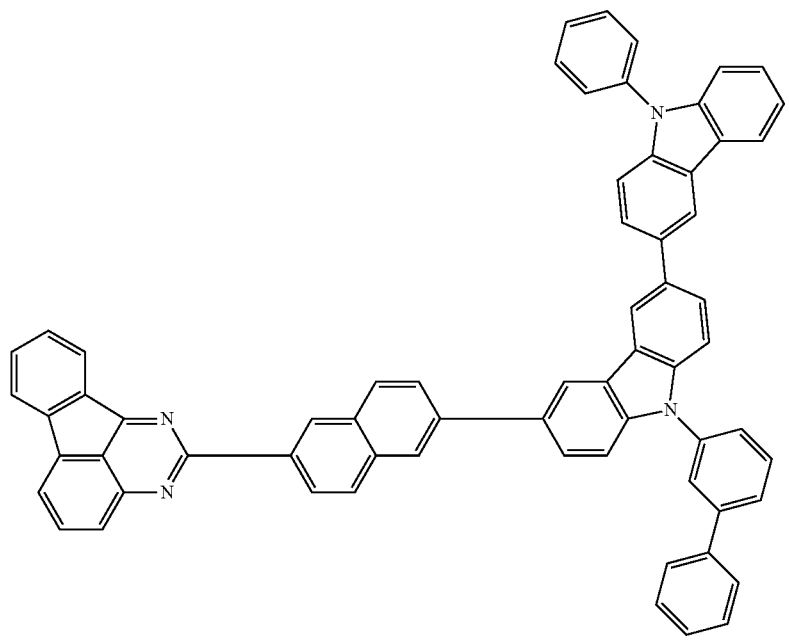
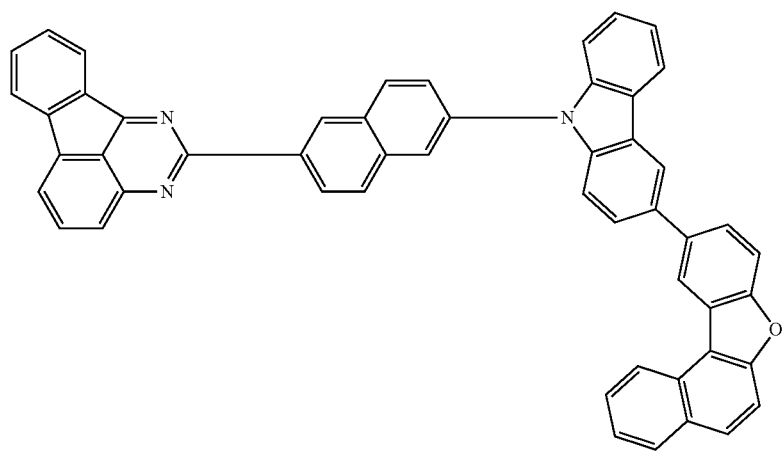
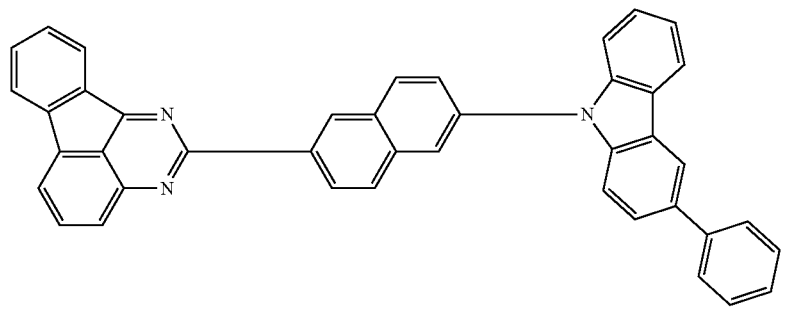

-continued
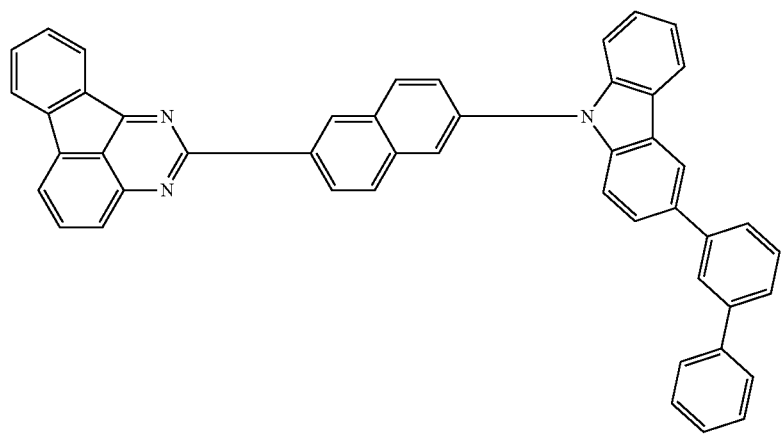
[Chem. 24]
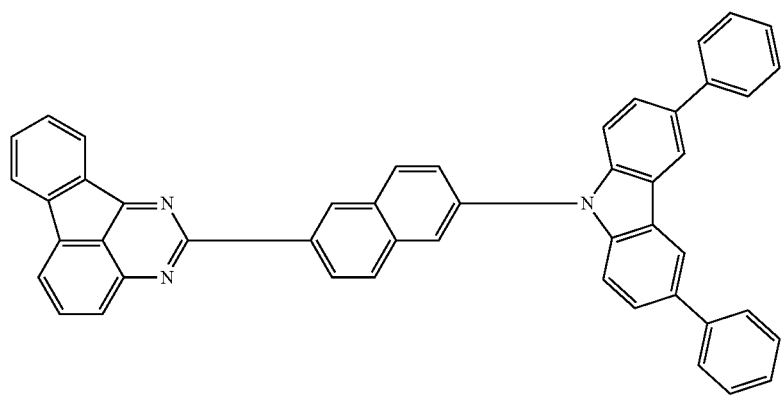
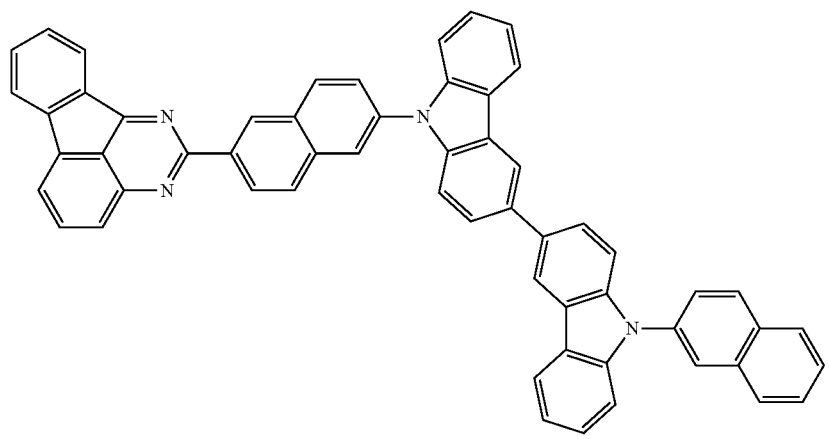
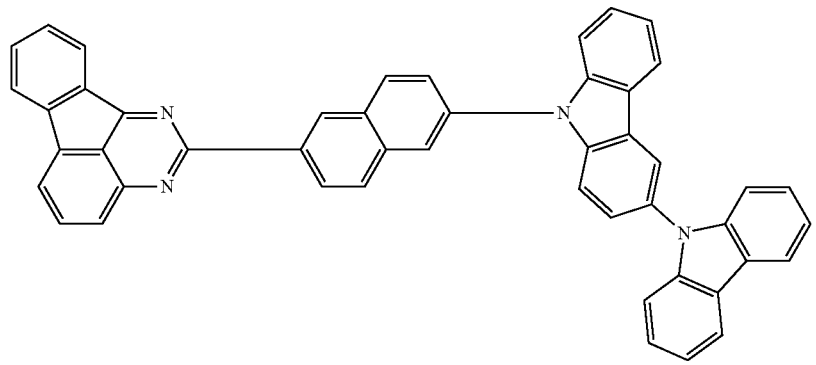

-continued
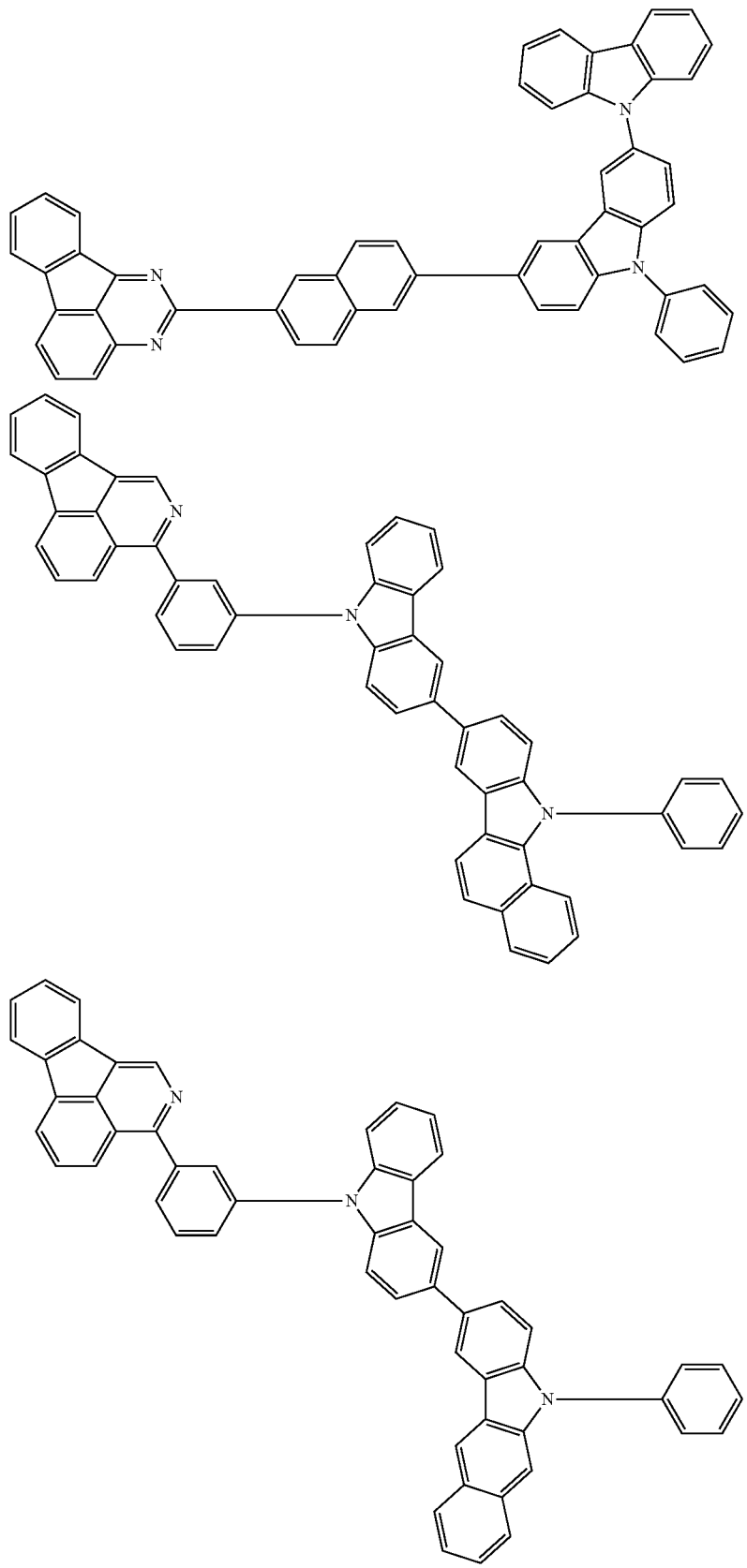

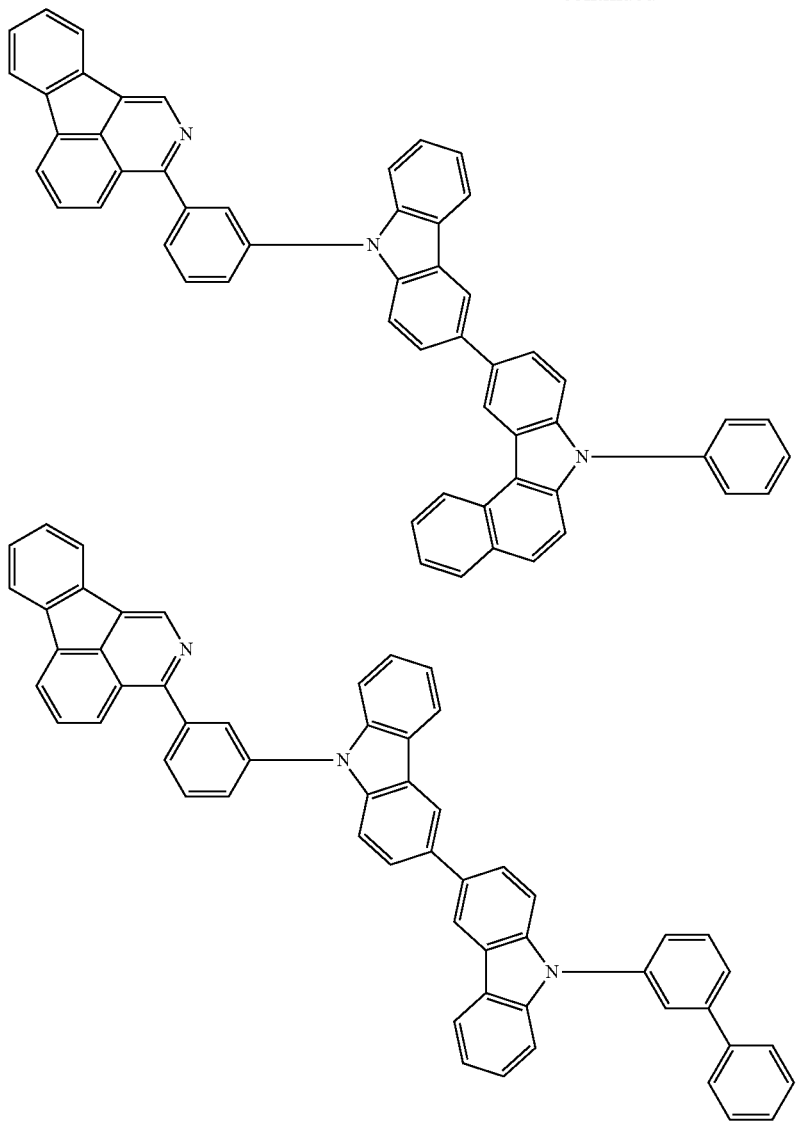
[Chem. 25]
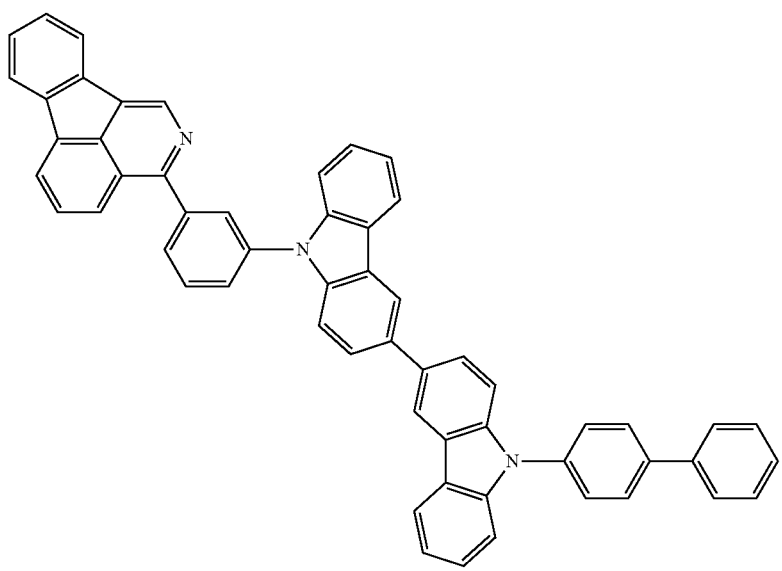

-continued
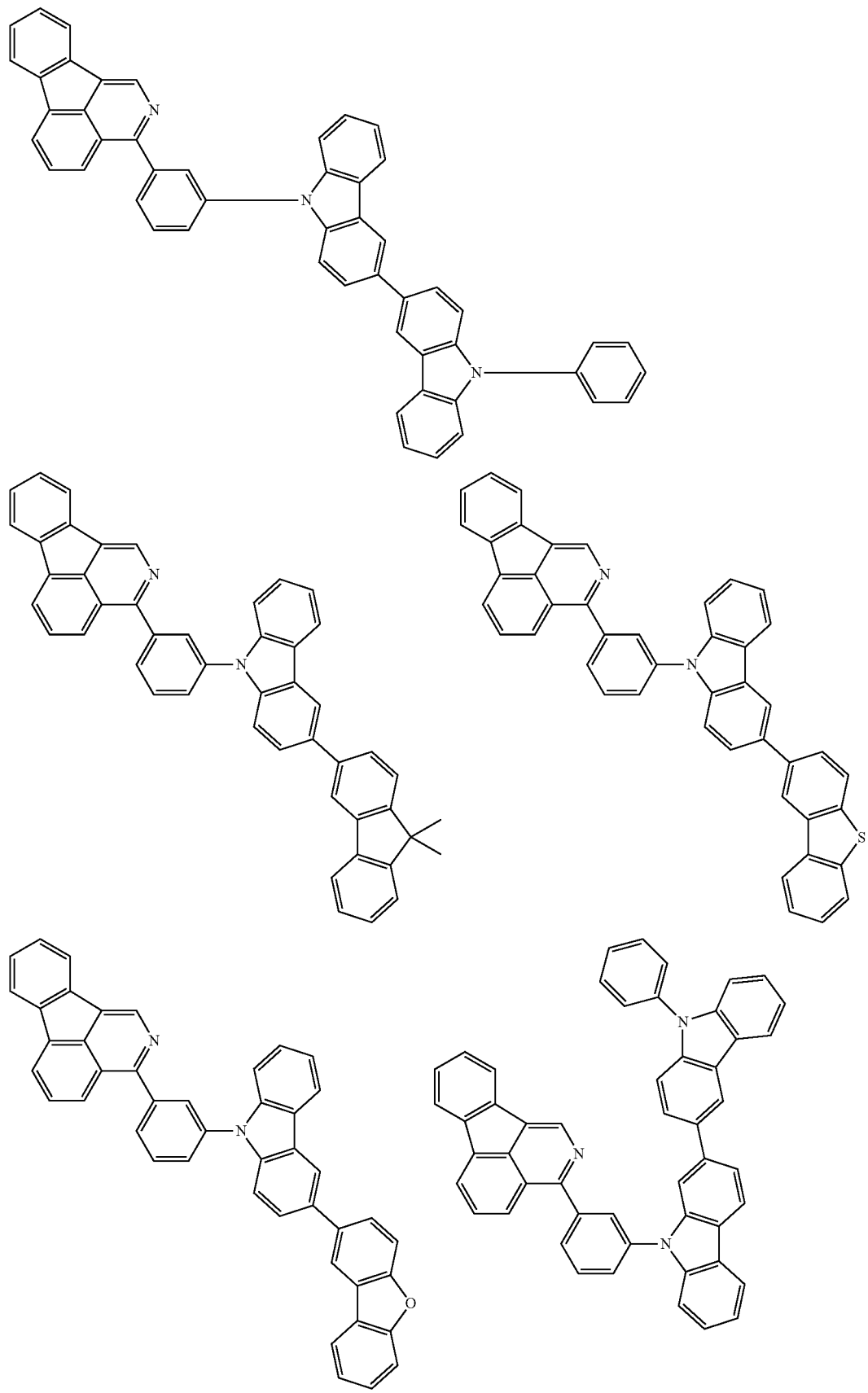

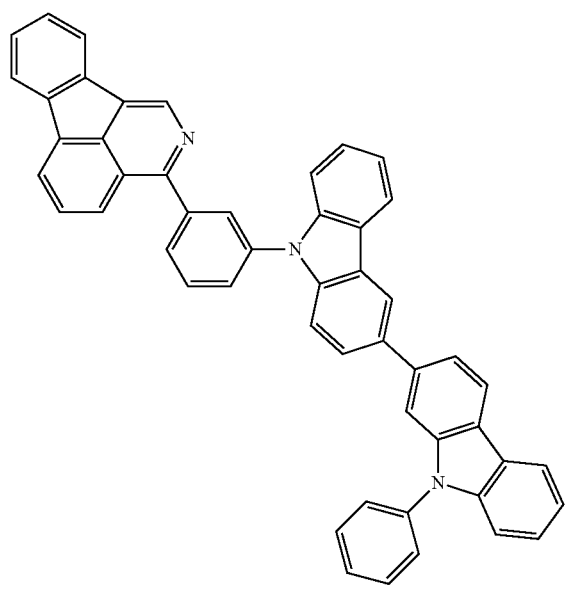
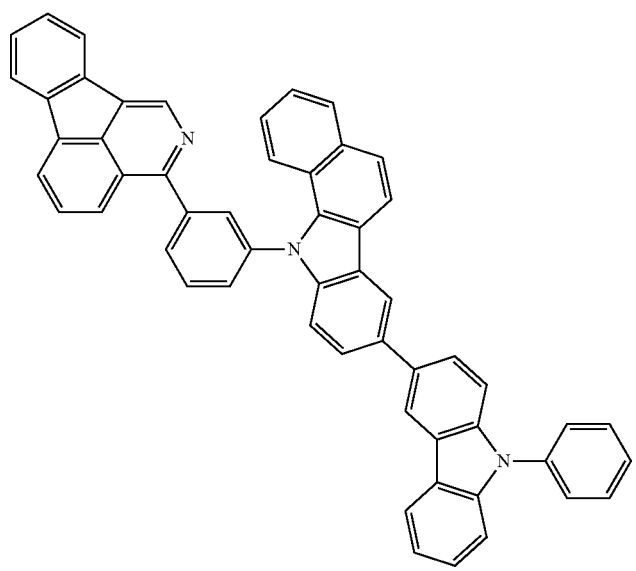
[Chem. 26]
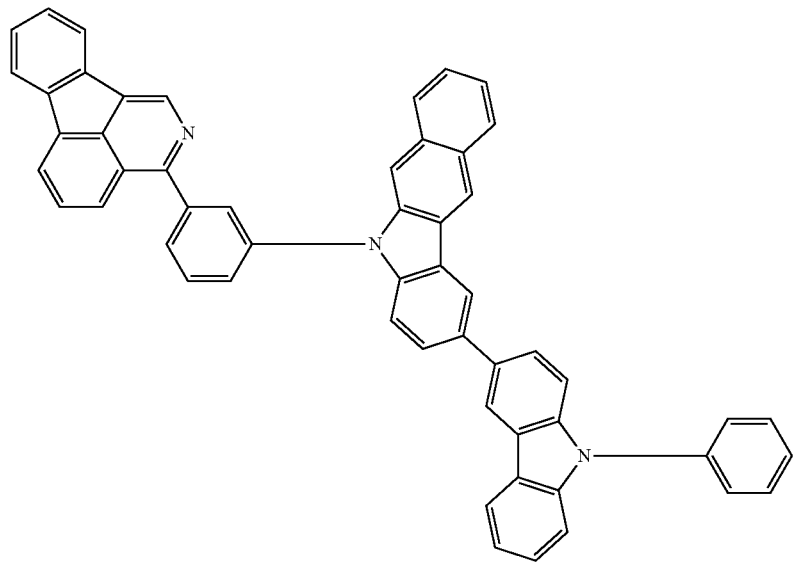

-continued
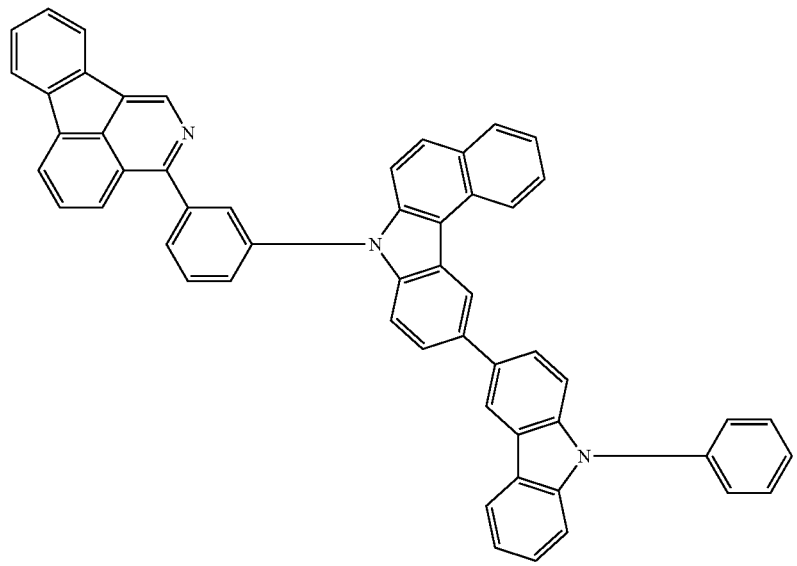
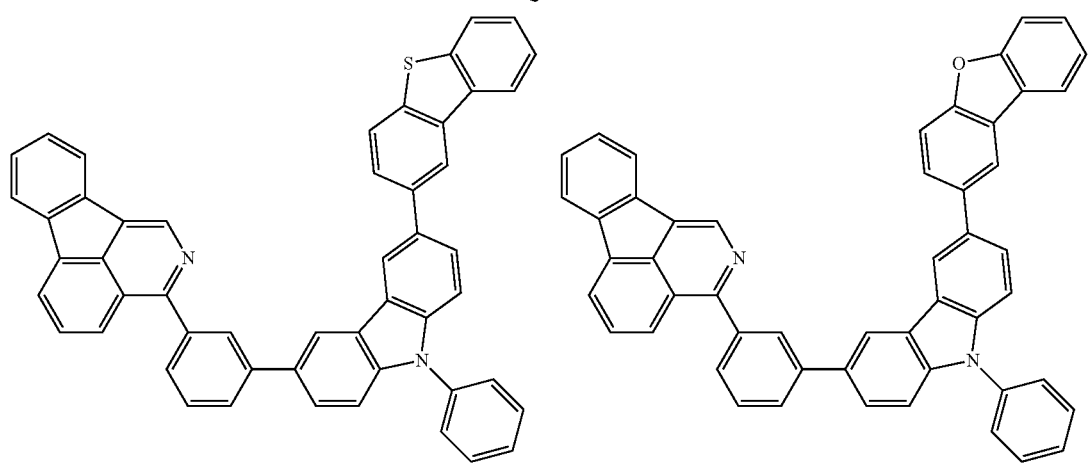
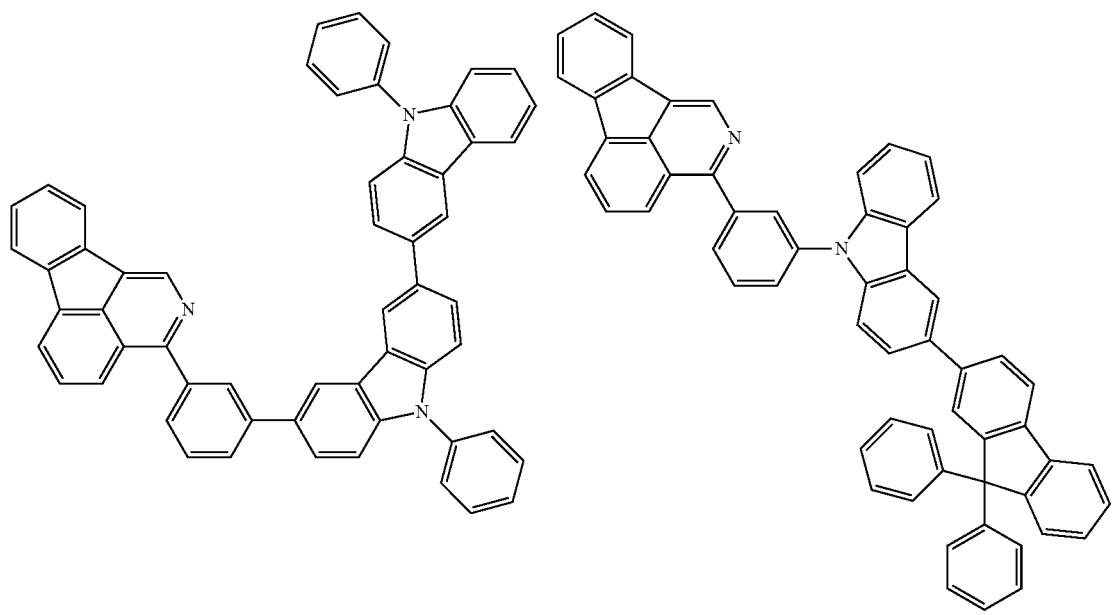

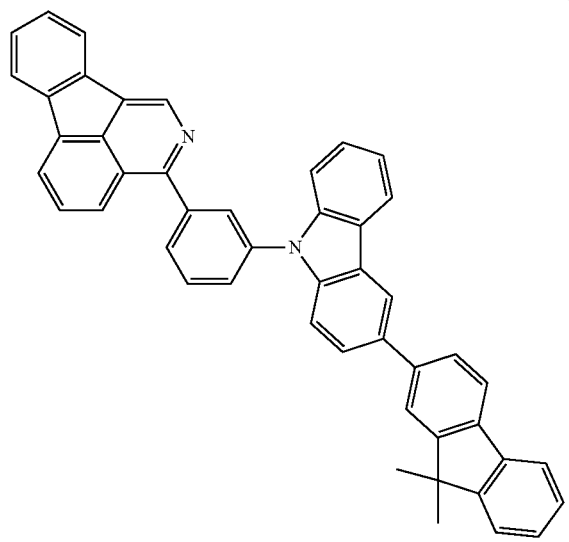
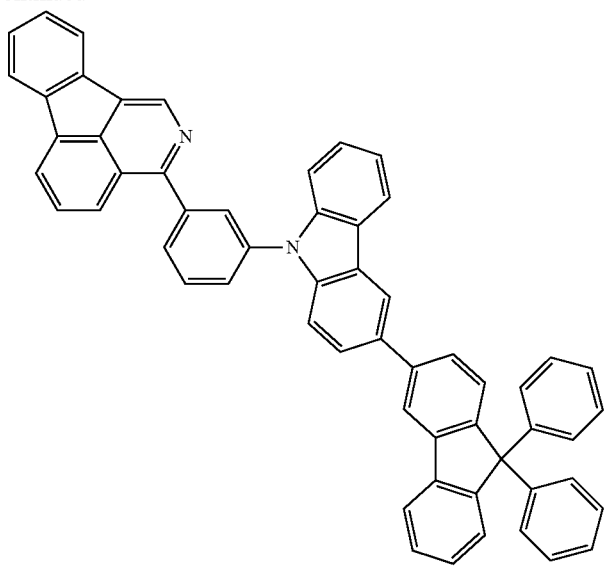
-continued
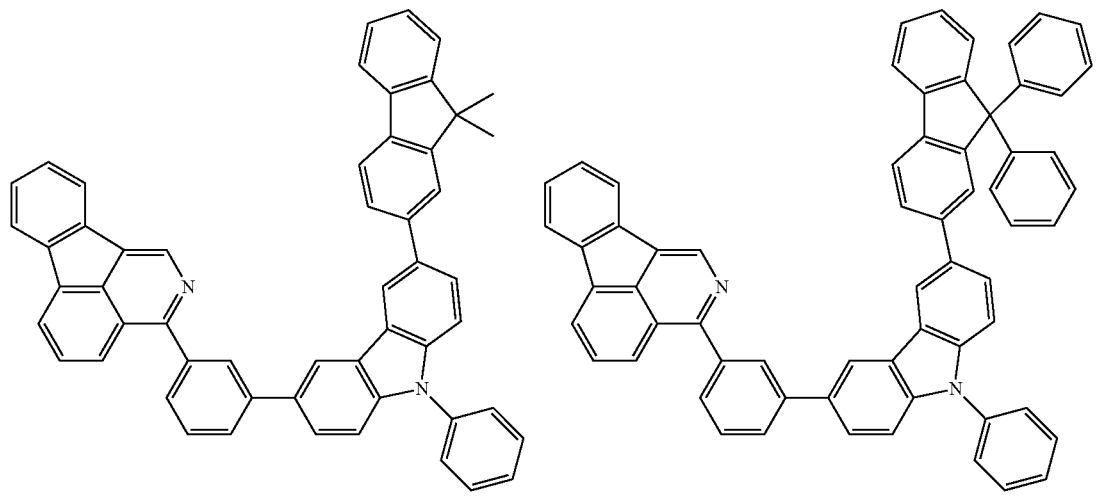
[Chem. 27]
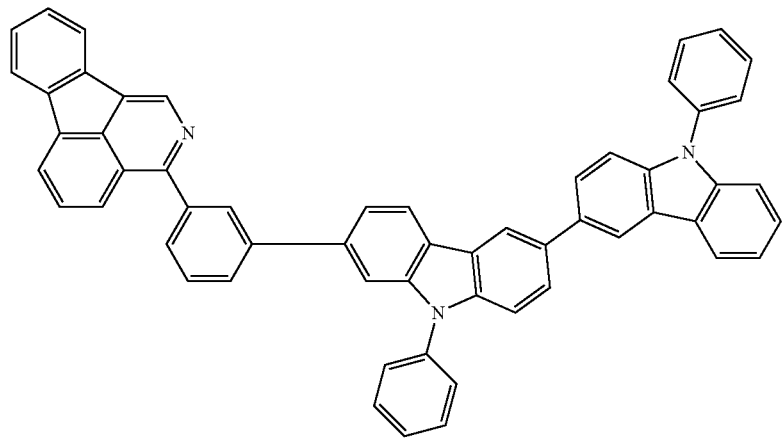

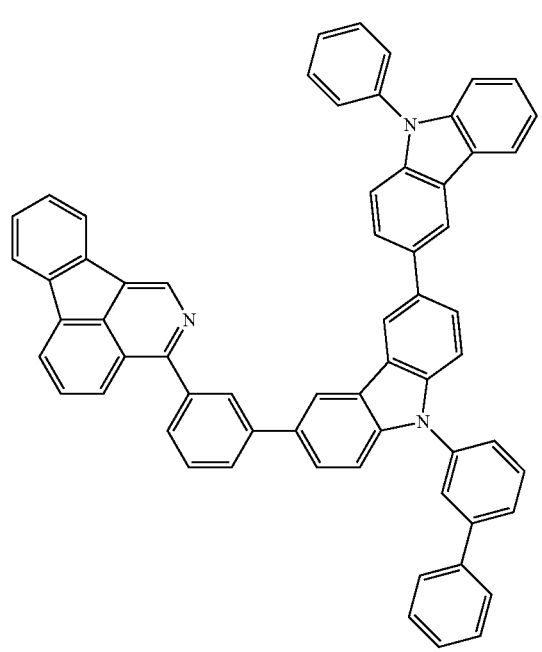
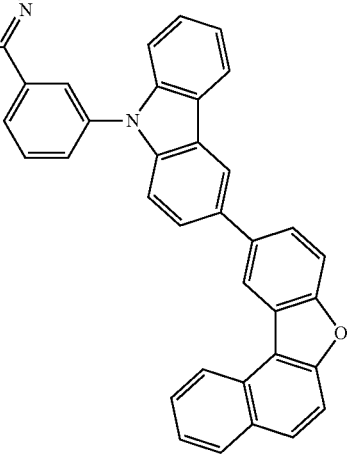
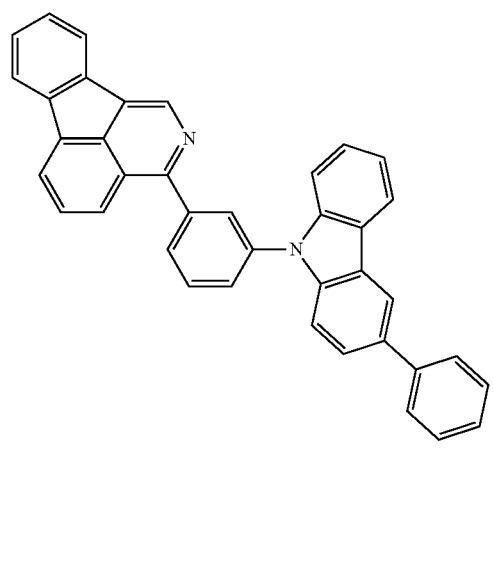

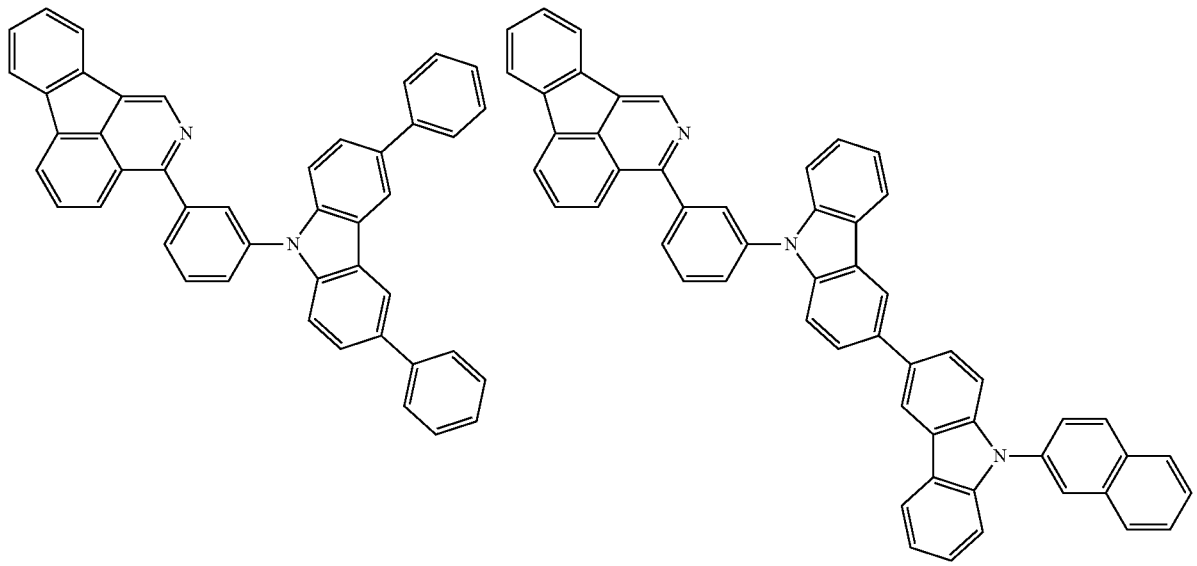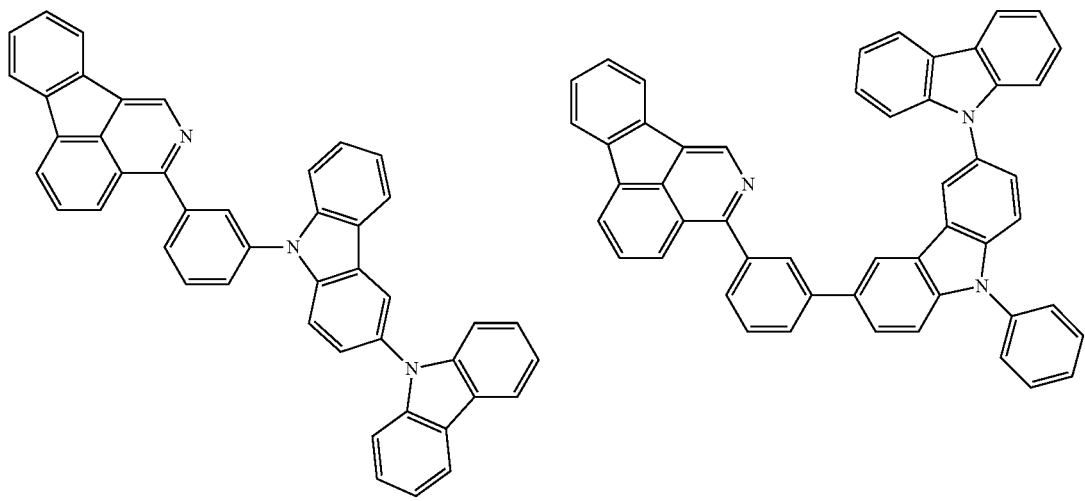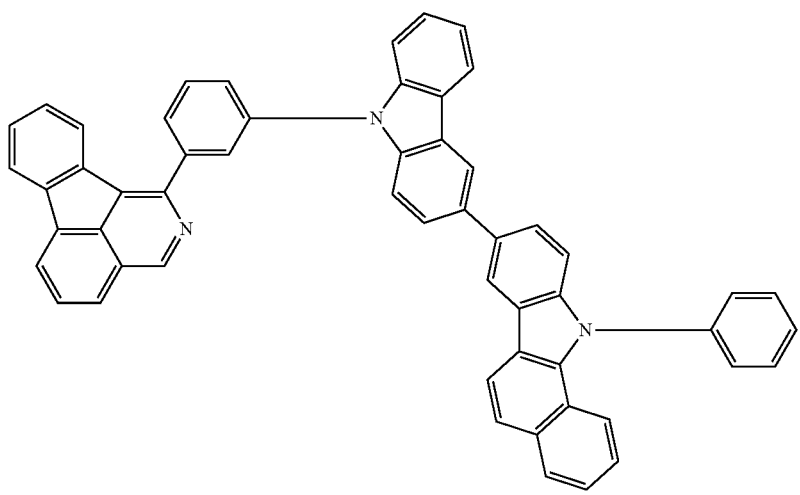

[Chem. 28]
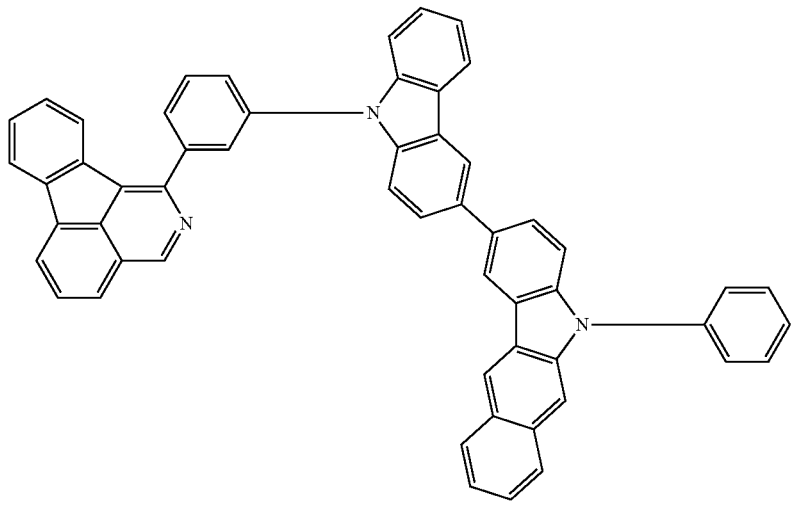
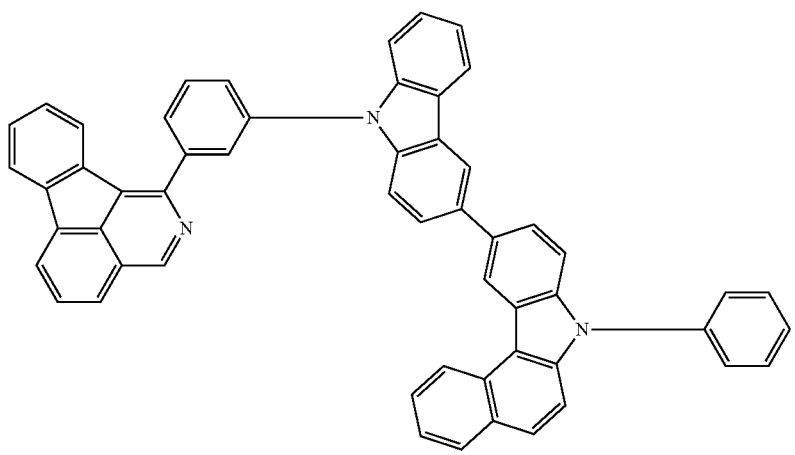
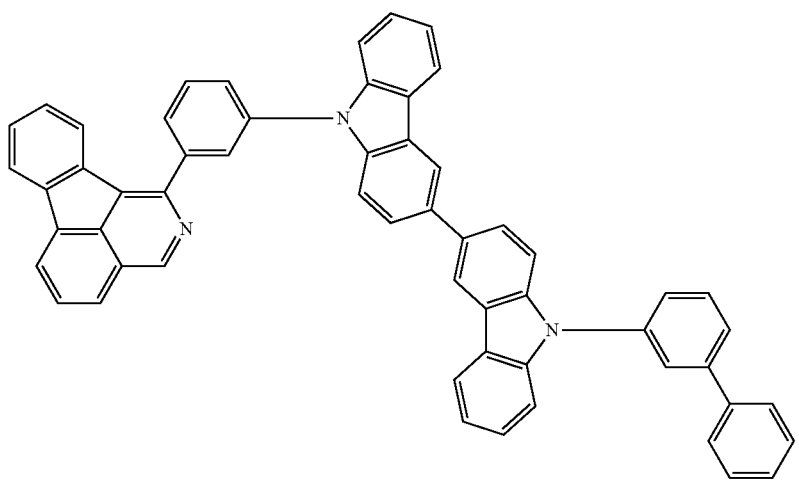

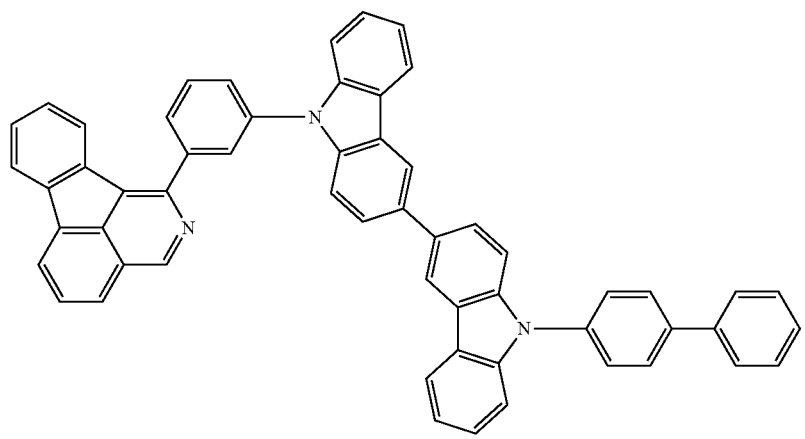
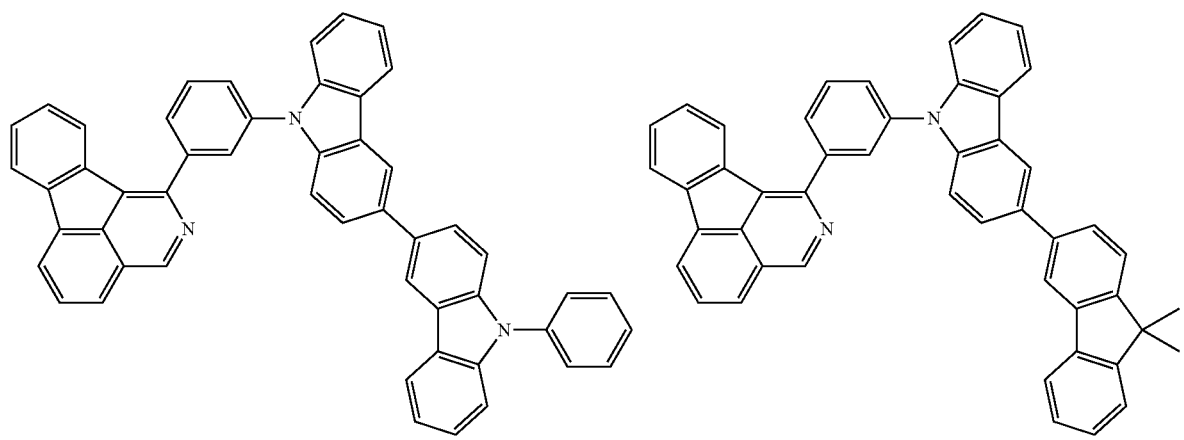
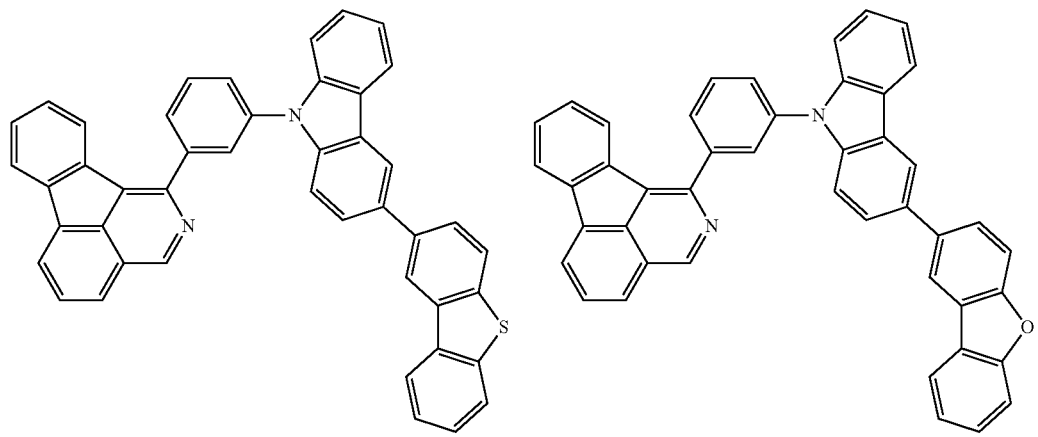

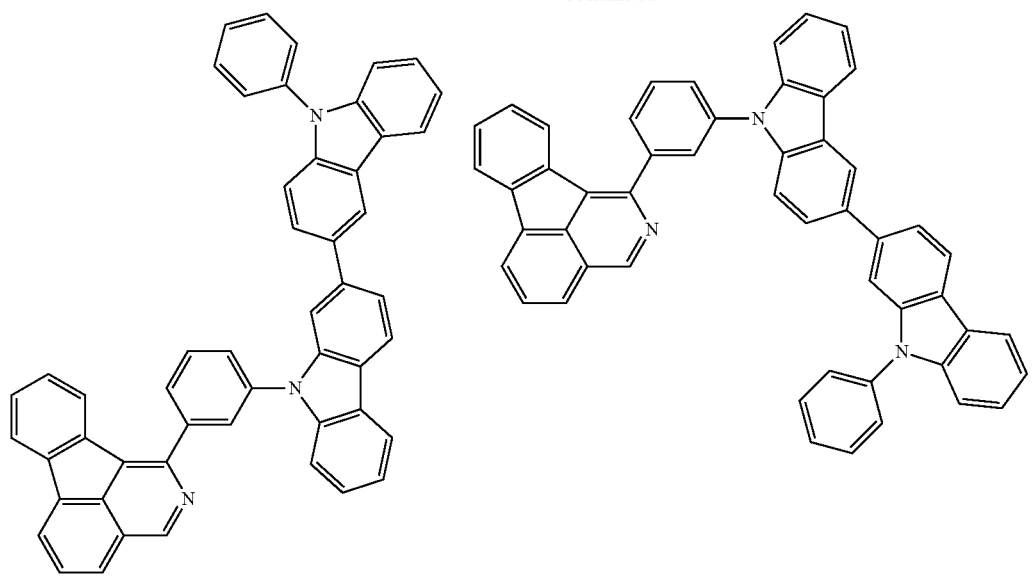
[Chem. 29]
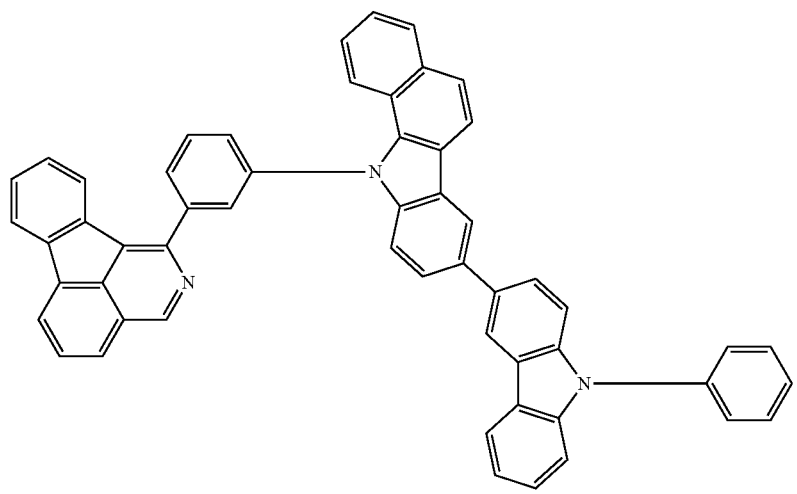
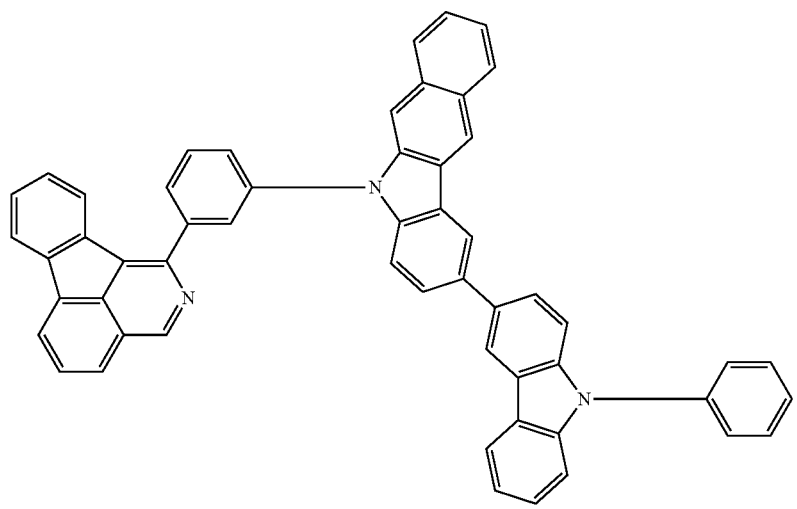

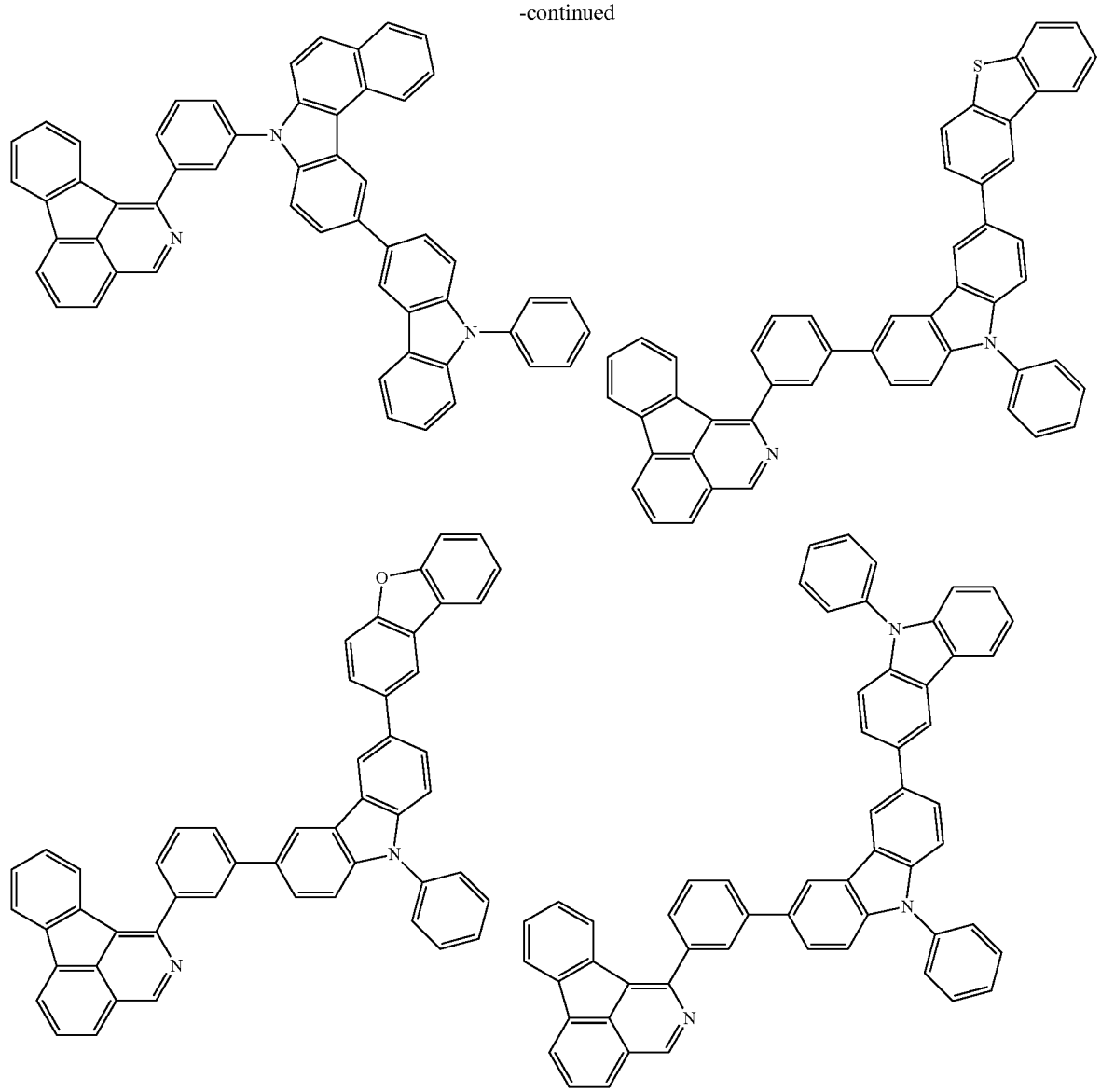
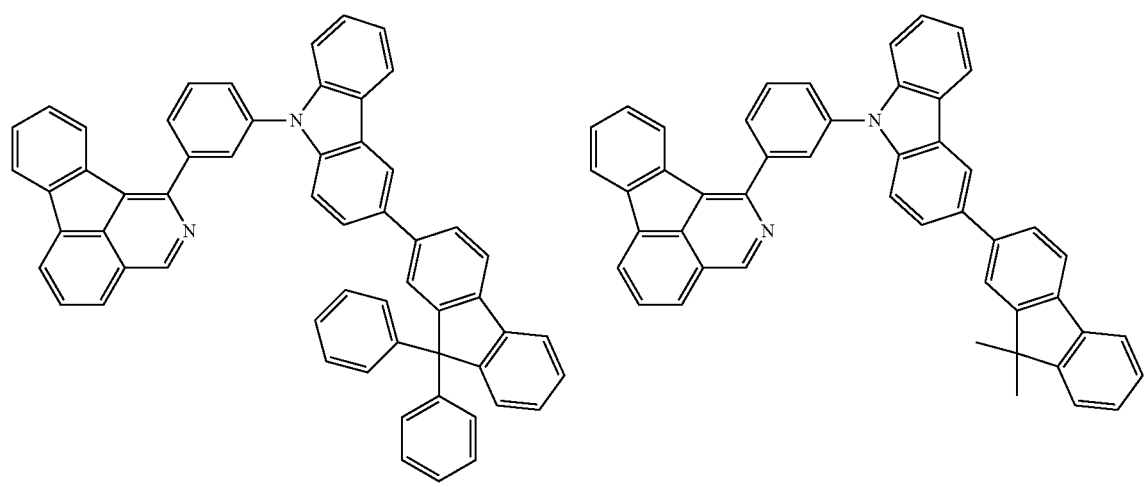

[Chem. 30]
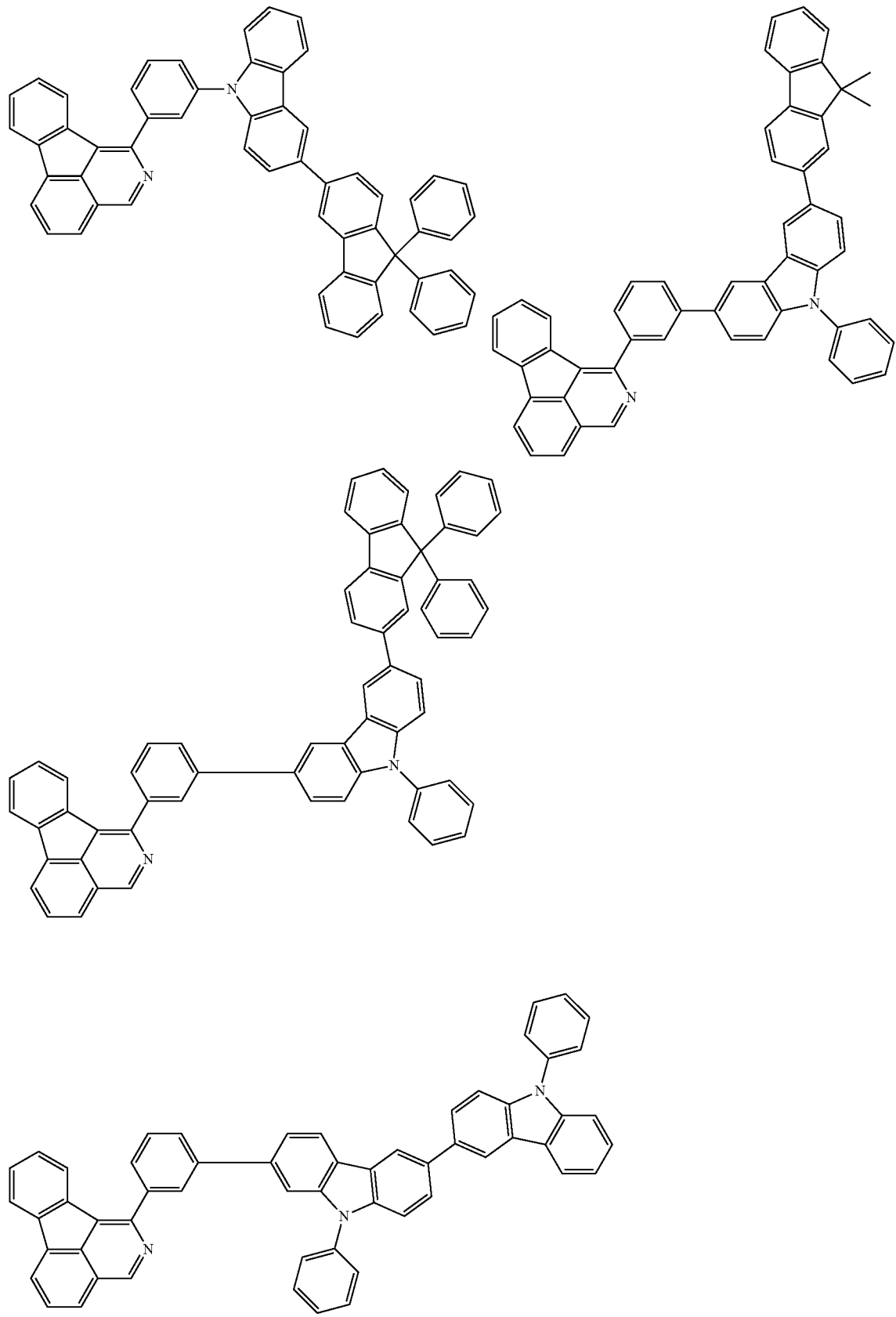

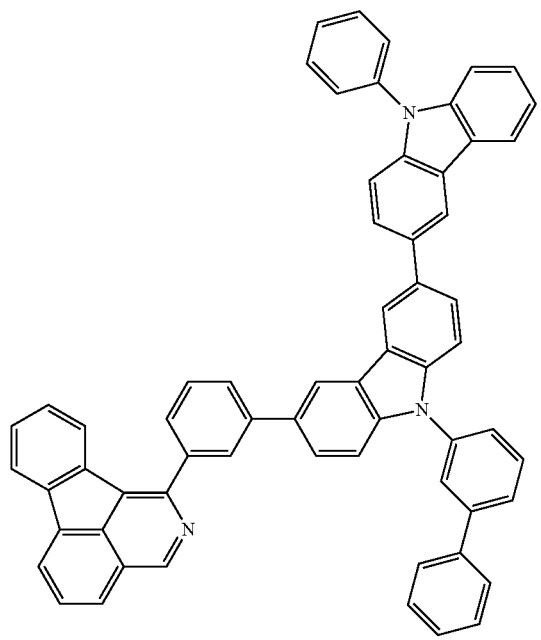
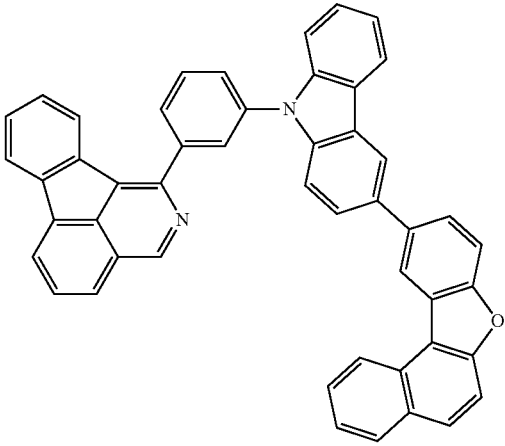
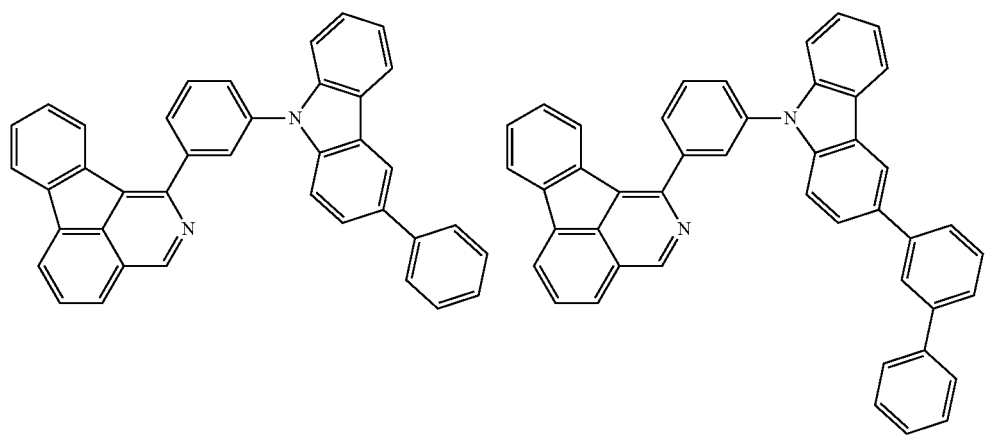
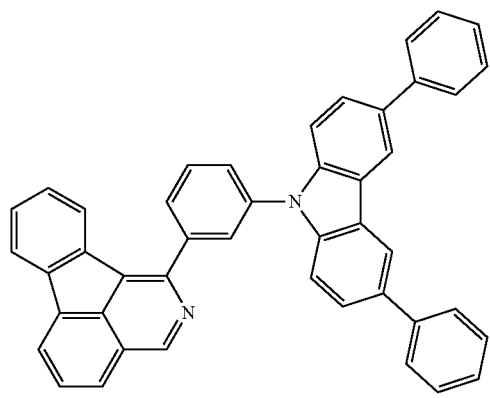

-continued
[Chem. 31]
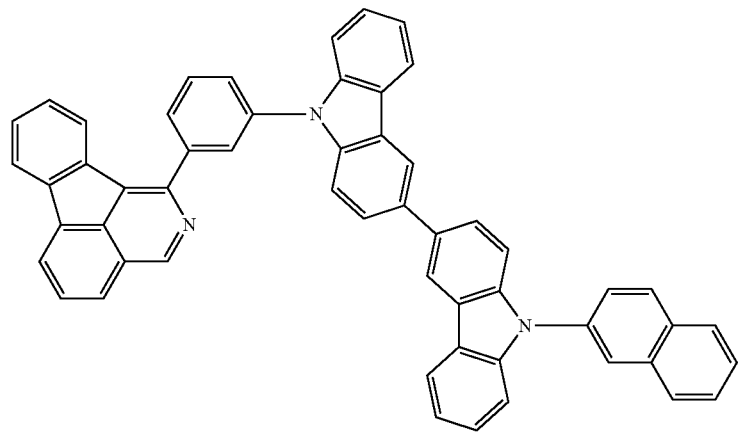
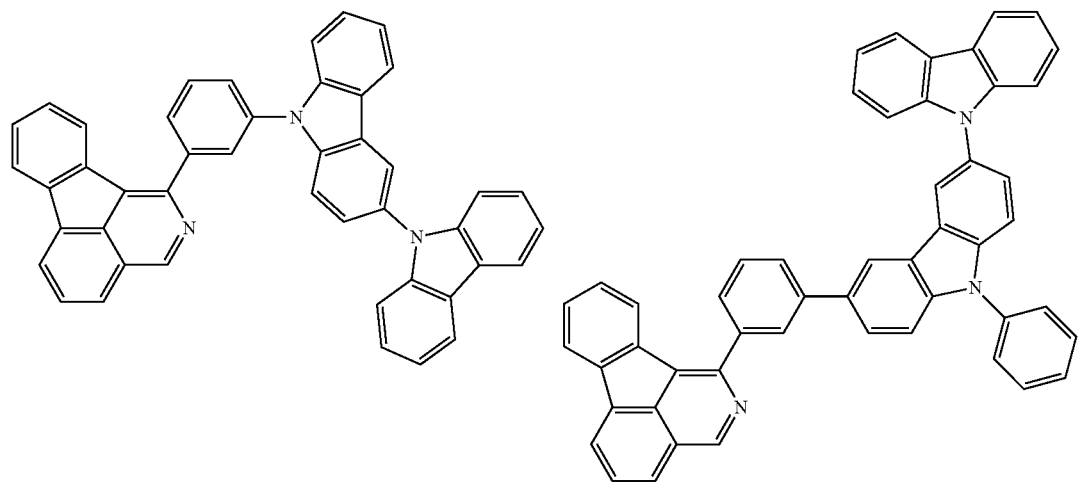
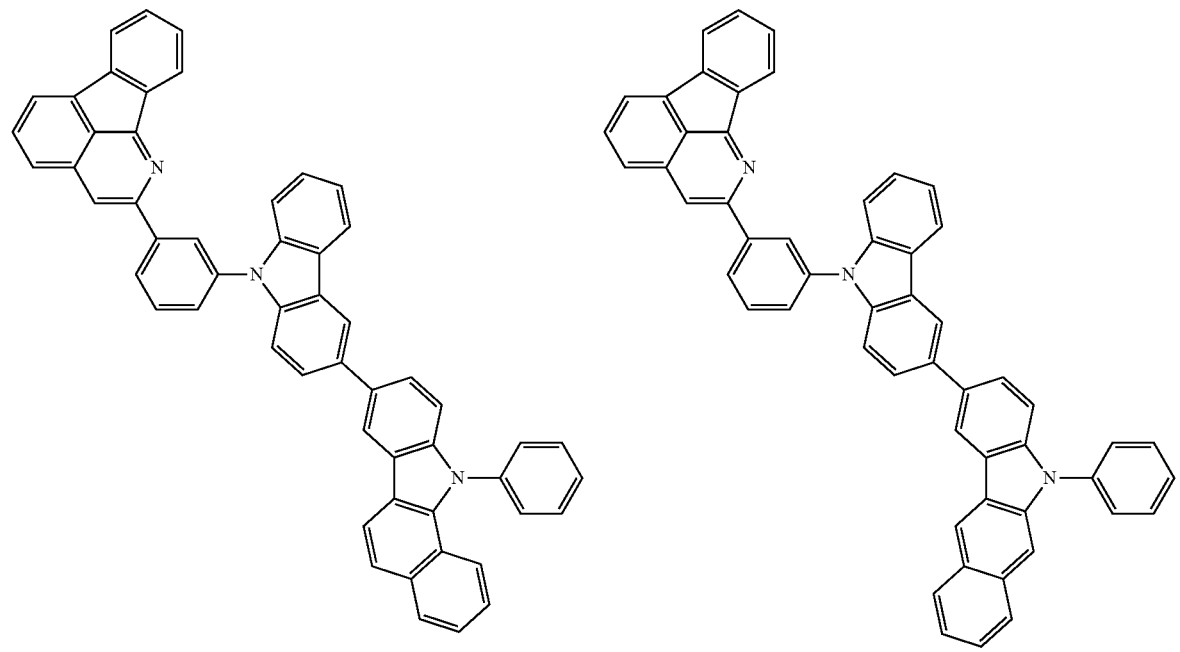

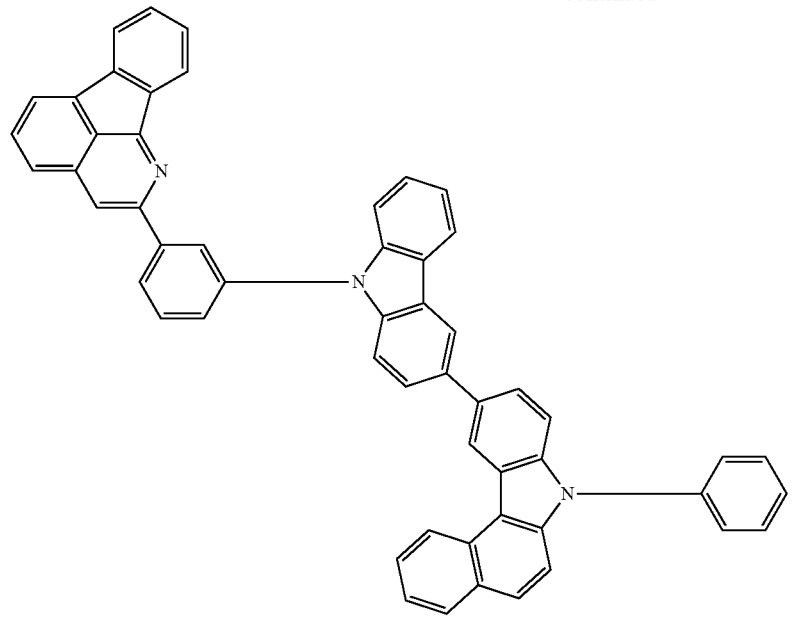
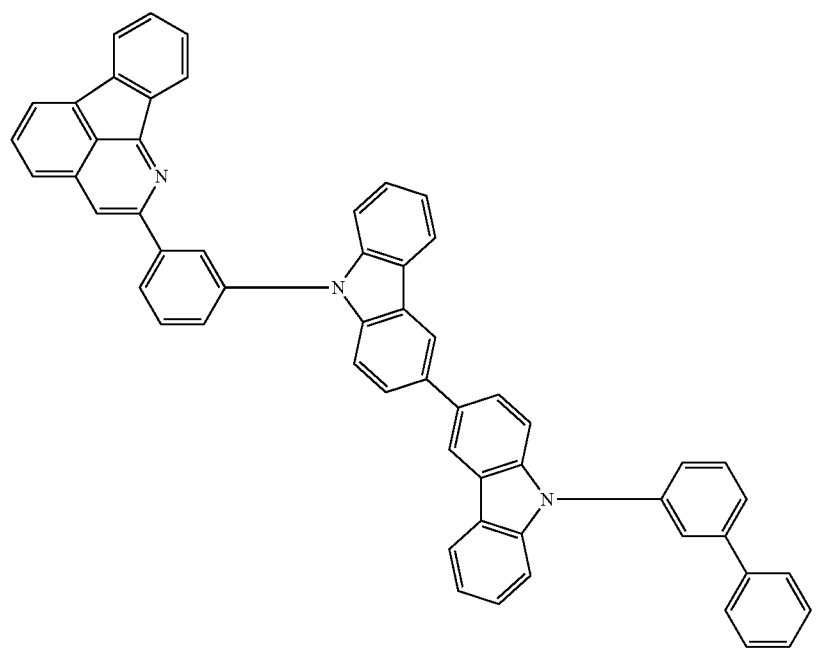

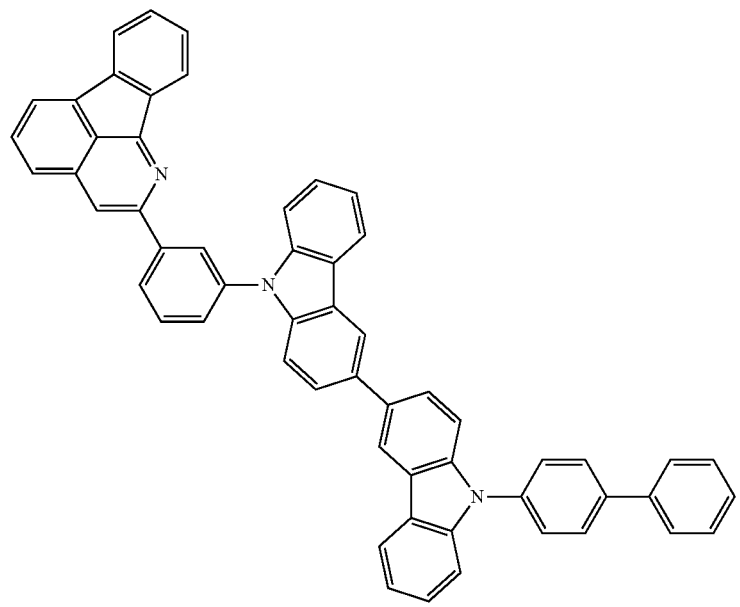
[Chem. 32]
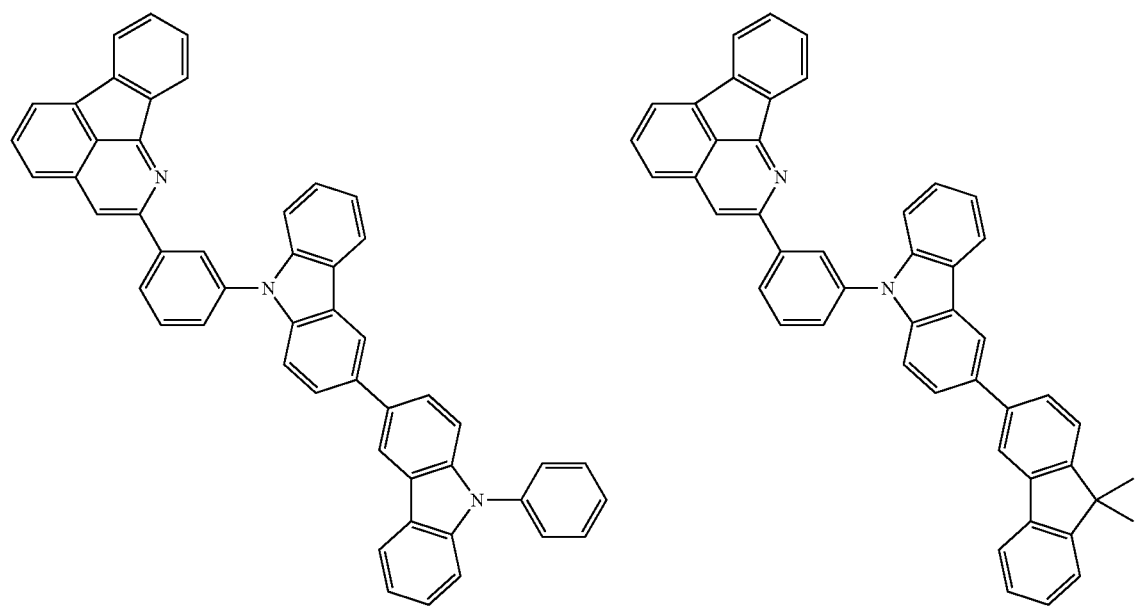

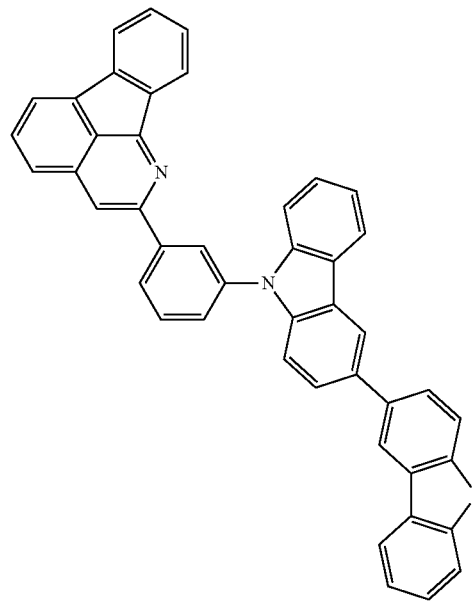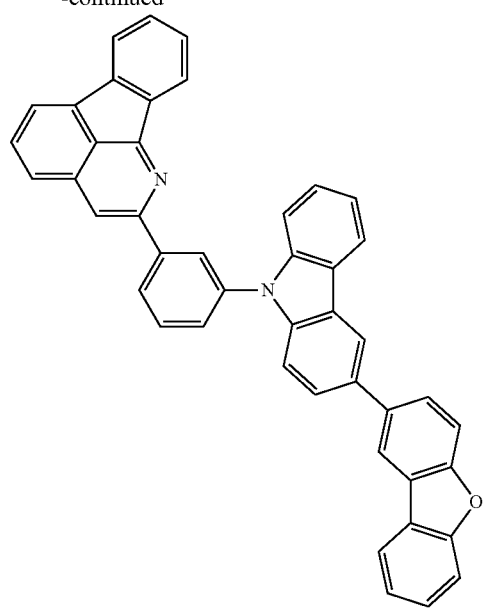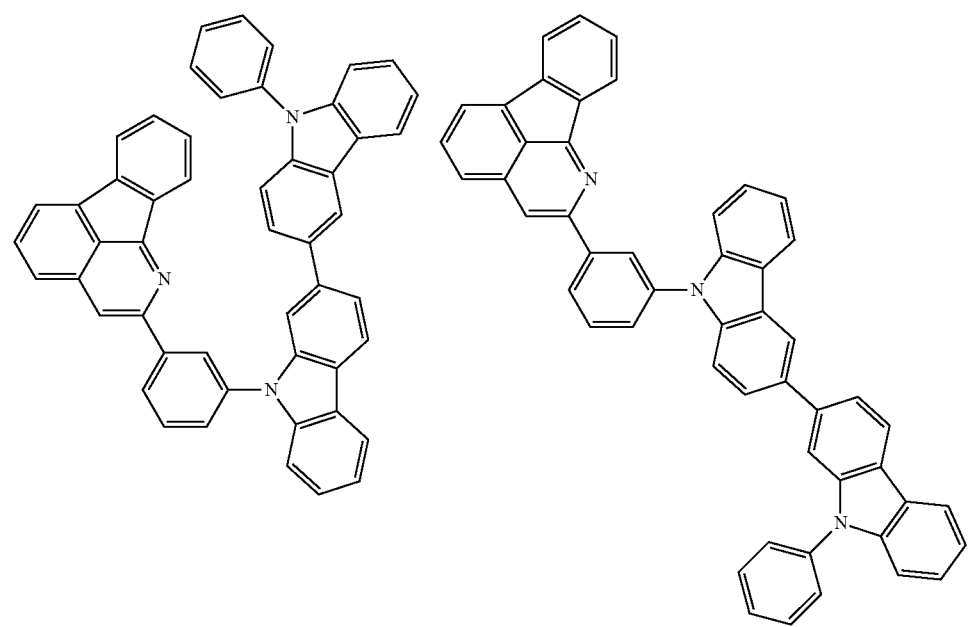

-continued
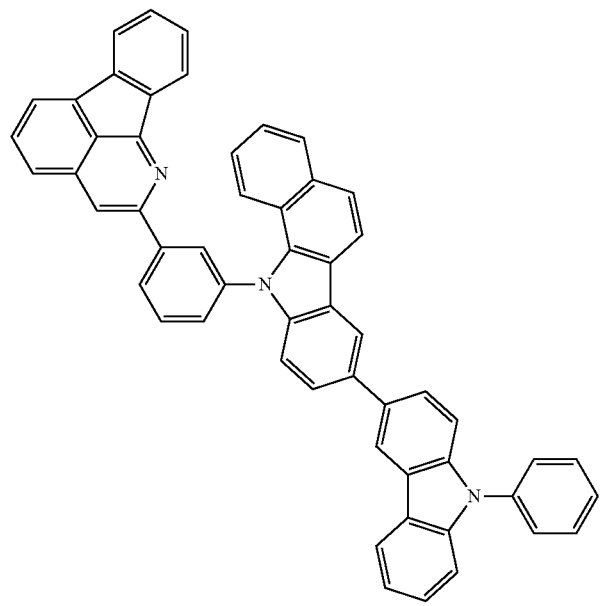
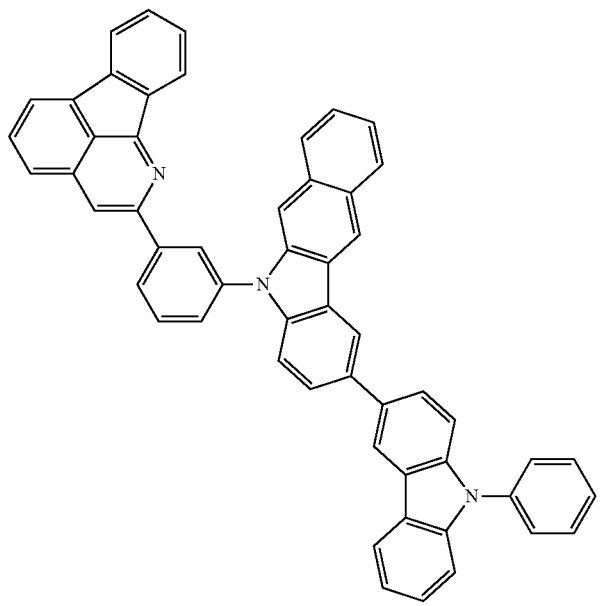
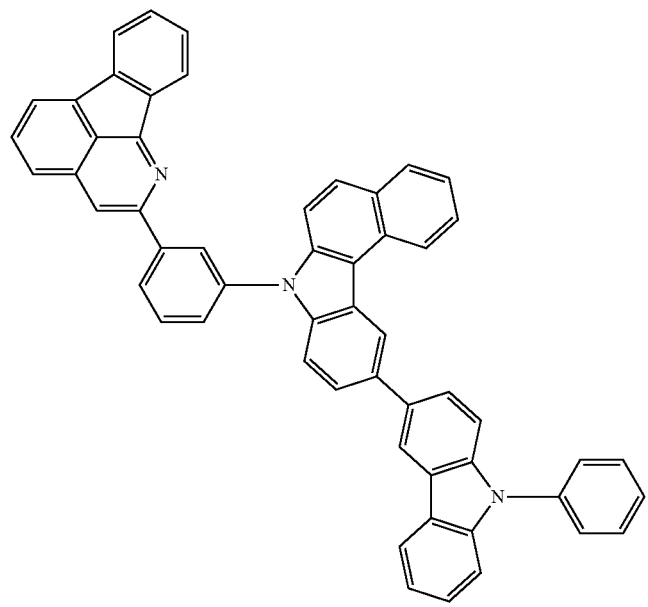
[Chem. 33]
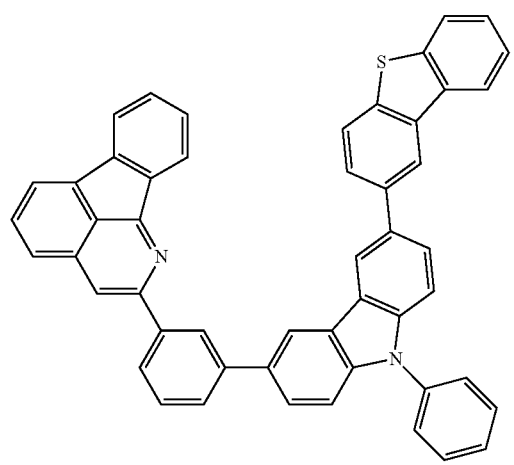
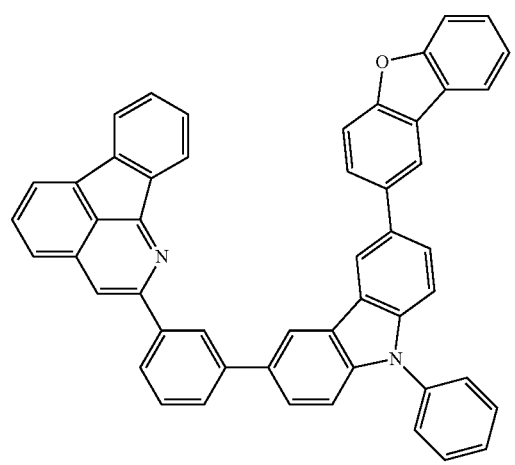

-continued
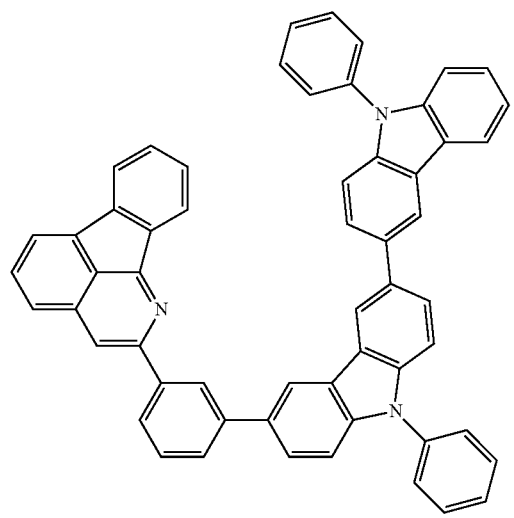
87
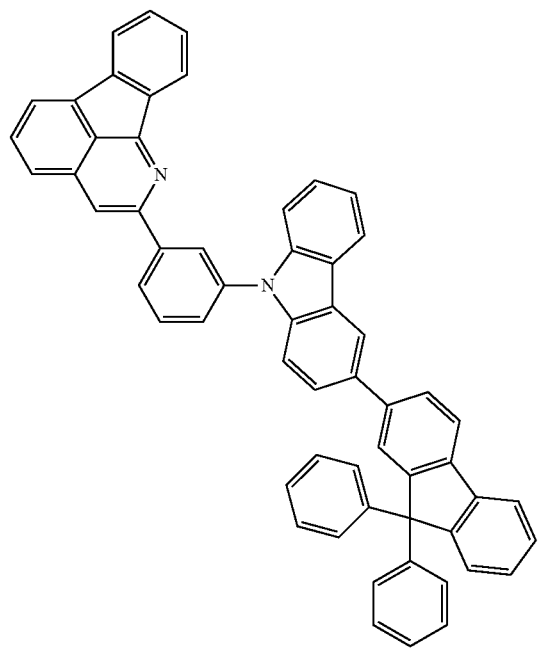
88
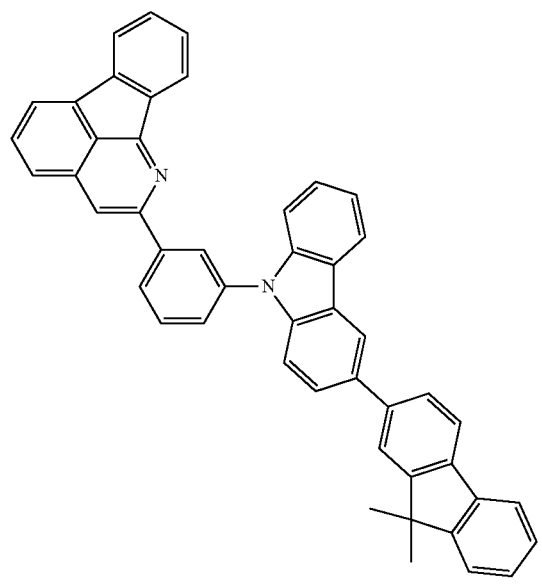
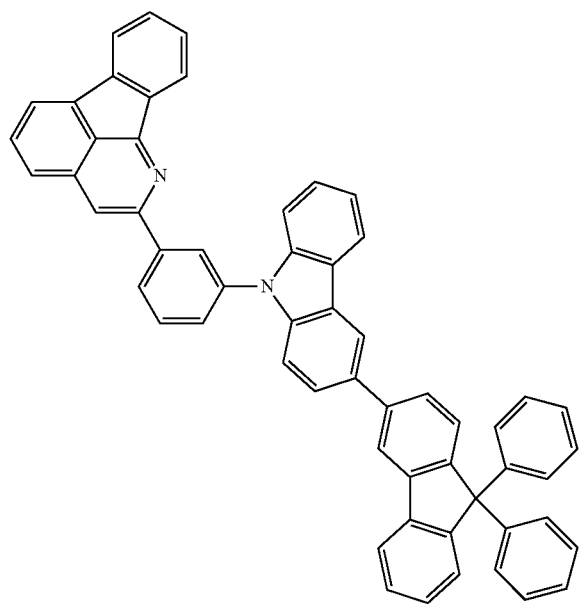

89
90
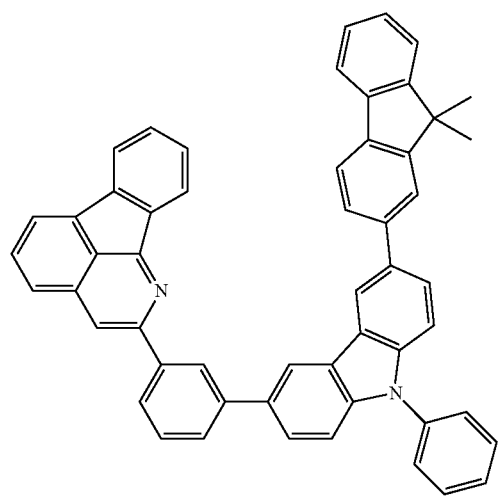
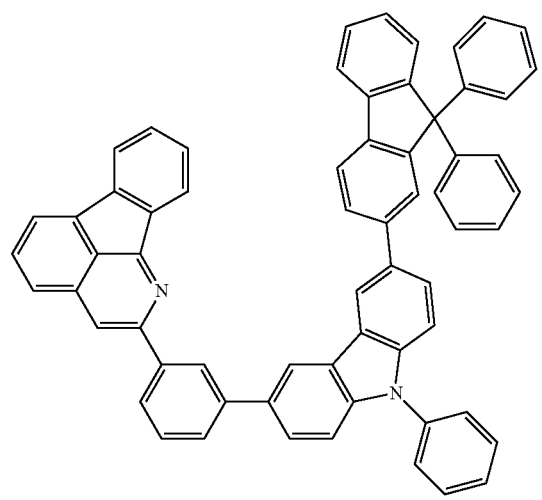
[Chem. 34]
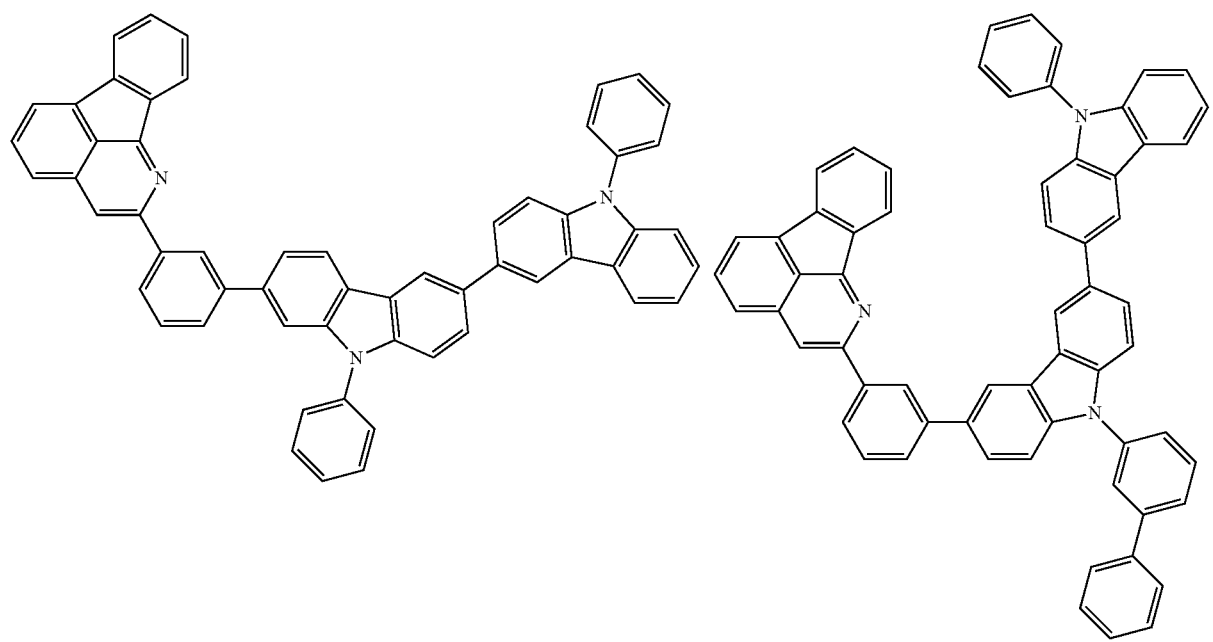

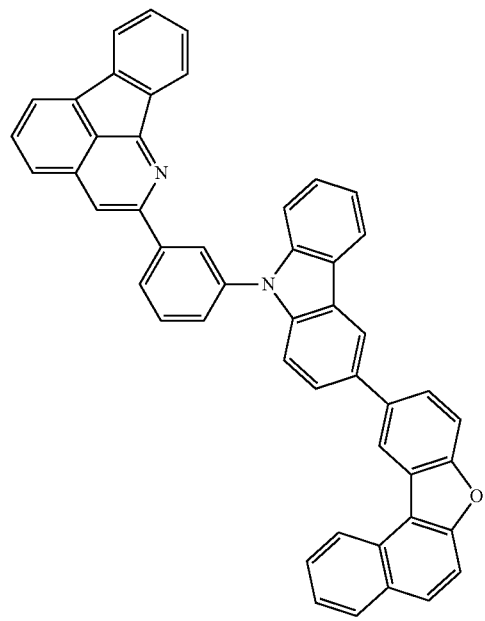
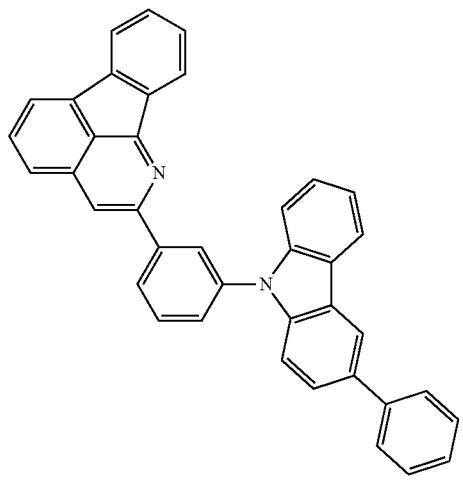
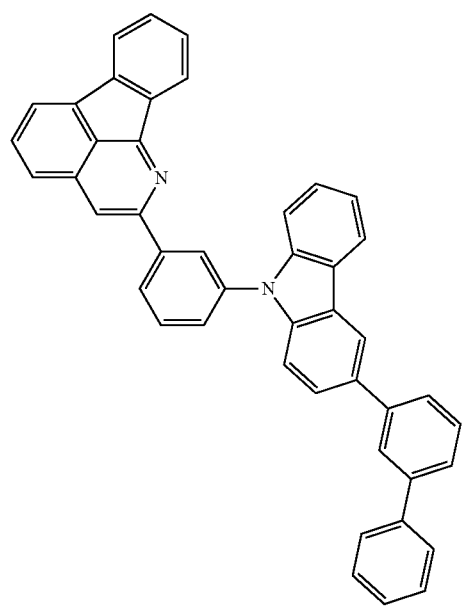
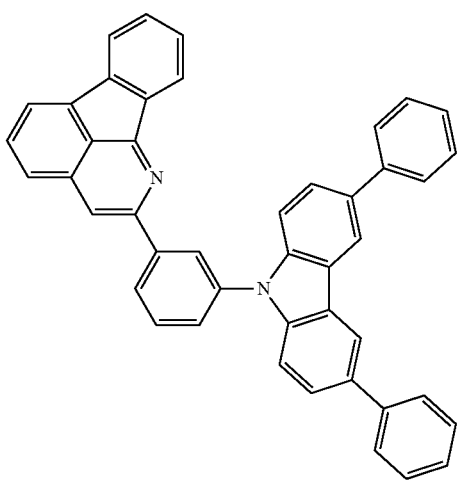

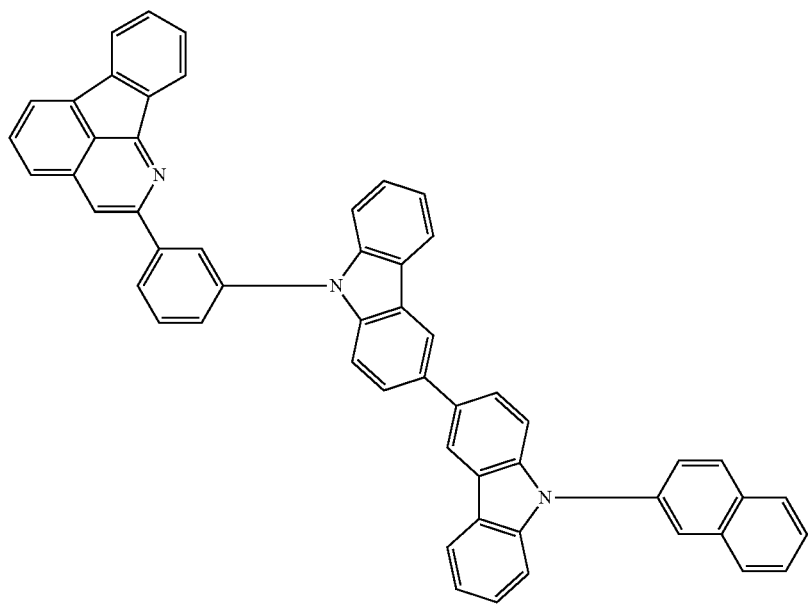
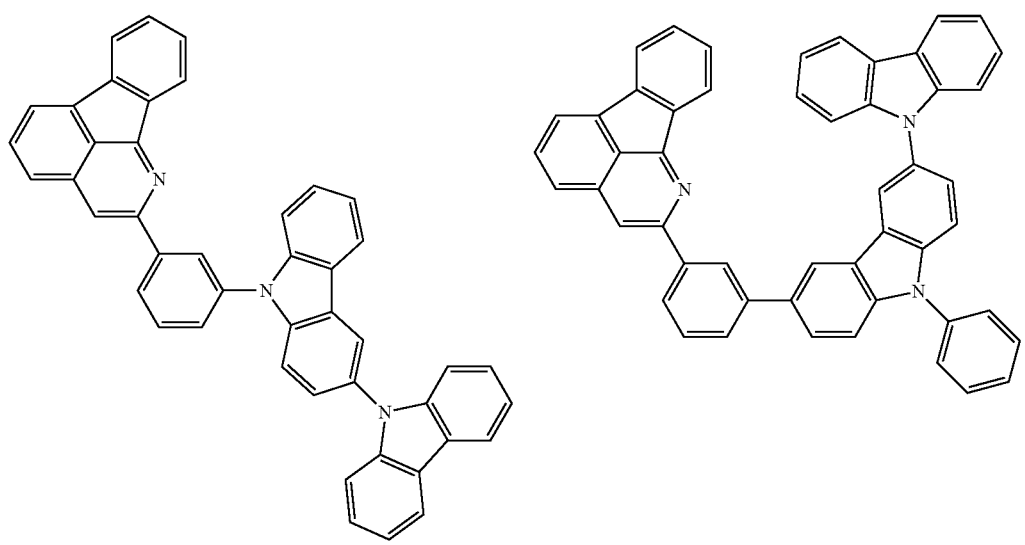
[Chem. 35]
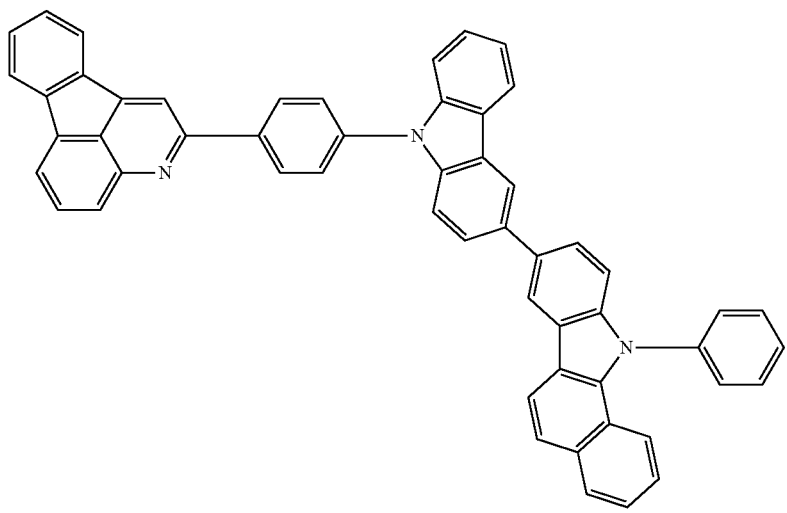

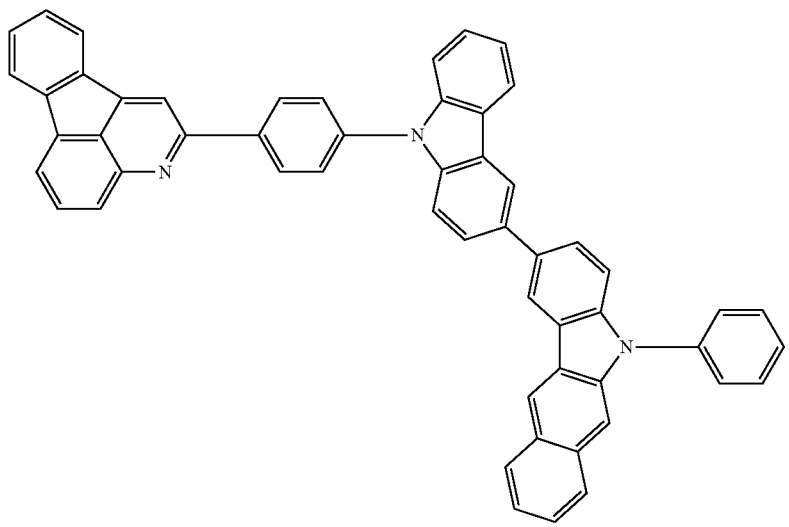
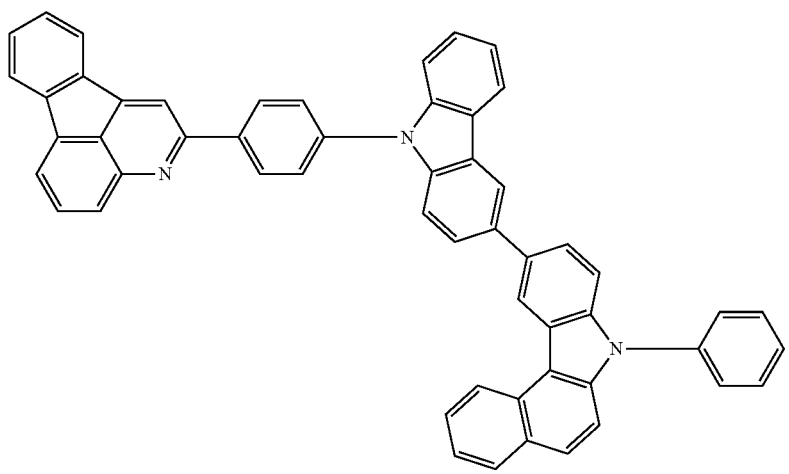
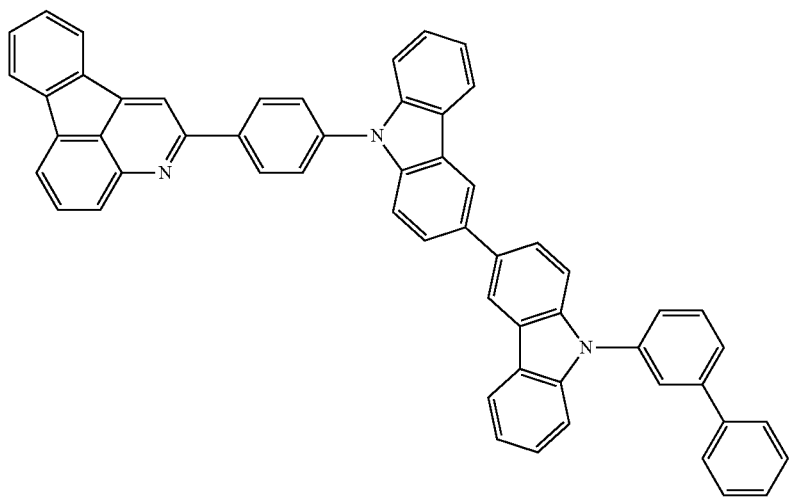

-continued
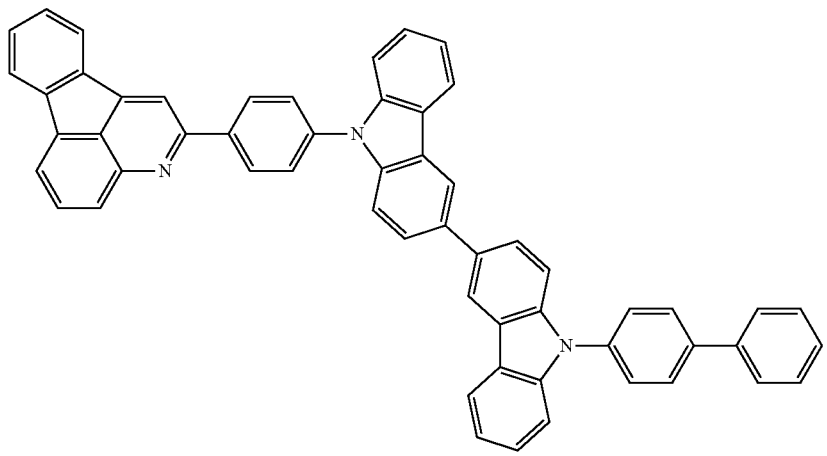
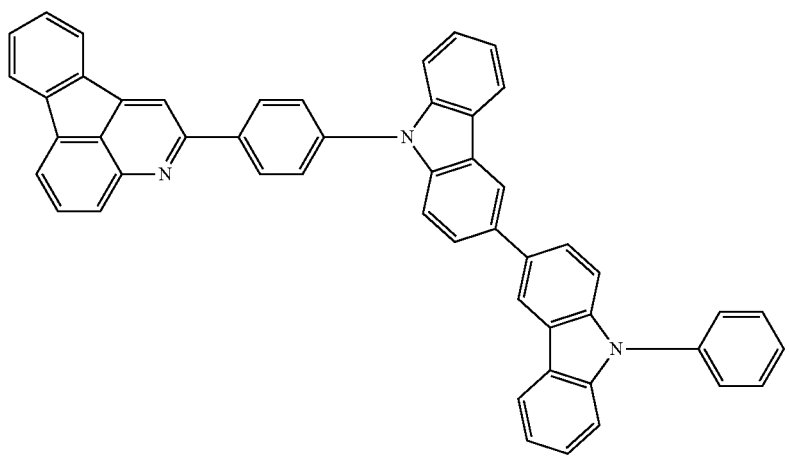
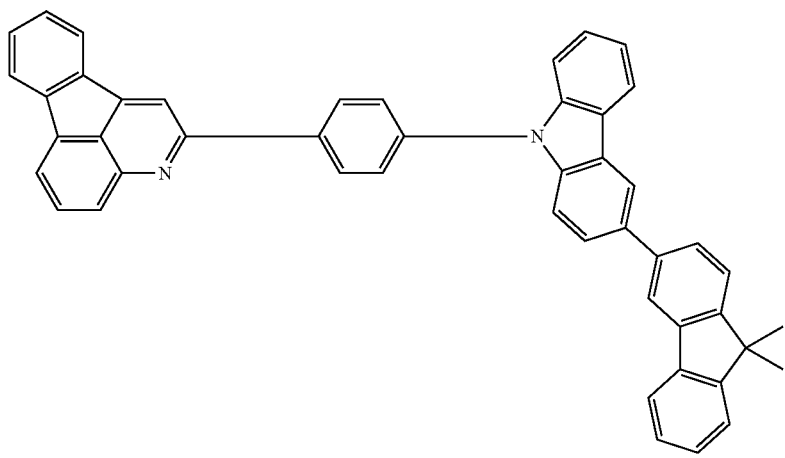

99
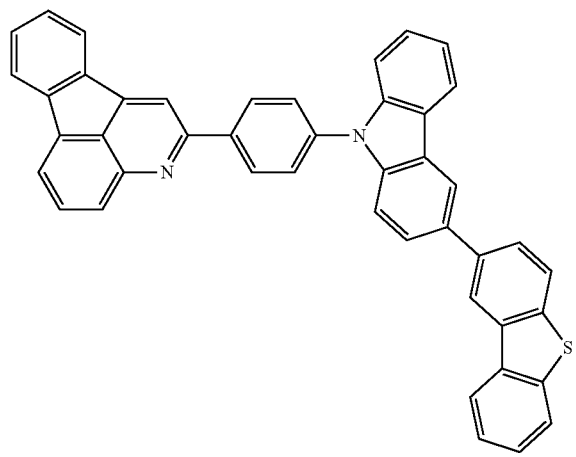
100
-continued
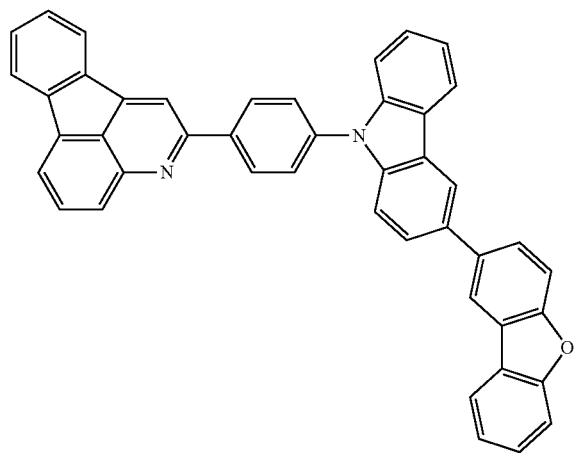
[Chem. 36]
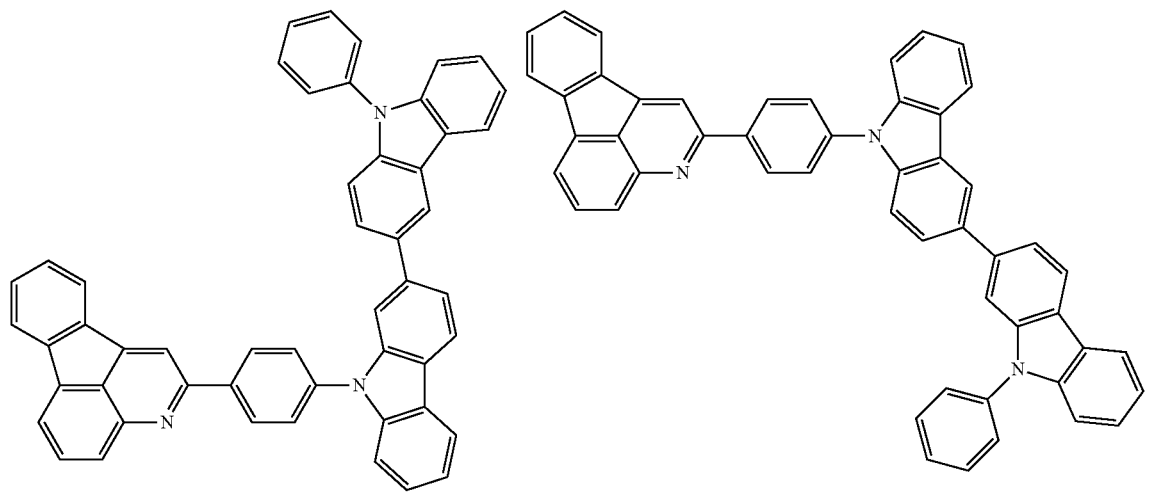
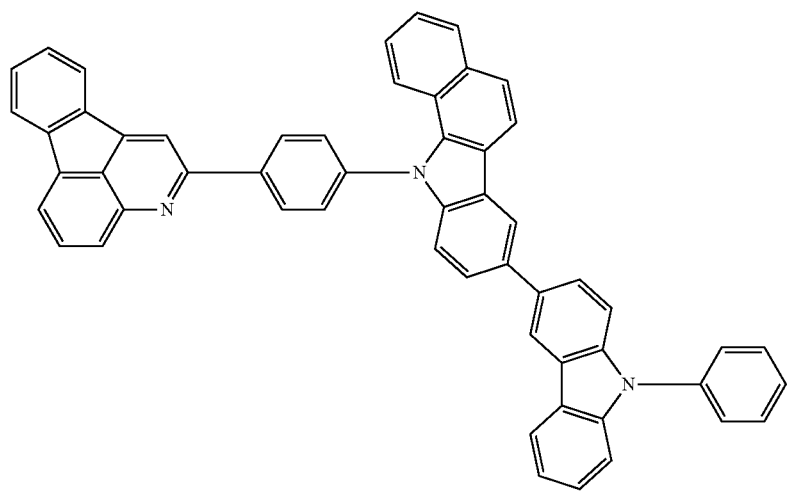

101 102
-continued
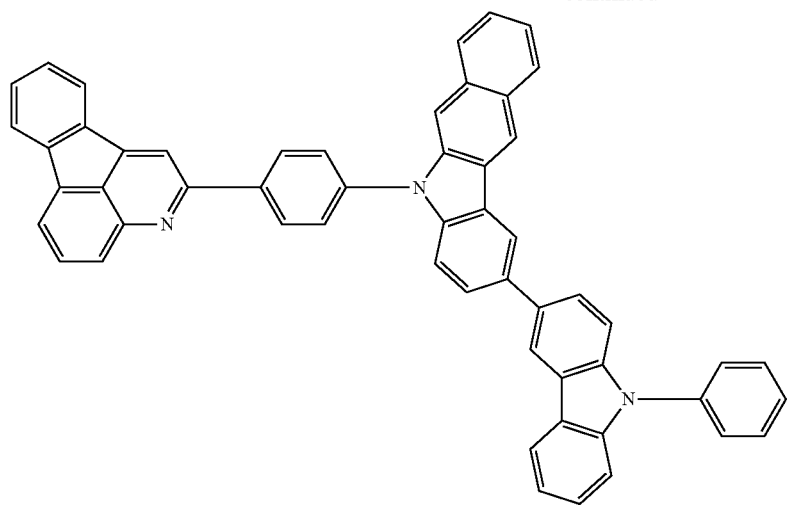
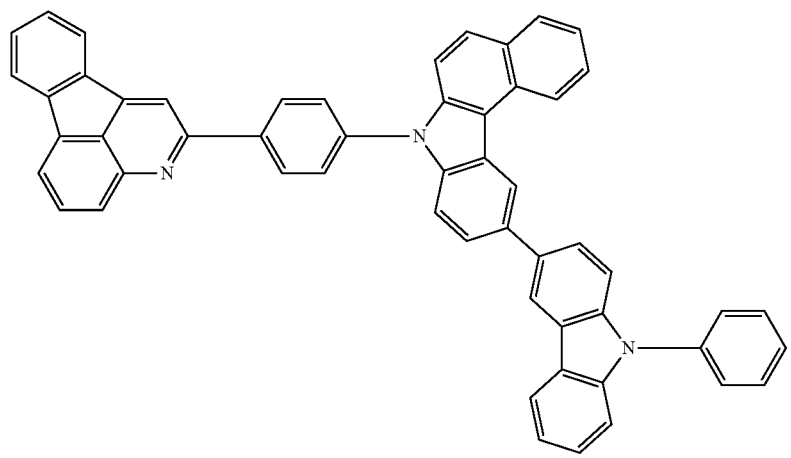
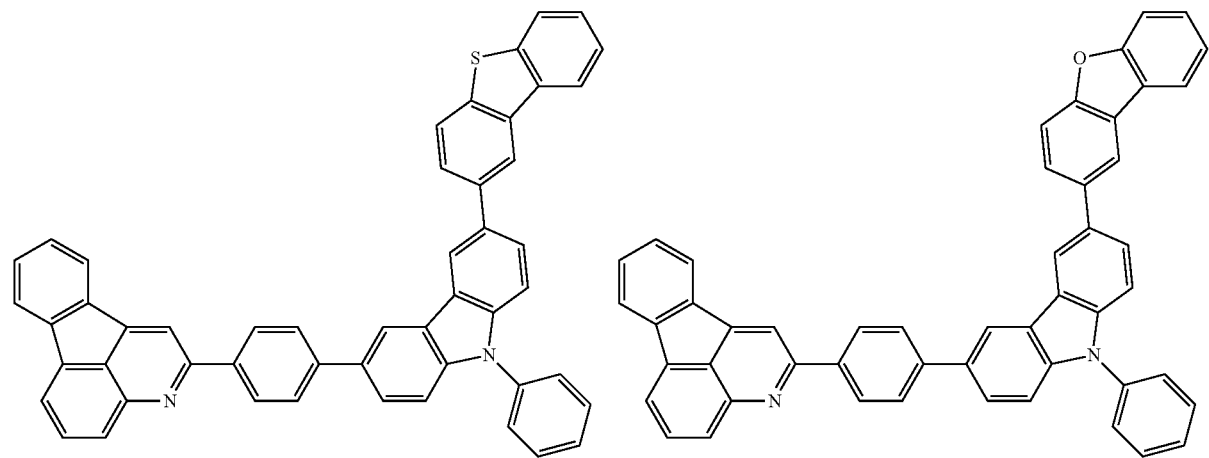

-continued
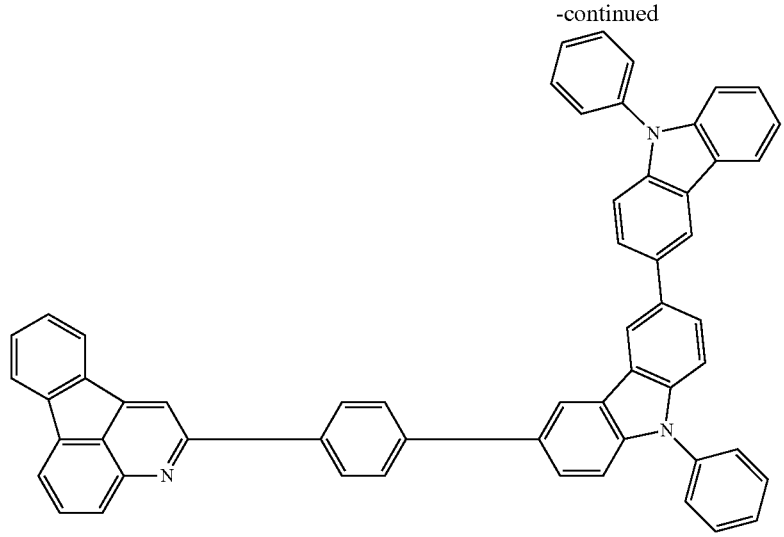
[Chem. 37]
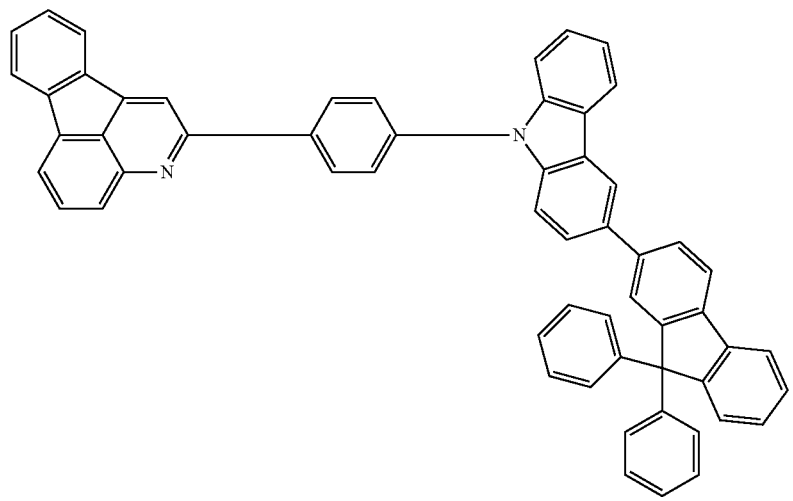
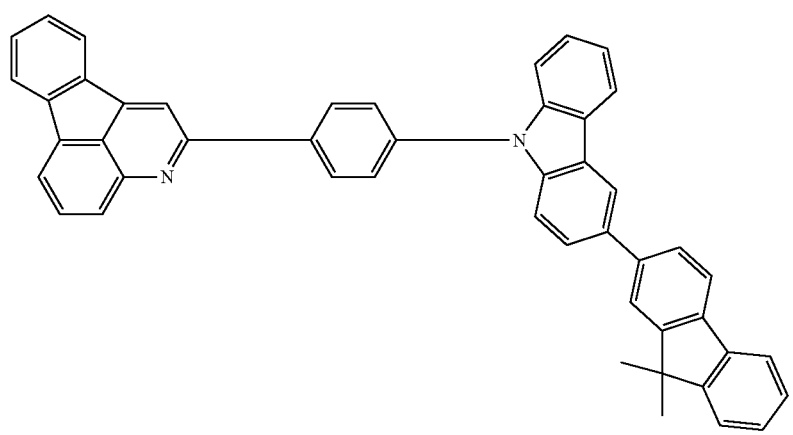

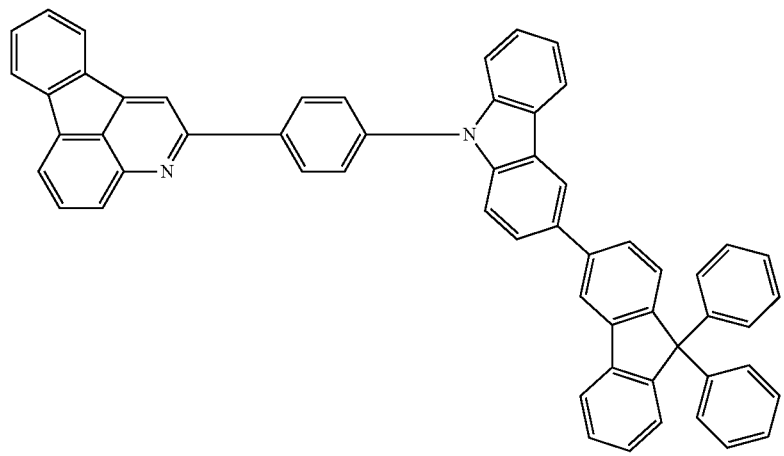
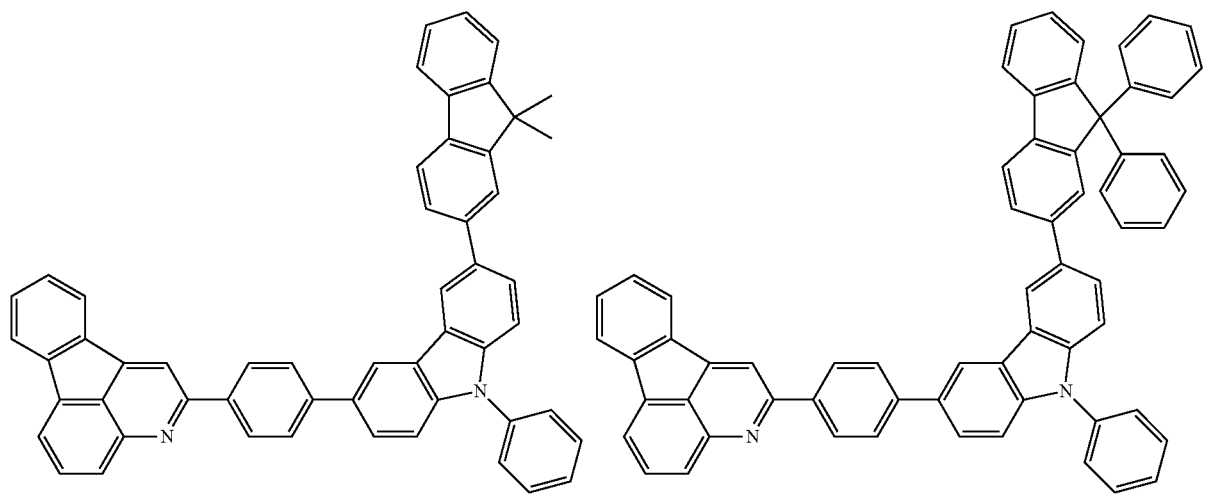
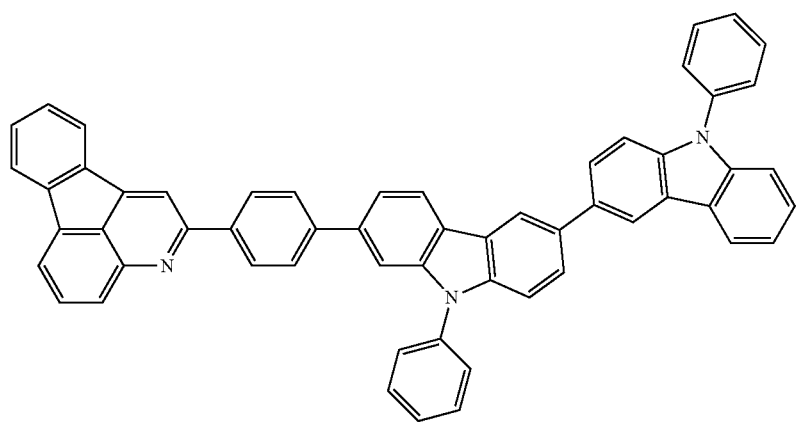

107 108
-continued
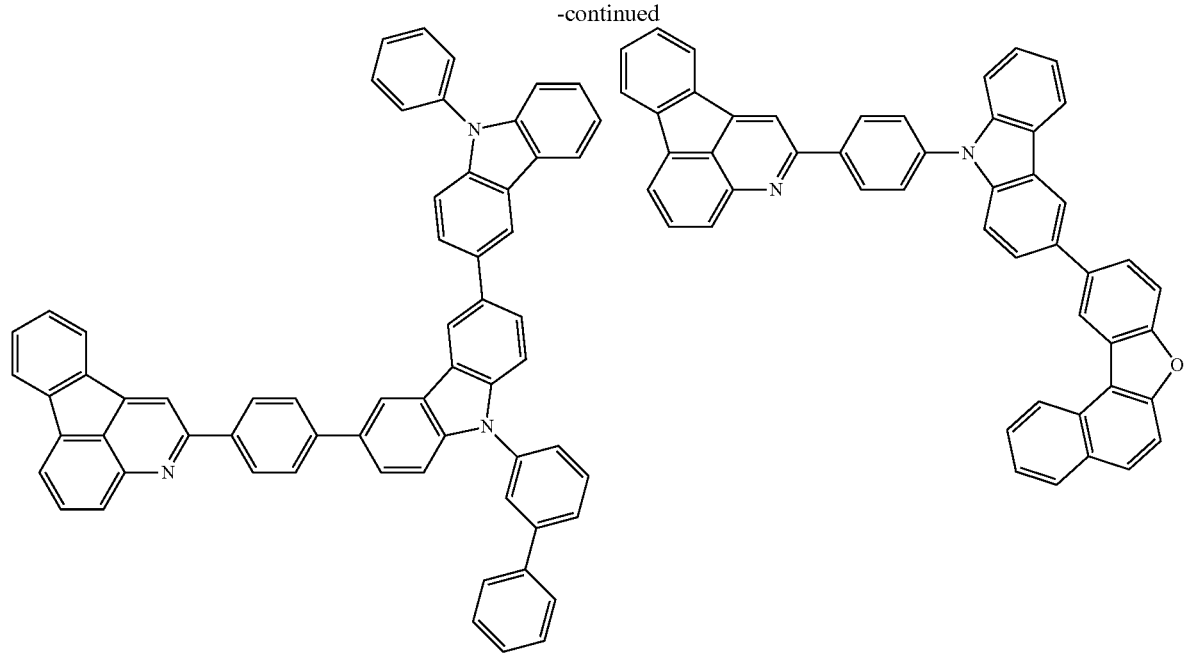
[Chem. 38]
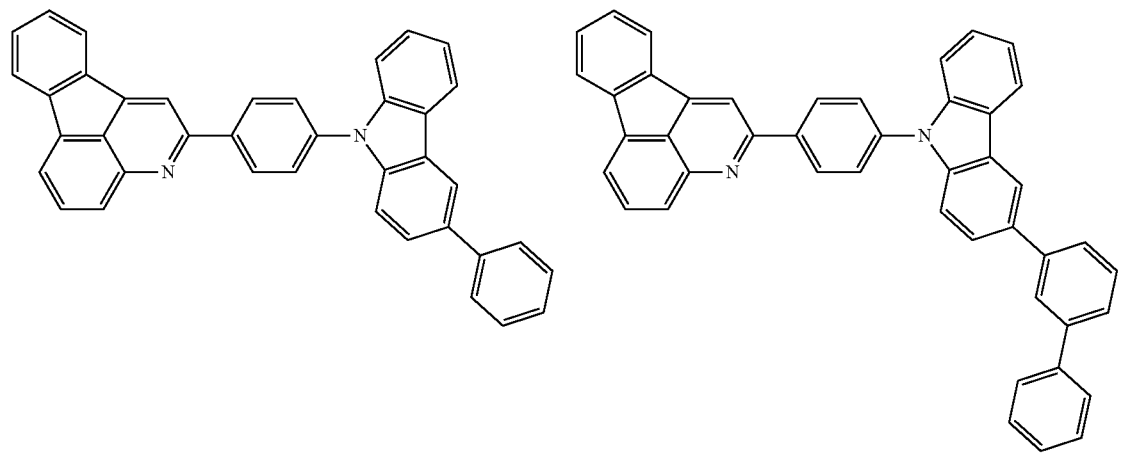
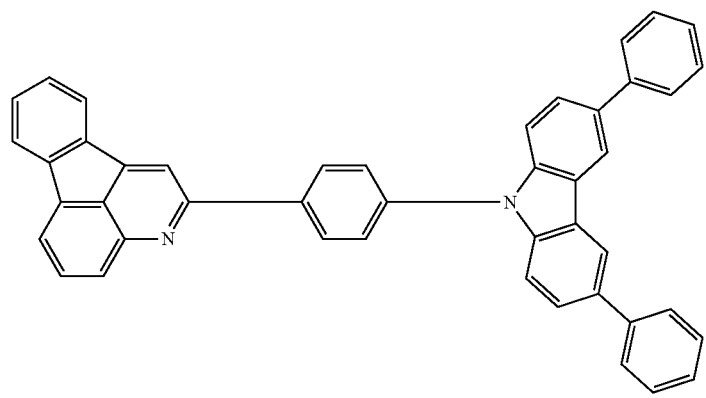

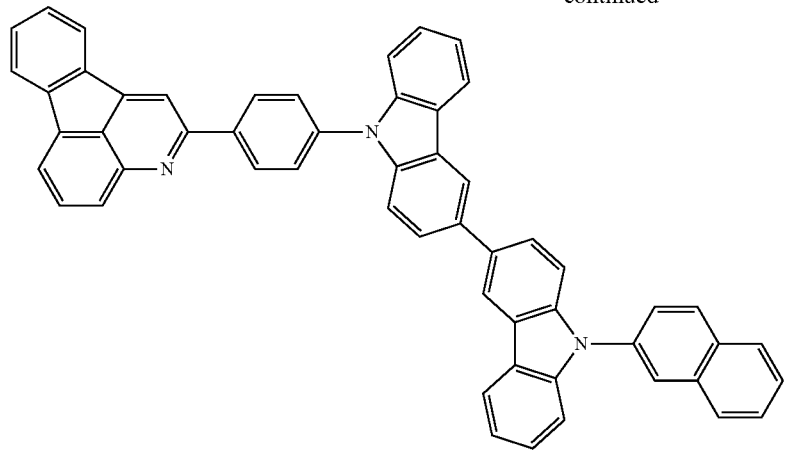
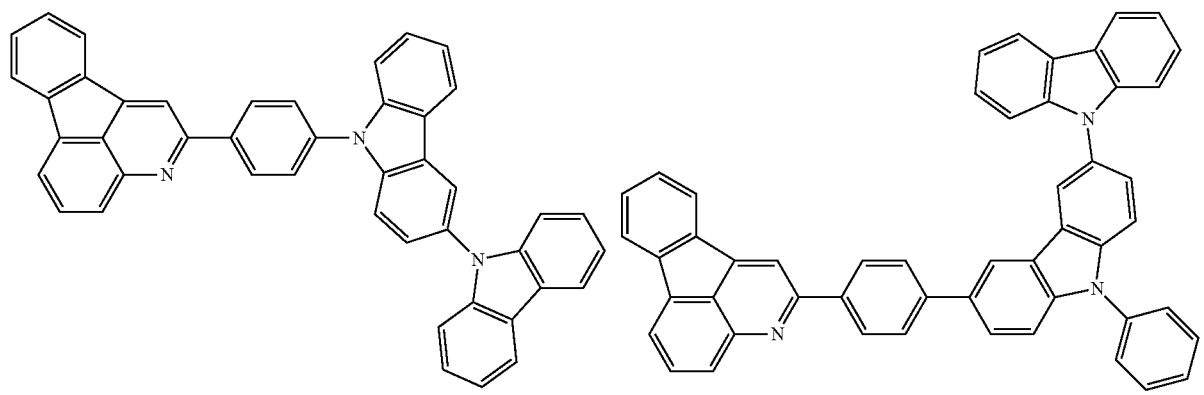
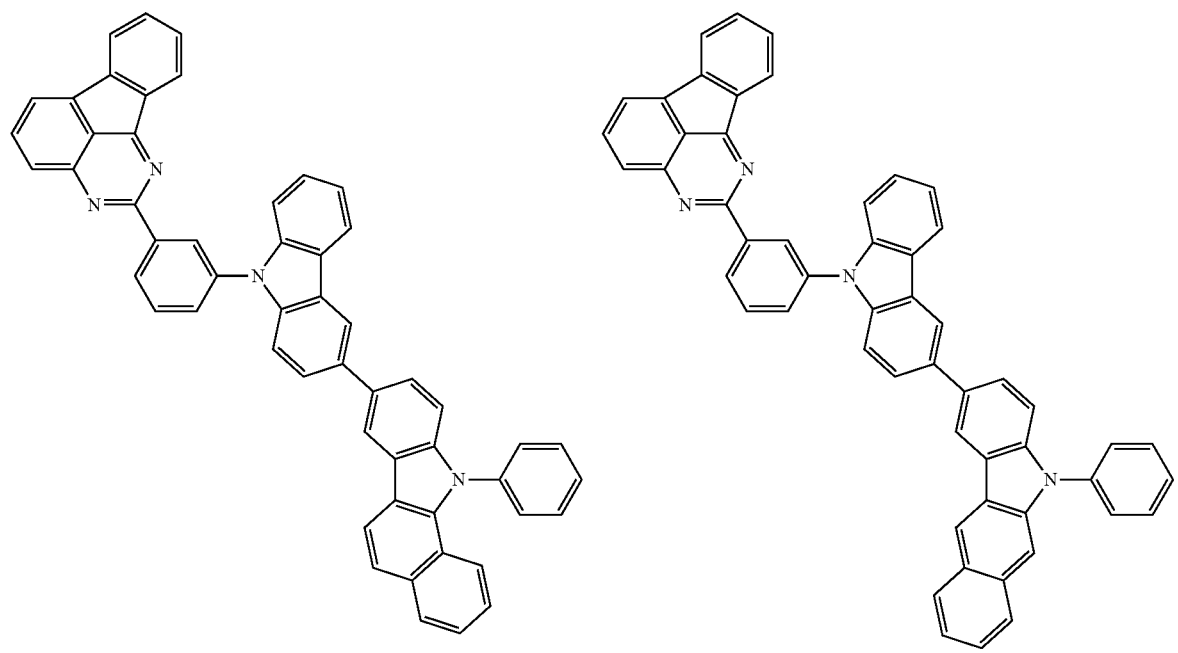

[Chem. 39]
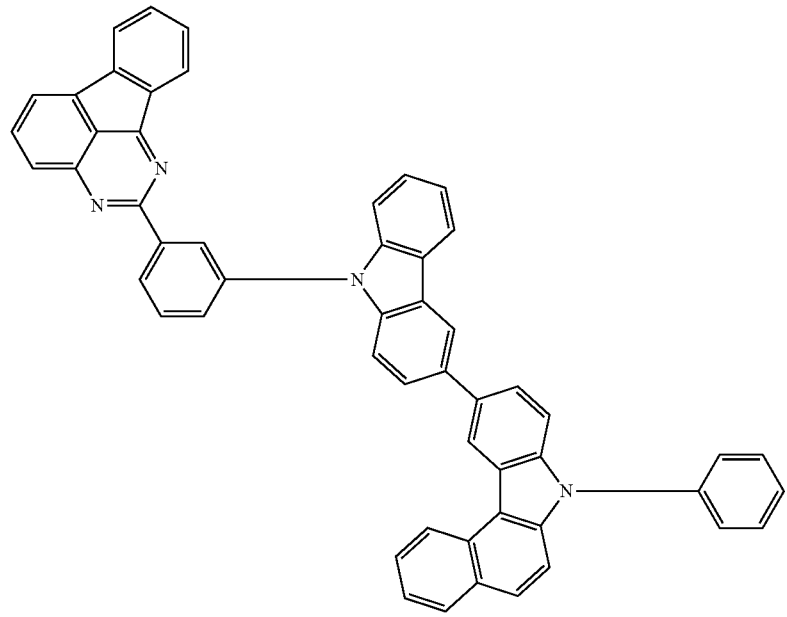
-continued
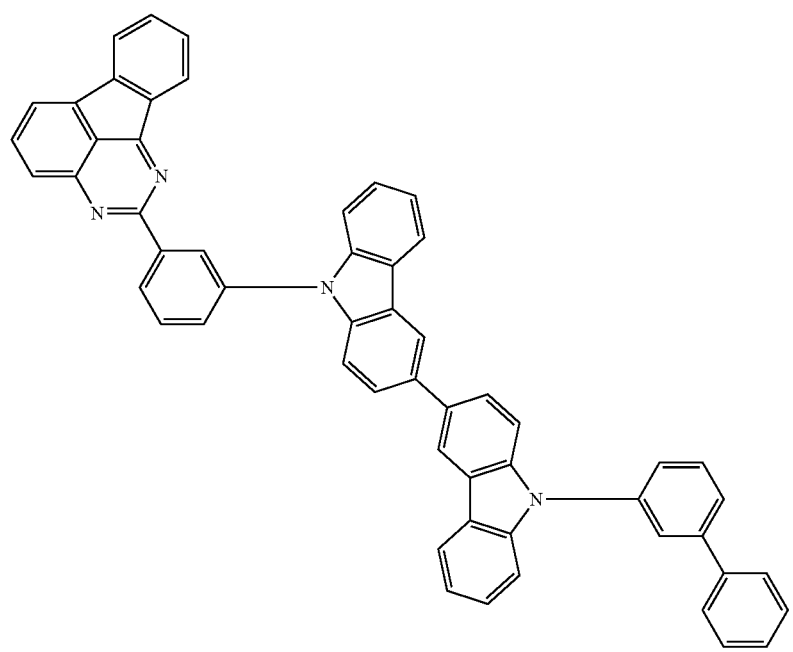

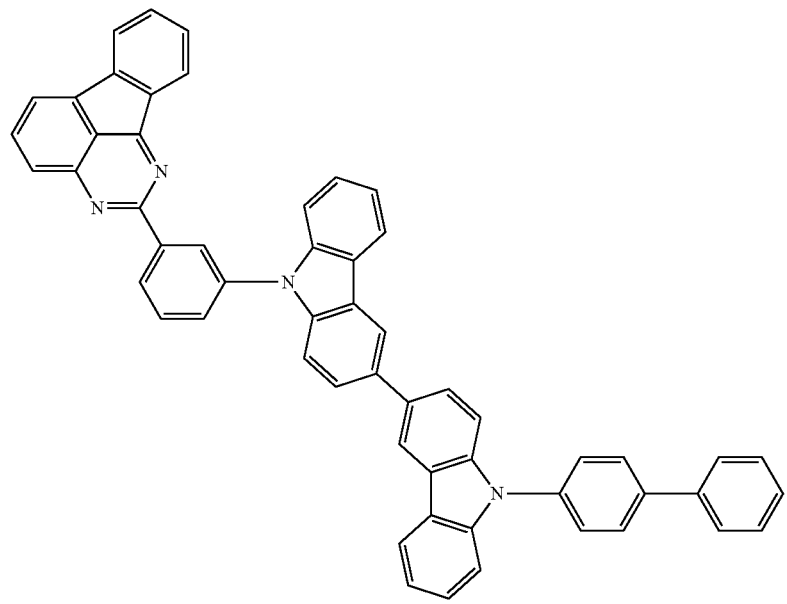
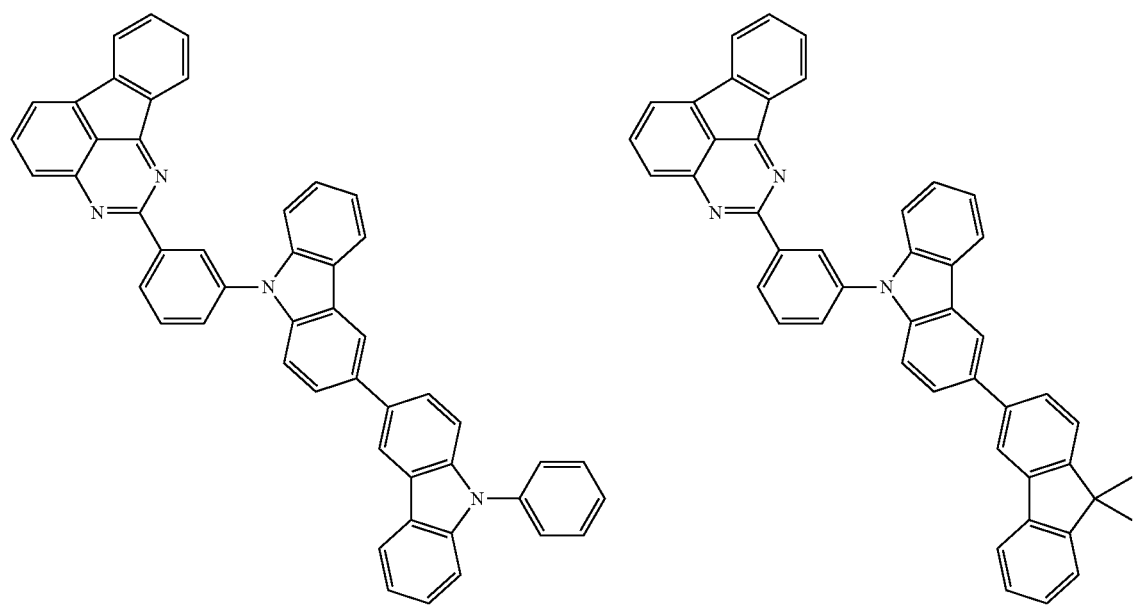

115
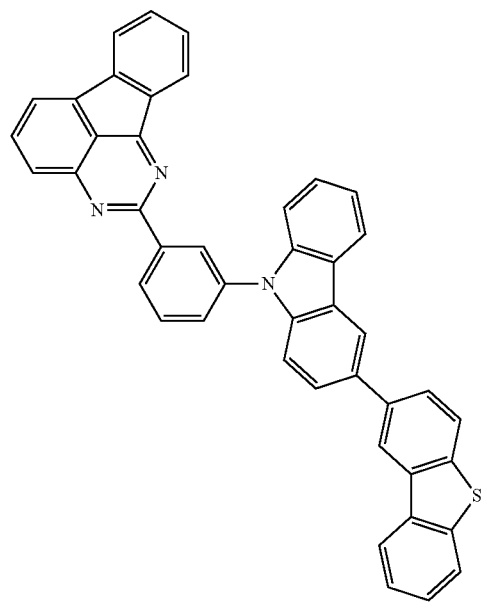
116
-continued
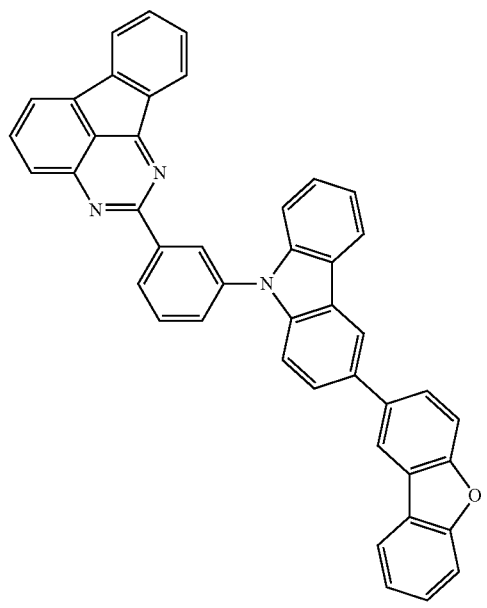
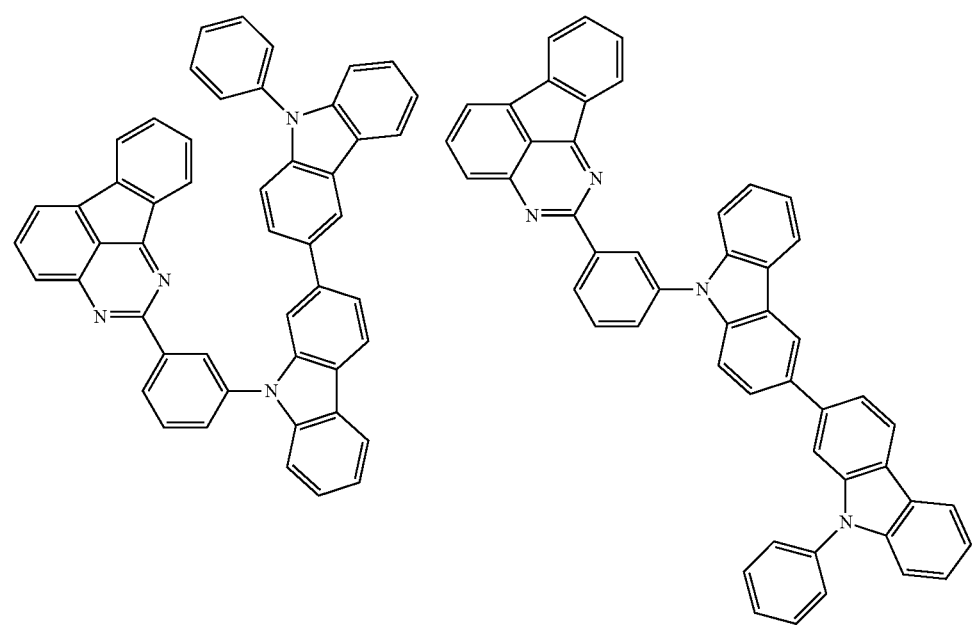

-continued
[Chem. 40]
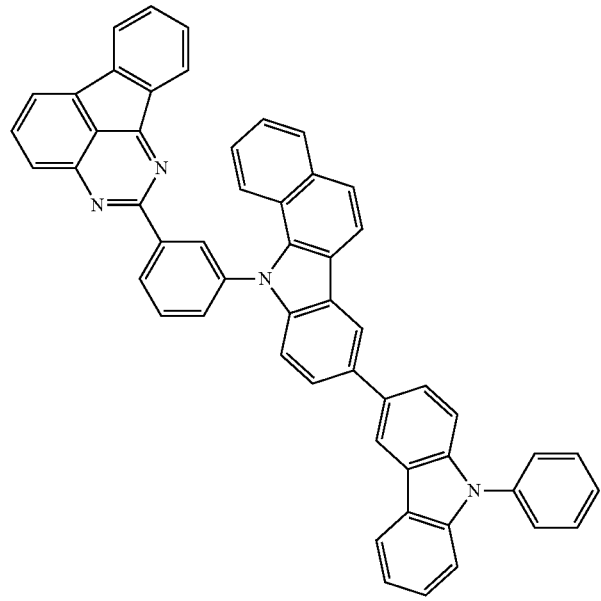
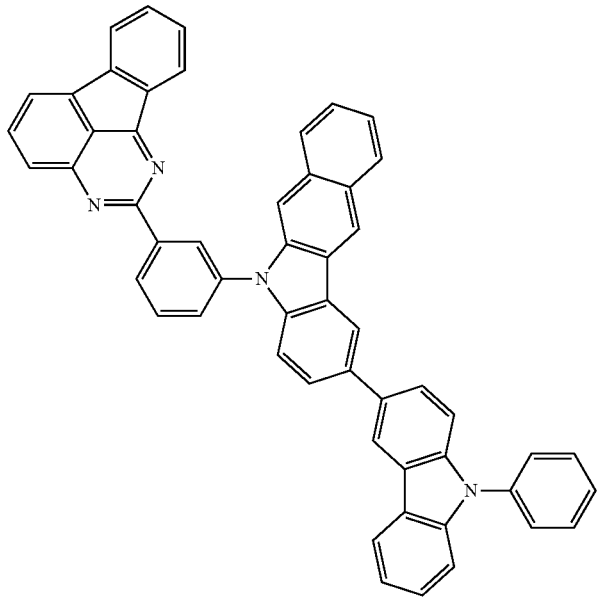
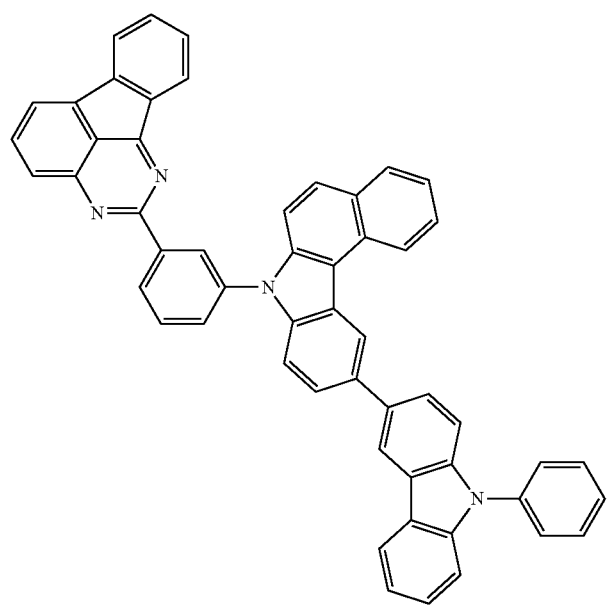
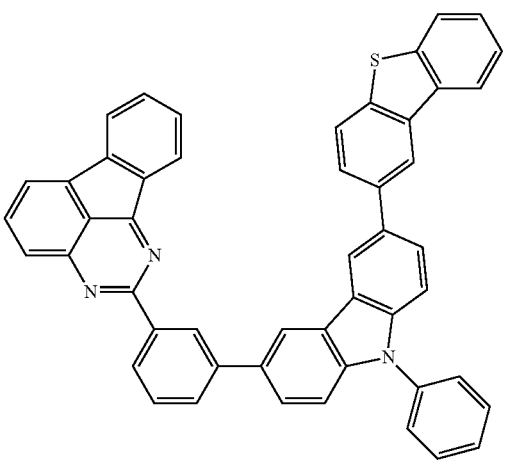

119
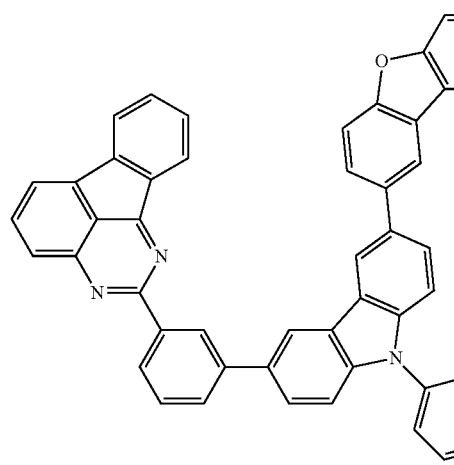
120
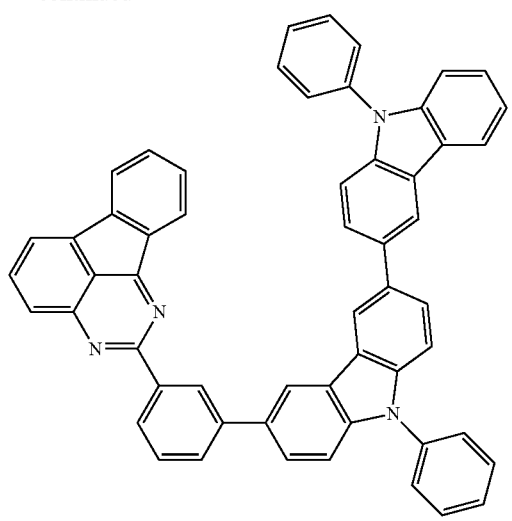
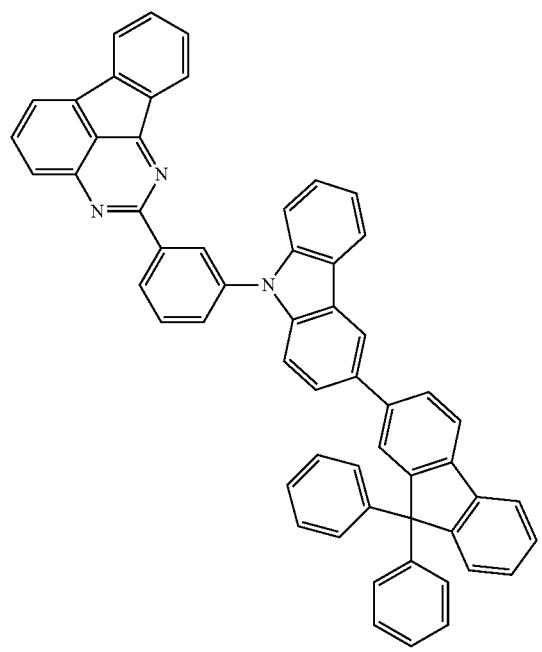
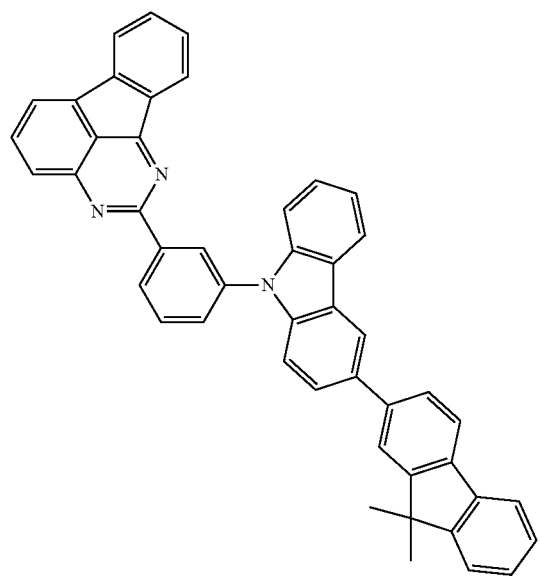

[Chem. 41]
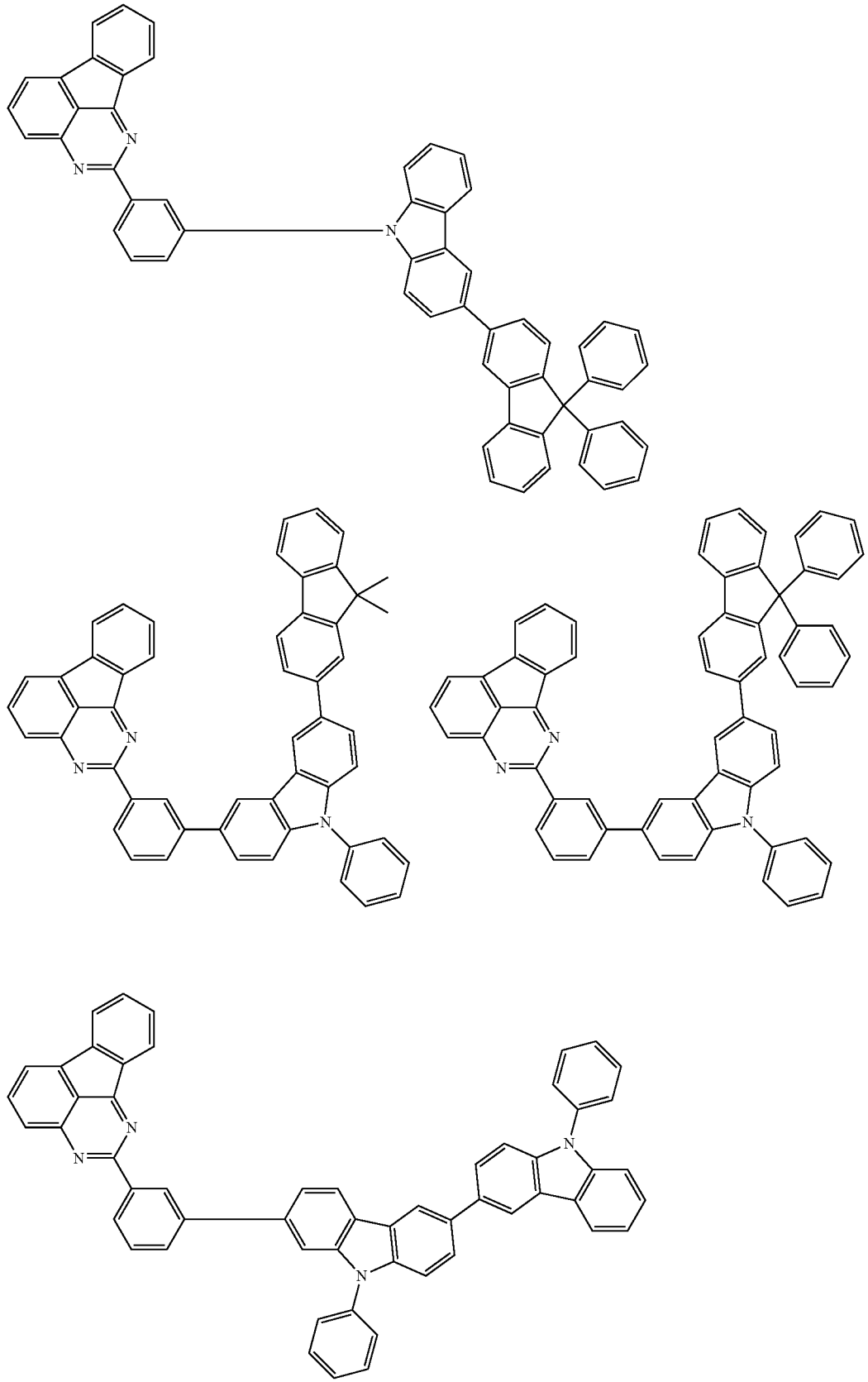

-continued
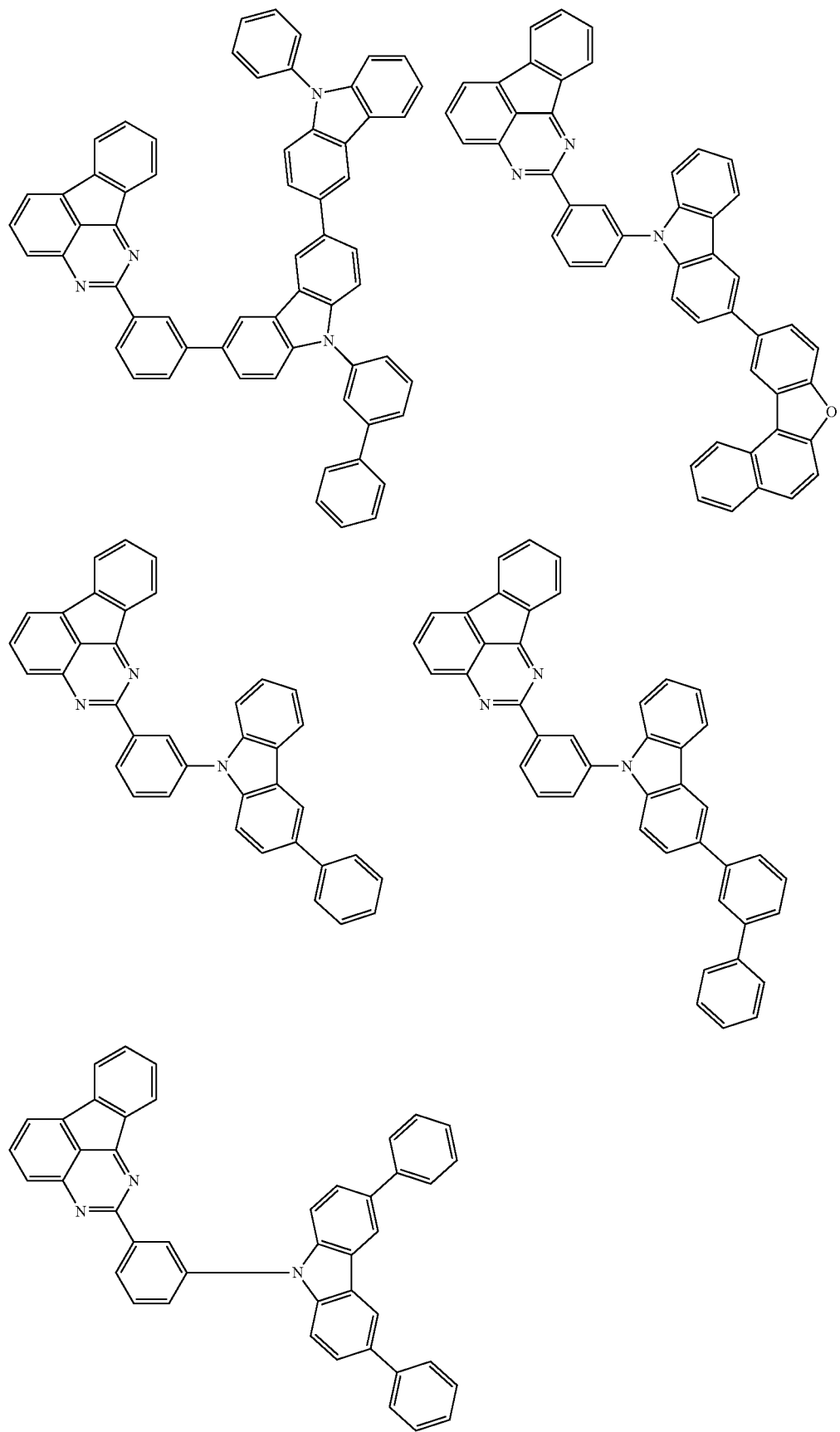

[Chem. 42]
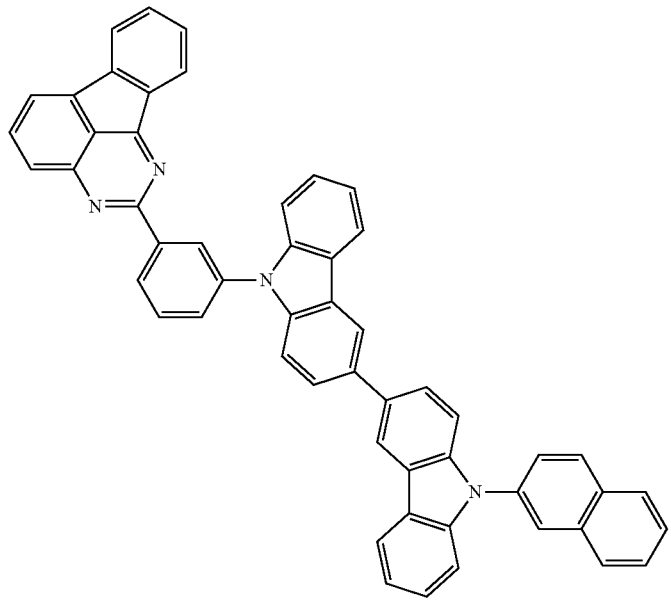
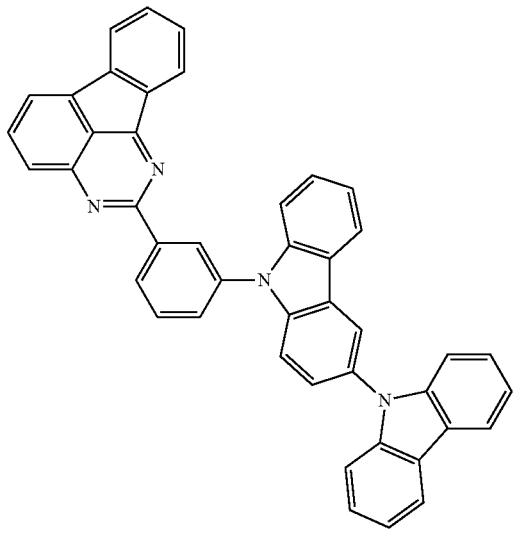
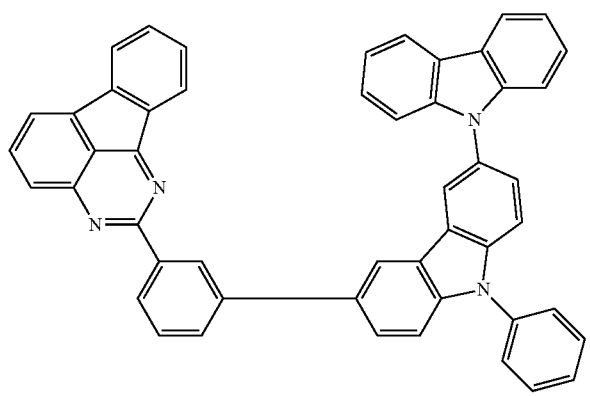
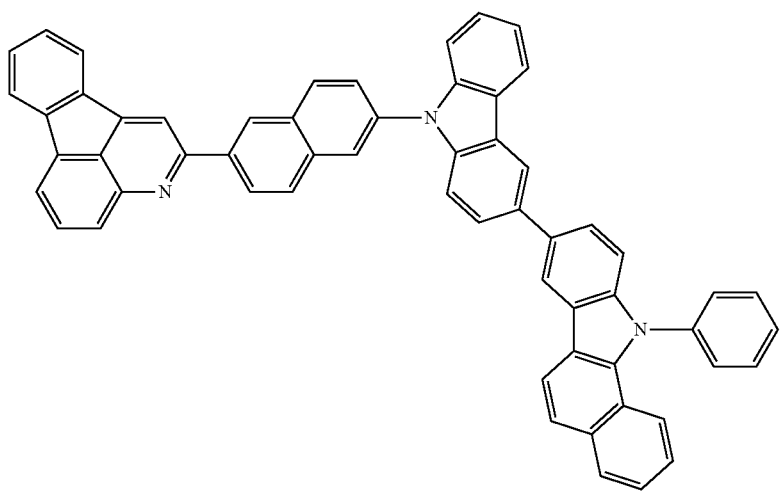

-continued
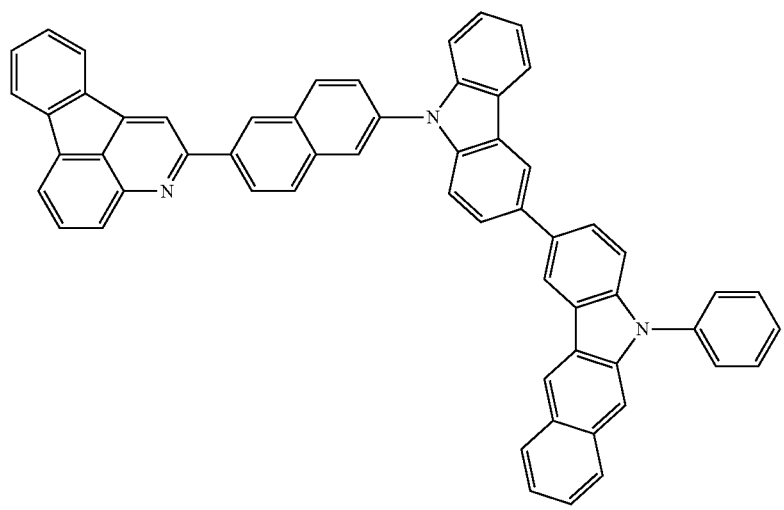
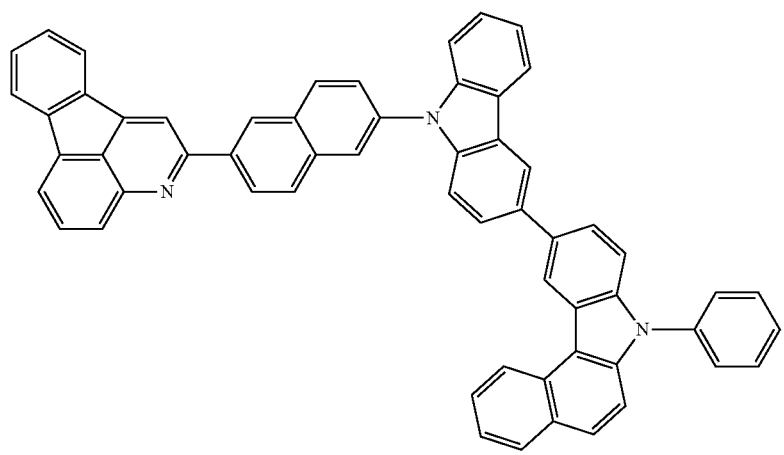
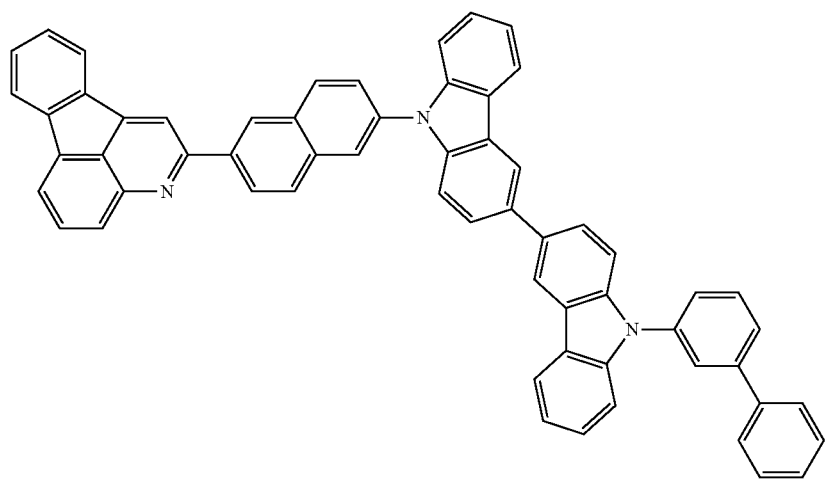

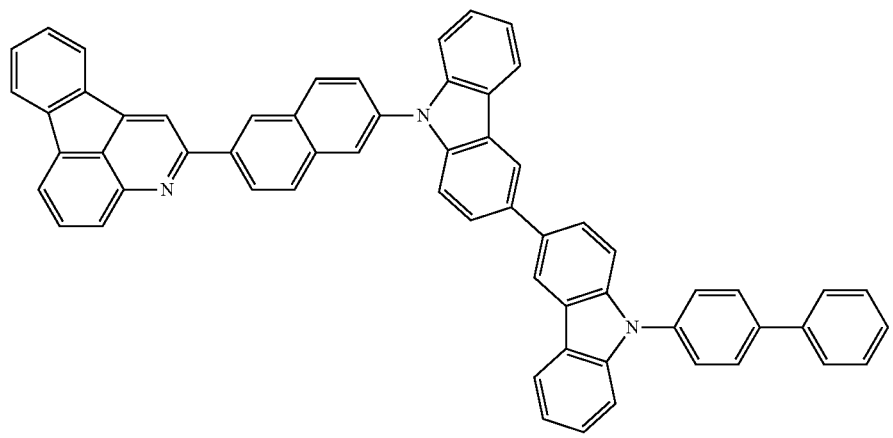
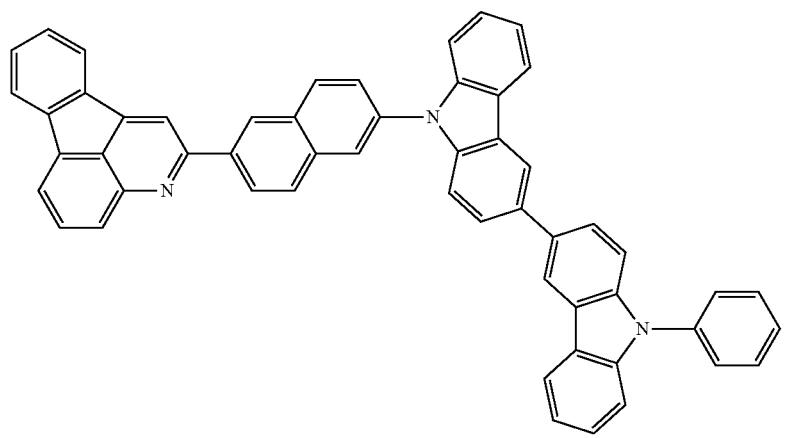
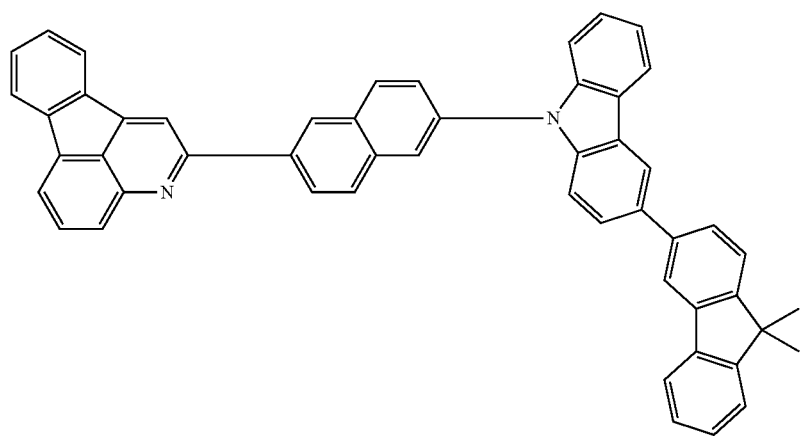

[Chem. 43]
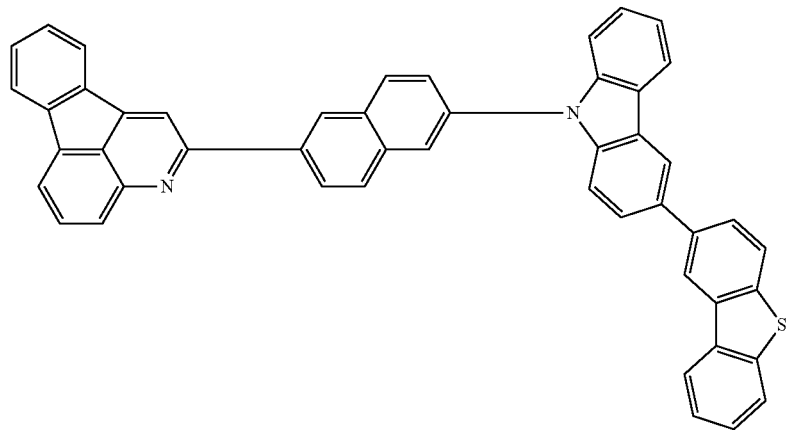
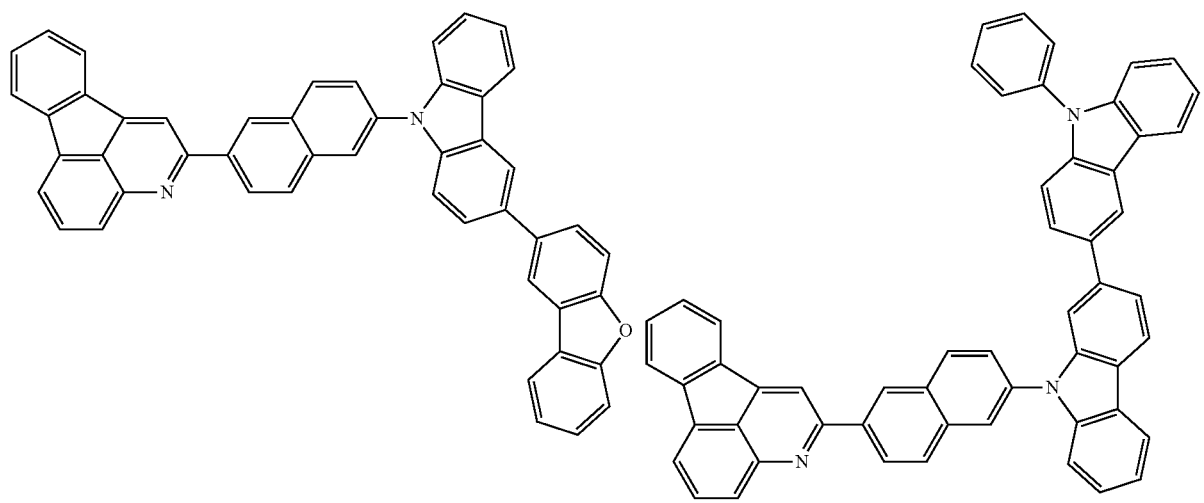
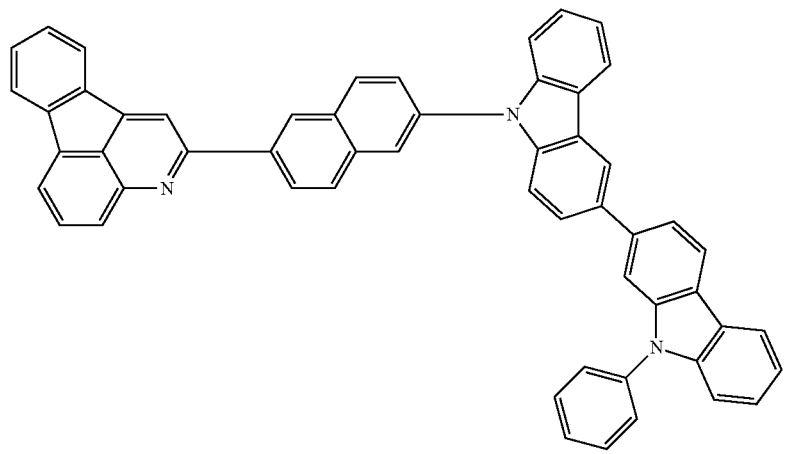

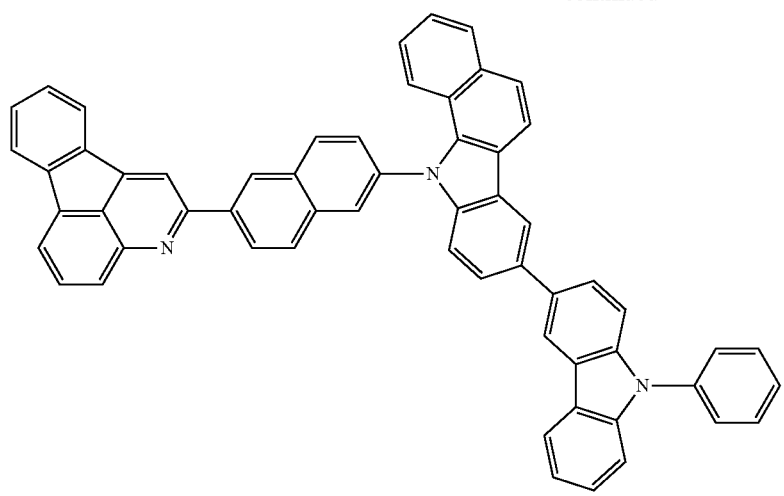
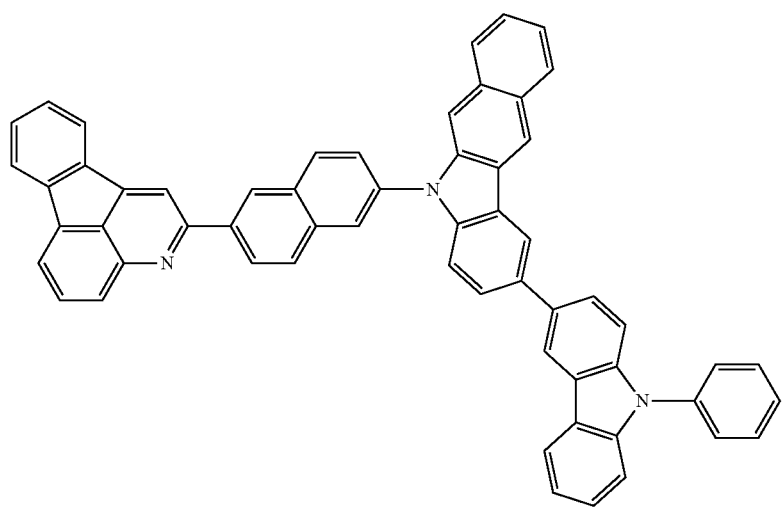
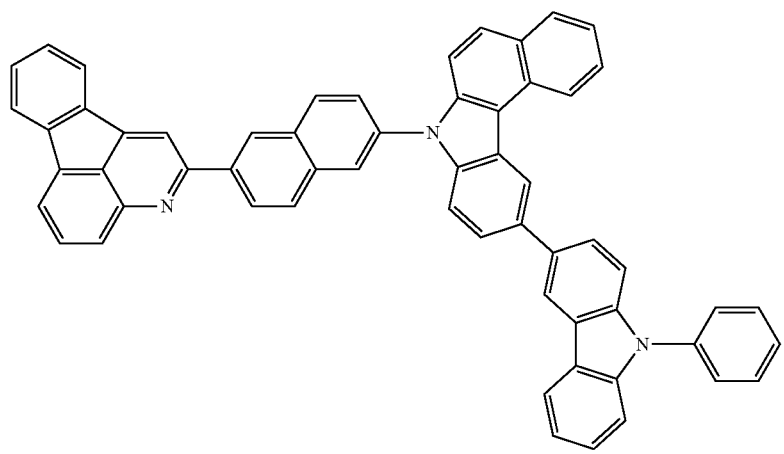

-continued
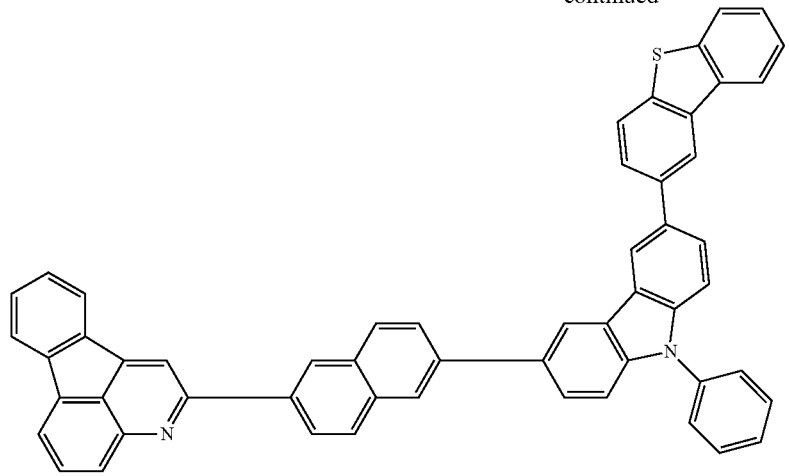
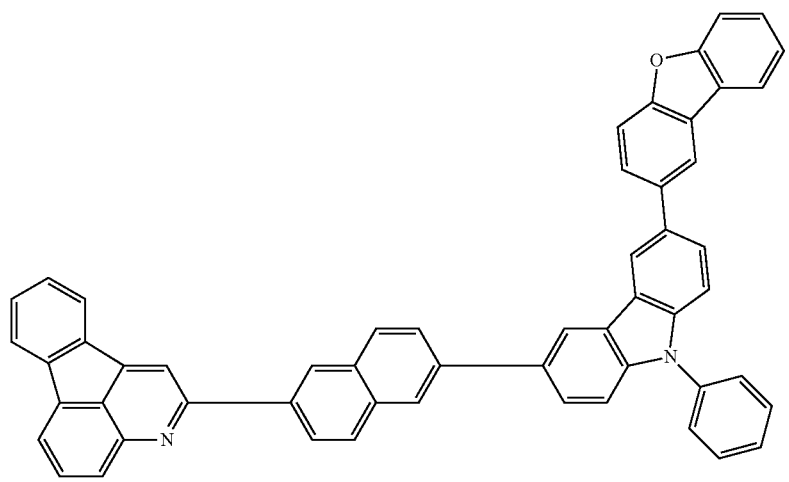
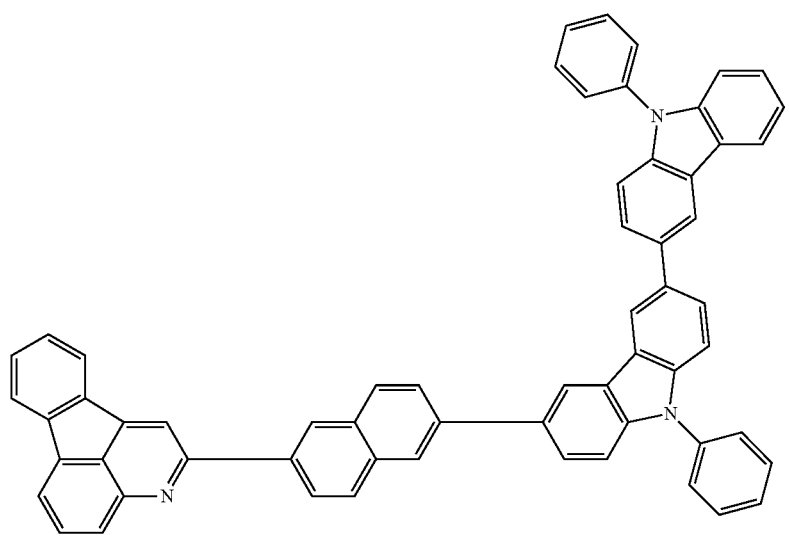

[Chem. 44]
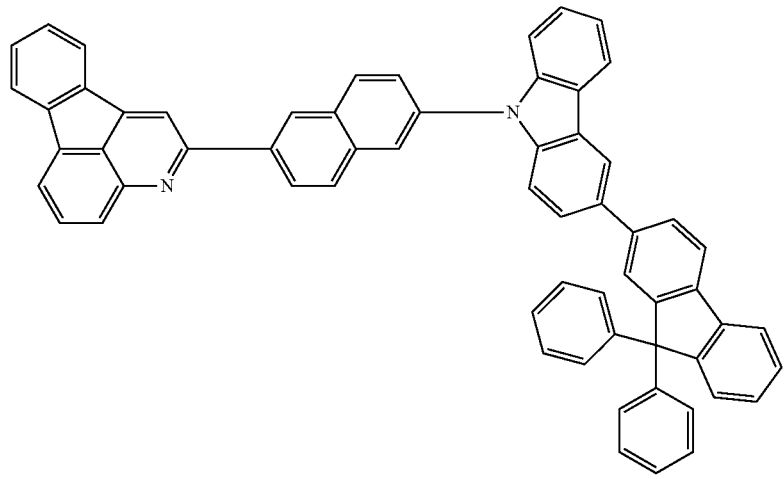
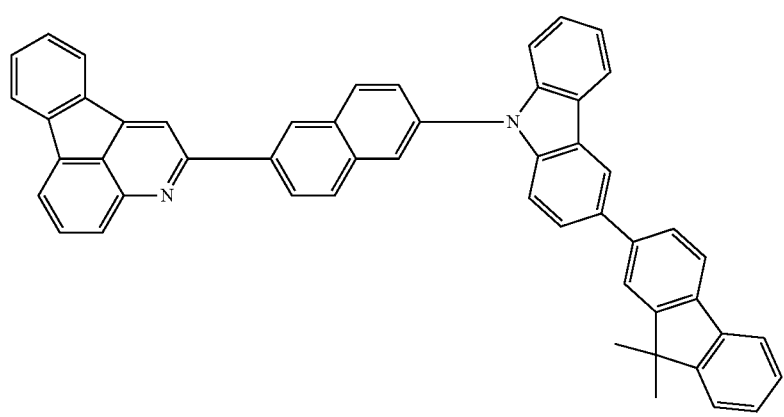
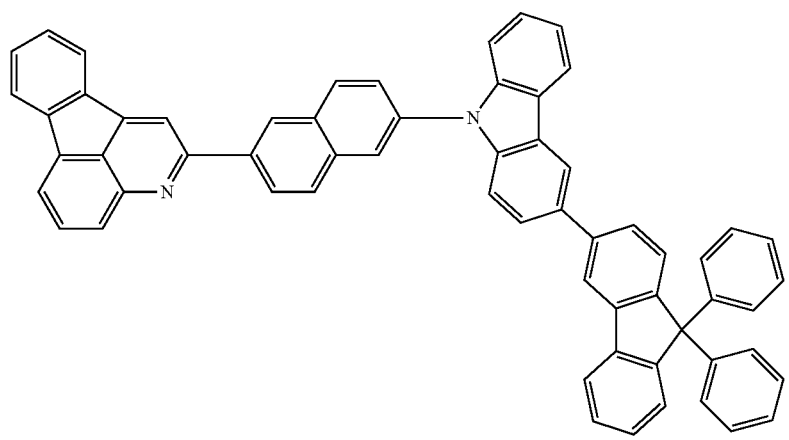

-continued
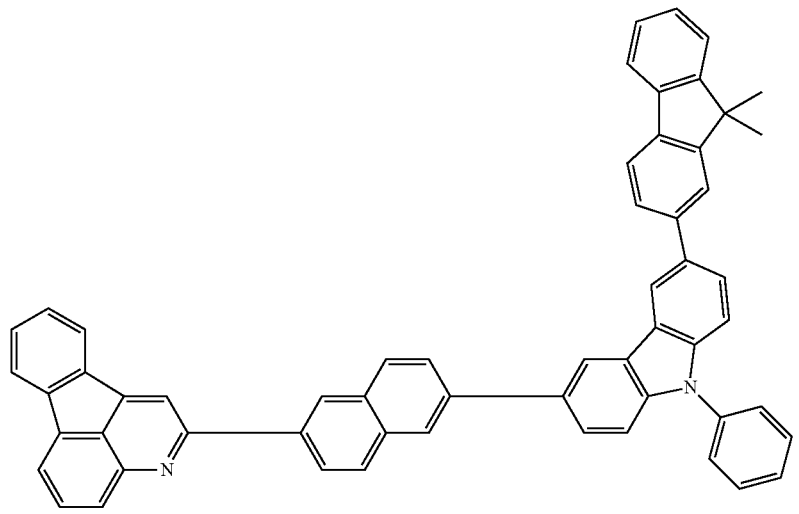
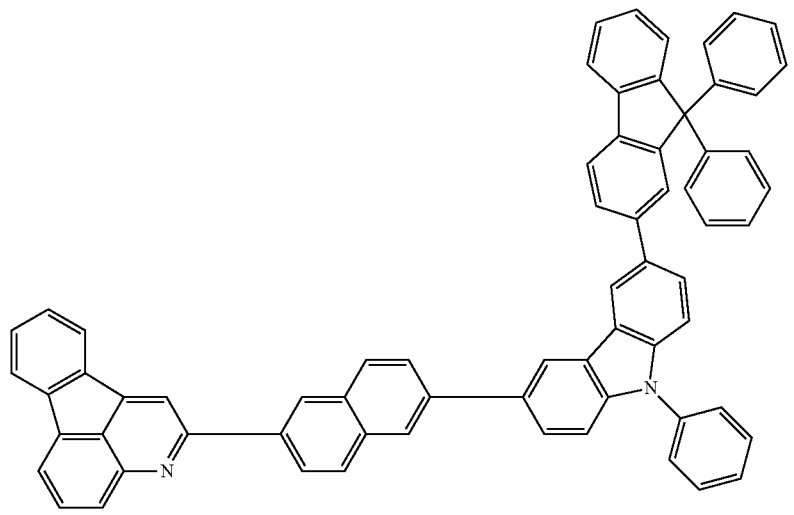
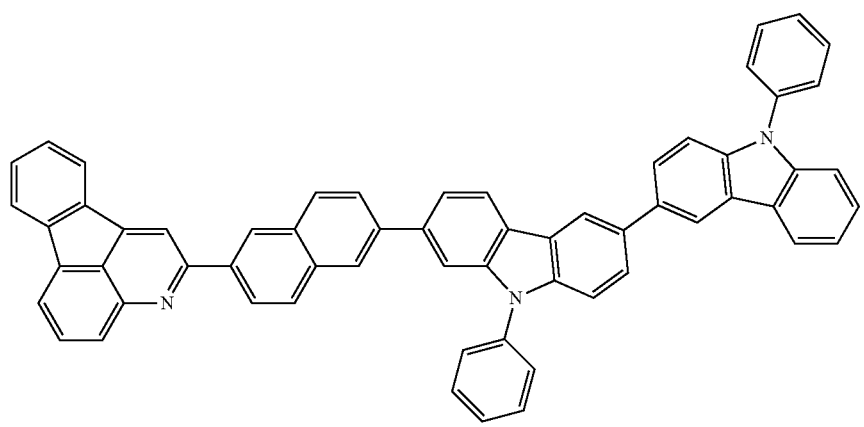

-continued
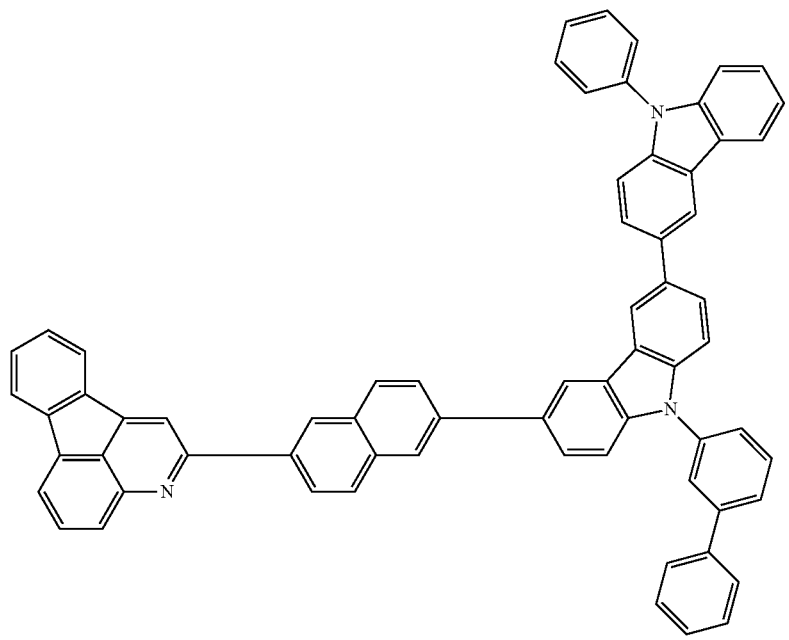
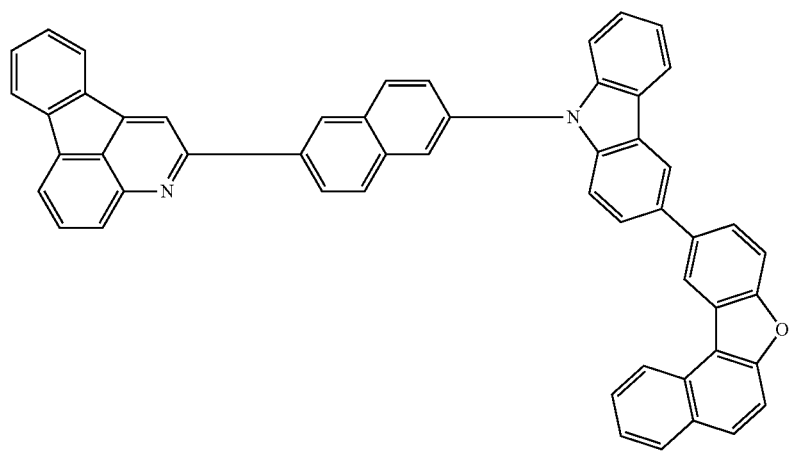
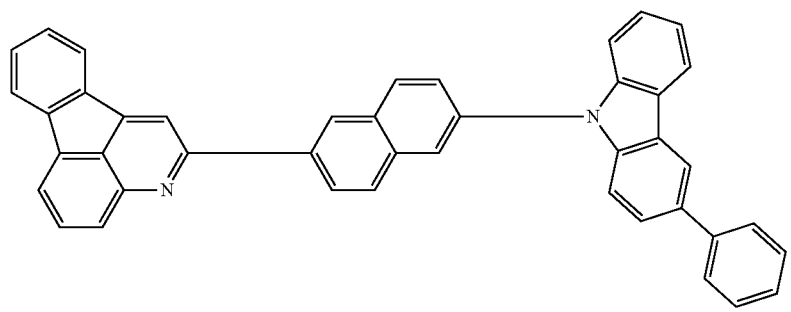

-continued
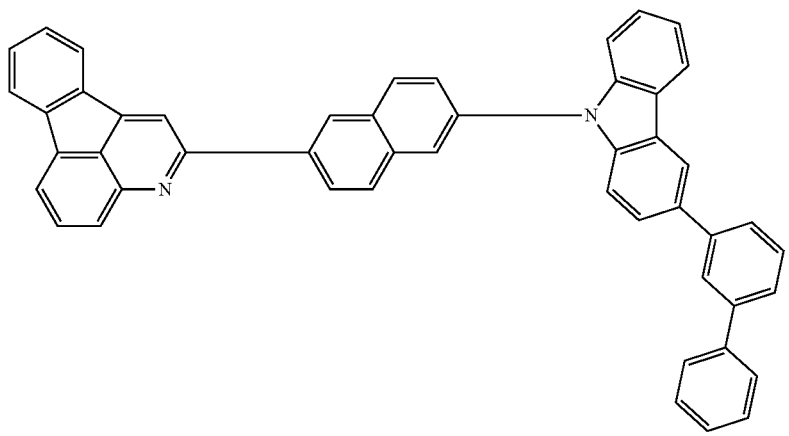
[Chem. 45]
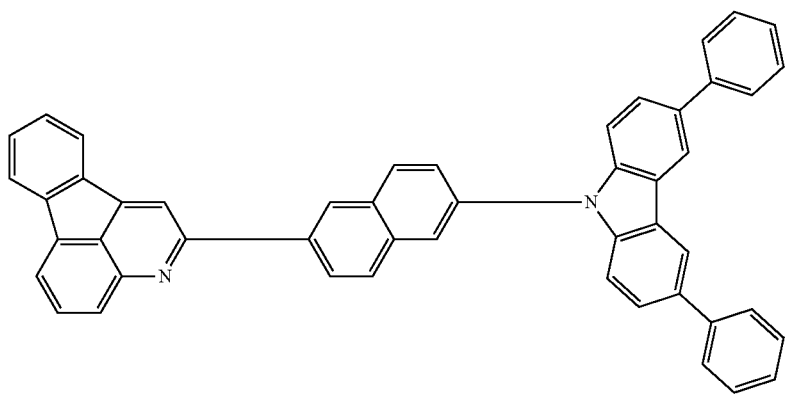
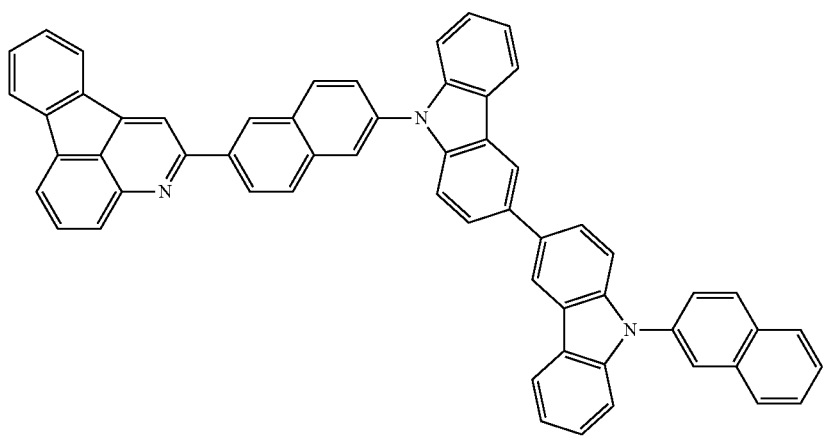
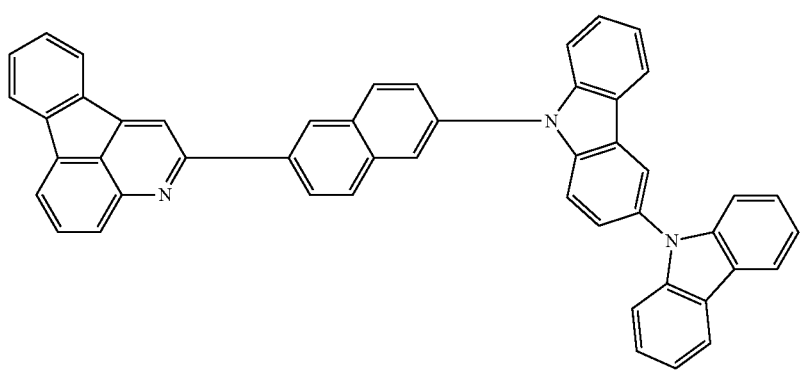

-continued
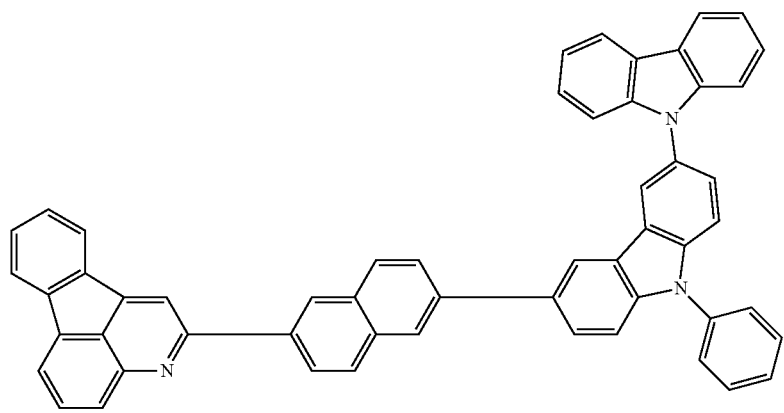
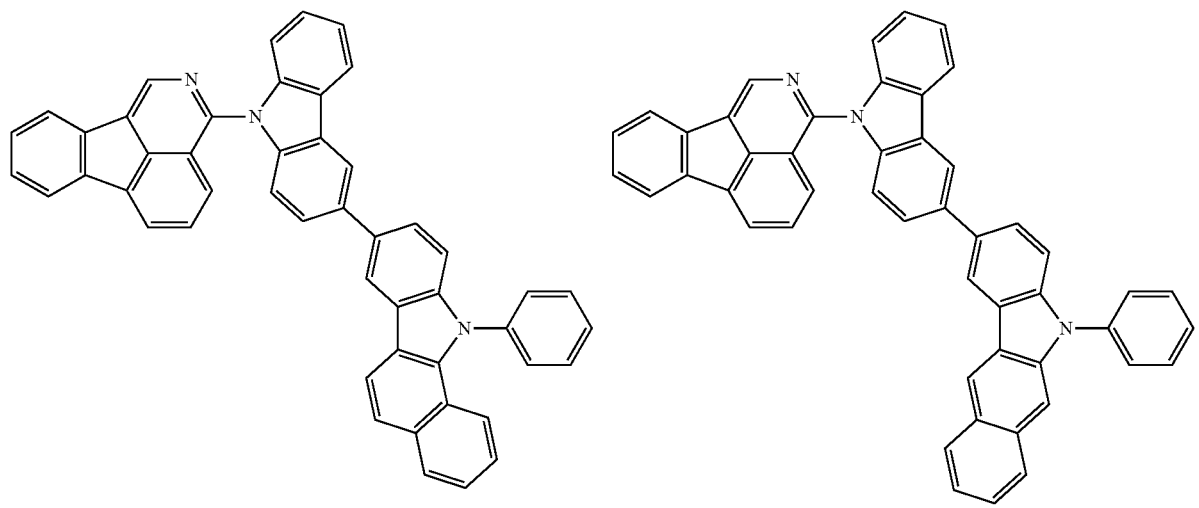
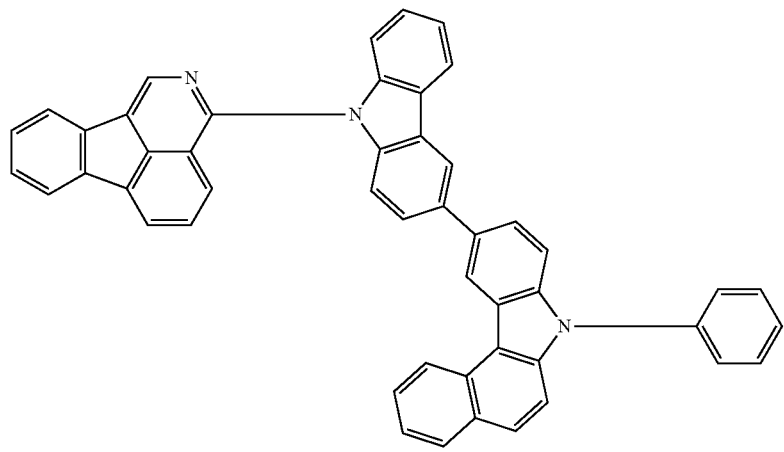

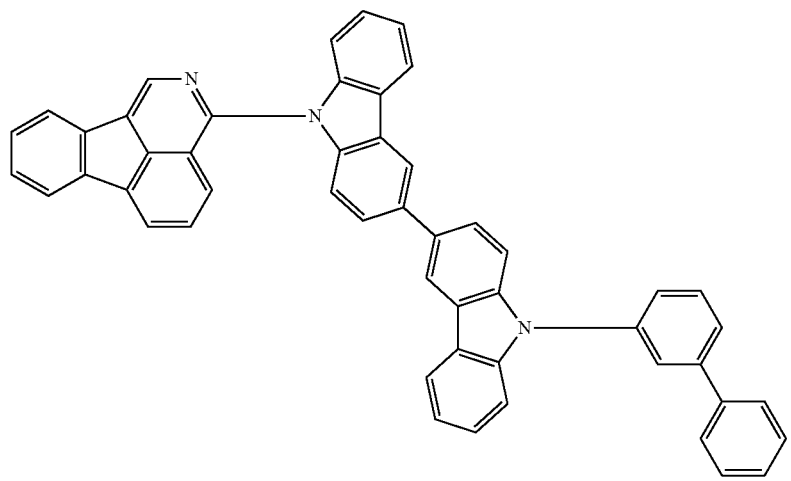
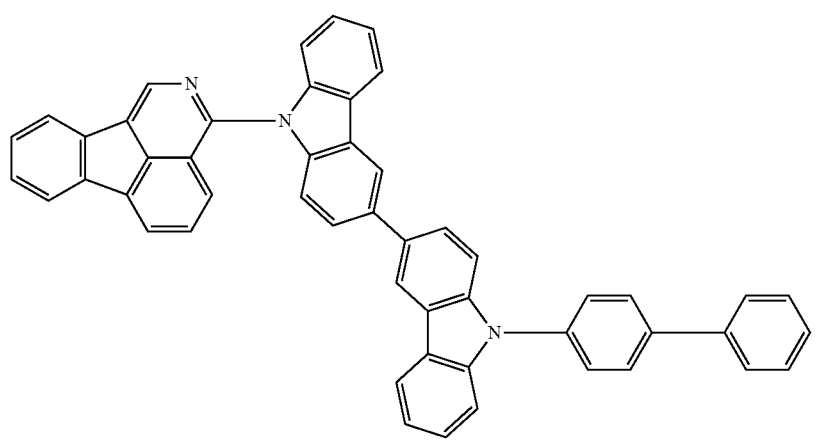
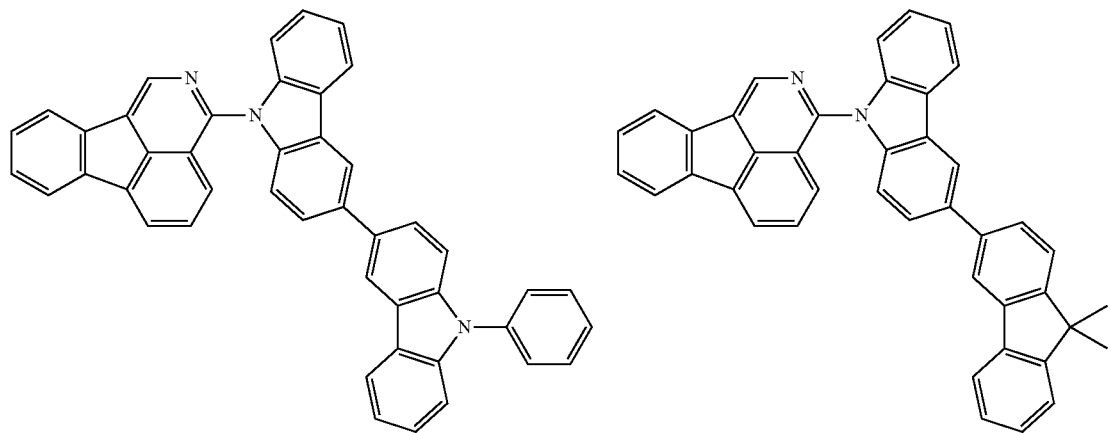

149 150
-continued
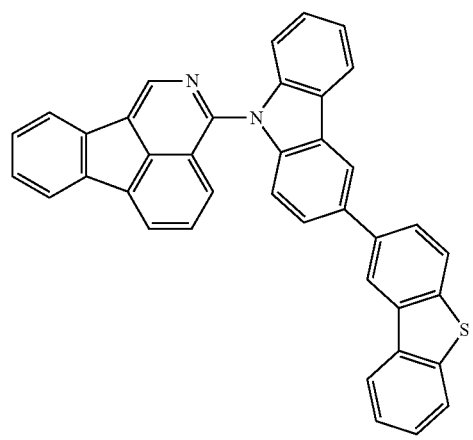
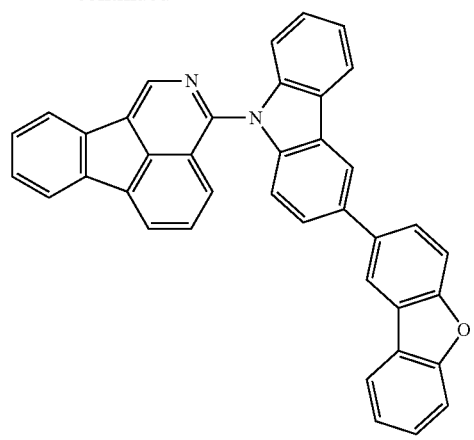
[Chem. 46]
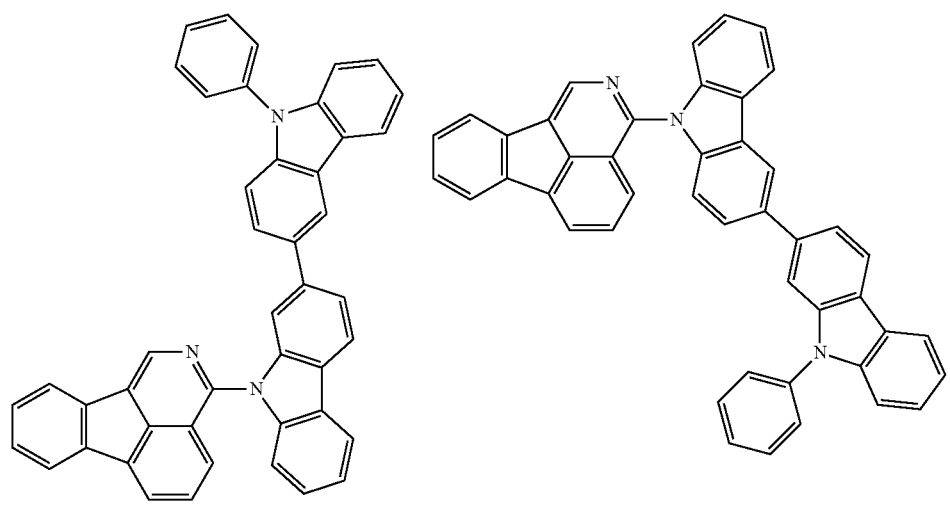
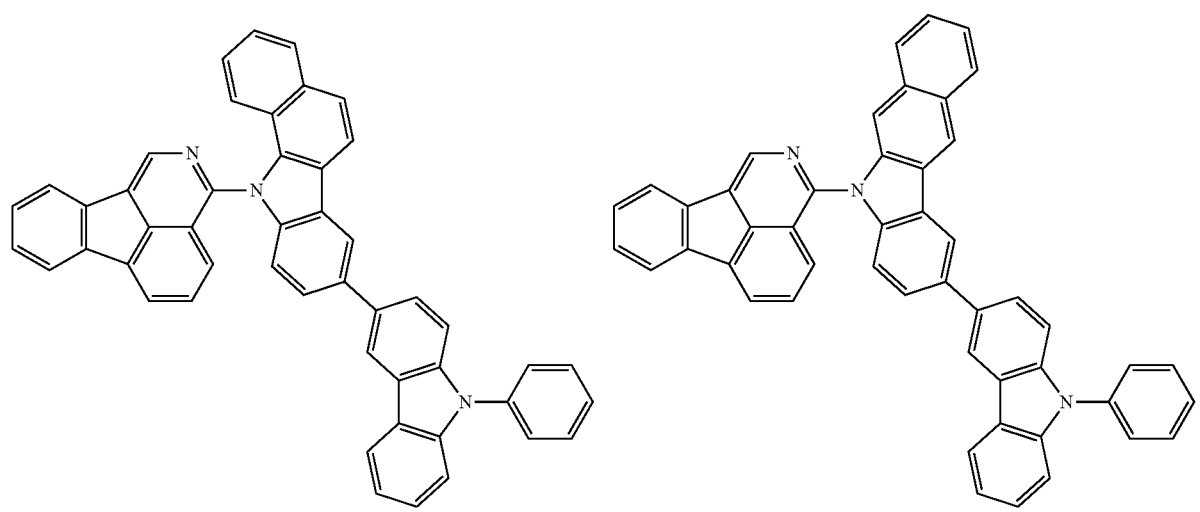

-continued
151
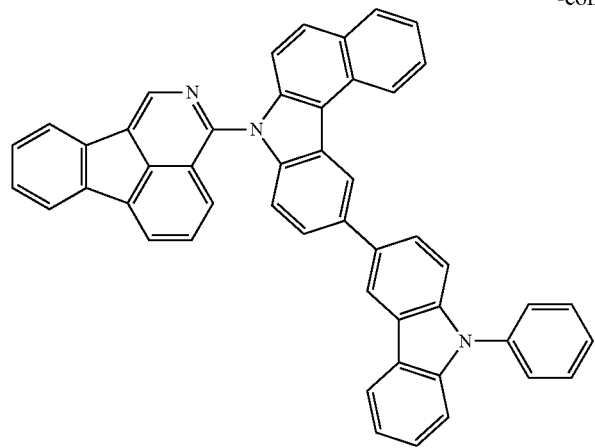
152
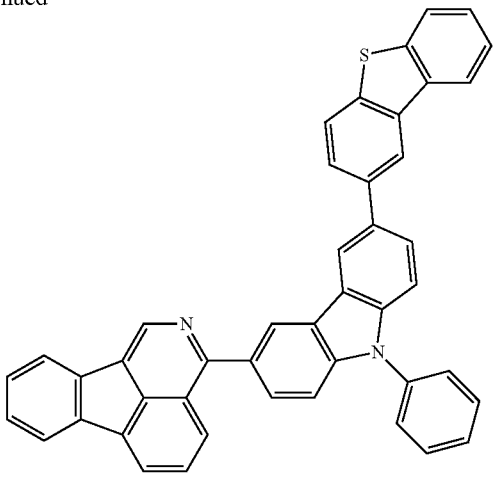
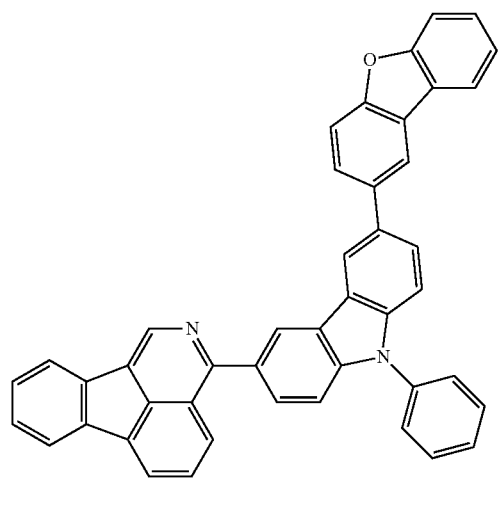
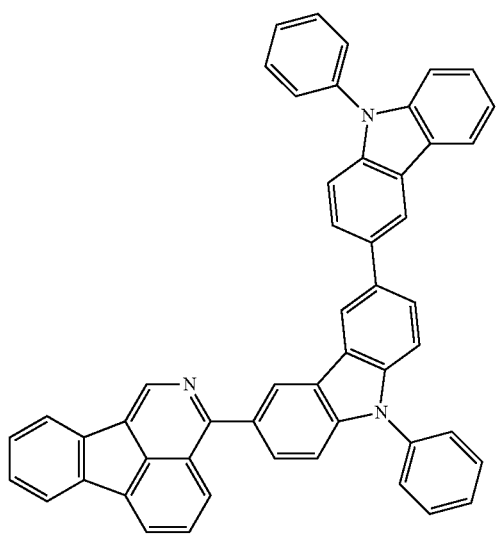
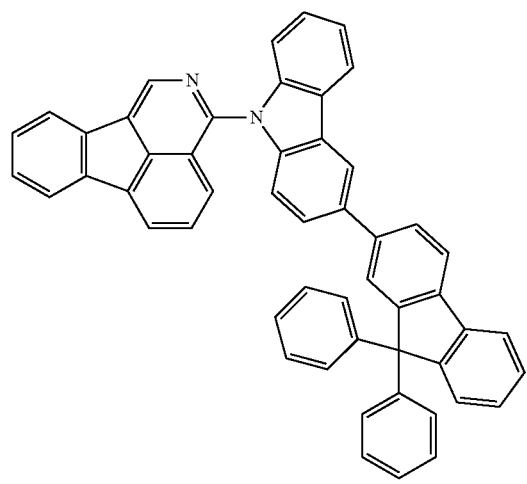
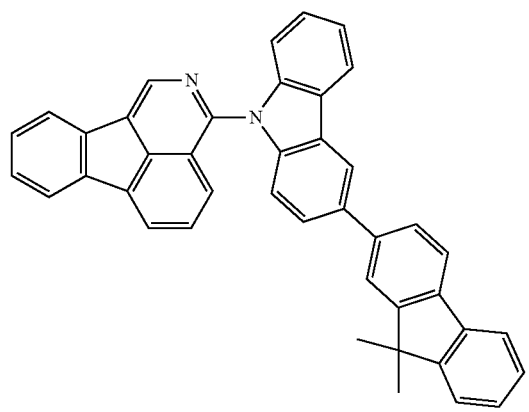

-continued
[Chem. 47]
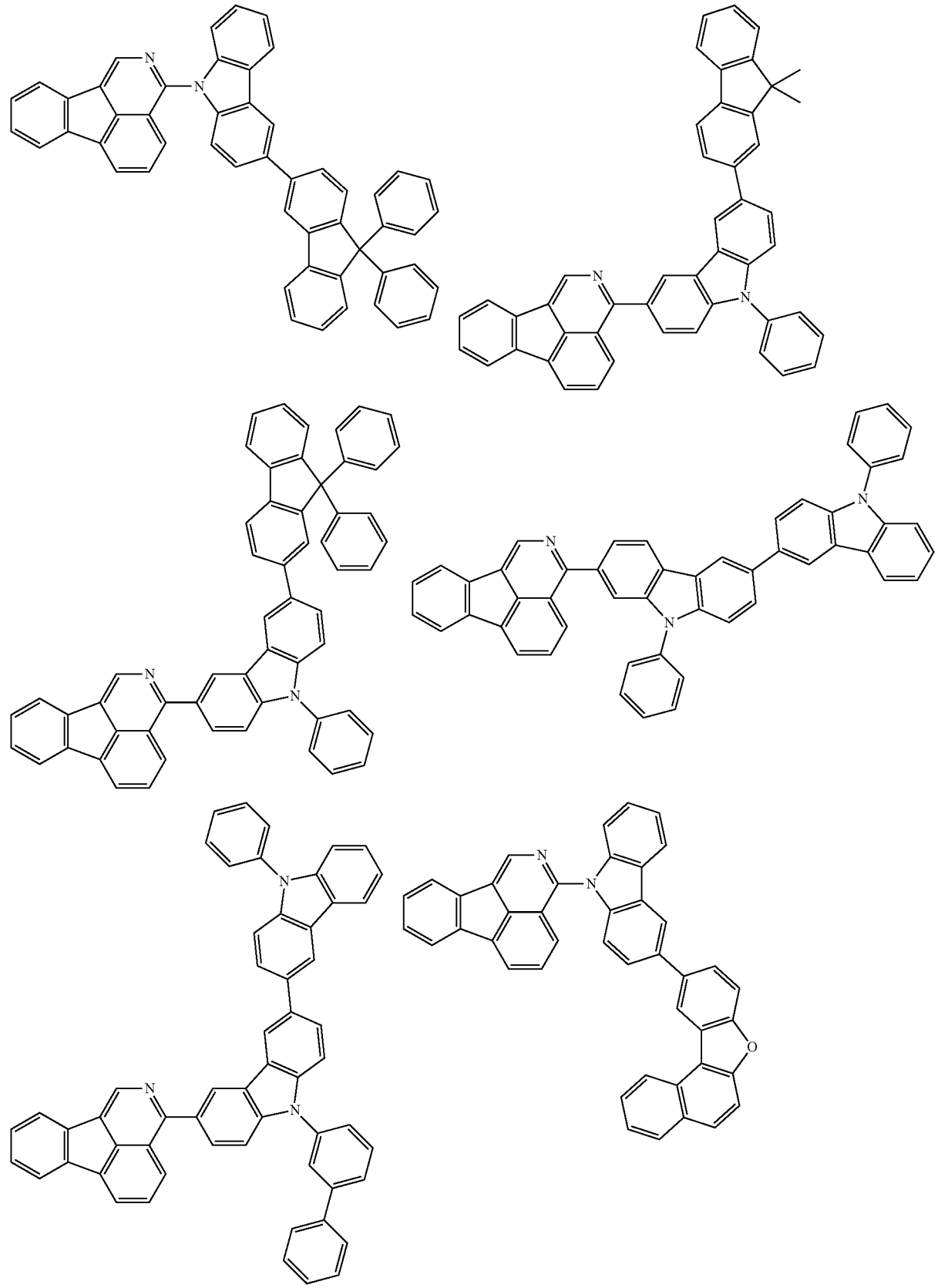

-continued
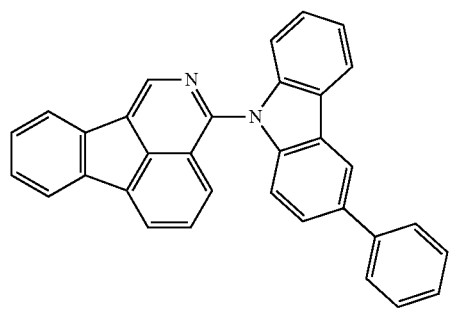
155
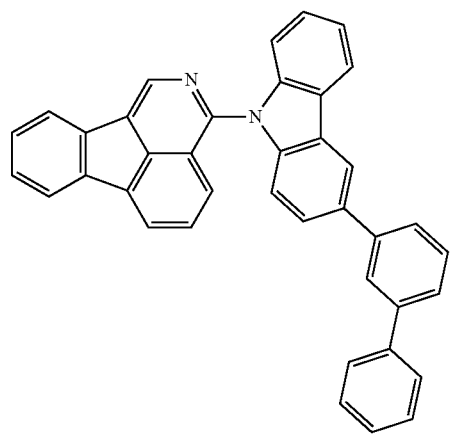
156
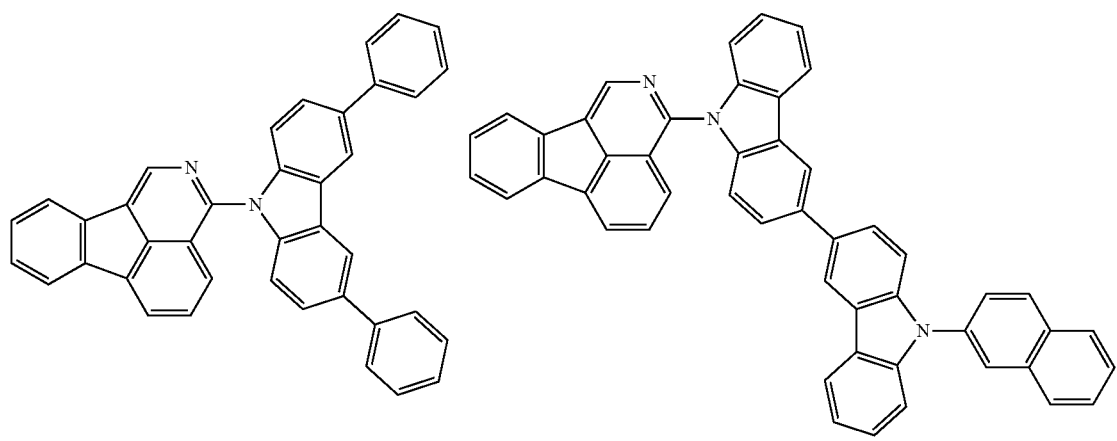
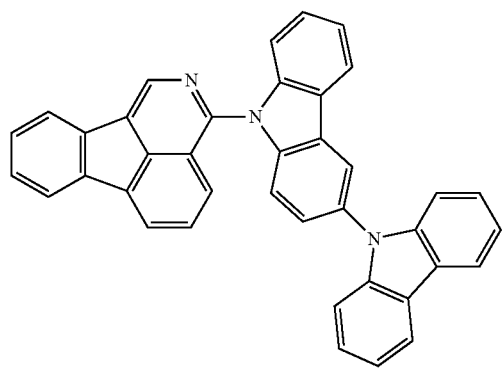

[Chem. 48]
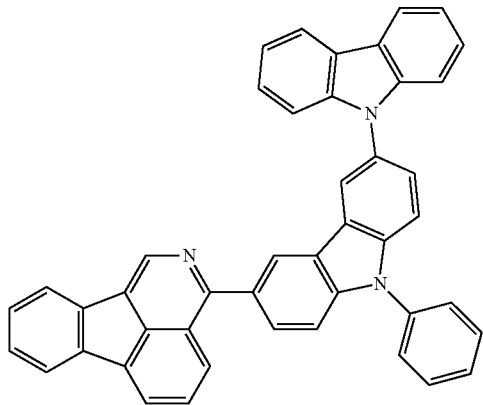
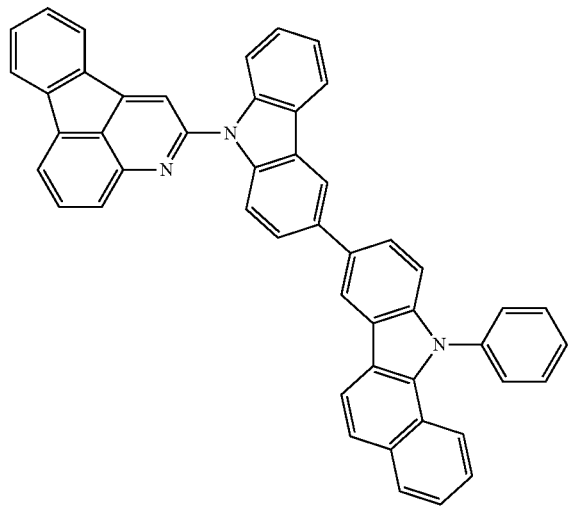
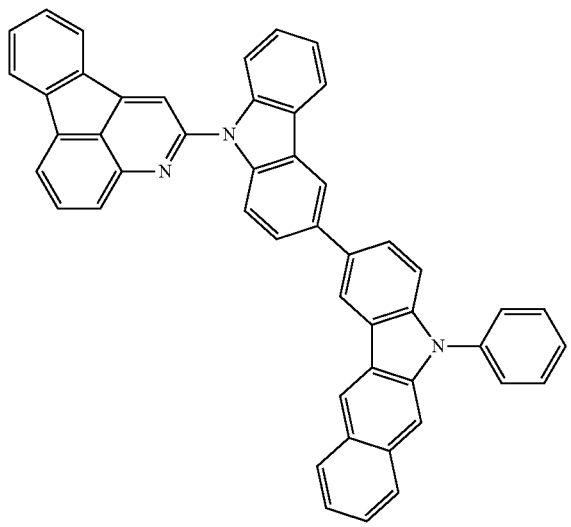
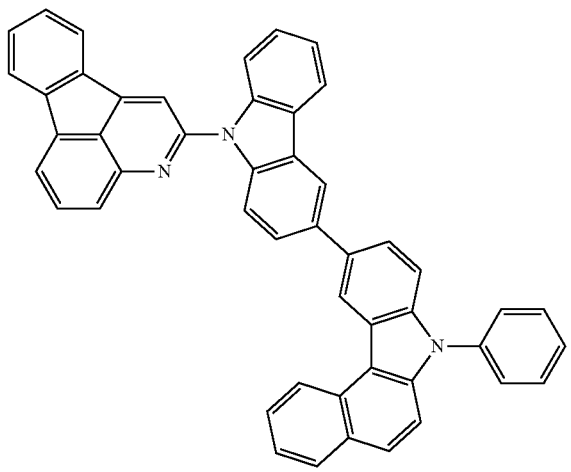
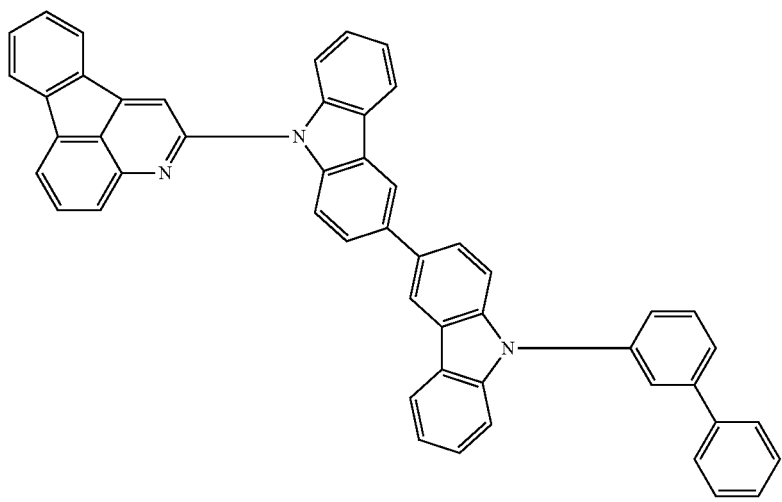

-continued
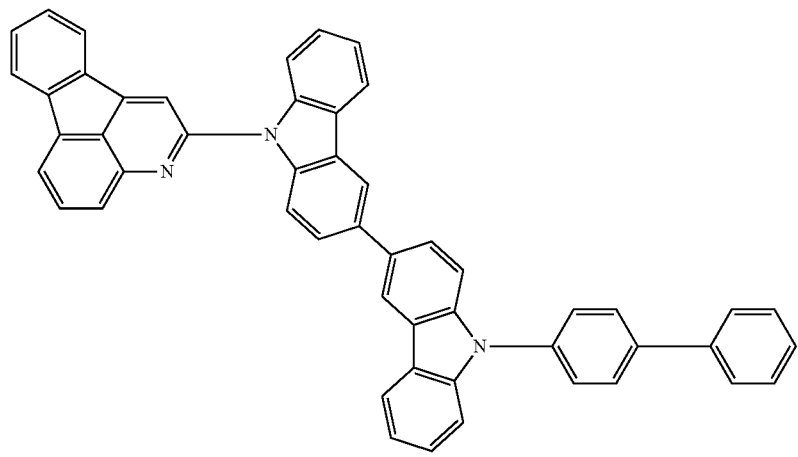
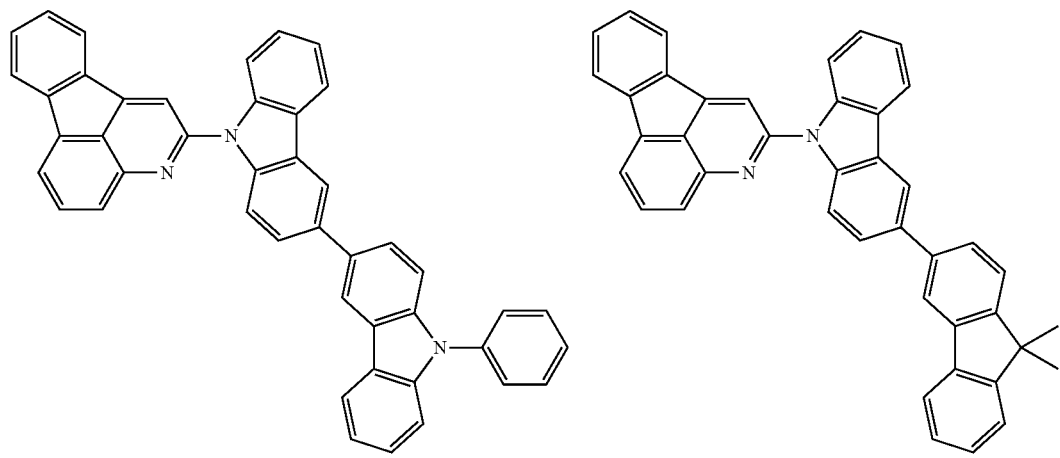
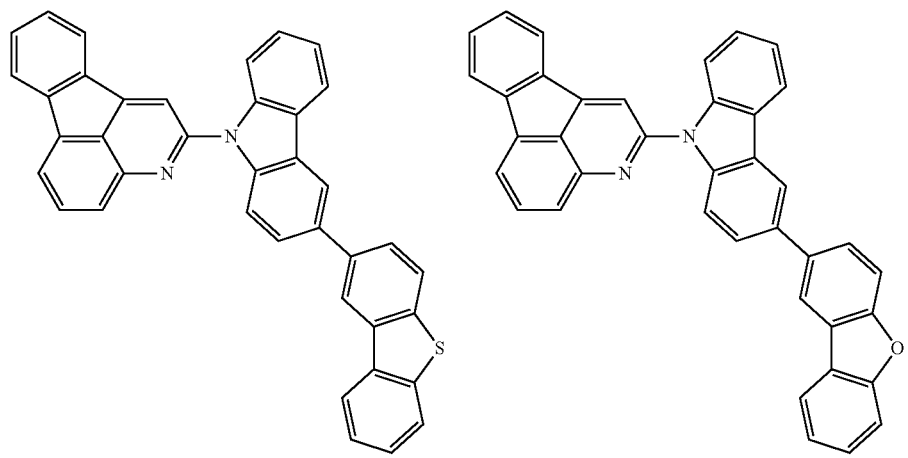

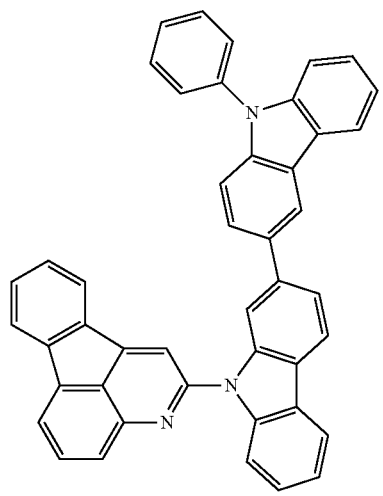
[Chem. 49]
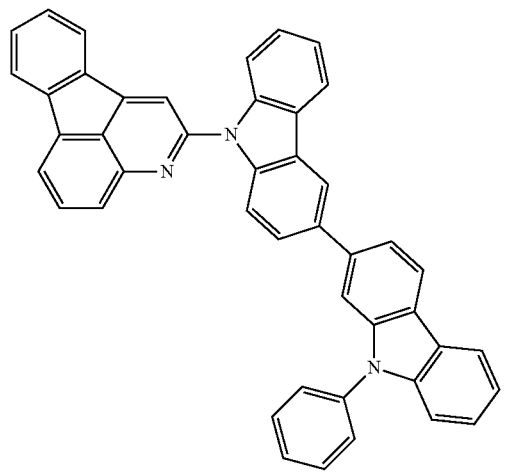
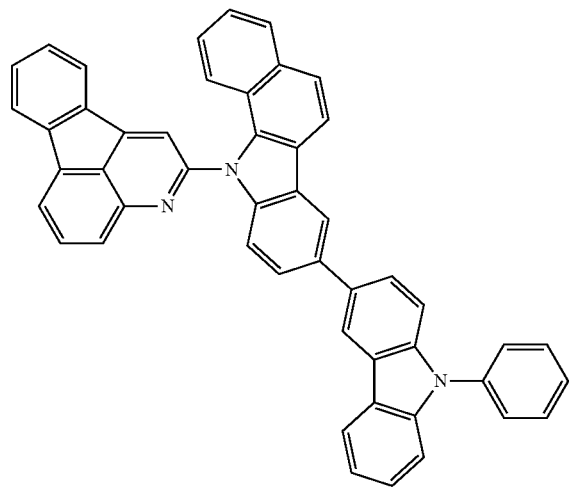
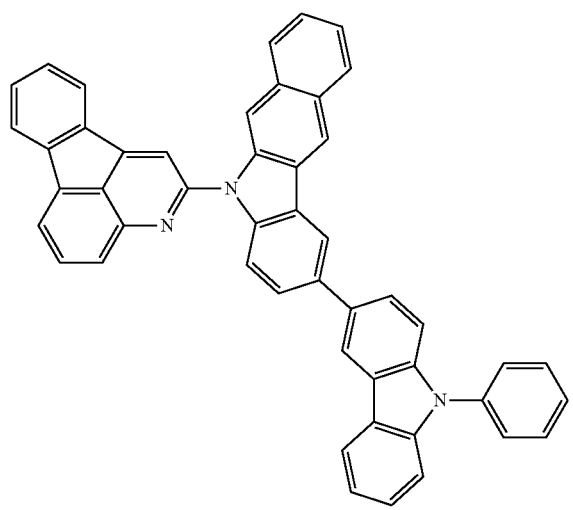
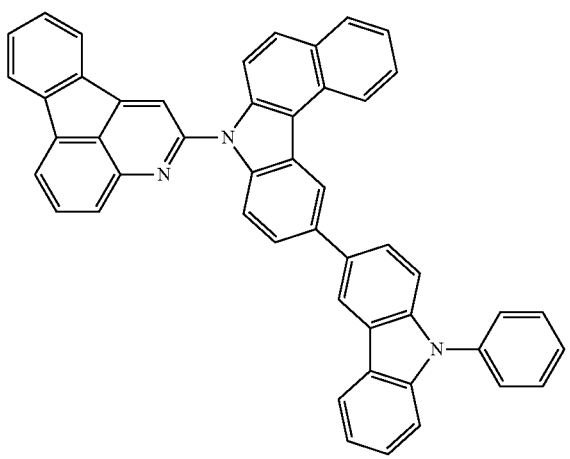

-continued
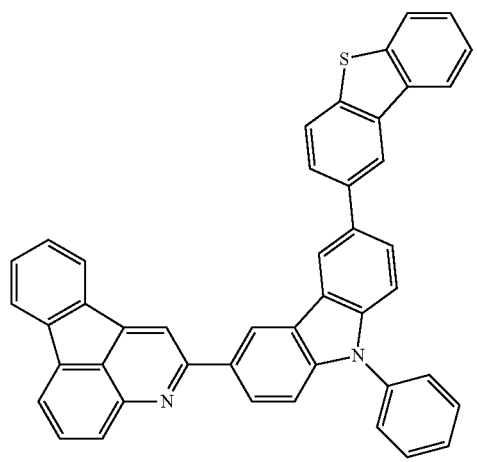
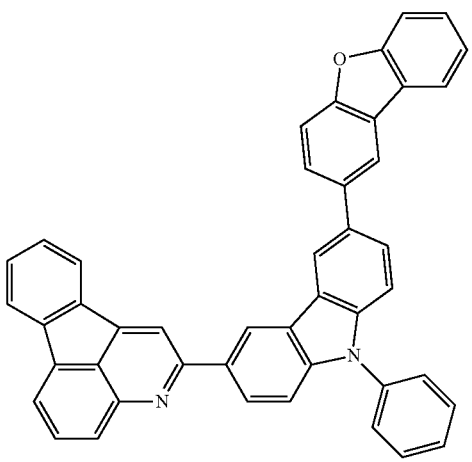
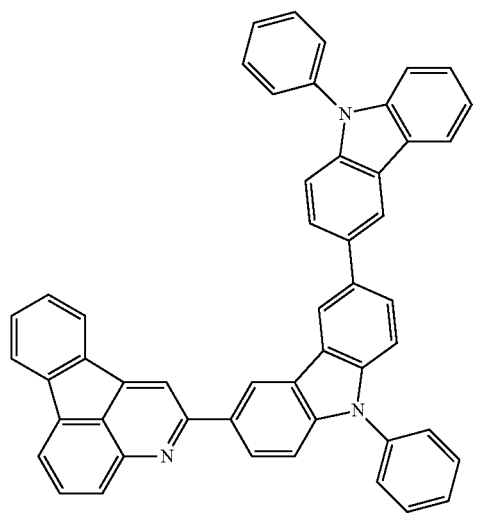
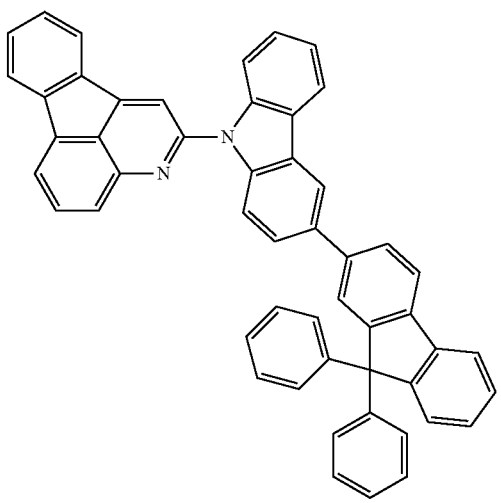
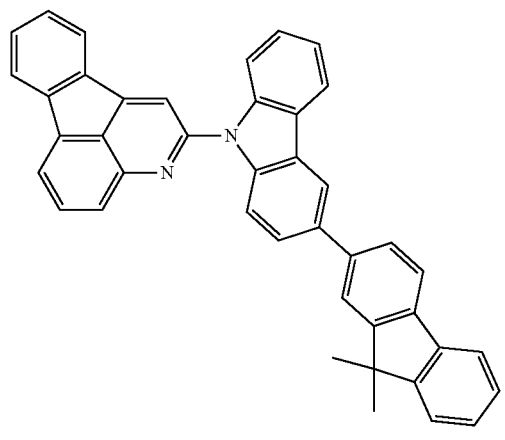
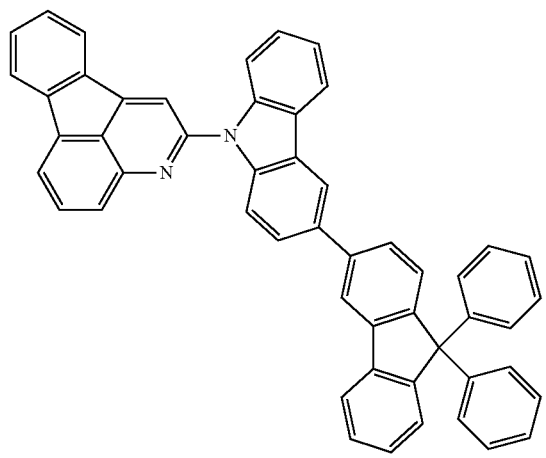

-continued
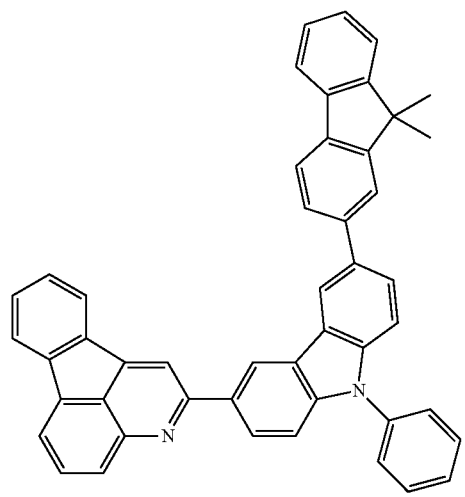
[Chem. 50]
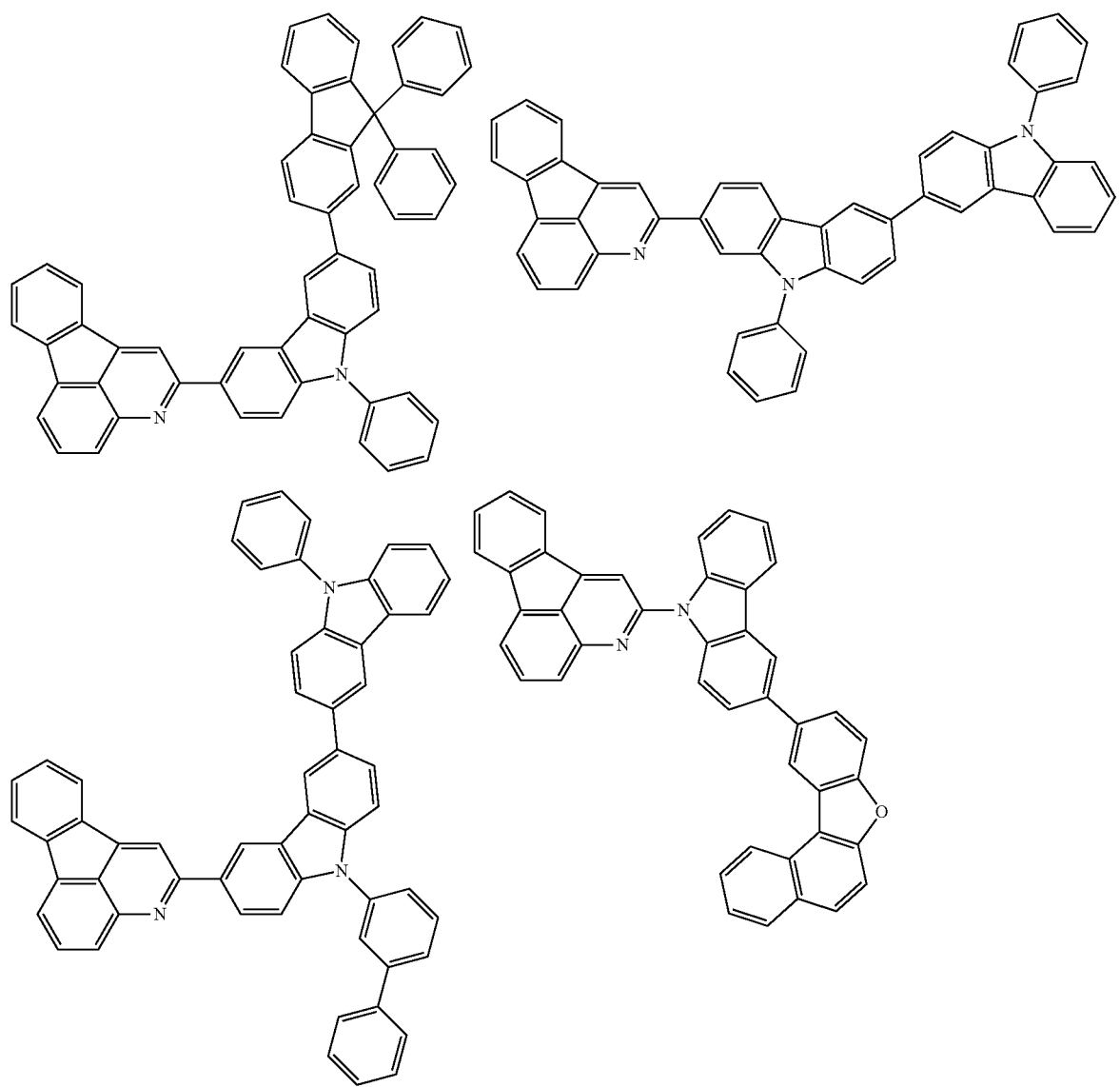

-continued
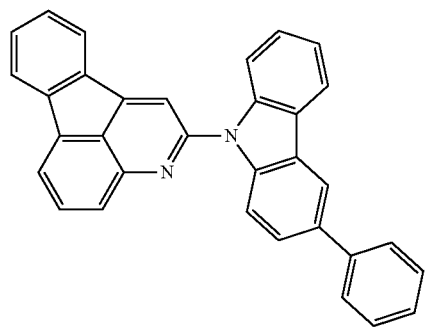
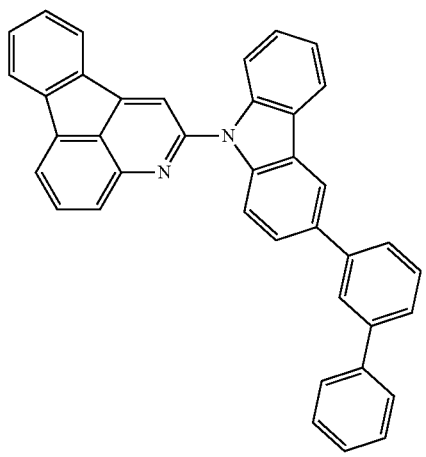
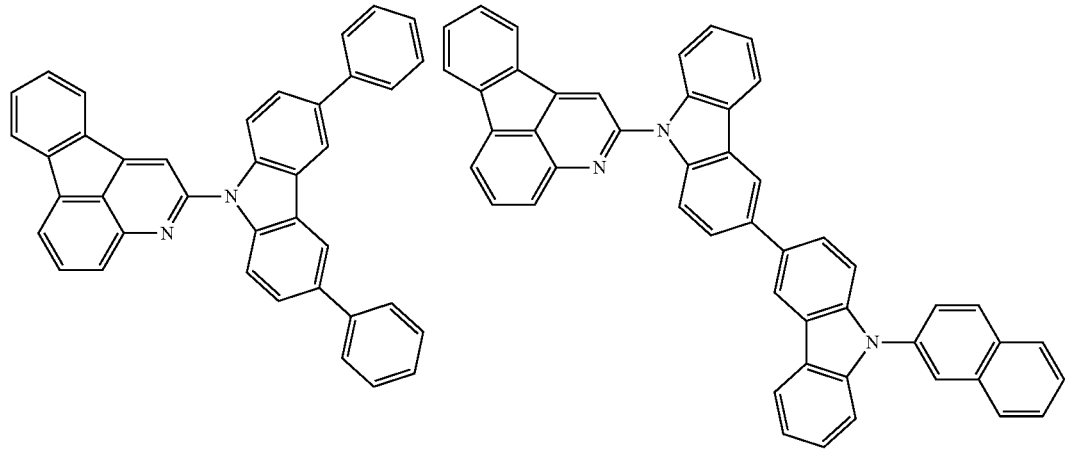
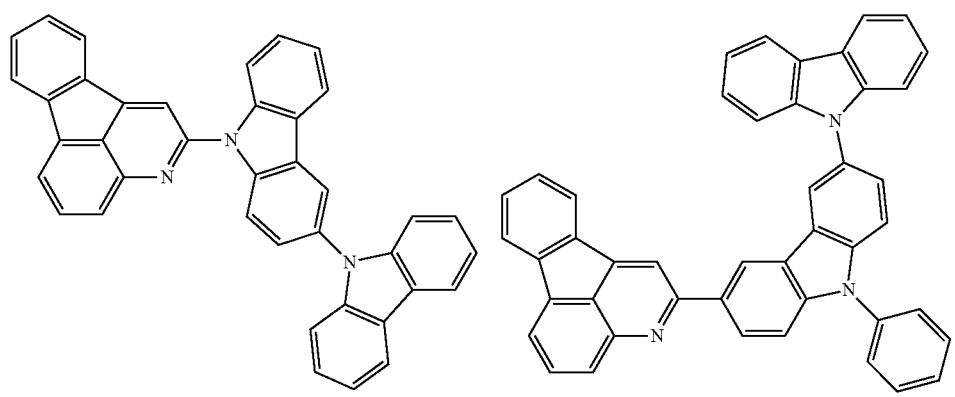

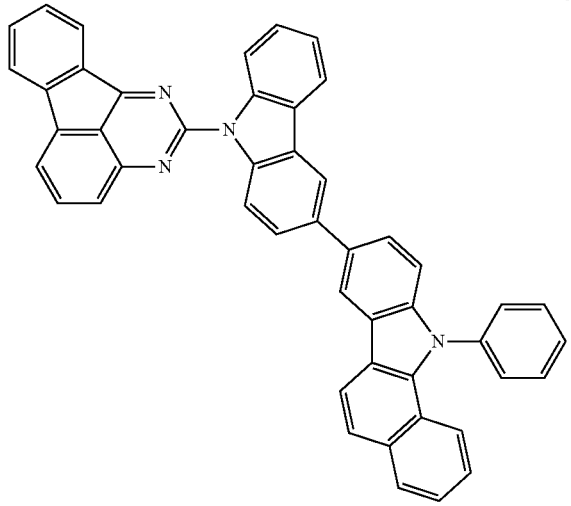
[Chem. 51]
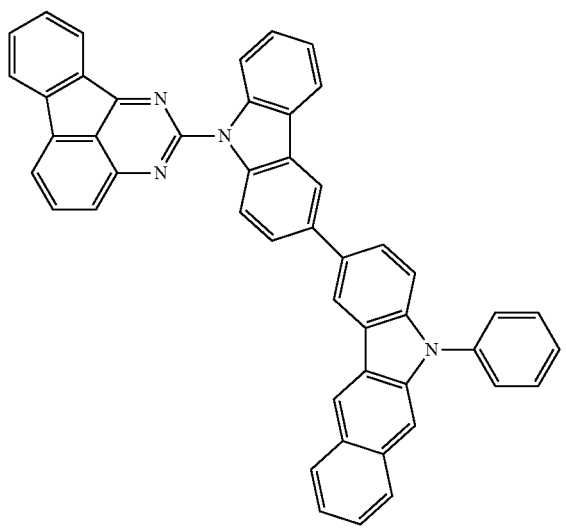
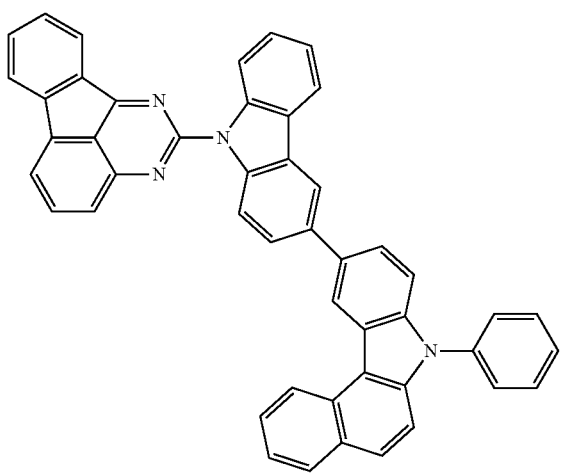
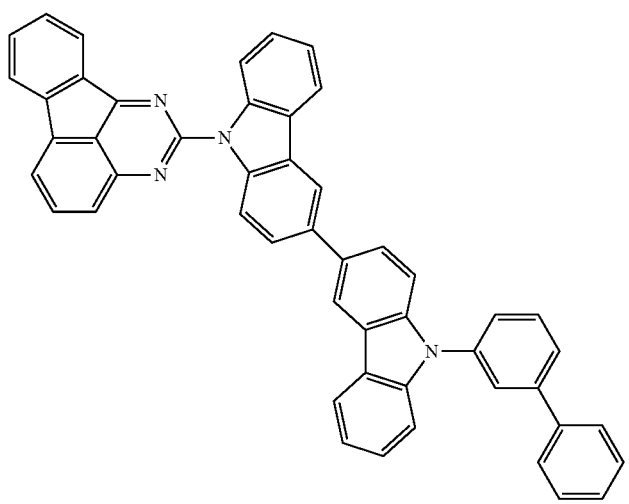

-continued
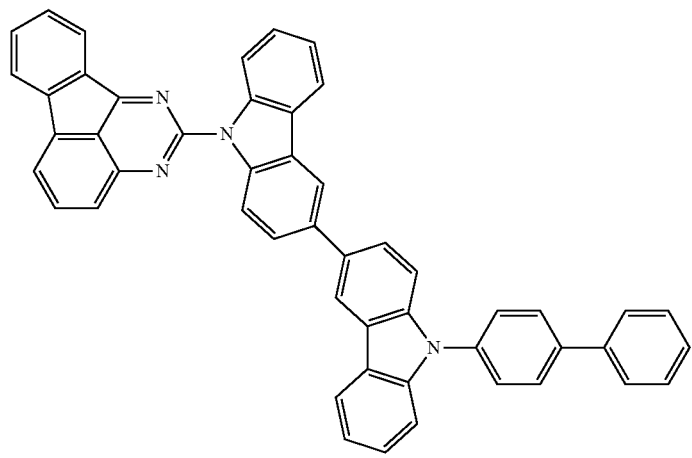
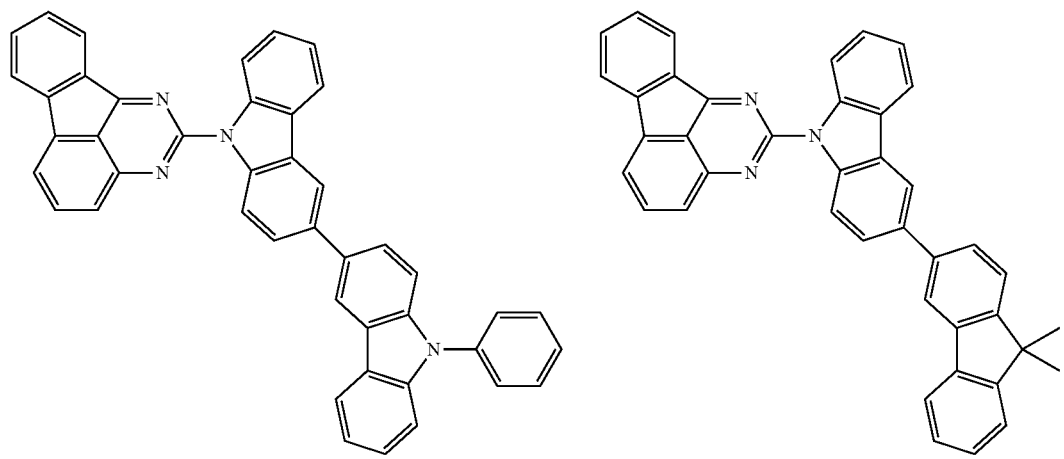
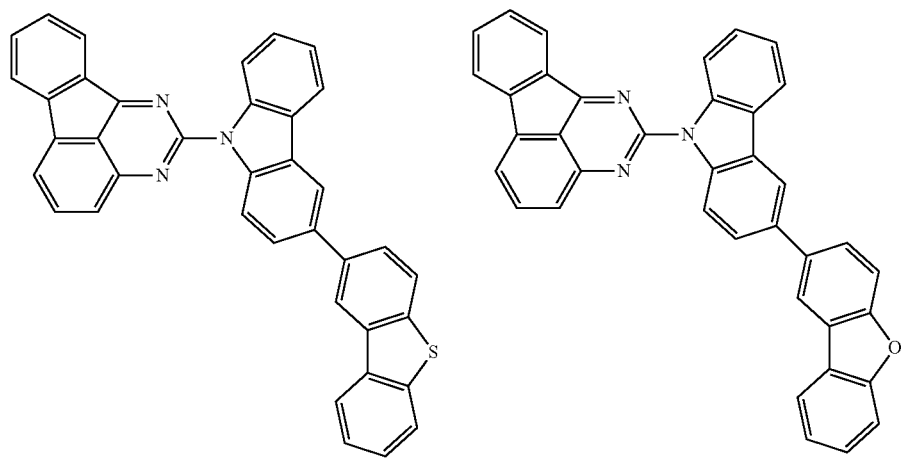

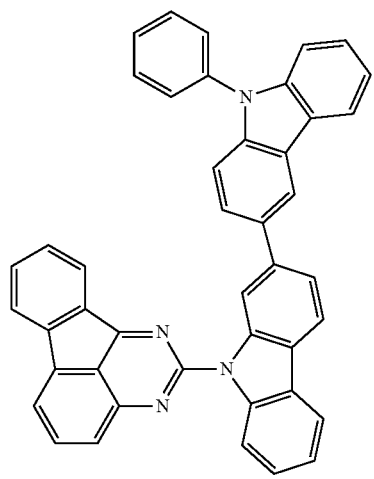
[Chem. 52]
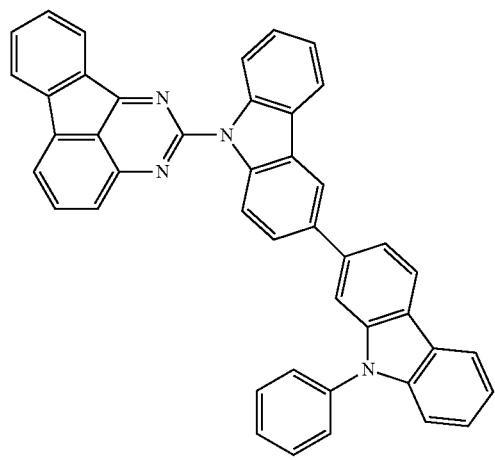
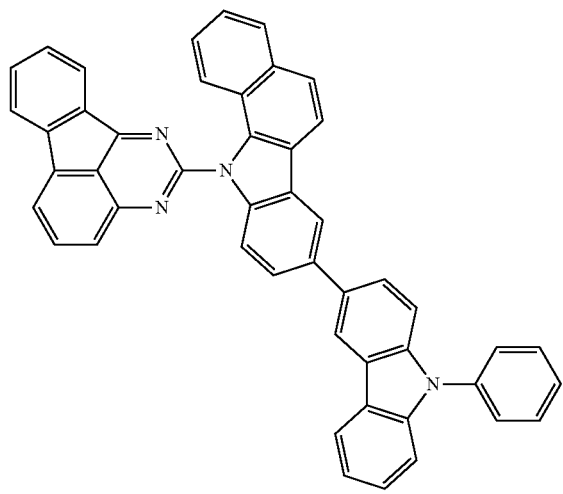
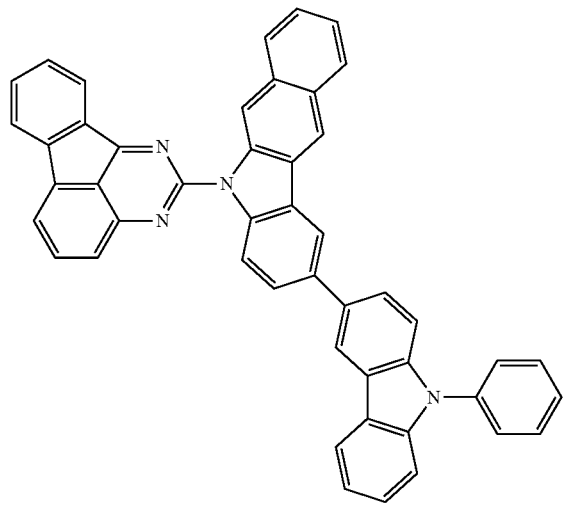
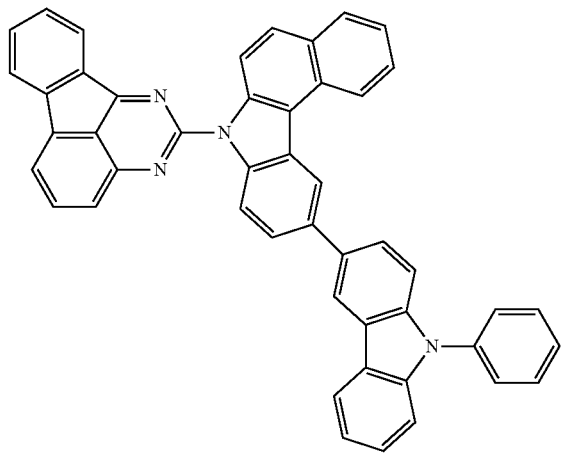

-continued
175
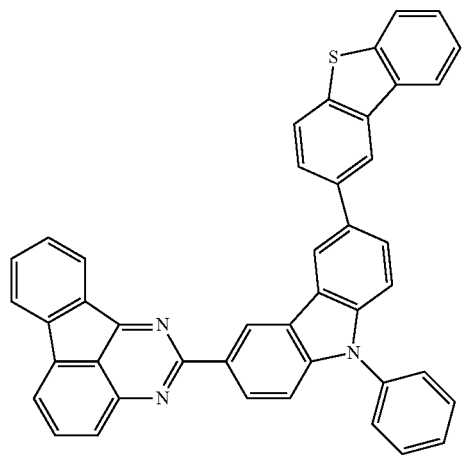
176
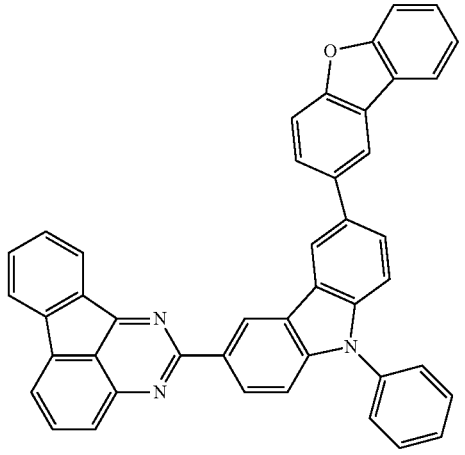
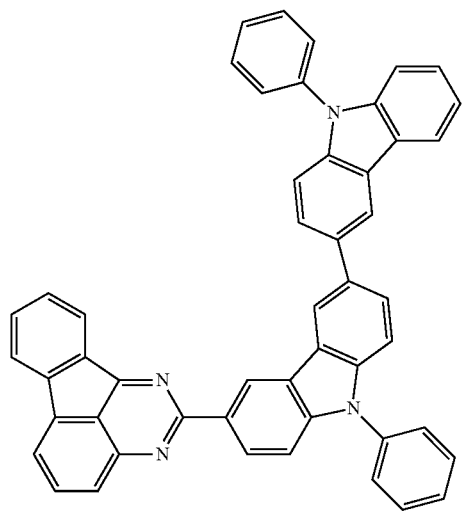
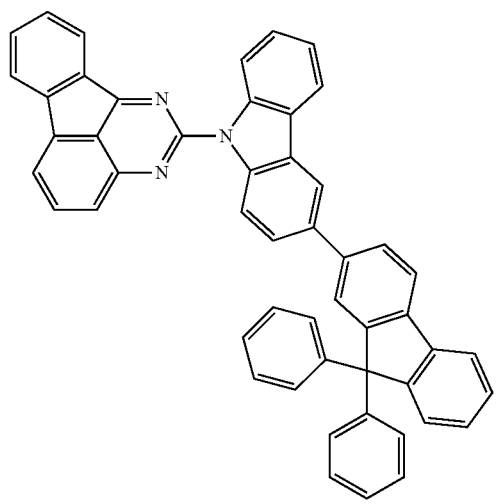
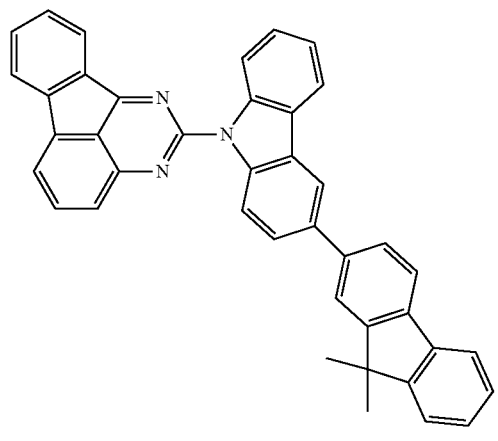
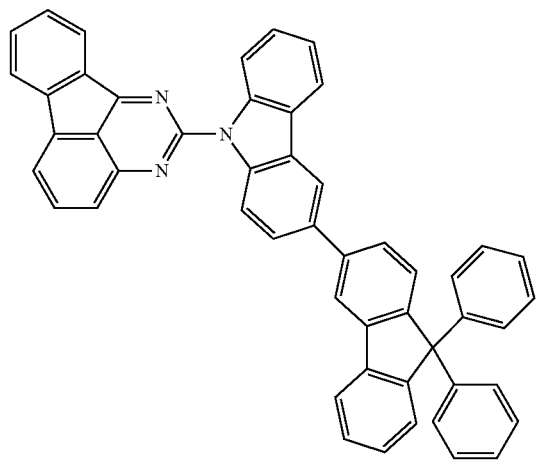

-continued
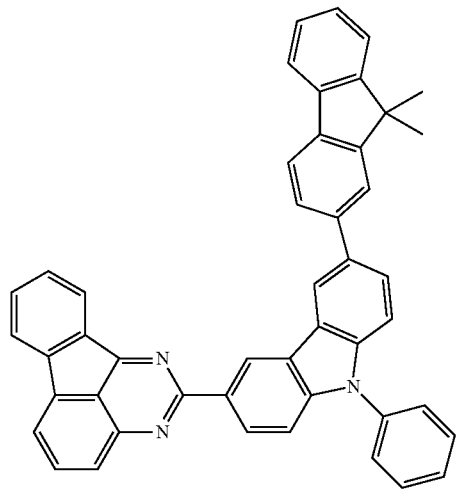
[Chem. 53]
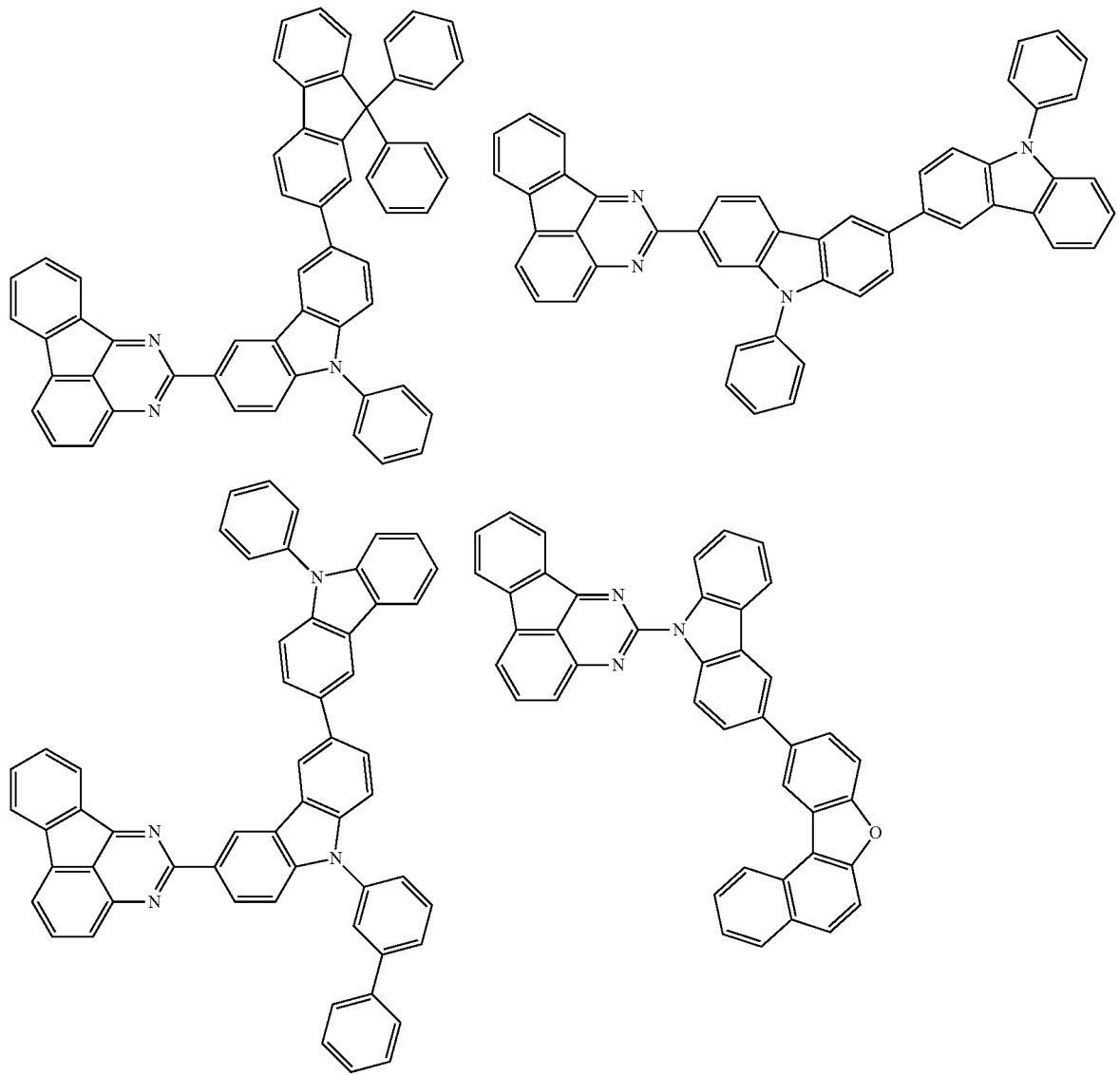

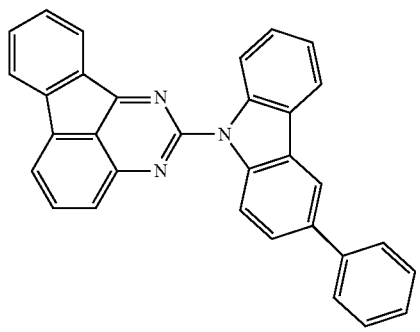
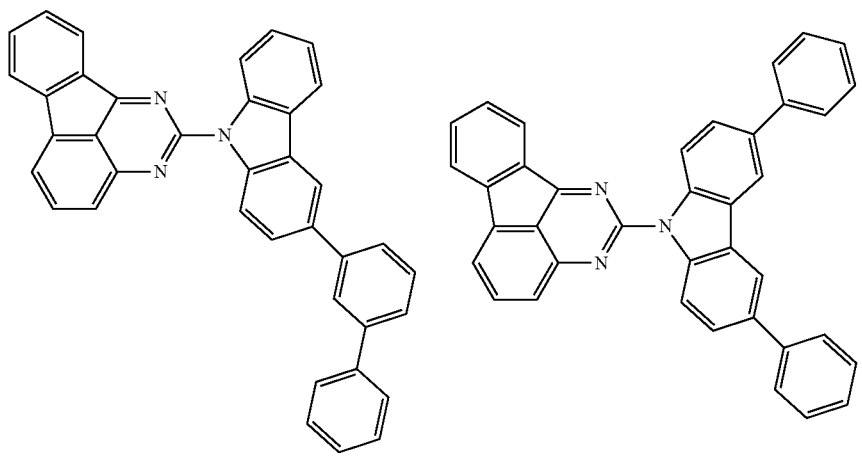
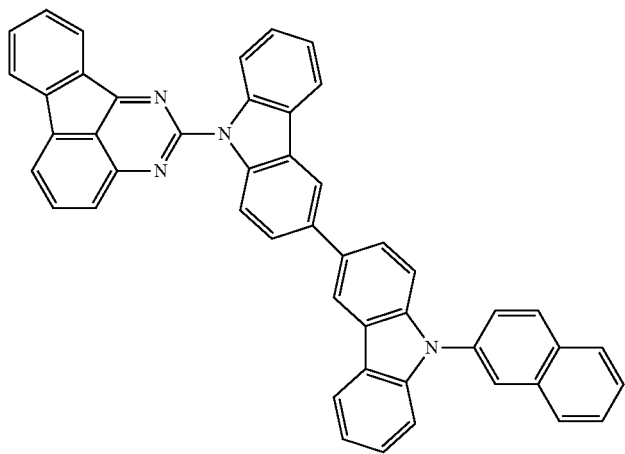
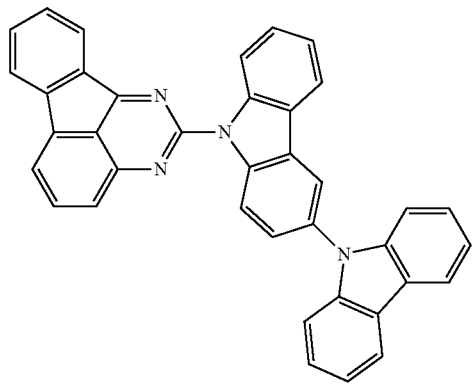

-continued
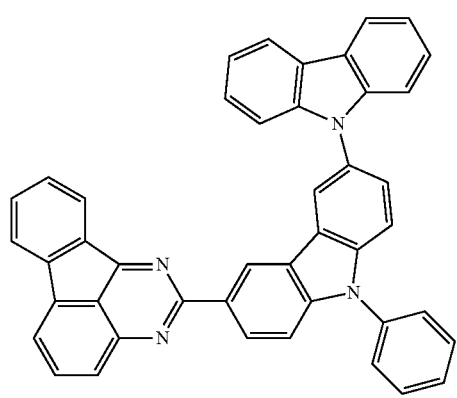
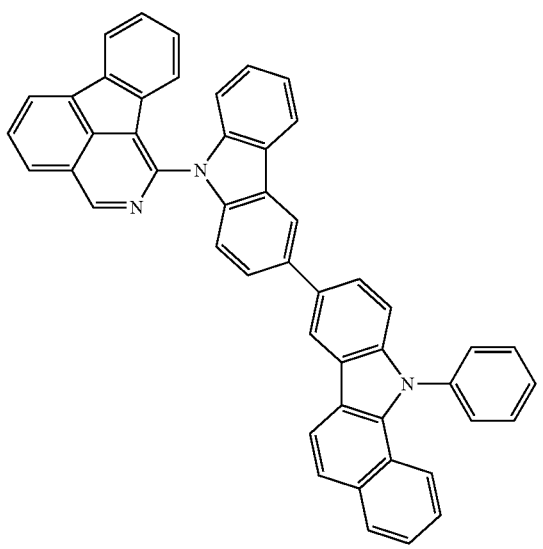
[Chem. 54]
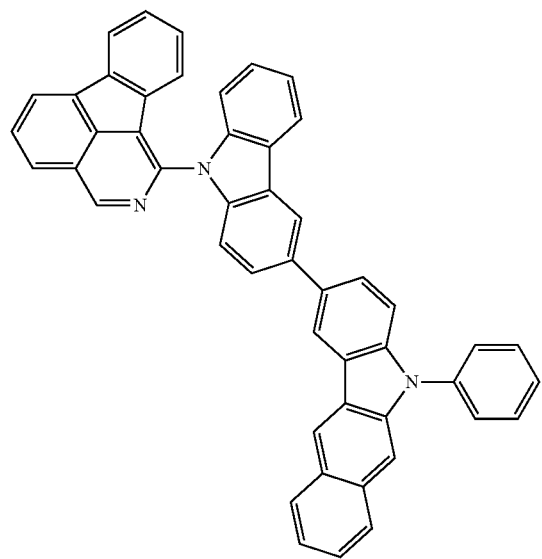
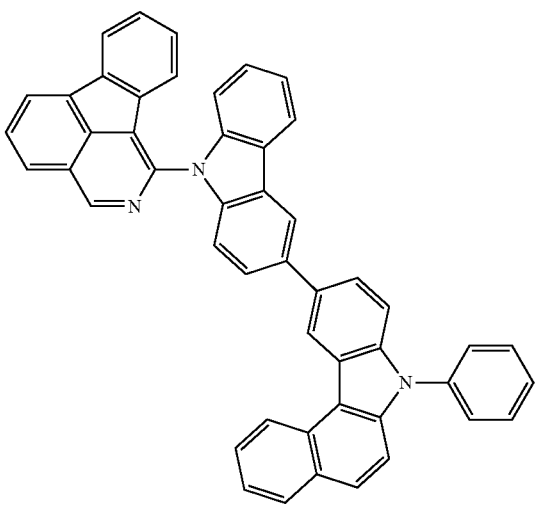
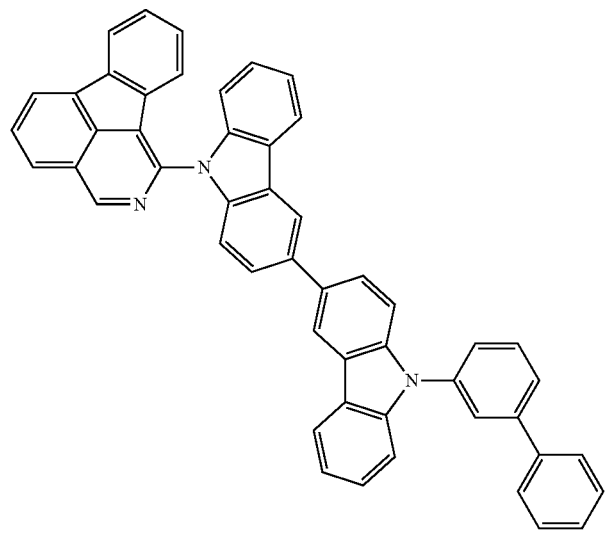

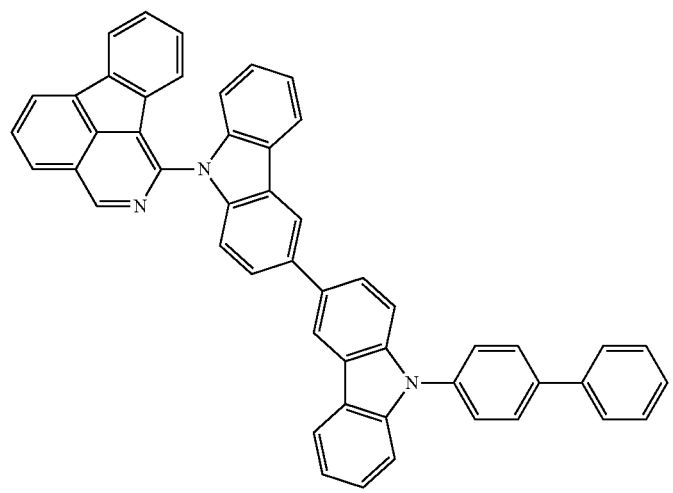
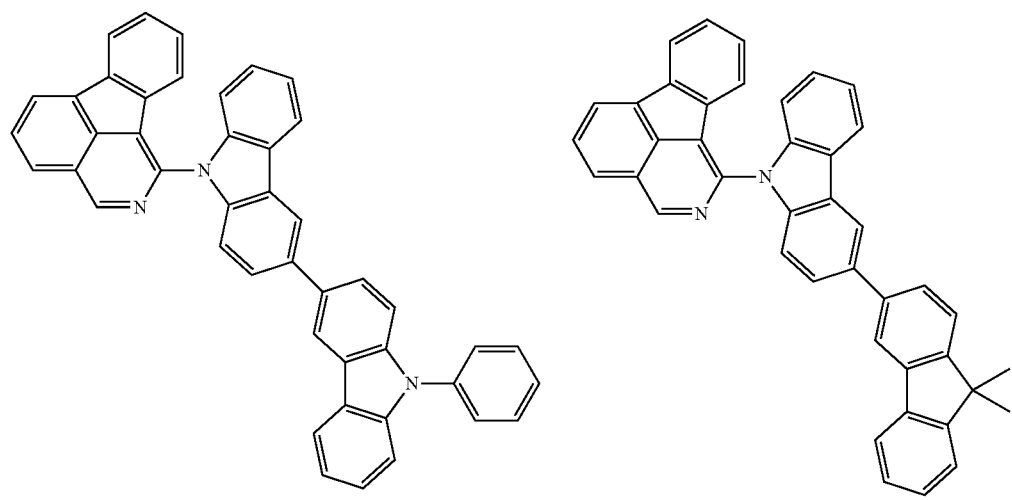
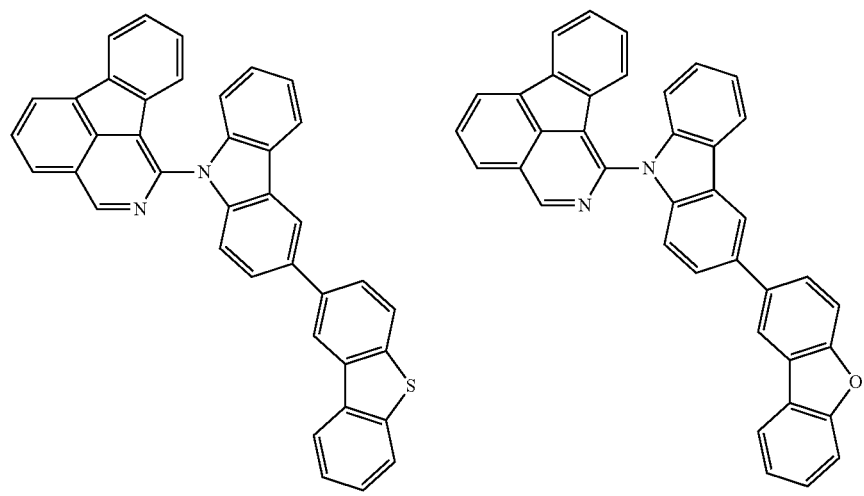

-continued
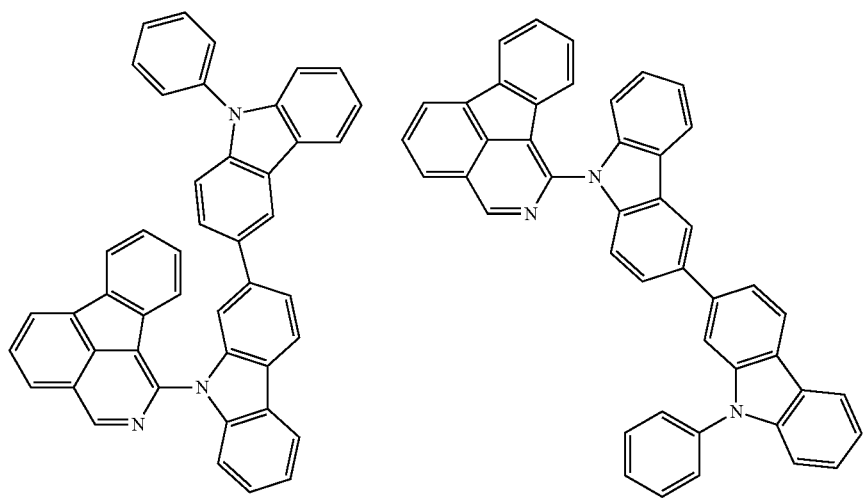
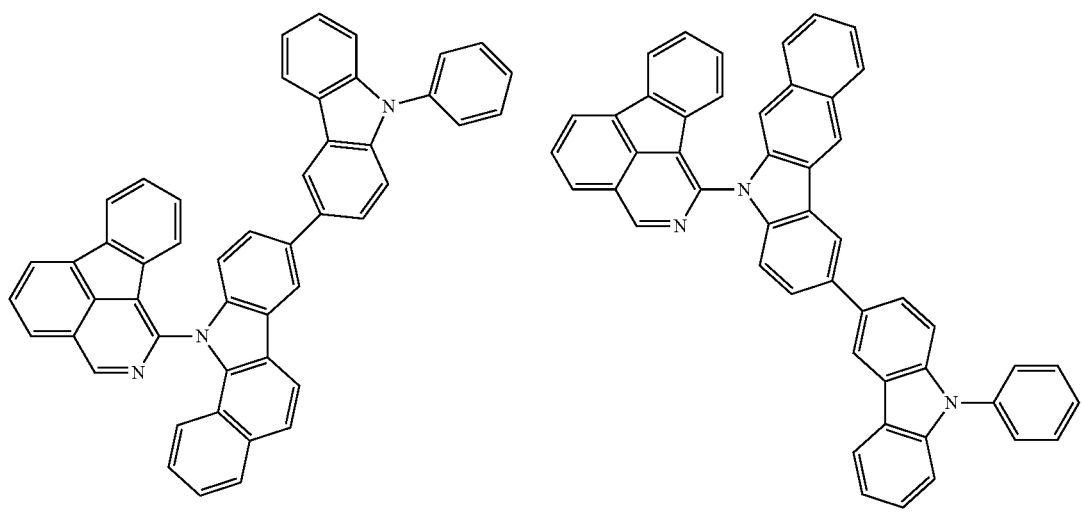
[Chem. 55]
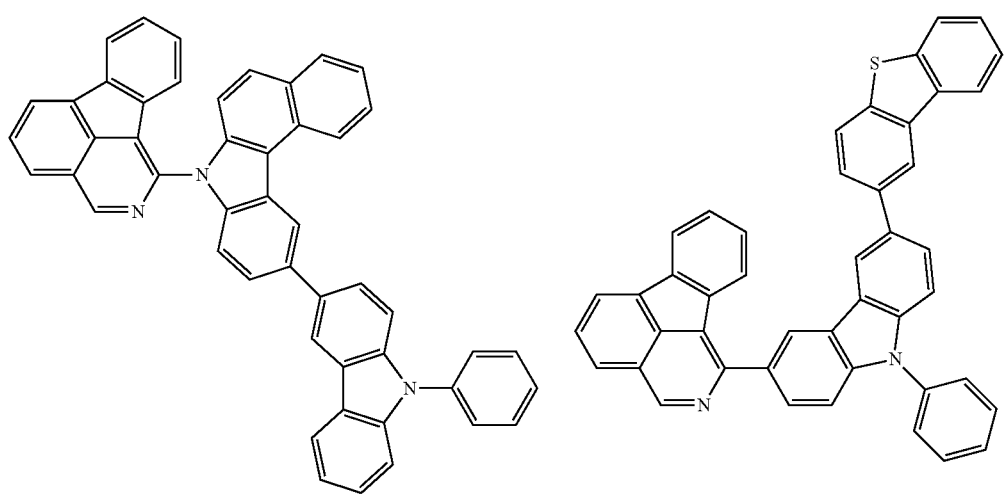

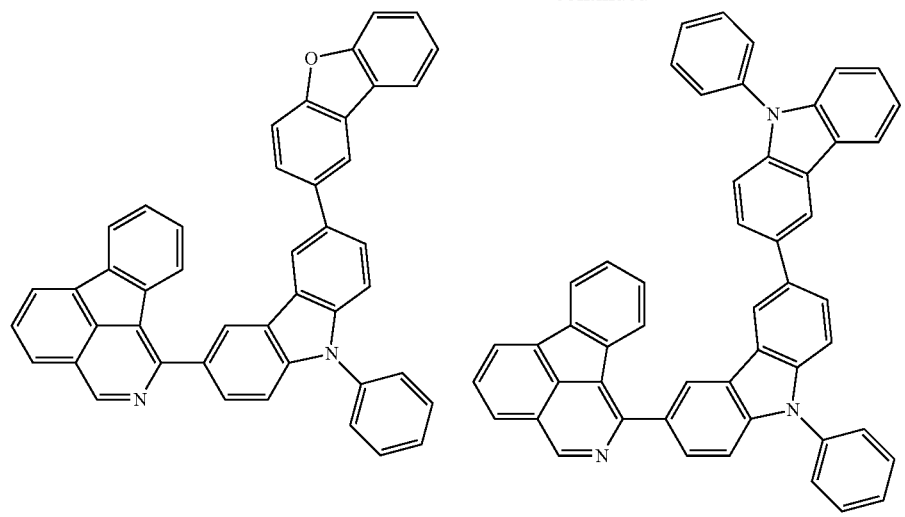
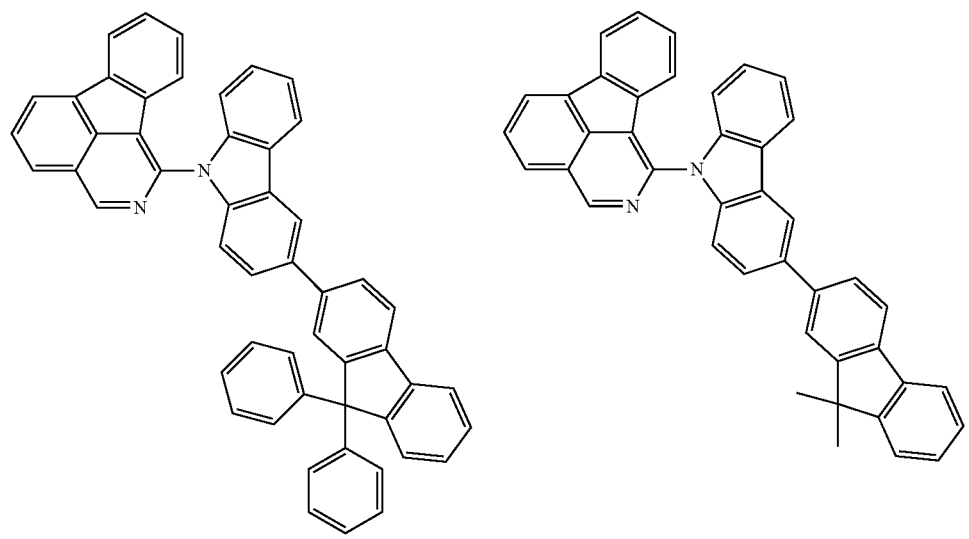
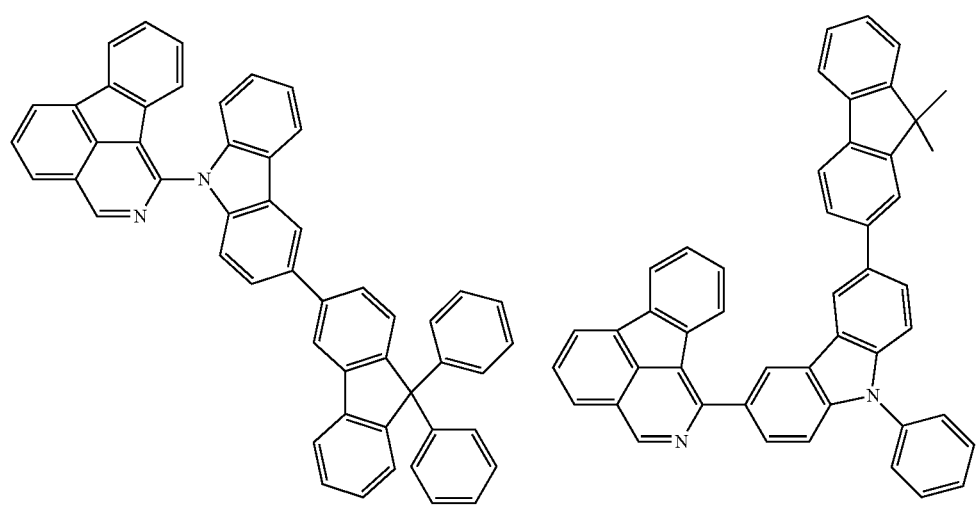

189                                              190
-continued
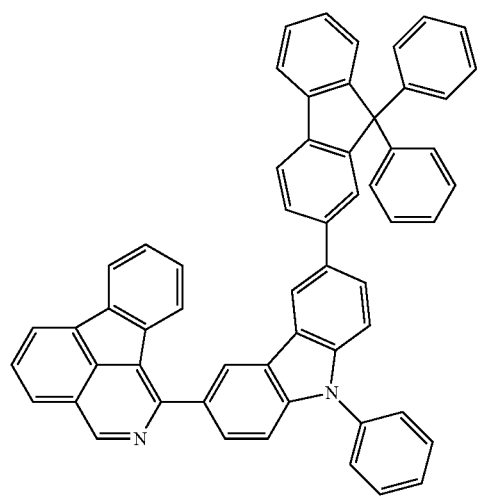
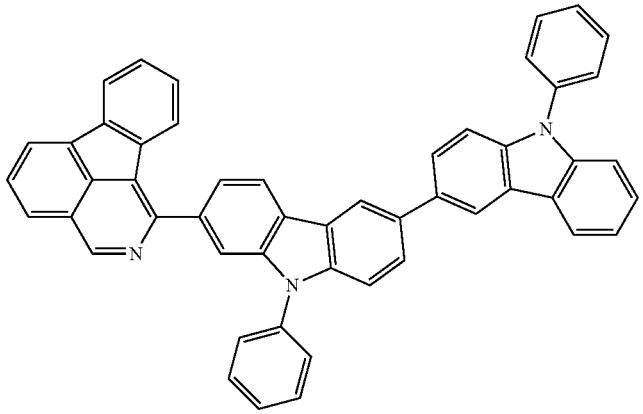
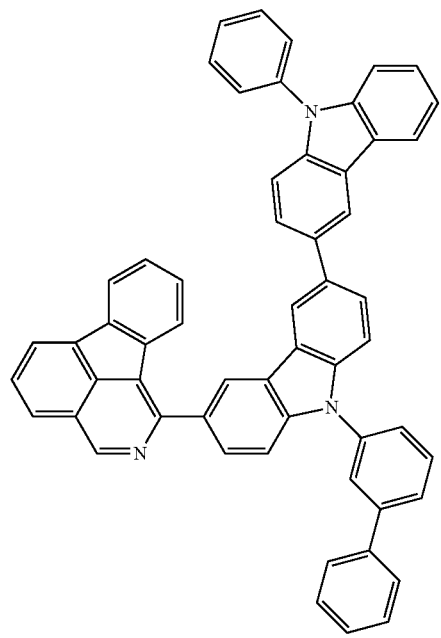
[Chem. 56]
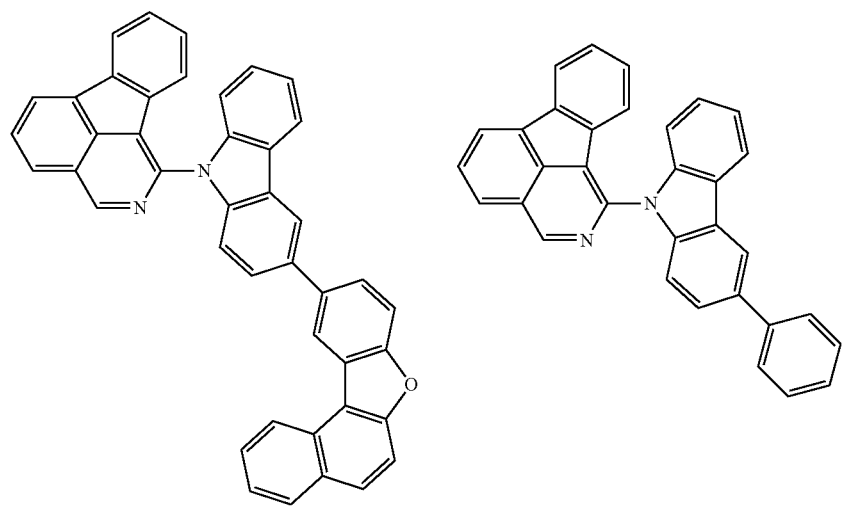

191
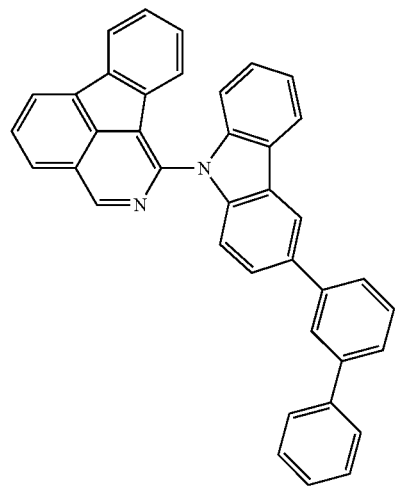
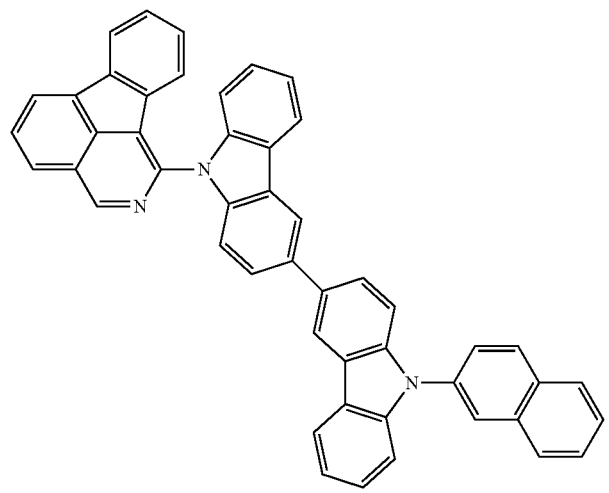
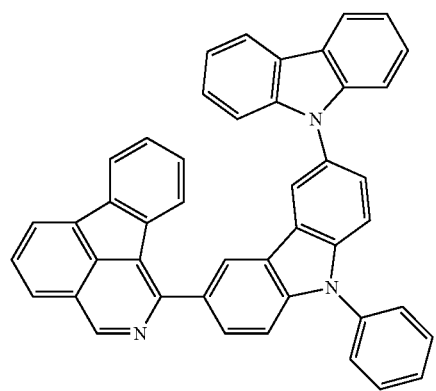
192
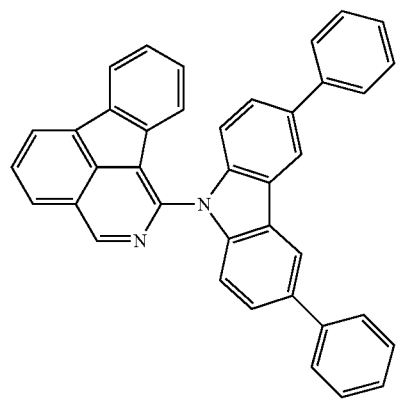
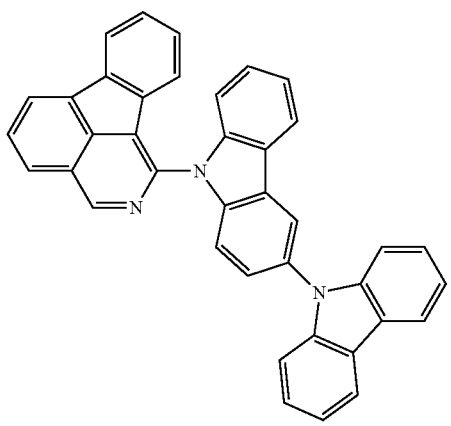
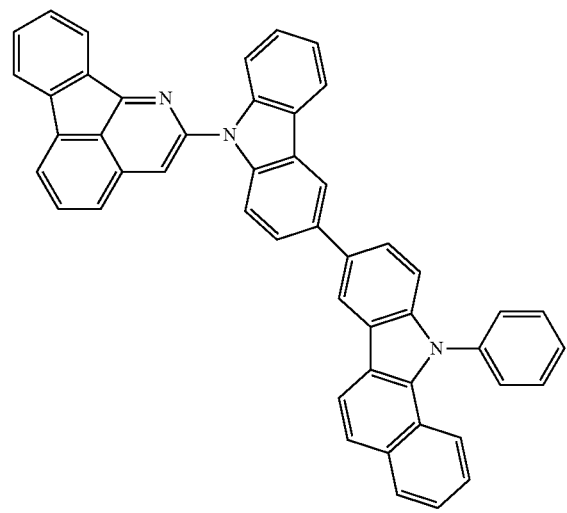

193
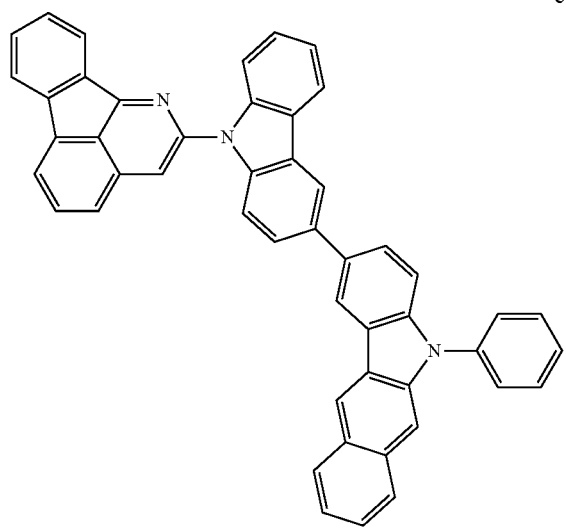
194
-continued
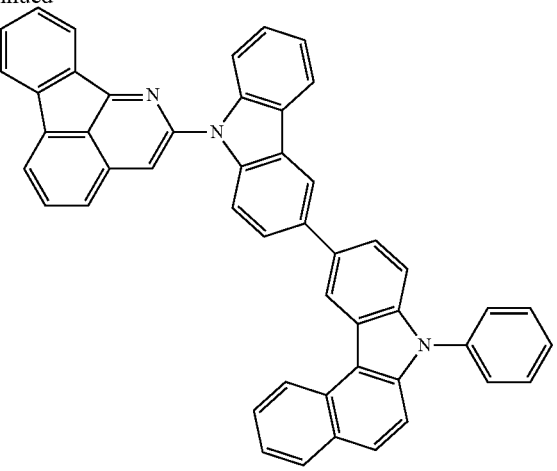
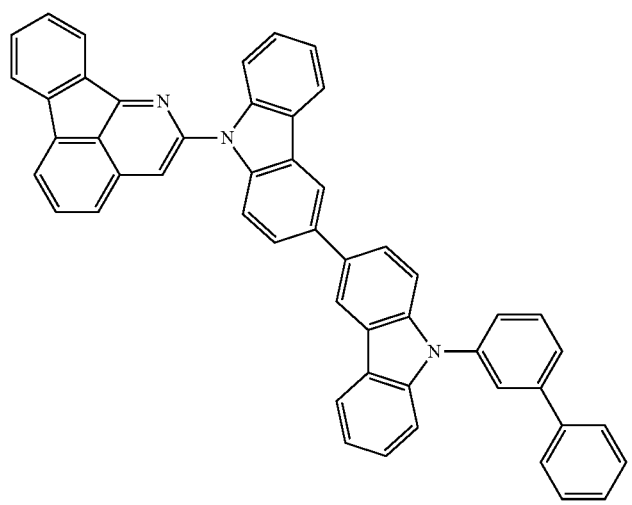
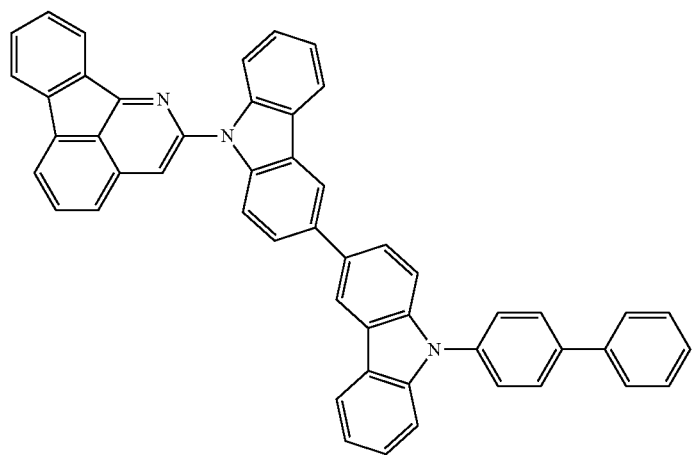

-continued
[Chem. 57]
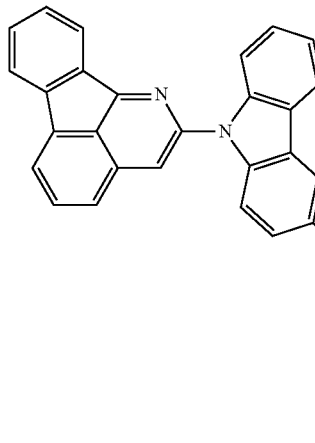
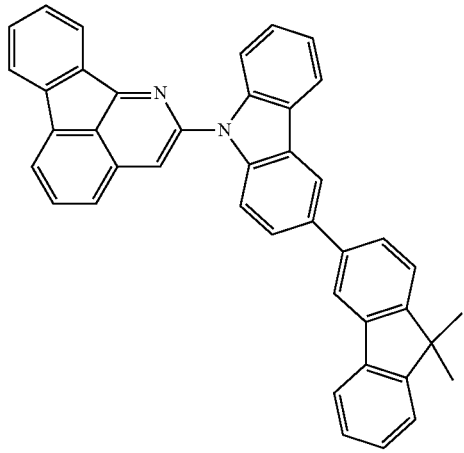
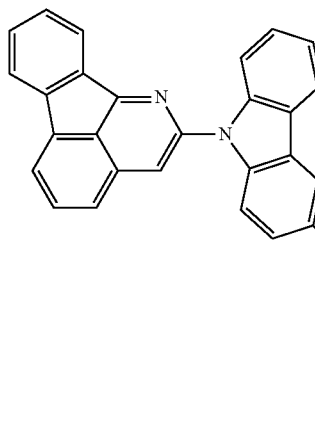
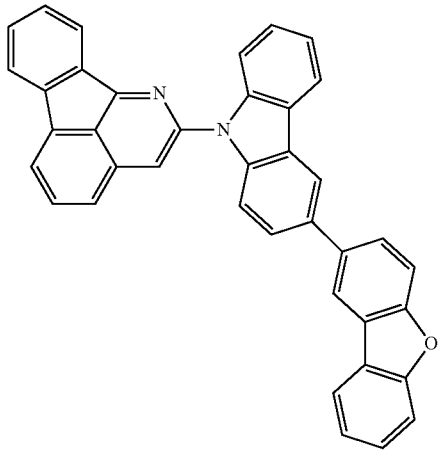
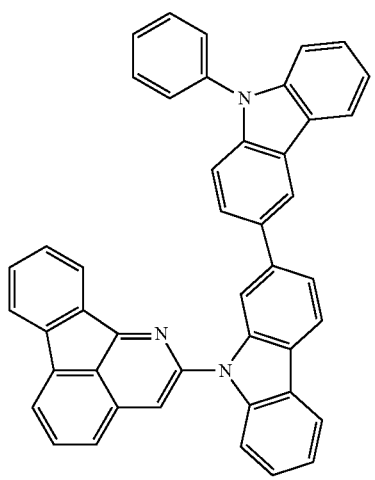
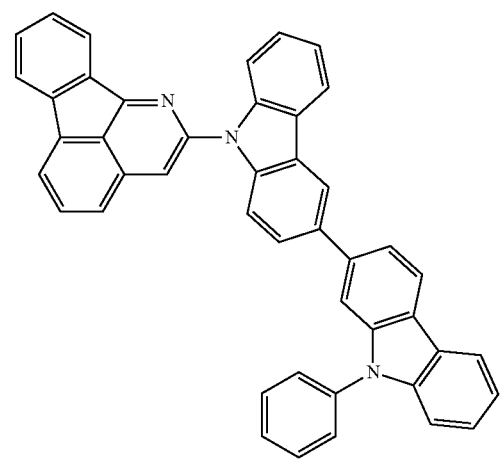

197
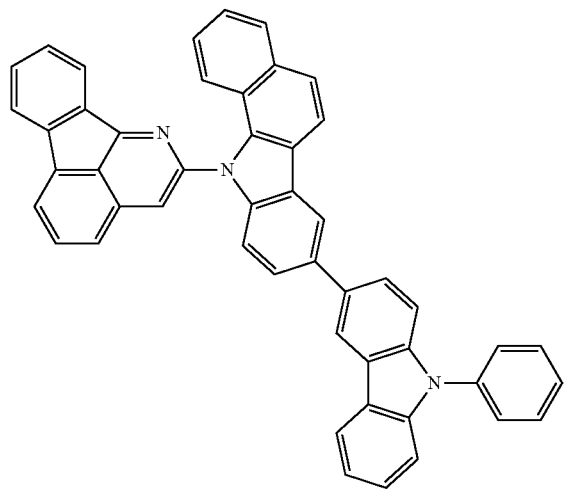
198
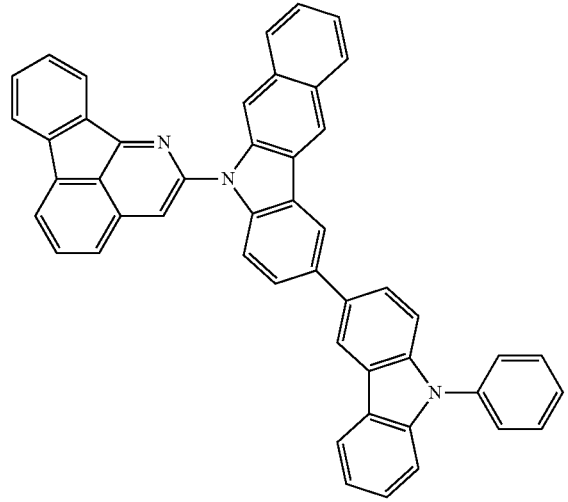
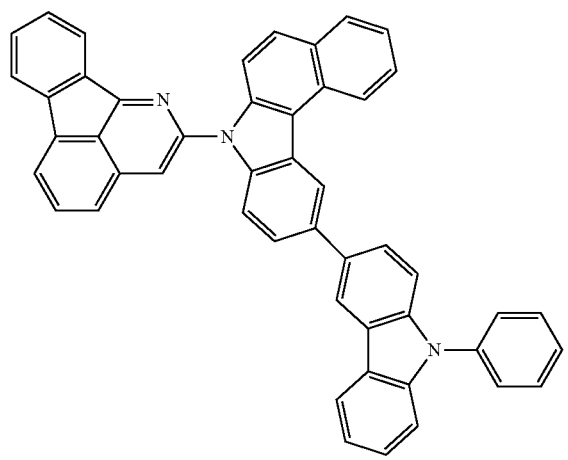
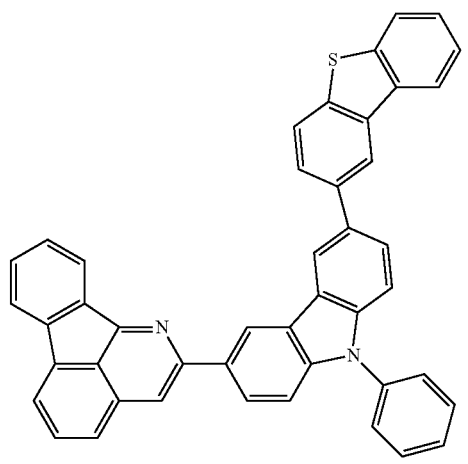
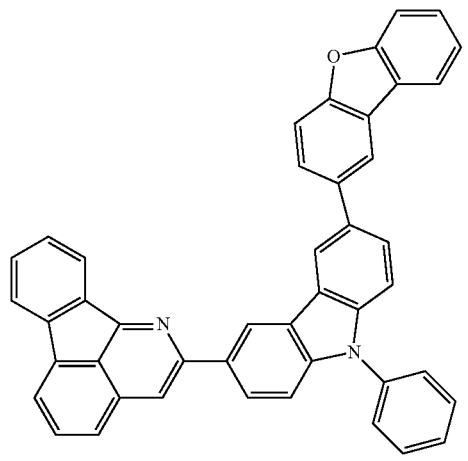
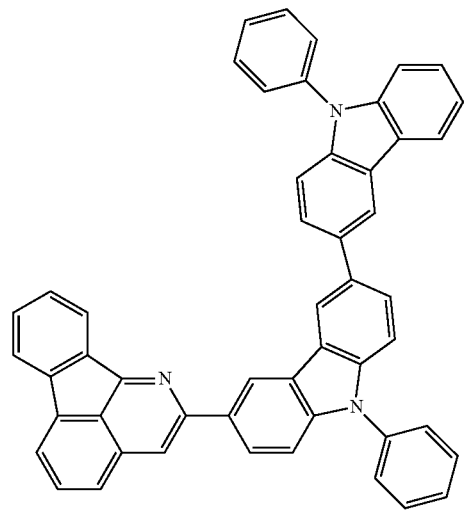

[Chem. 58]
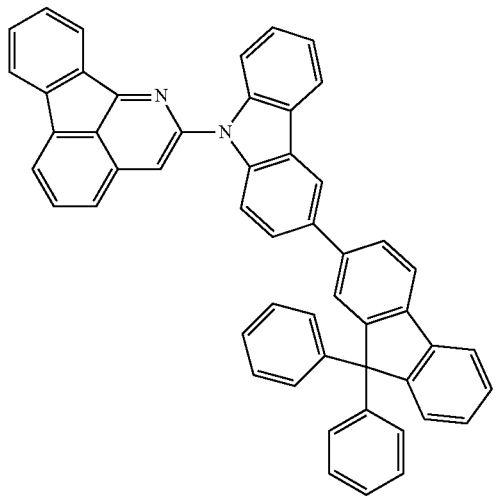
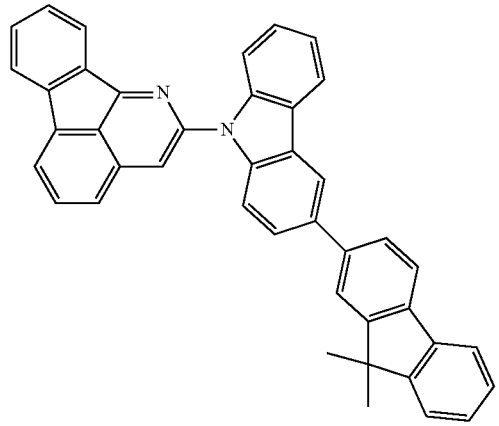
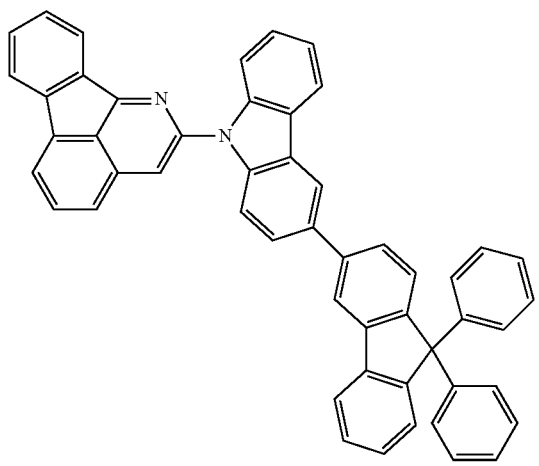
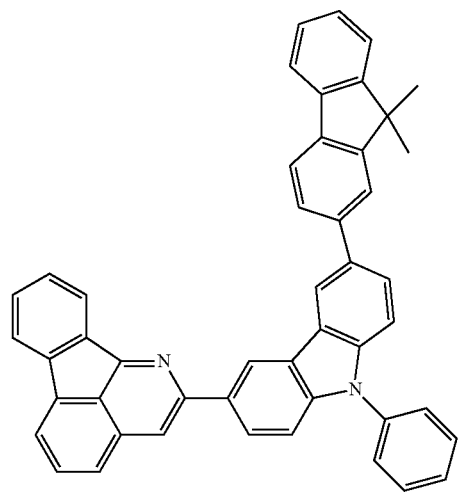
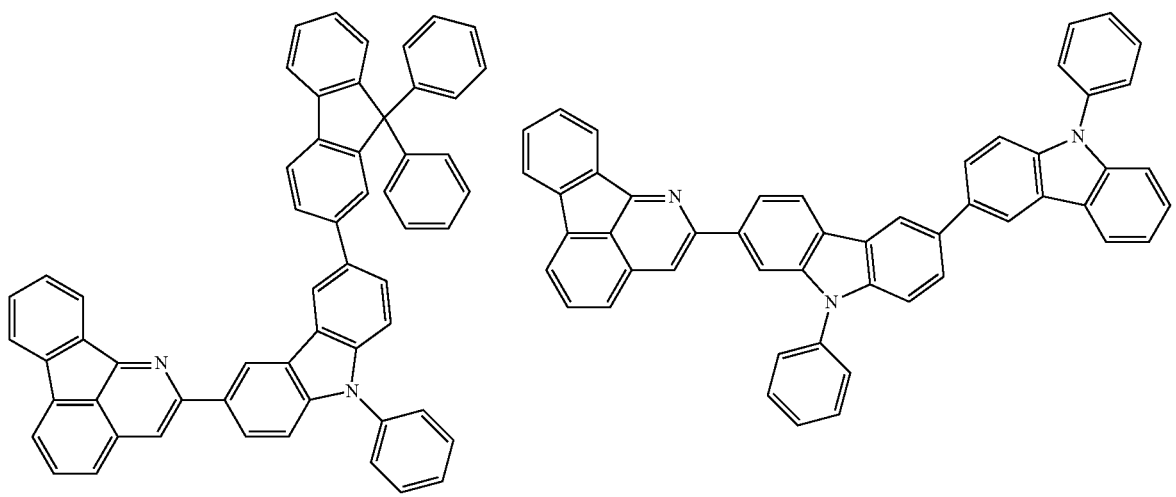

201
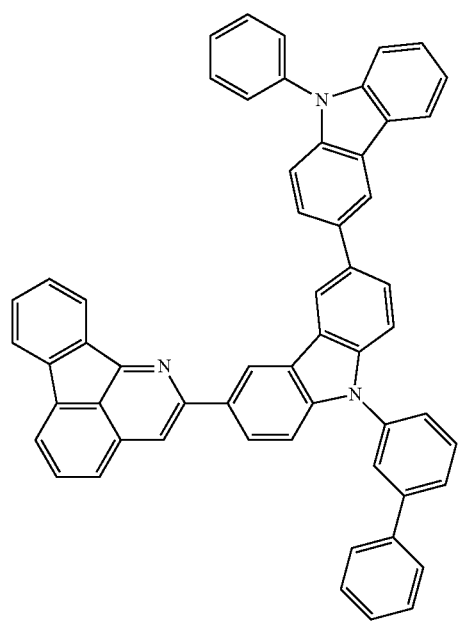
202
-continued
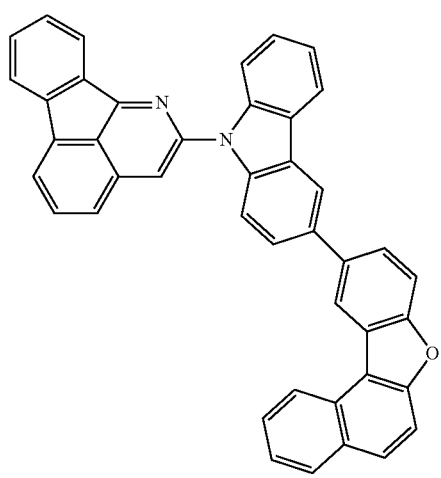
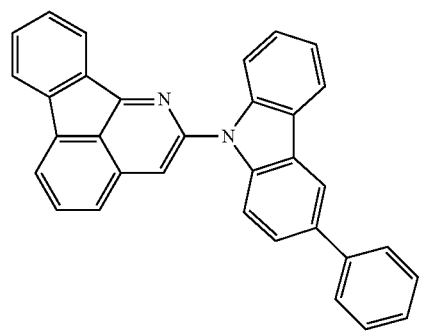
[Chem. 59]
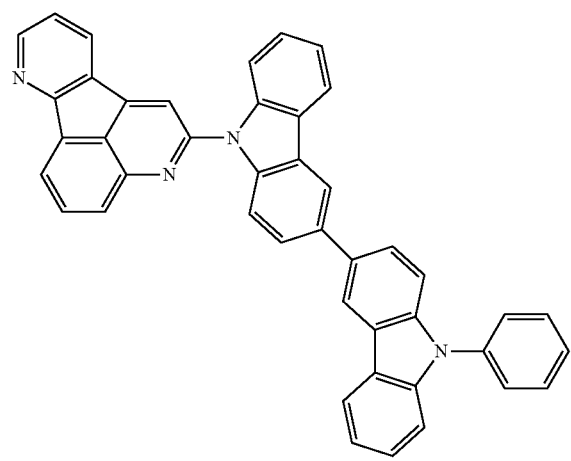
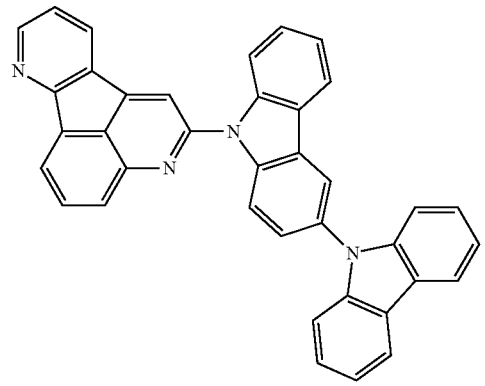

-continued
203
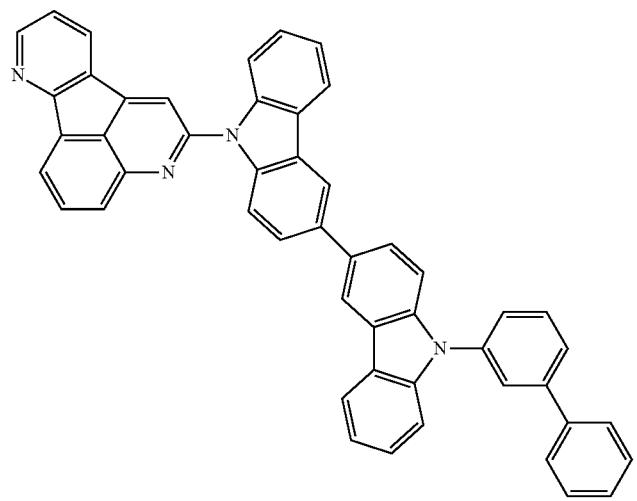
204
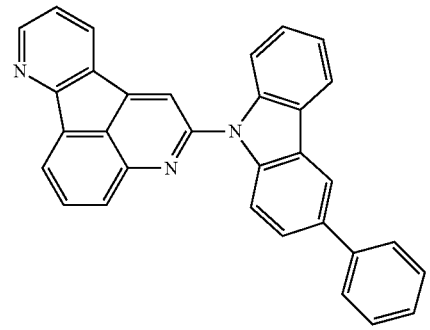
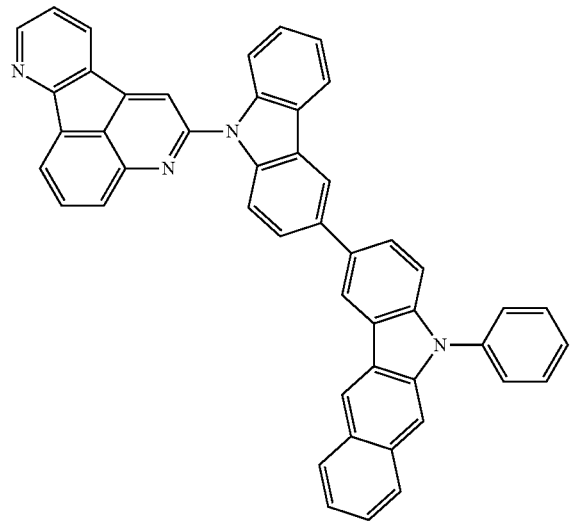
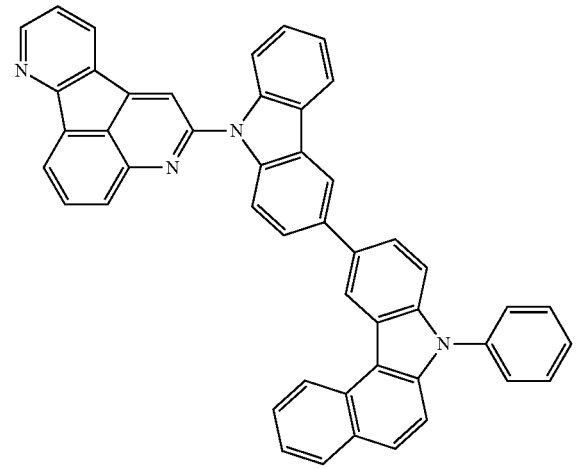
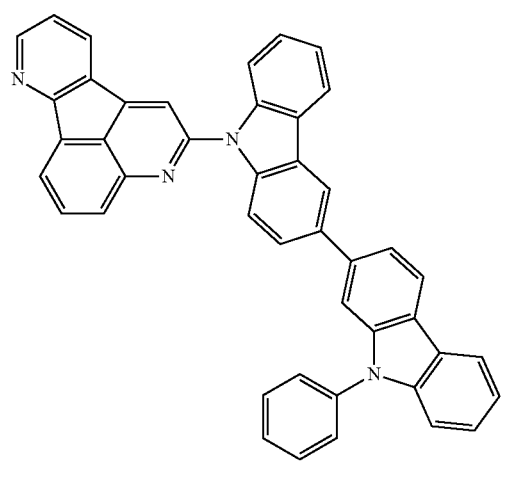
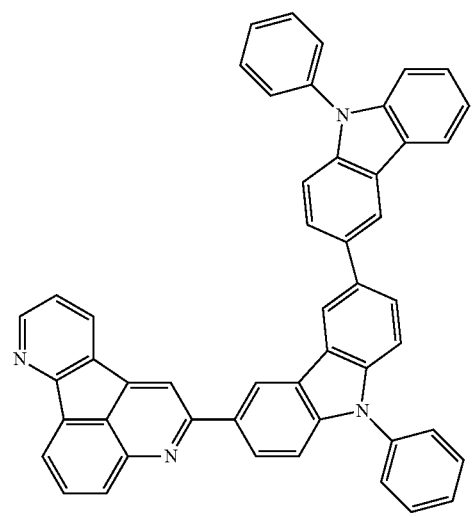

-continued
205
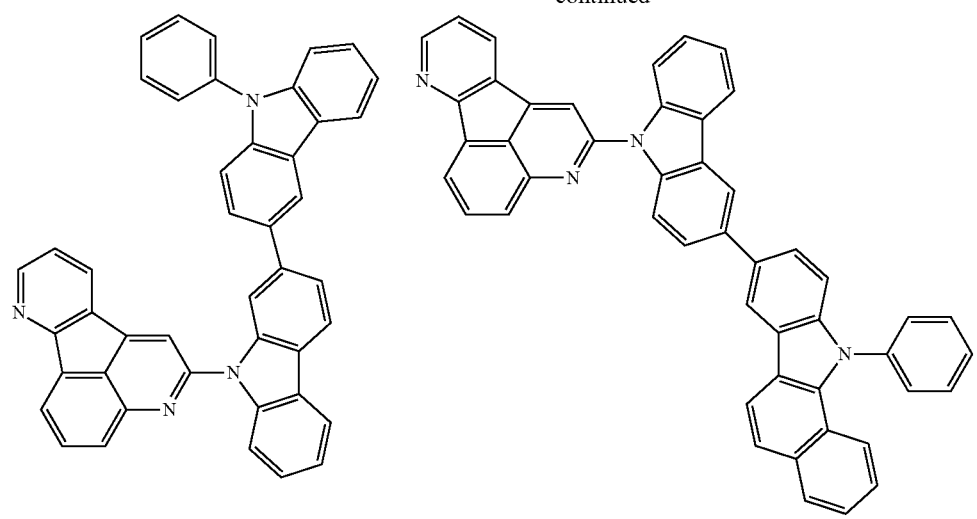
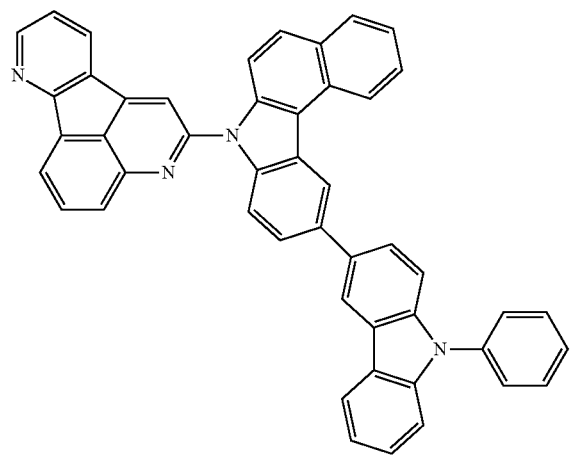
[Chem. 60]
206
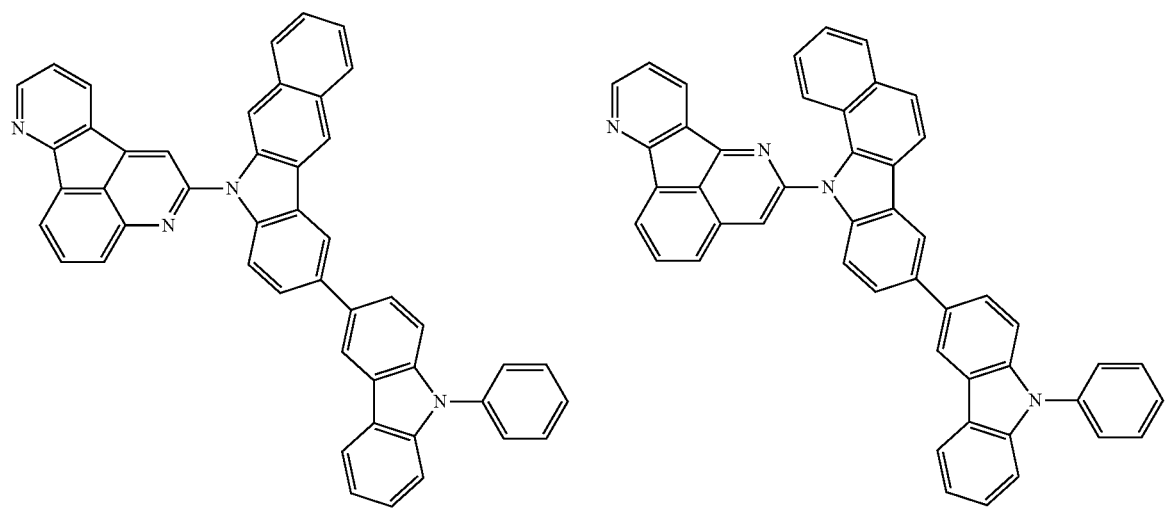

207 208
-continued
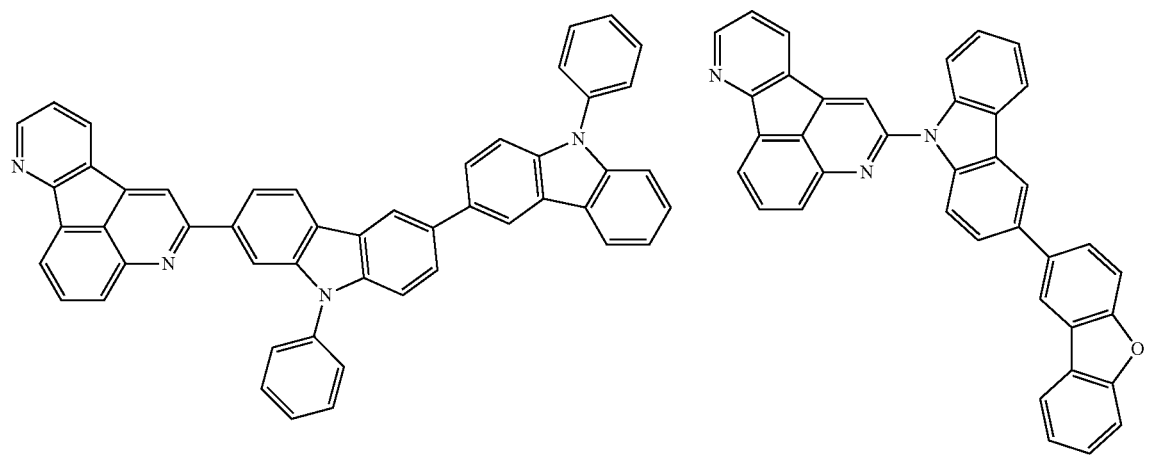
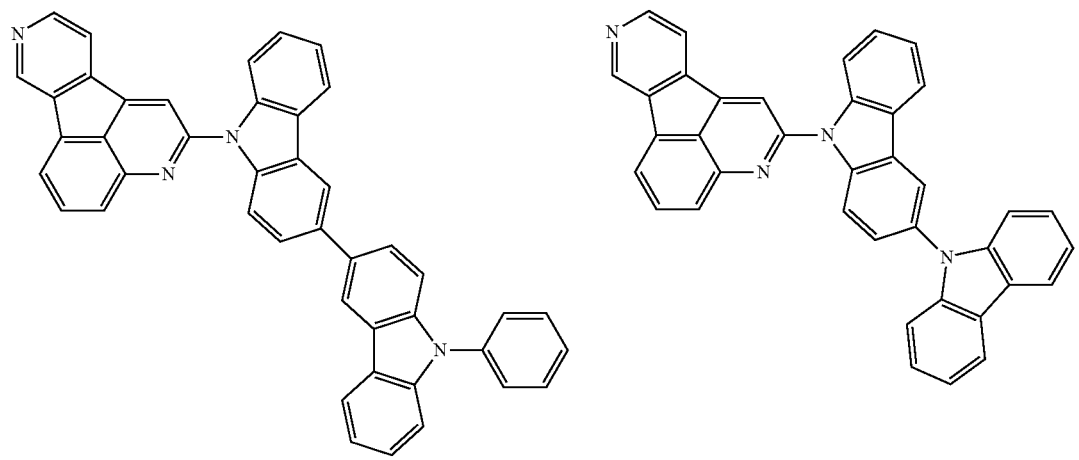
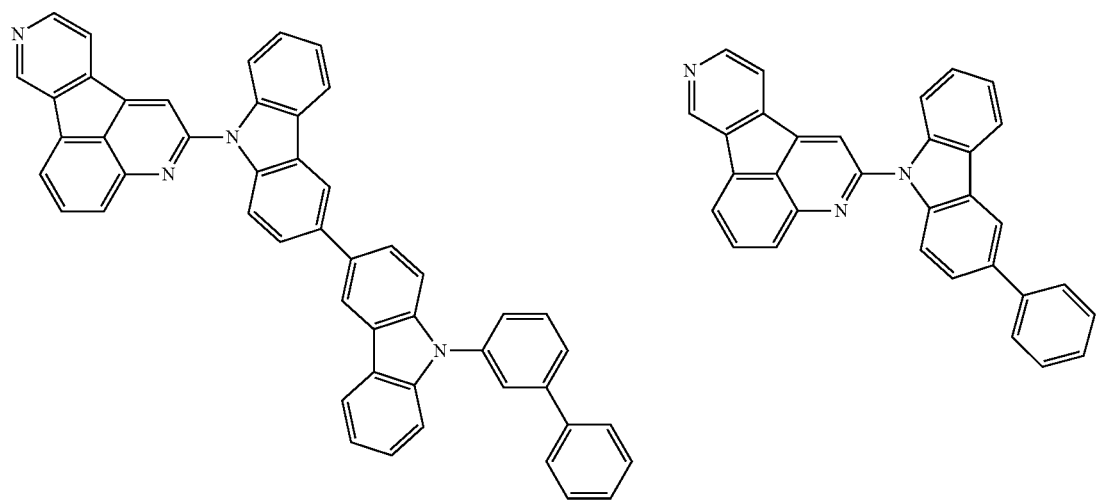

209
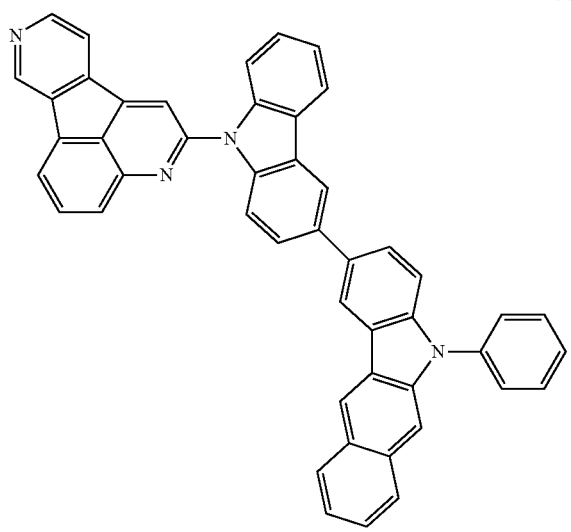
210
-continued
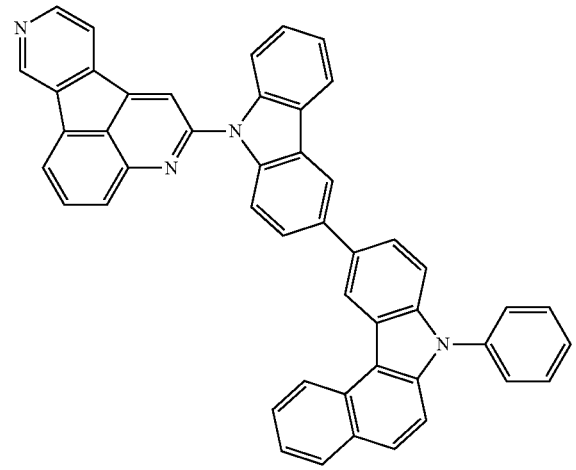
[Chem. 61]
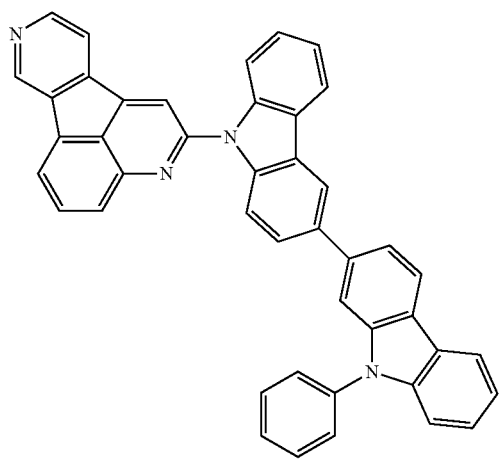
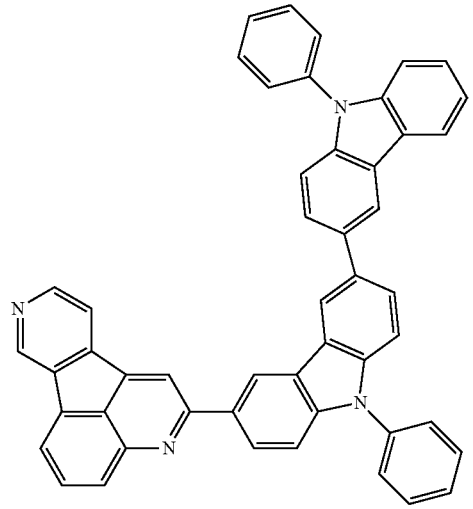
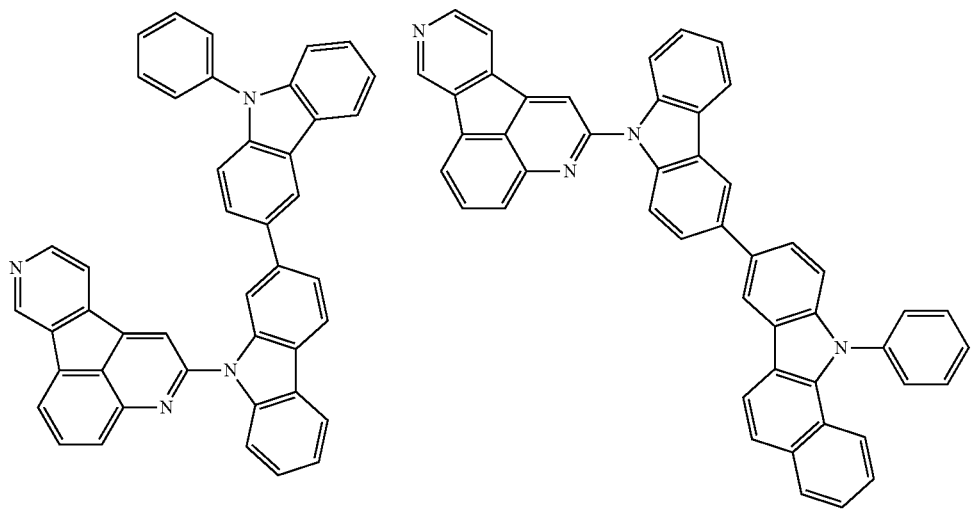

-continued
211
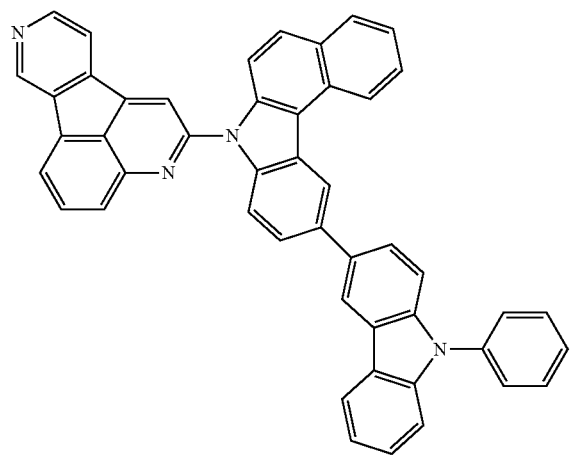
212
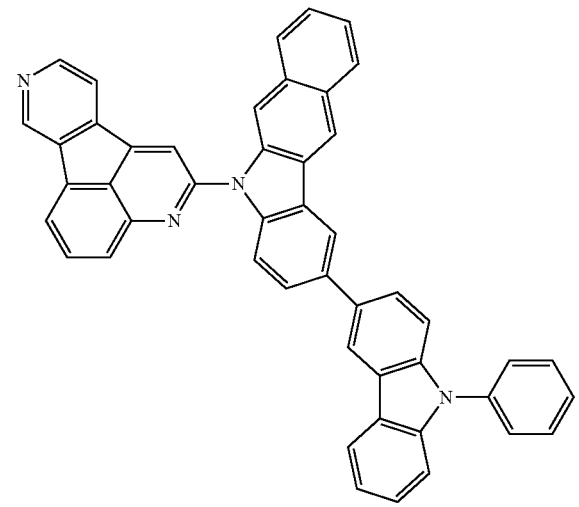
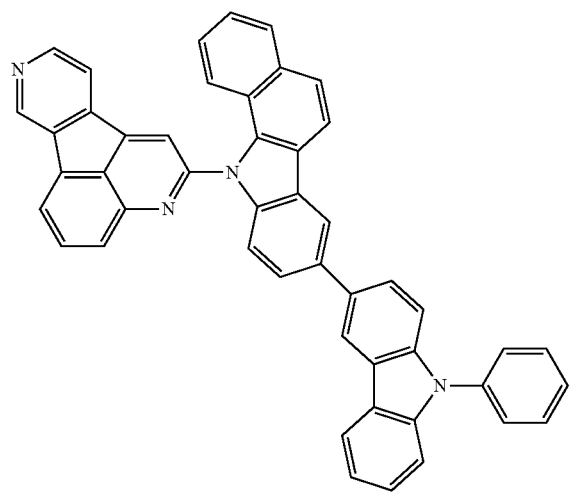
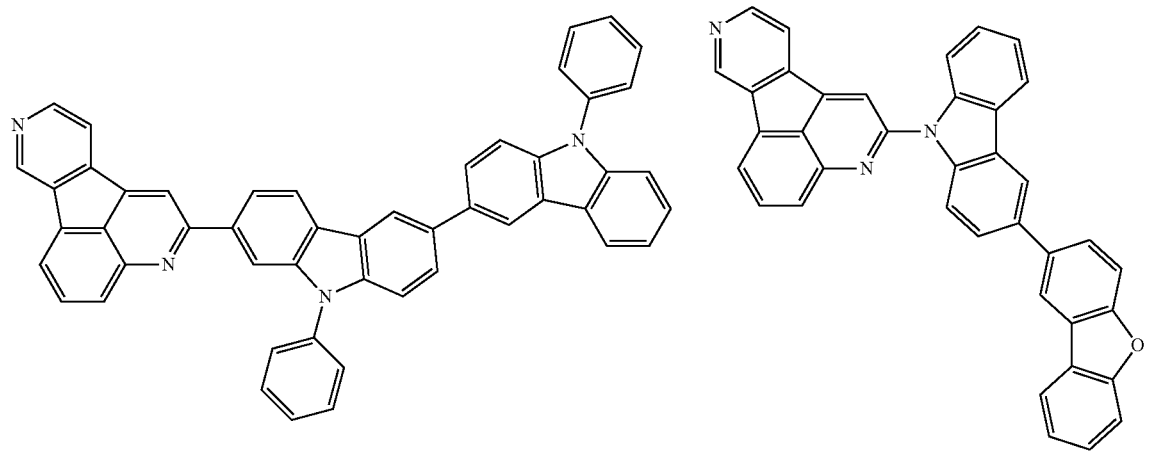

213
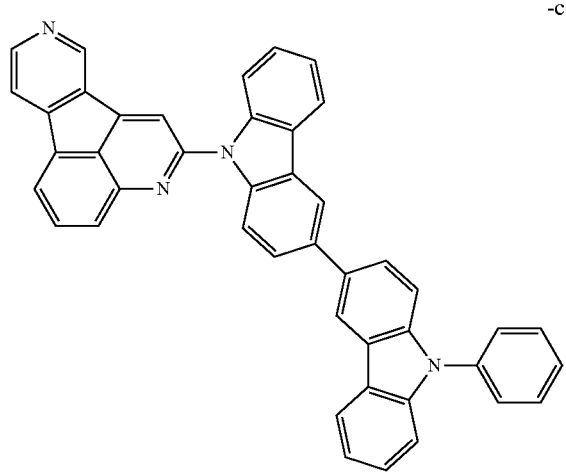
214
-continued
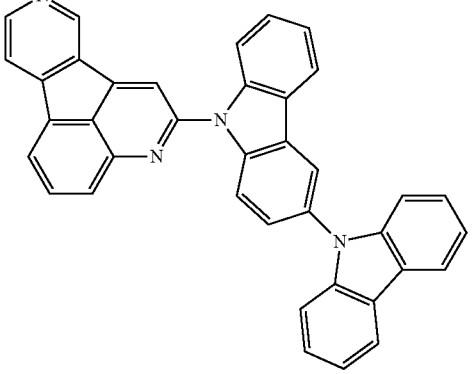
[Chem. 62]
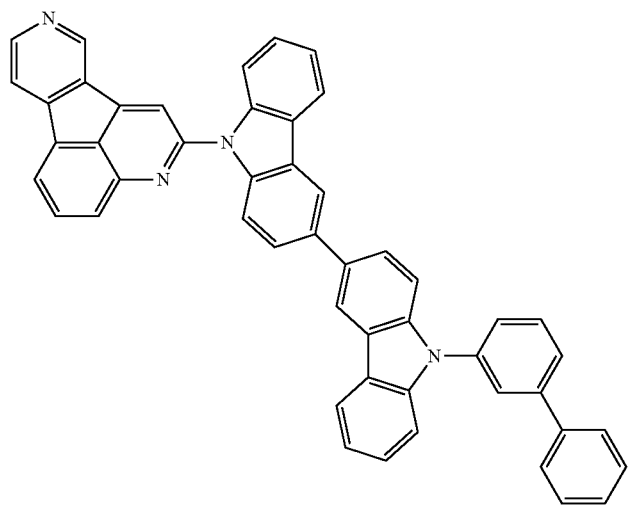
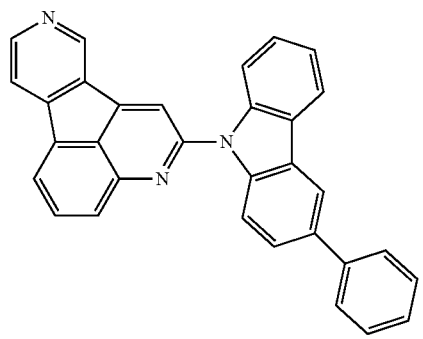
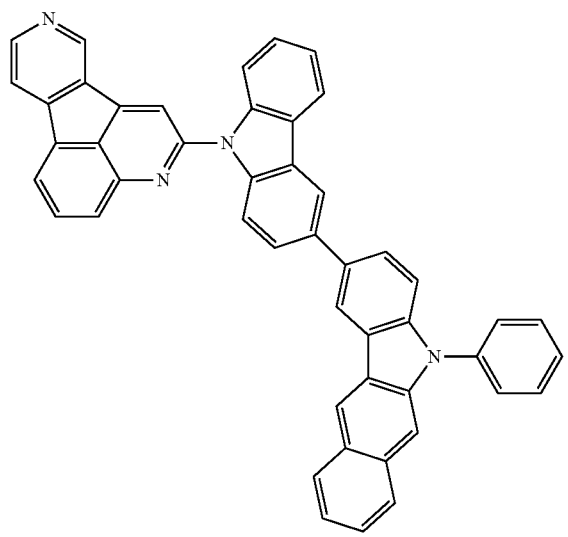
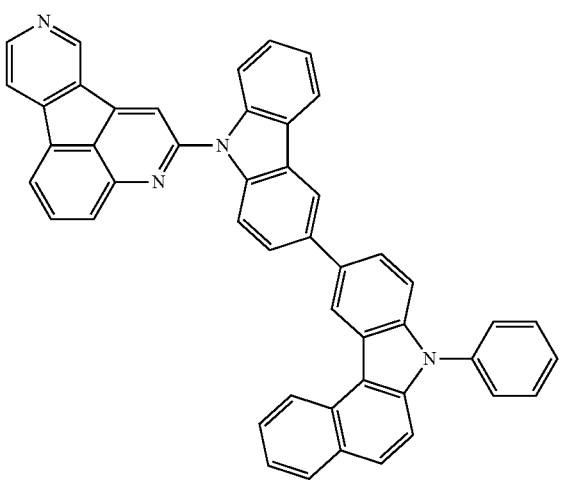

215 216
-continued
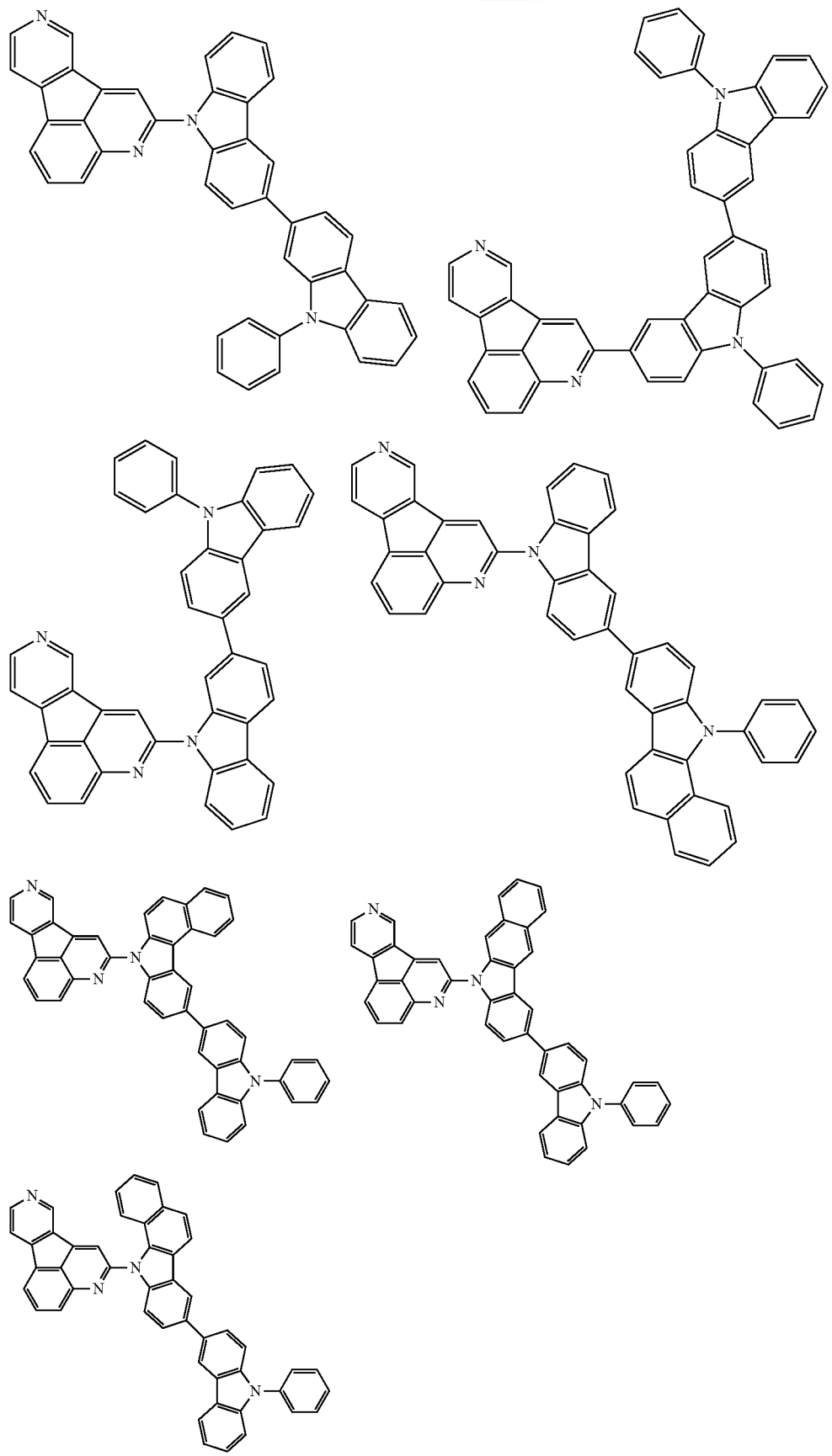

[Chem. 63]
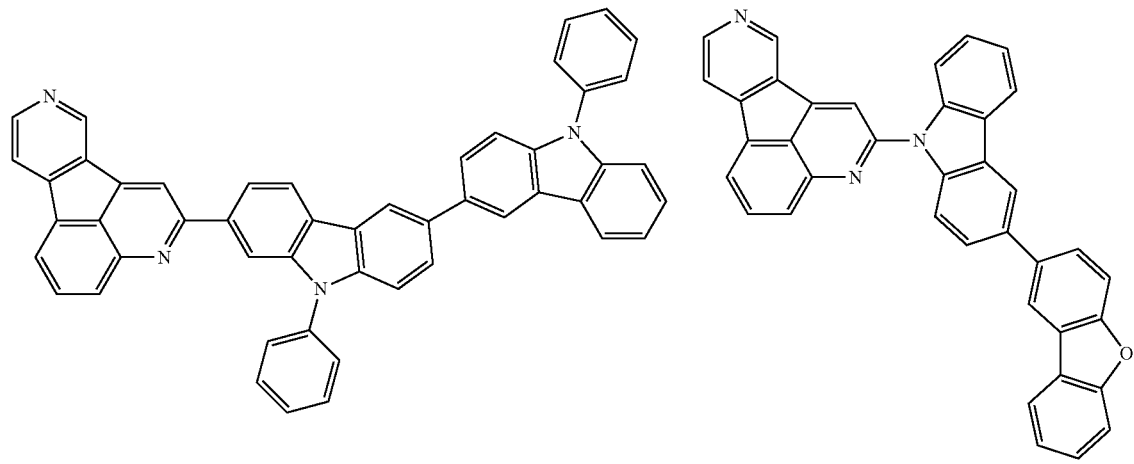
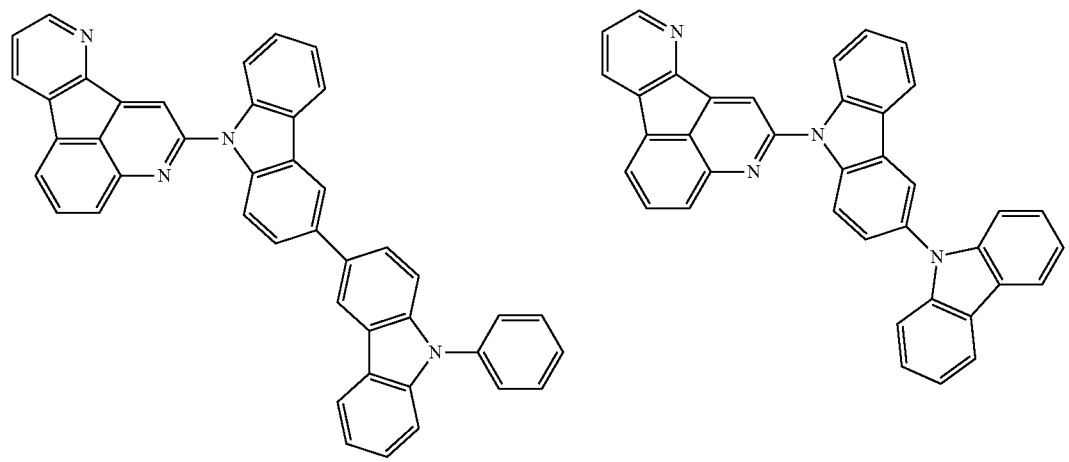
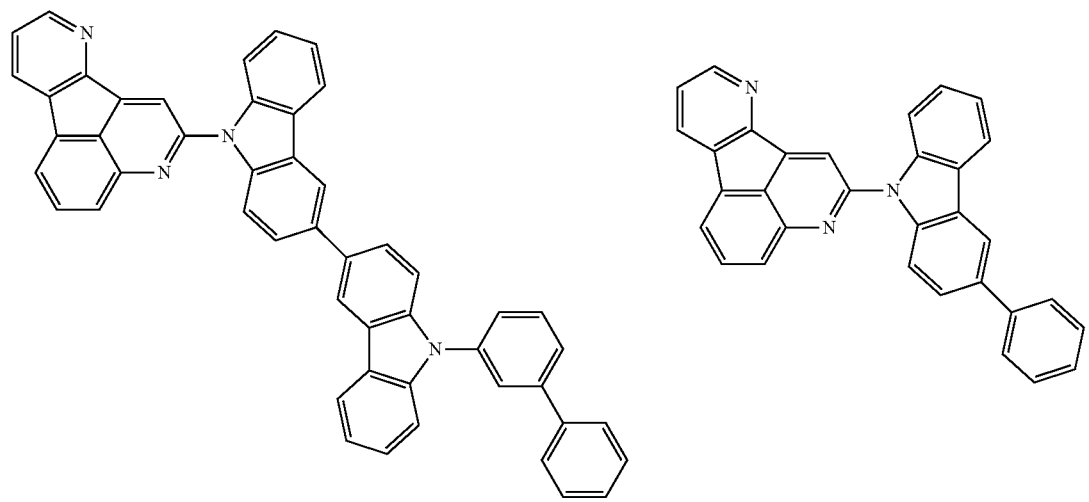

219
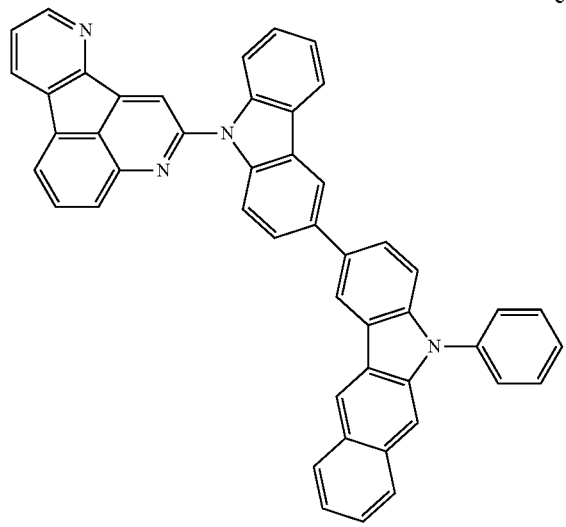
220
-continued
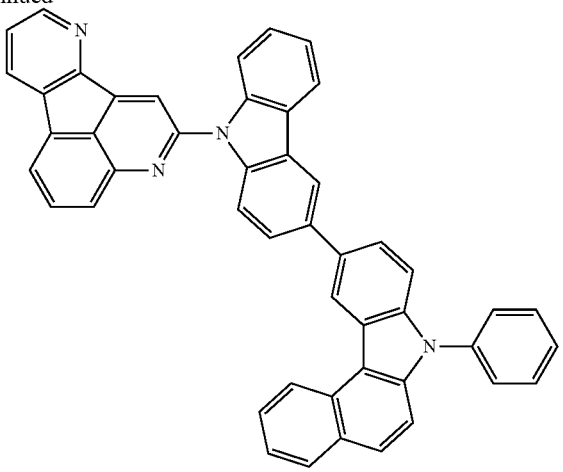
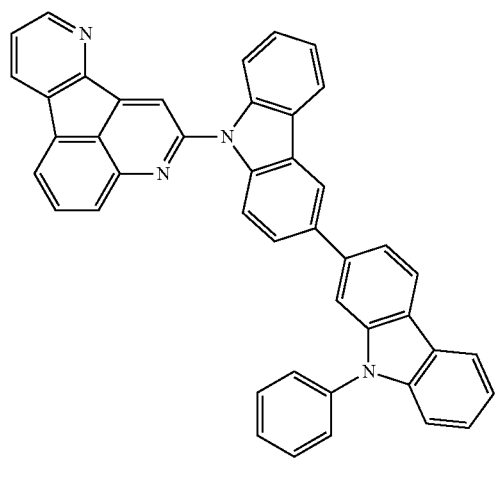
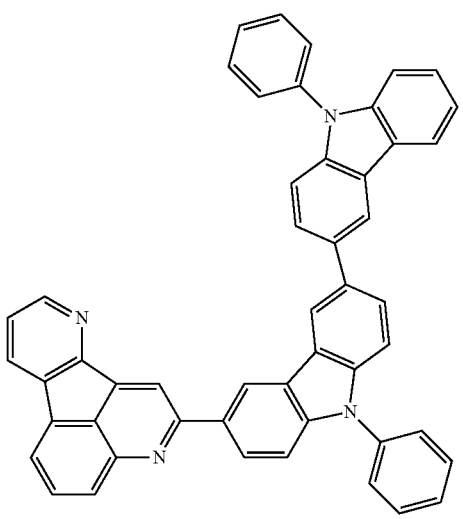
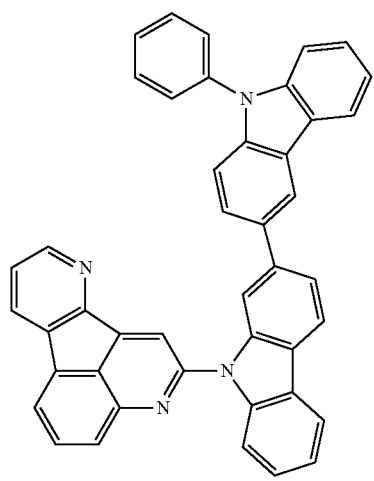

221
222
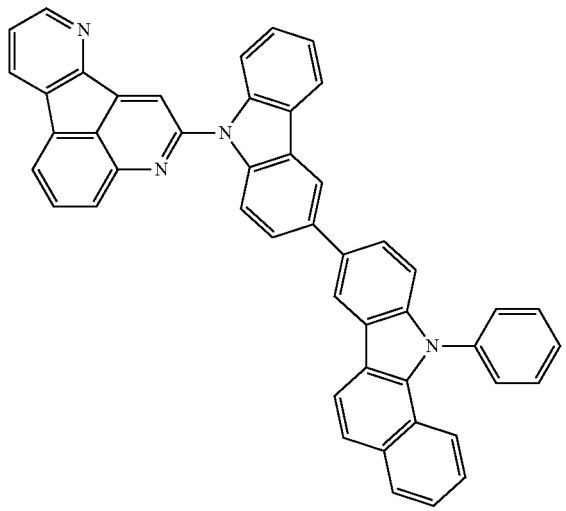
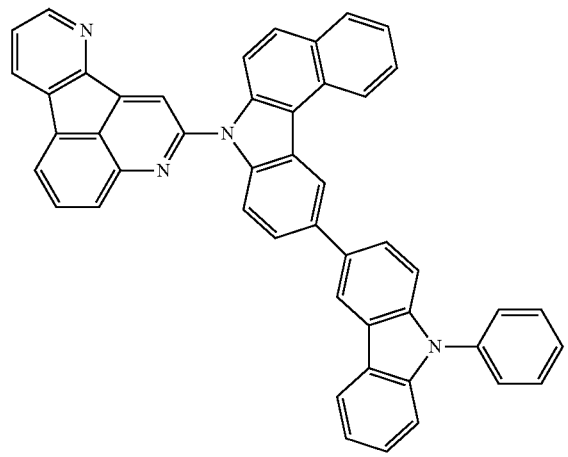
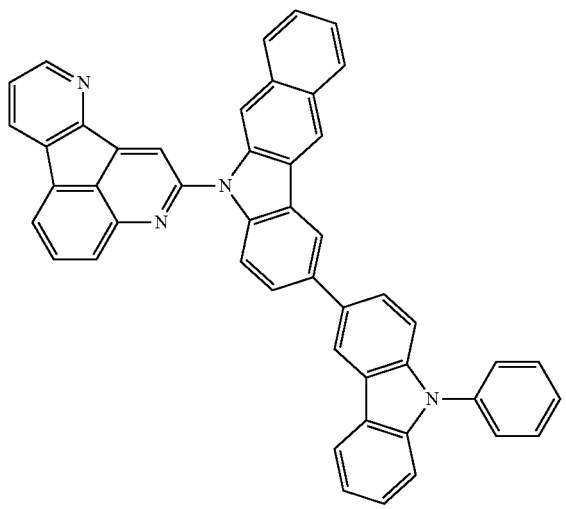
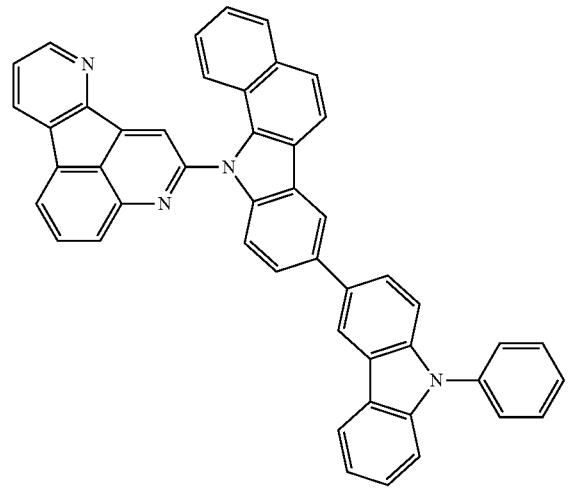
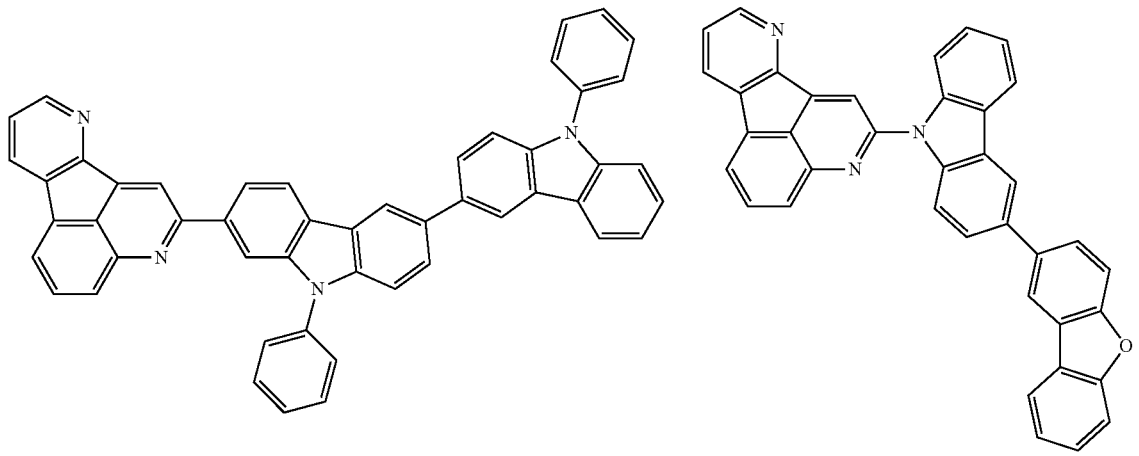

223
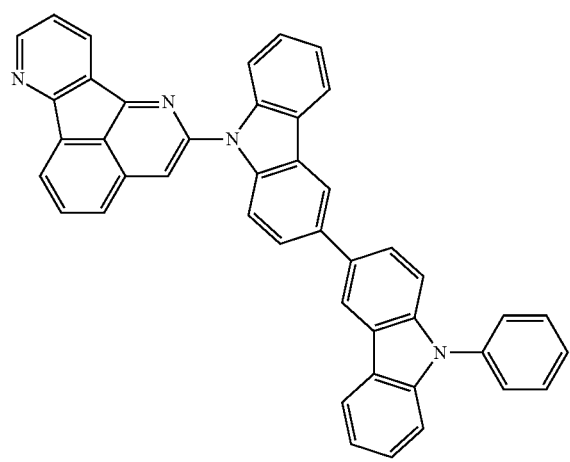
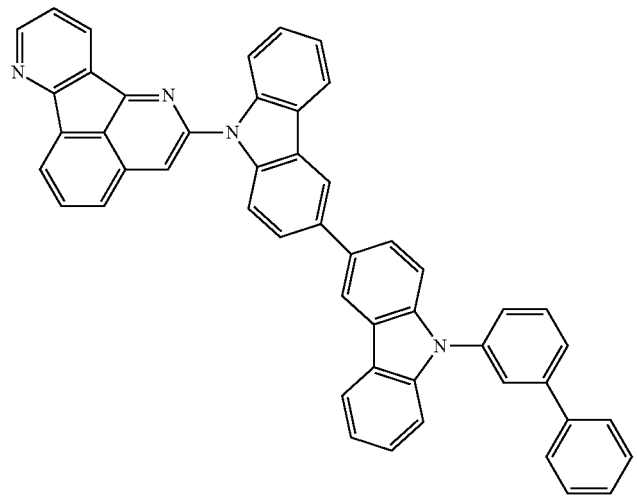
[Chem. 65]
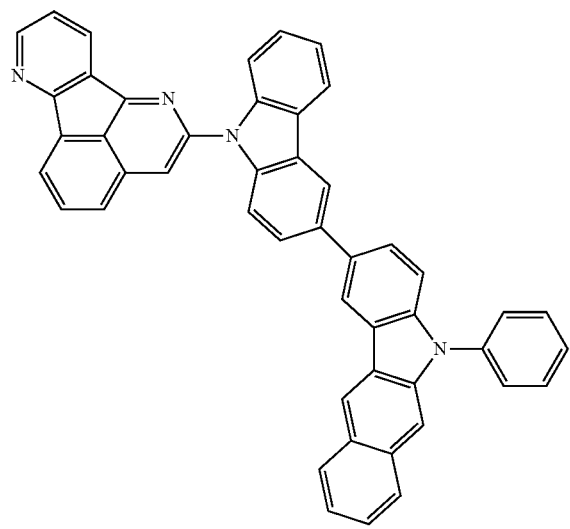
224
-continued
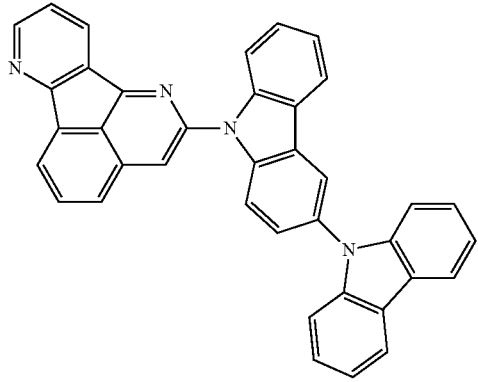
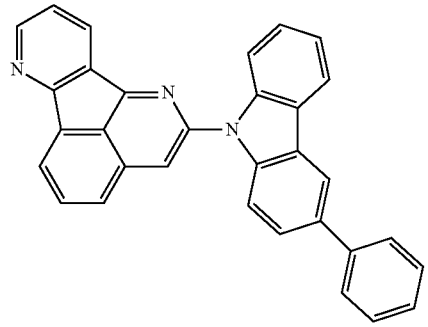
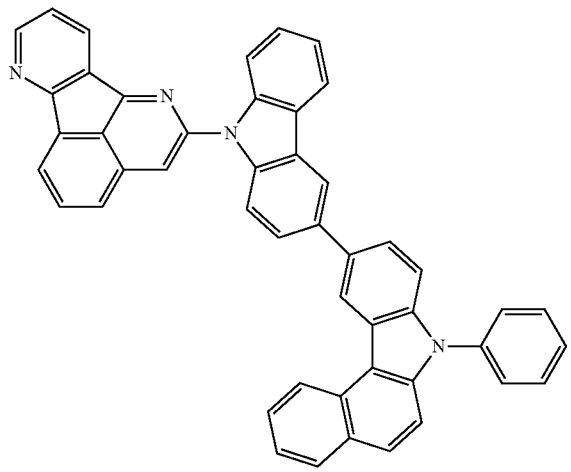

225  226
-continued
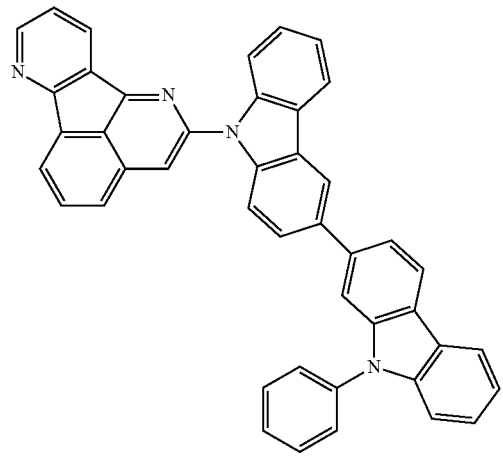
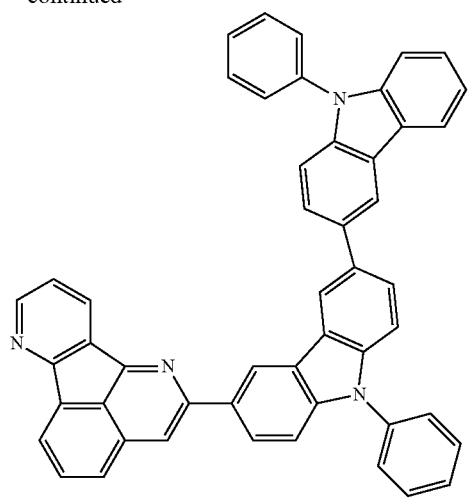
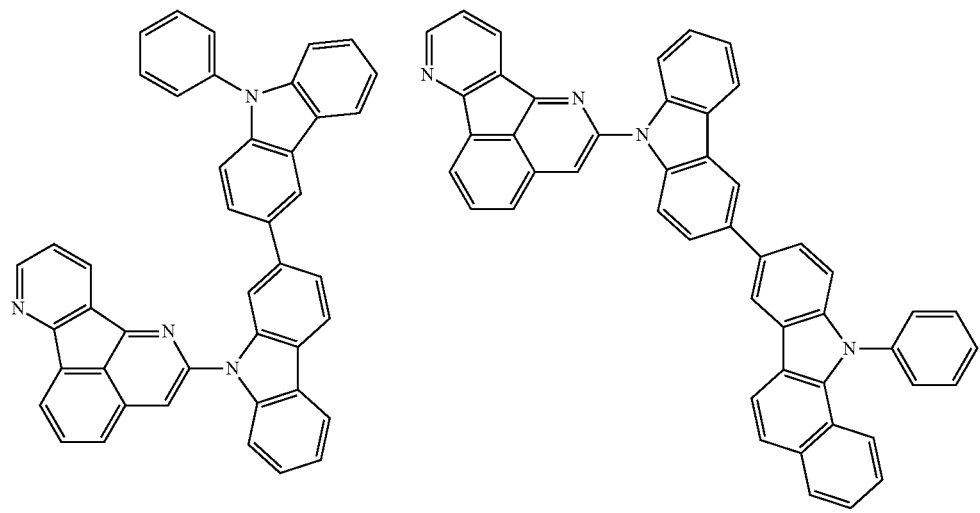
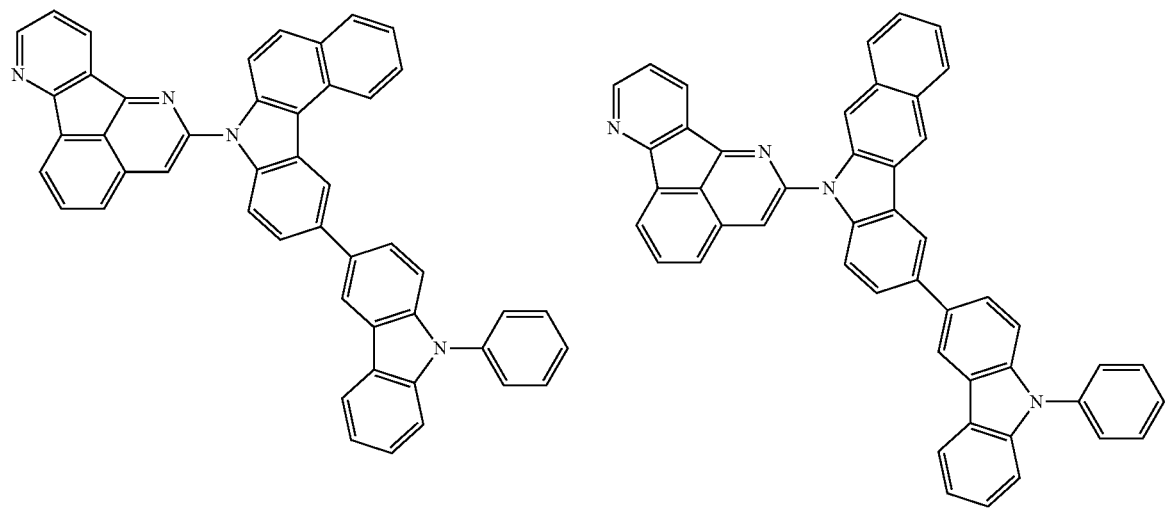

227
228
-continued
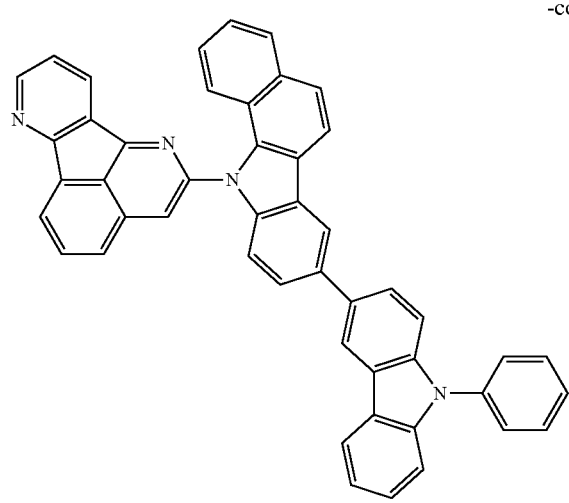
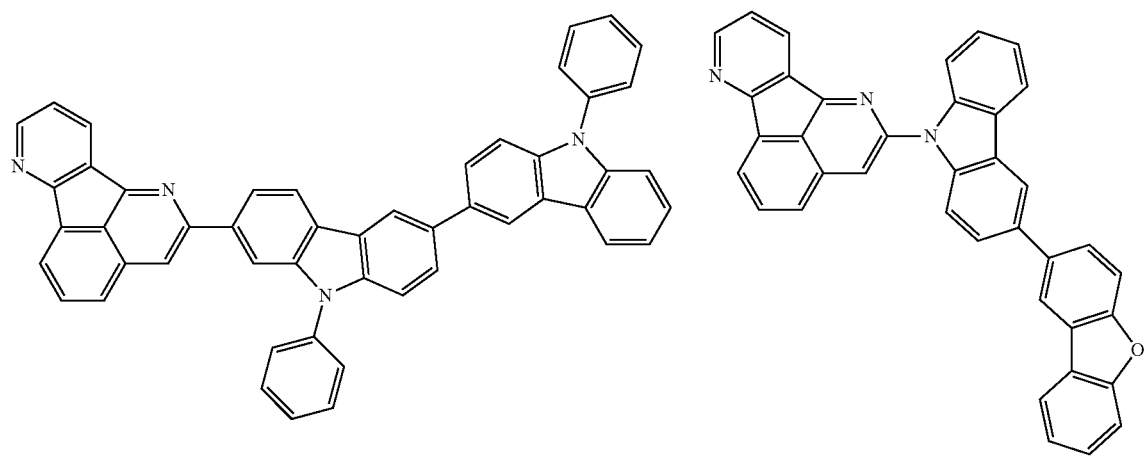
45
[Chem. 66]
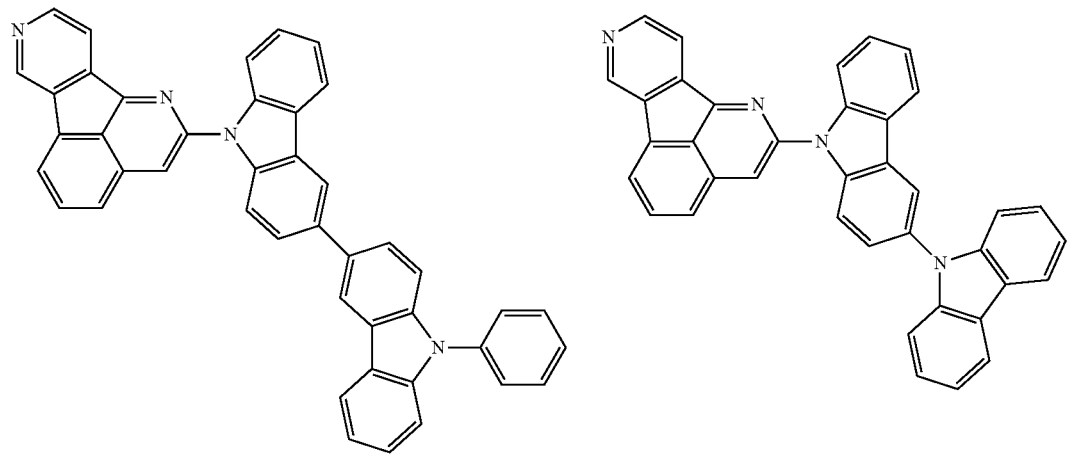

-continued
229
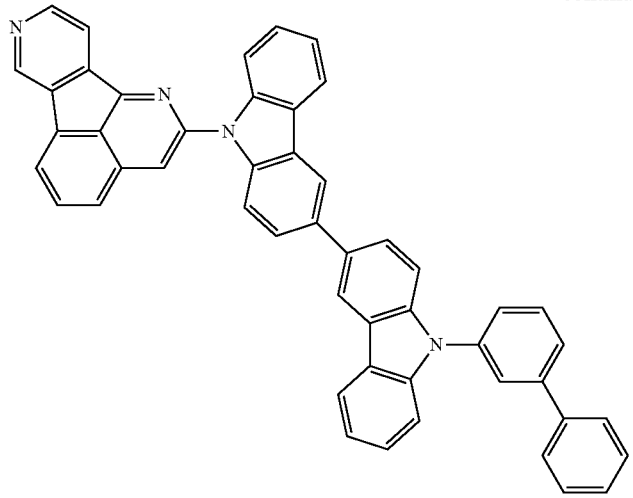
230
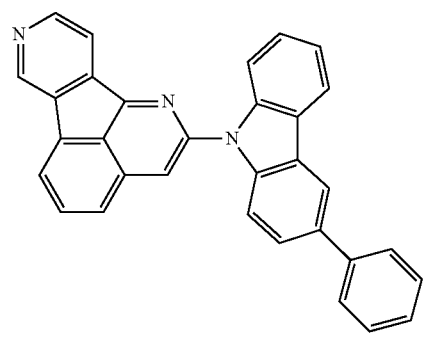
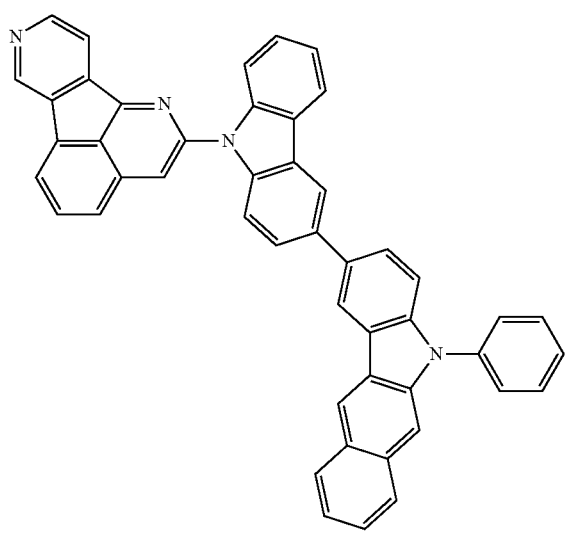
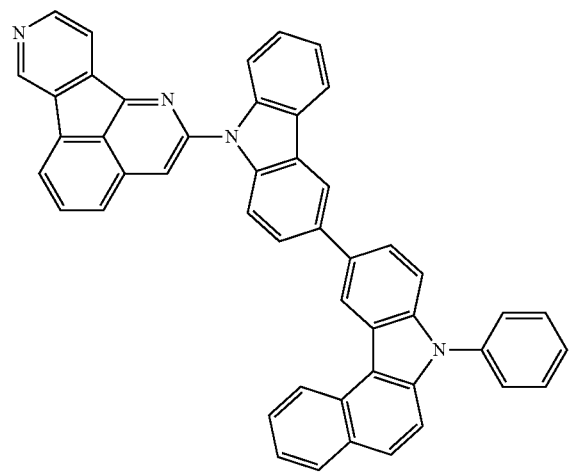
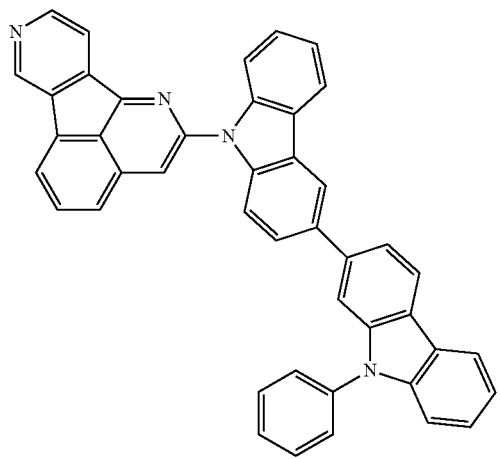
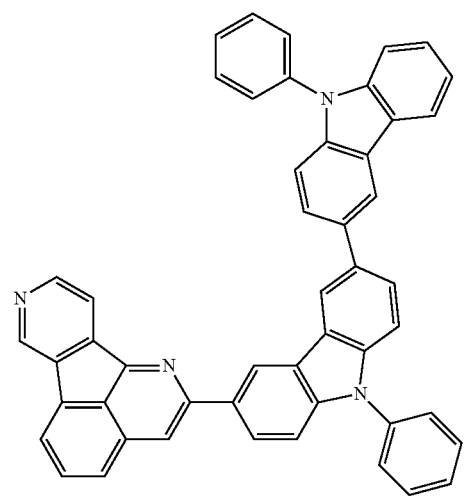

231
232
-continued
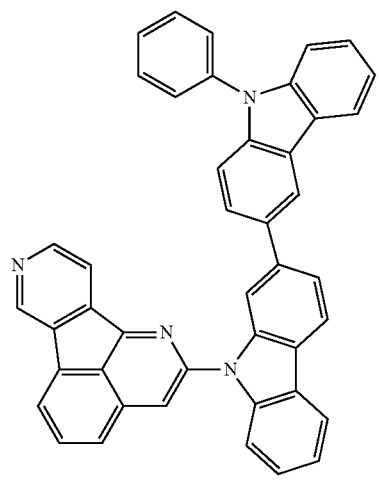
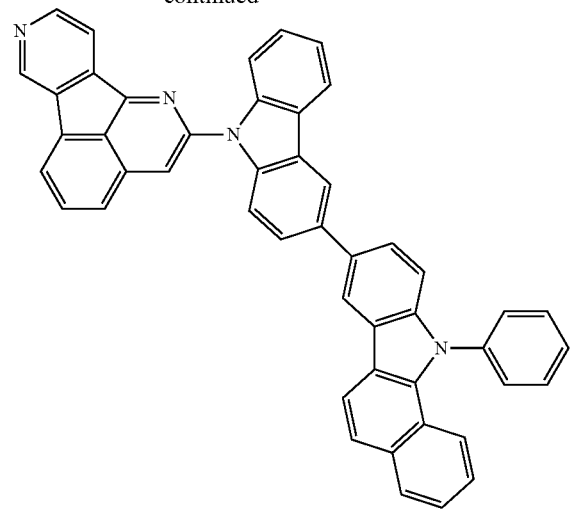
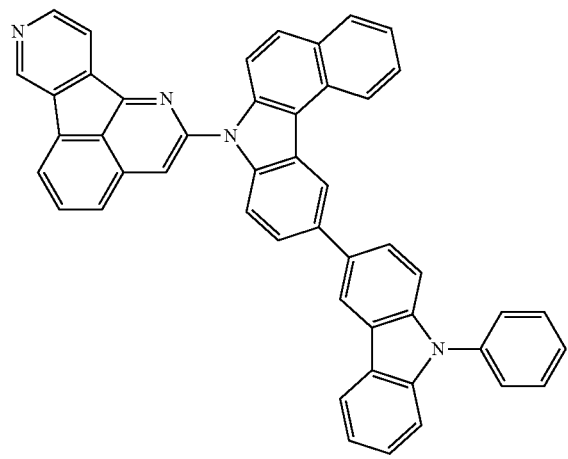
[Chem. 67]
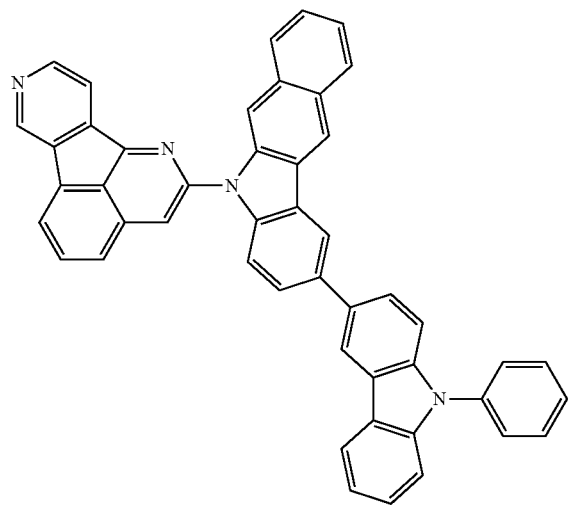
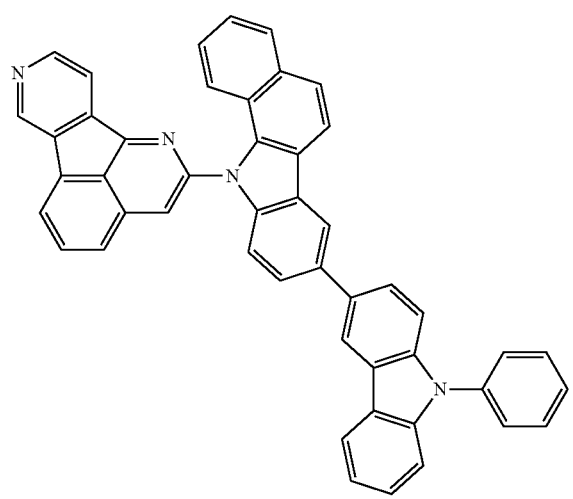

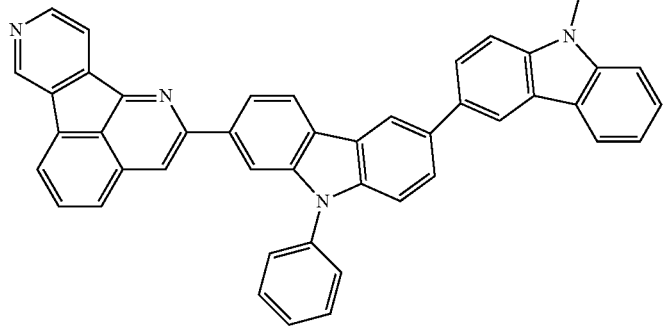
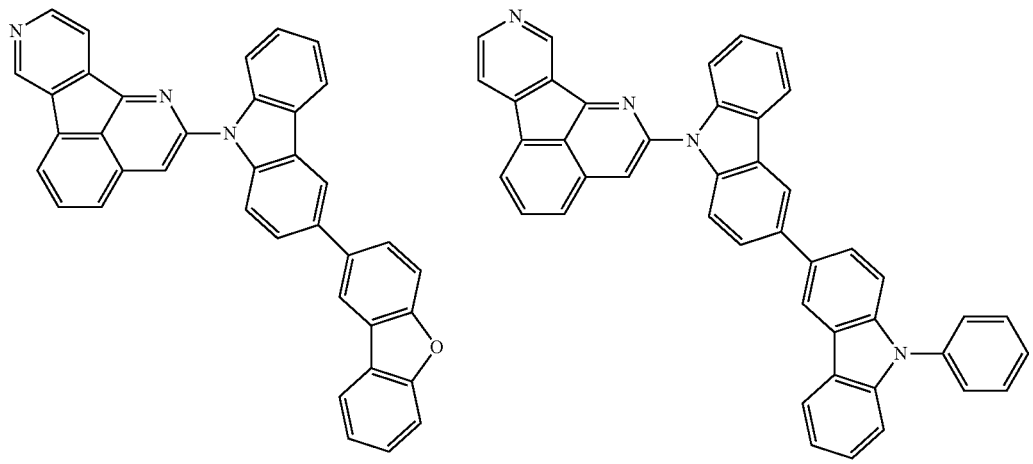
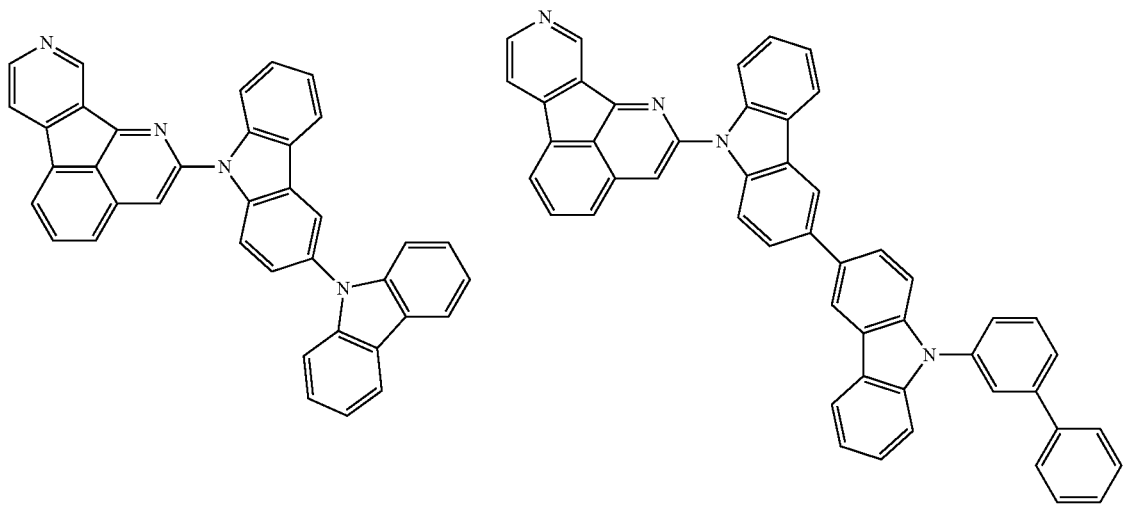

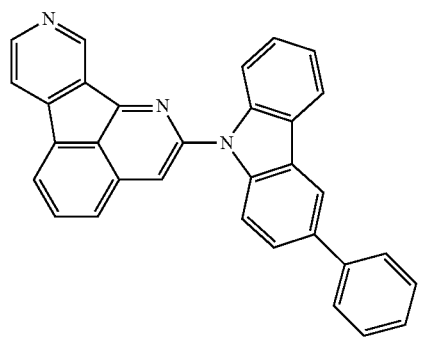
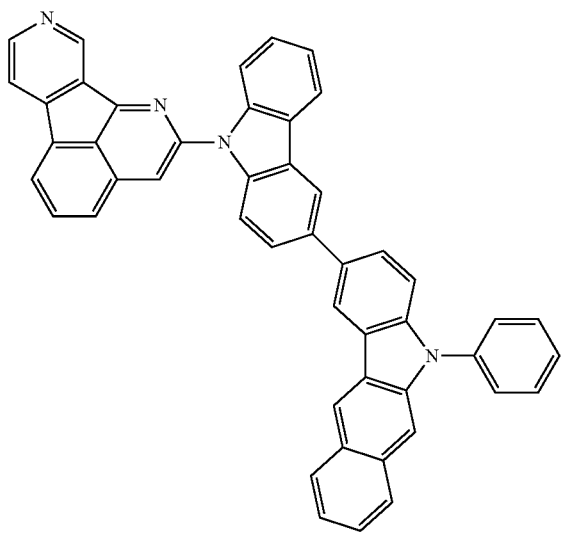
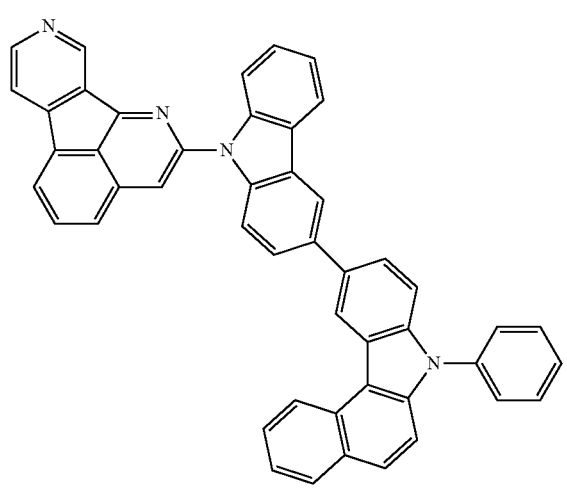
[Chem. 68]
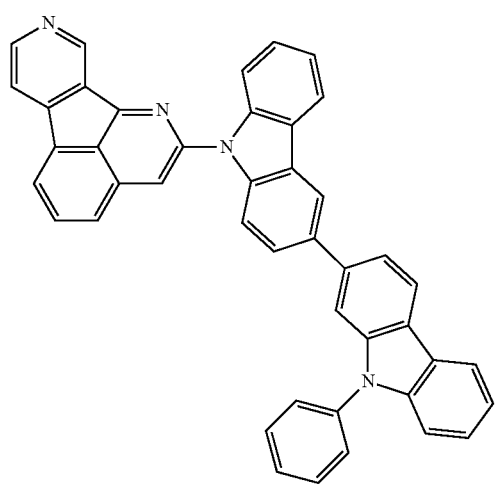
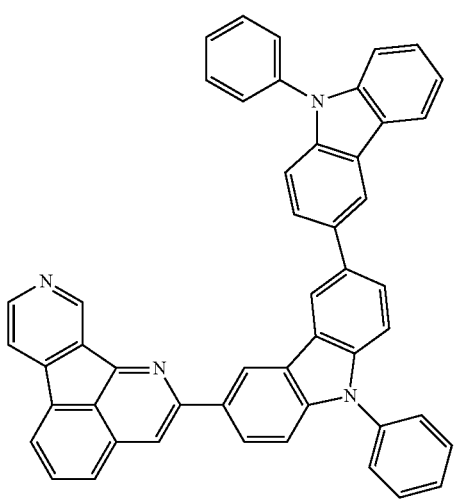

-continued
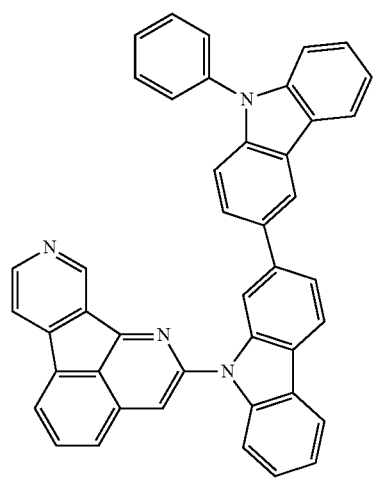
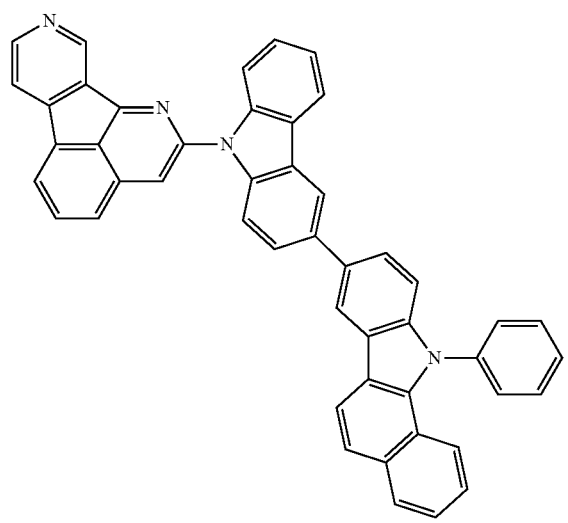
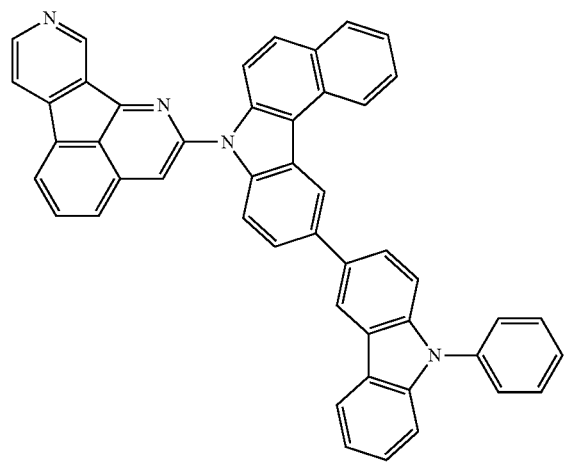
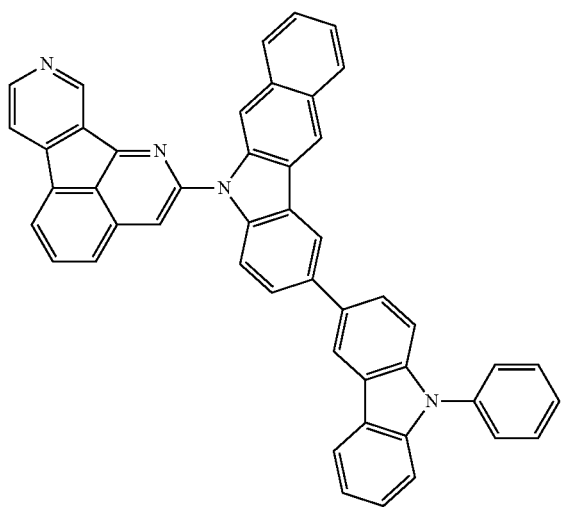
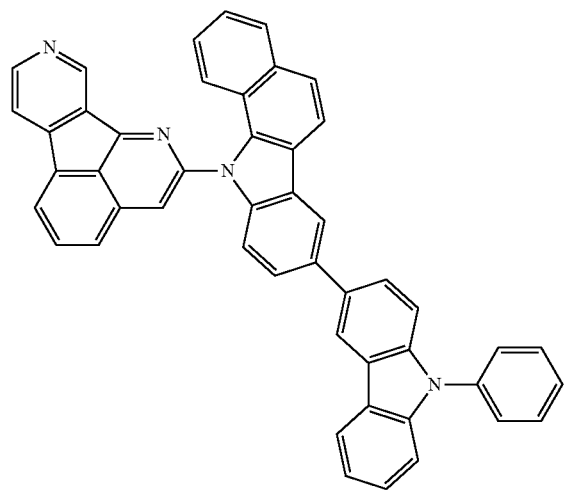

-continued
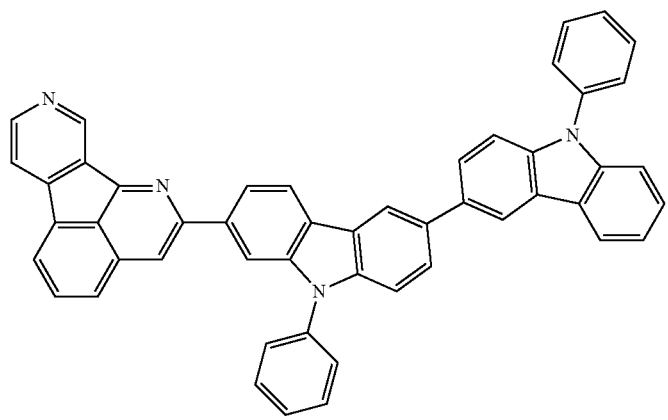
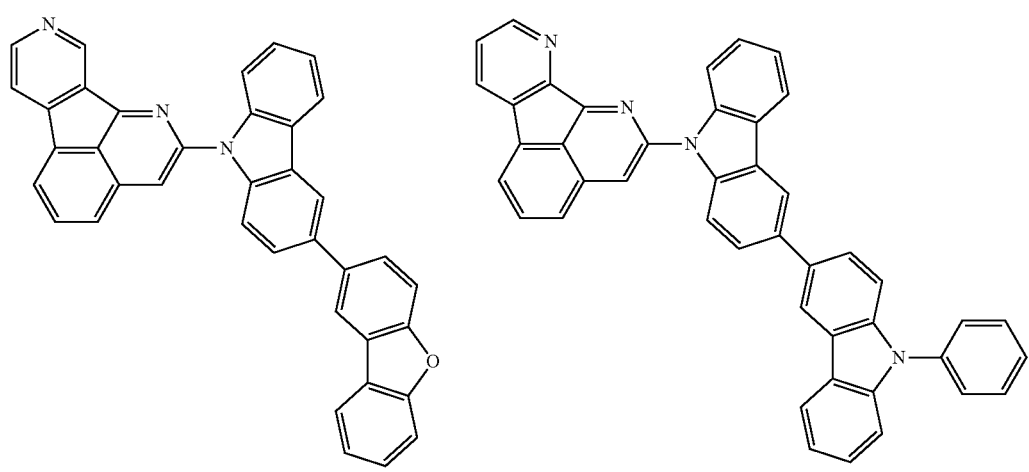
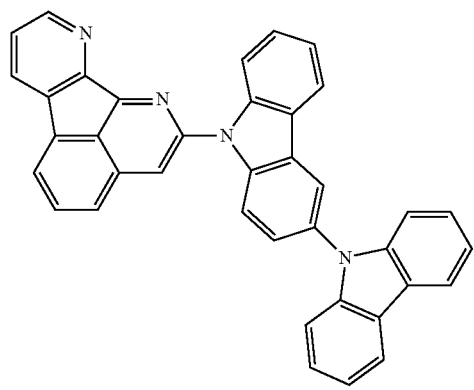

-continued
[Chem. 69]
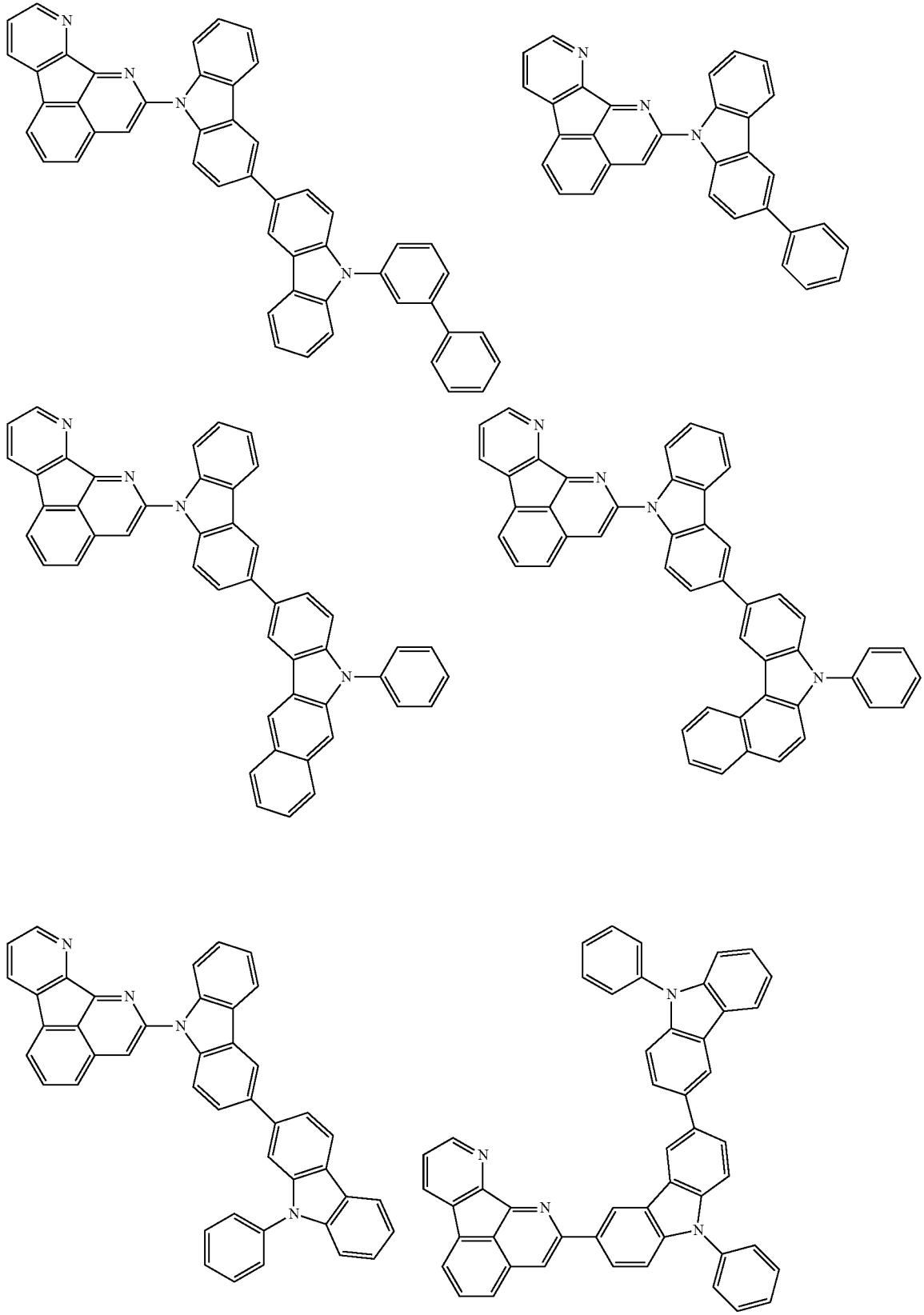

-continued
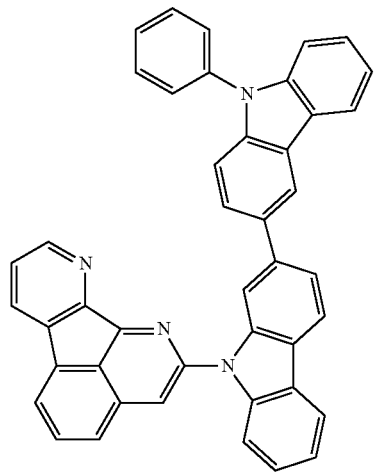
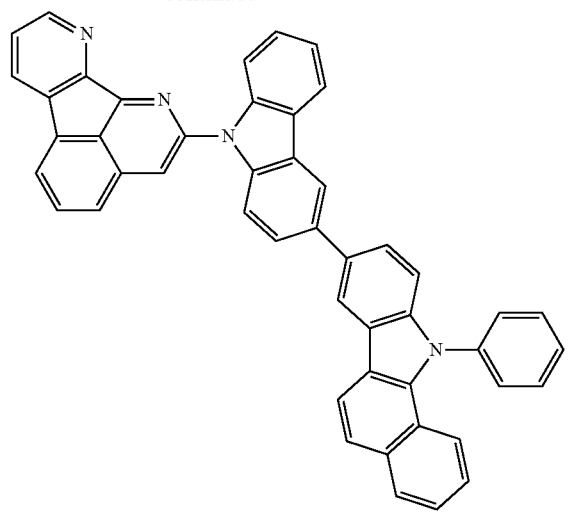
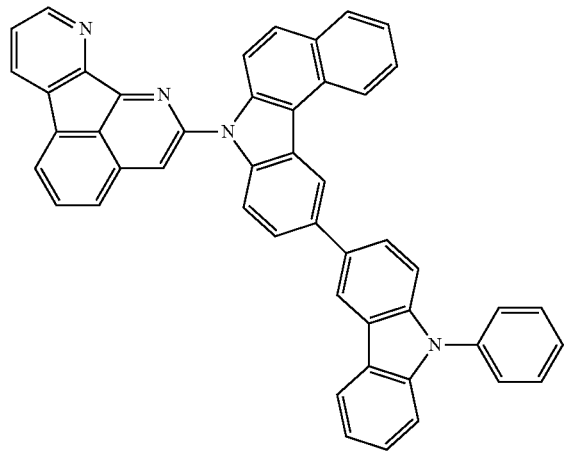
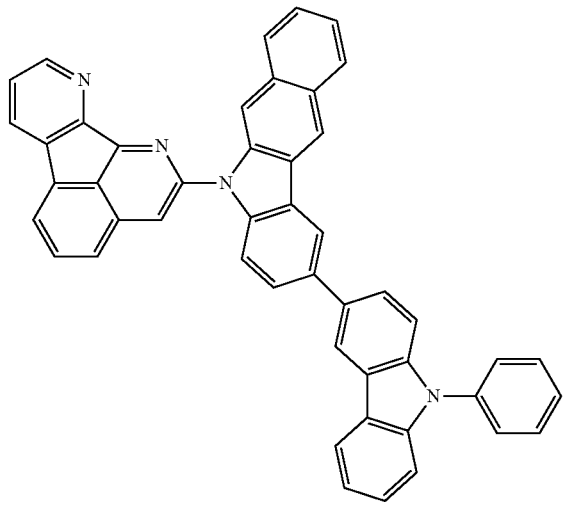
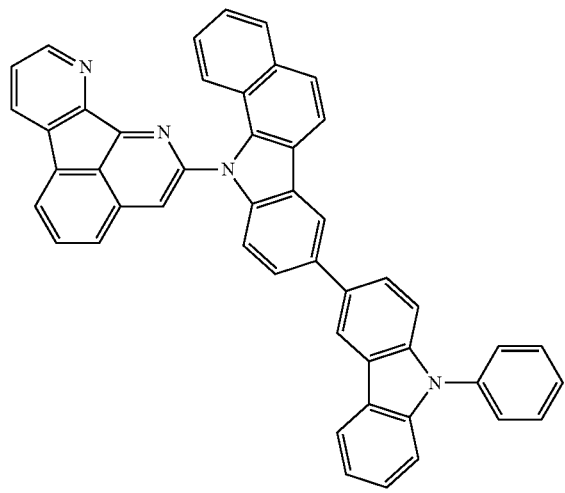

[Chem. 70]
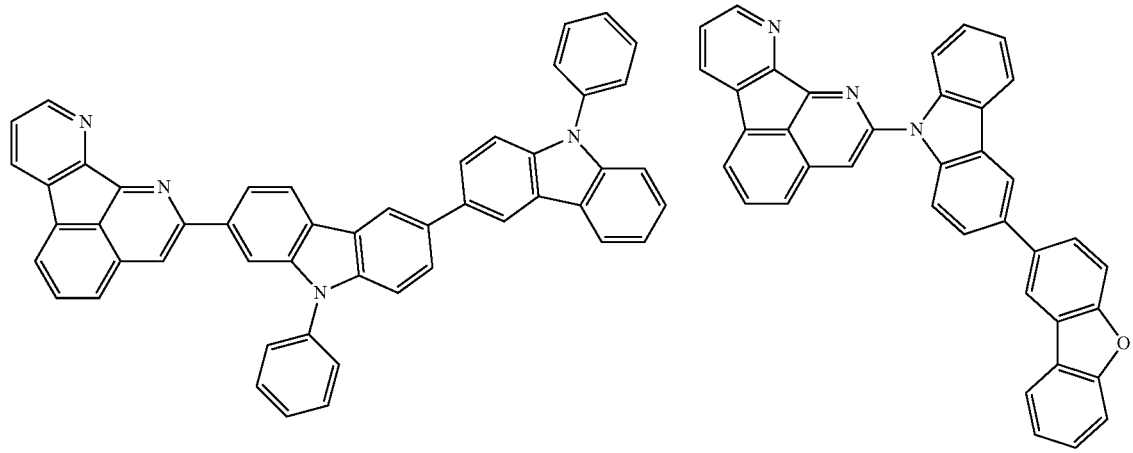
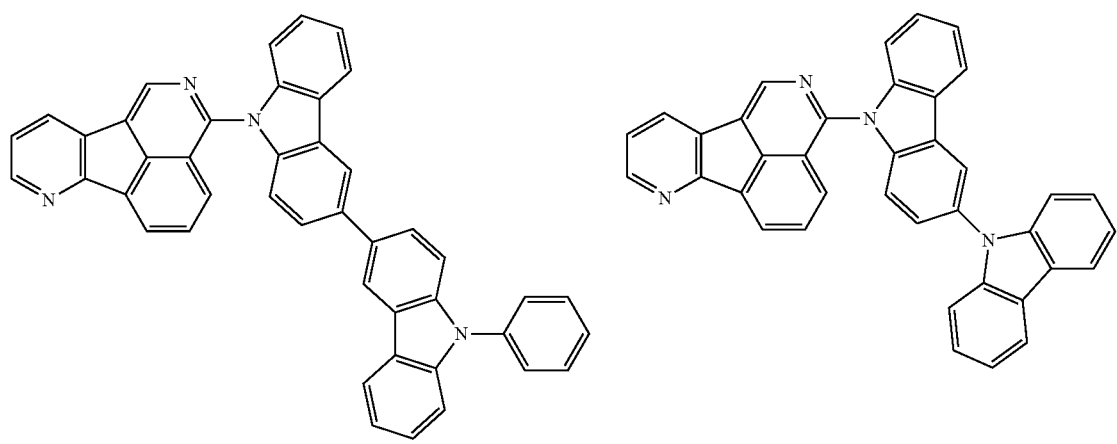
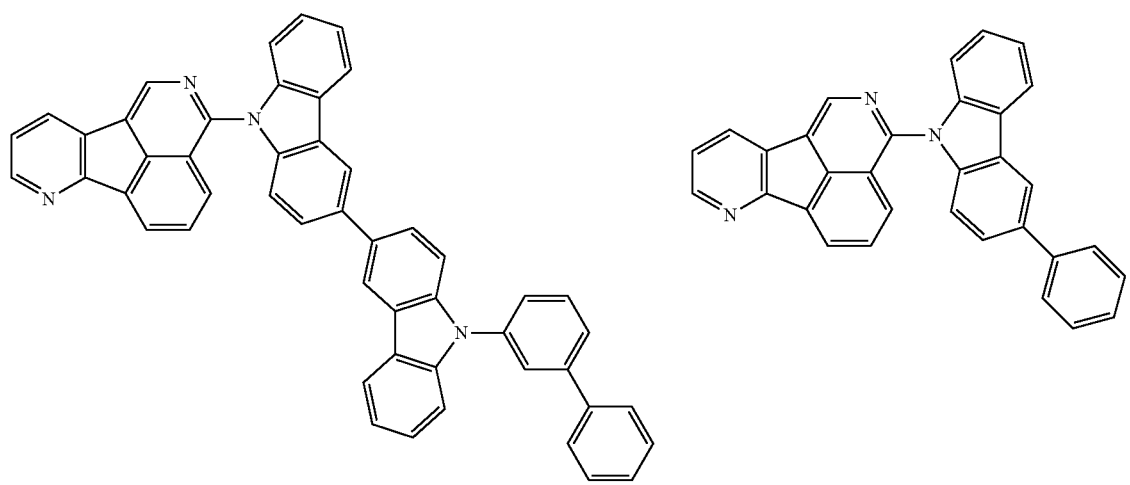

-continued
247
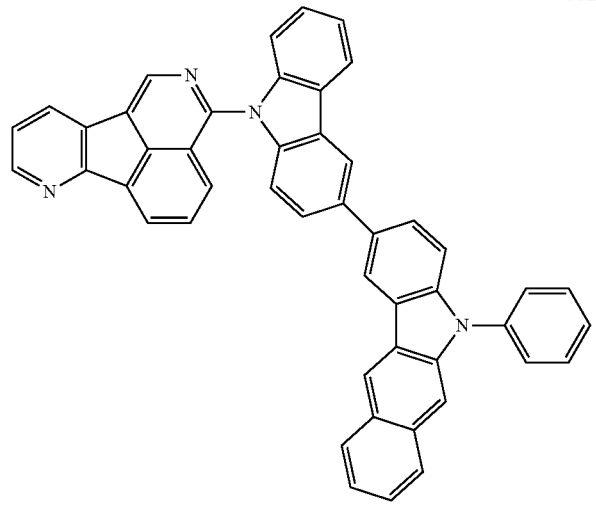
248
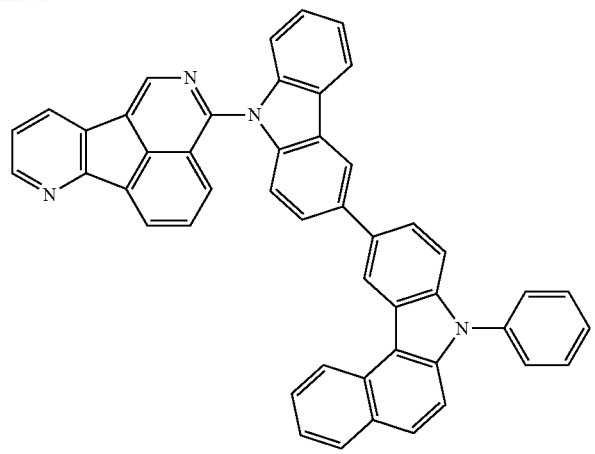
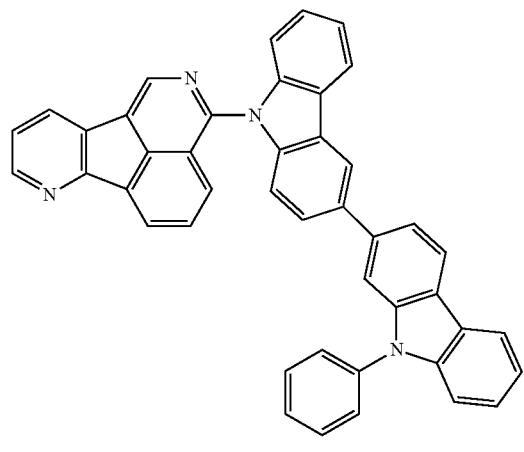
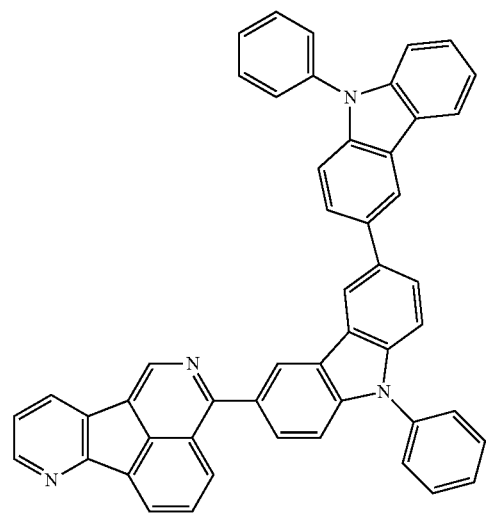
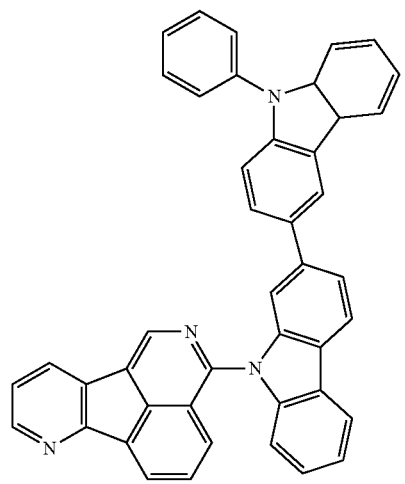

[Chem. 71]
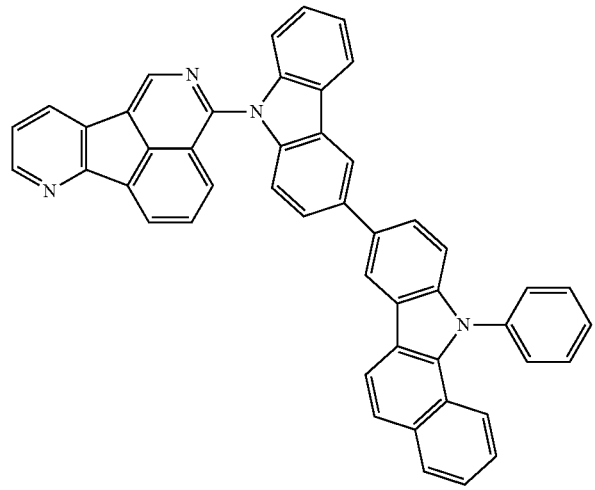
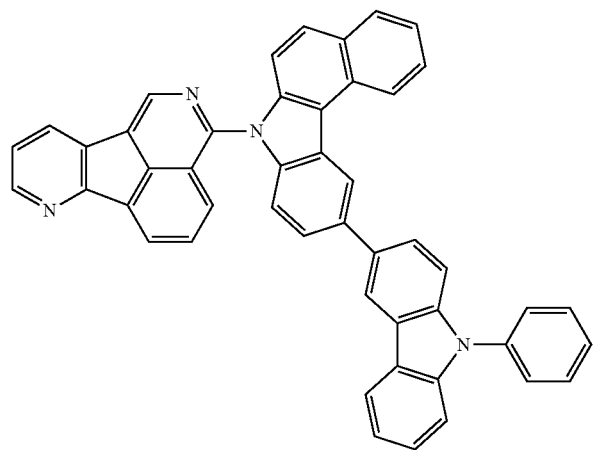
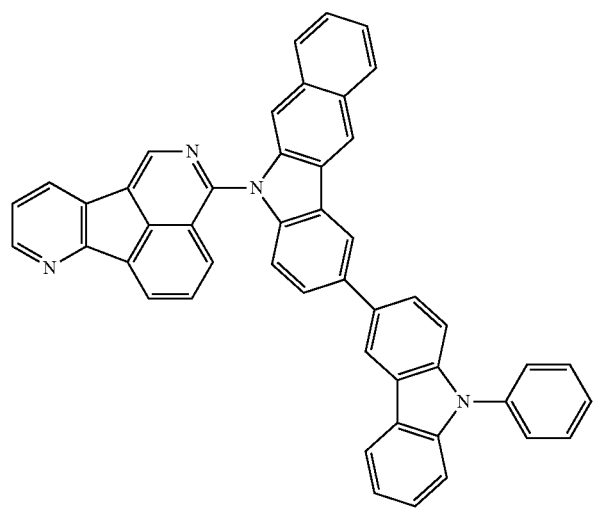

251 252
-continued
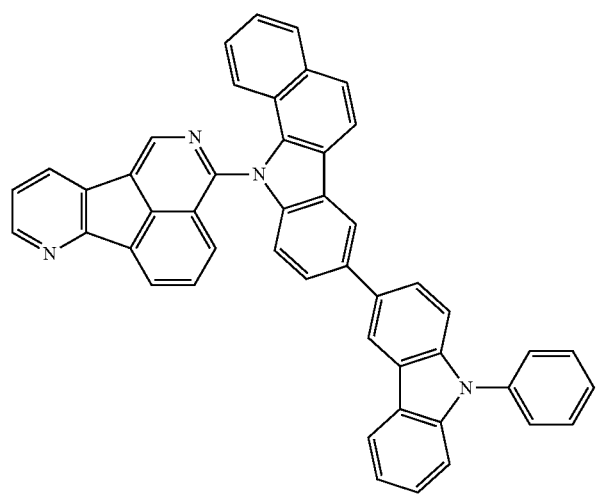
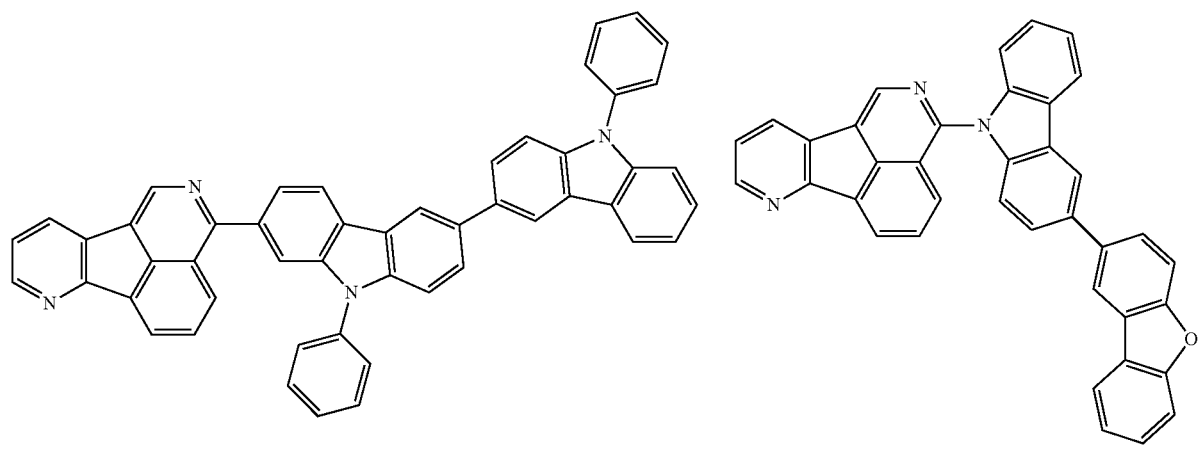
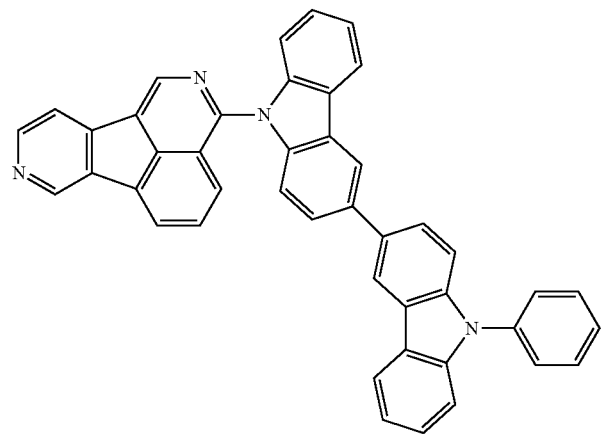
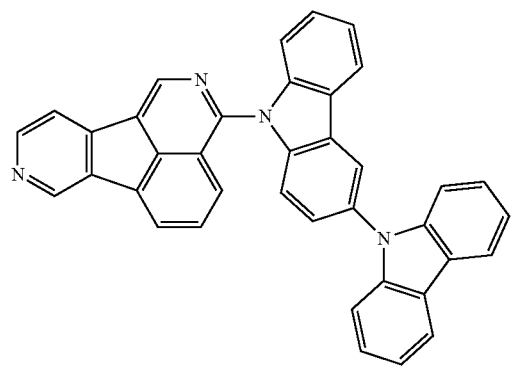

253
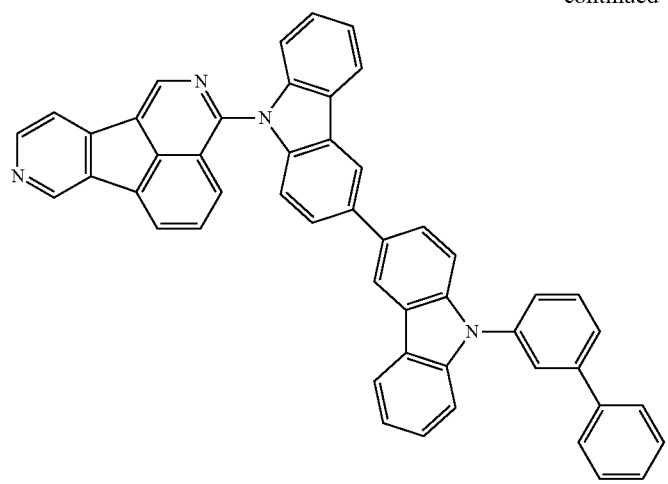
254
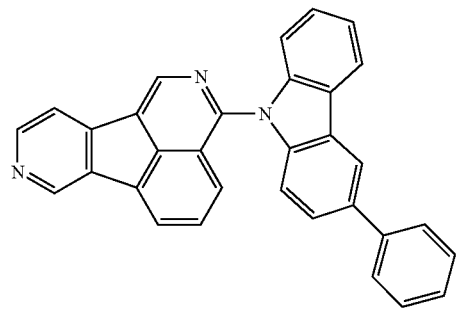
[Chem. 72]
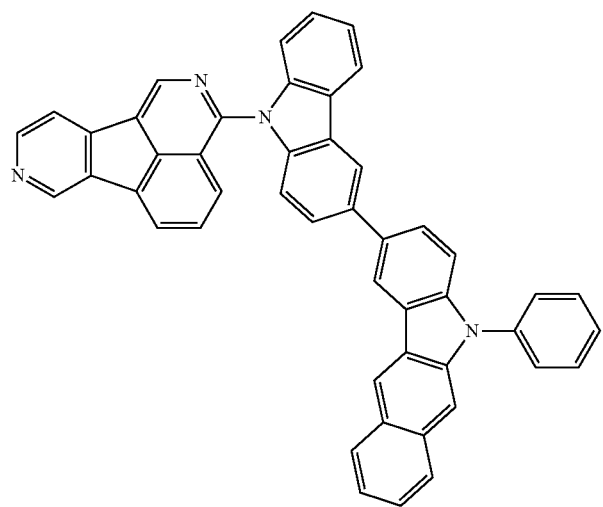
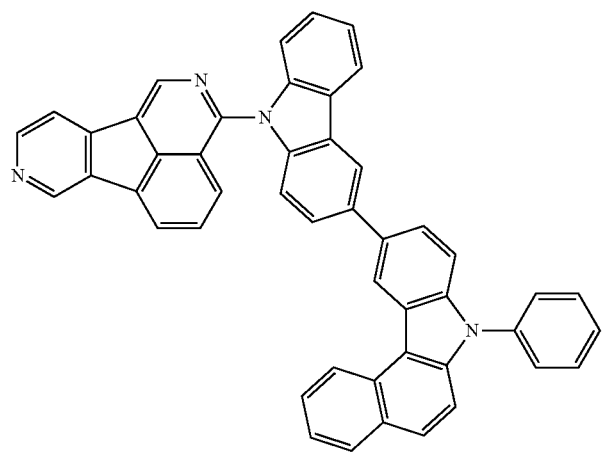

255
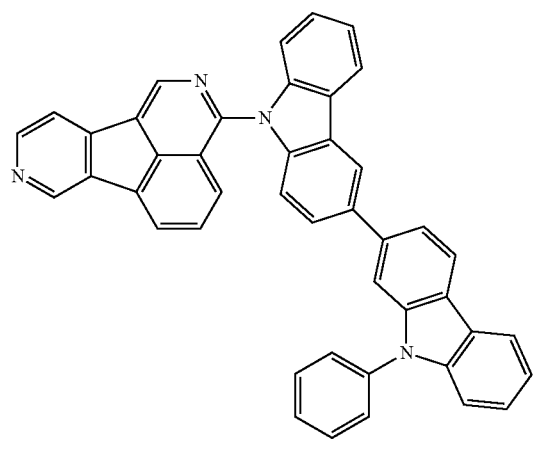
256
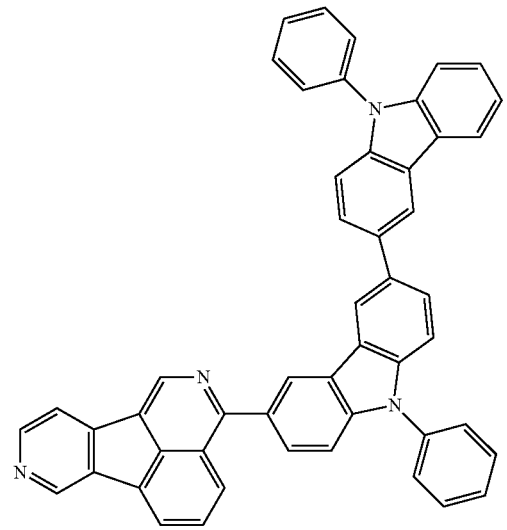
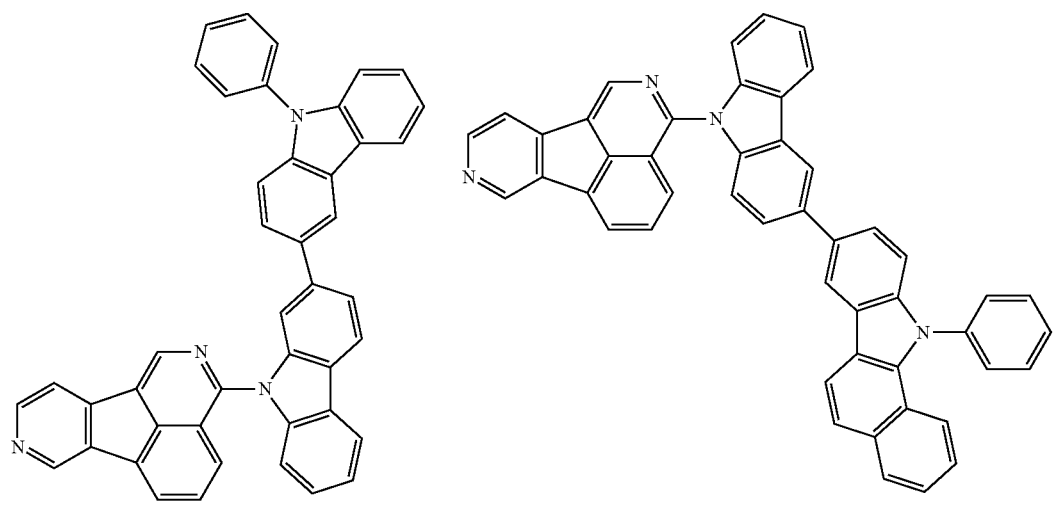
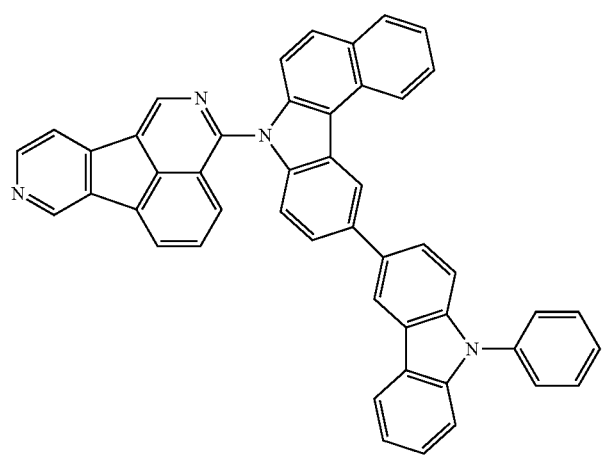

-continued
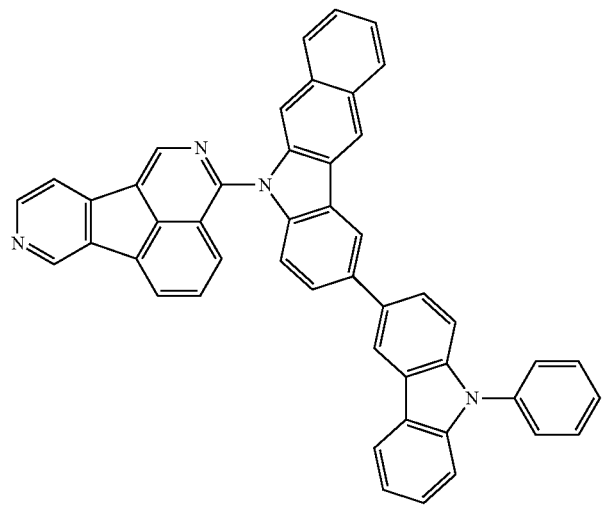
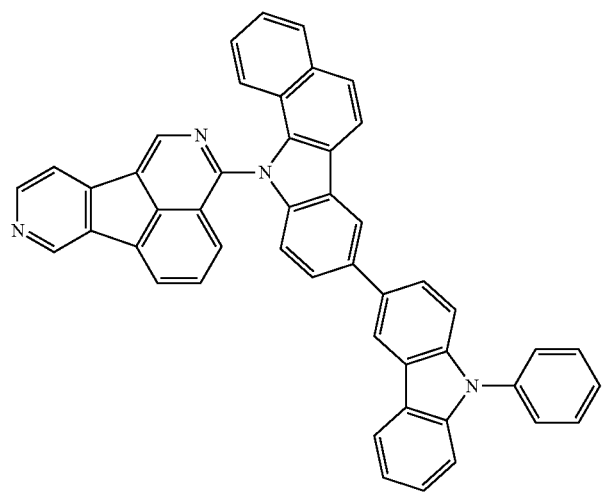
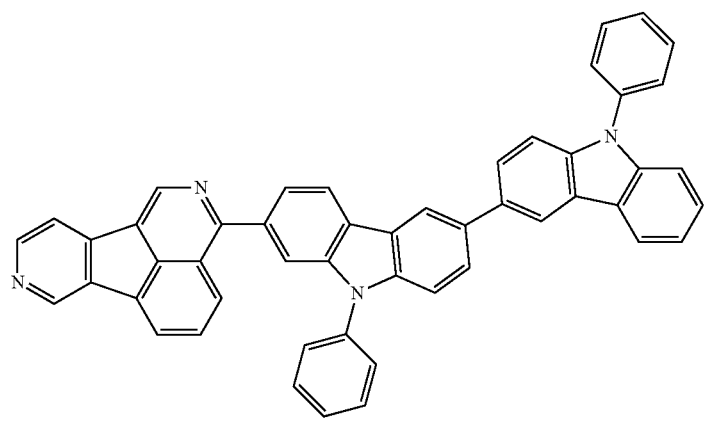

[Chem. 73]
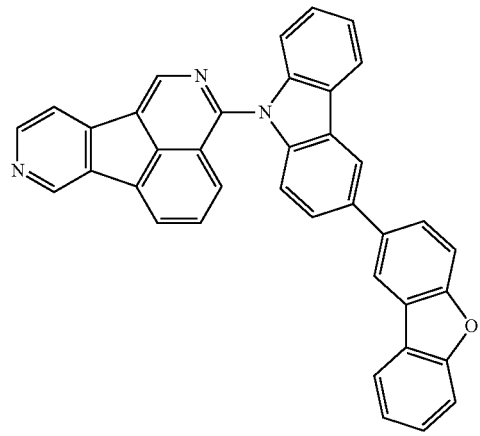
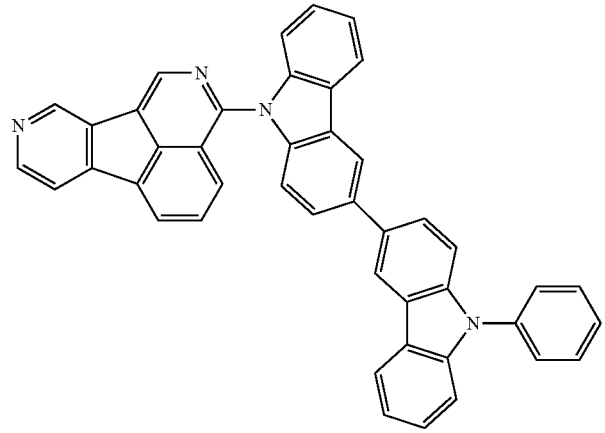
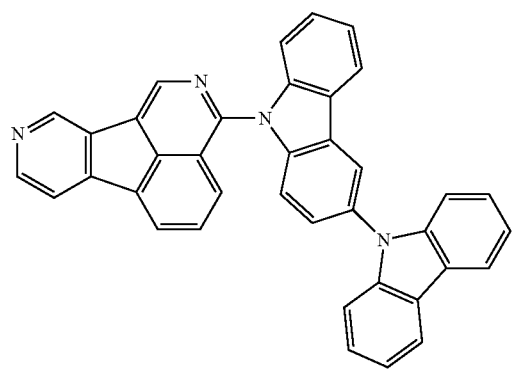
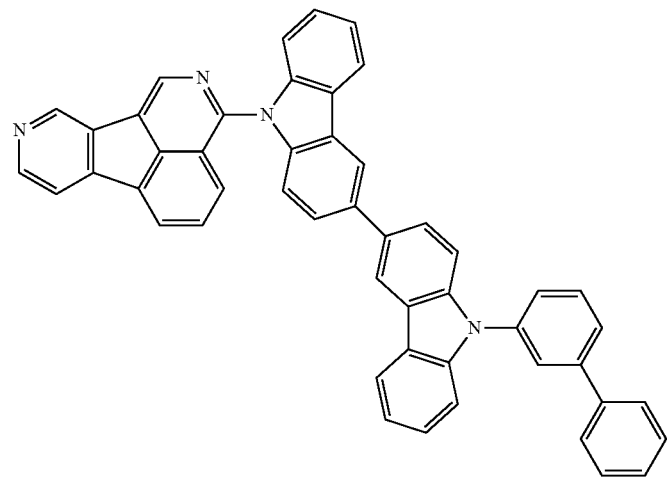
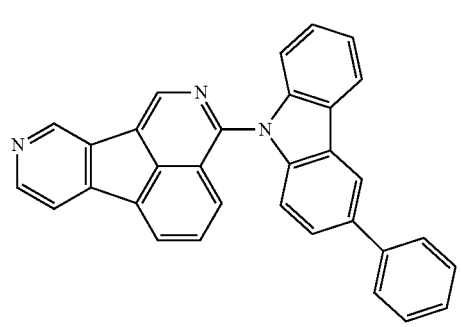
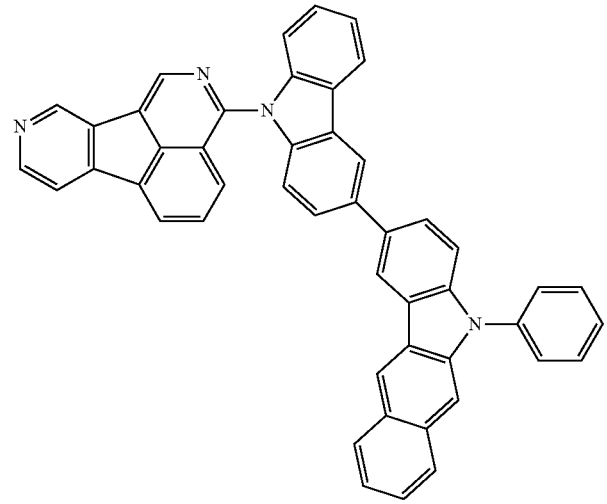

-continued
261
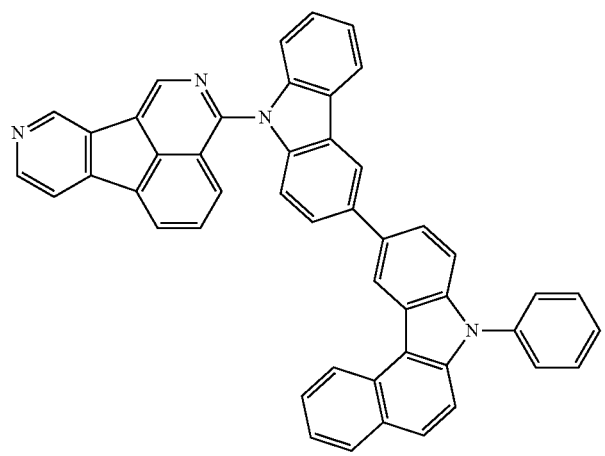
262
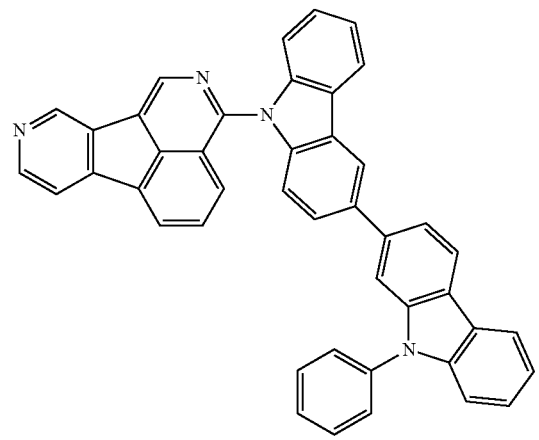
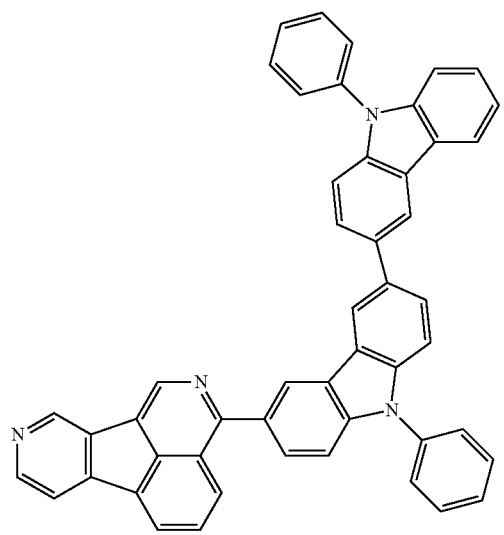
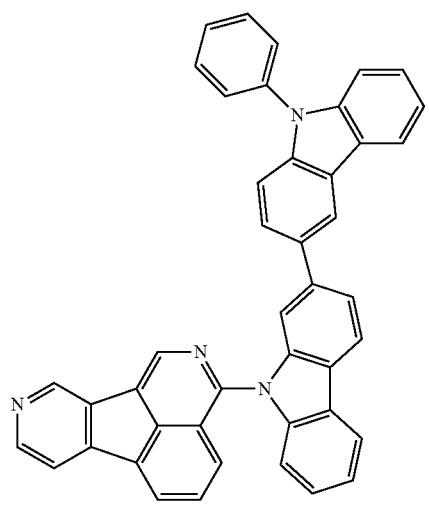
[Chem. 74]
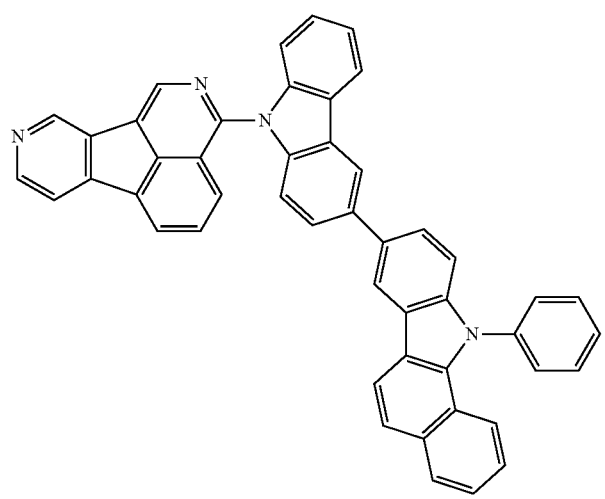

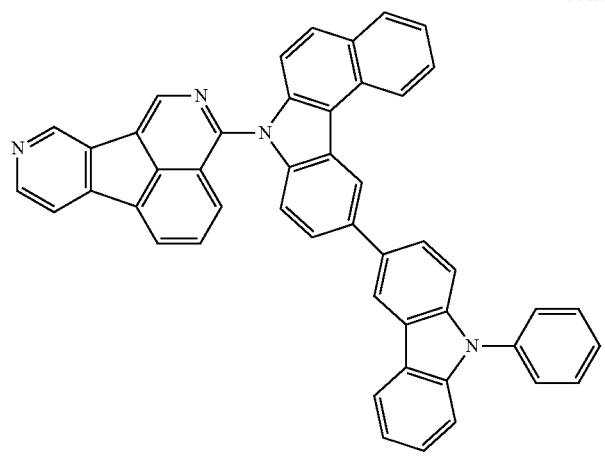
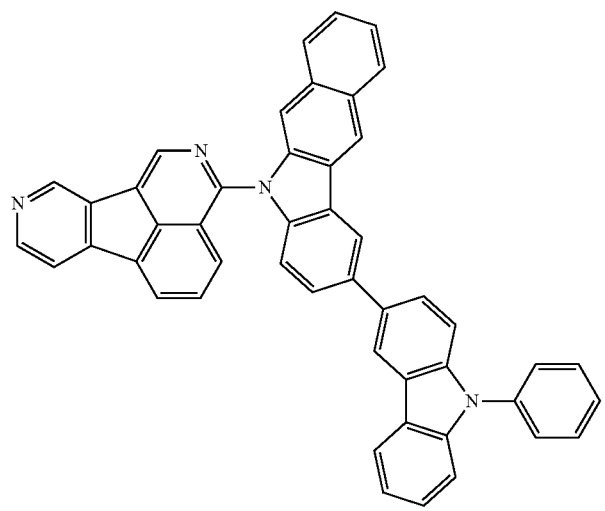
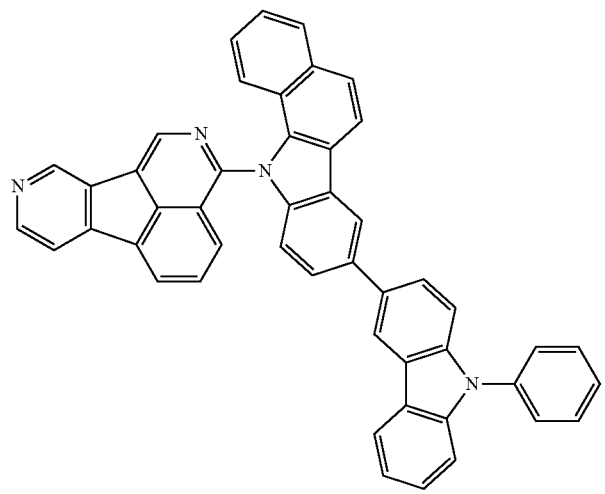

-continued
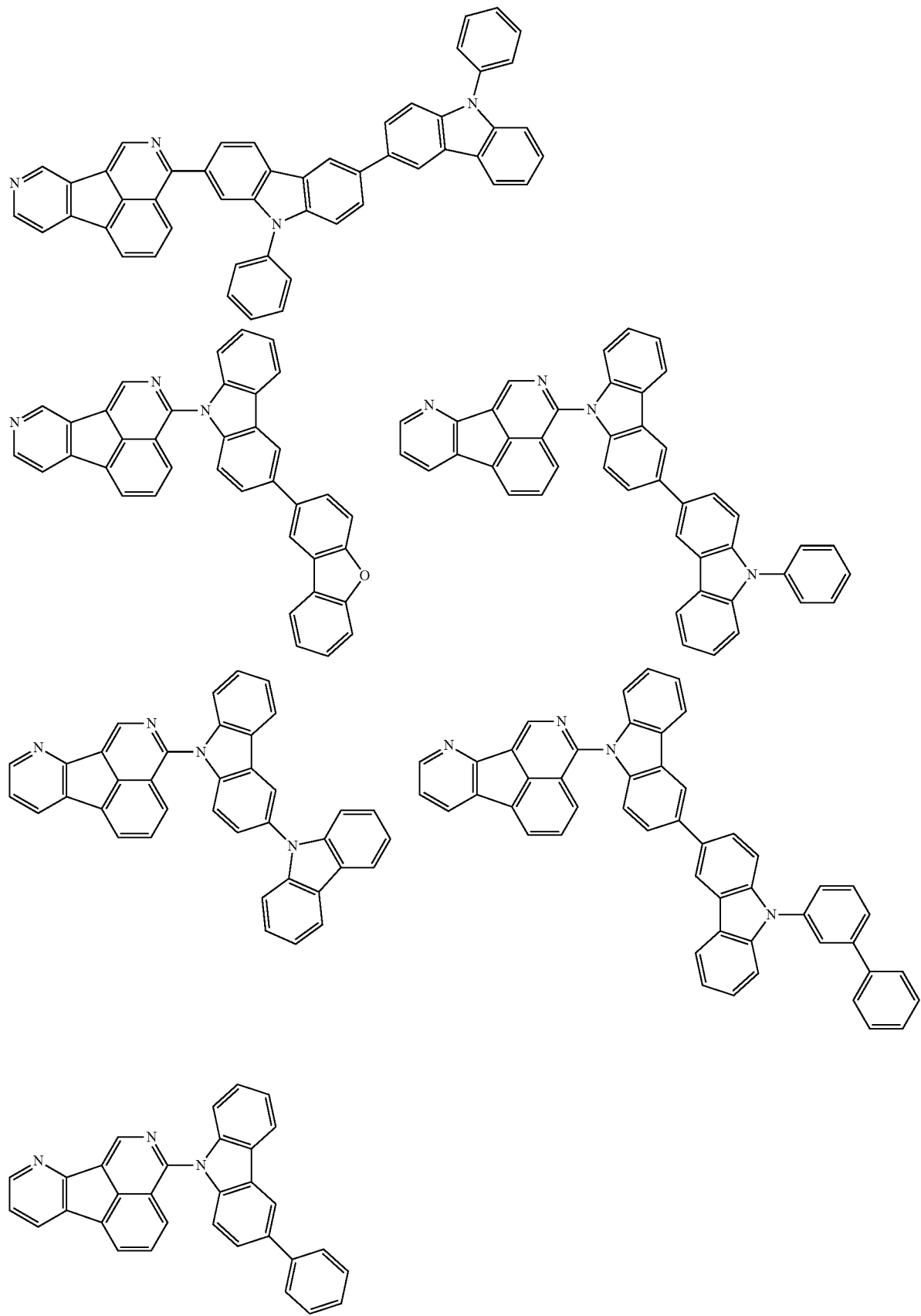

[Chem. 75]
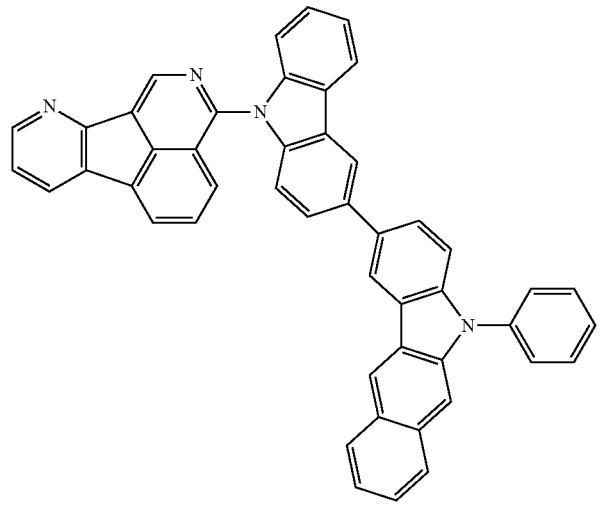
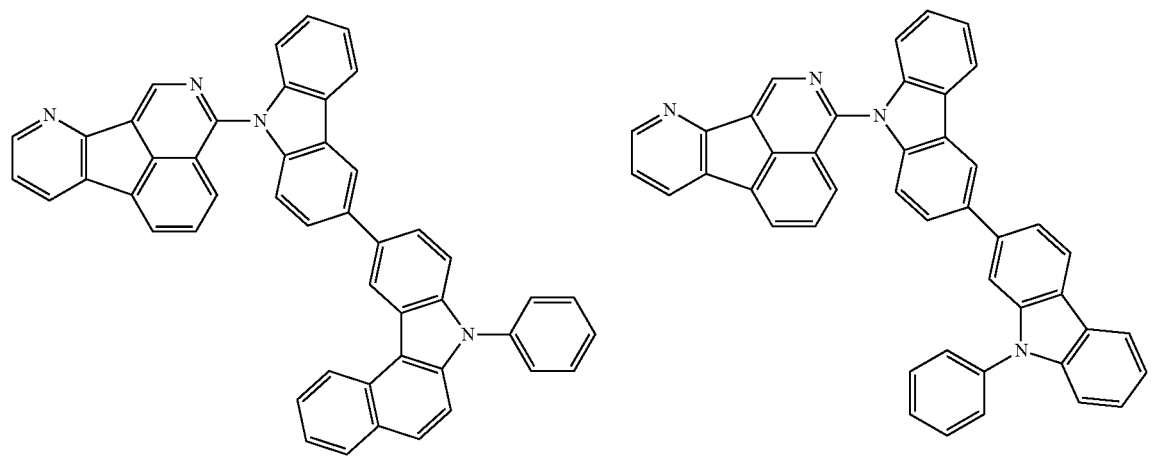
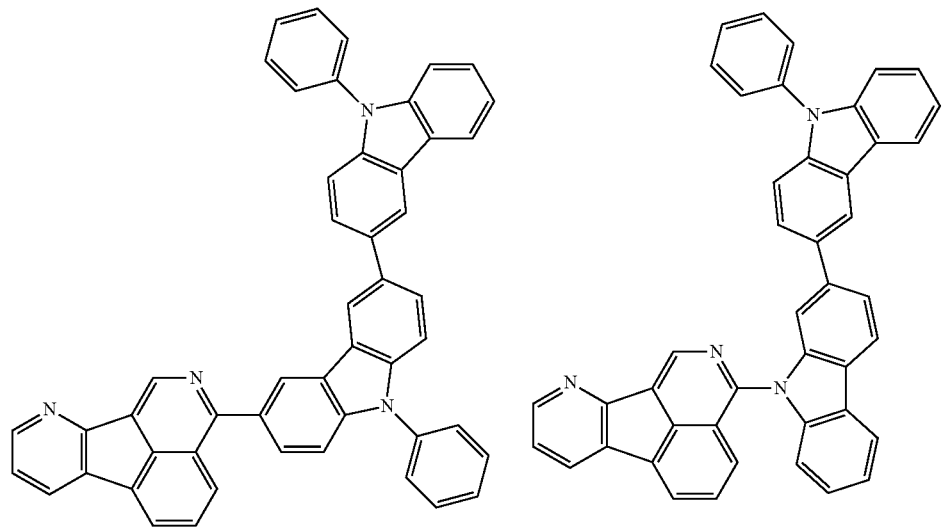

-continued
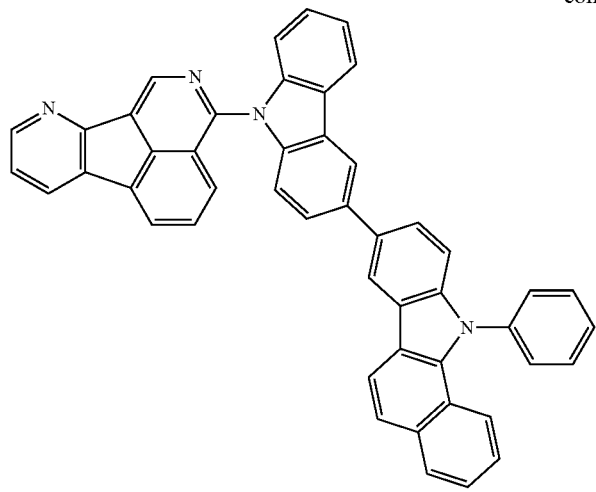
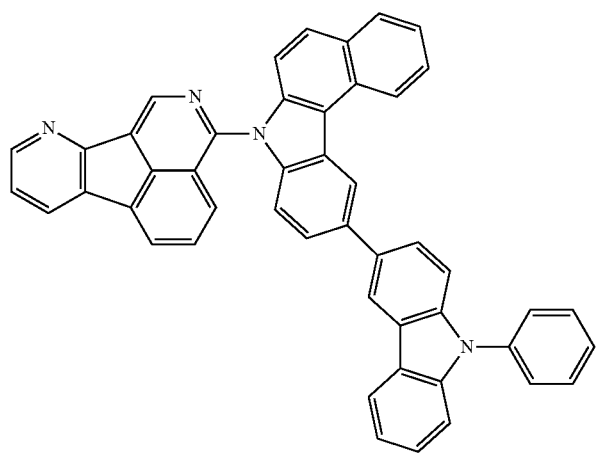
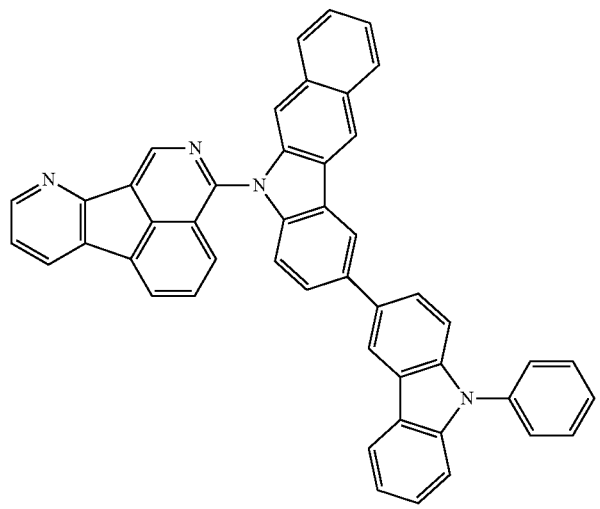

271
272
-continued
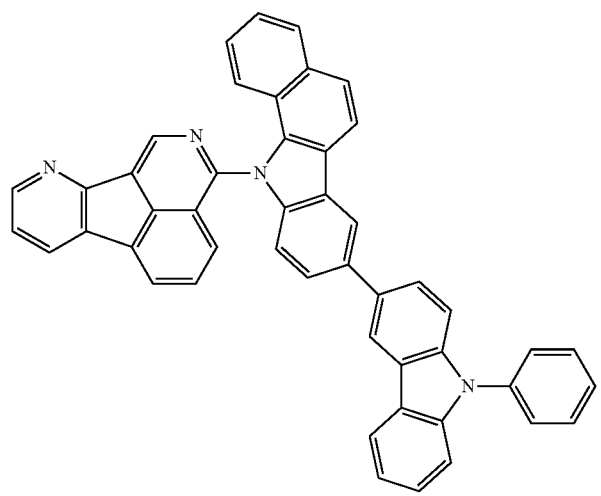
[Chem. 76]
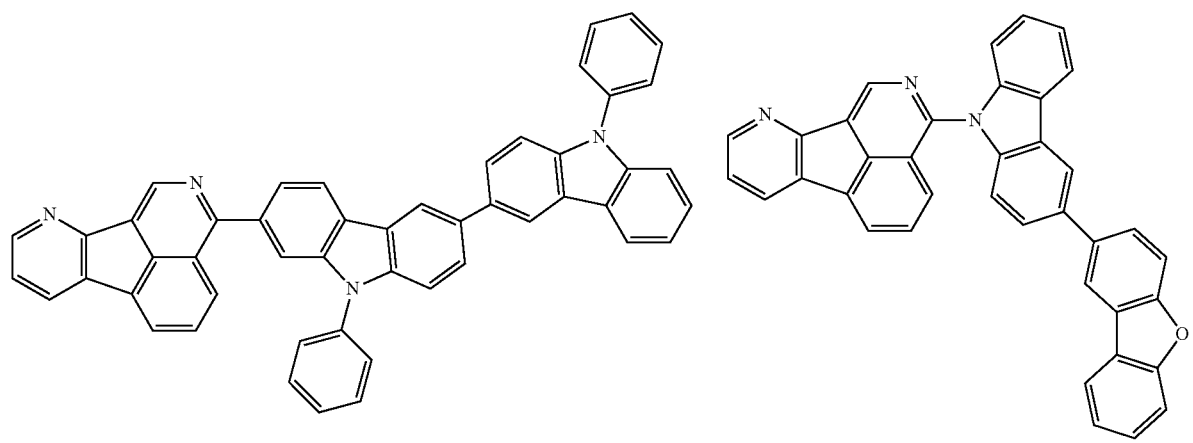
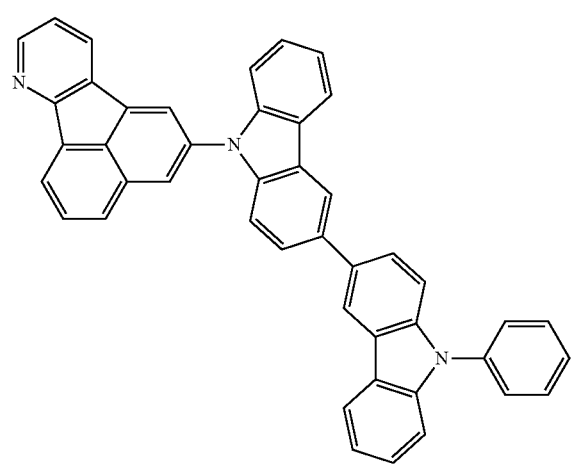
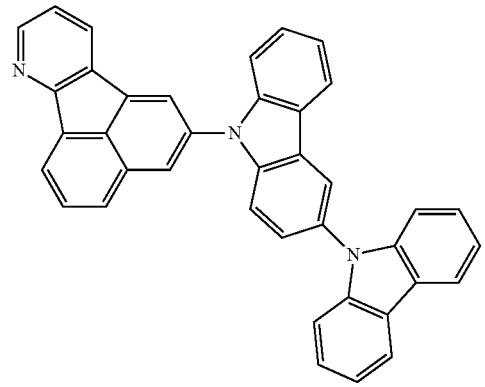

273
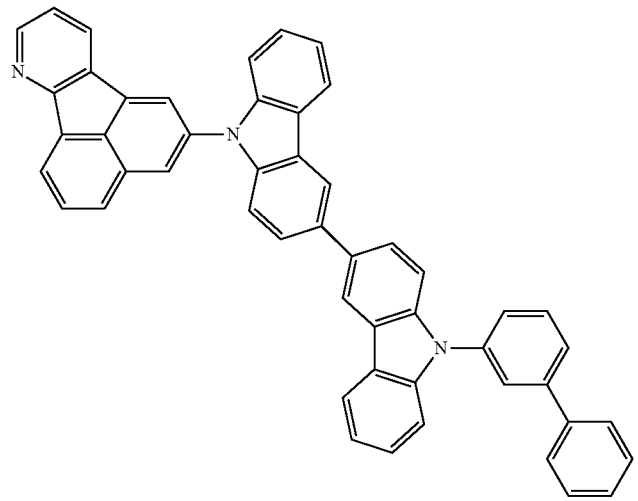
274
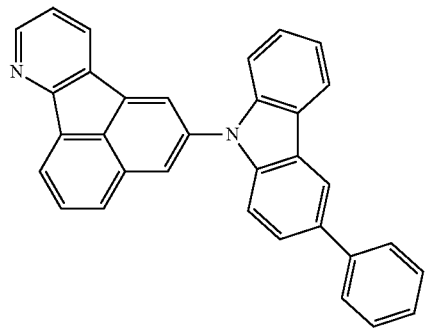
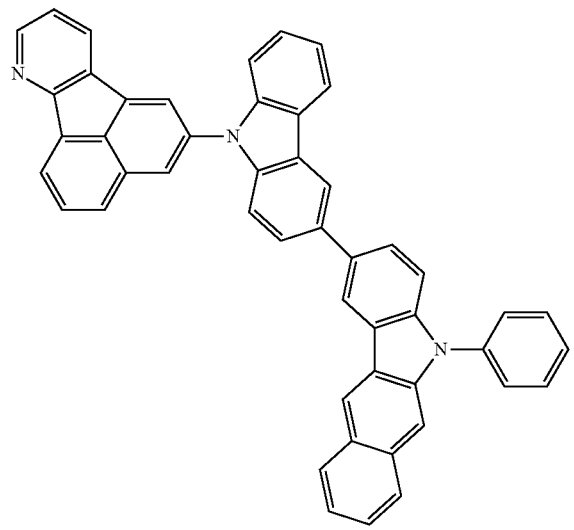
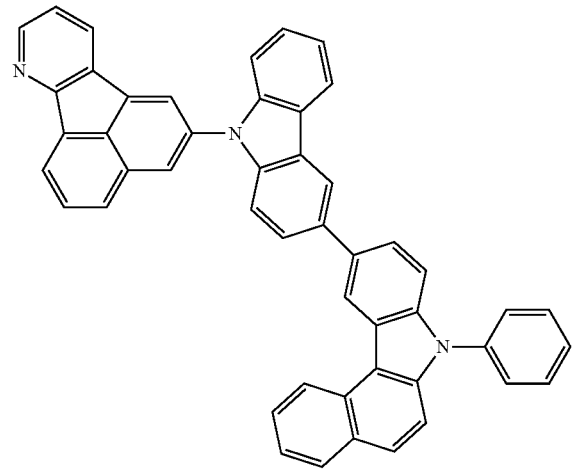
[Chem. 77]
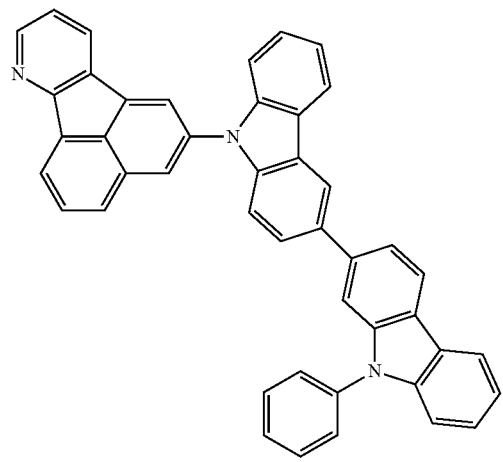
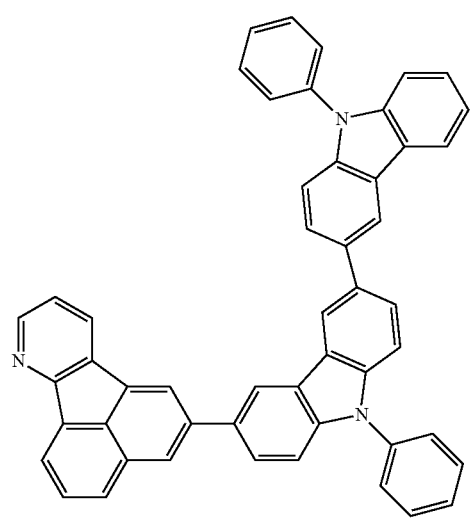

275 276
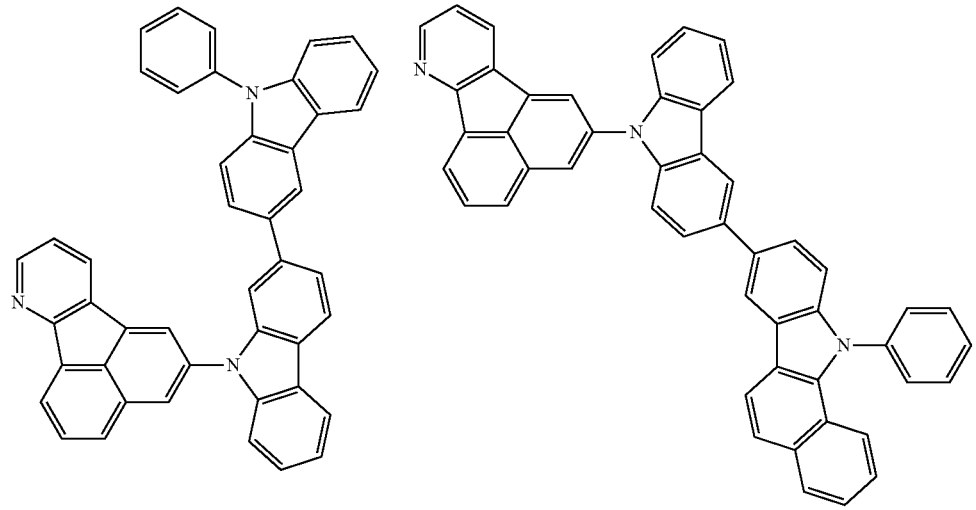
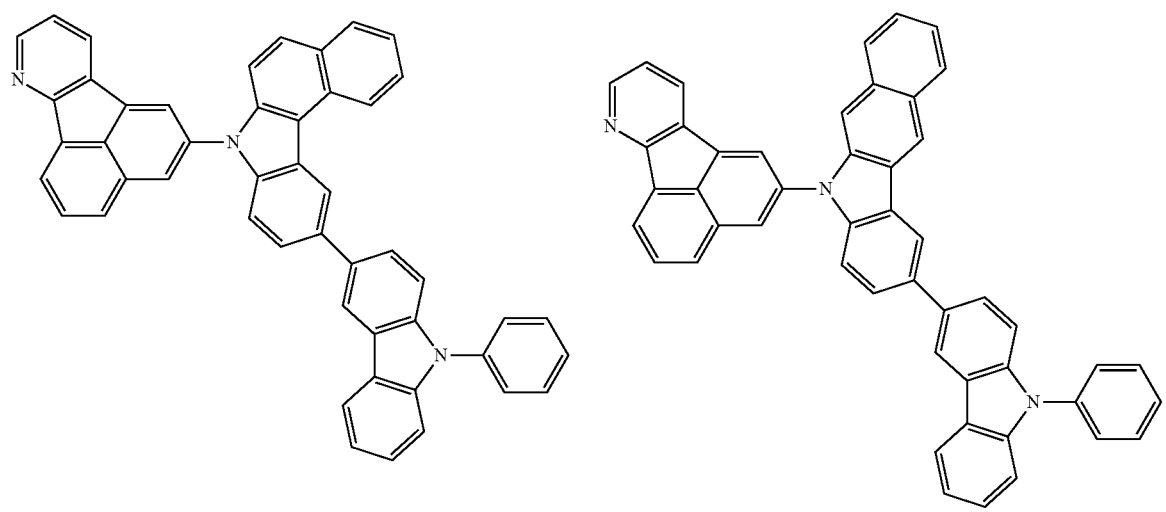
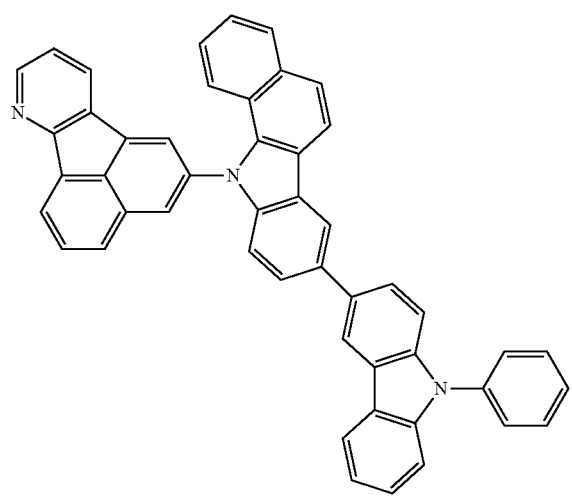

-continued
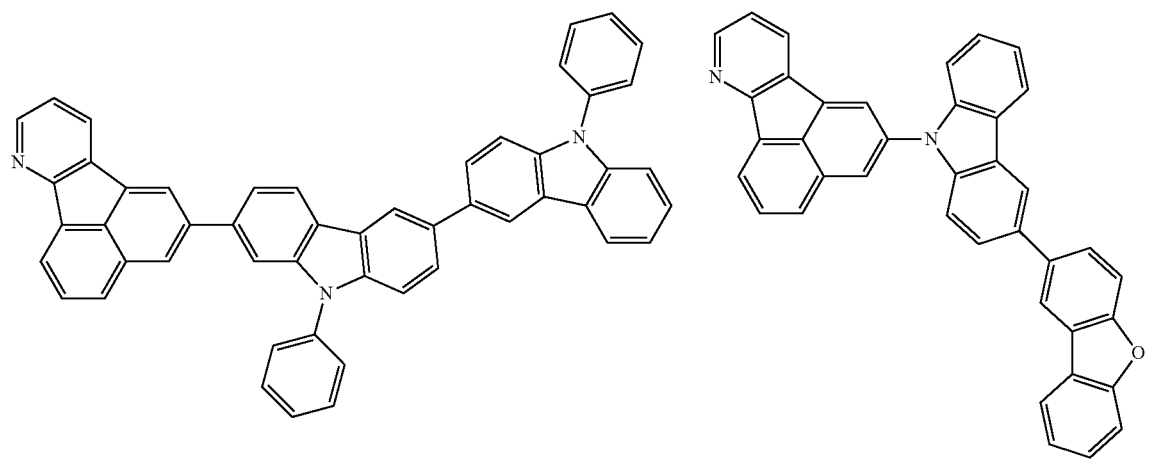
[Chem. 78]
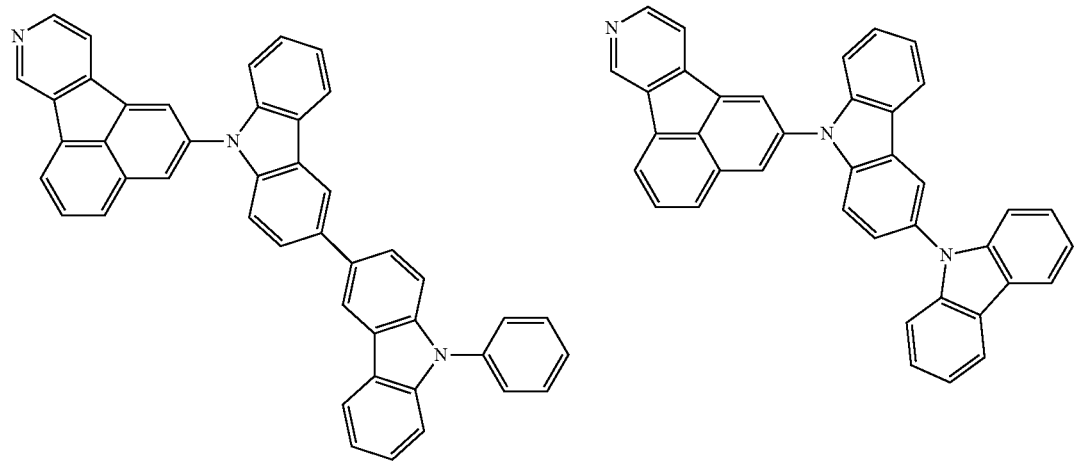
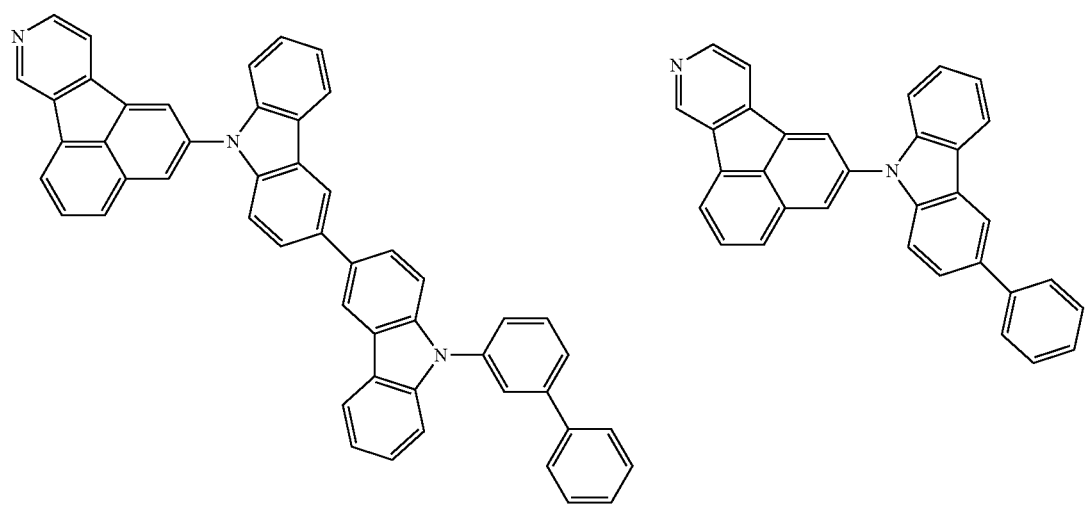

-continued
279
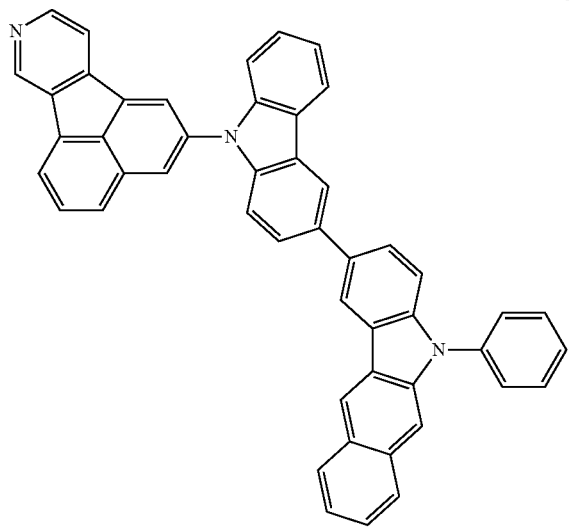
280
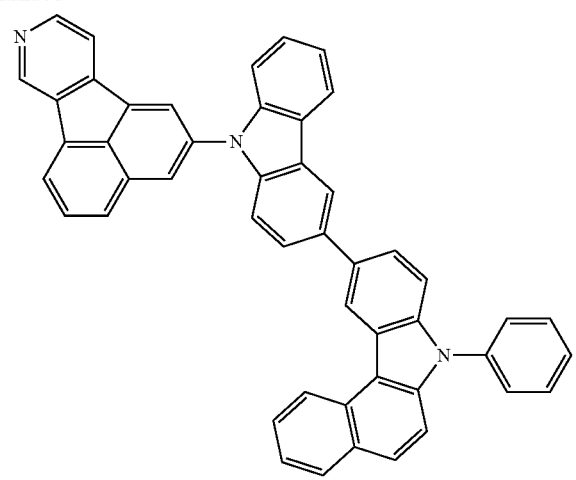
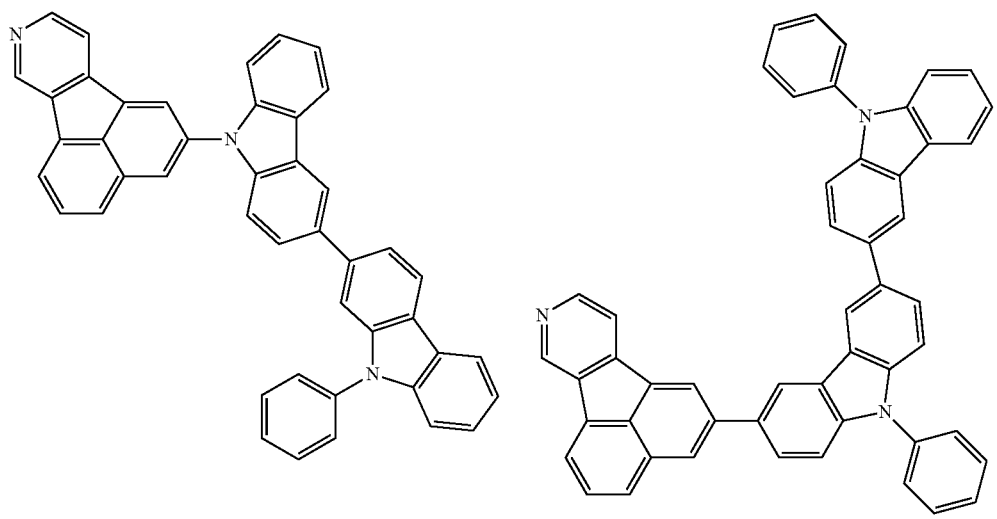
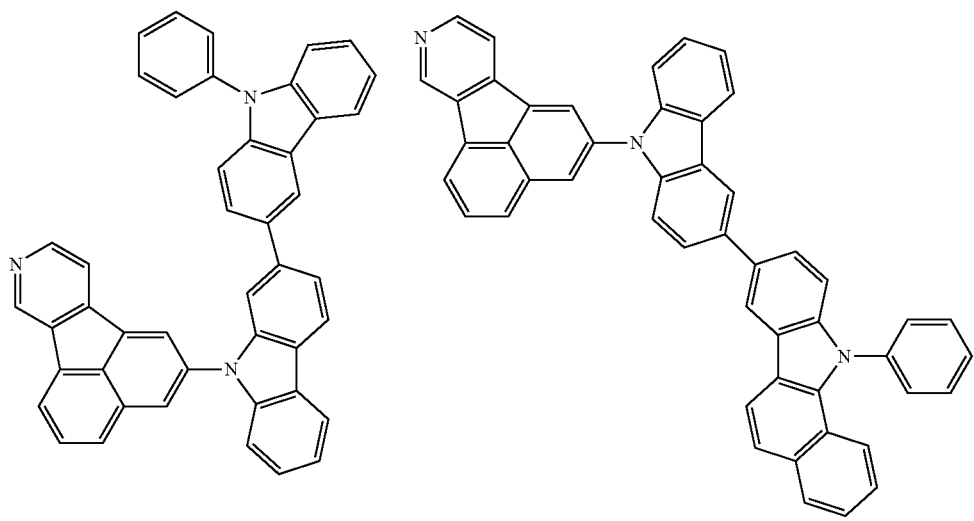

281
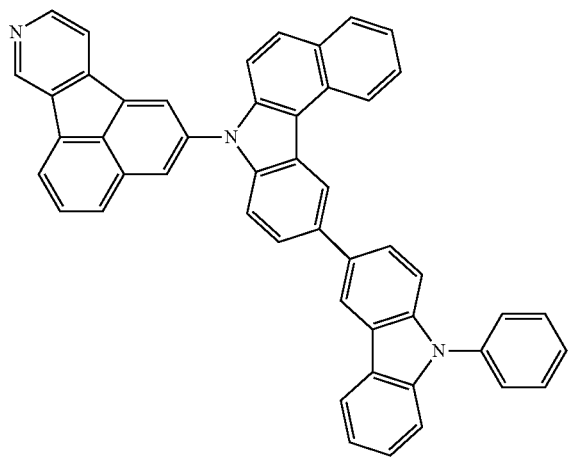
282
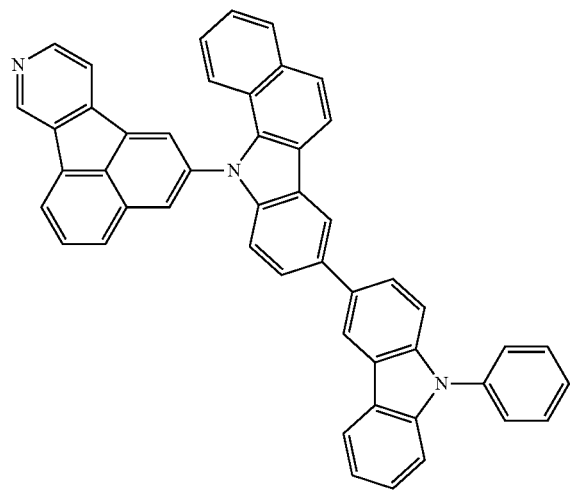
[Chem. 79]
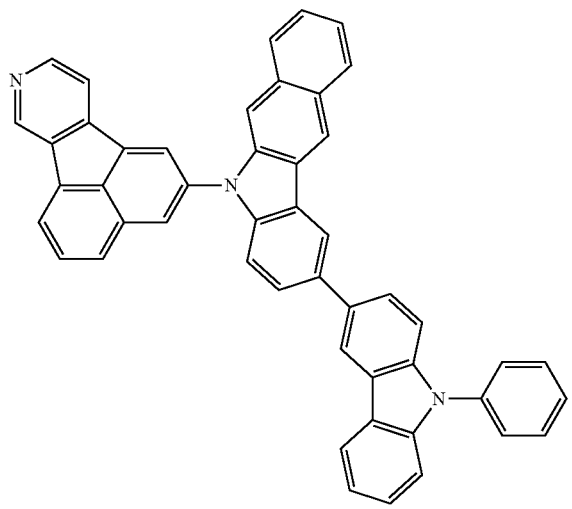
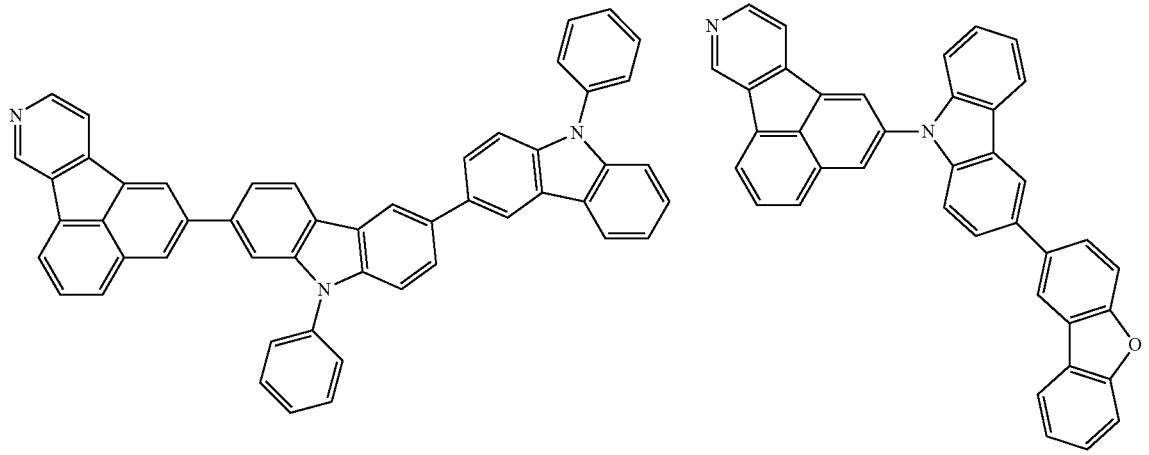

-continued
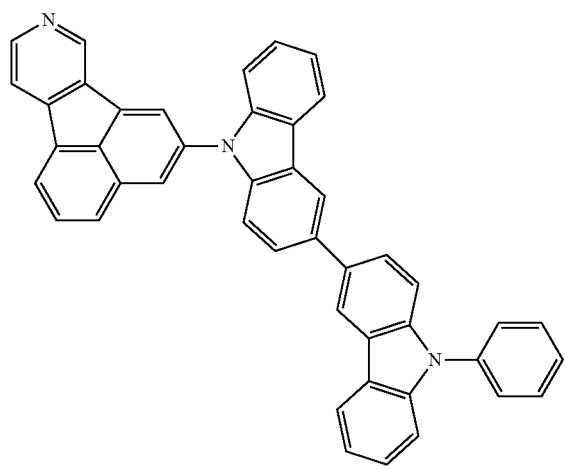
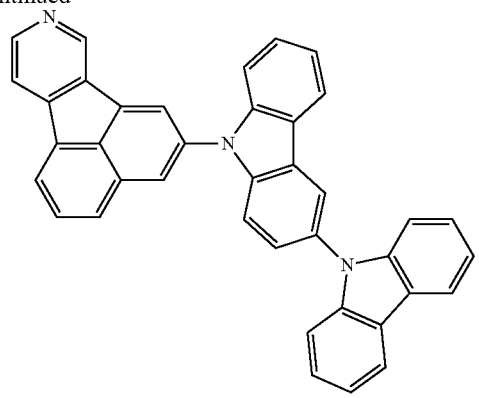
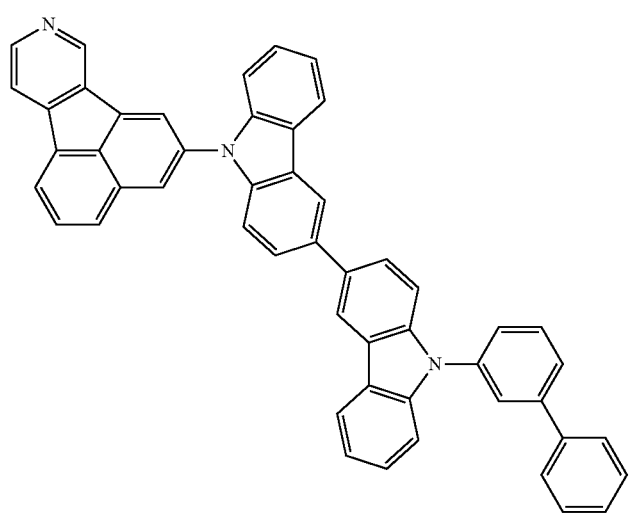
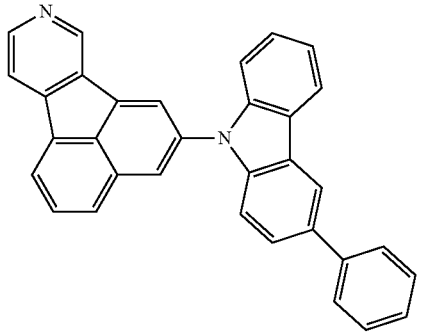
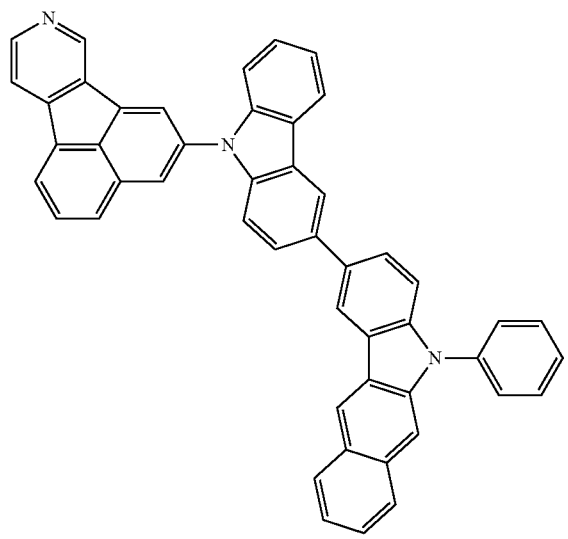
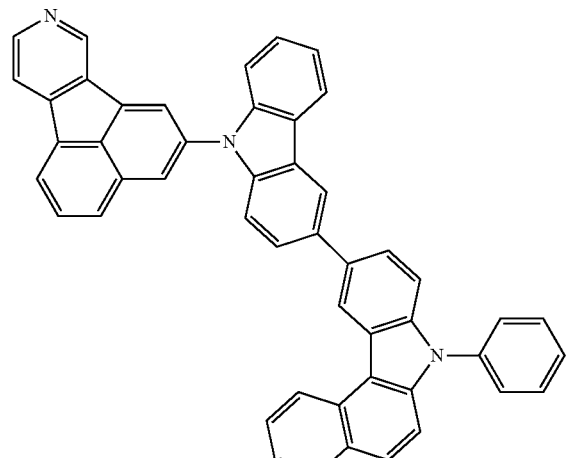

[Chem. 80]
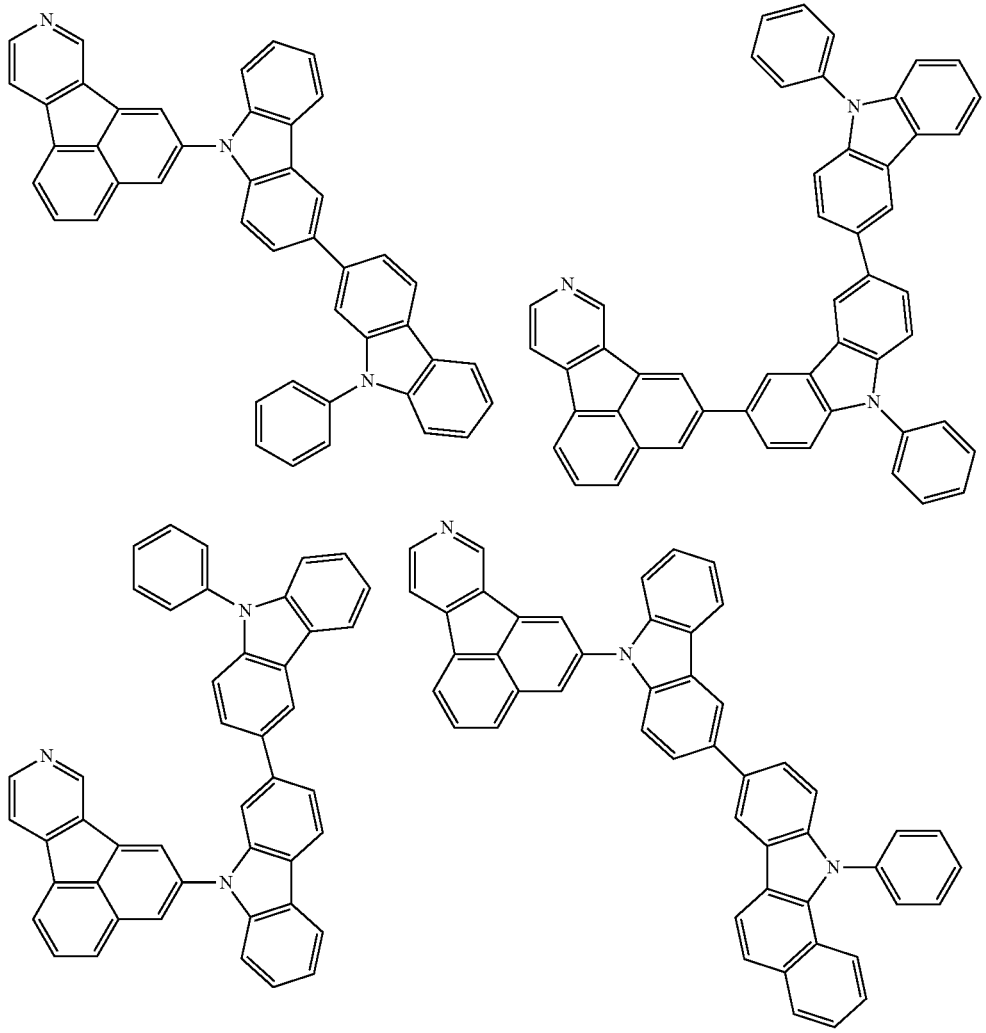
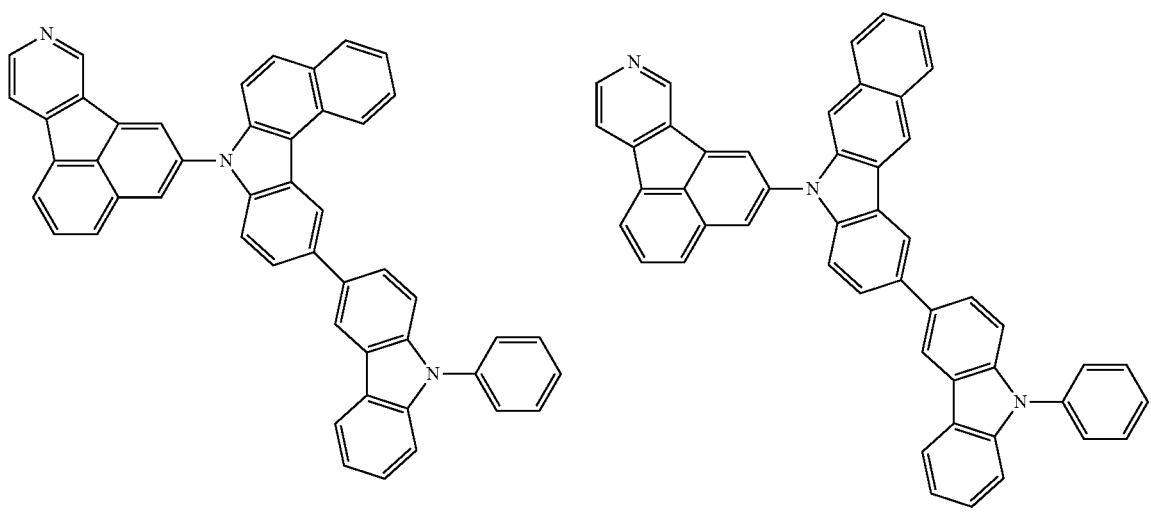

287
288
-continued
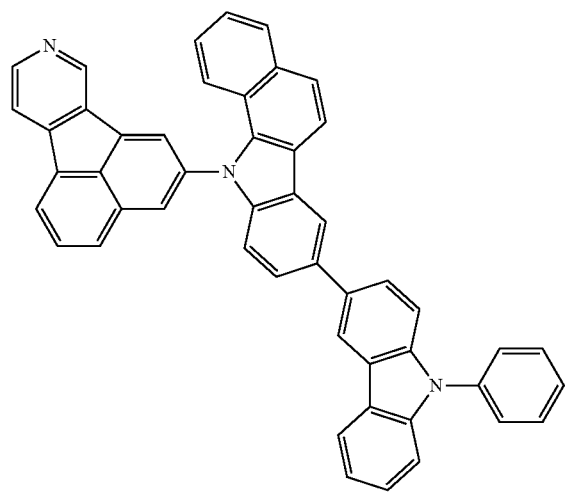
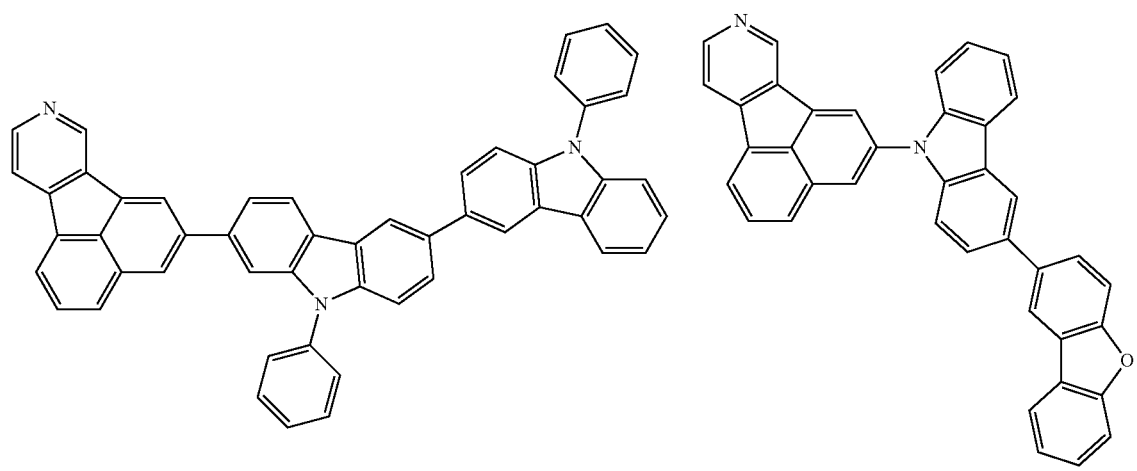
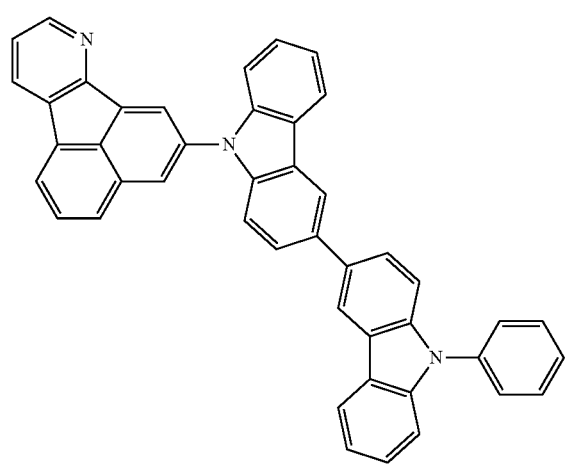

[Chem. 81]
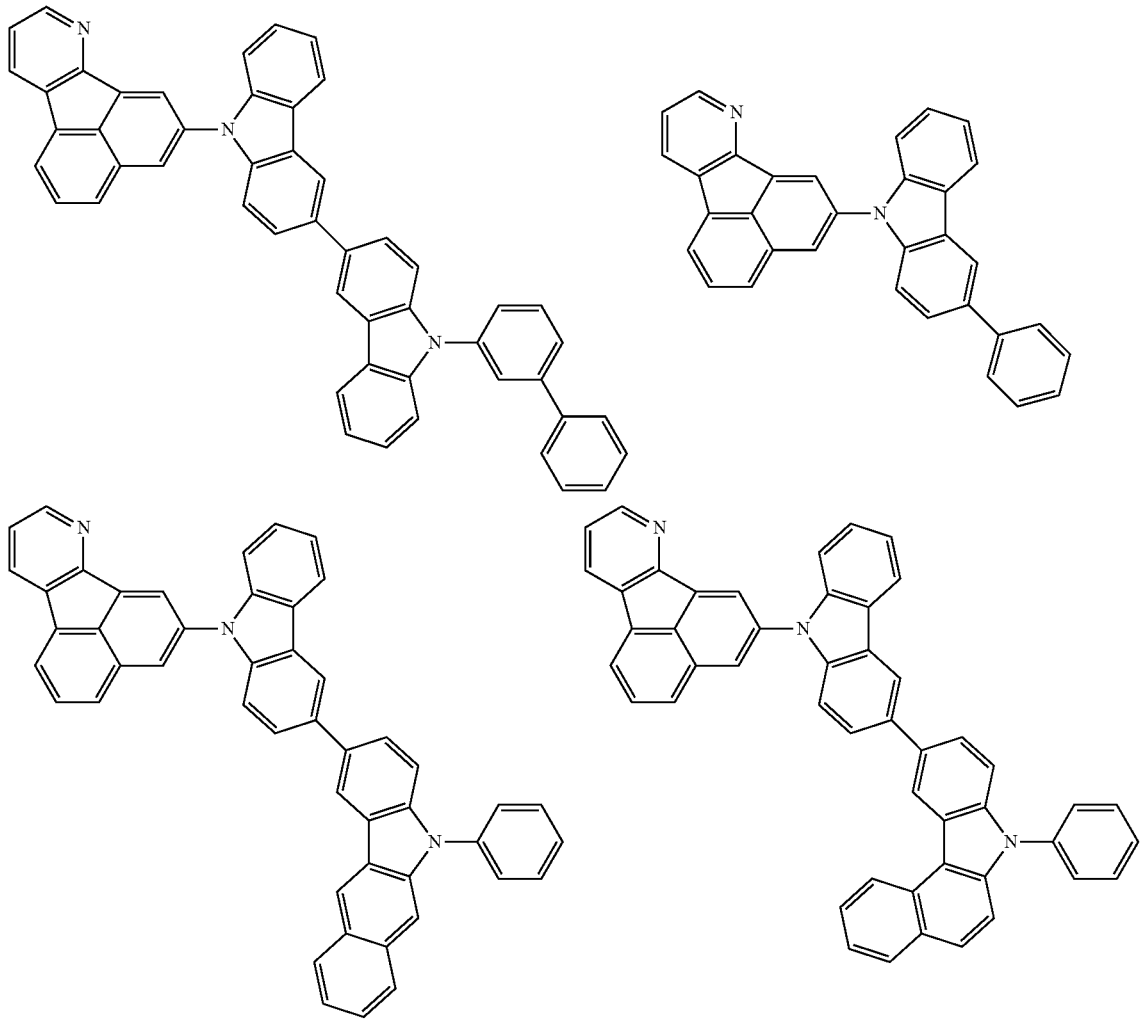
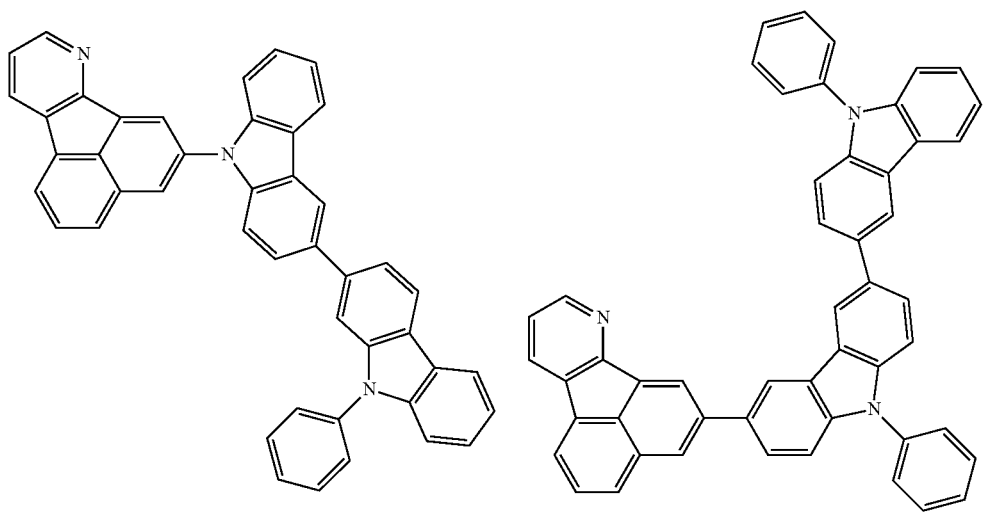

291
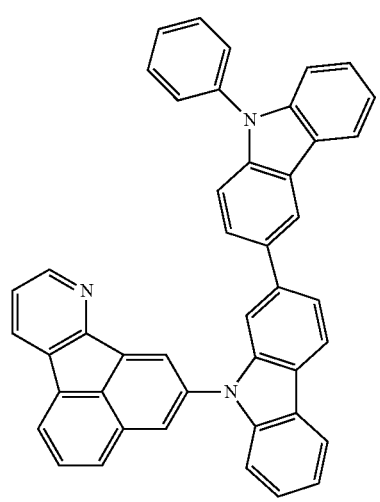
292
-continued
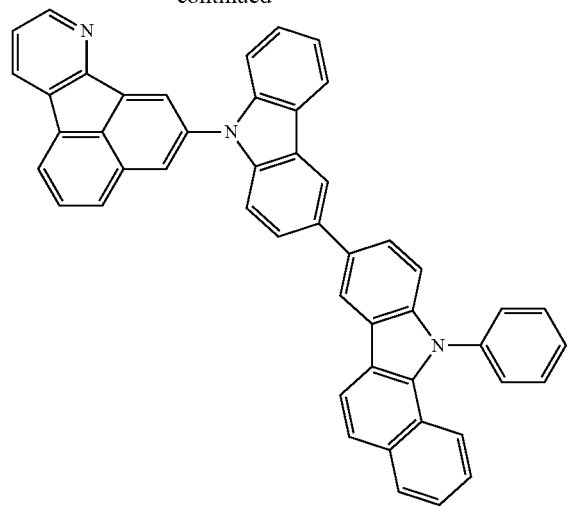
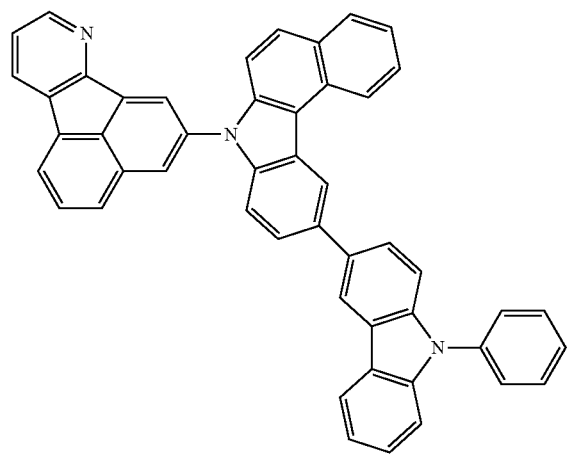
[Chem. 82]
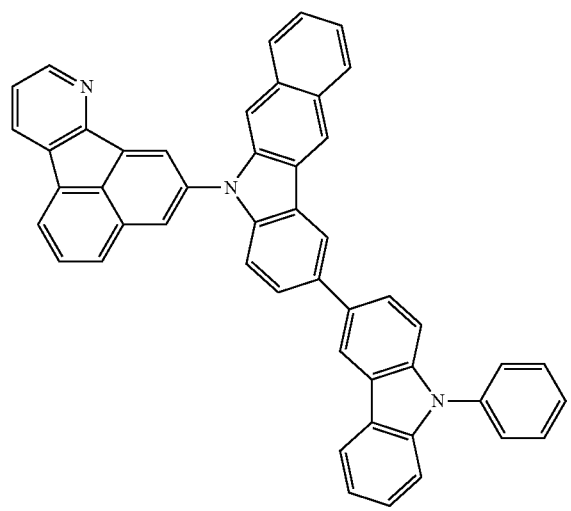
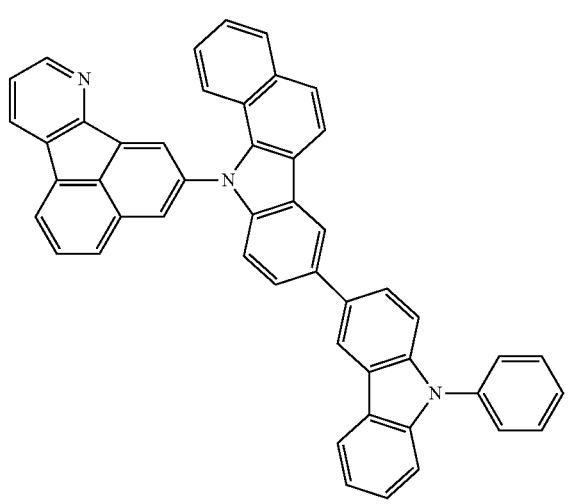

293 294
-continued
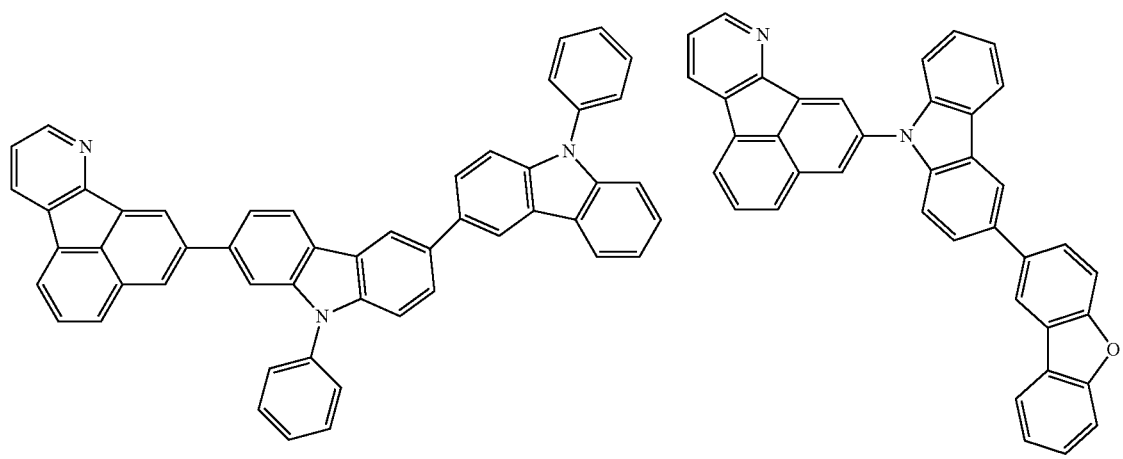
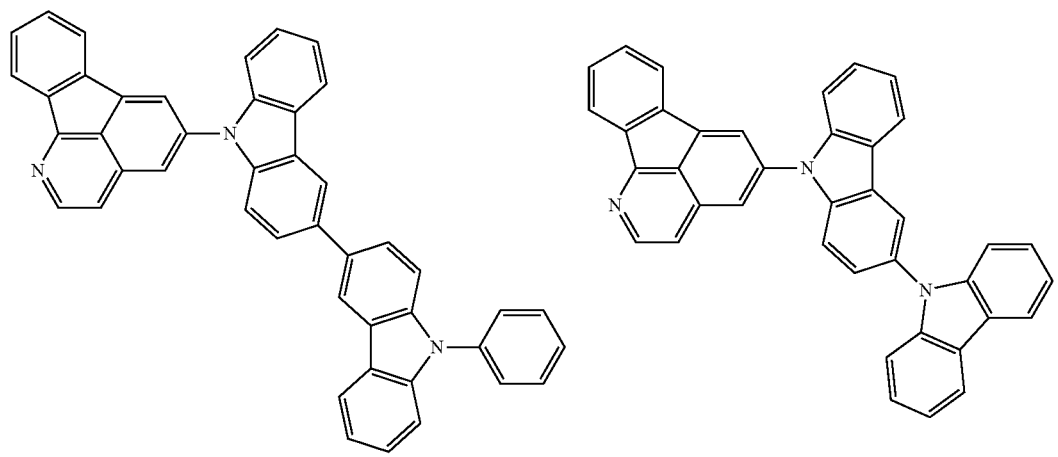
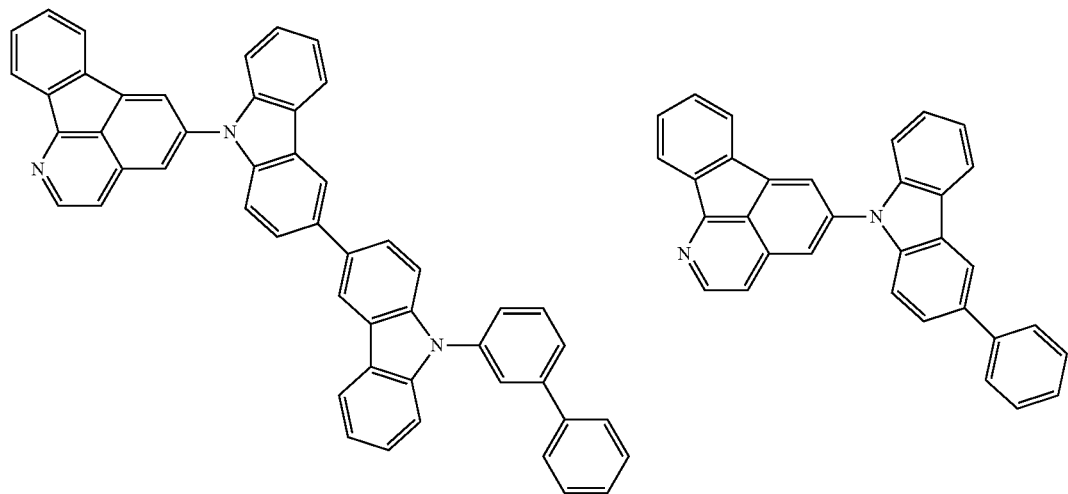

295
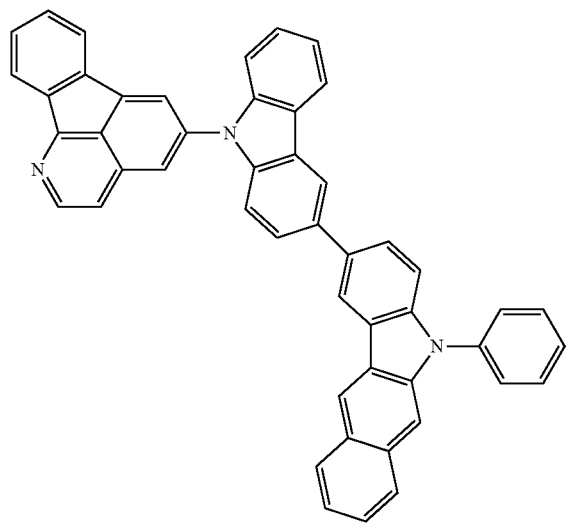
296
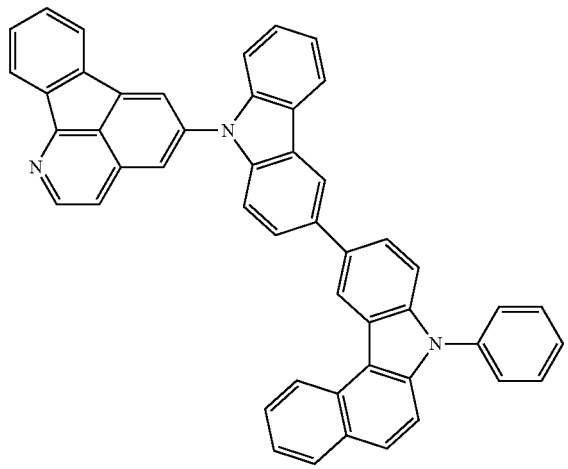
[Chem. 83]
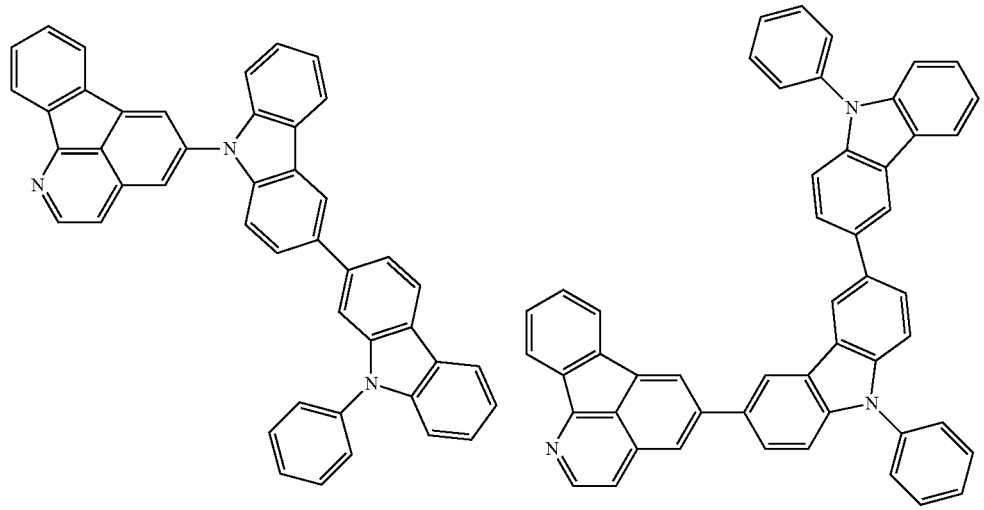
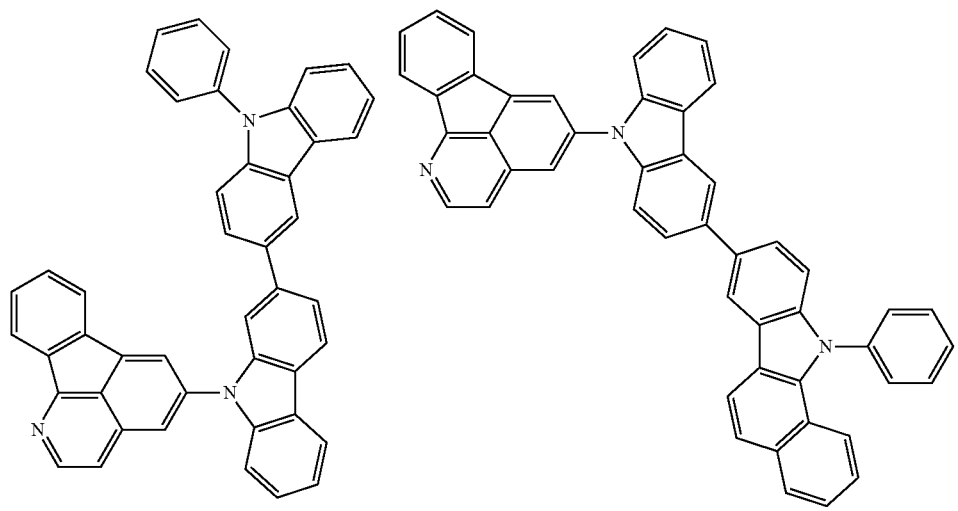

-continued
297 298
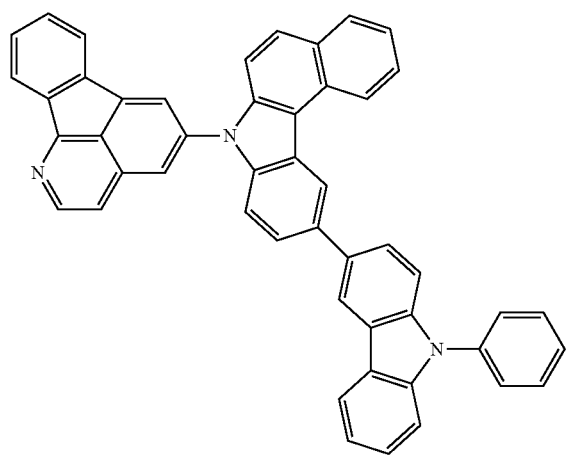 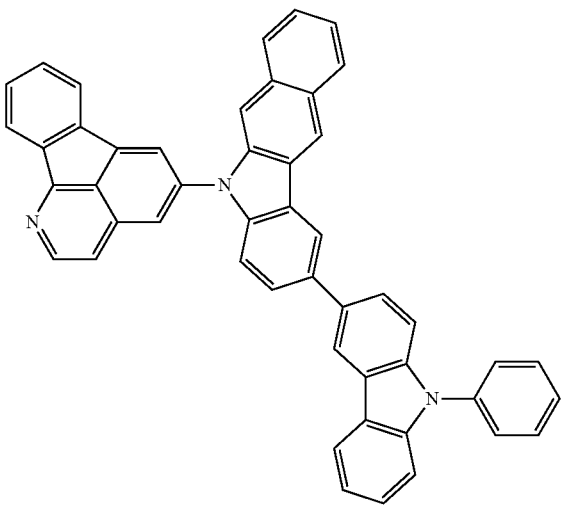
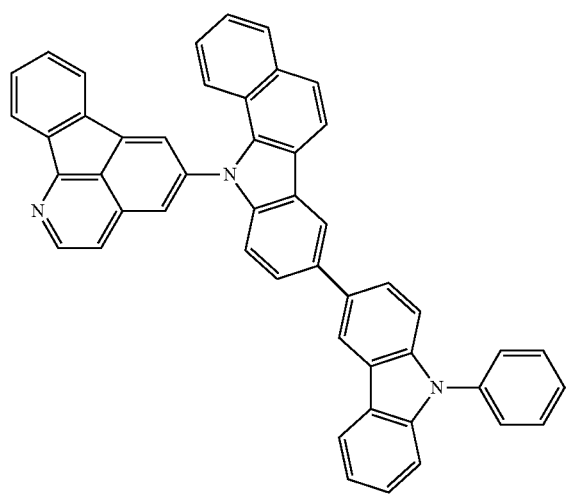
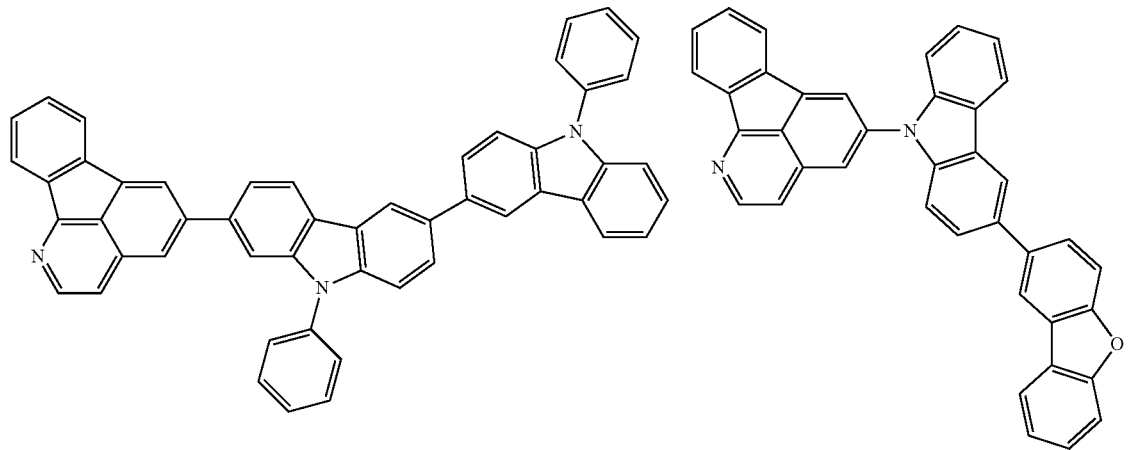

299
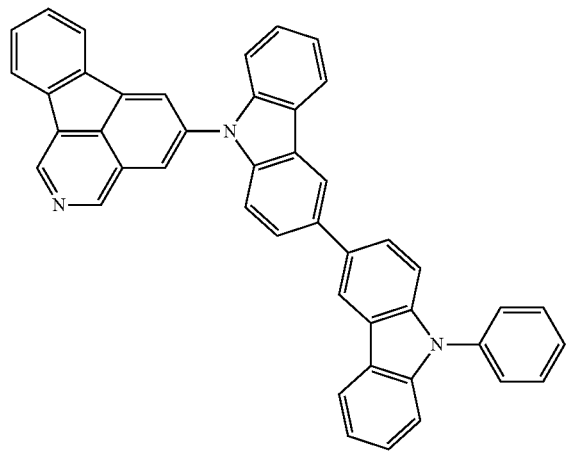
300
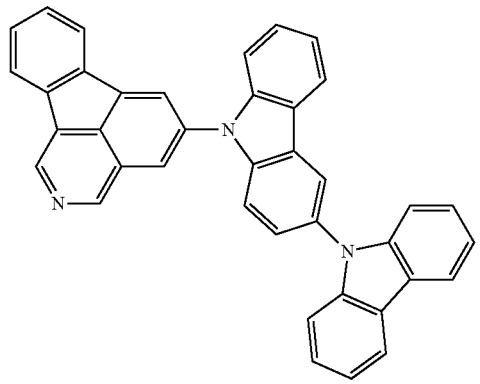
[Chem. 84]
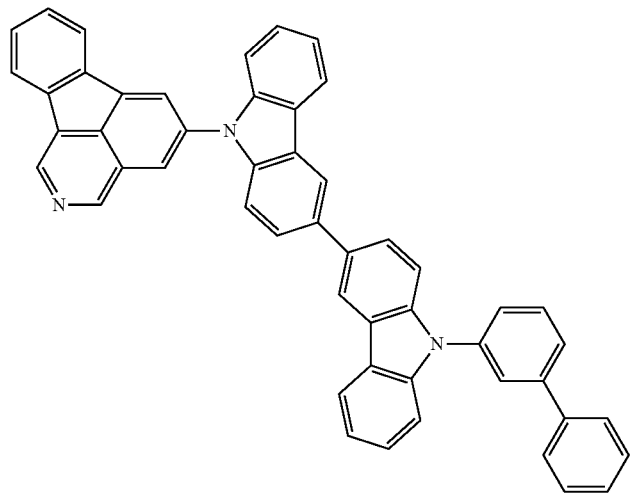
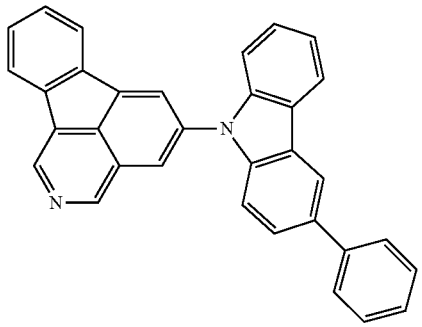
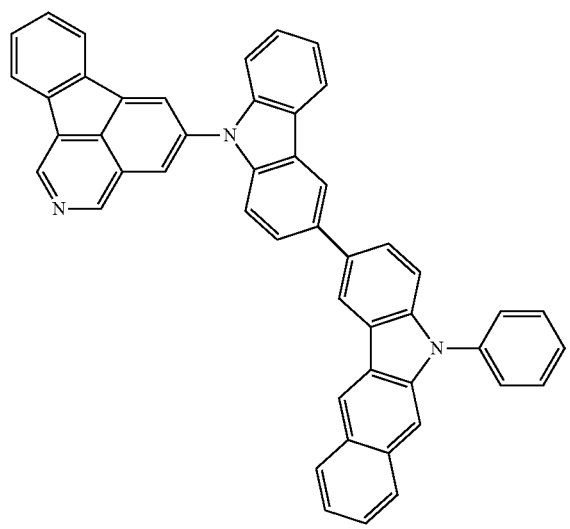
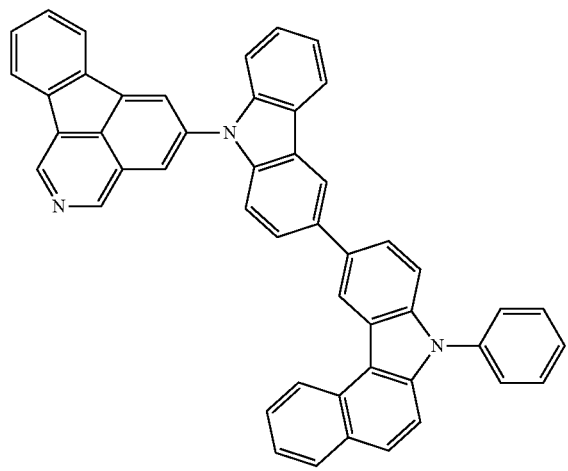

-continued
301 302
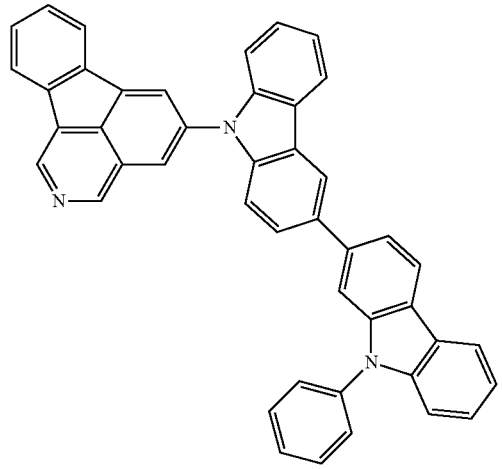 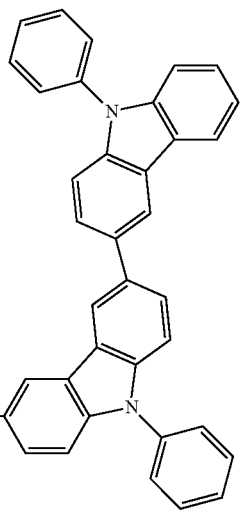
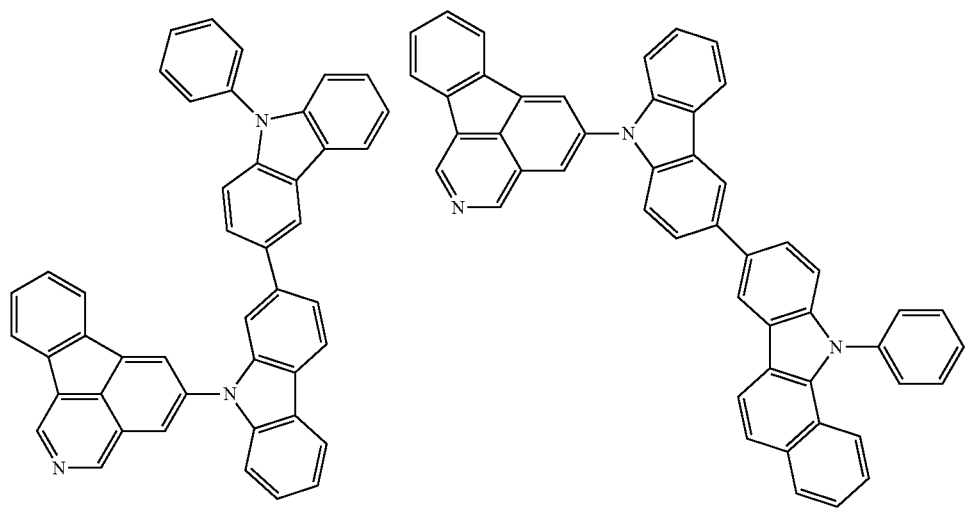
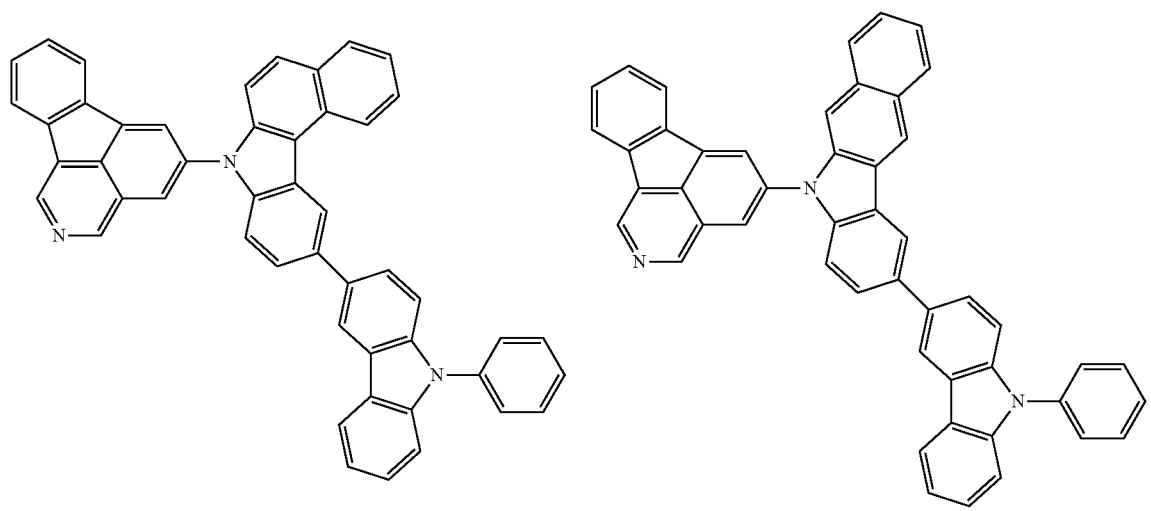

303
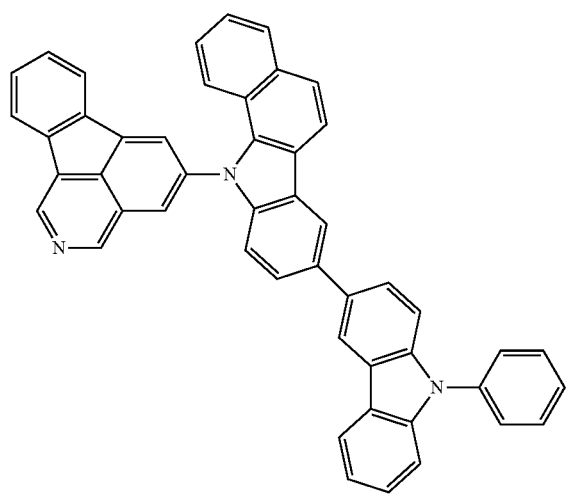
304
-continued
[Chem. 85]
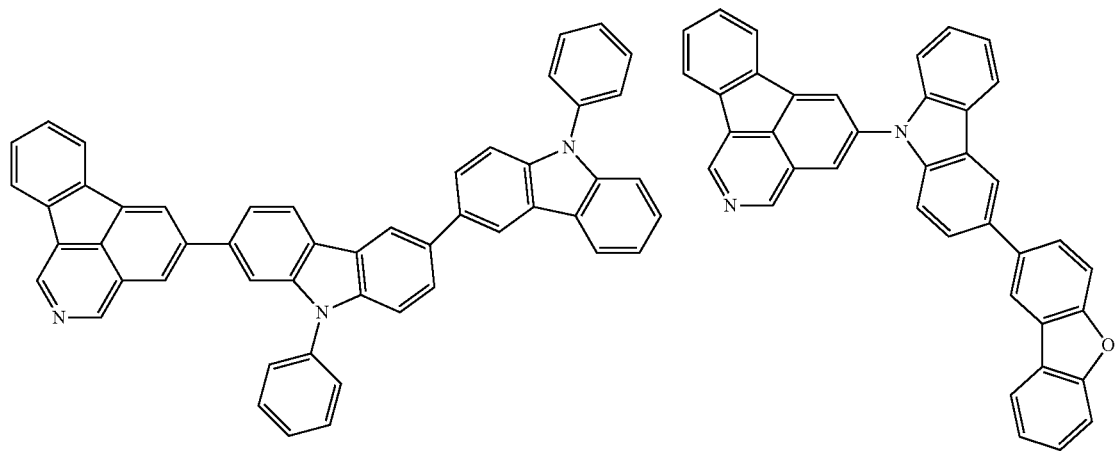
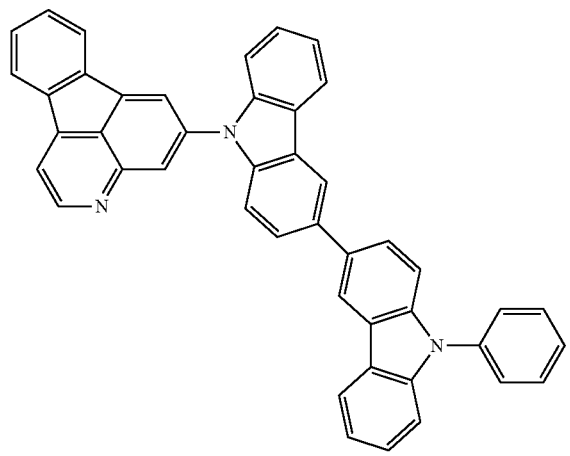
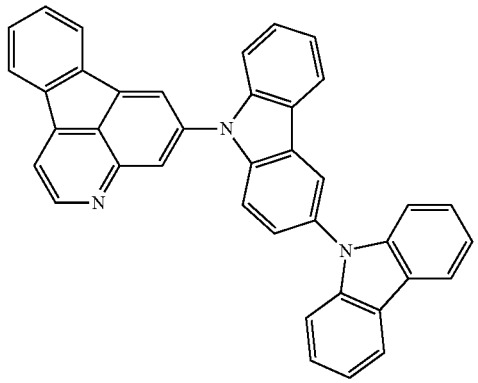

-continued
305
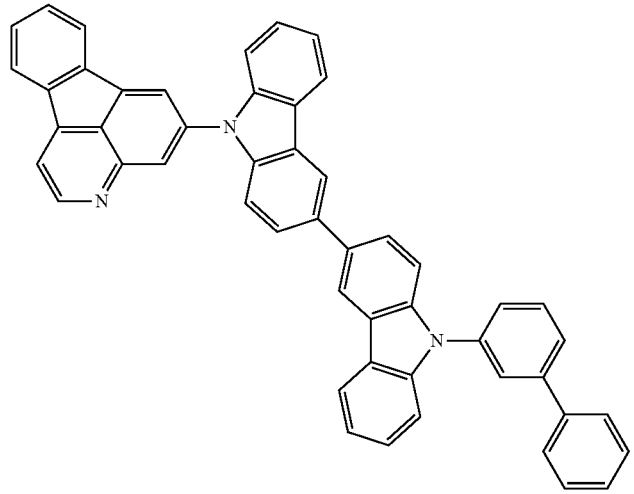
306
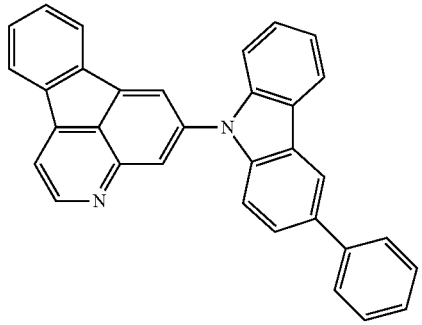
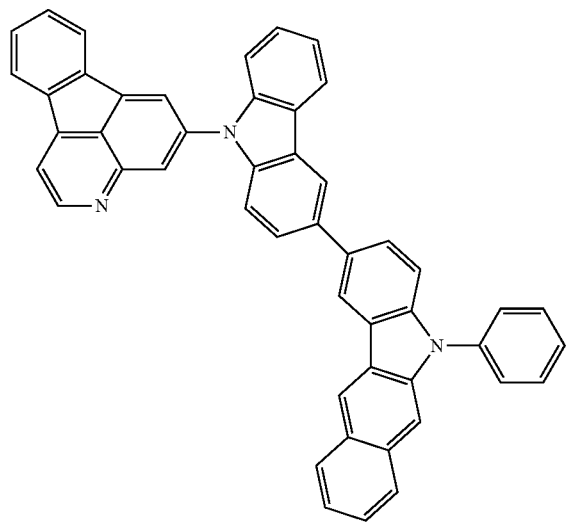
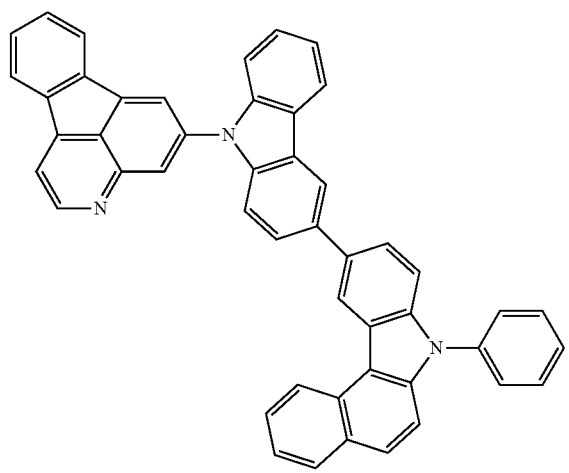
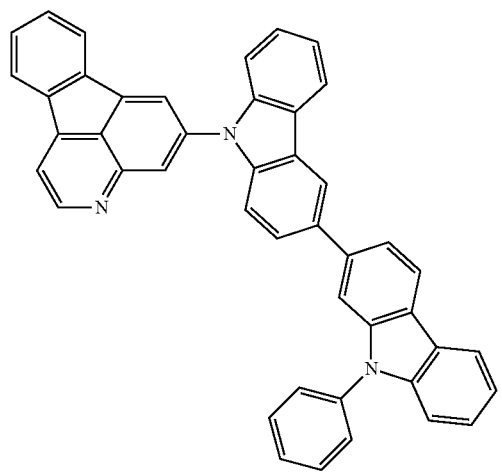
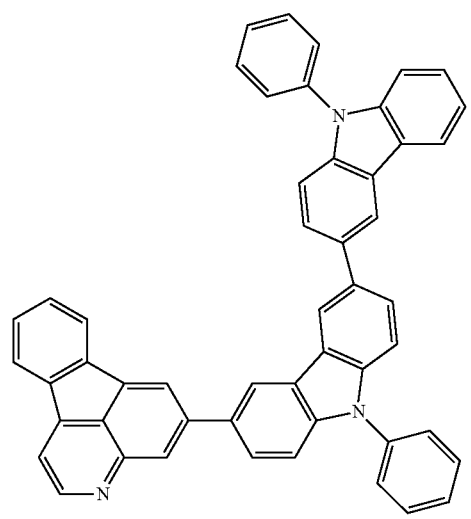

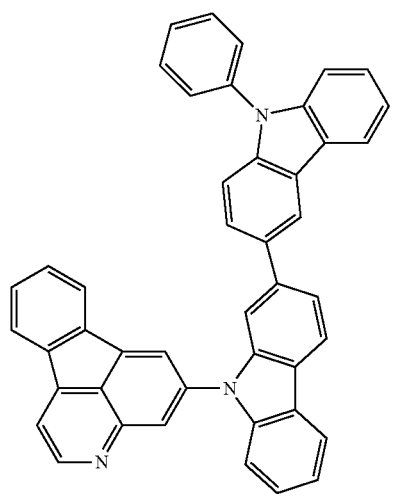
[Chem. 86]
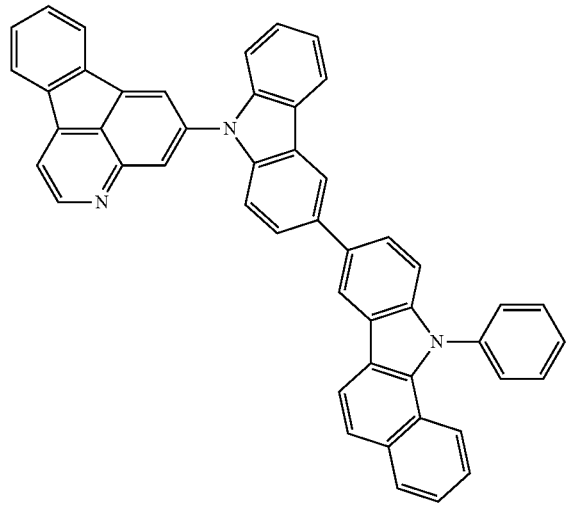
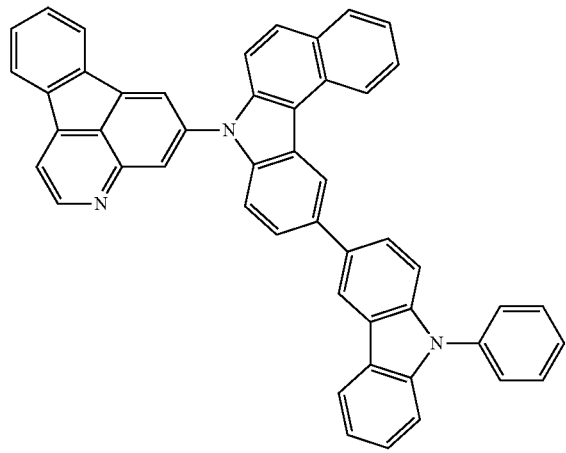
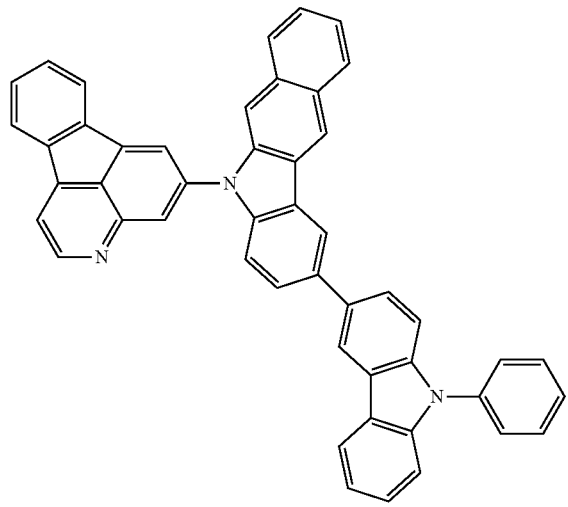
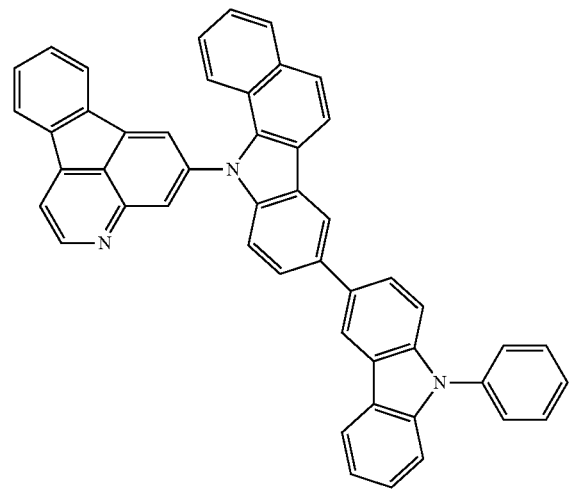

309                                                310
-continued
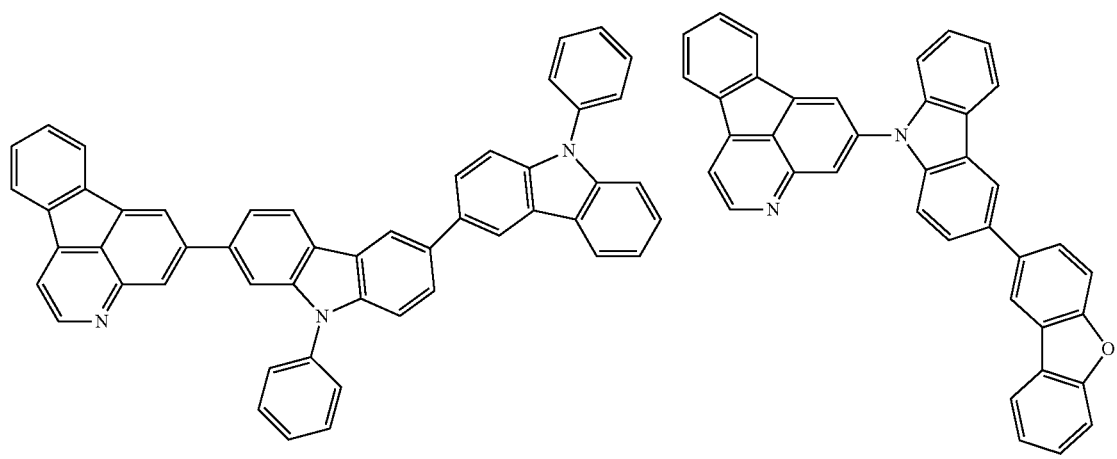
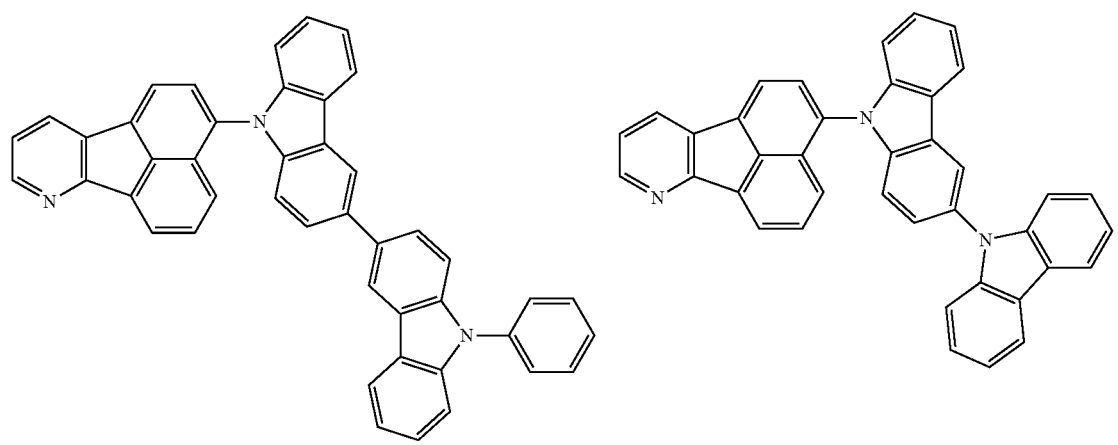
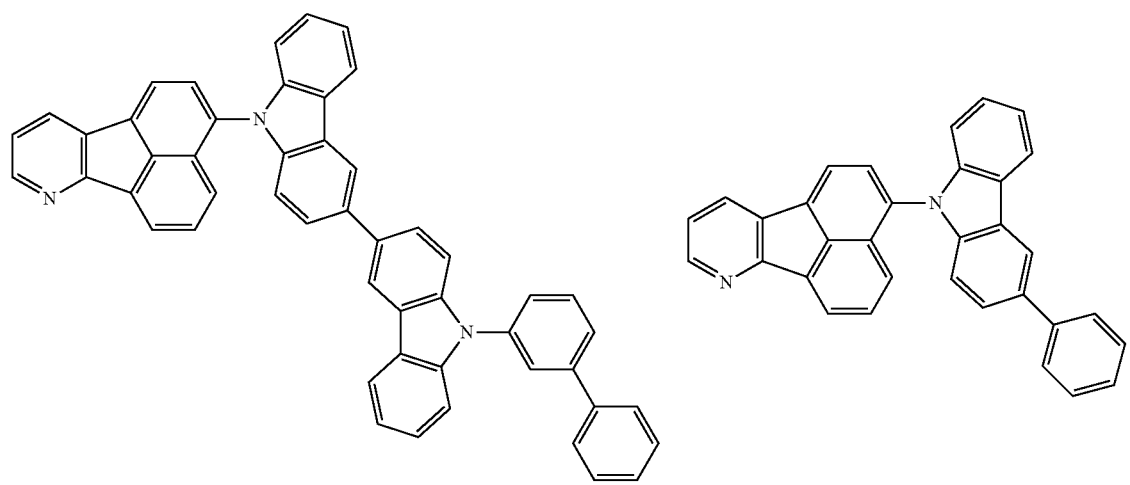

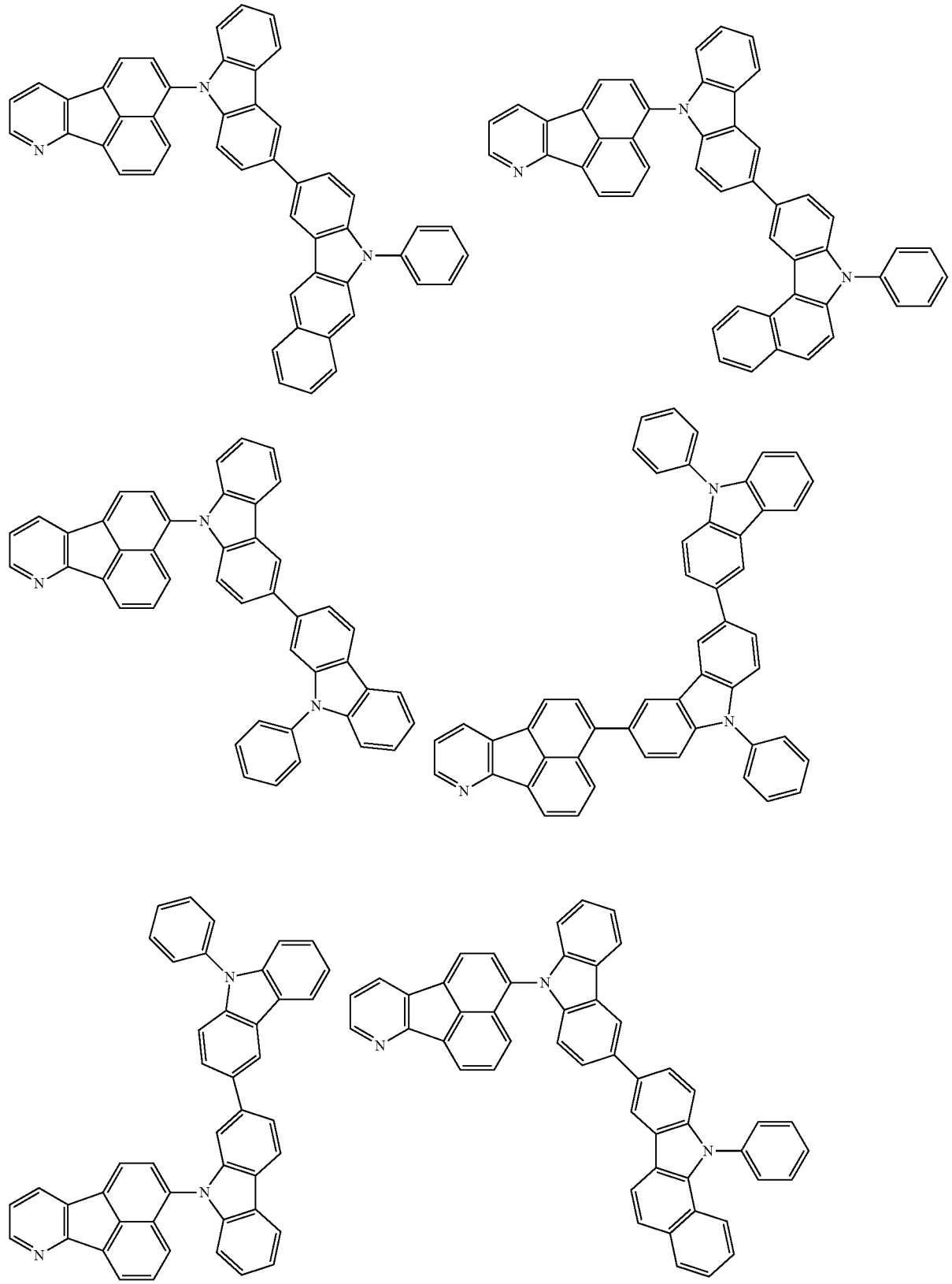

-continued
313
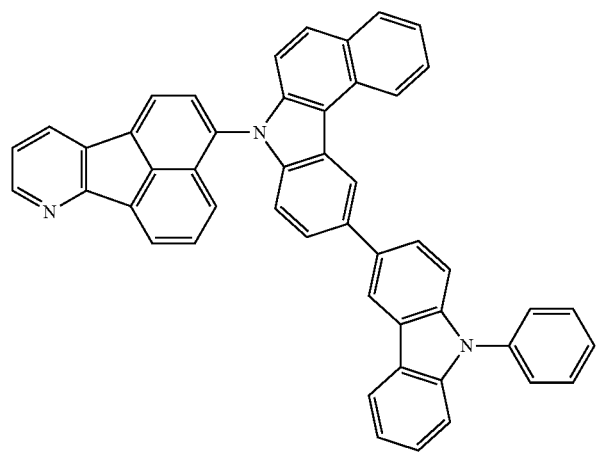
314
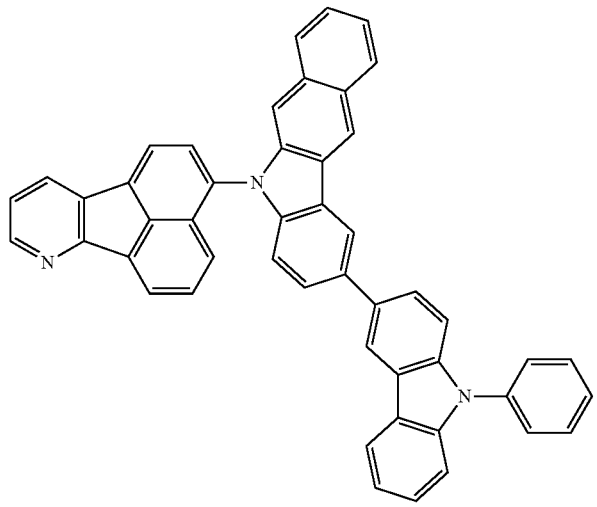
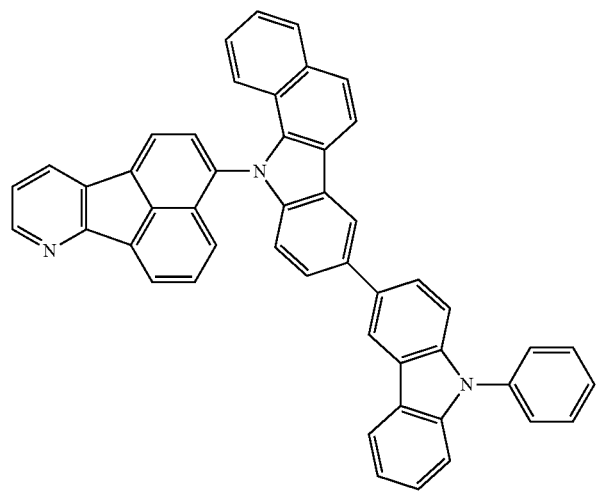
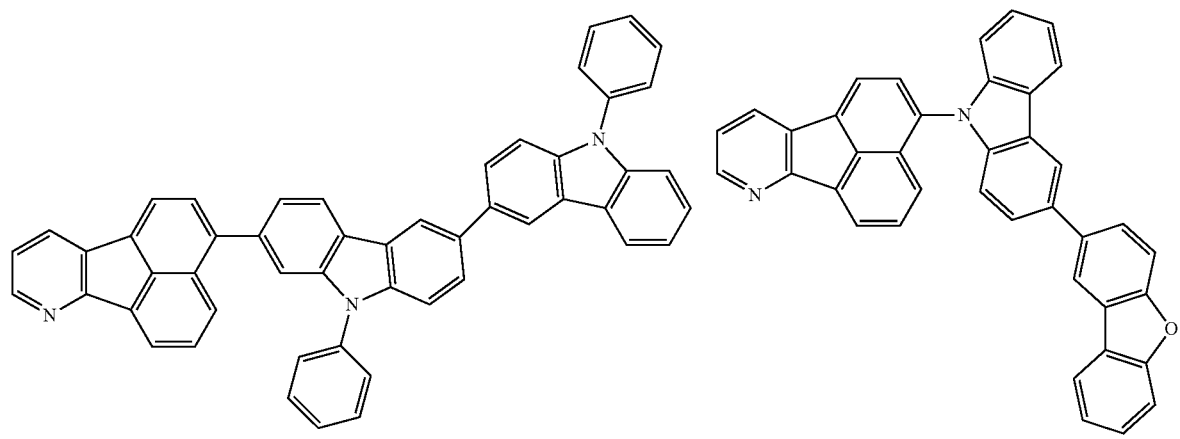

[Chem. 88]
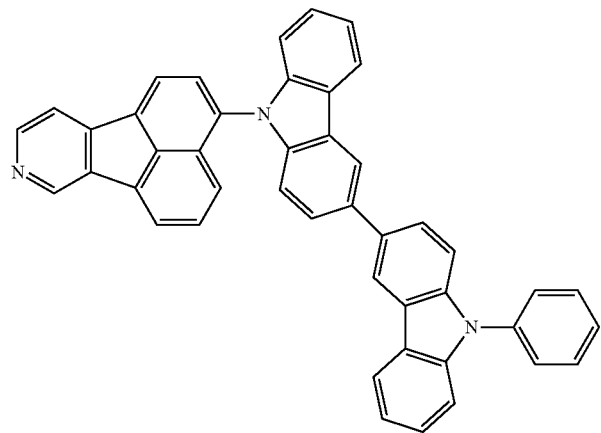
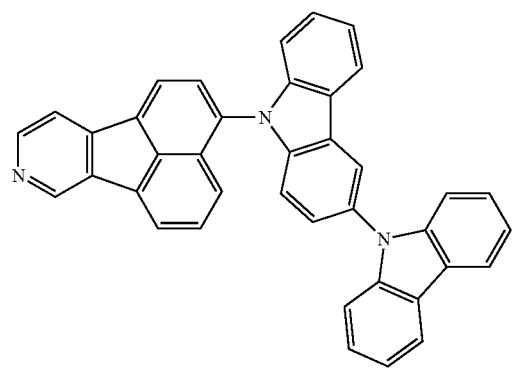
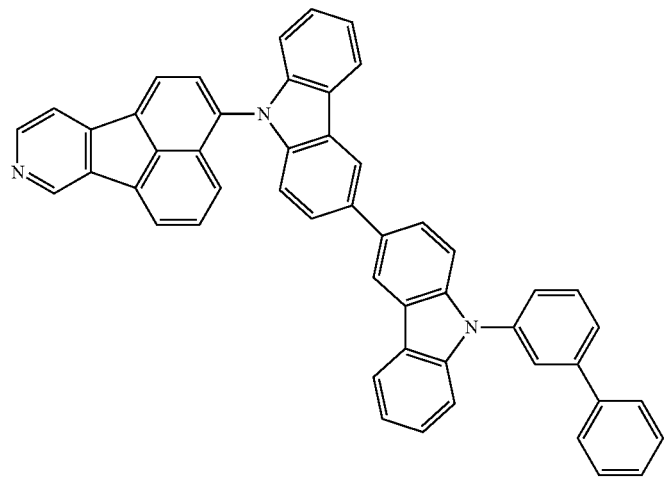
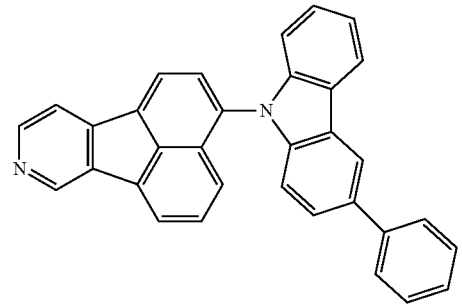
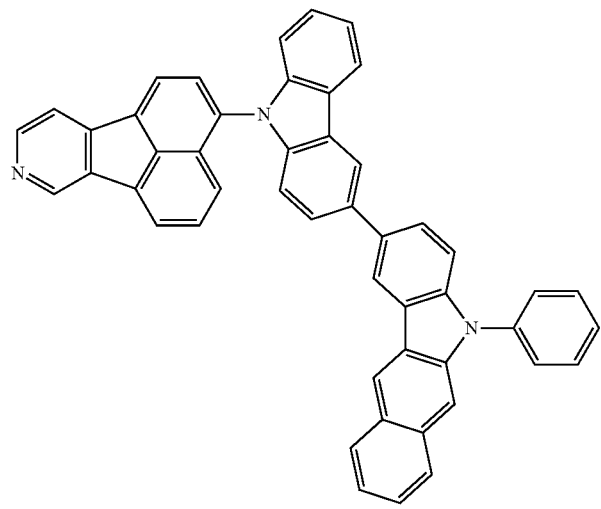
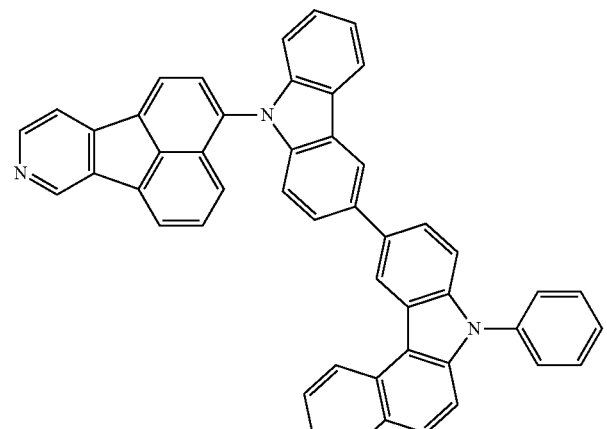

317 318
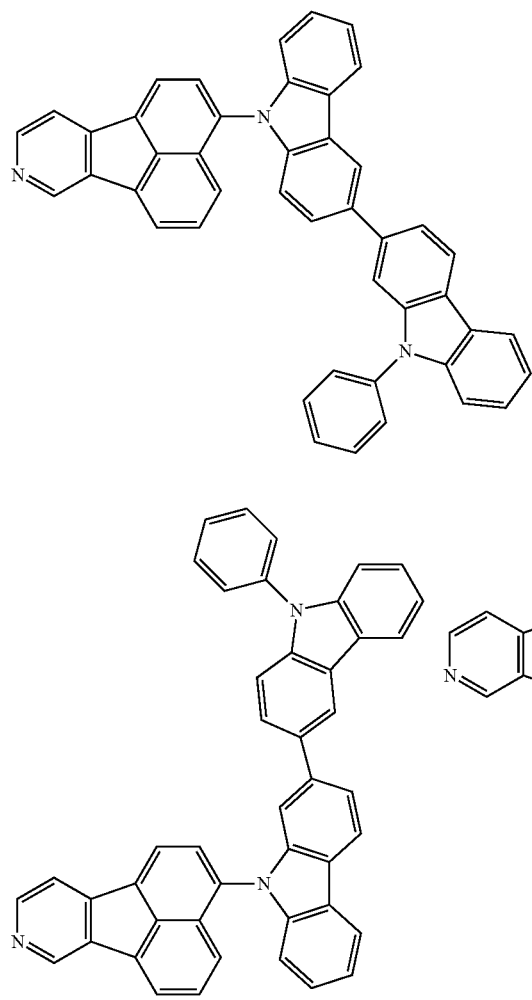
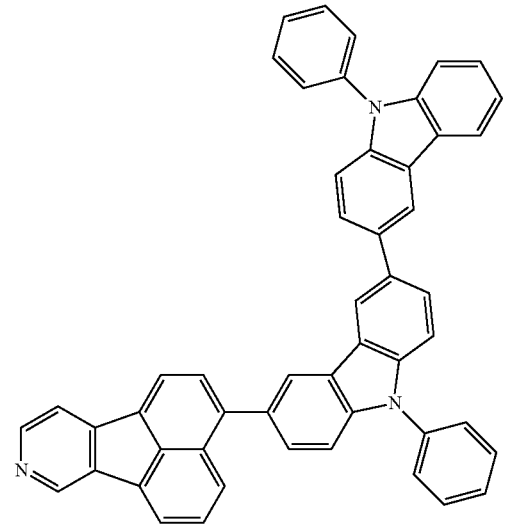
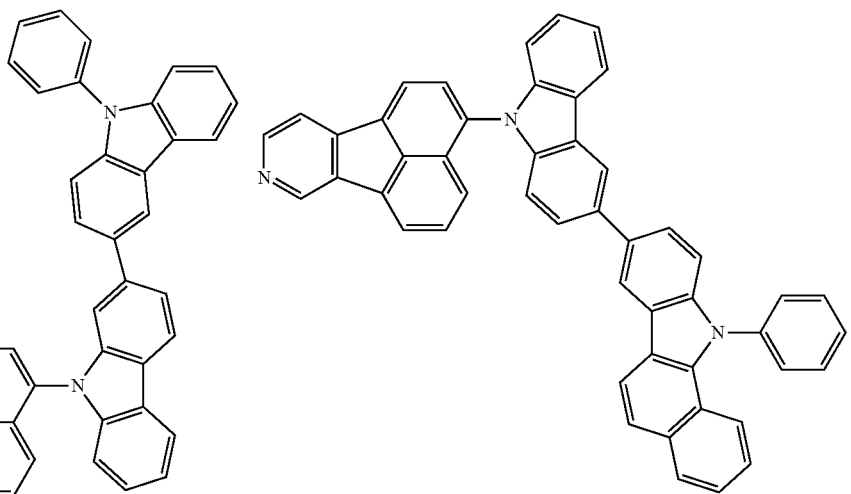
[Chem. 89]
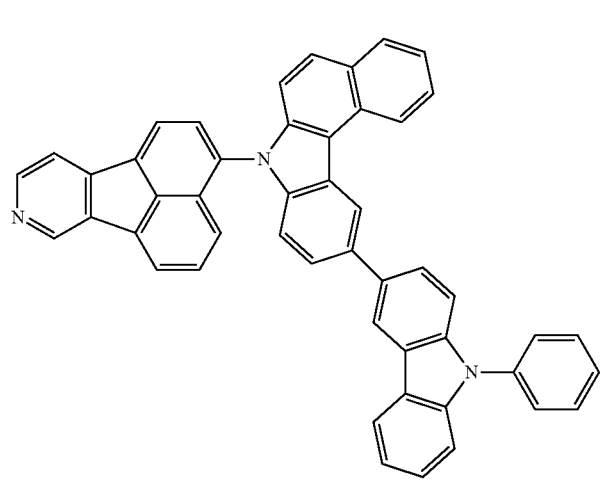
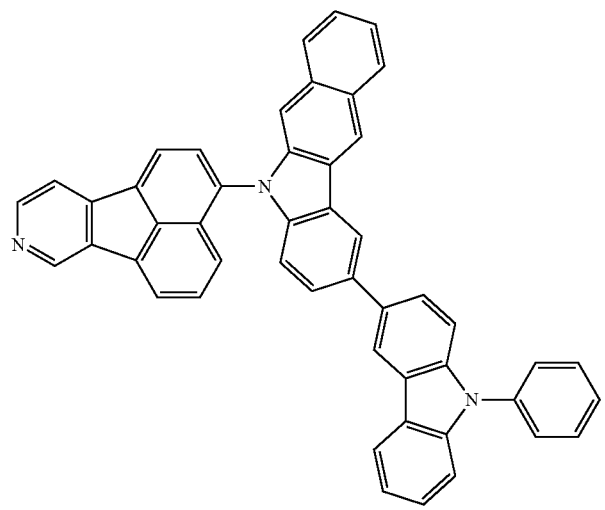

319 320
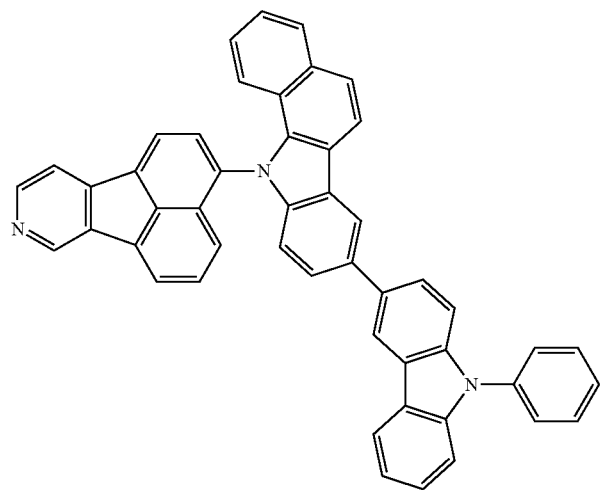
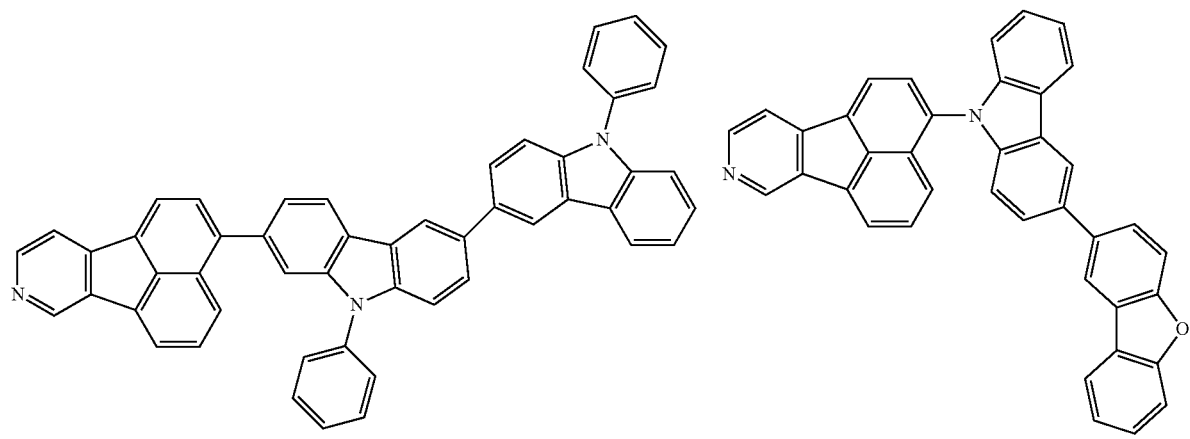
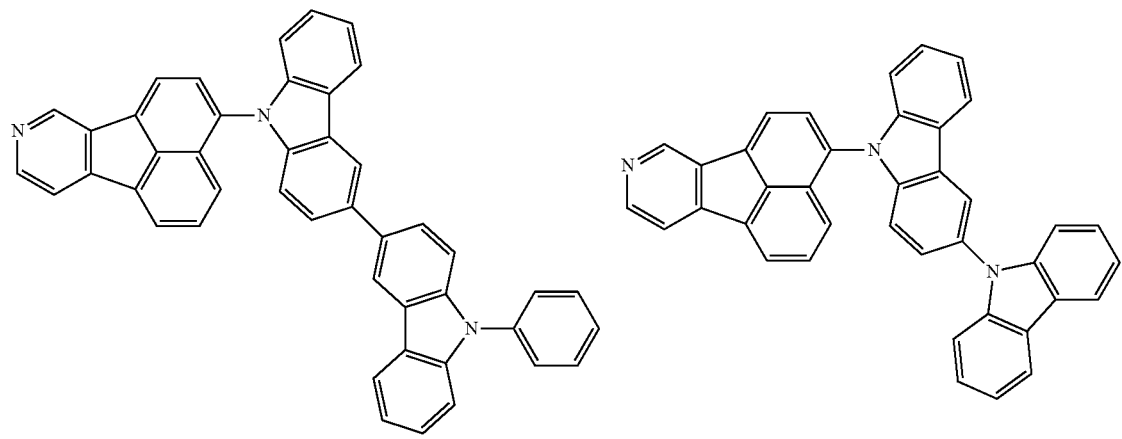

321
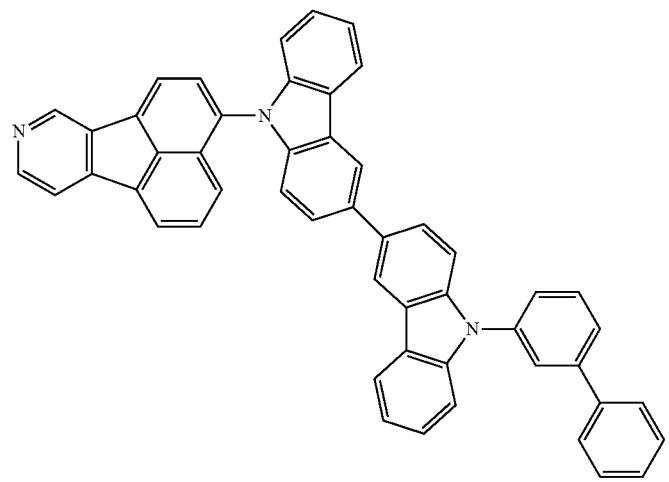
322
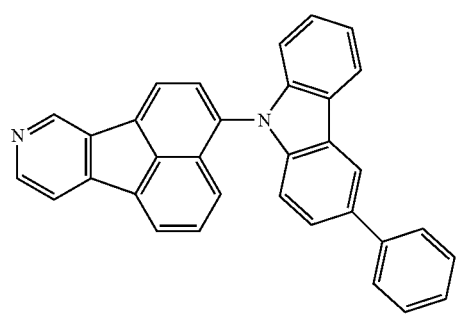
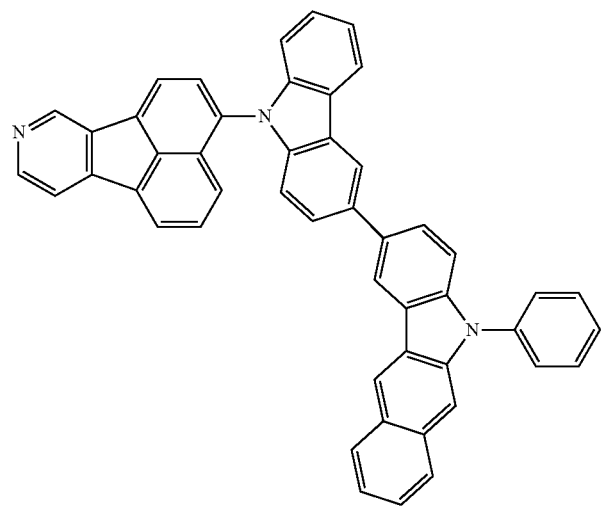
[Chem. 90]
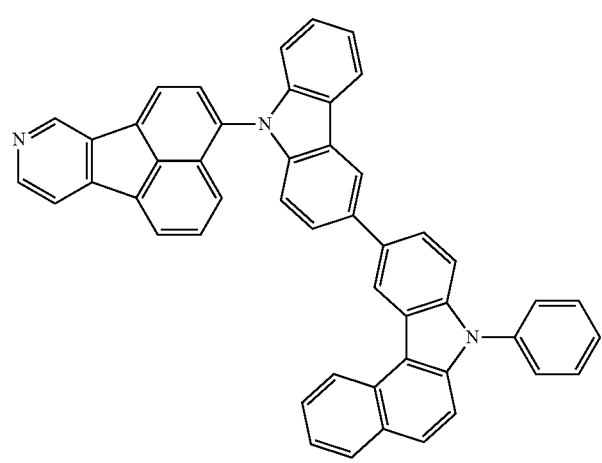
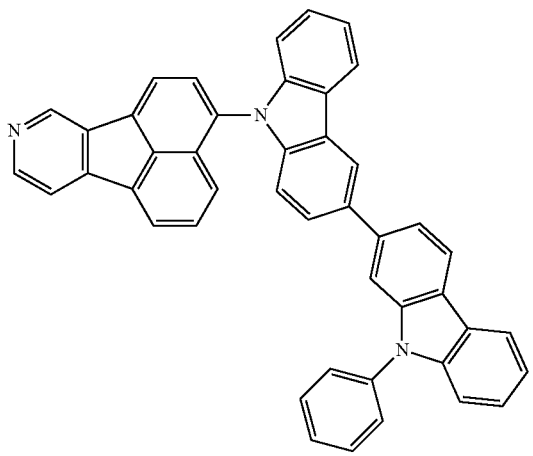

323 324
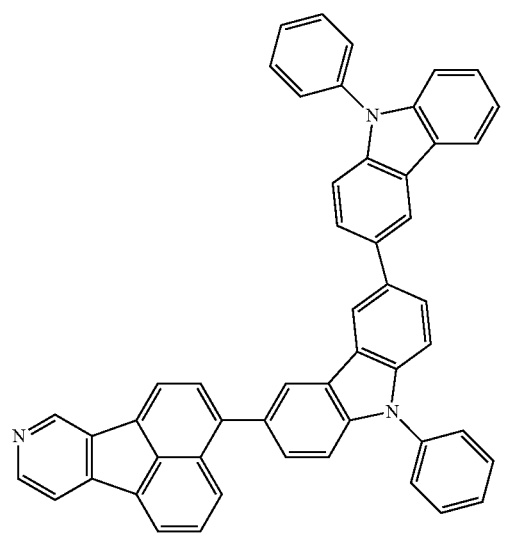 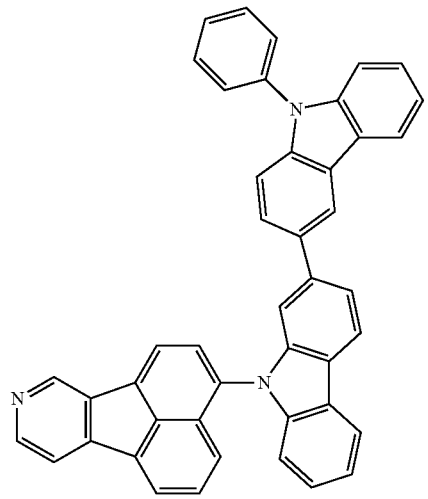
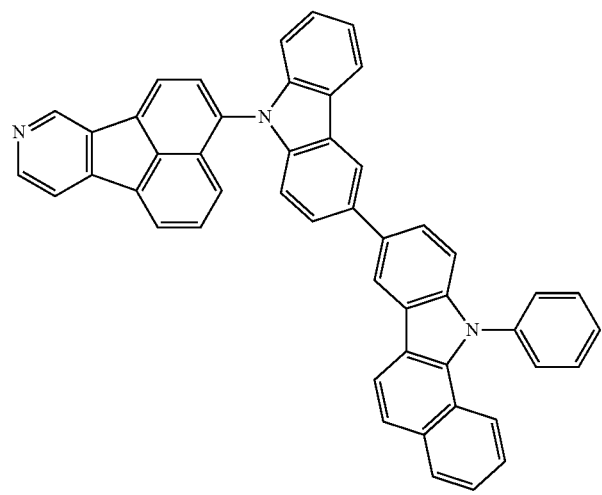 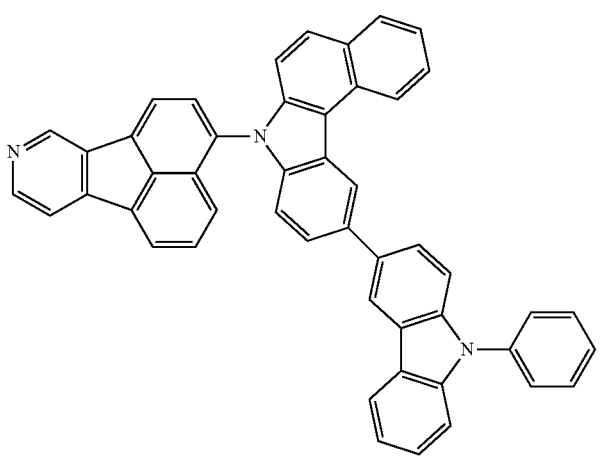
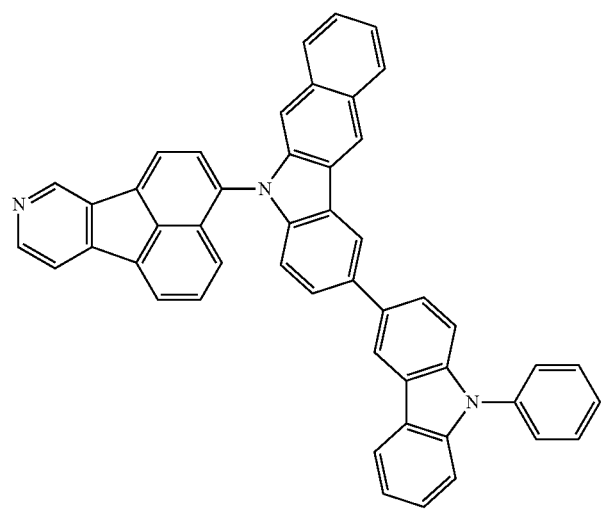

325
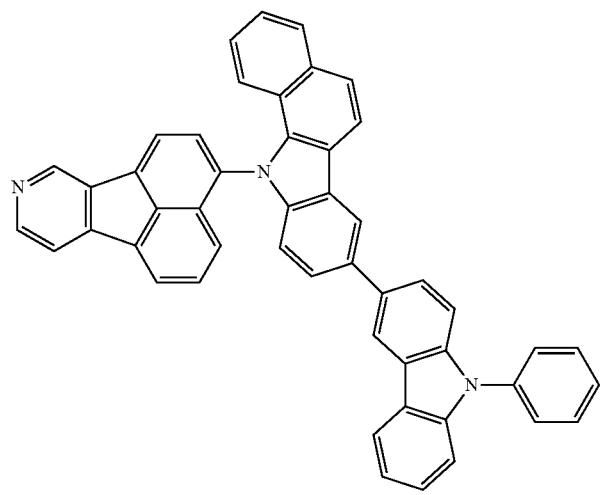
326
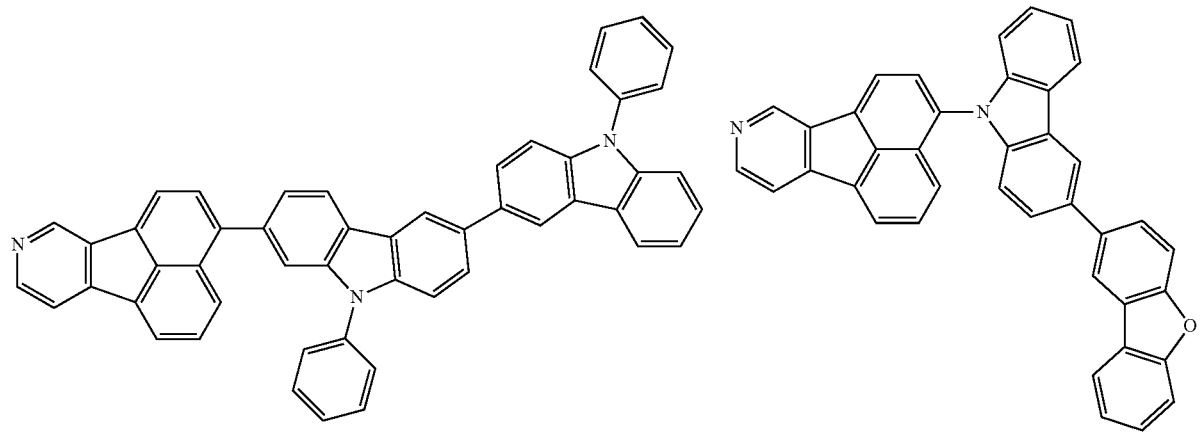
[Chem. 91]
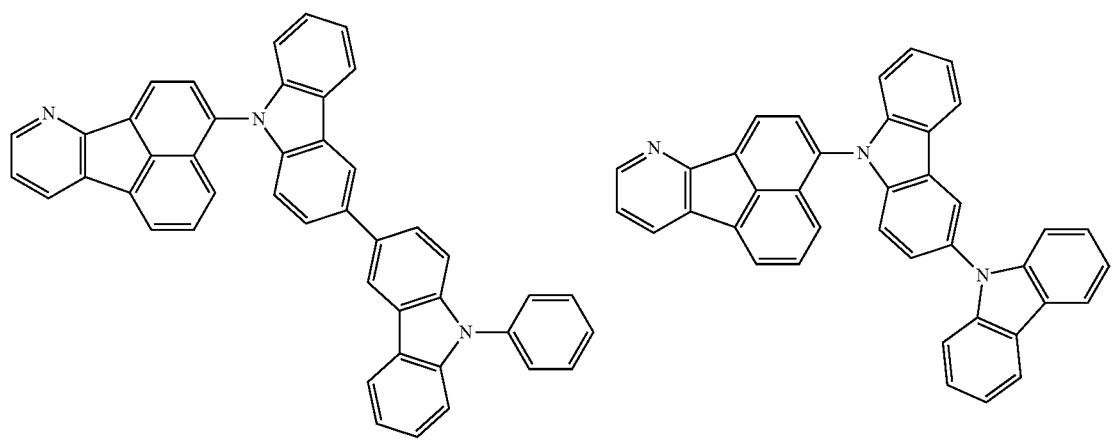

-continued
327
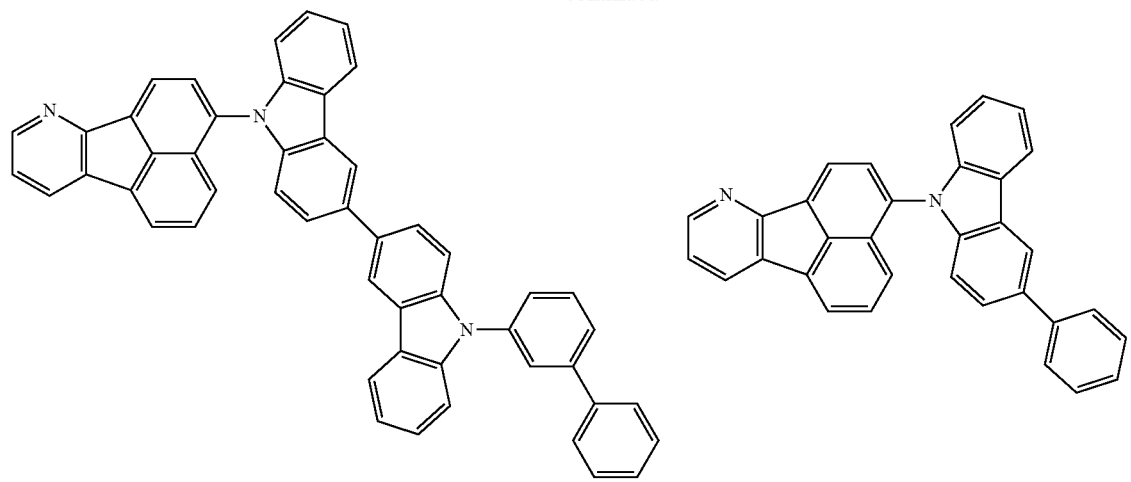
328
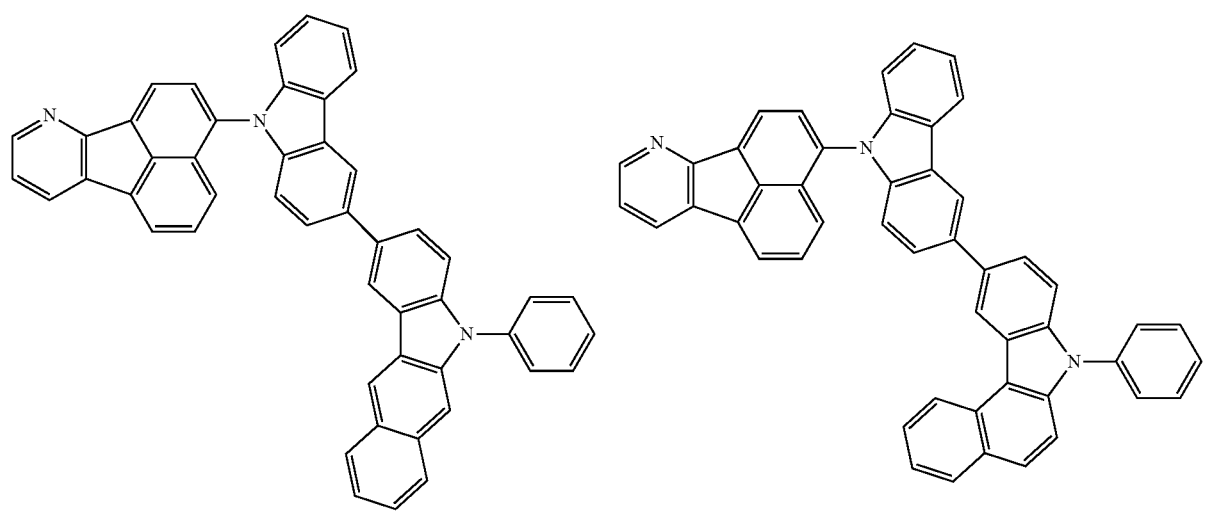
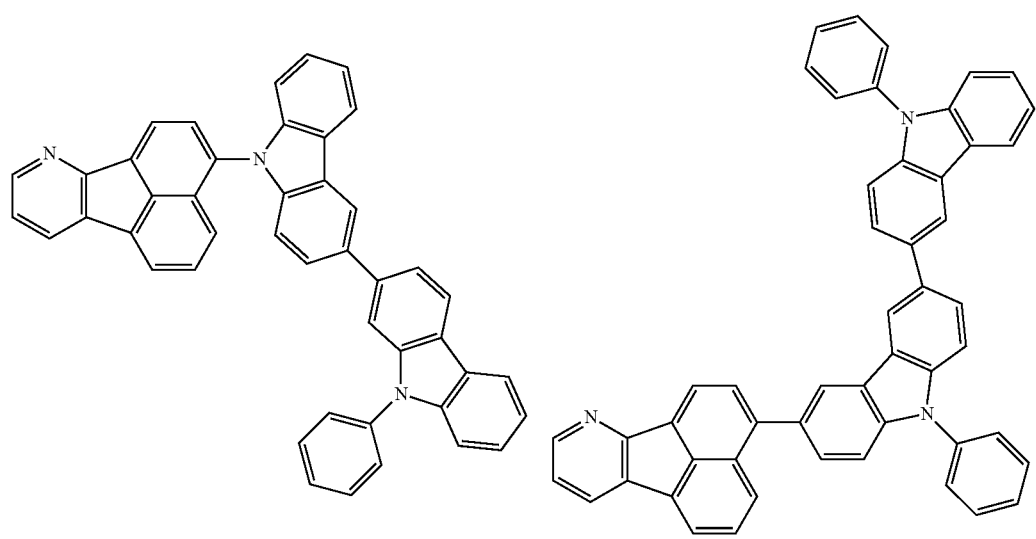

329 330
-continued
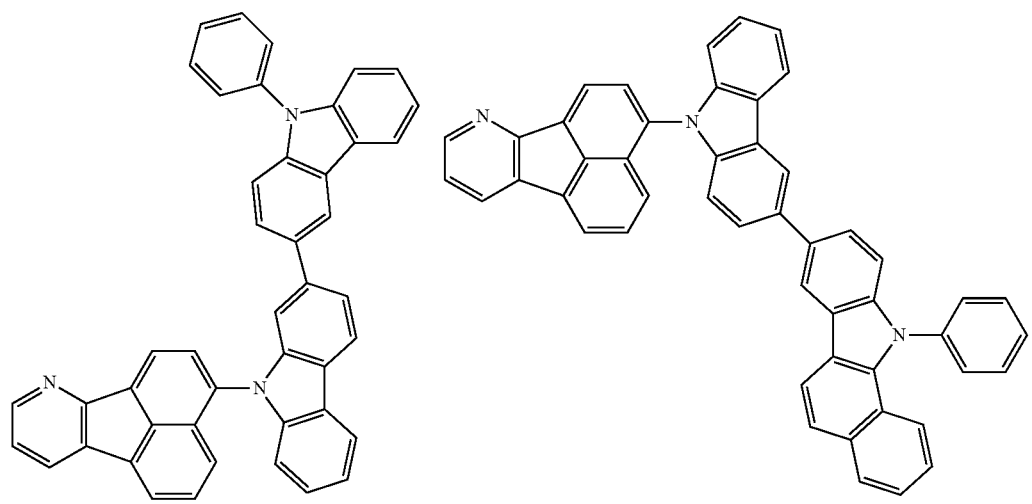
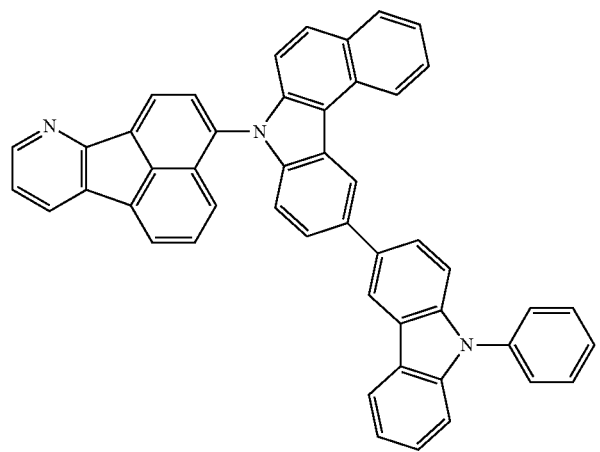
[Chem. 92]
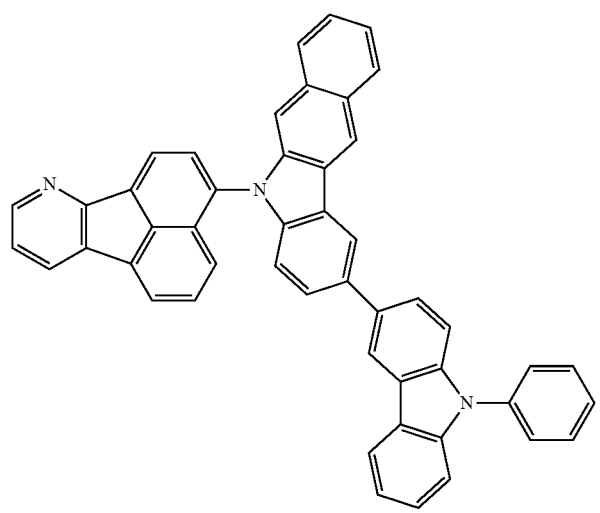
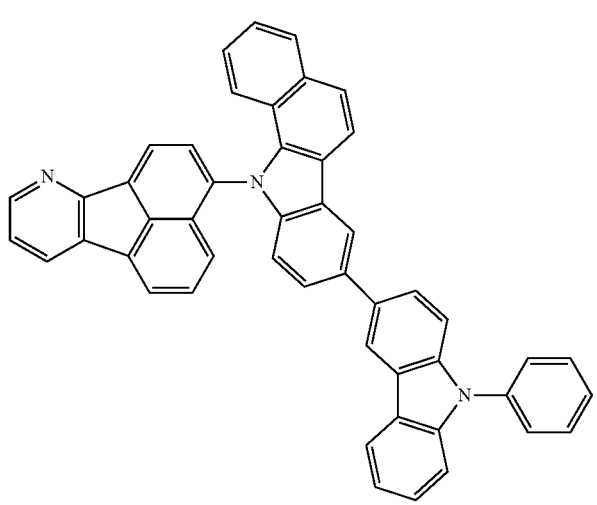

331 332
-continued
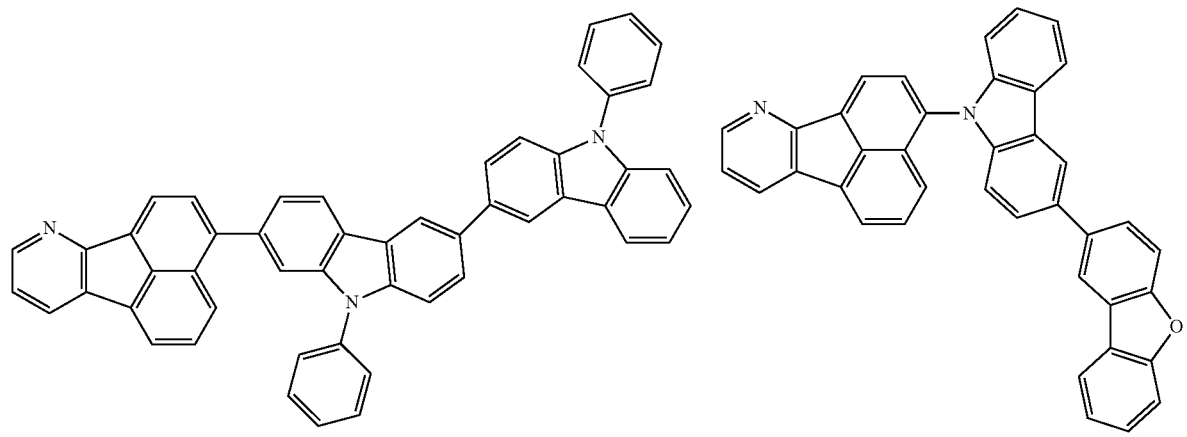
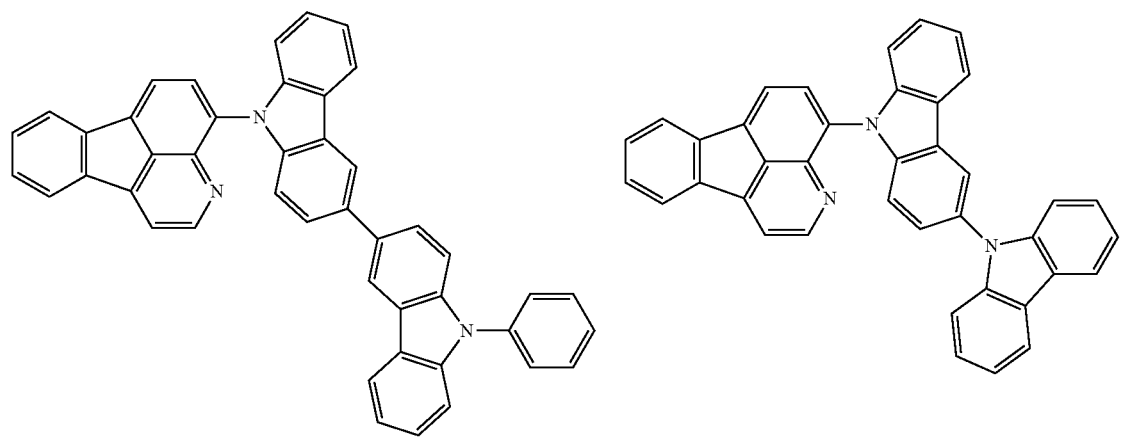
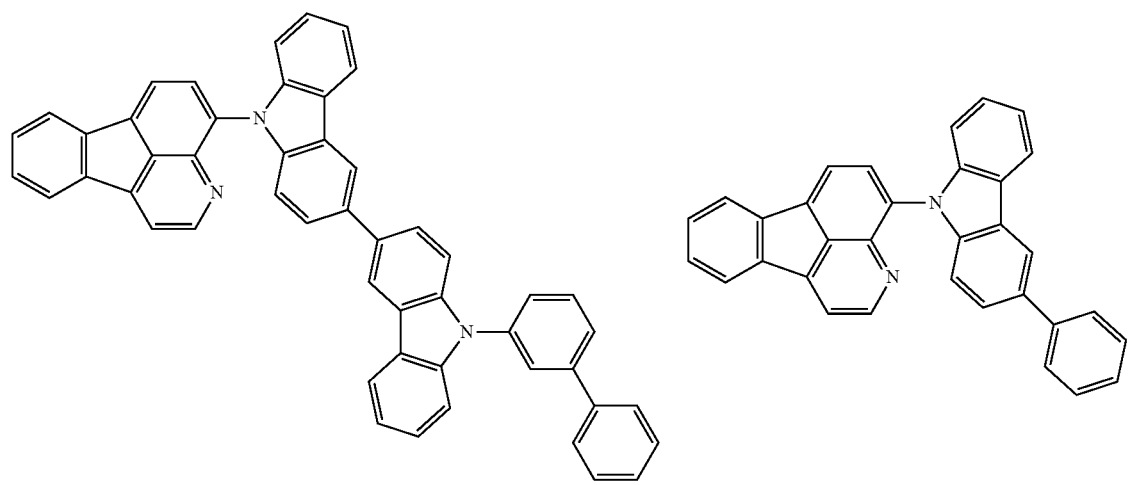

-continued
333
334
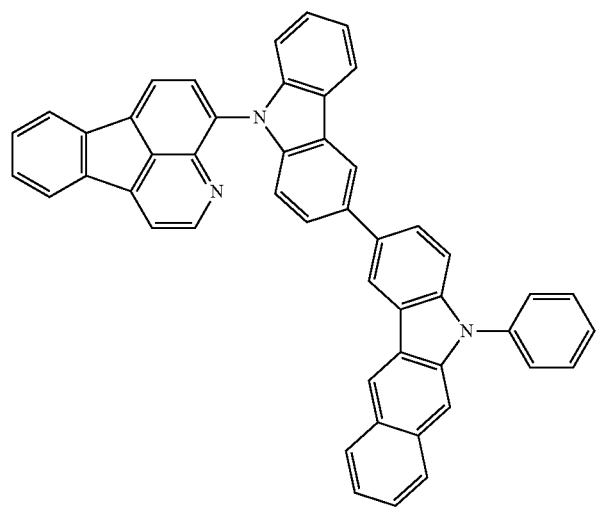
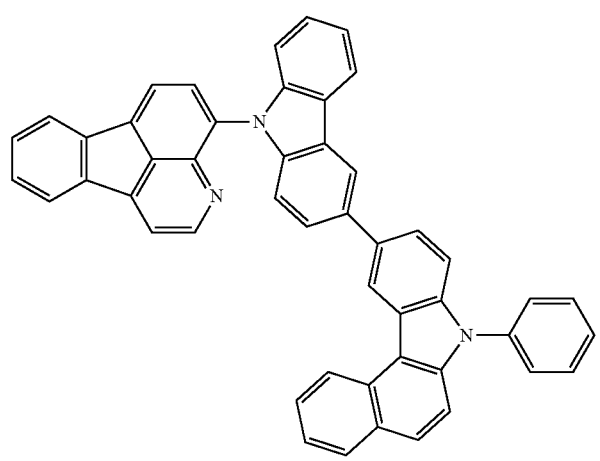
[Chem. 93]
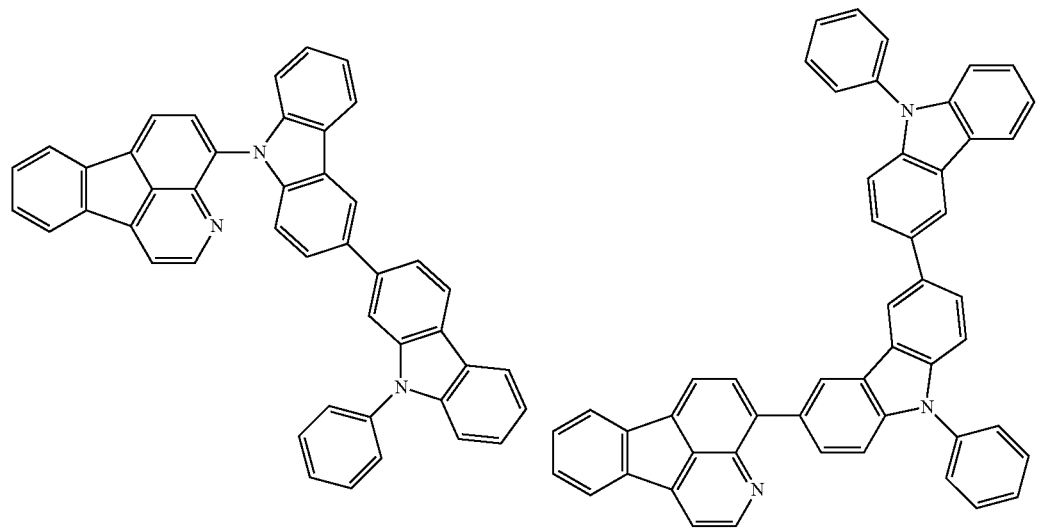
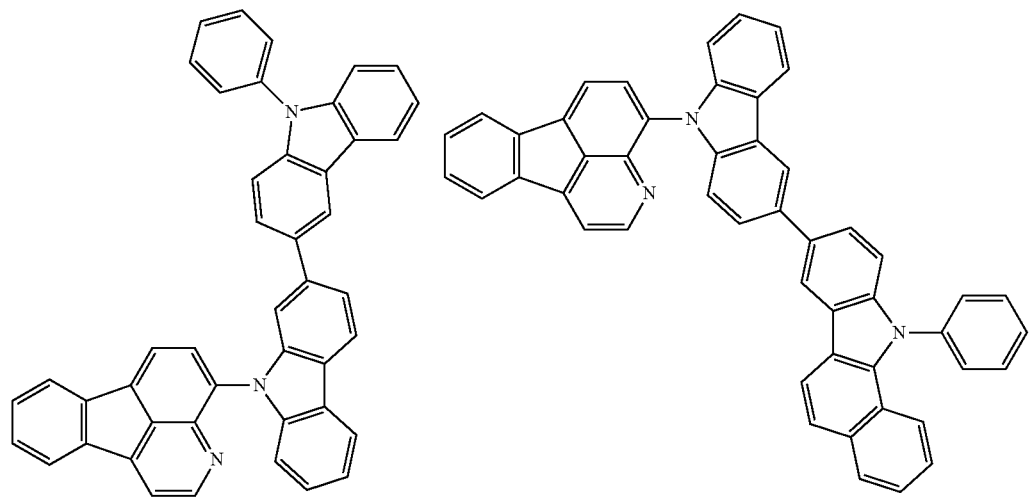

335 336
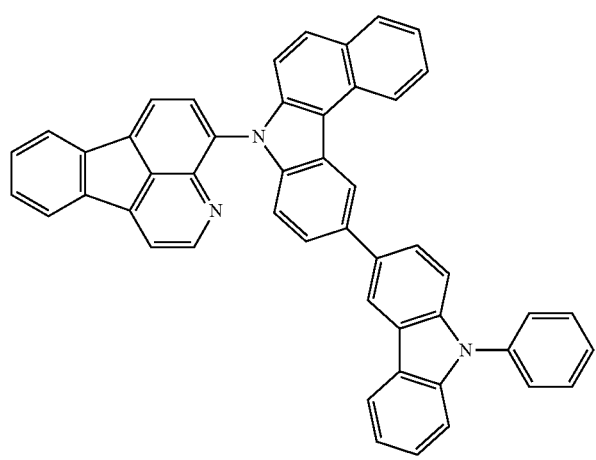
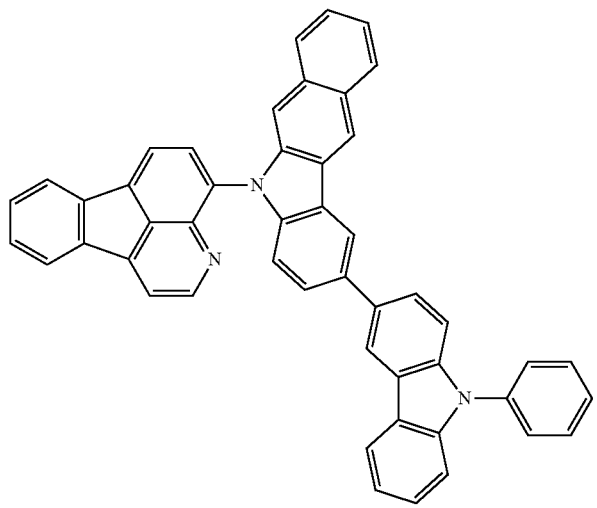
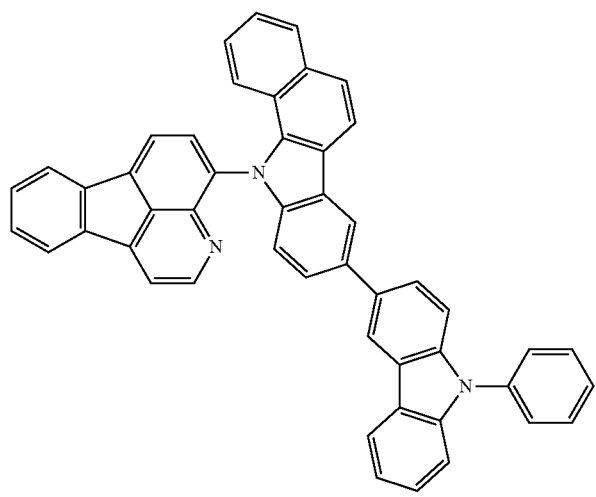
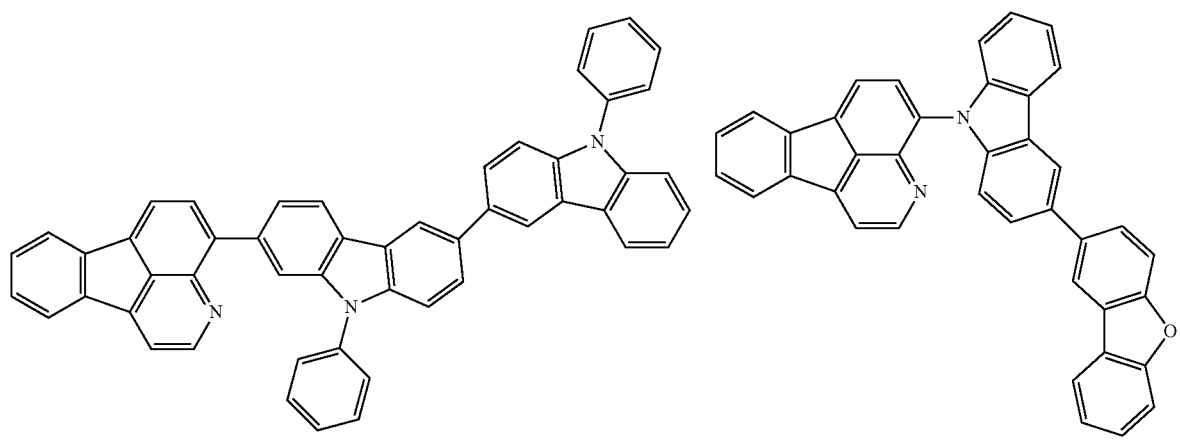

337
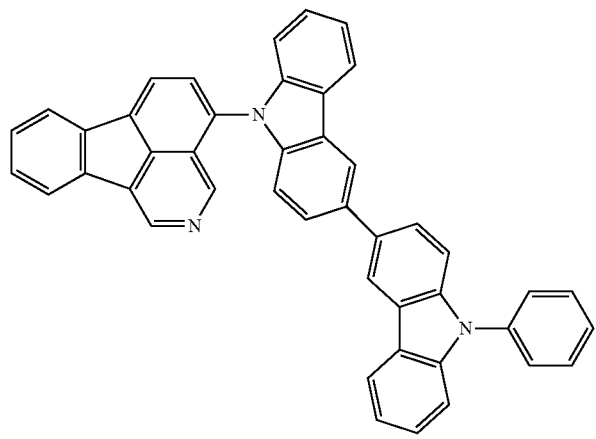
338
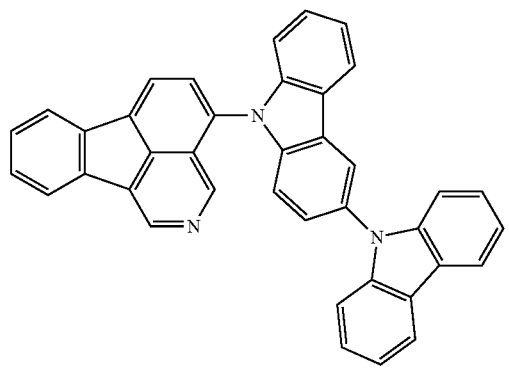
[Chem. 94]
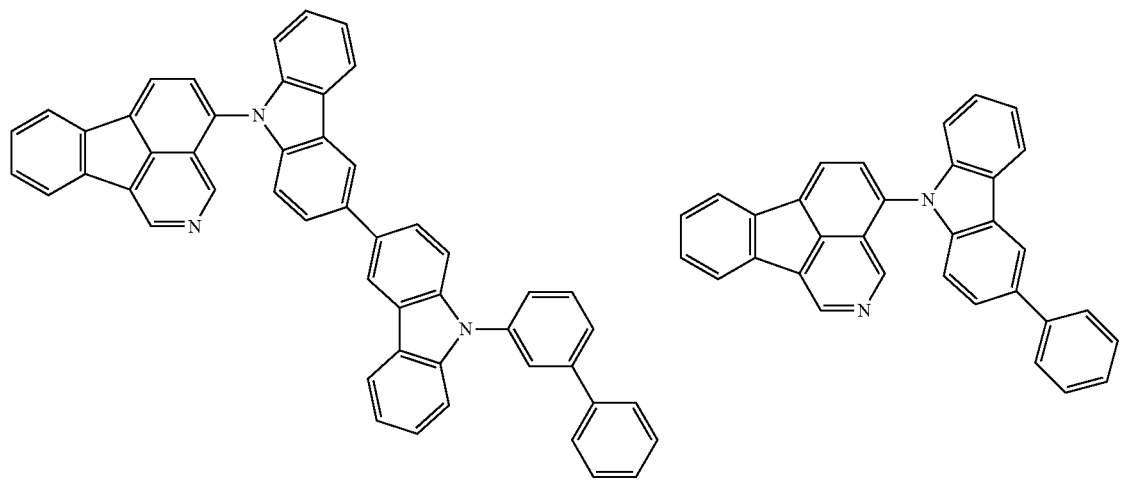
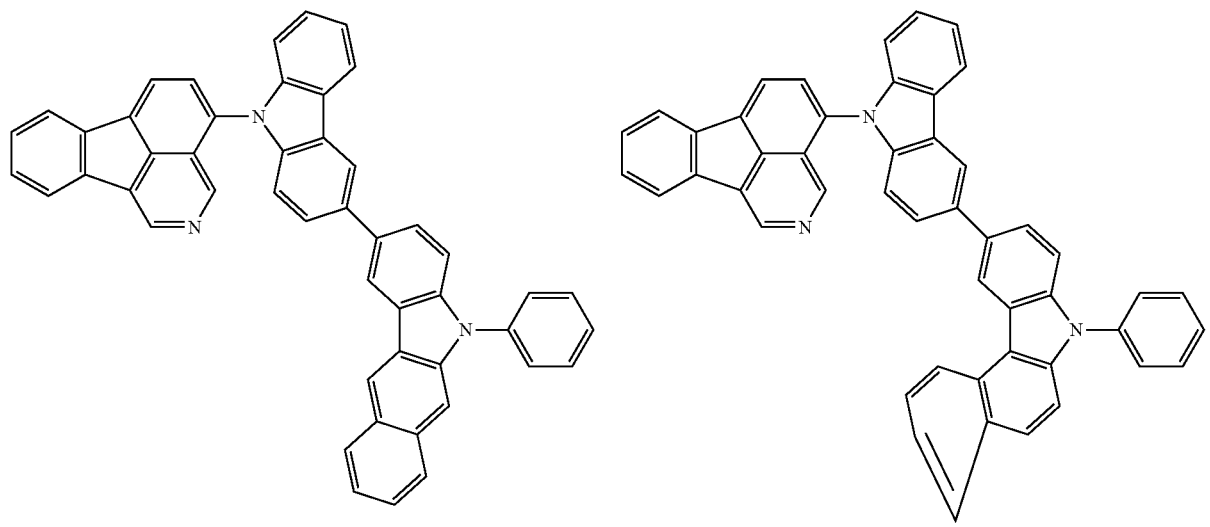

339 340
-continued
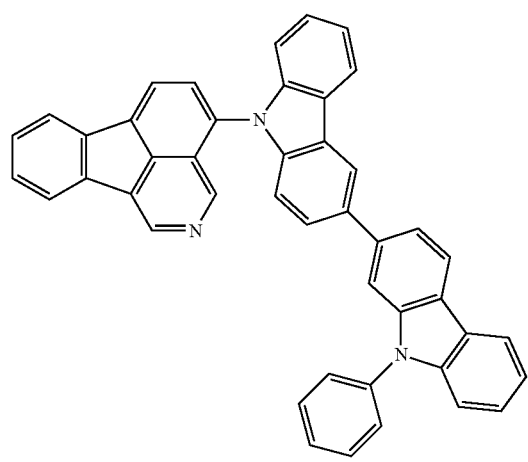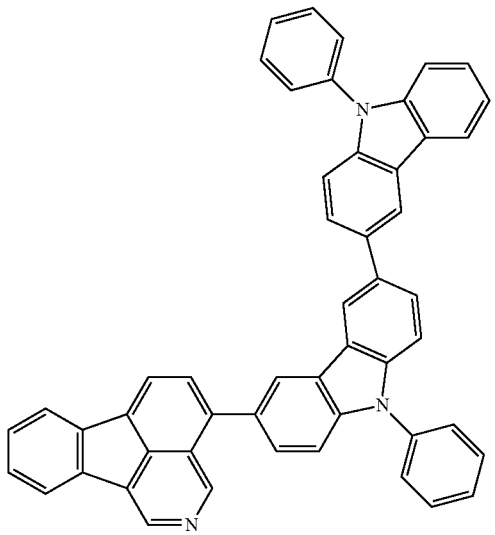
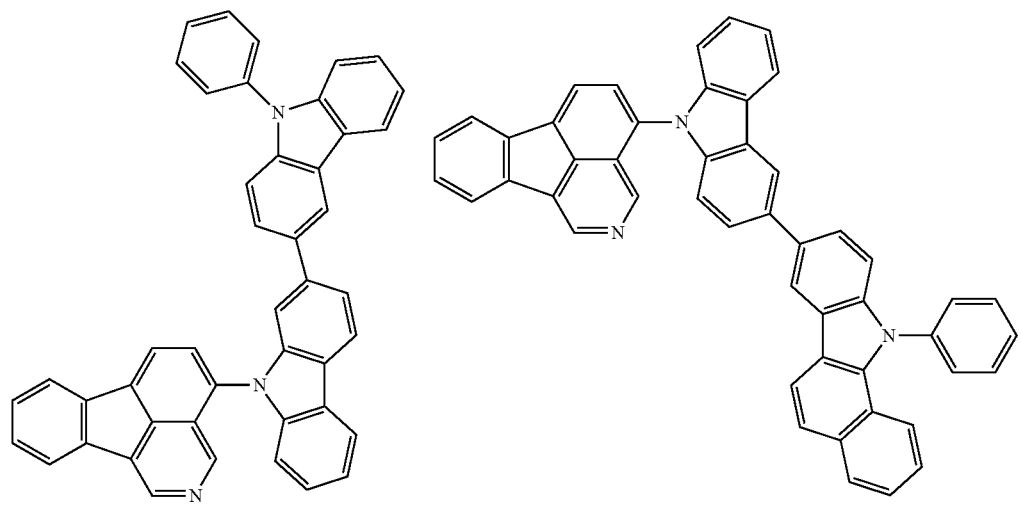
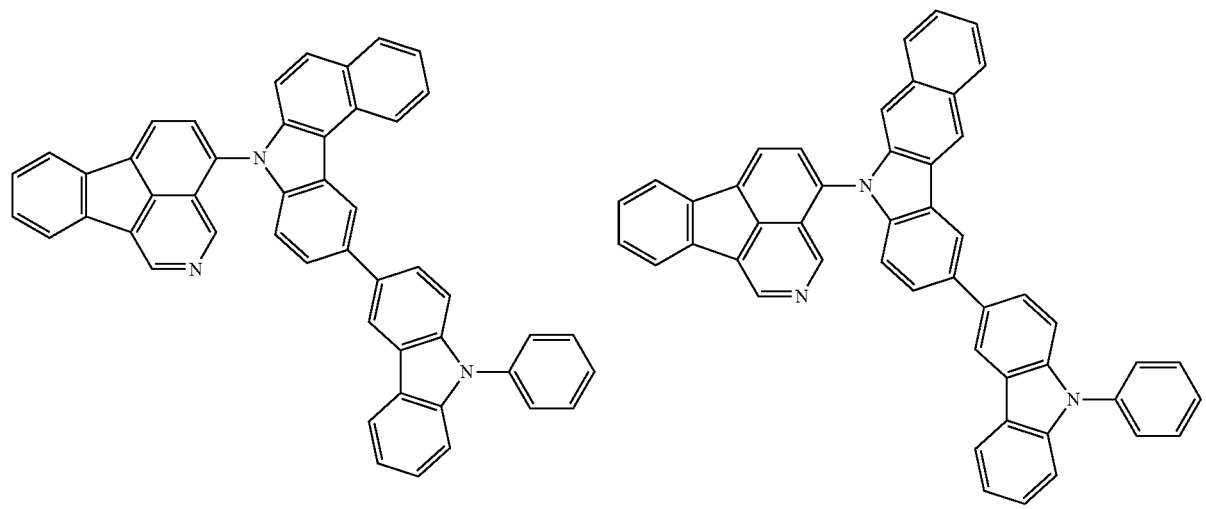

341 342
-continued
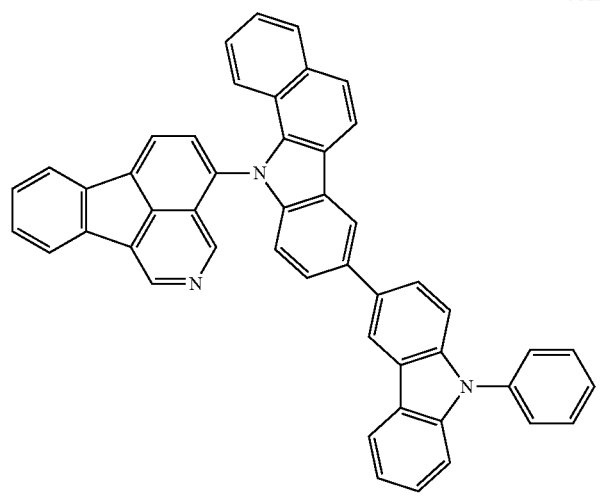
[Chem. 95]

343 344
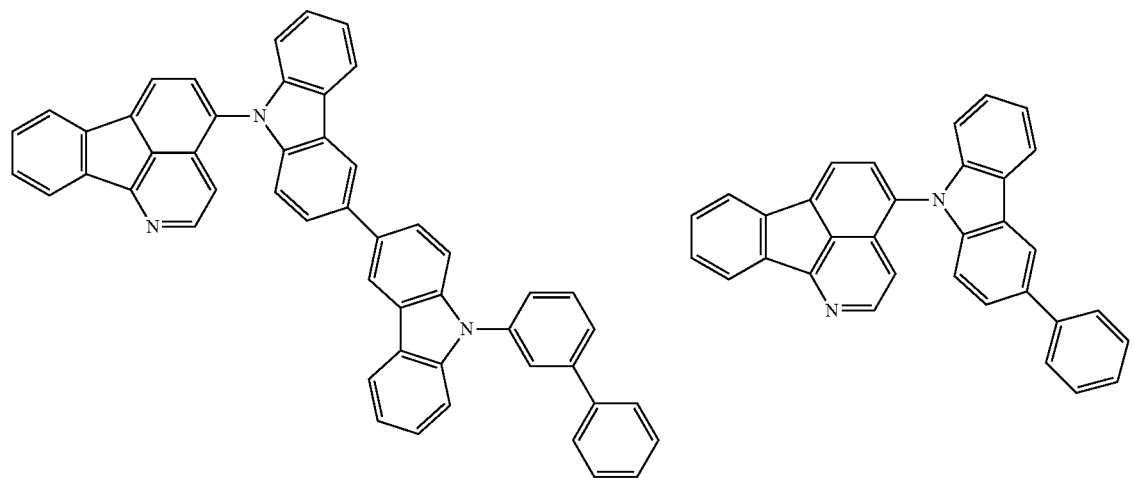
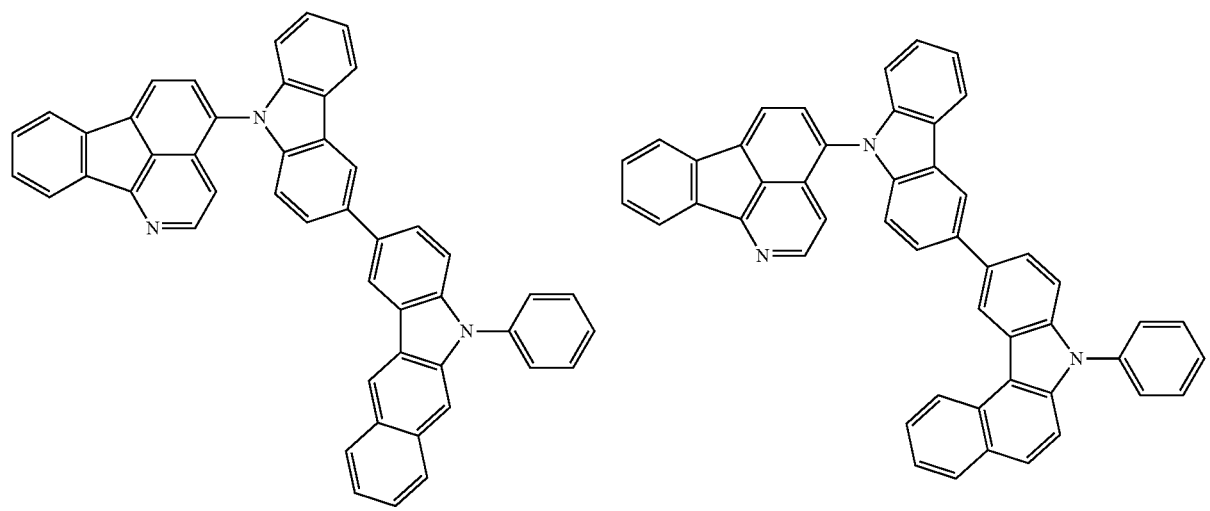
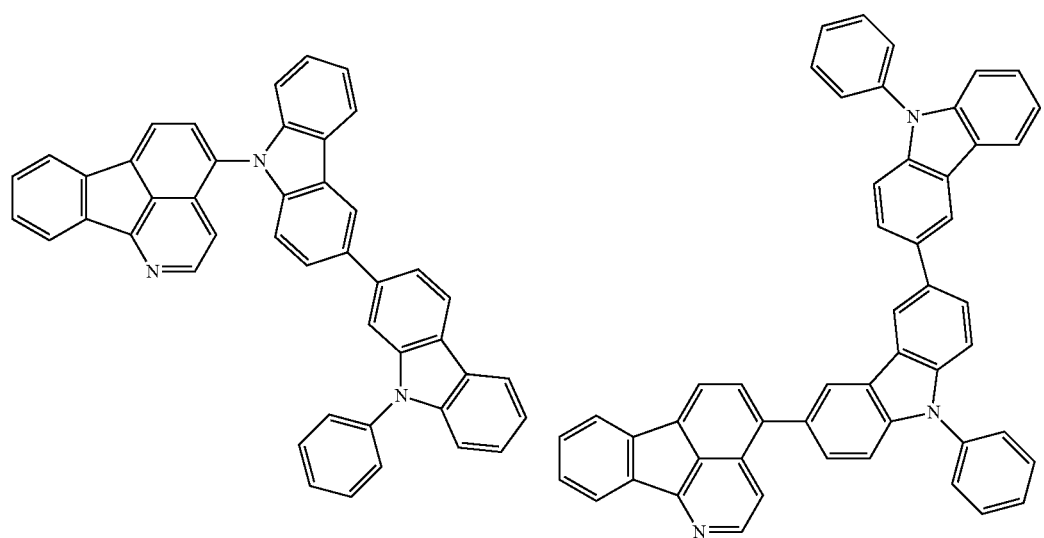

345
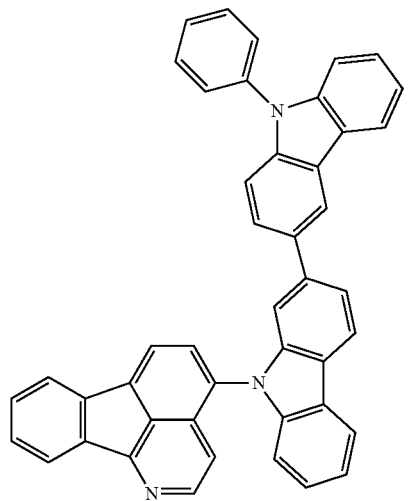
346
[Chem. 96]
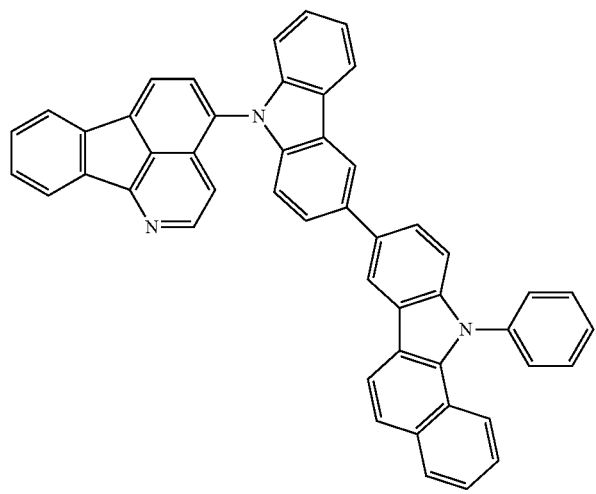
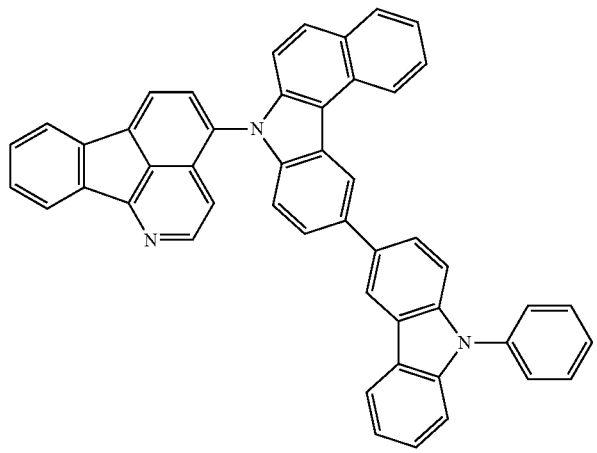
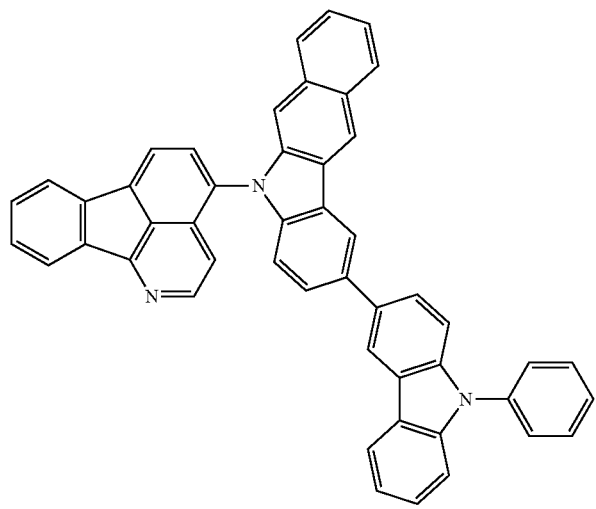
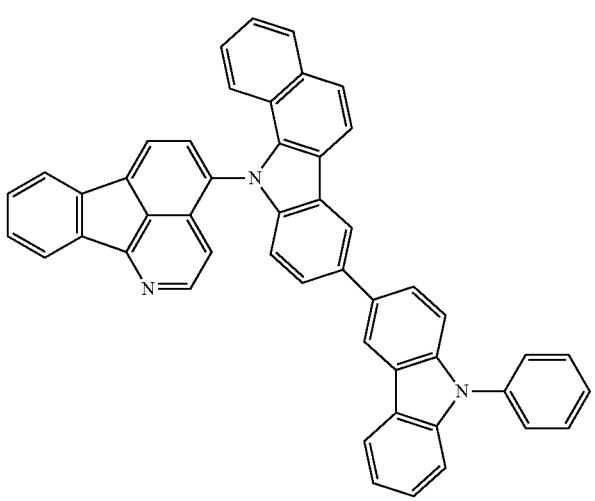

347 348
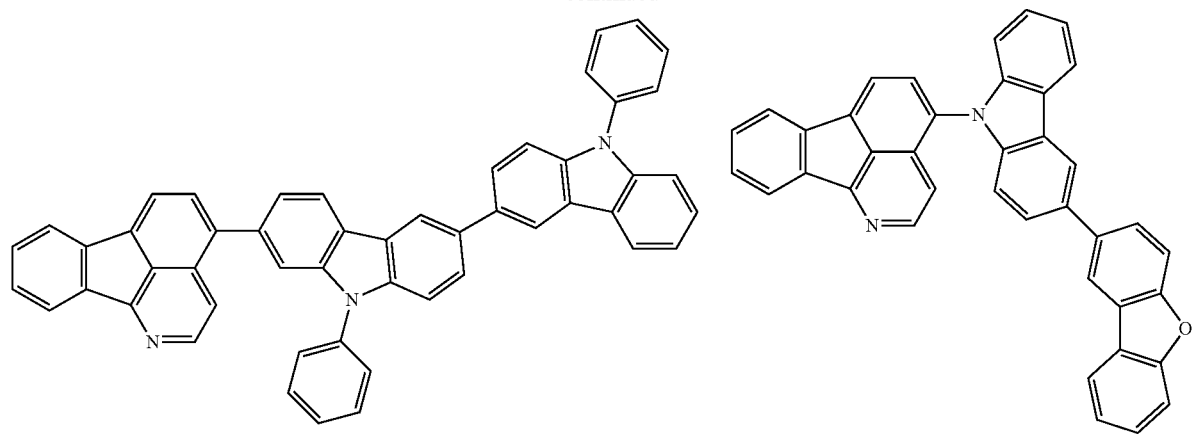
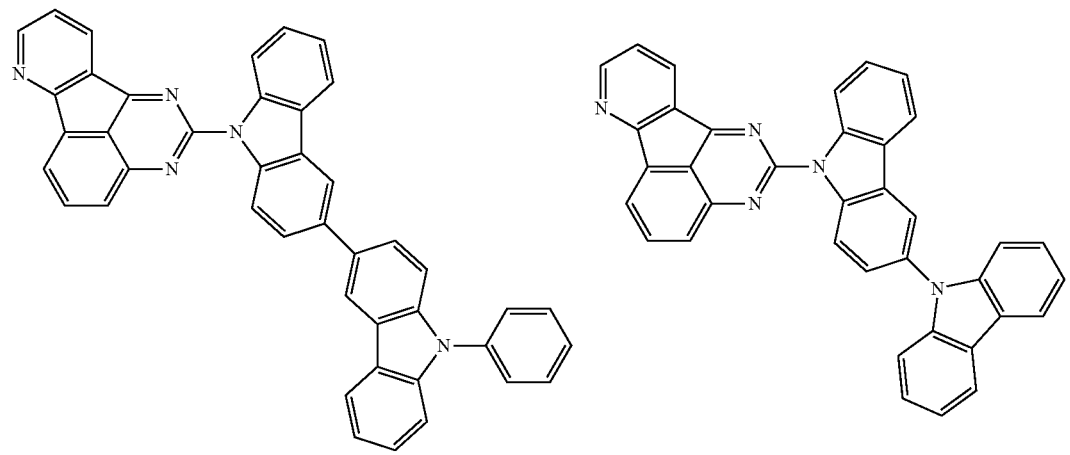
[Chem. 97]
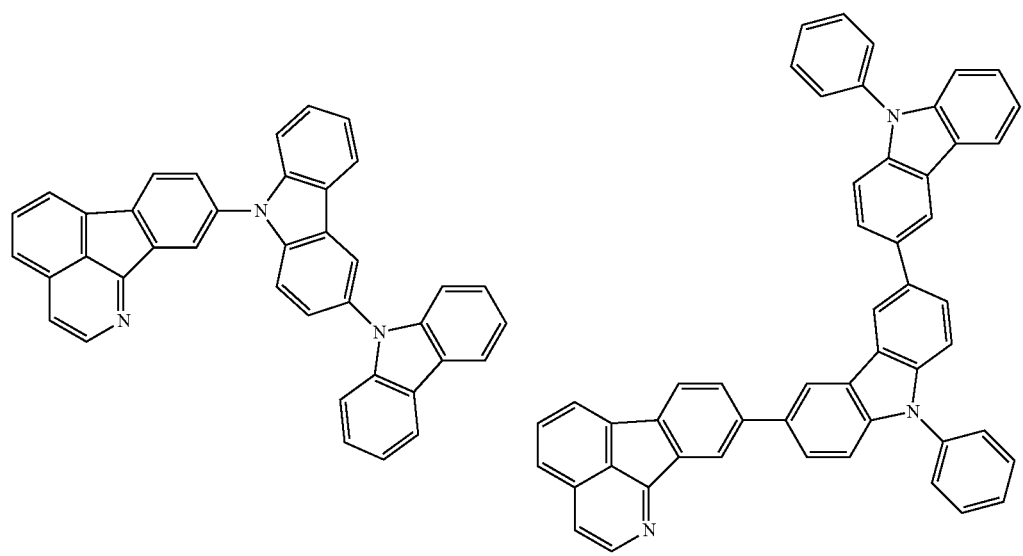

-continued
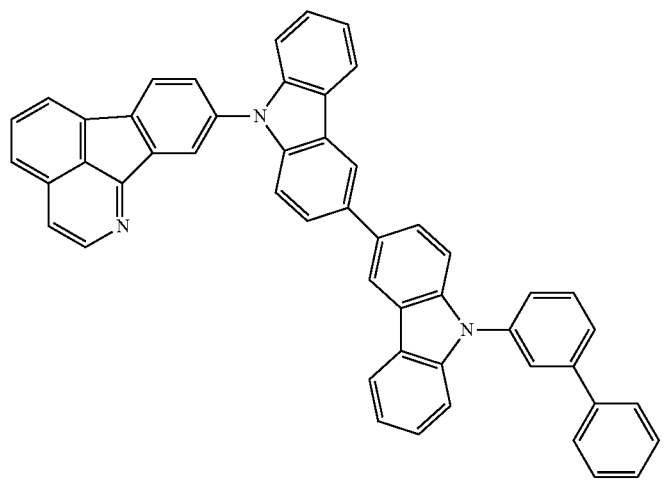
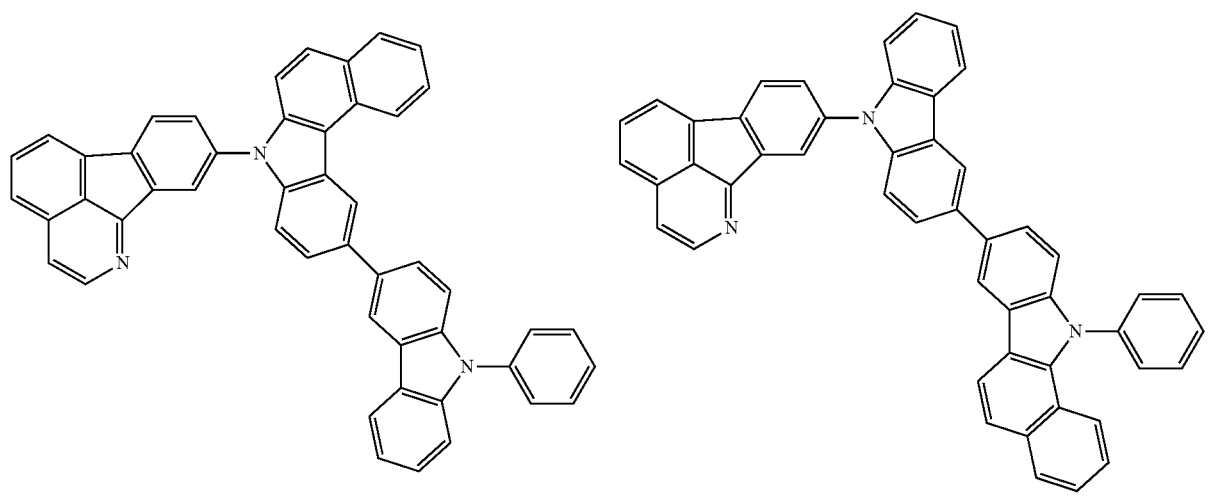
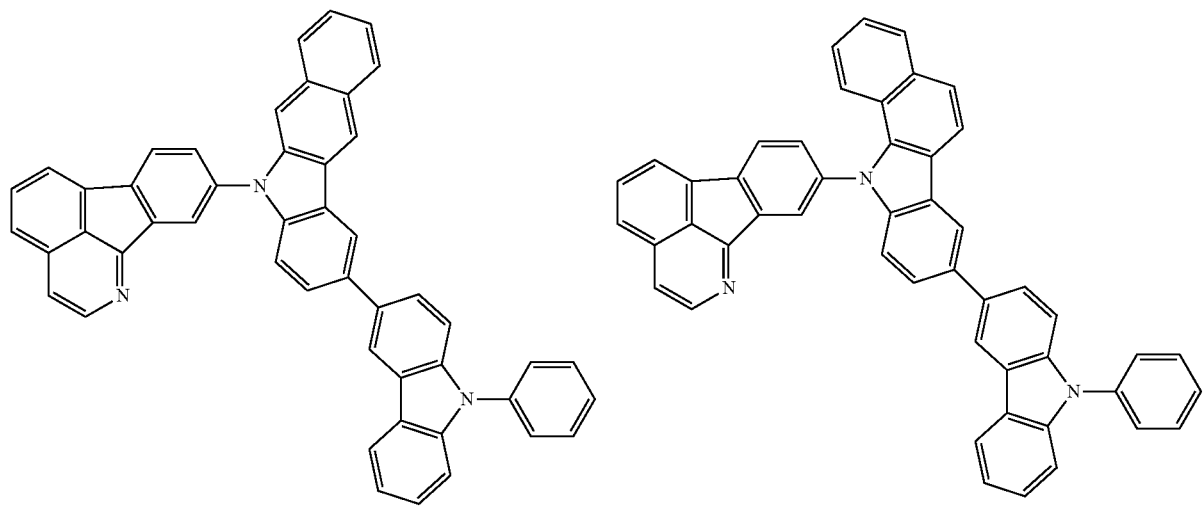

351
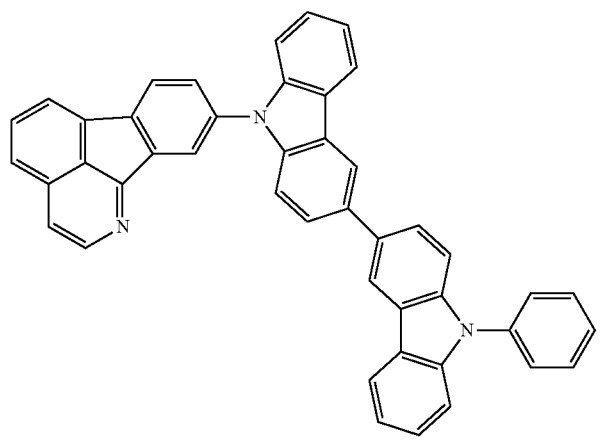
352
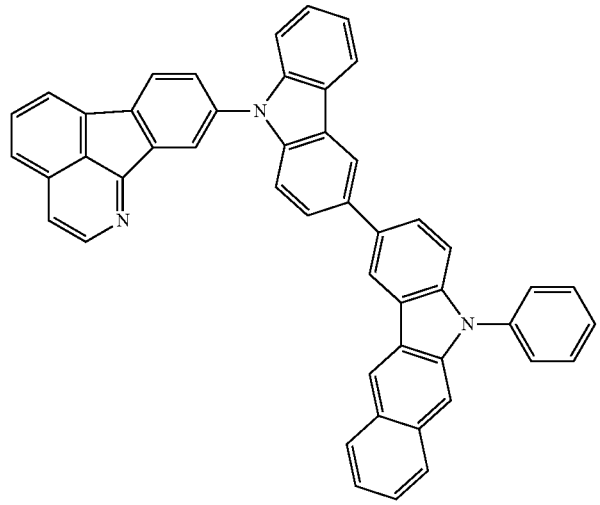
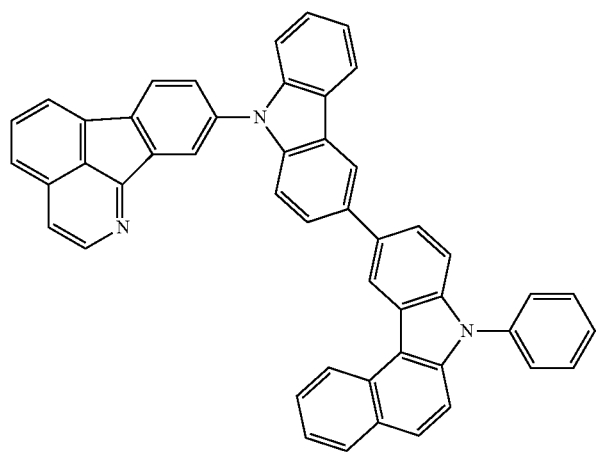
[Chem. 98]
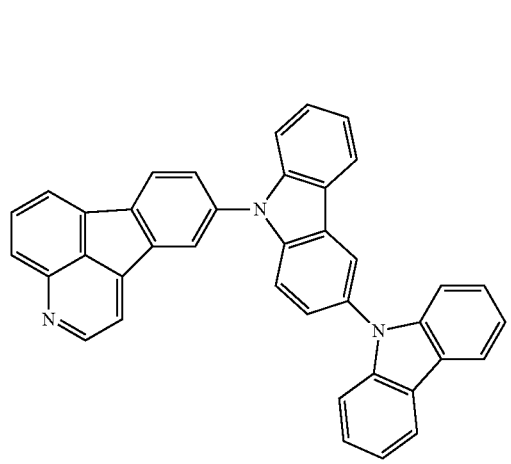
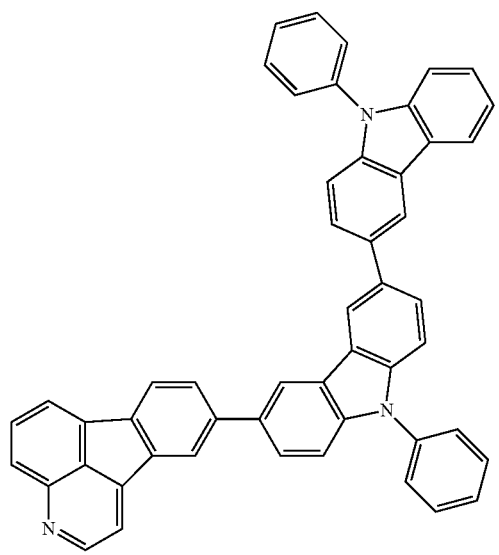

-continued
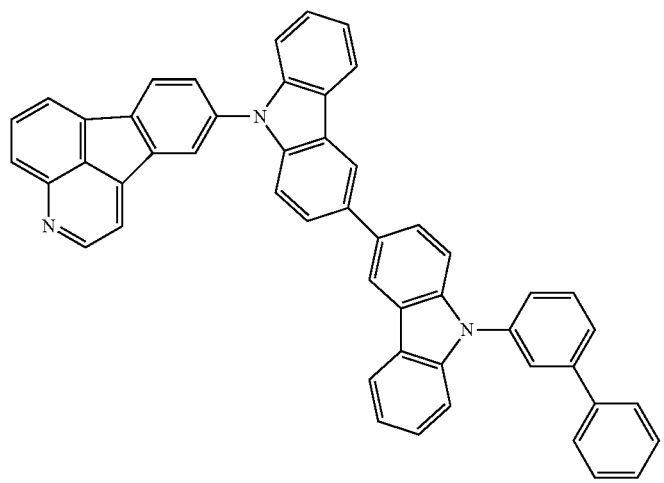
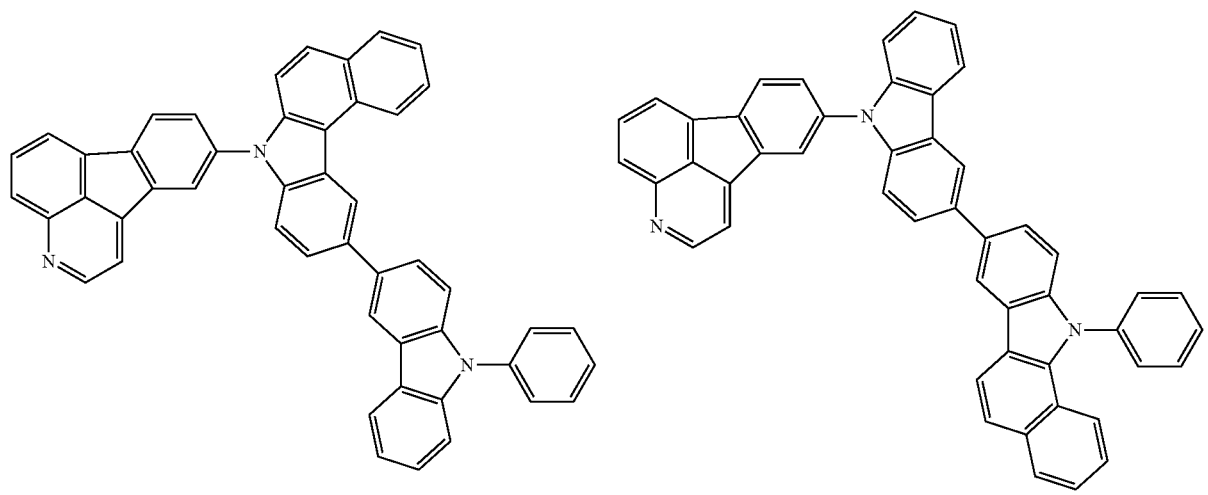
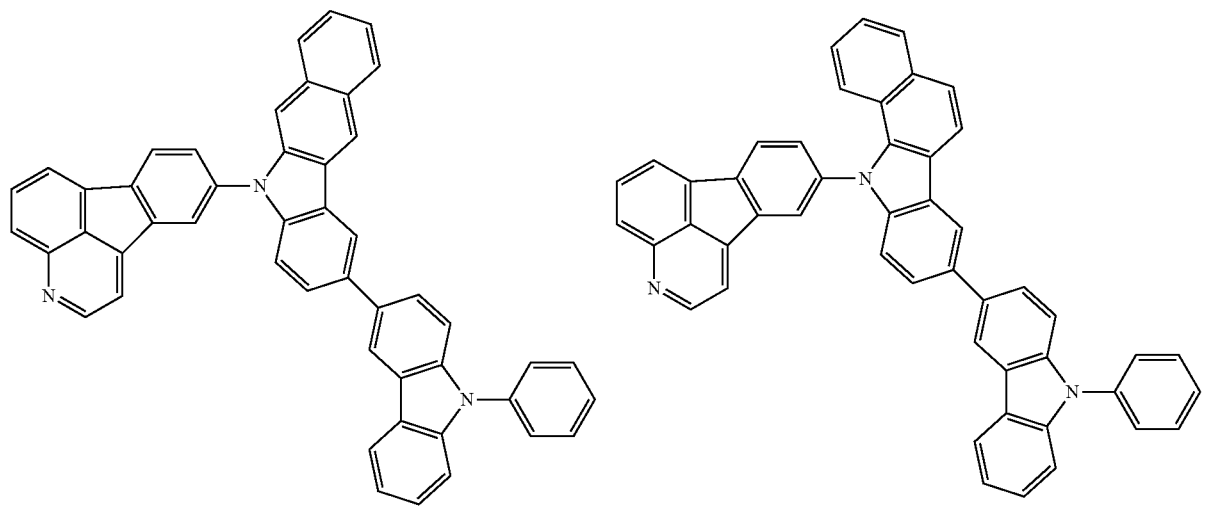

-continued
355
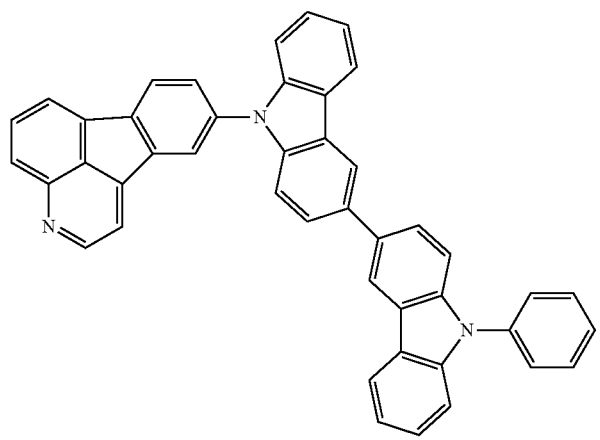
356
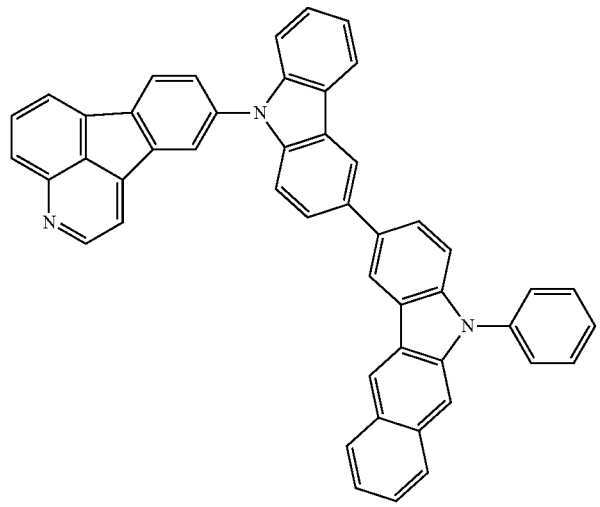
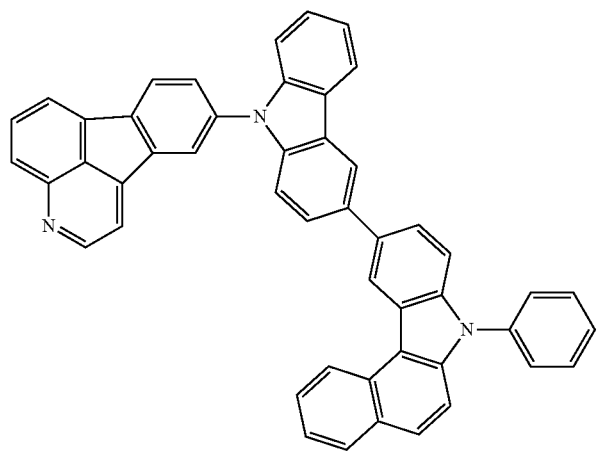
[Chem. 99]
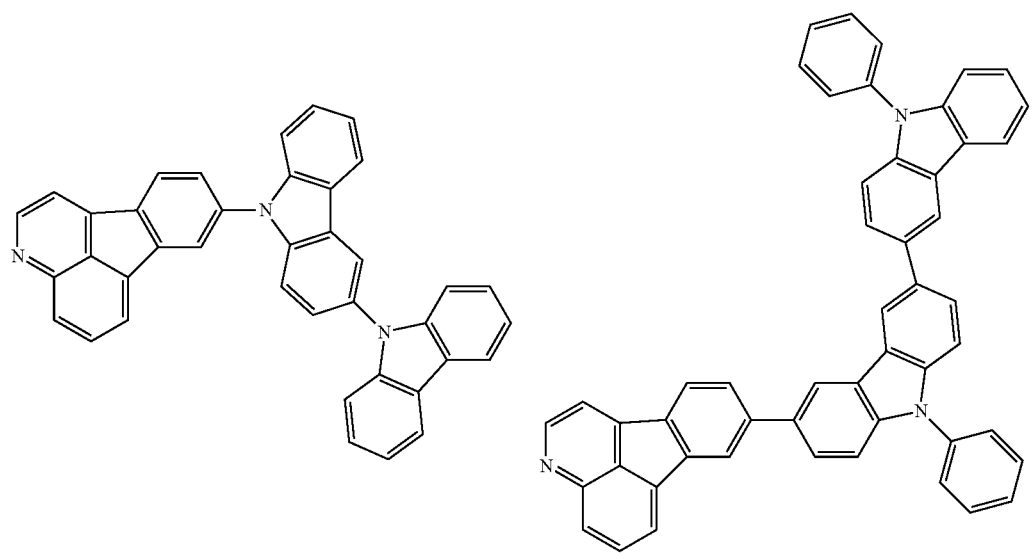

-continued
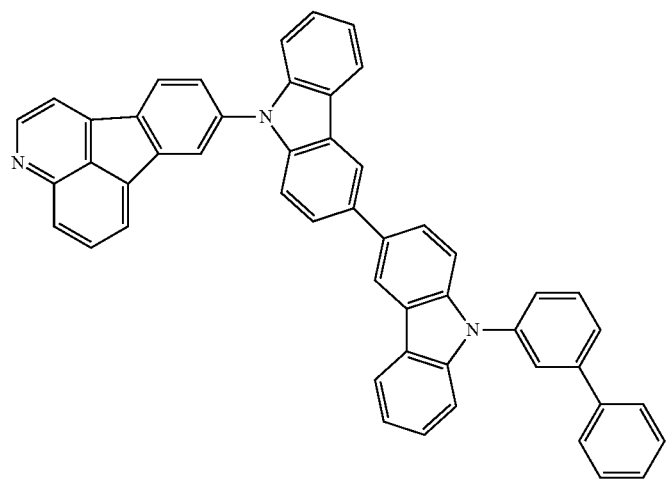
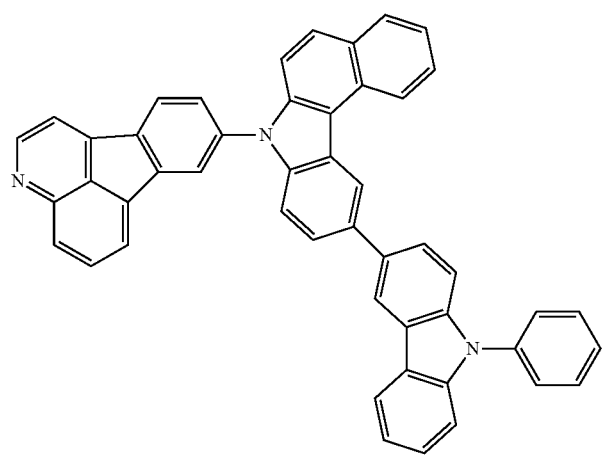
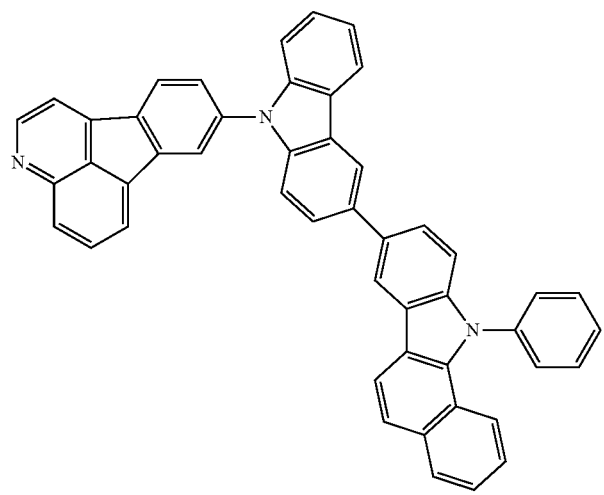

-continued
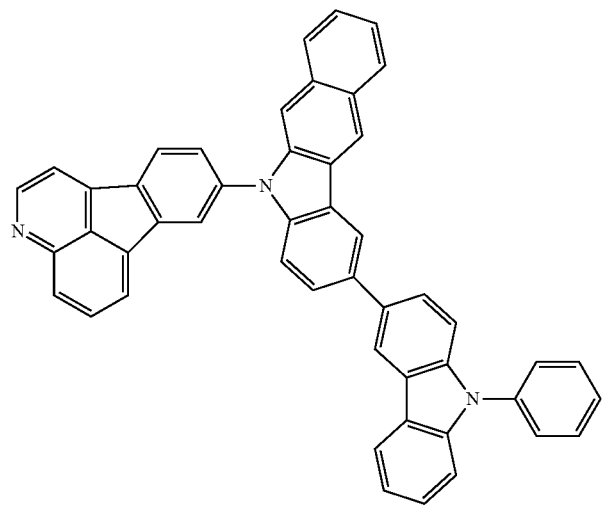
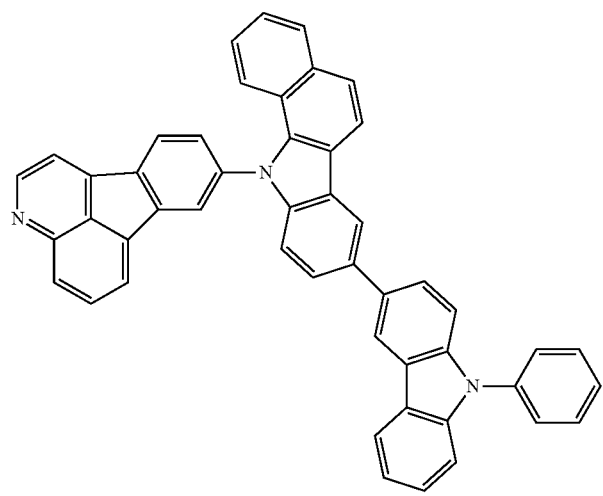
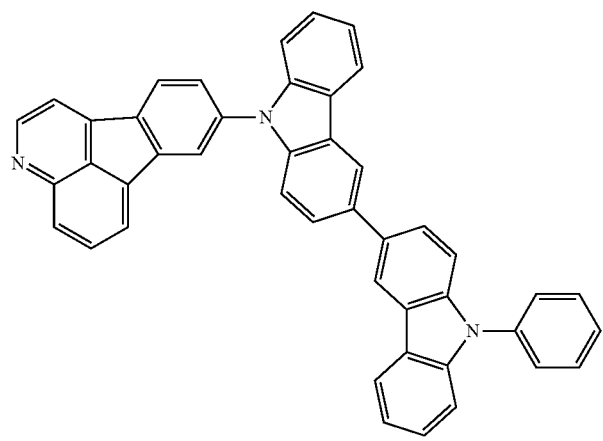

-continued
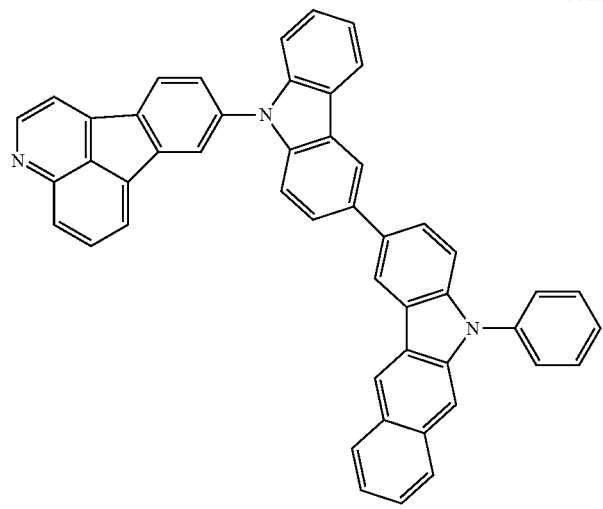
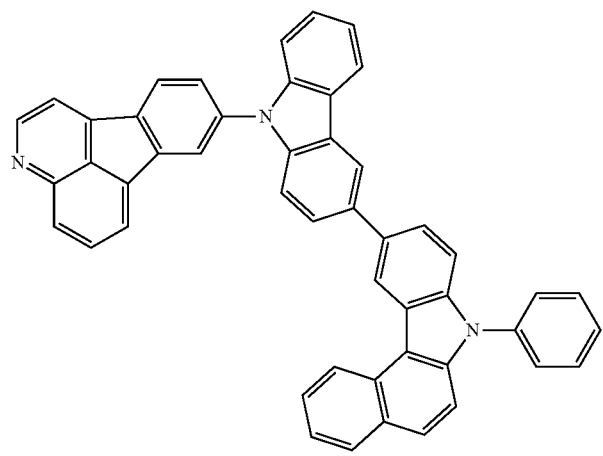
[Chem. 100]
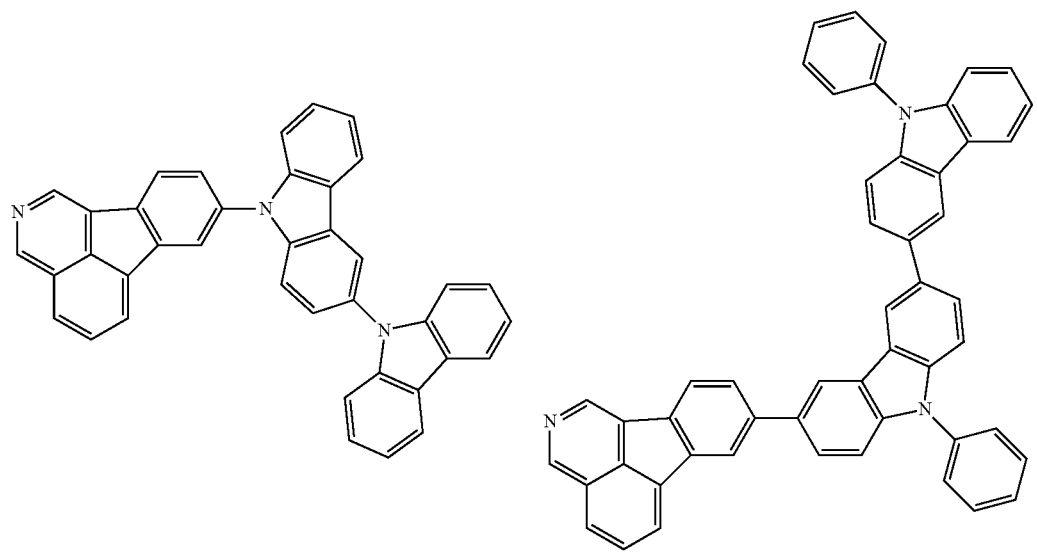

-continued
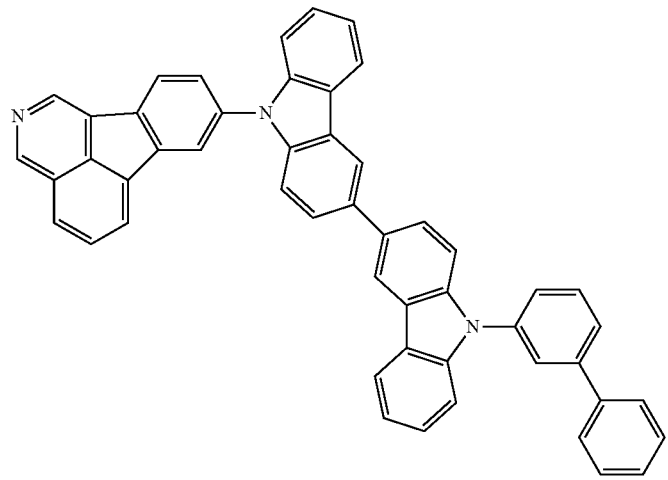
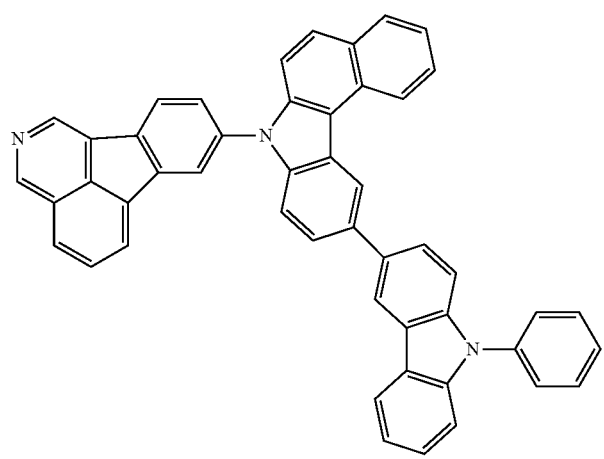
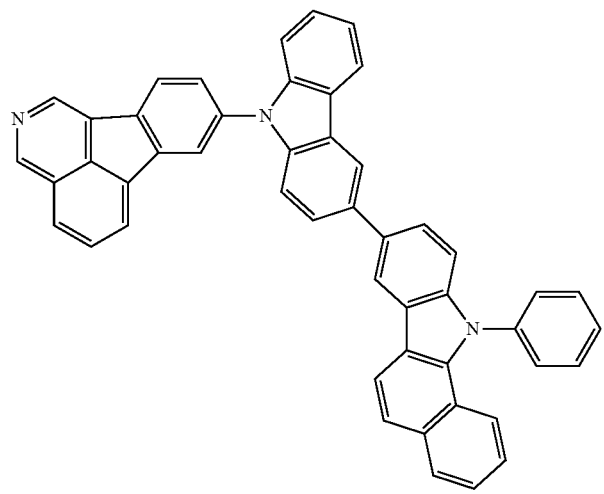

-continued
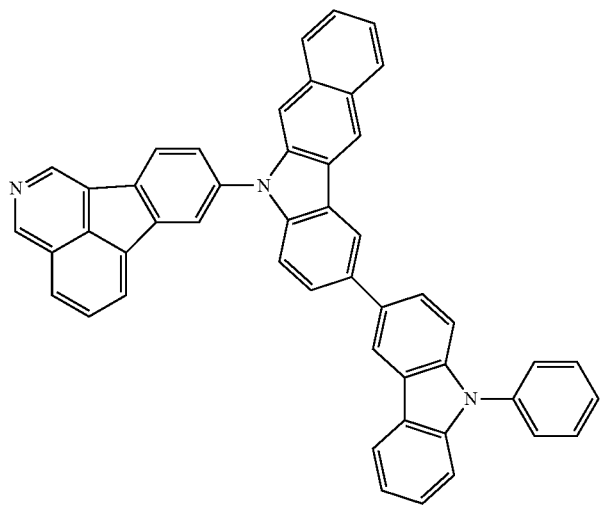
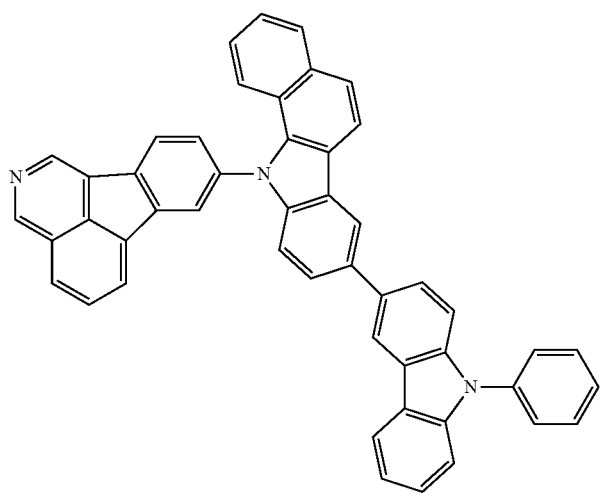
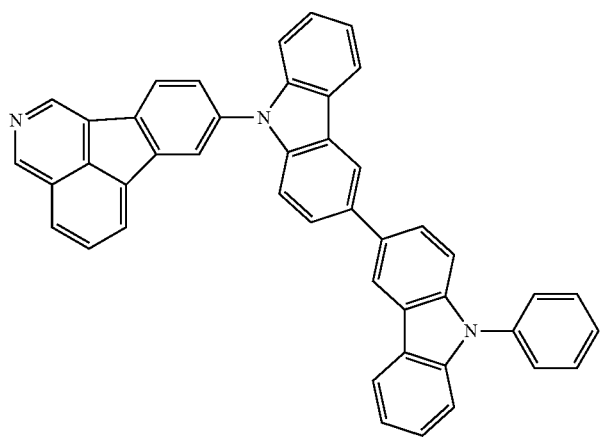

-continued
367
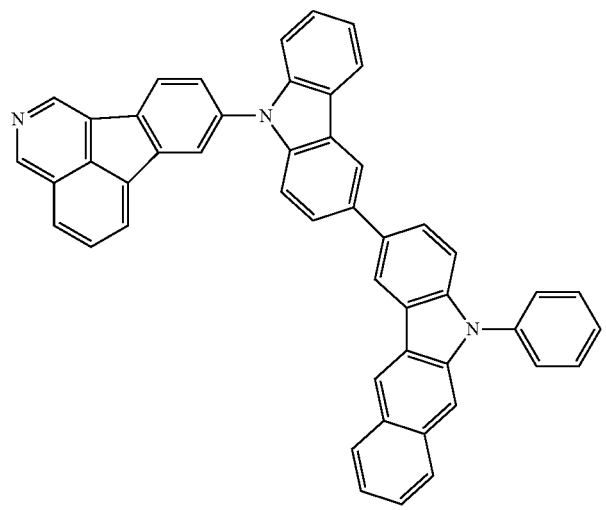
368
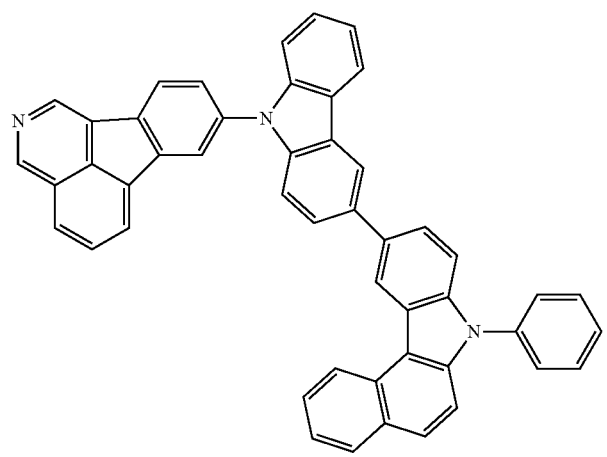
[Chem. 101]
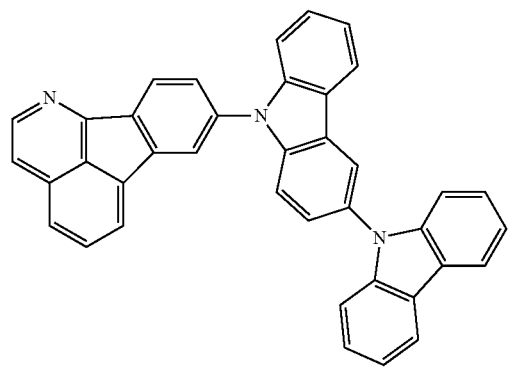
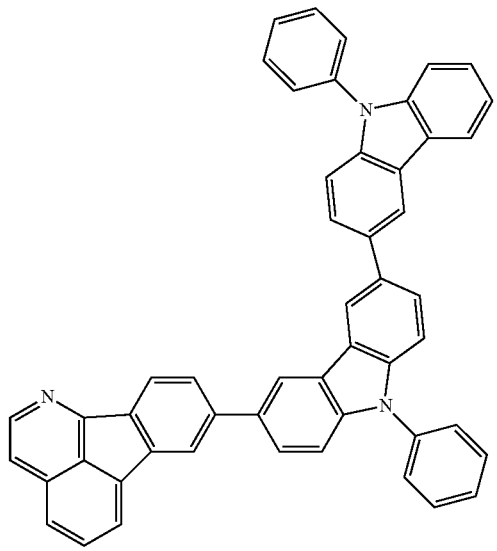
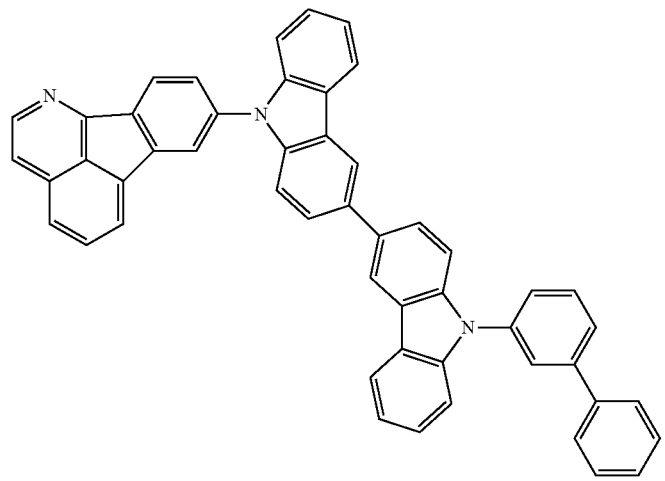

-continued
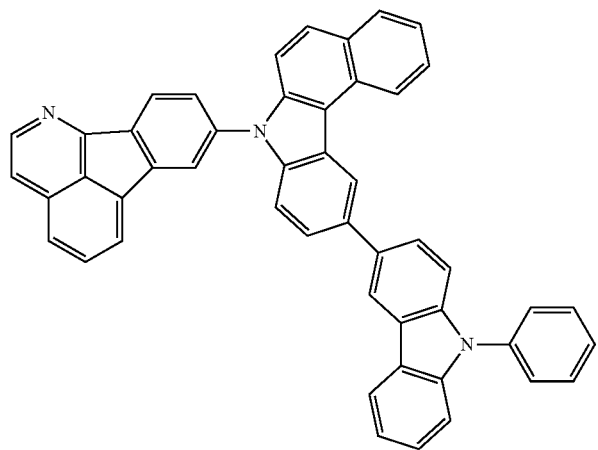
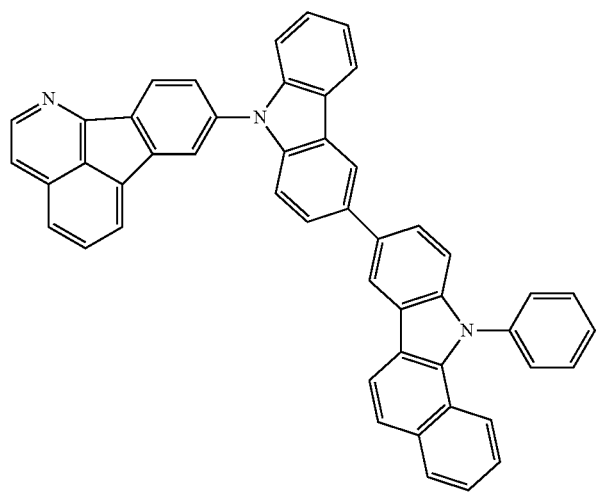
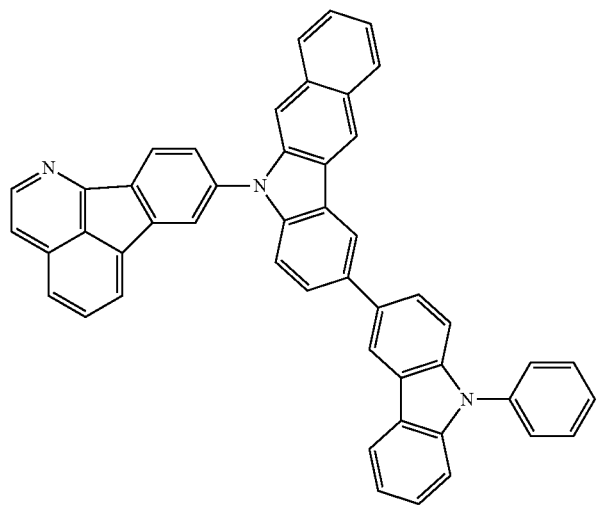

-continued
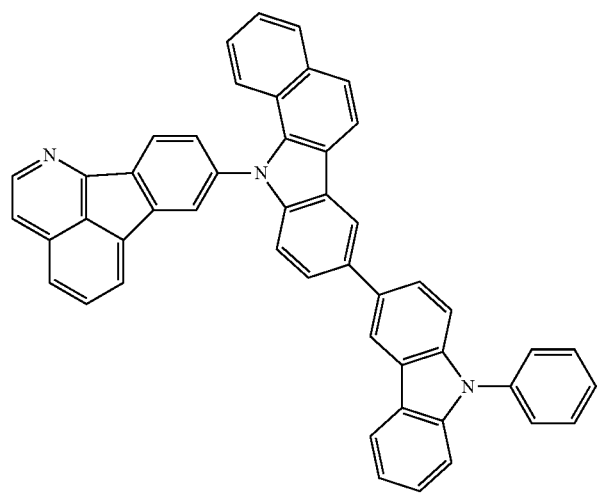
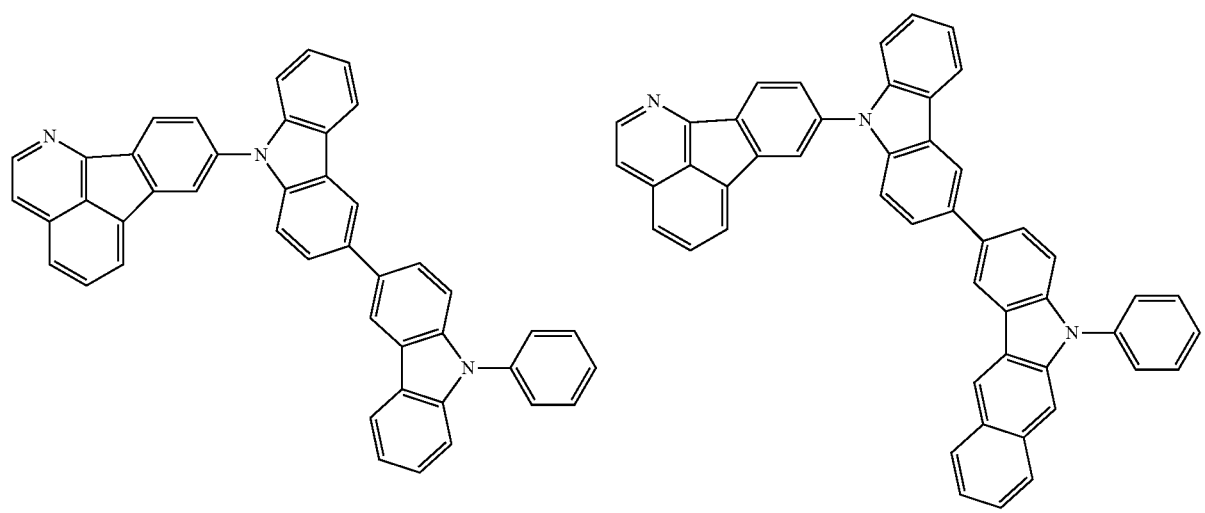
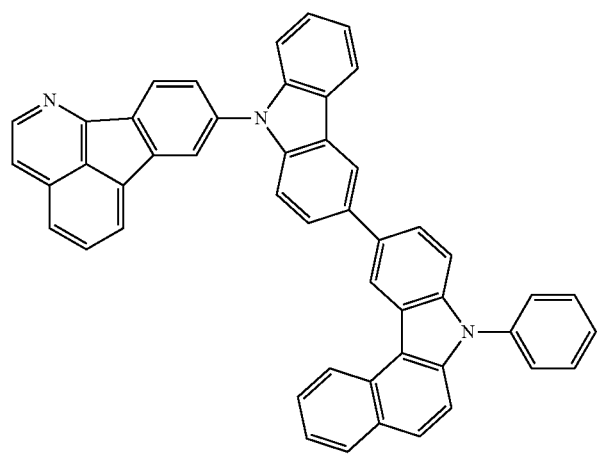

[Chem. 102]
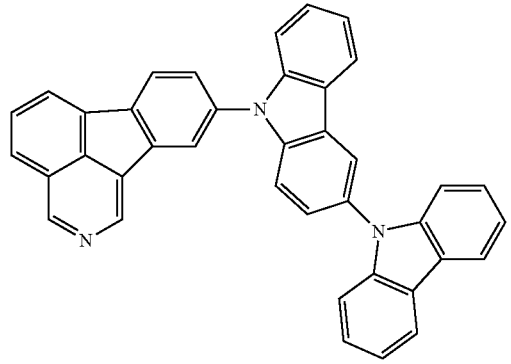
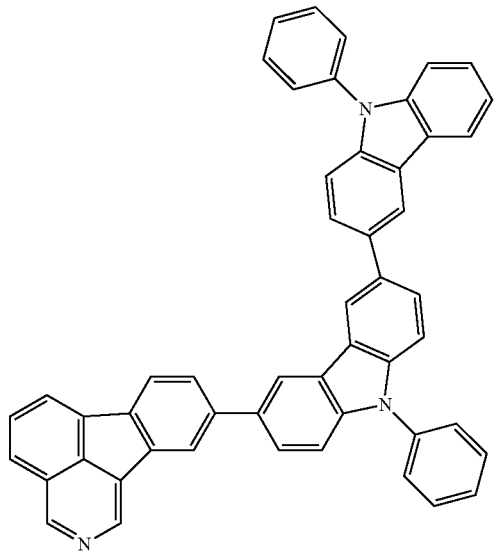
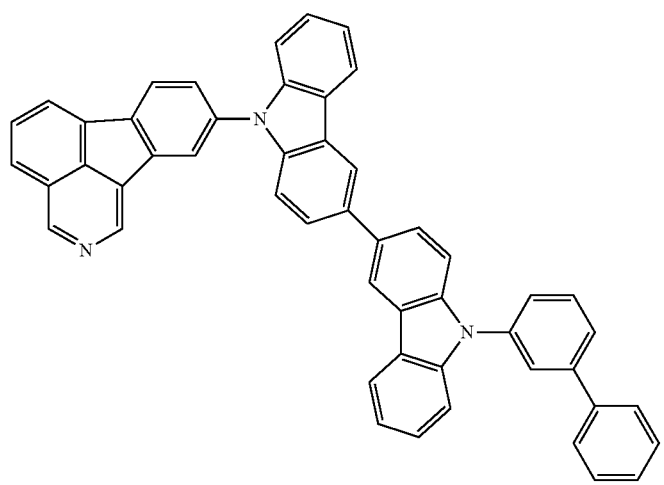
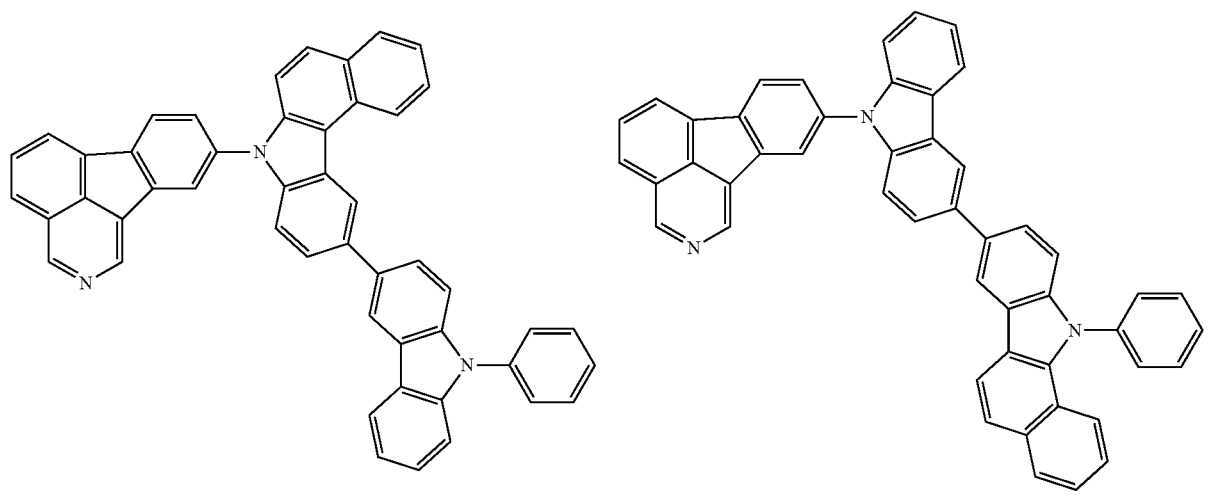

-continued
375
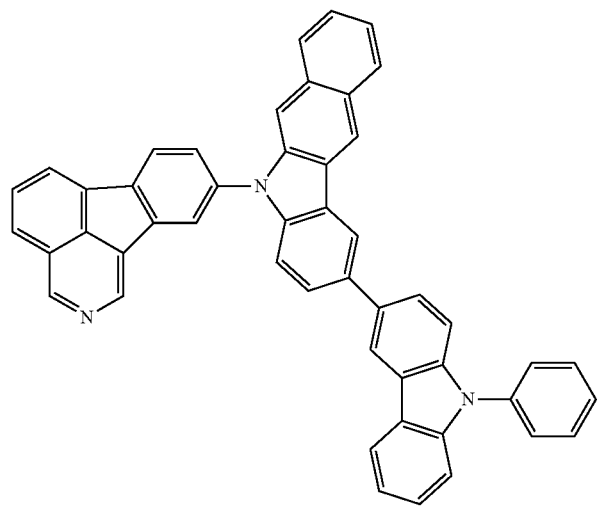
376
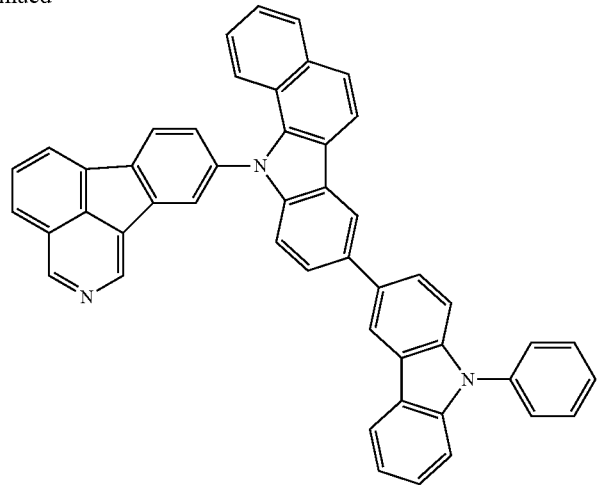
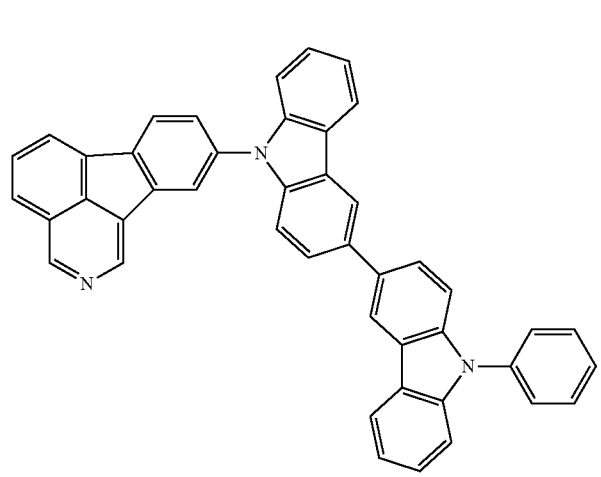
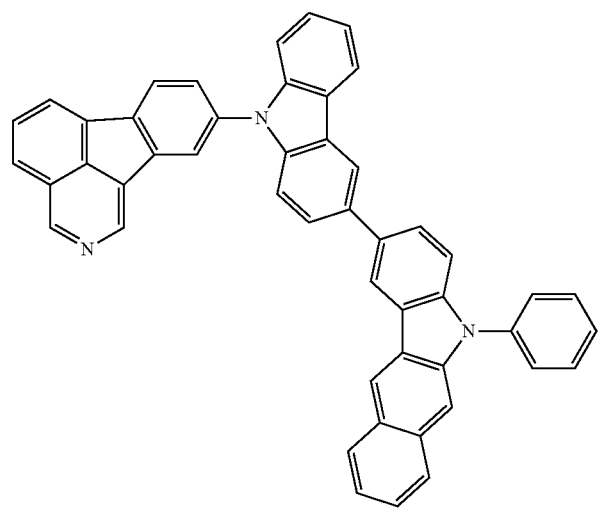
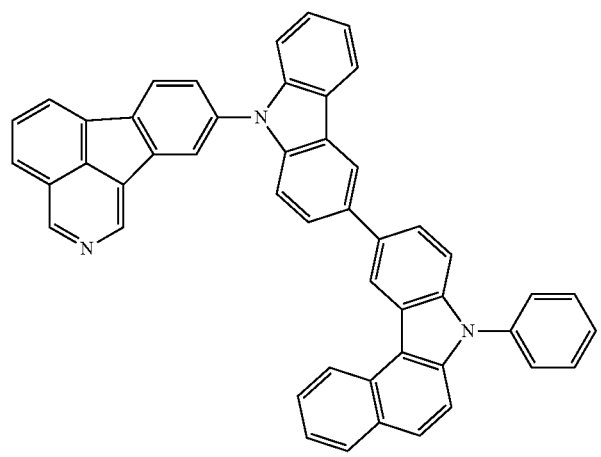

[Chem. 103]
-continued
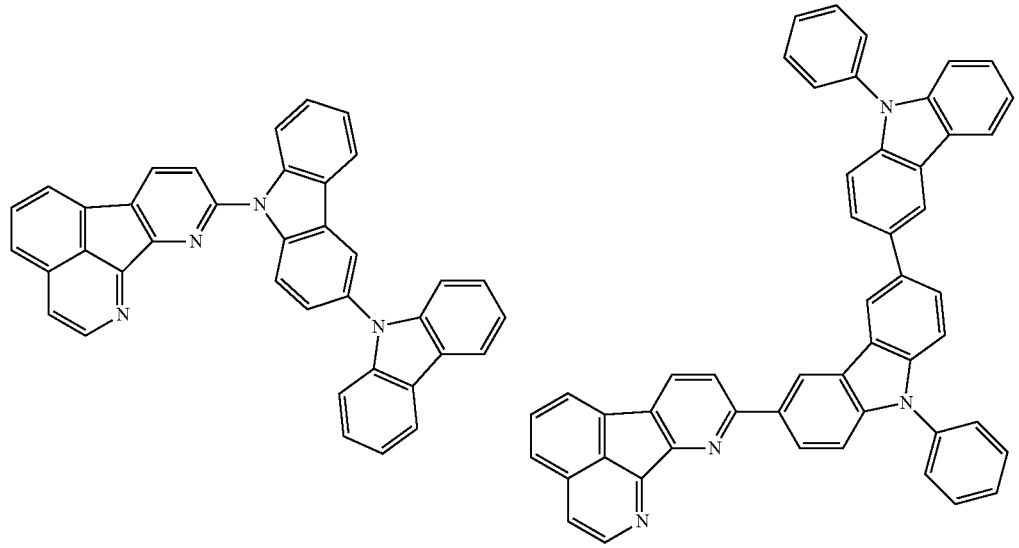
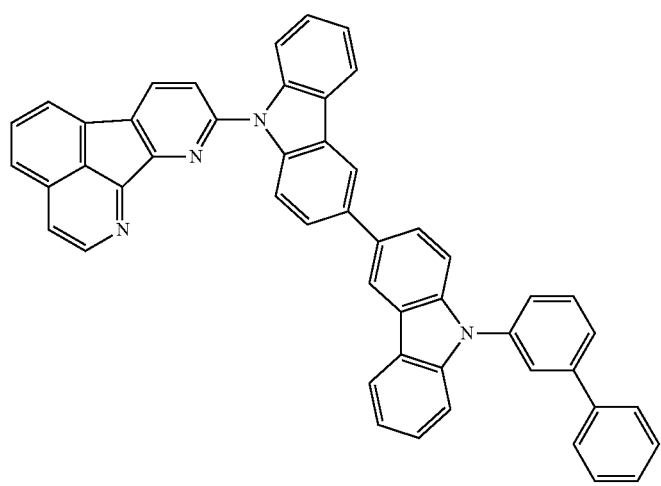
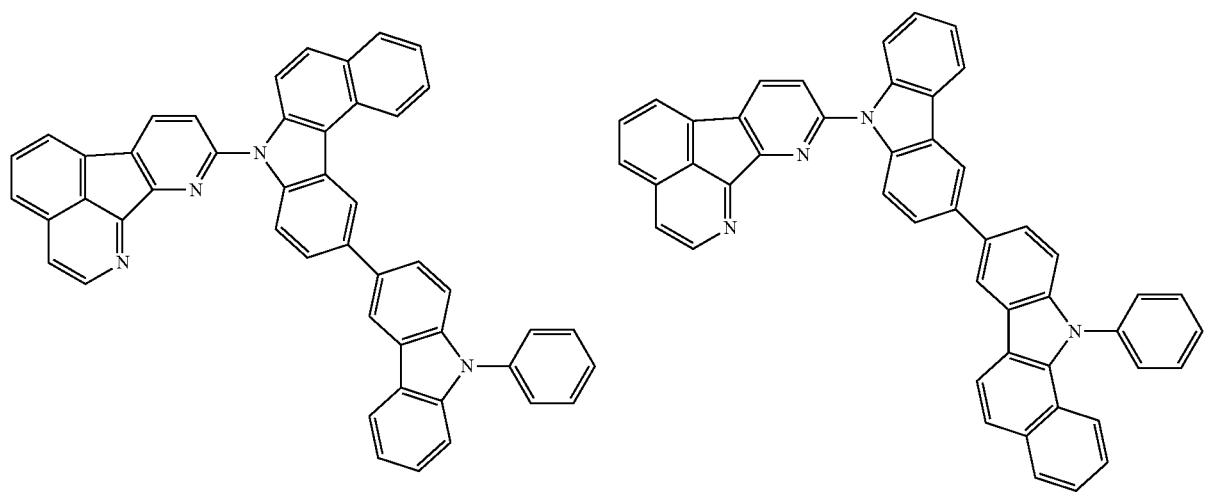

-continued
| 379 | 380 |
|---|---|
| 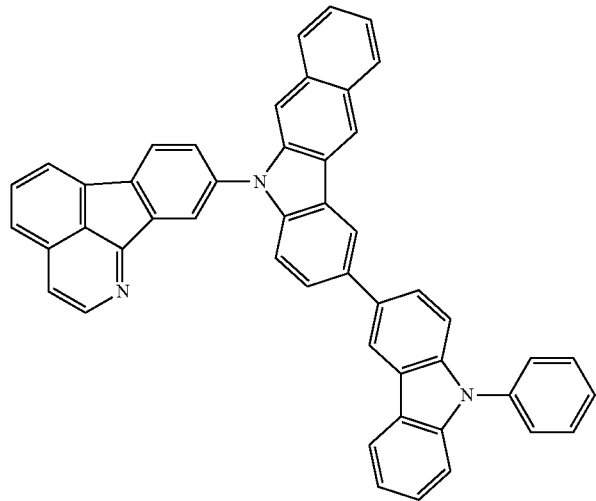 | 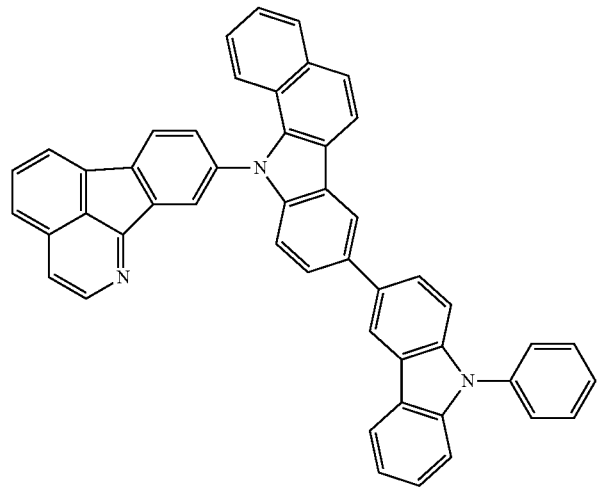 |
| 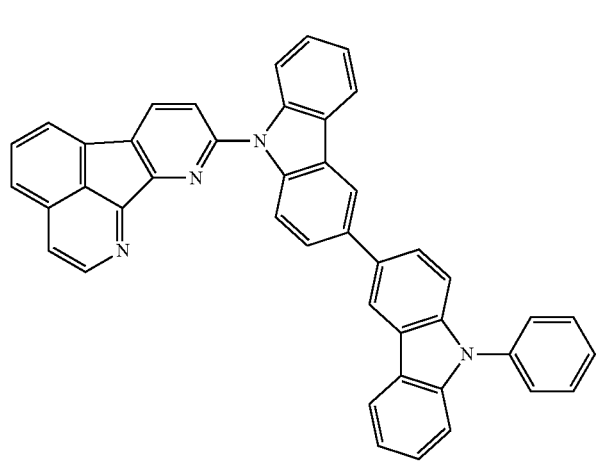 | 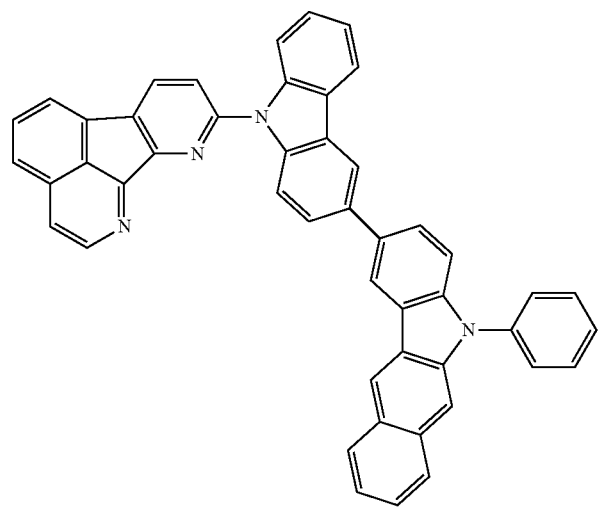 |
| 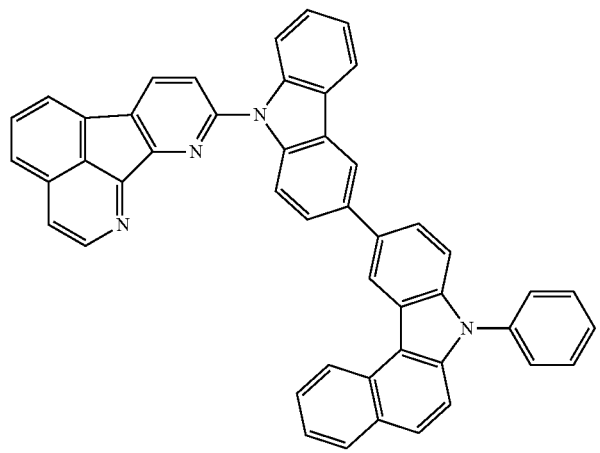 | |

381
382
-continued
[Chem. 104]
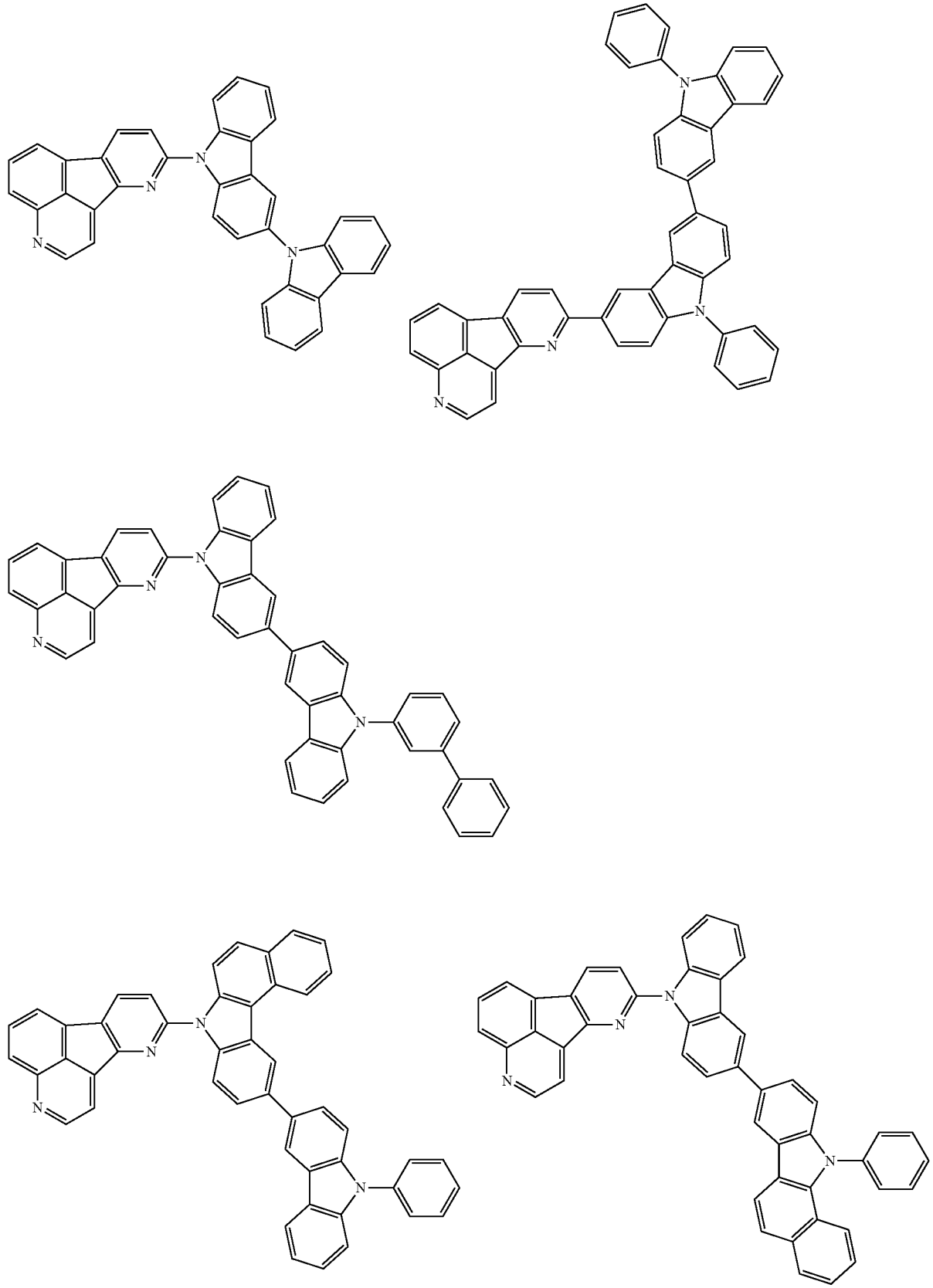

383 384
-continued
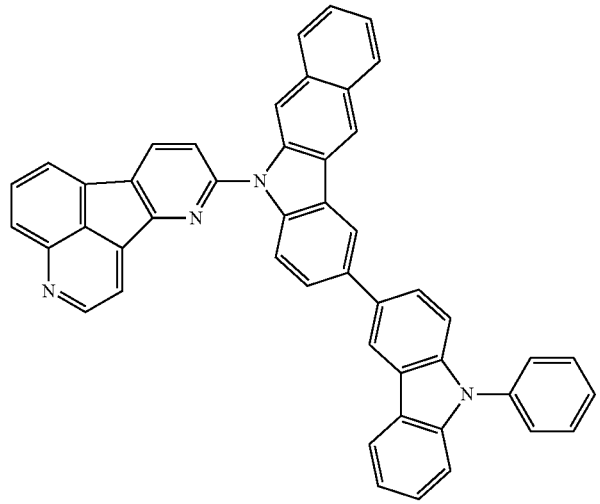
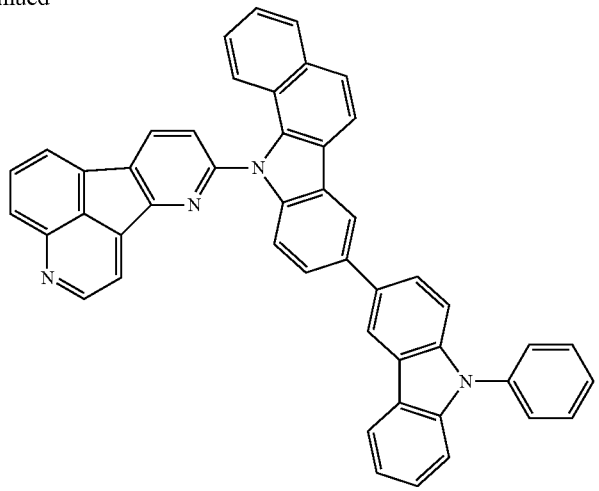
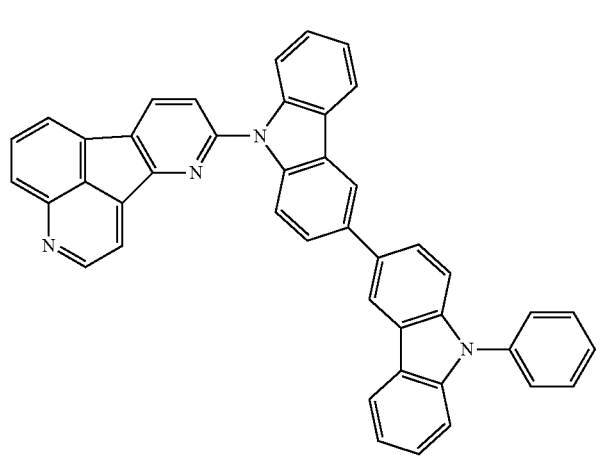
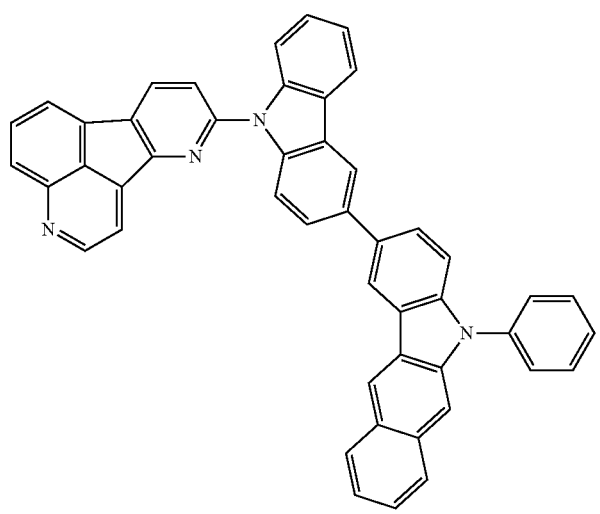
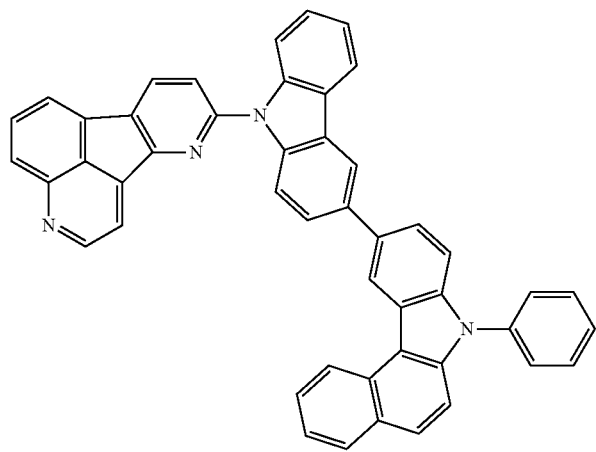

[Chem. 105]
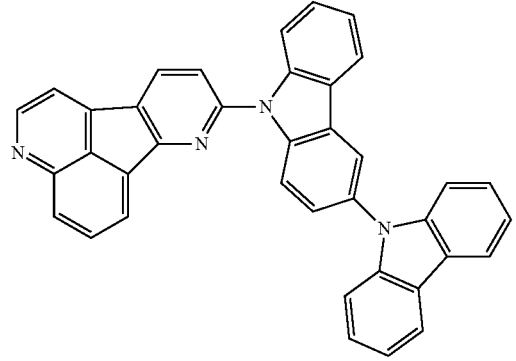
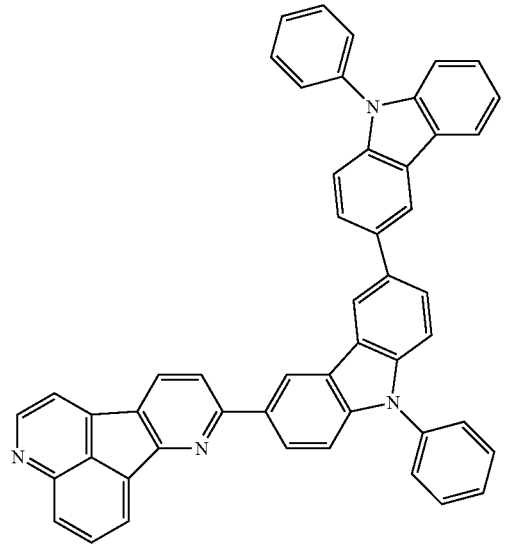
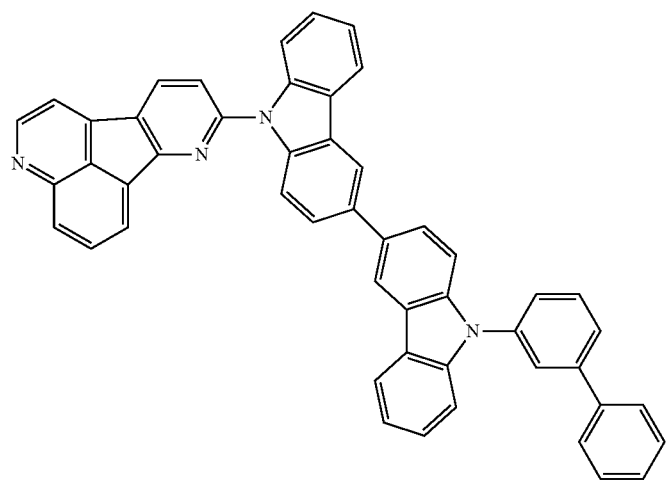
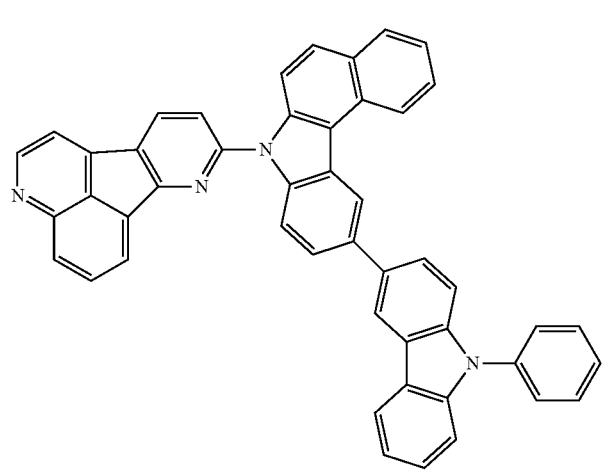
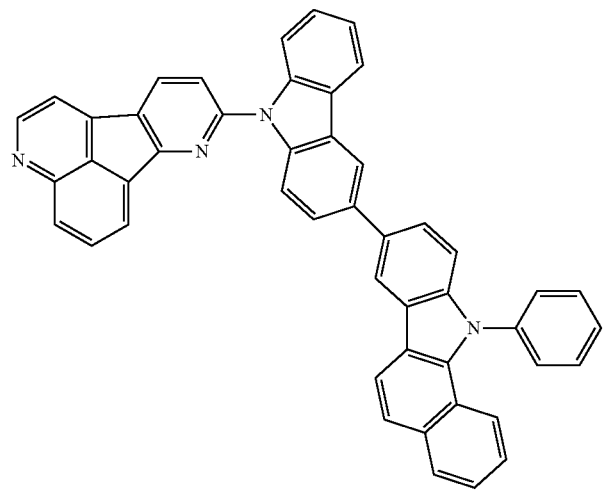

-continued
387 388
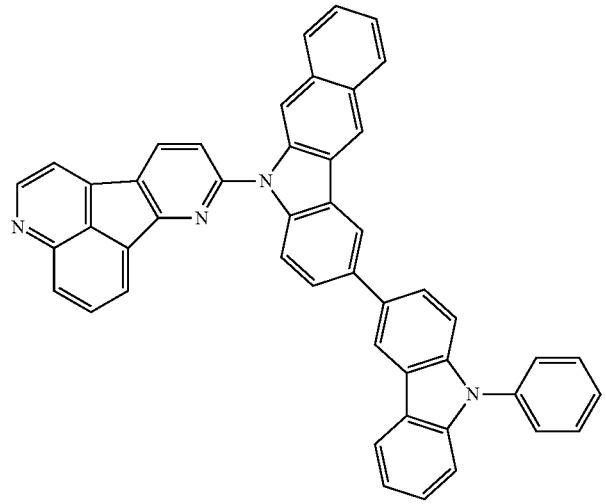 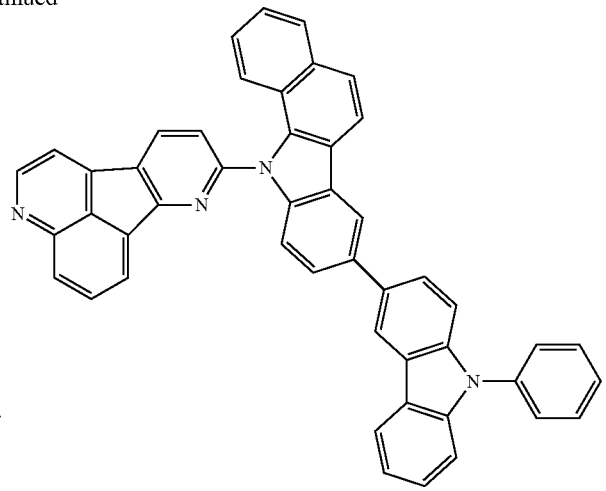
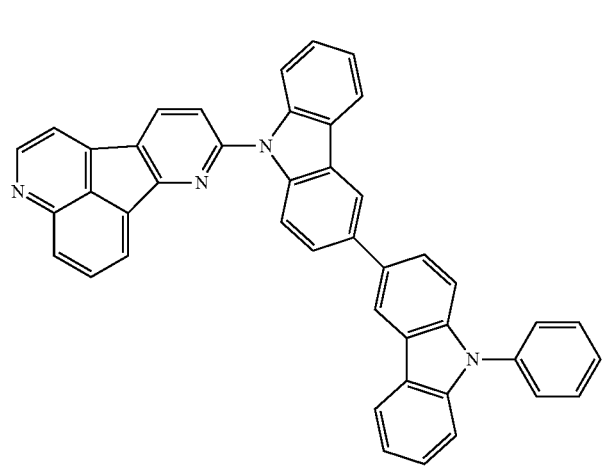 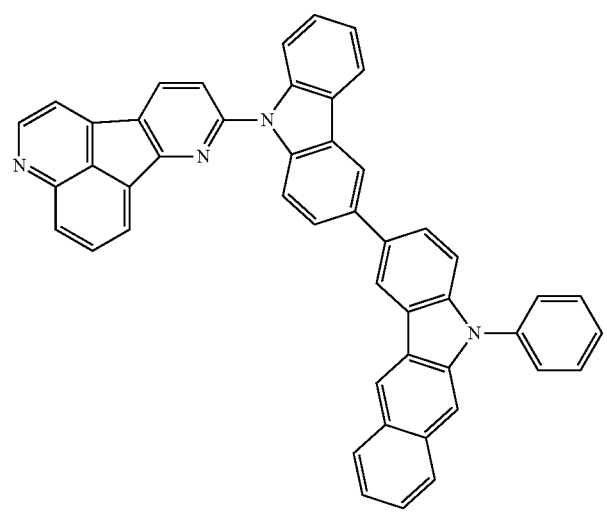
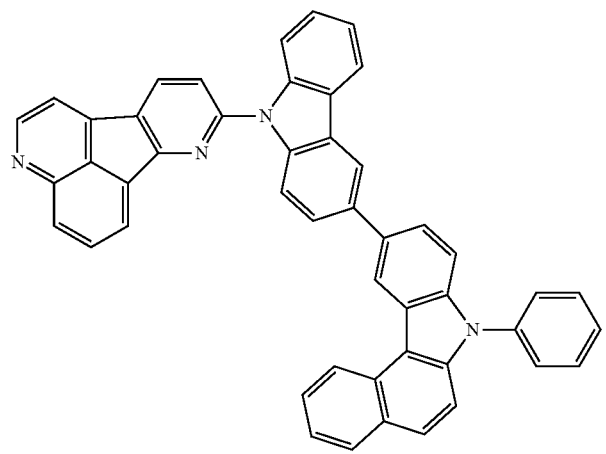

[Chem. 106]
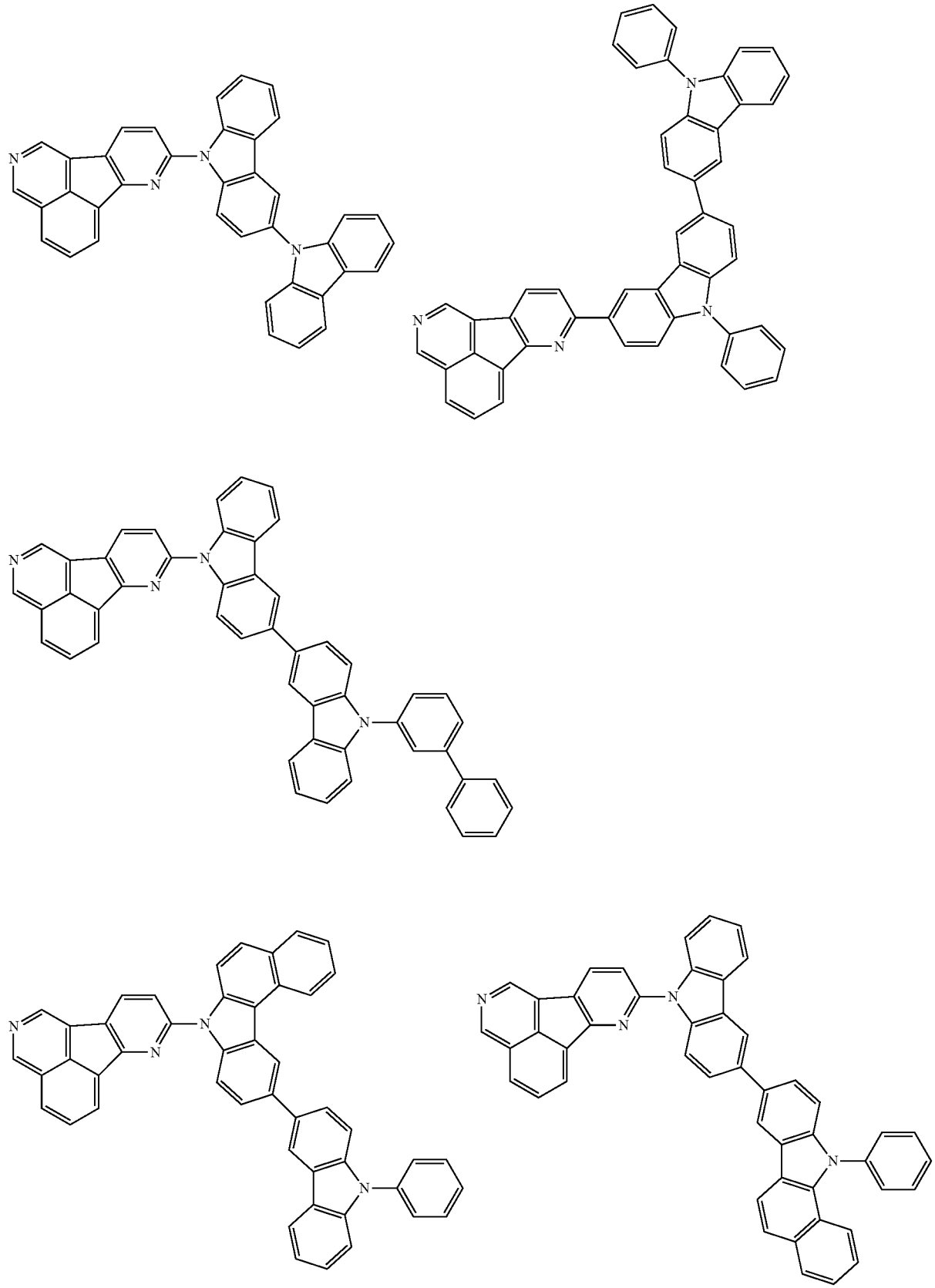

-continued
391
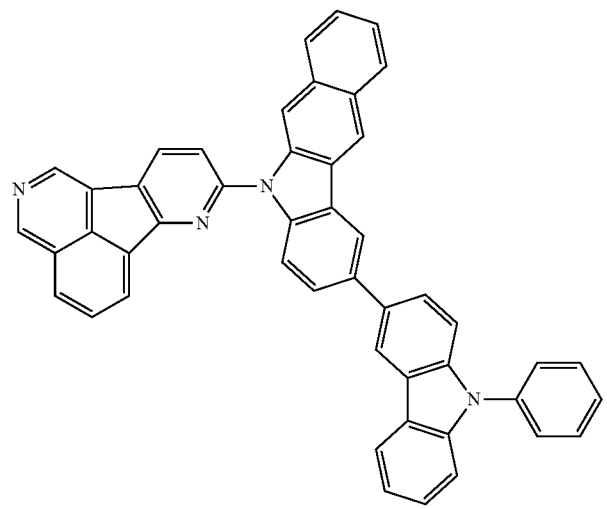
392
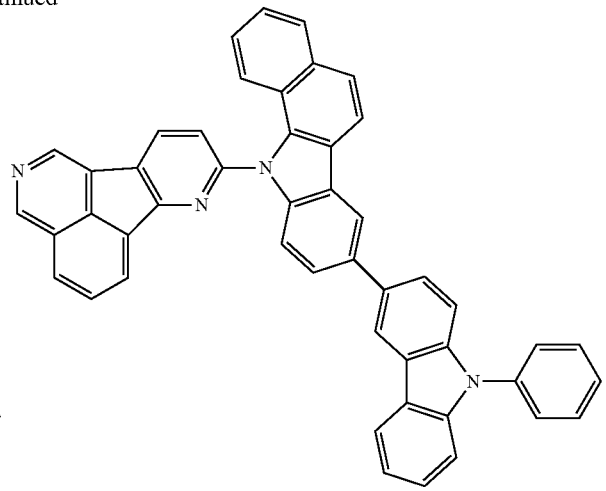
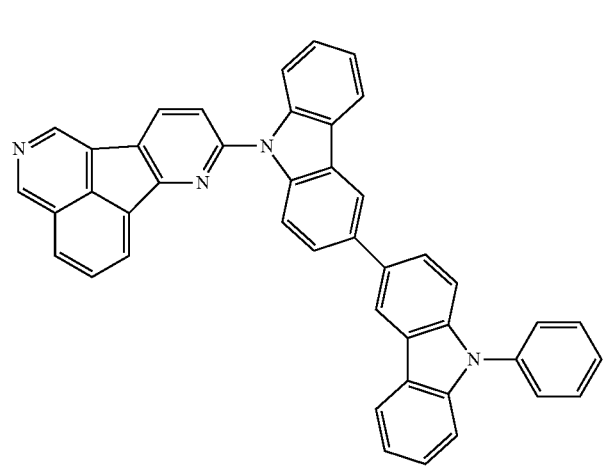
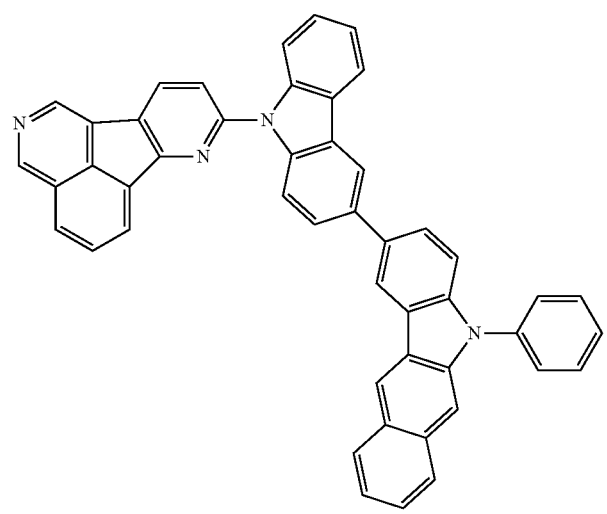
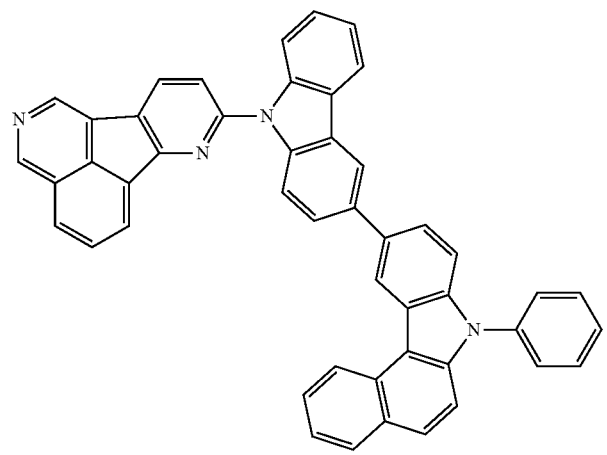

[Chem. 107]
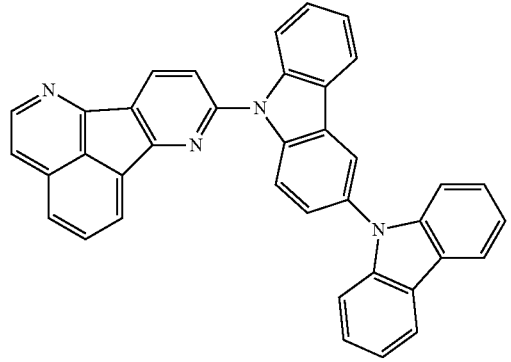
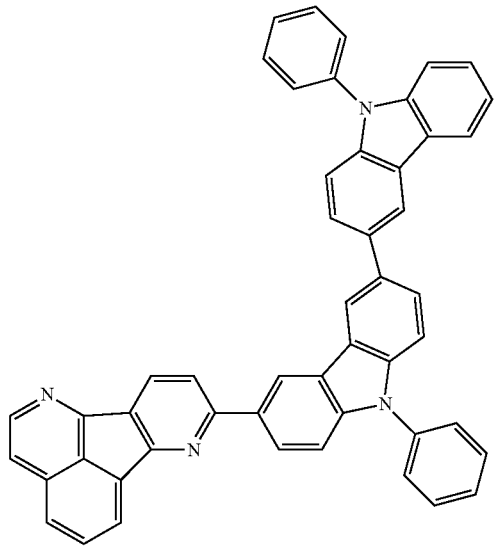
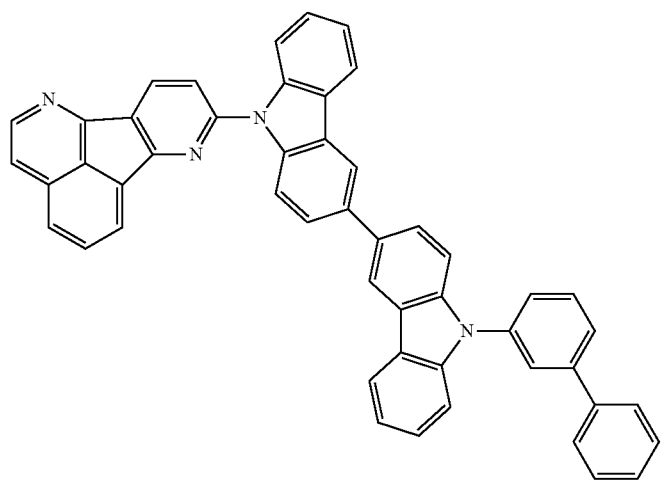
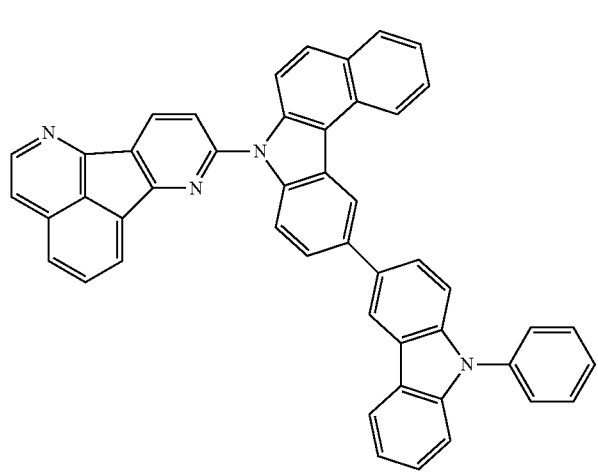
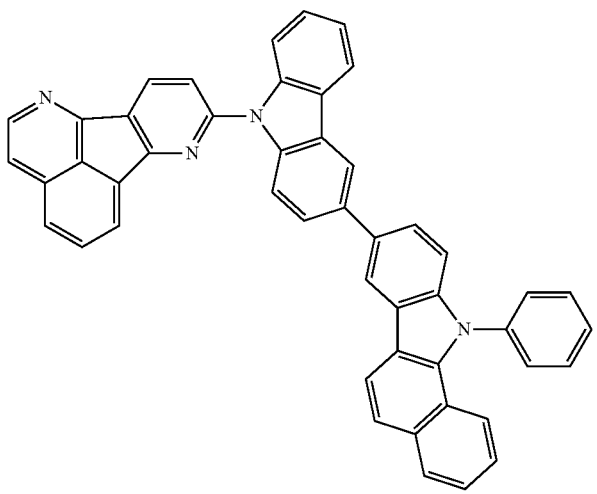

-continued
395 396
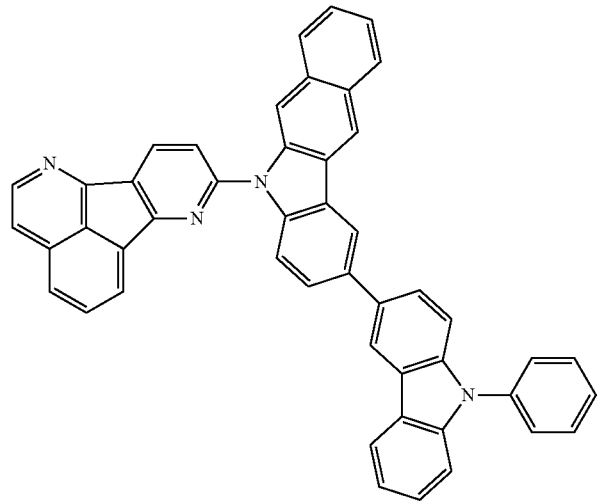 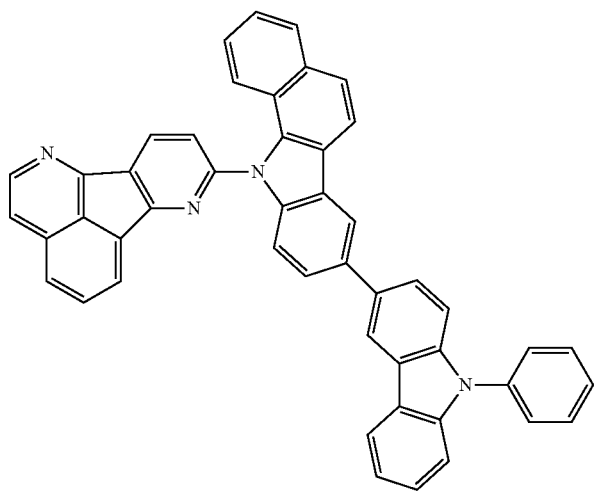
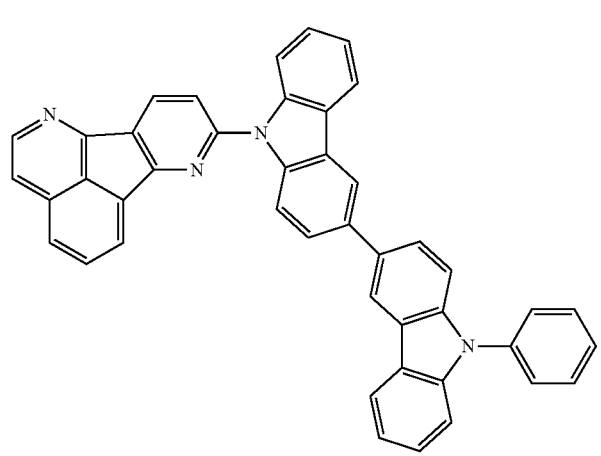 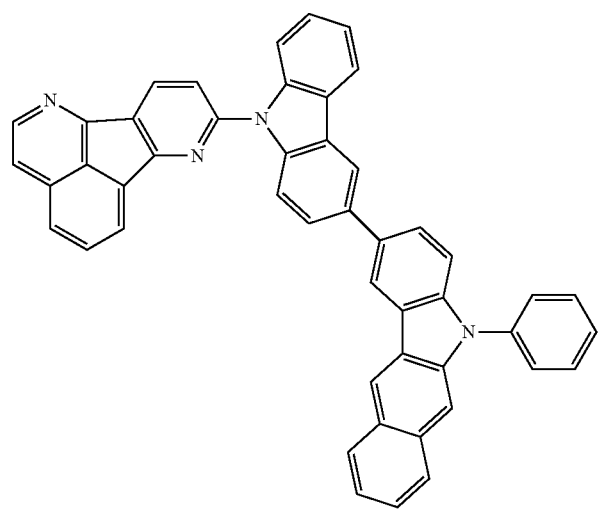
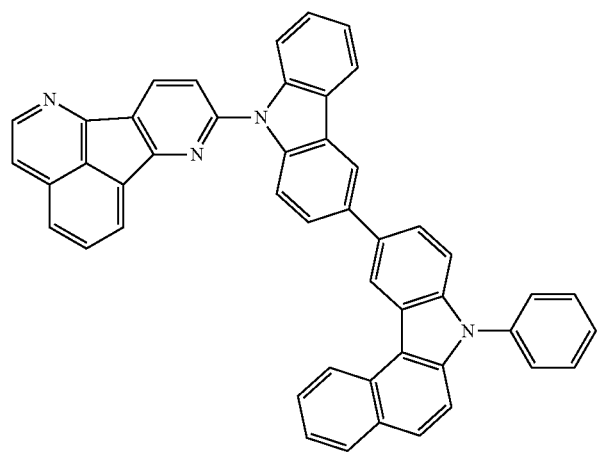

[Chem. 108]
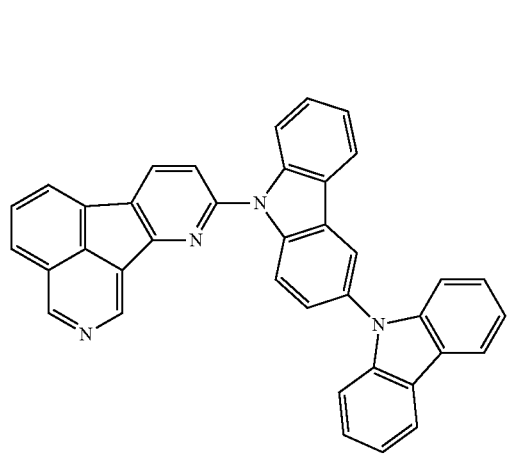
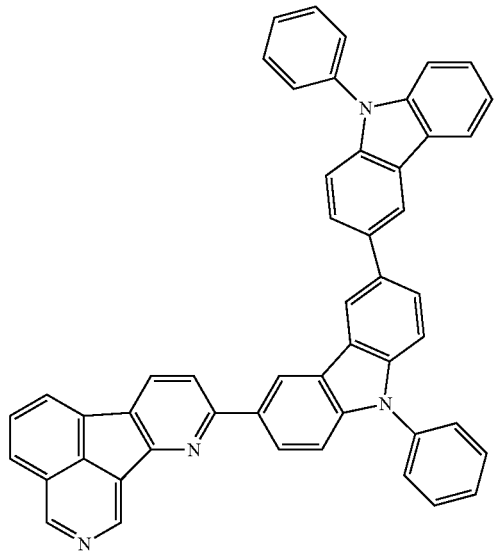
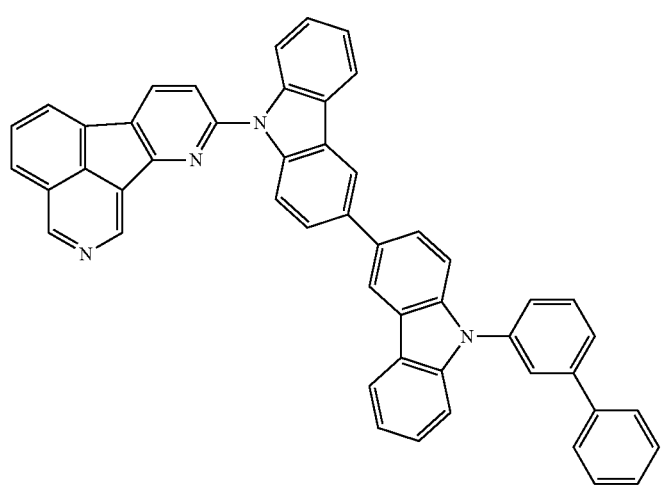
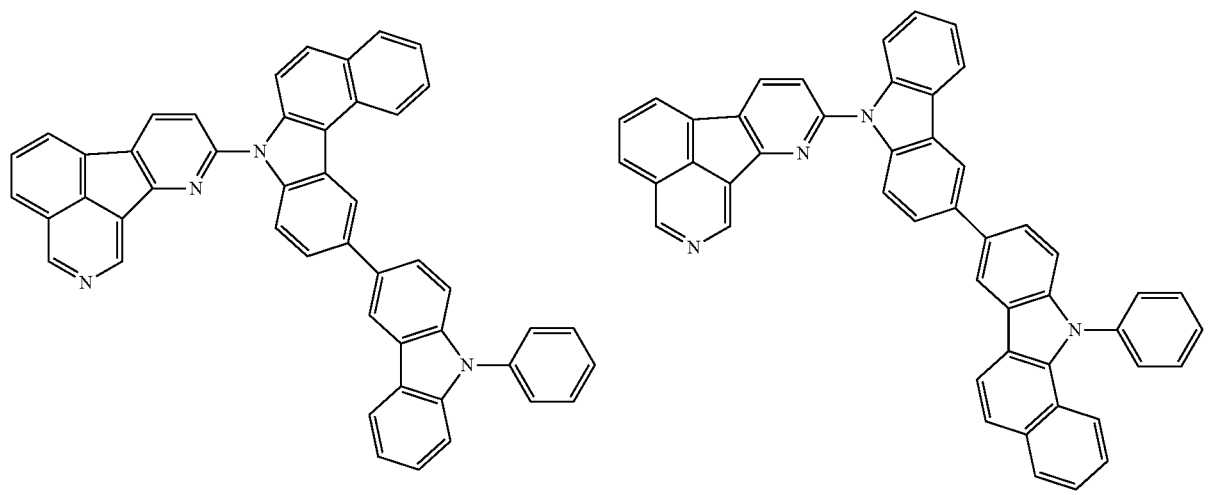

-continued
399
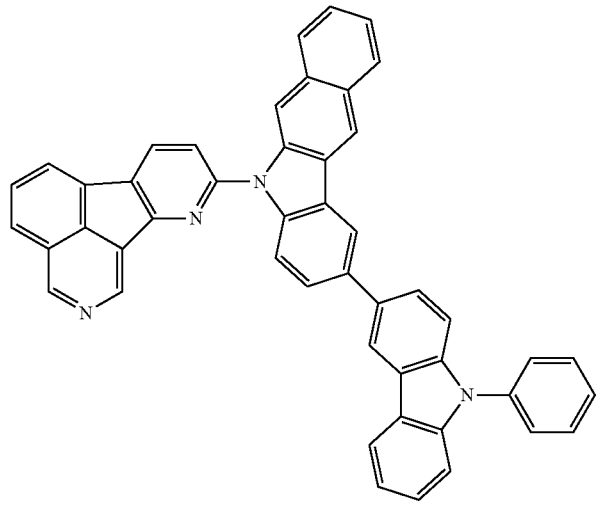
400
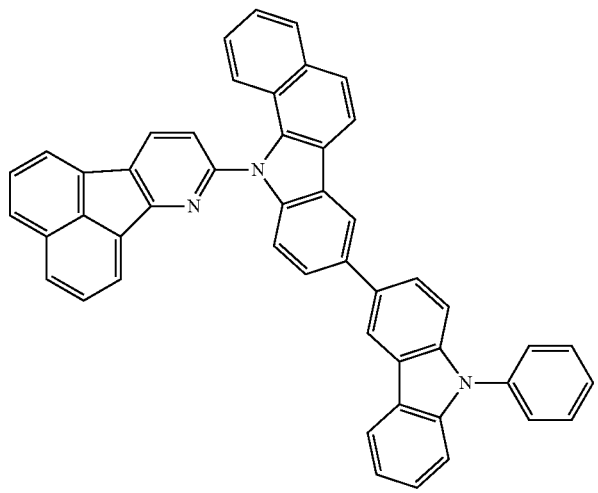
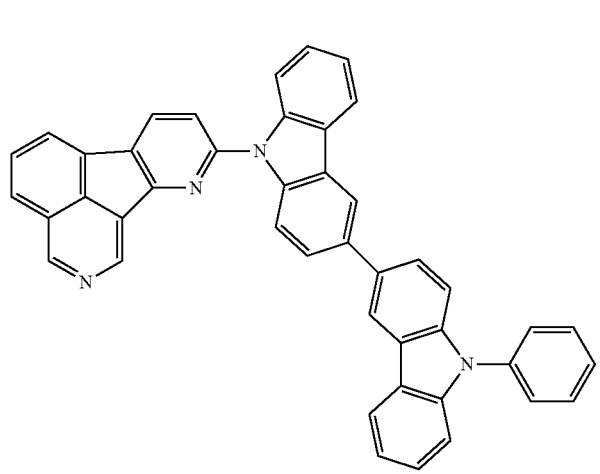
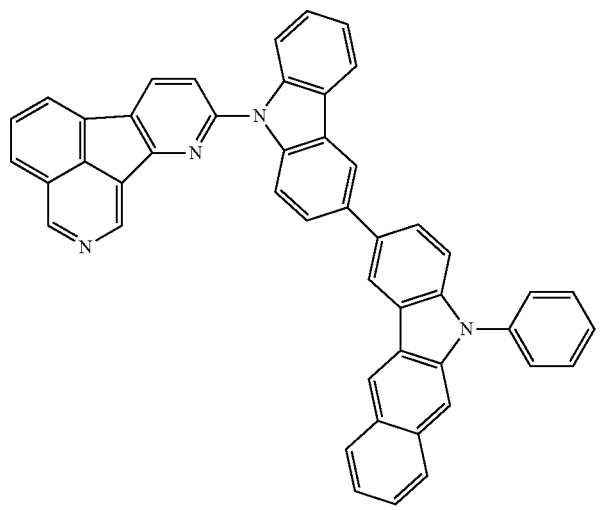
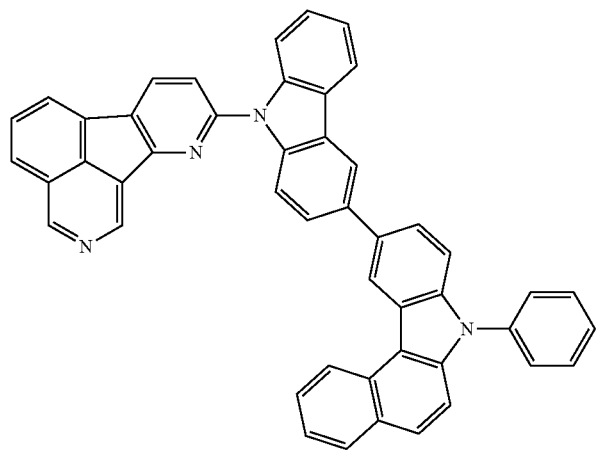

[Chem. 109]
401
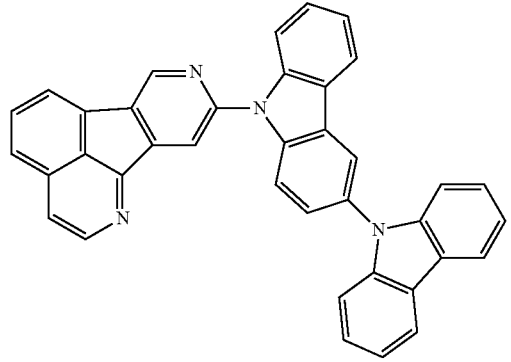
402
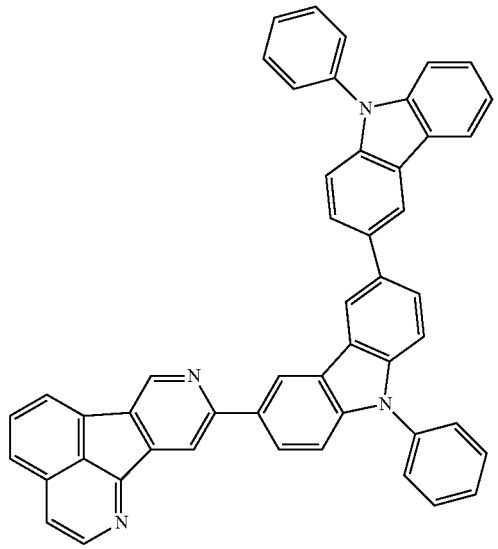
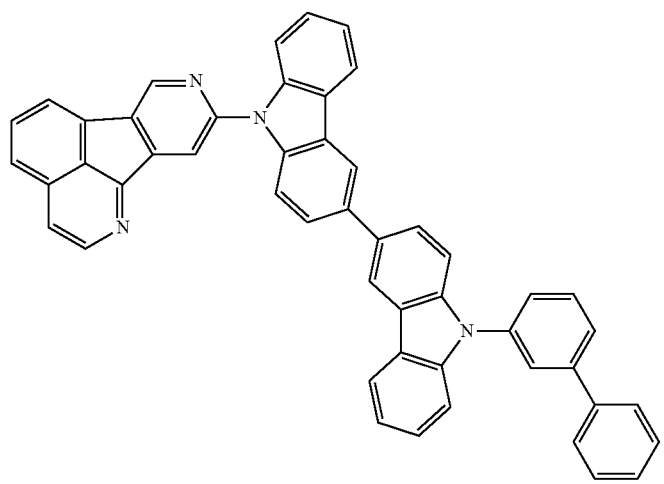
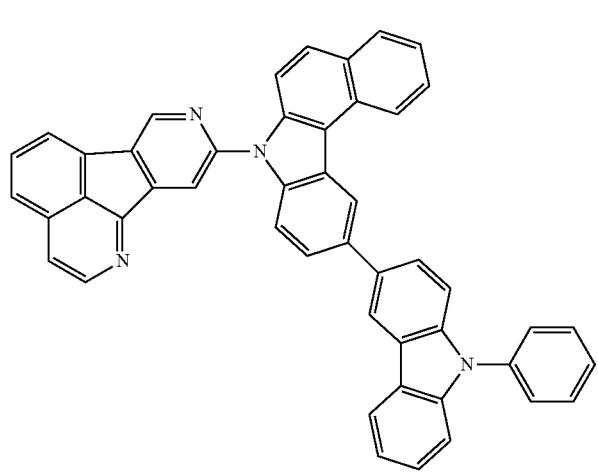
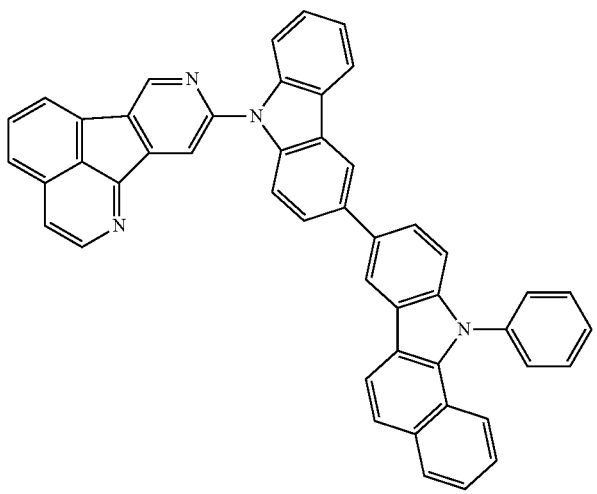

403
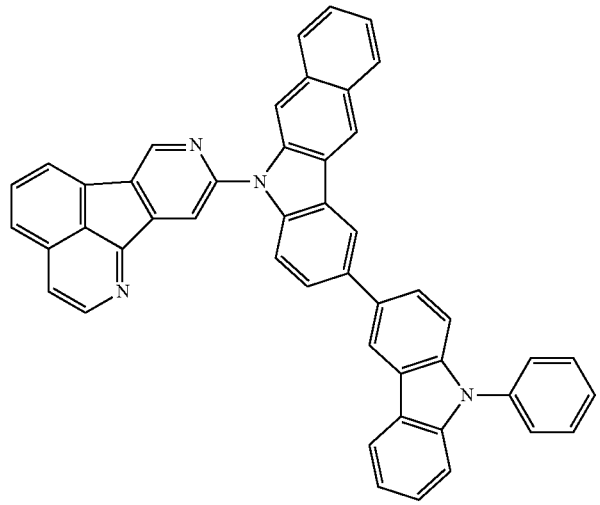
404
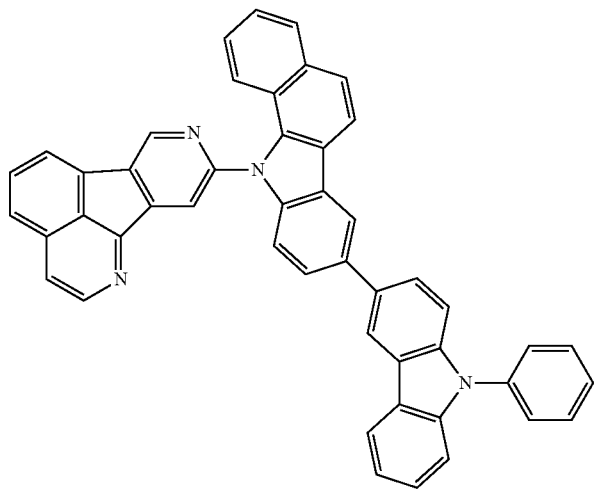
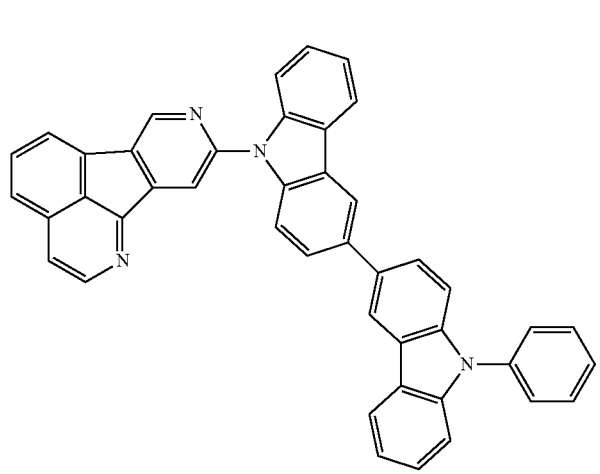
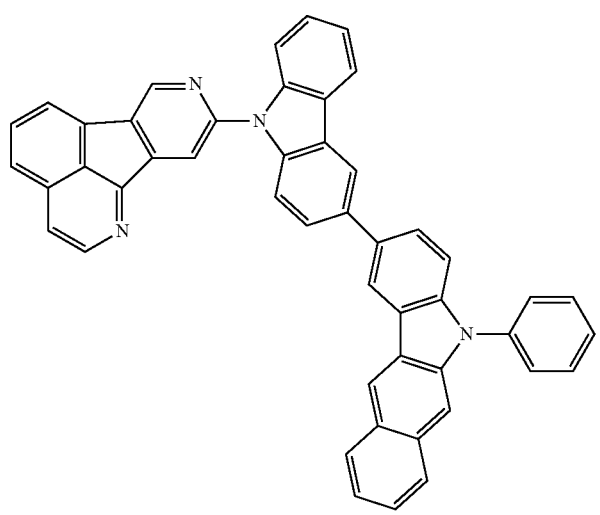
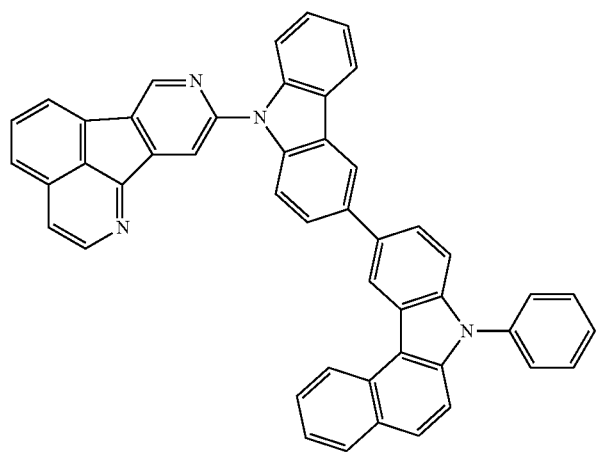

405 406
-continued
[Chem. 110]
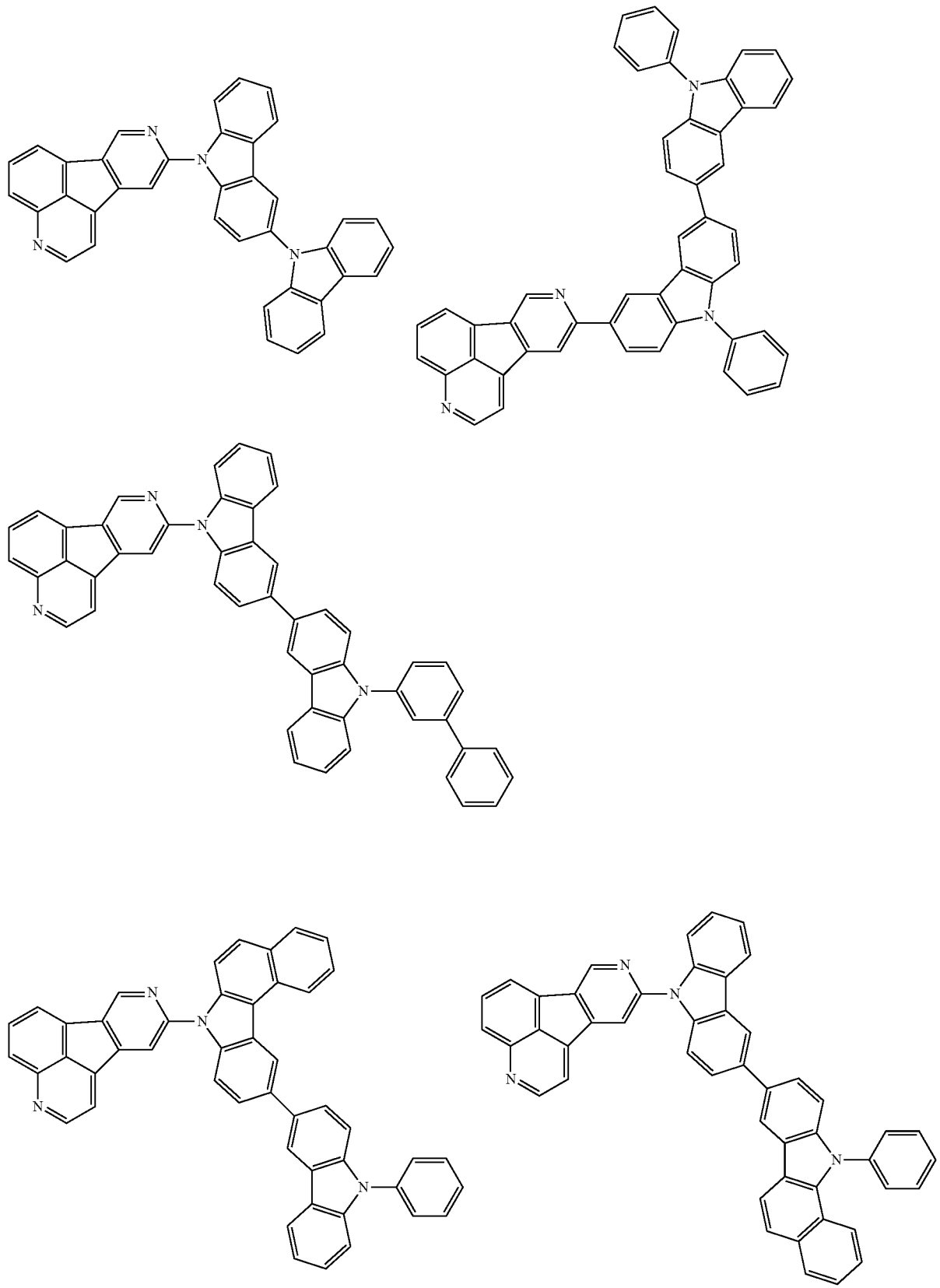

-continued
407
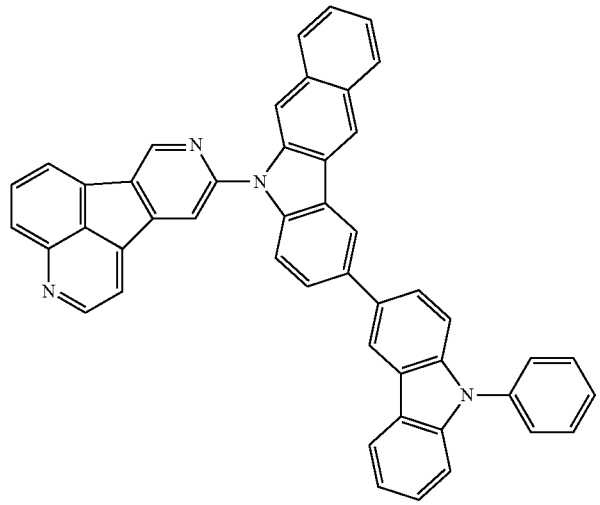
408
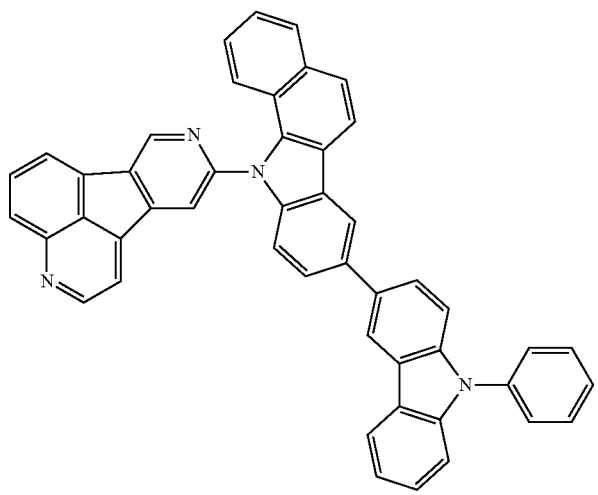
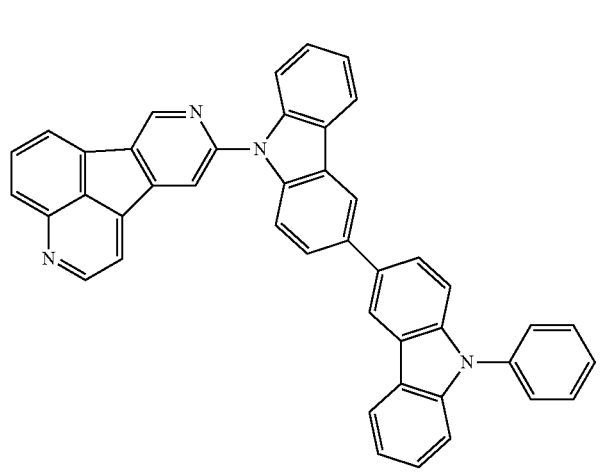
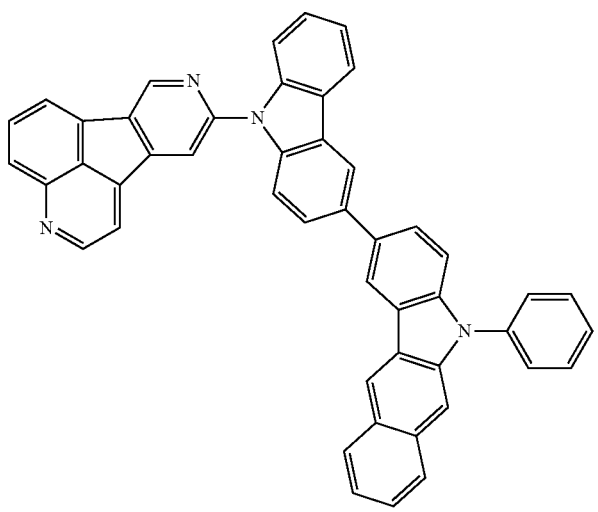
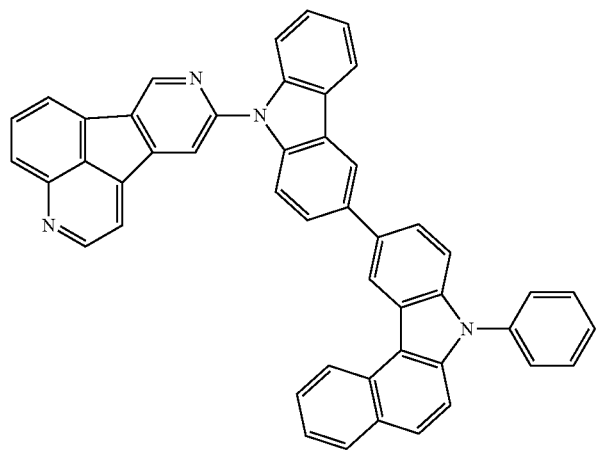

[Chem. 111]
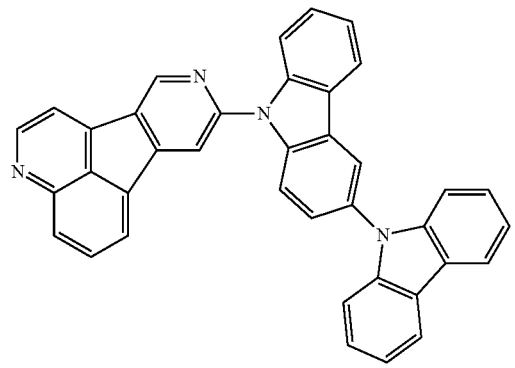
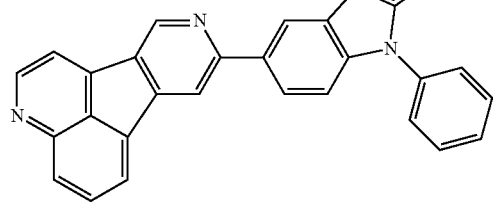
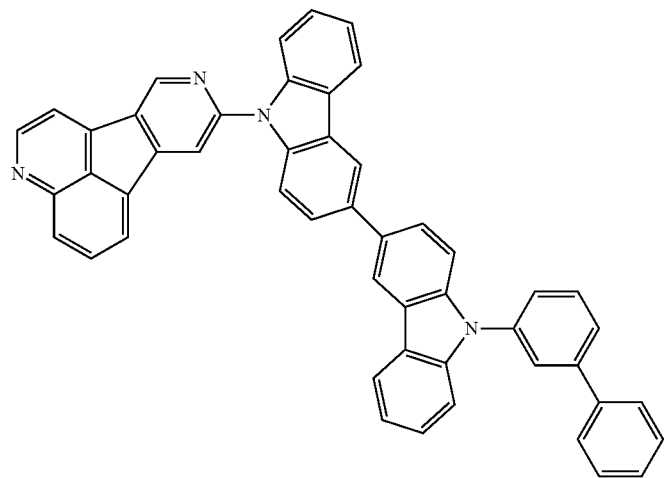
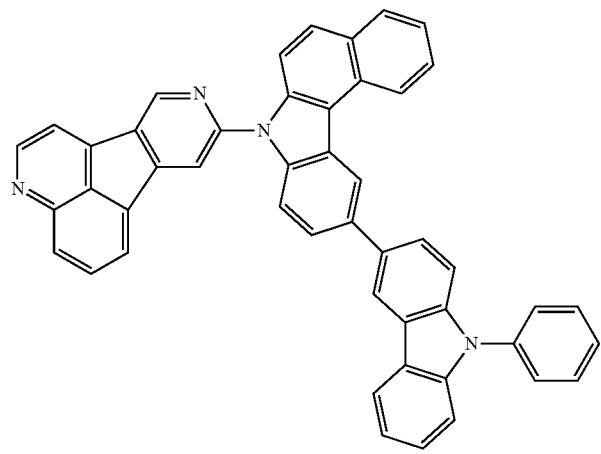

411 412
-continued
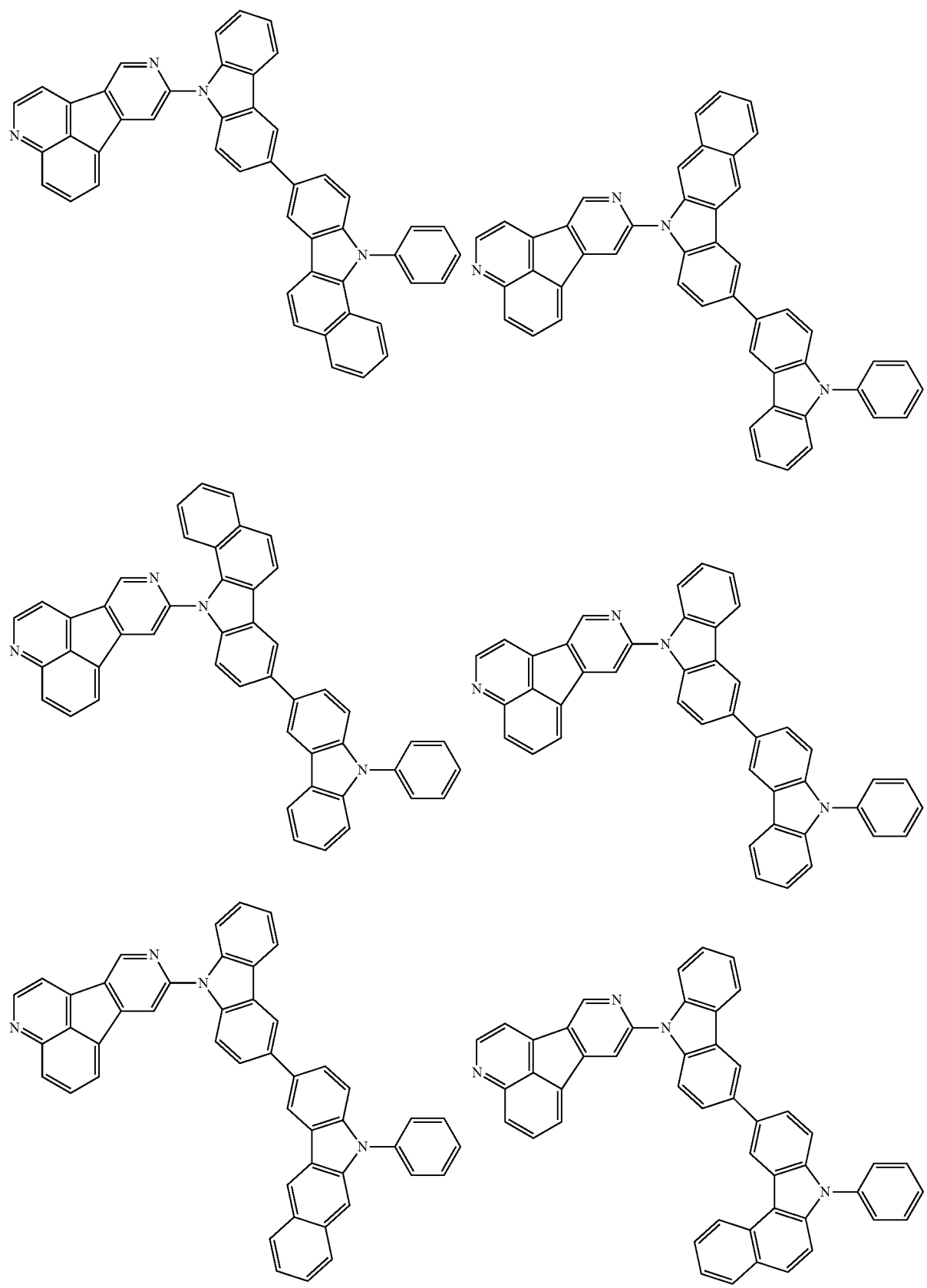

413
[Chem. 112]
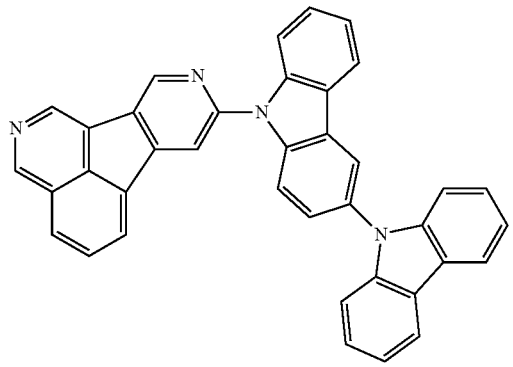
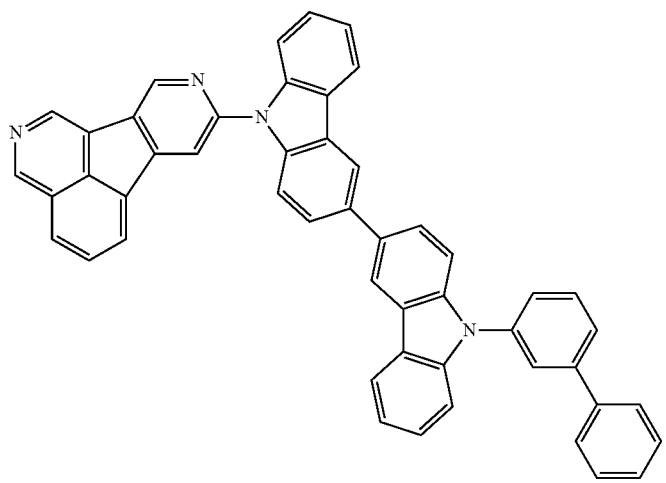
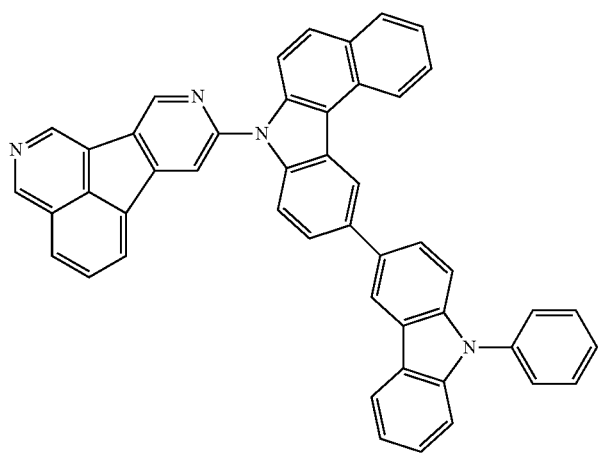
414
-continued
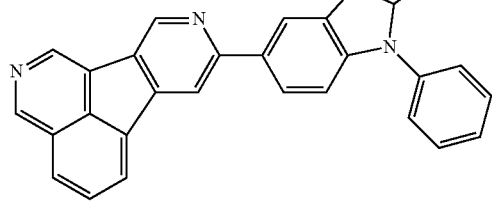

415 416
-continued
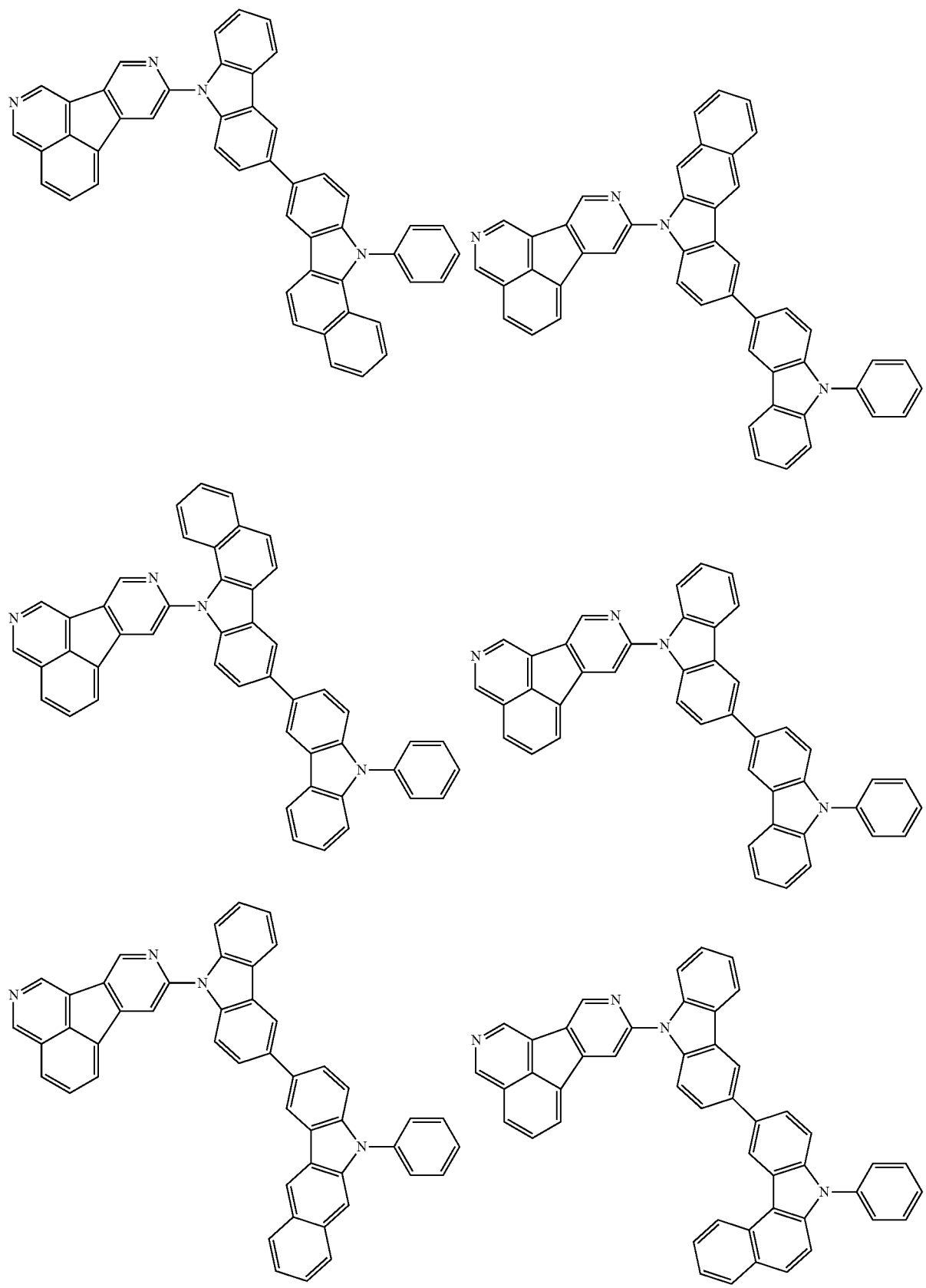

[Chem. 113]
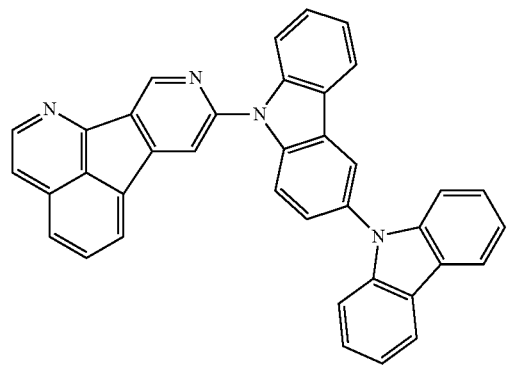
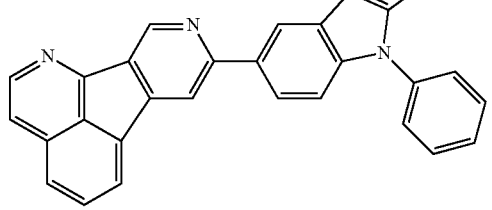
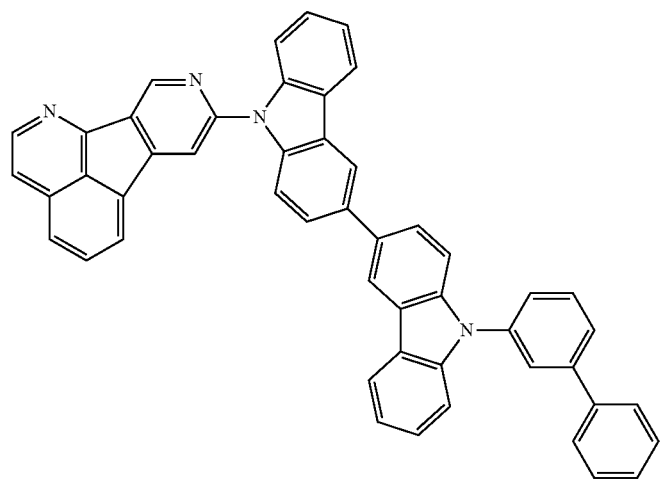
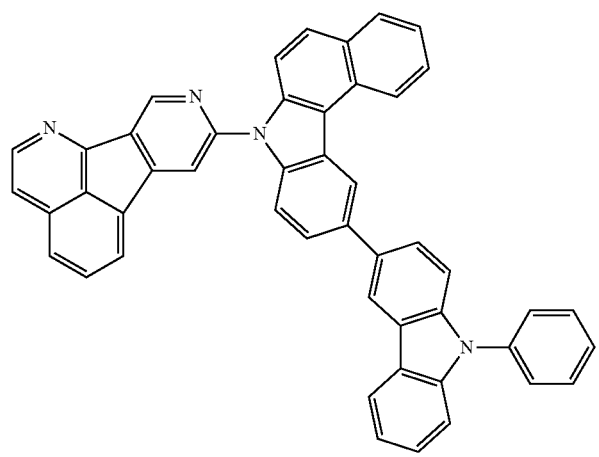

-continued
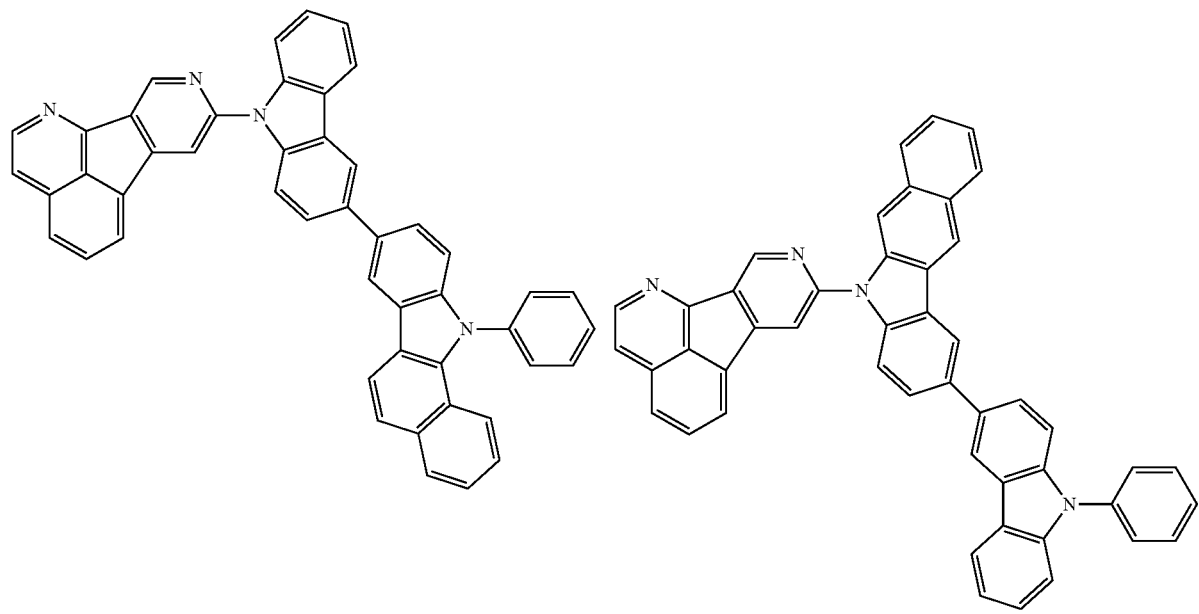
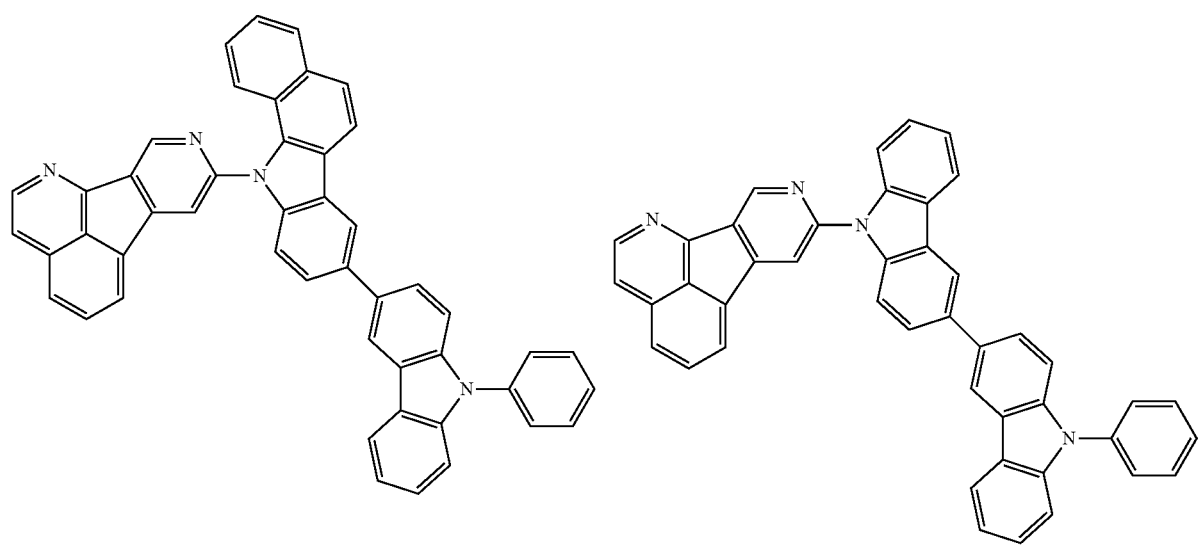
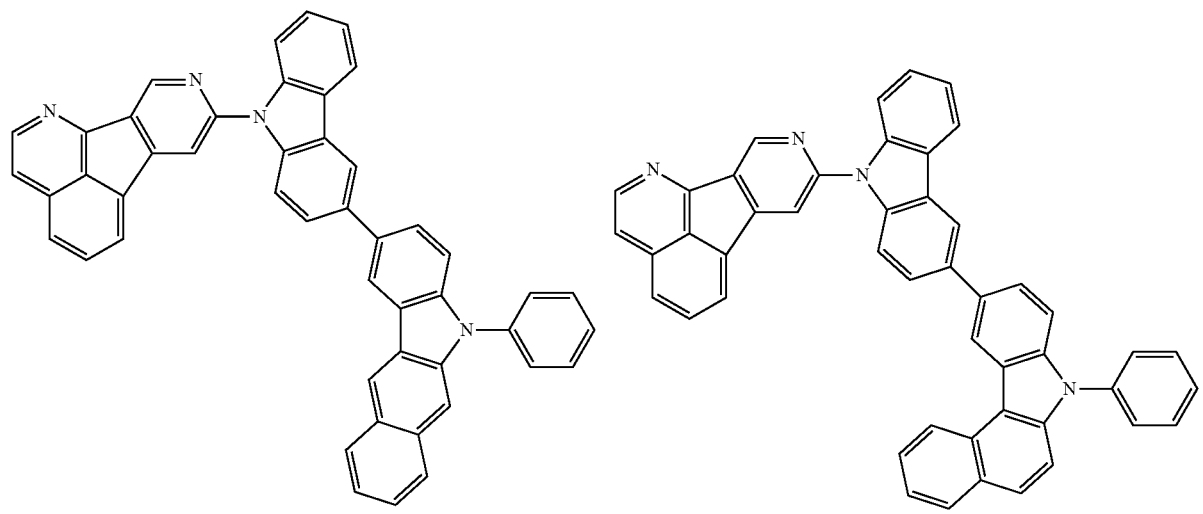

[Chem. 114]
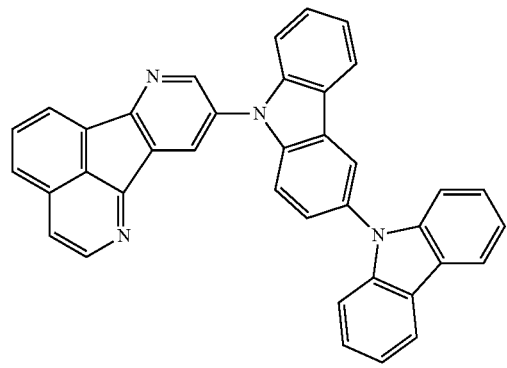
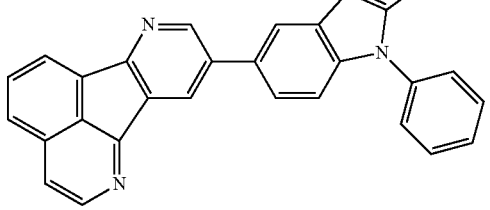
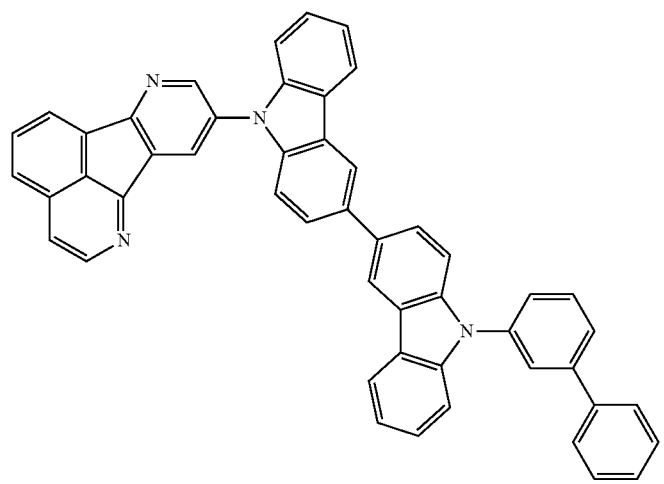
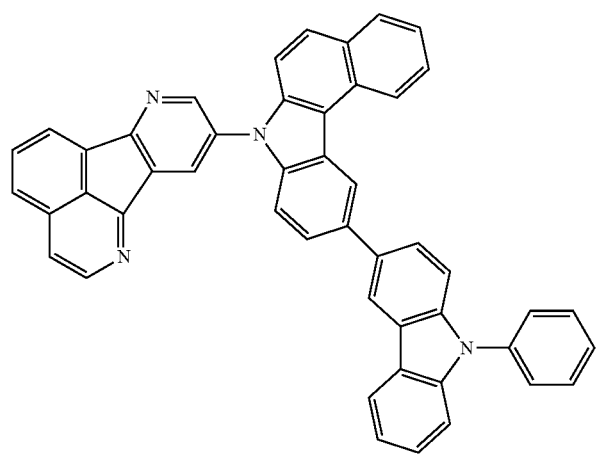

423 424
-continued
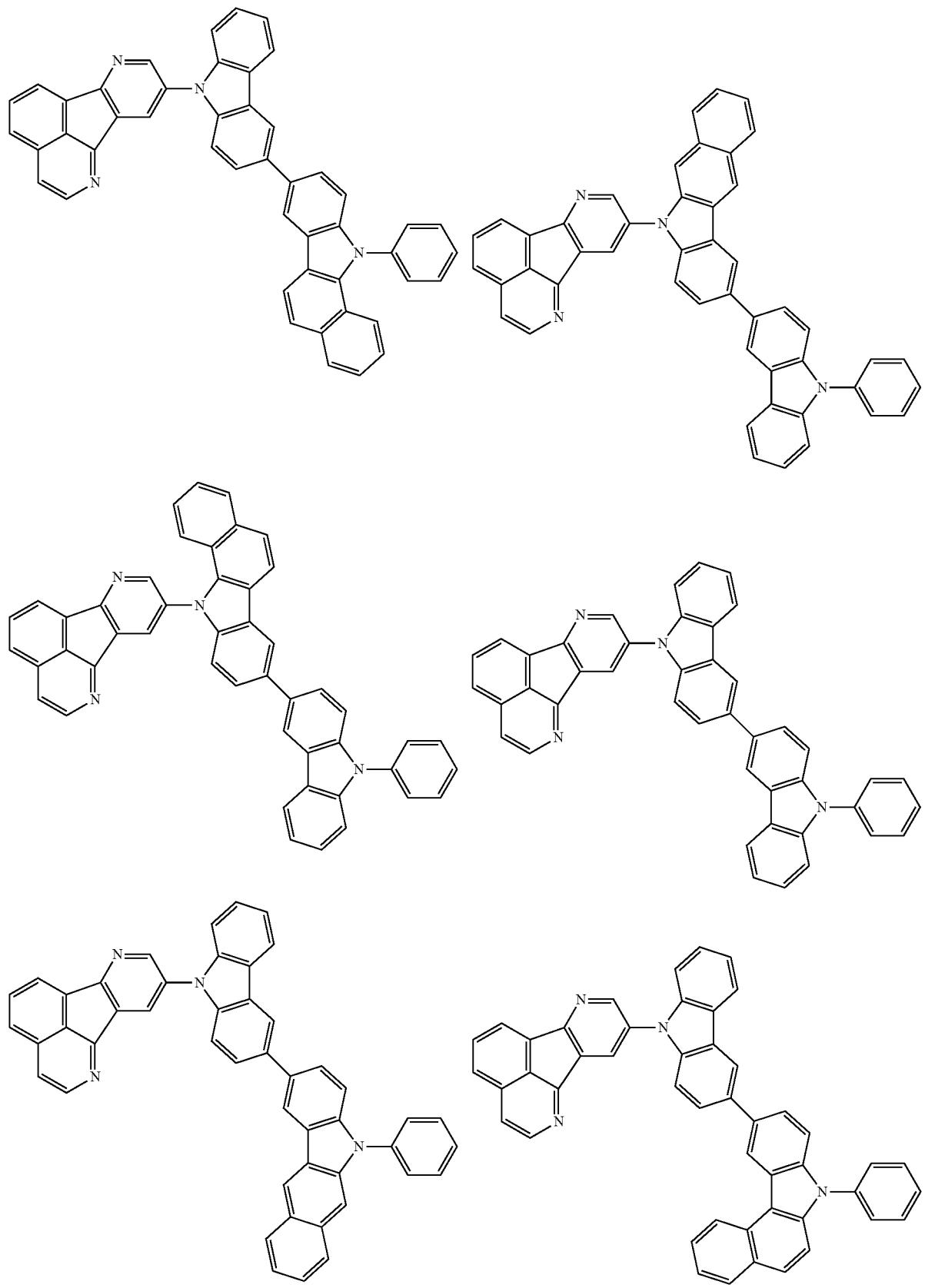

[Chem. 115]
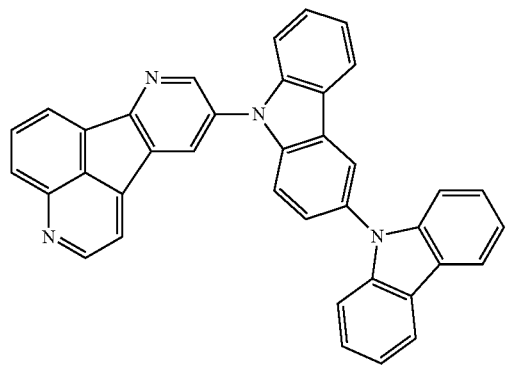
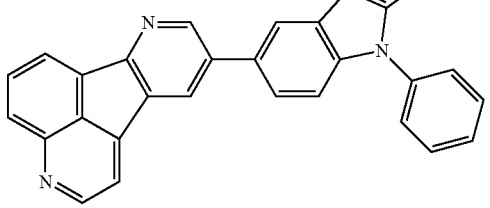
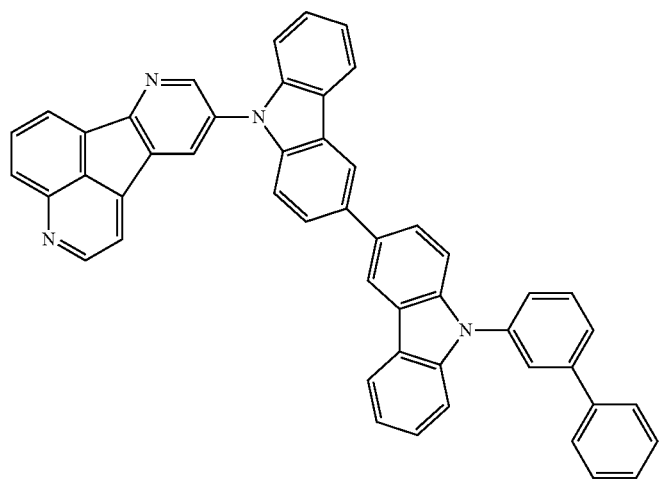
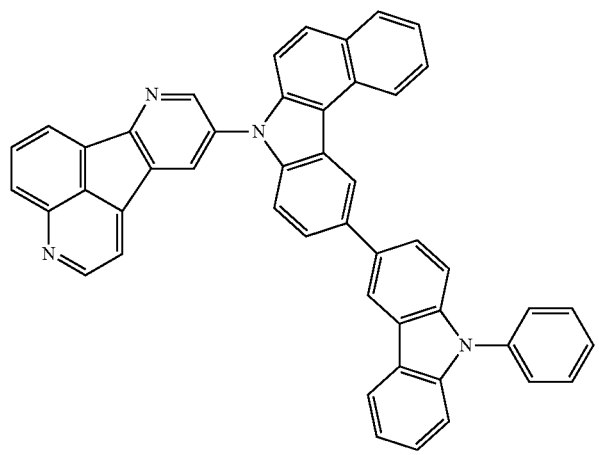

427 428
-continued
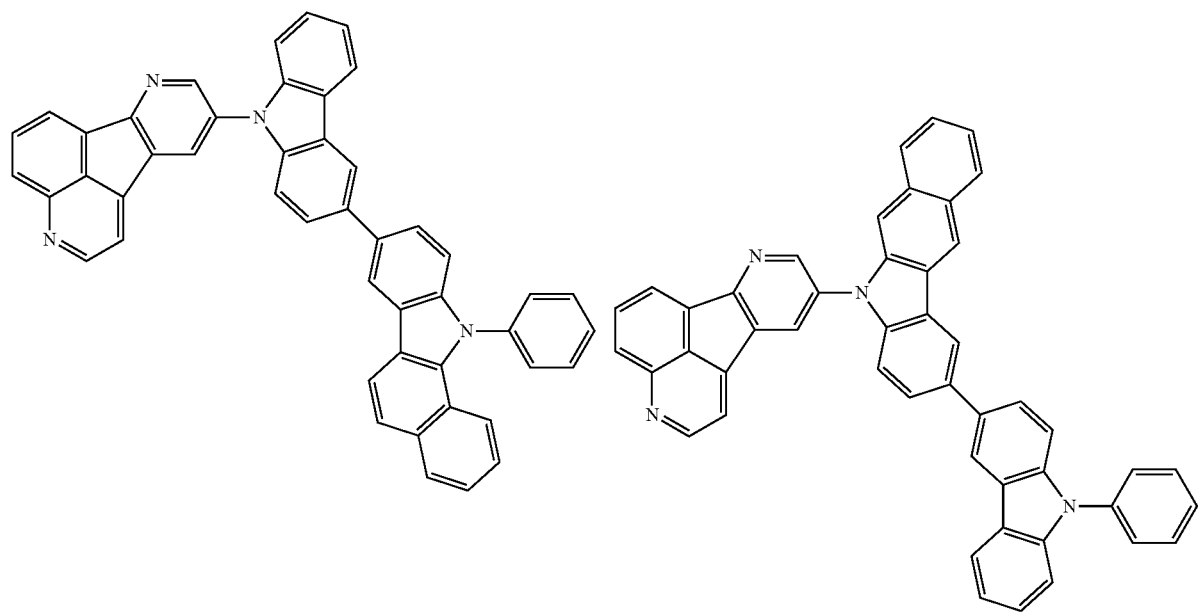
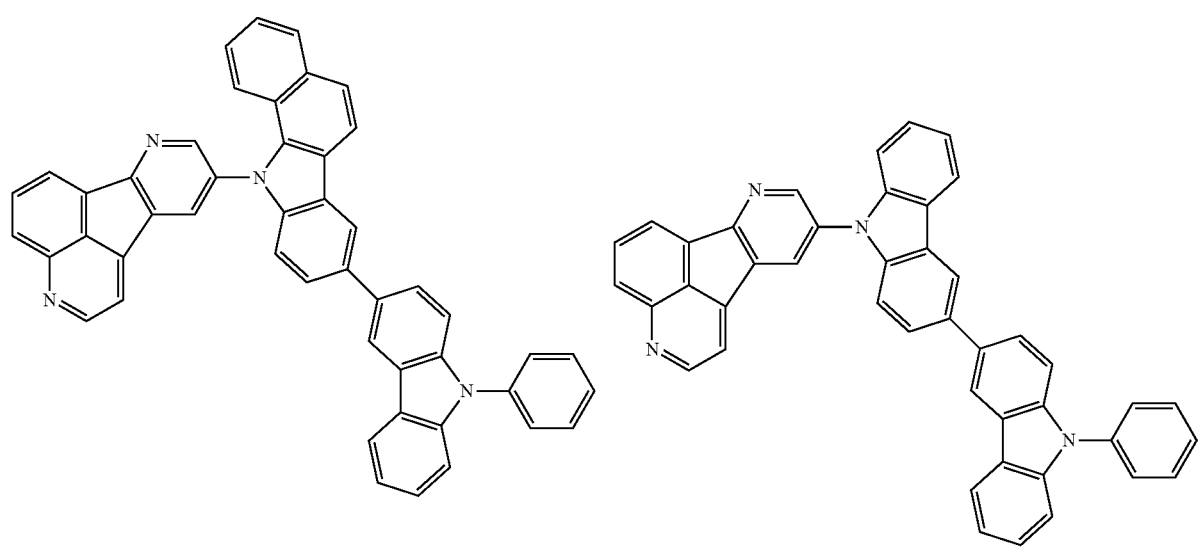
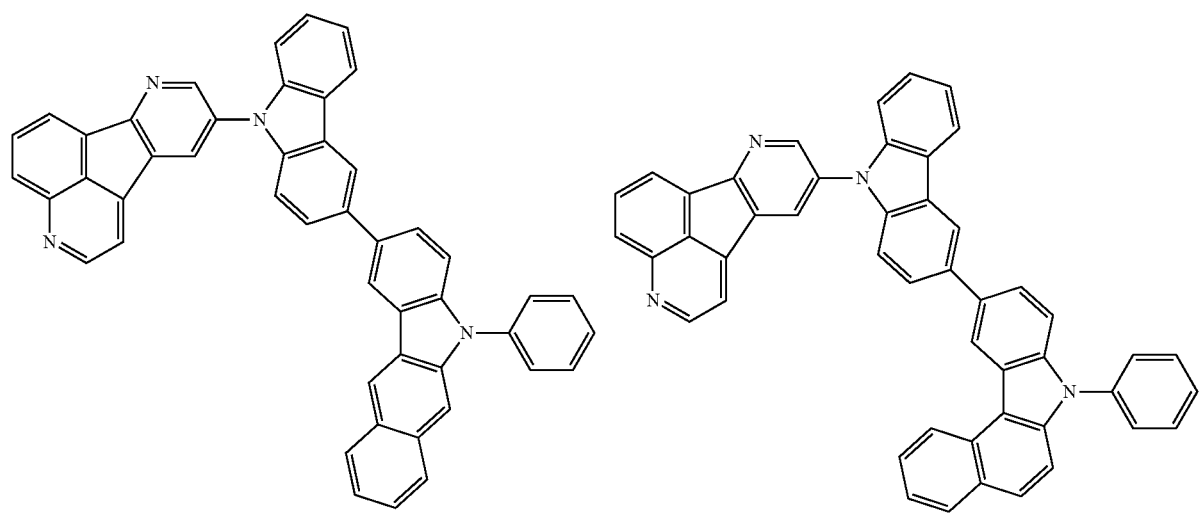

-continued
[Chem. 116]
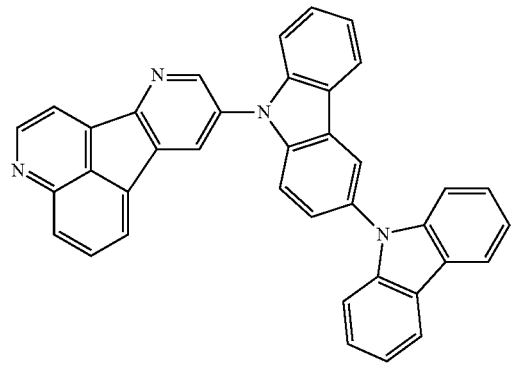
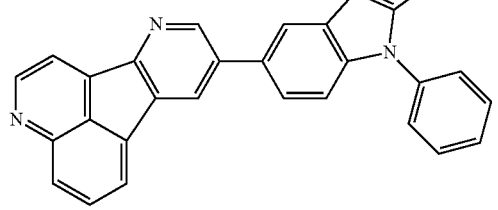
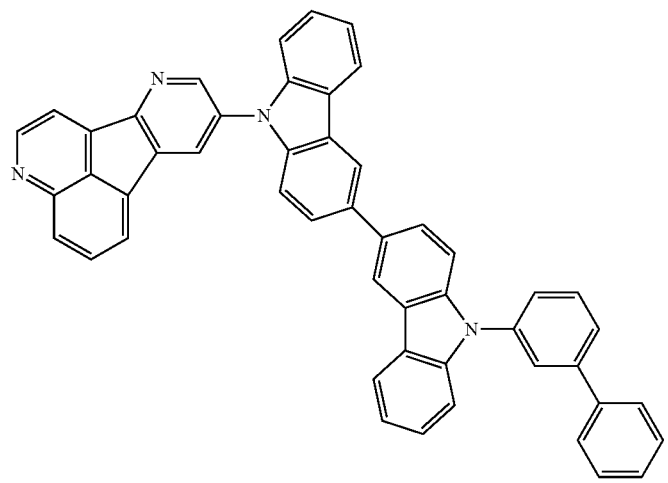
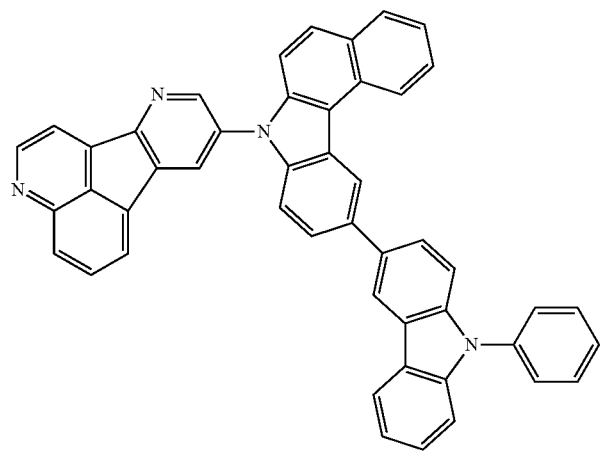

-continued
431
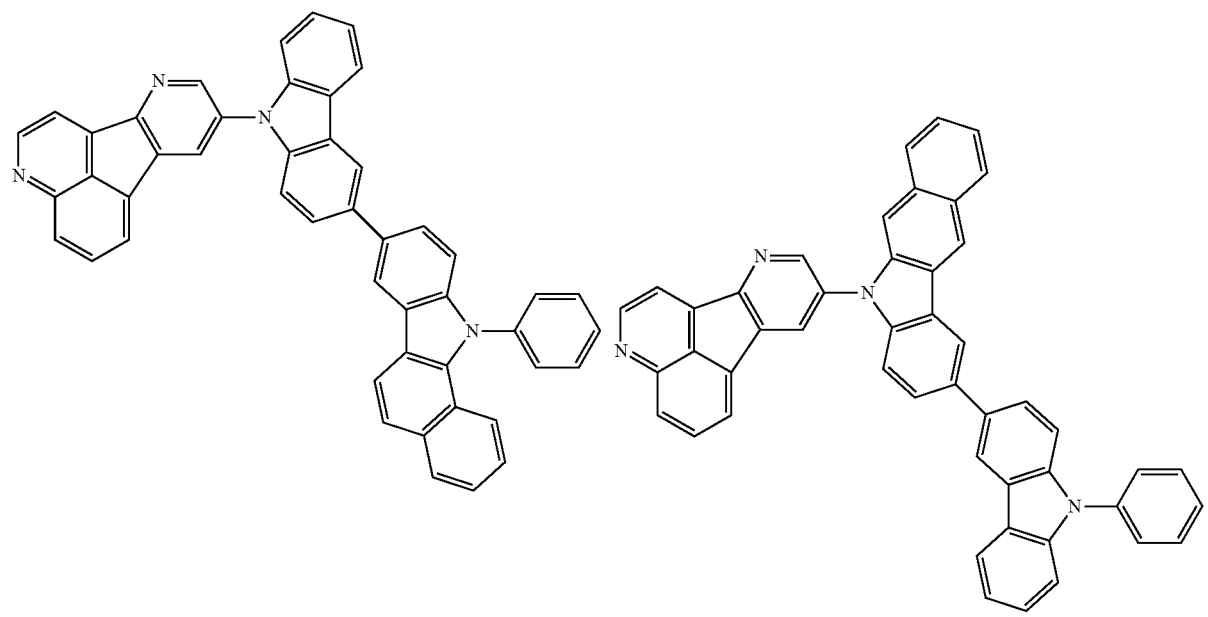
432
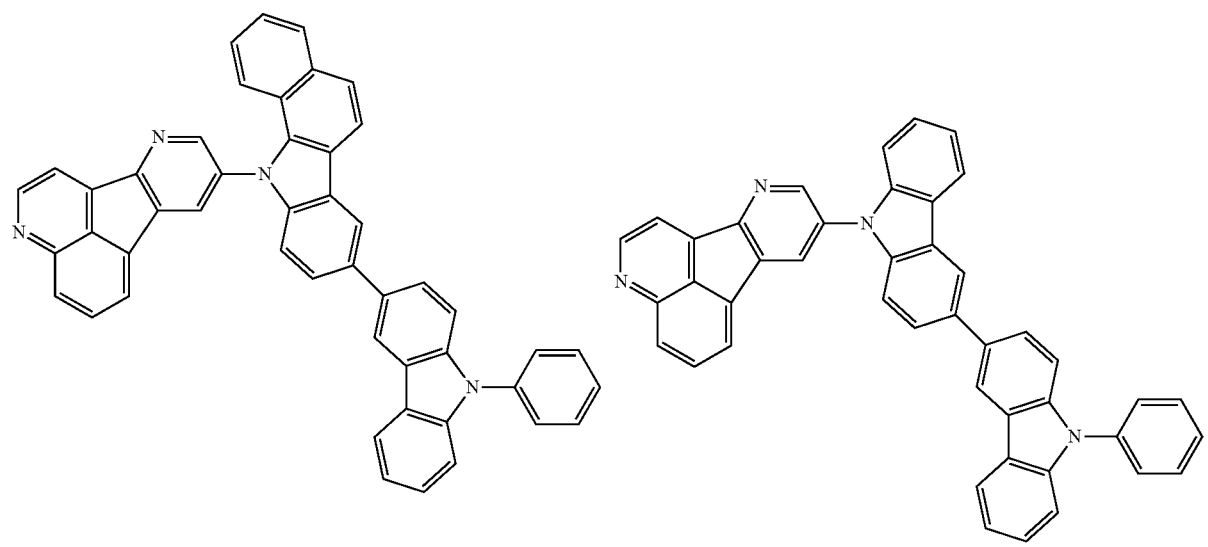
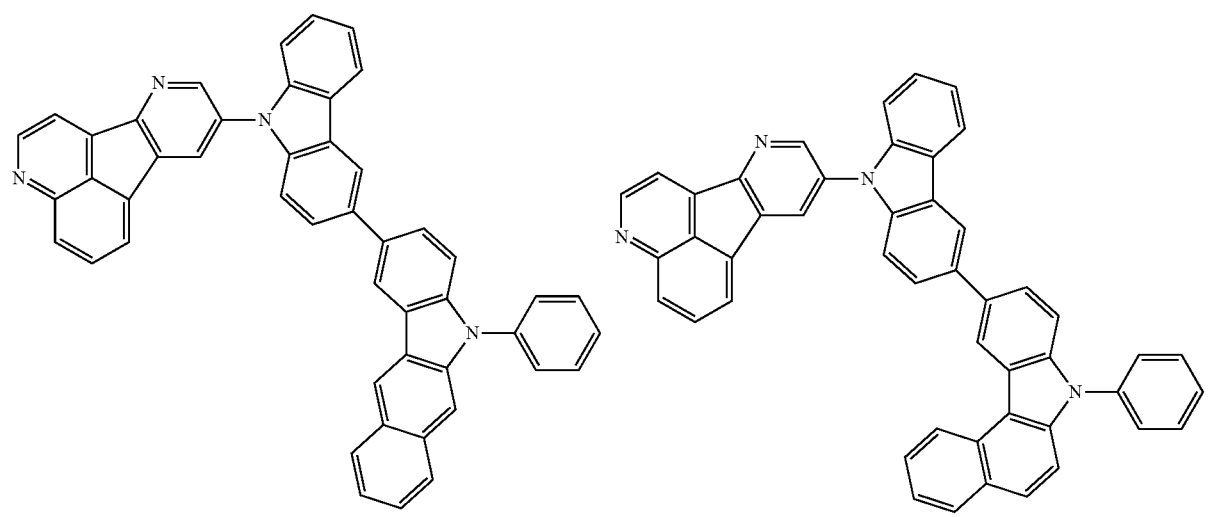

433
-continued
[Chem. 117]
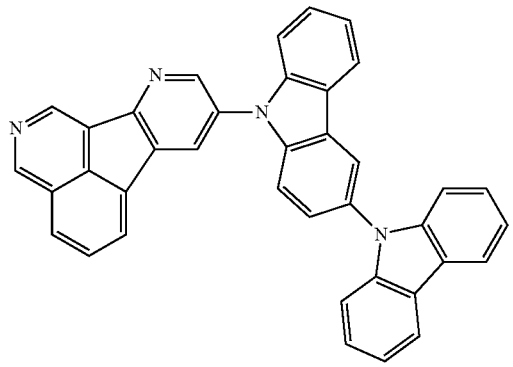
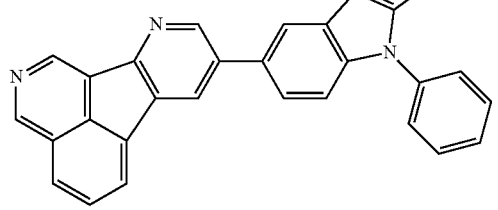
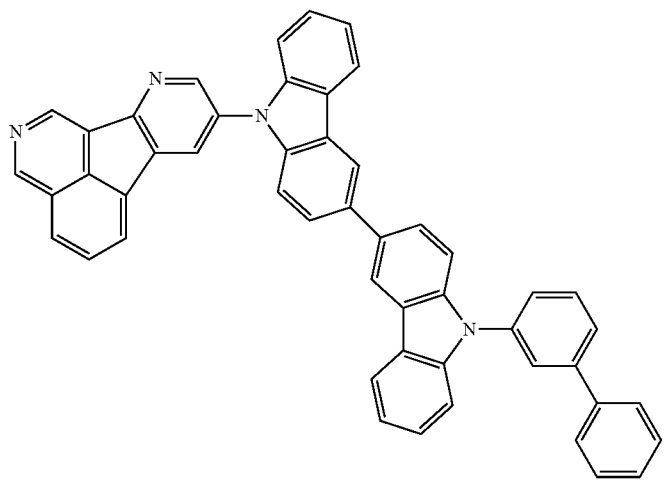
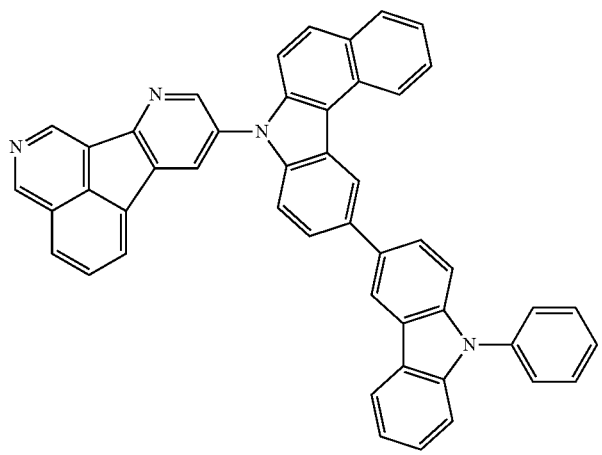

435 436
-continued
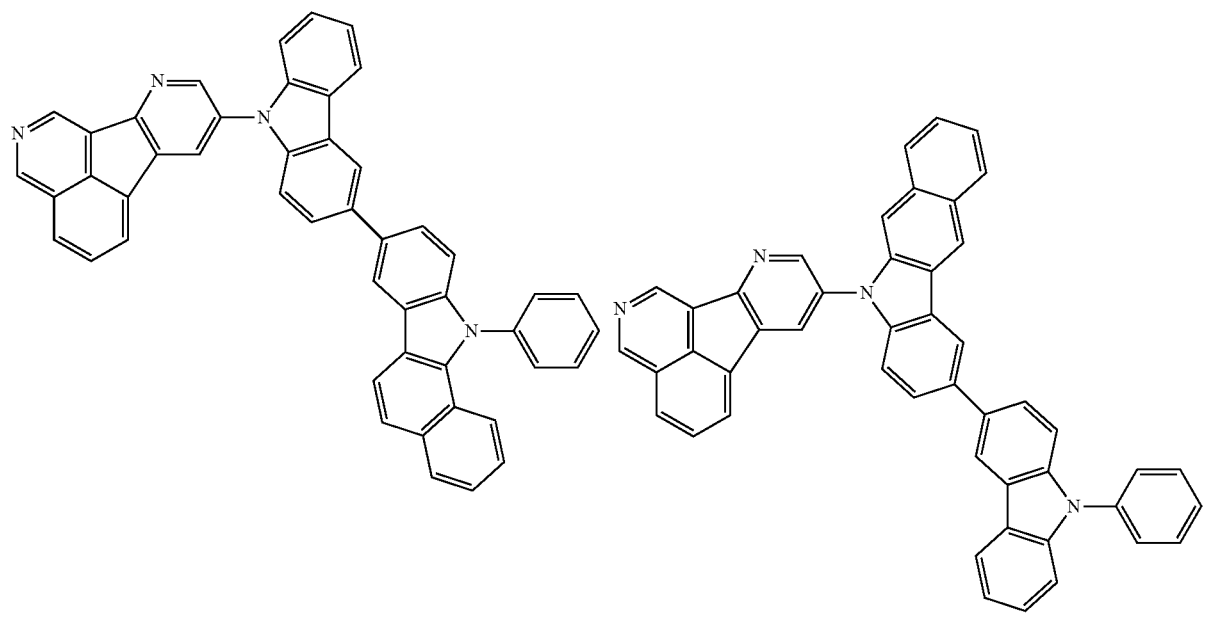
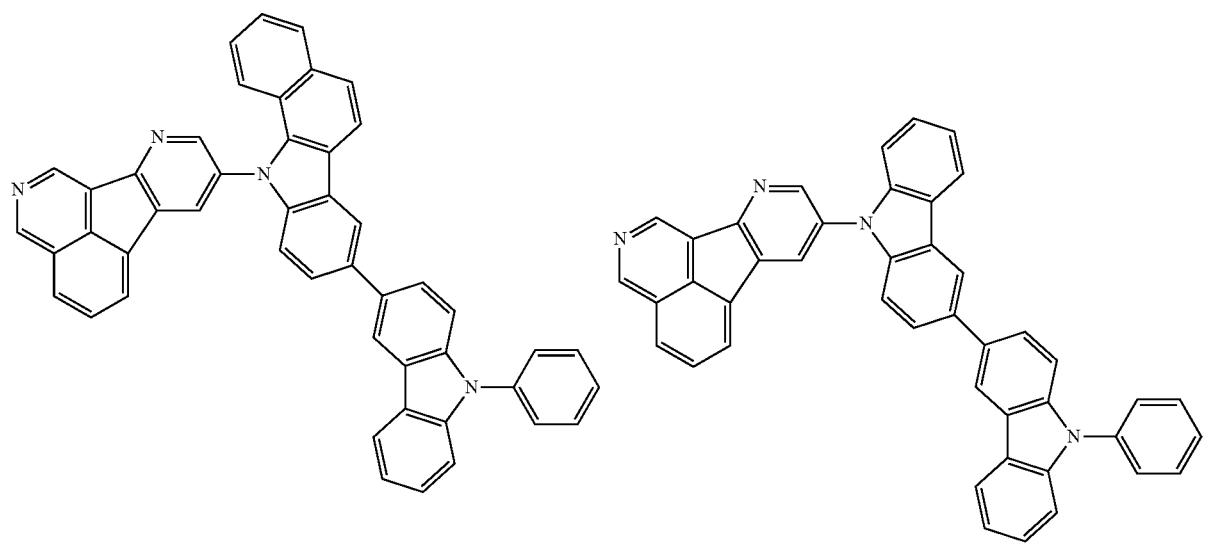
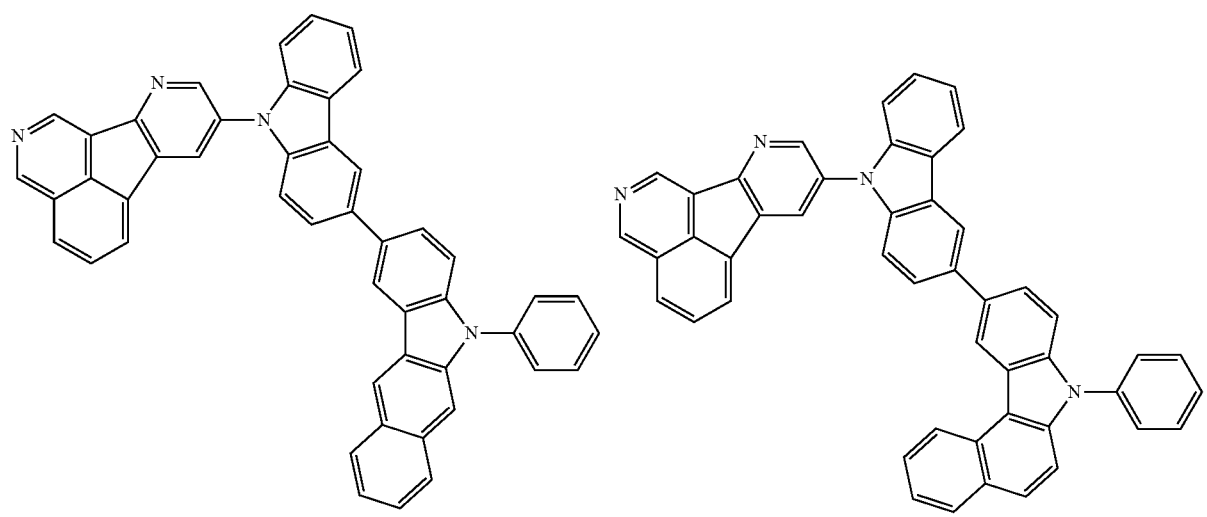

[Chem. 118]
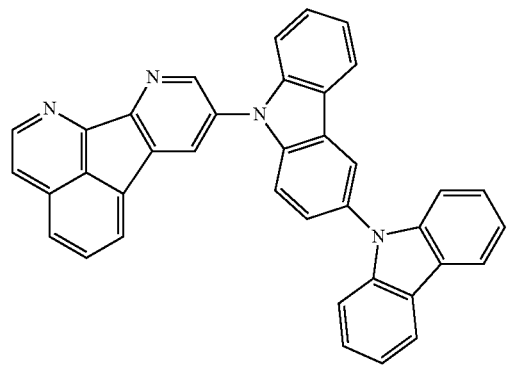
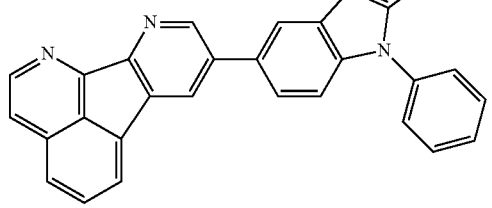
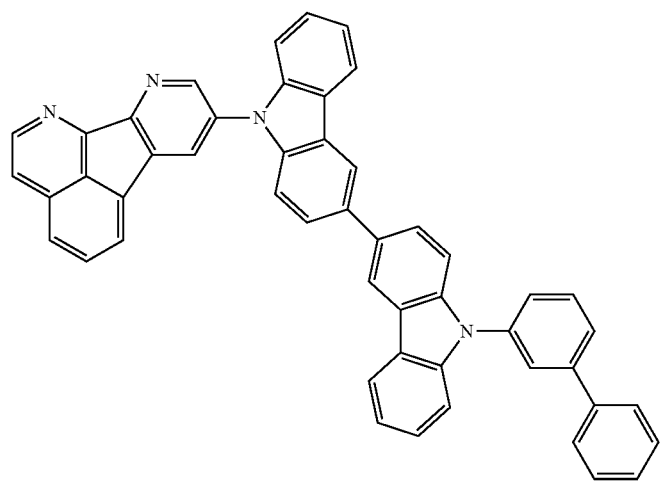
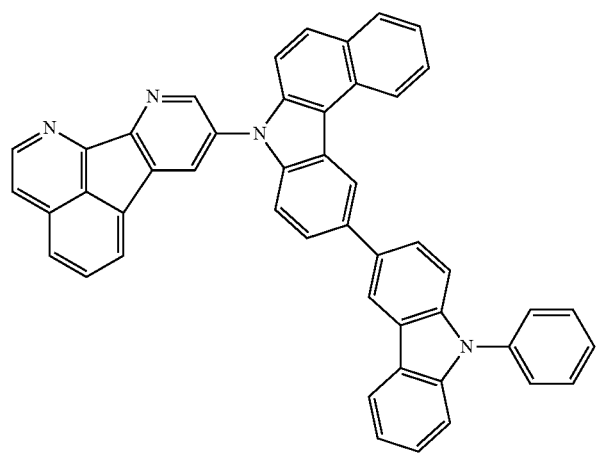

-continued
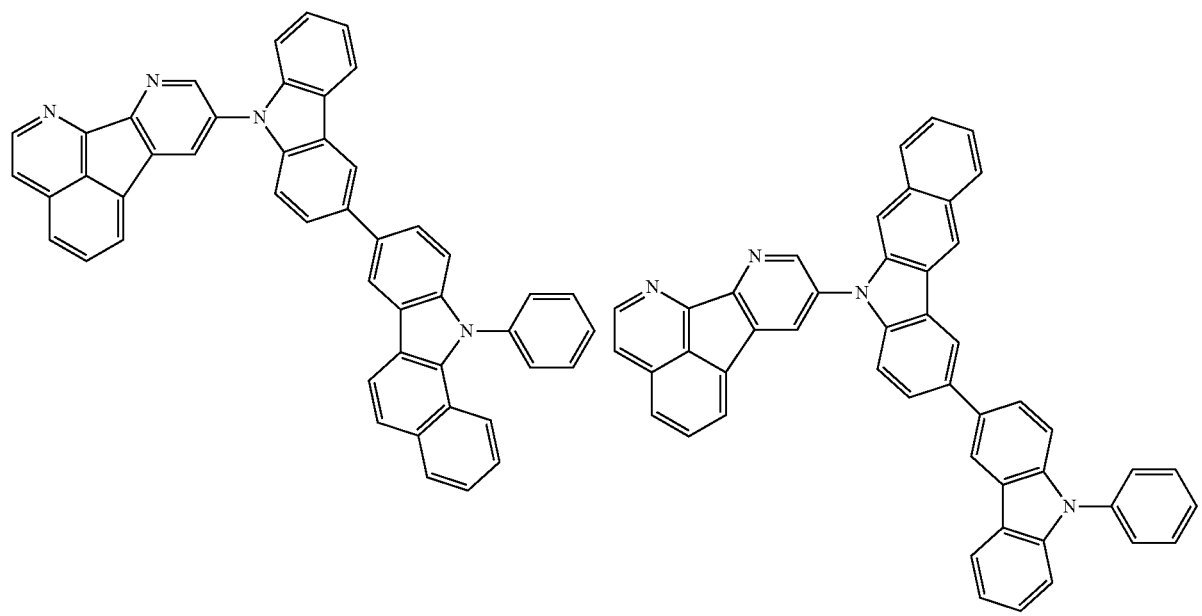
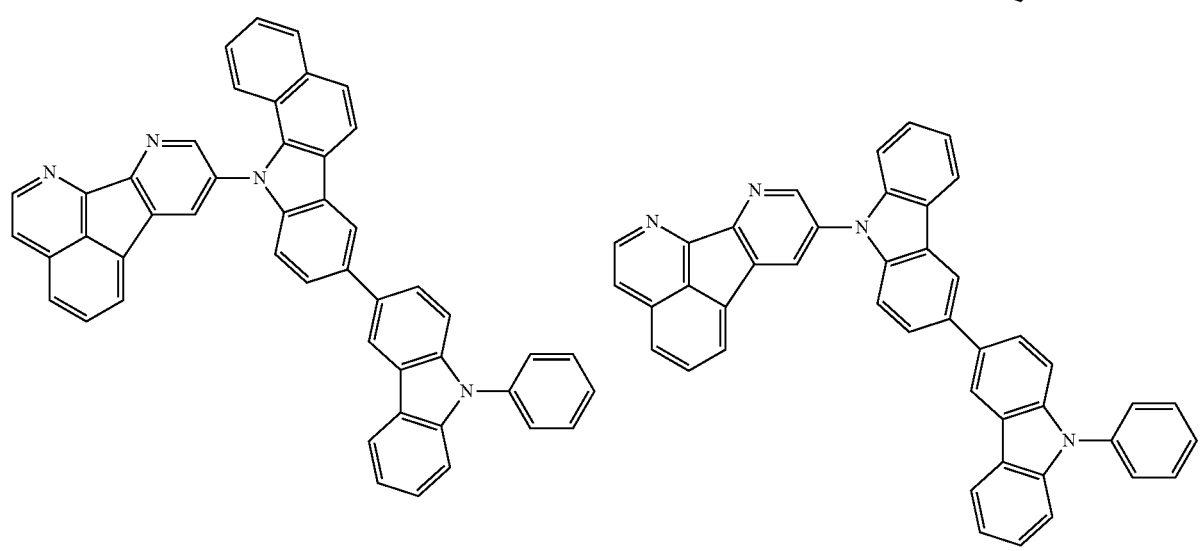
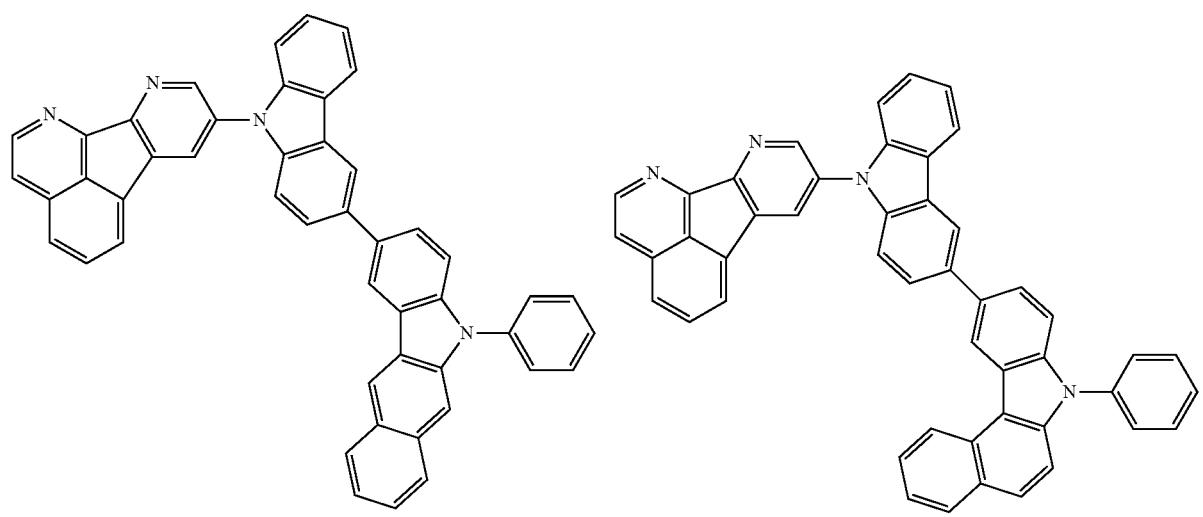

-continued
[Chem. 119]
441
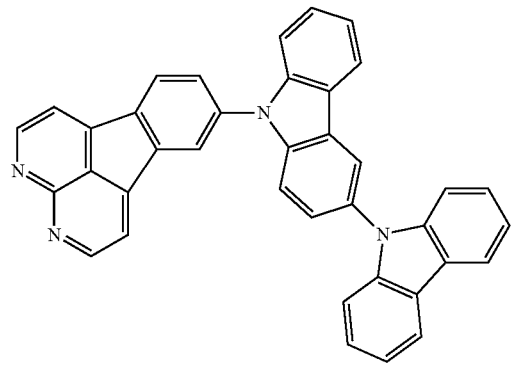
442
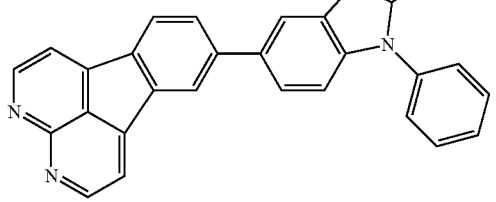
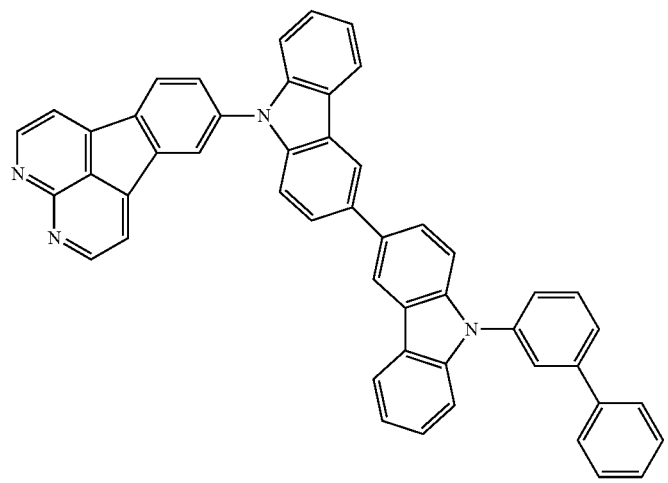
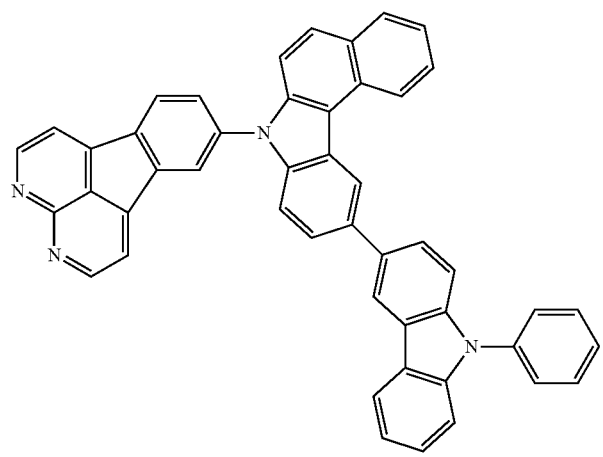

443  444
-continued
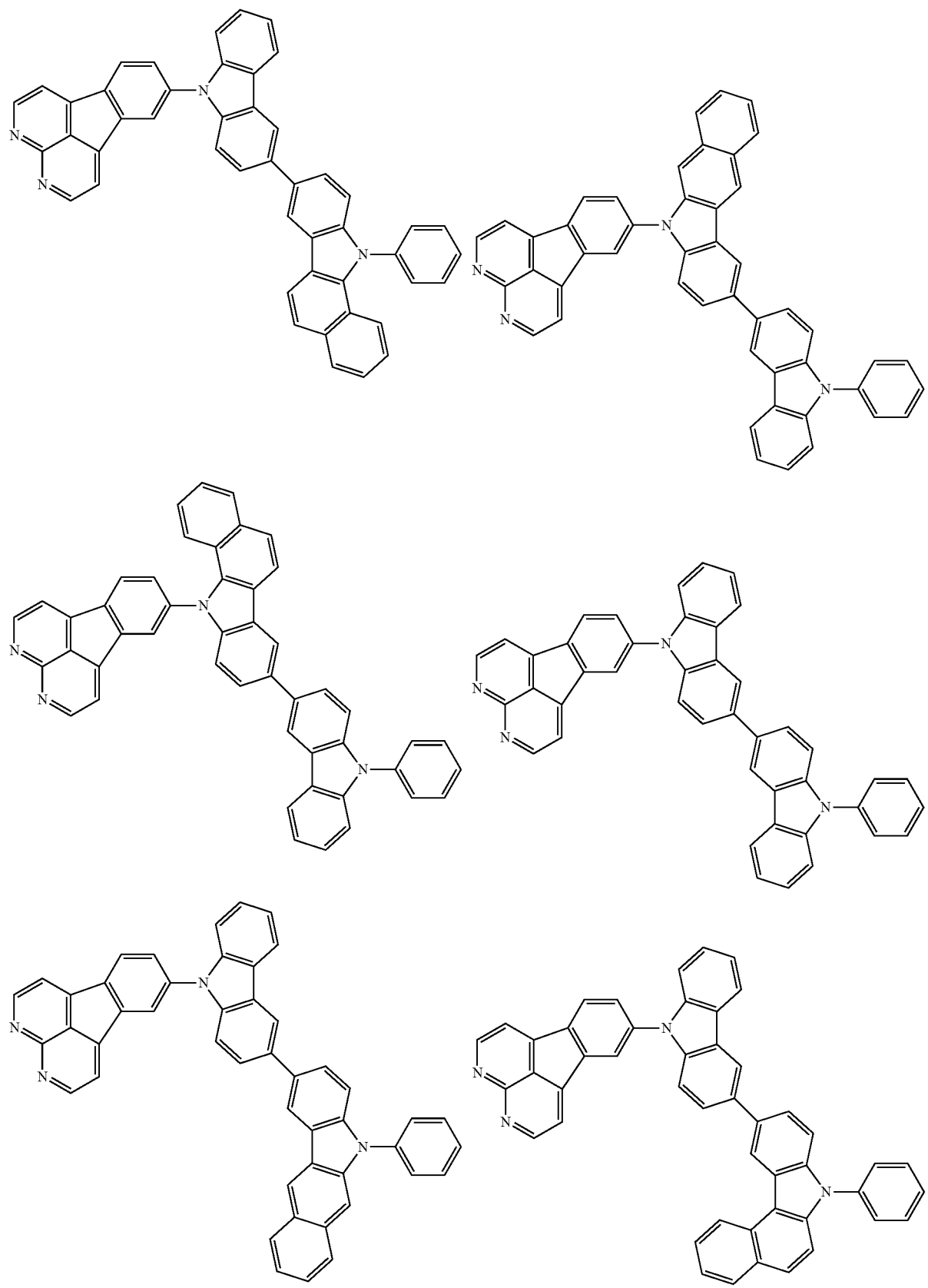

-continued
[Chem. 120]
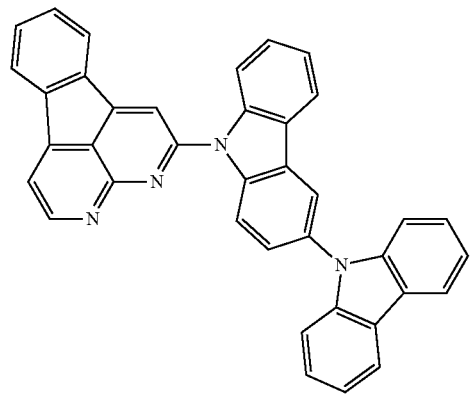
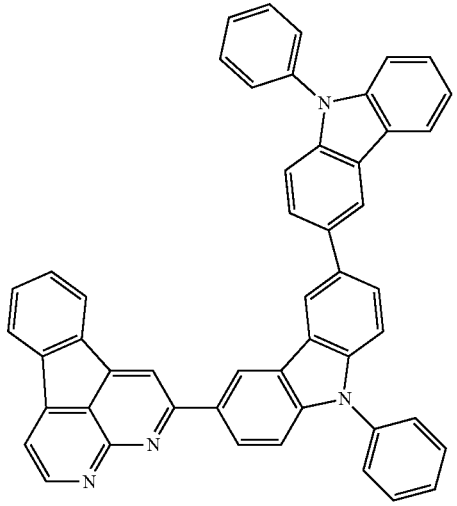
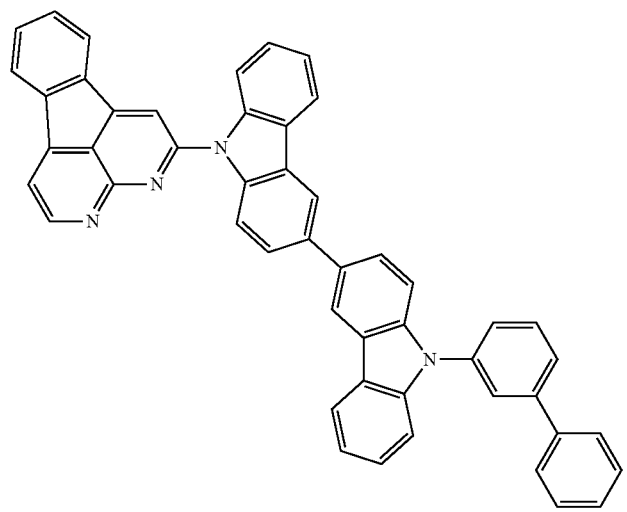
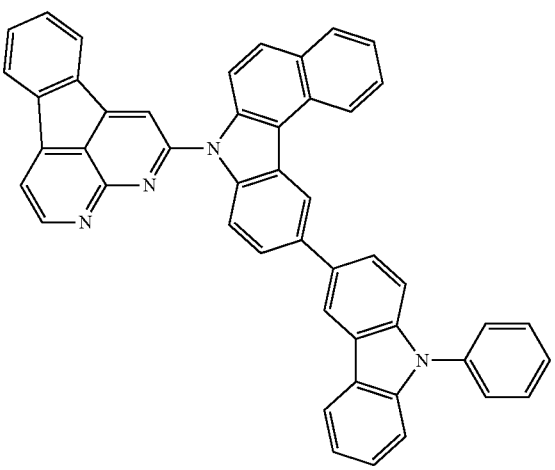
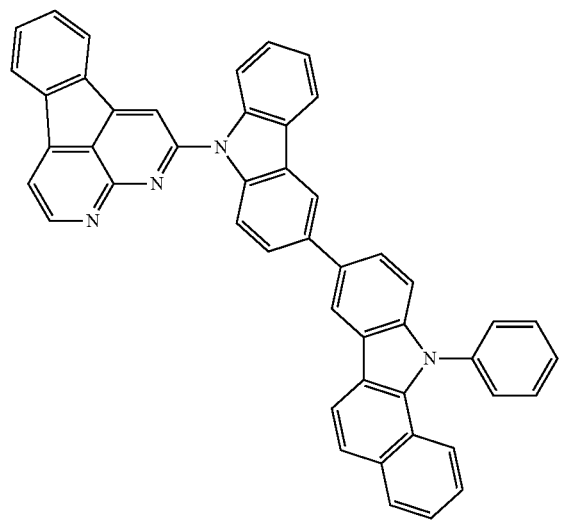
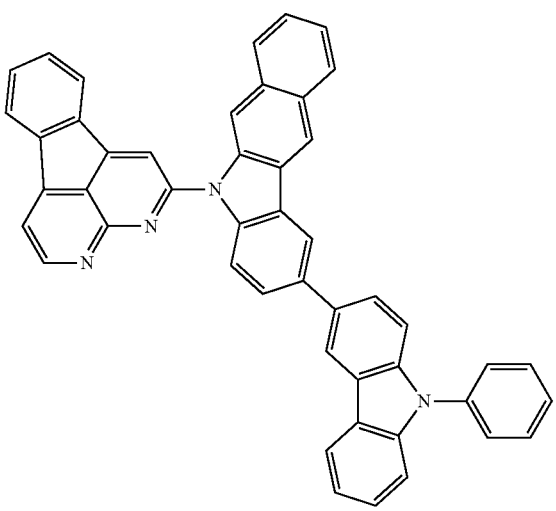

-continued
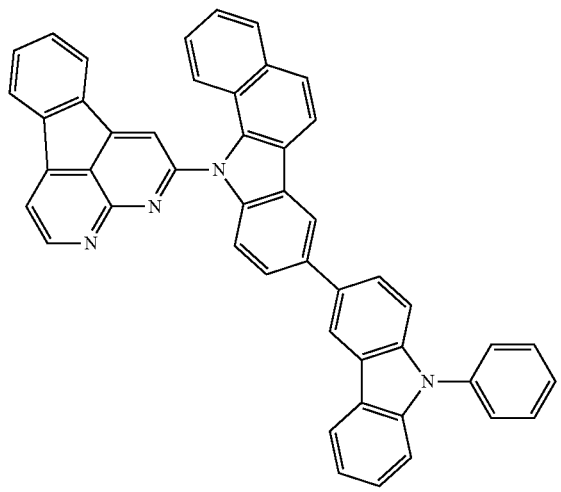
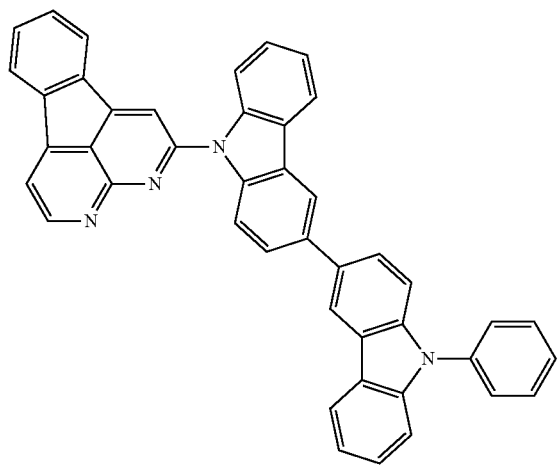
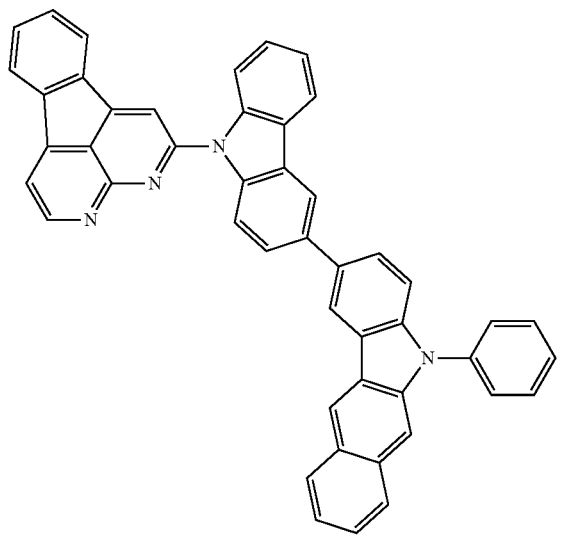
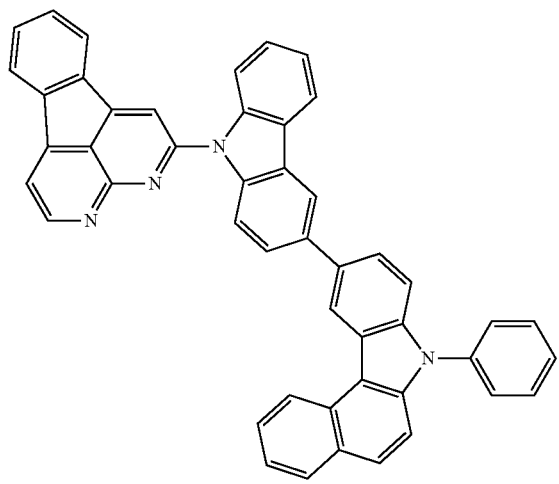
[Chem. 121]
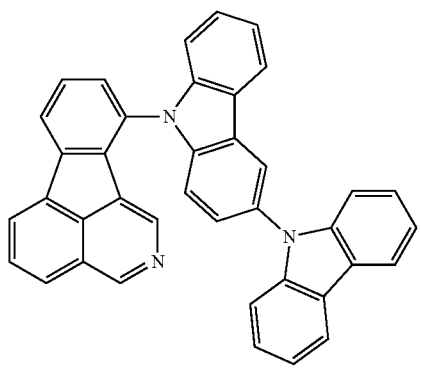
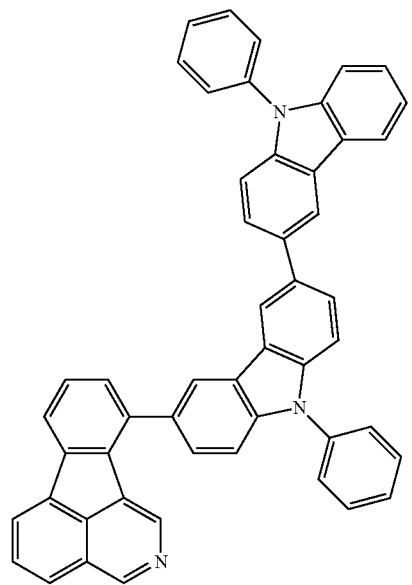

449
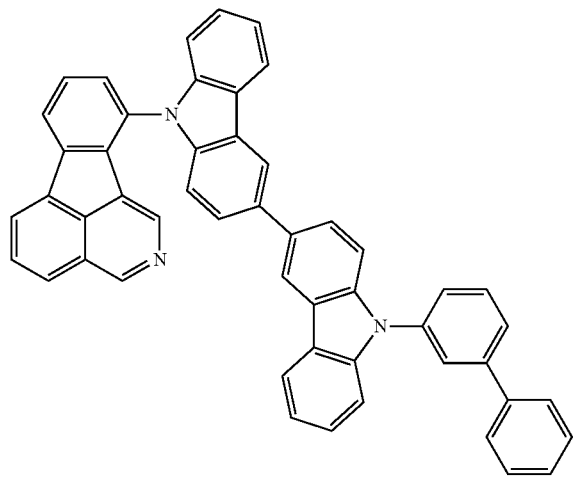
450
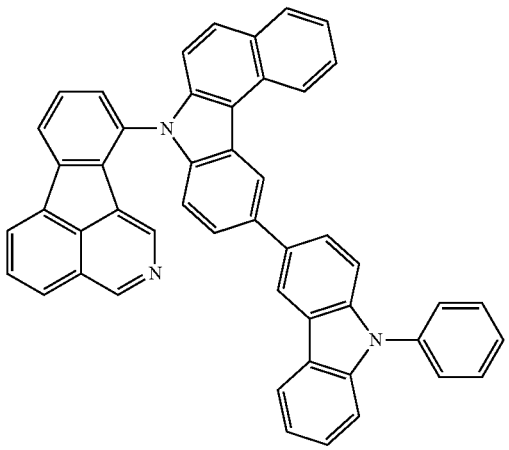
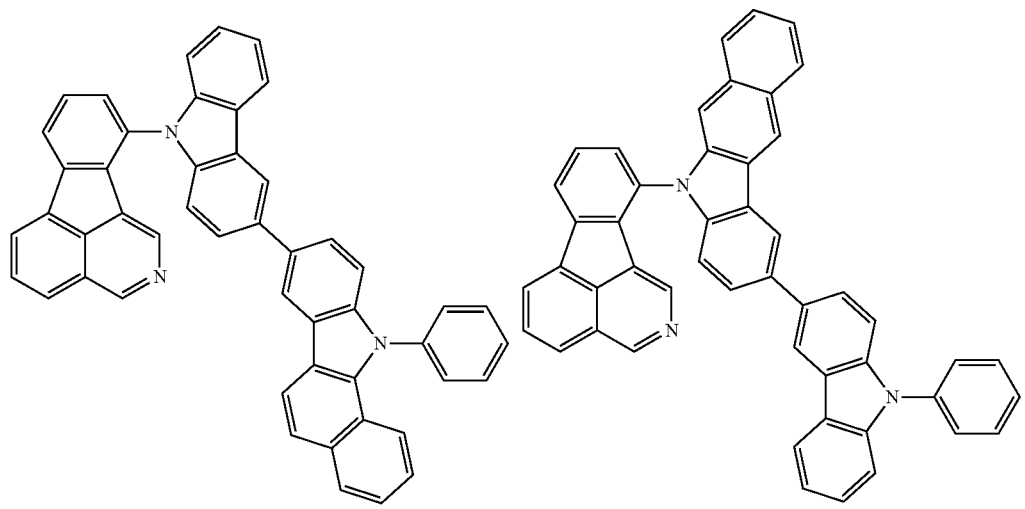
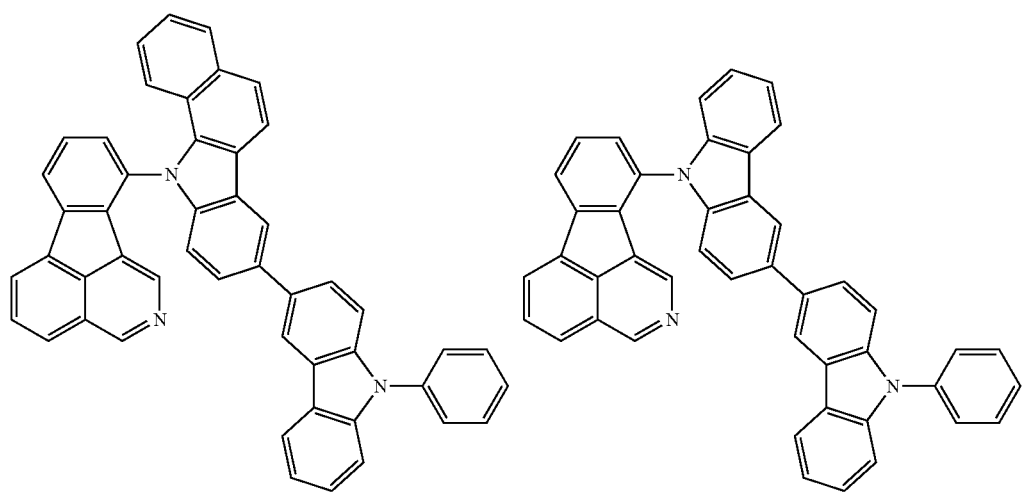

451
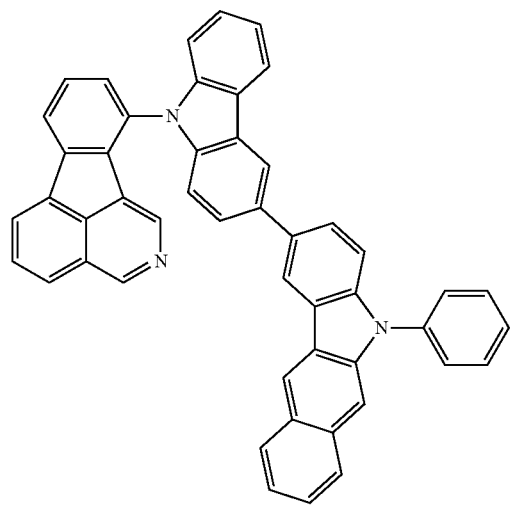
452
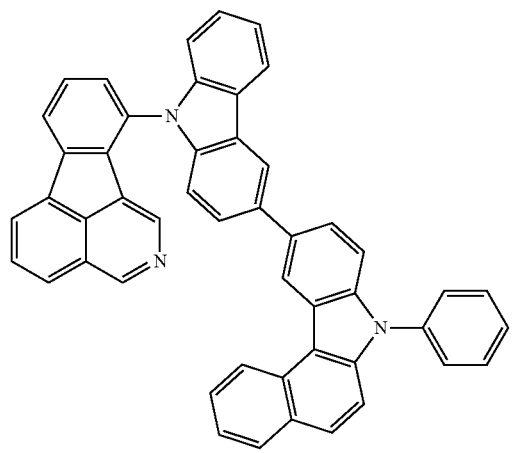
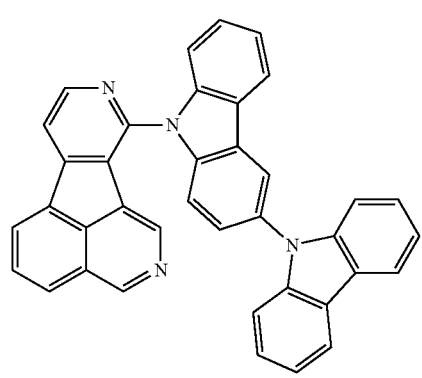
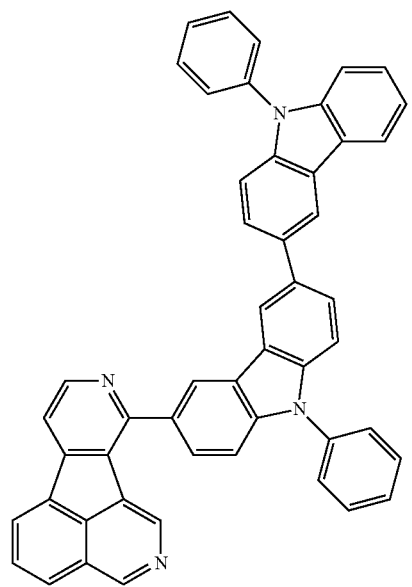
[Chem. 122]
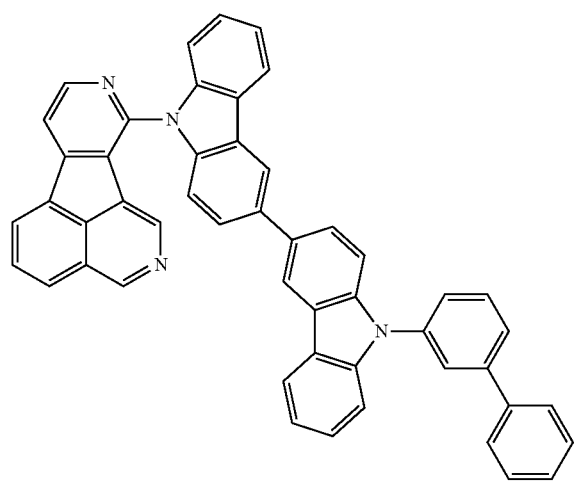
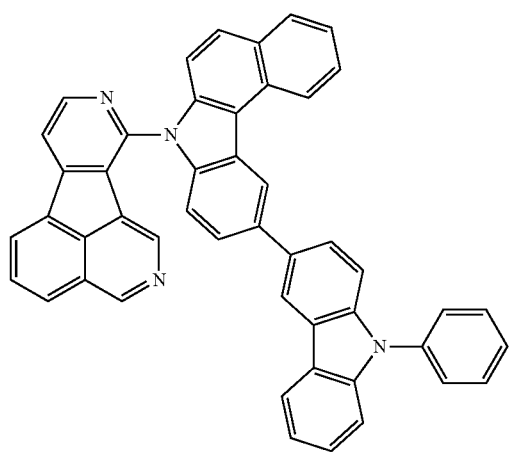

453
454
-continued
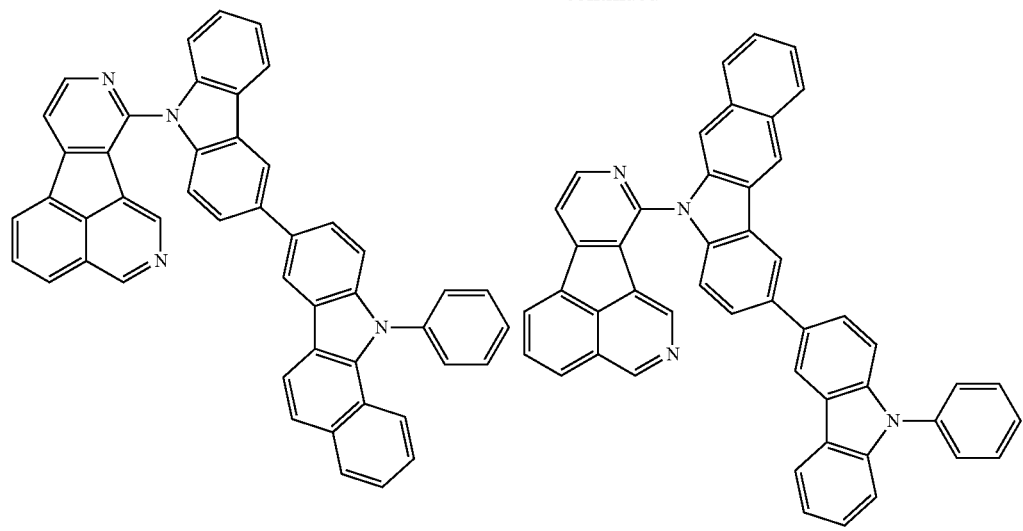
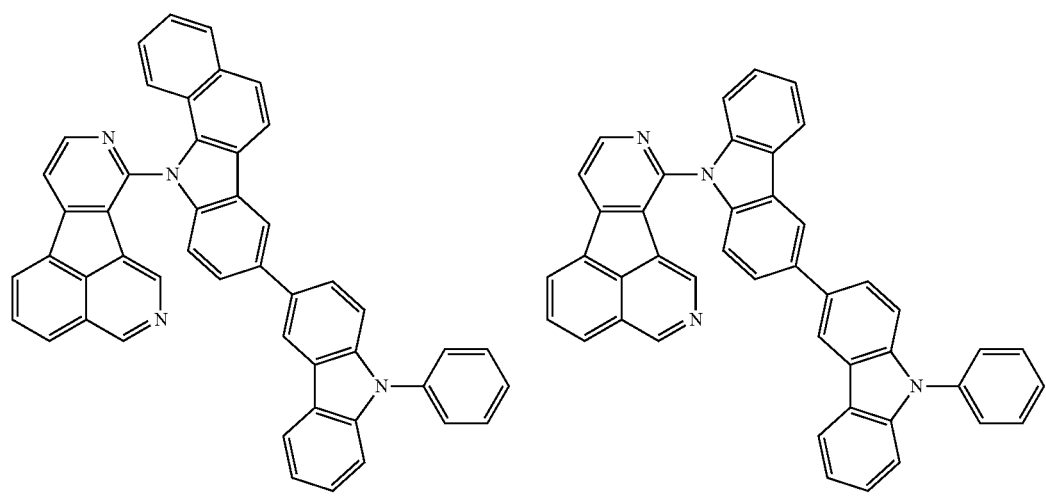
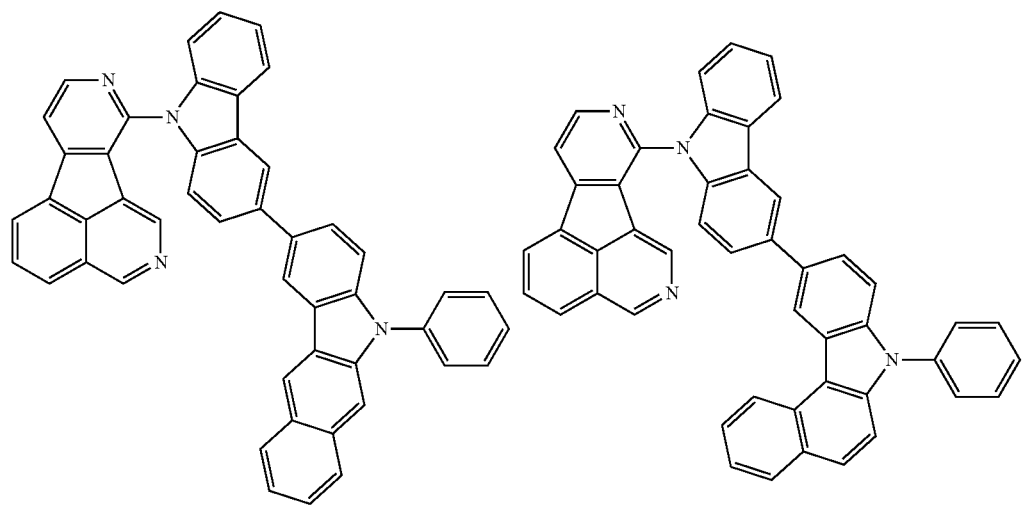

-continued
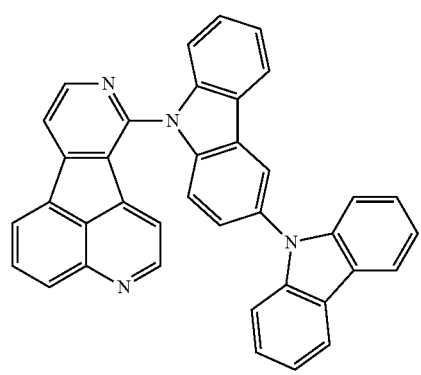
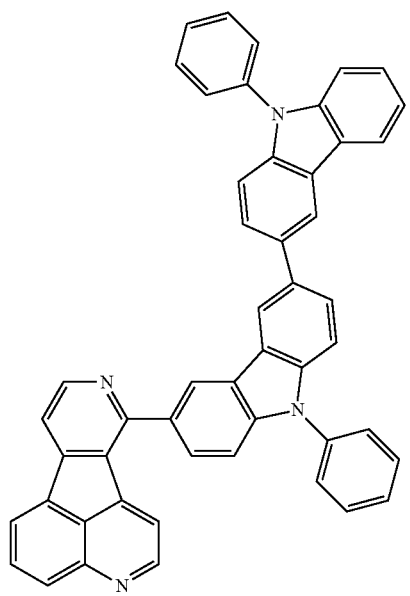
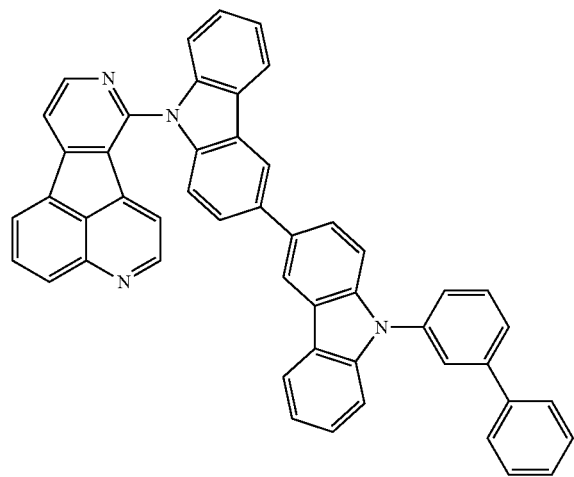
[Chem. 123]
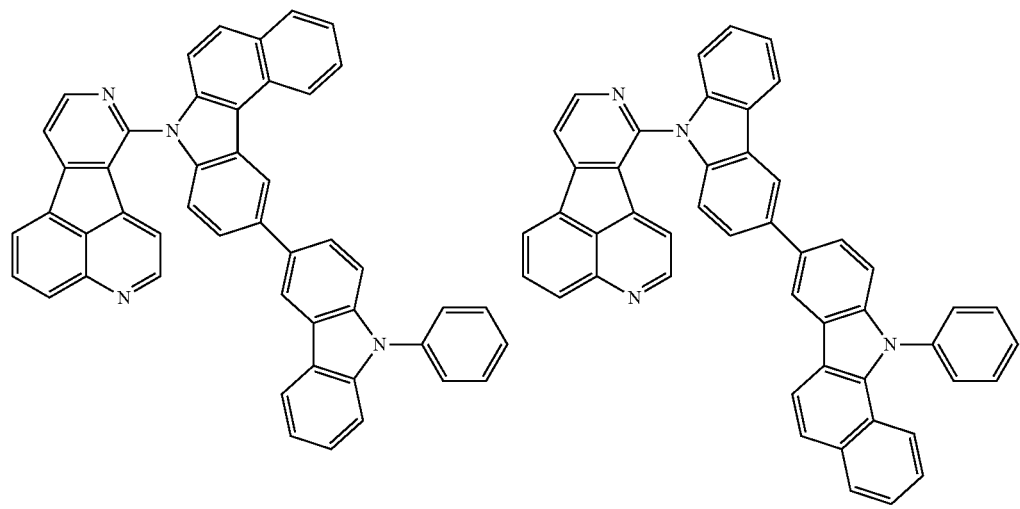

-continued
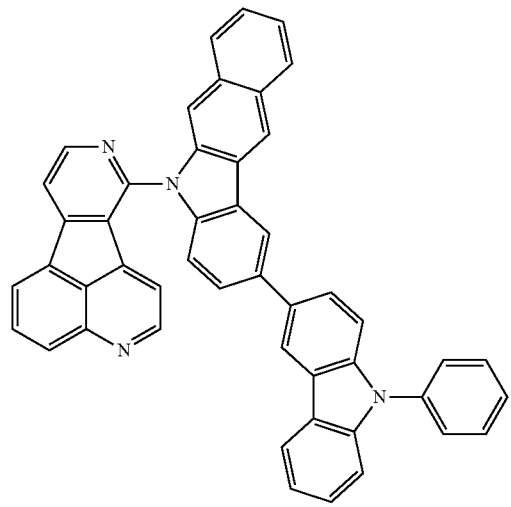
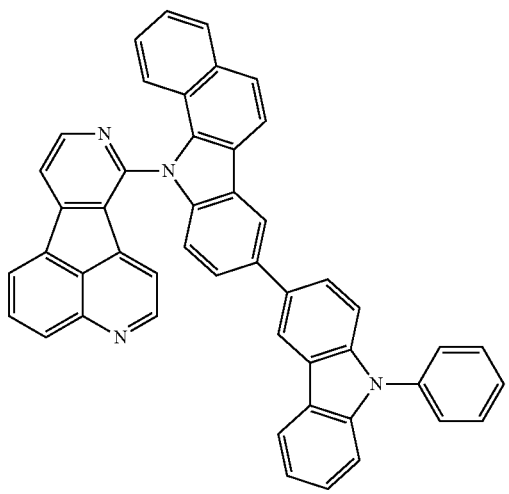
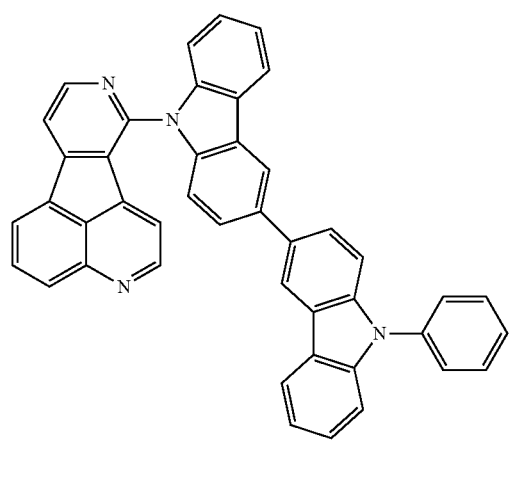
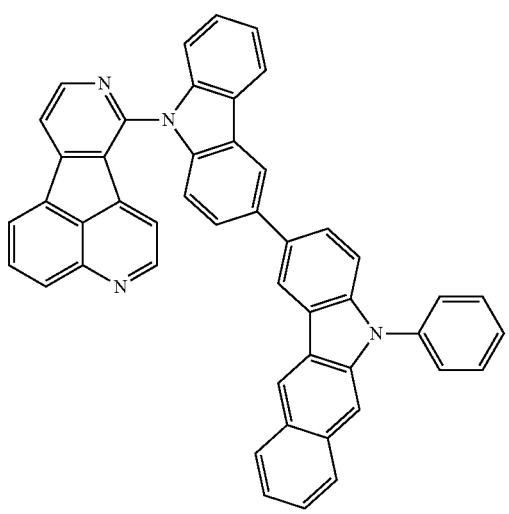
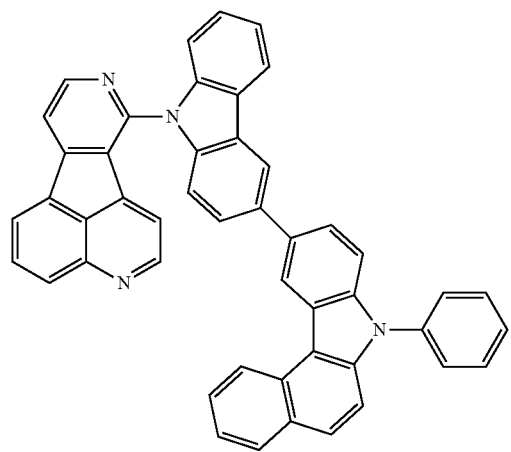 [SMILES: c1ccc(-n2c3ccc(-c4ccc5c(c4)c4ccccc4n5-c4nccc5c4-c4ccnc6cccc-5c46)cc3c3c4ccccc4ccc32)cc1]

[Chem. 124]
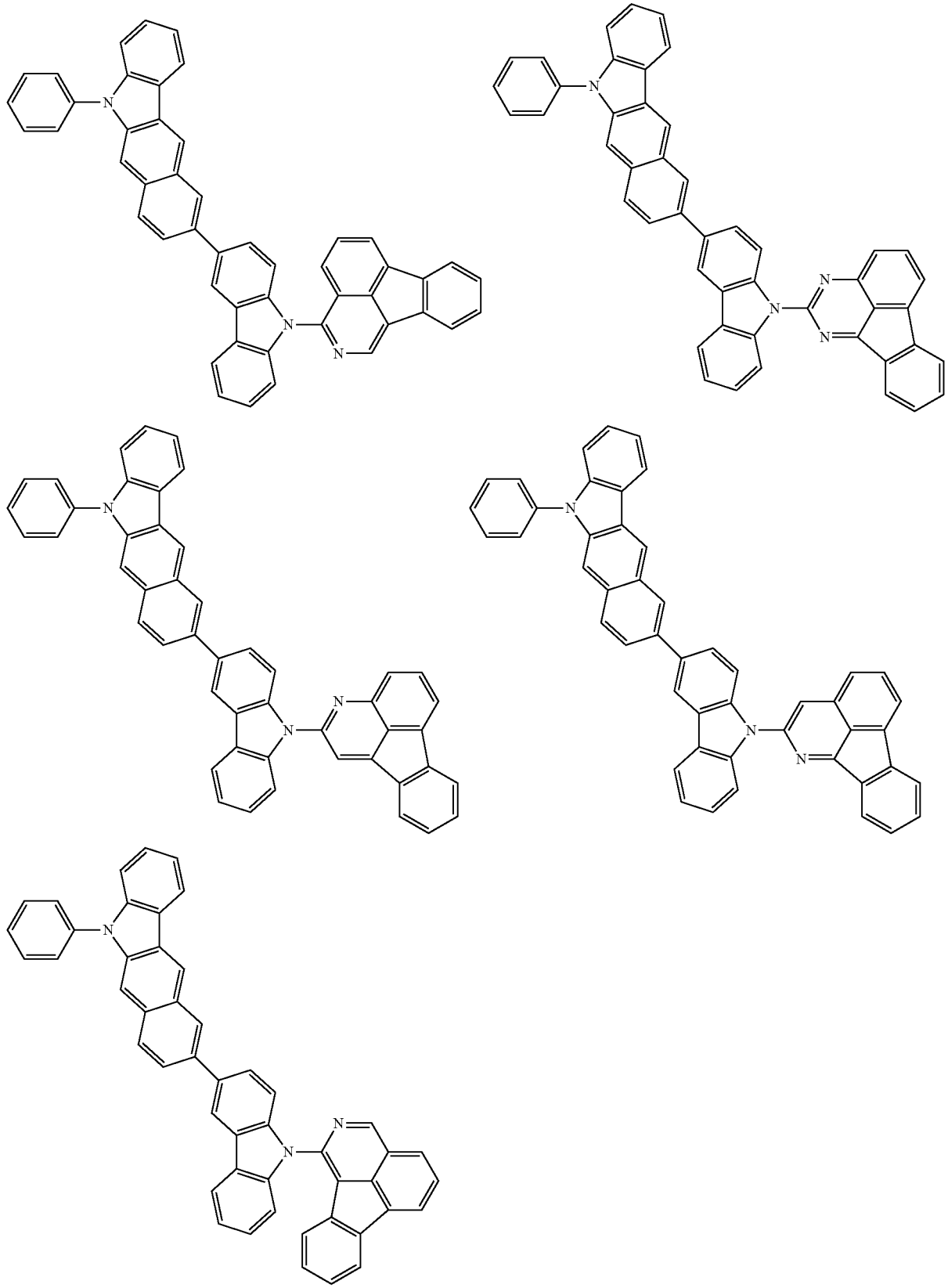

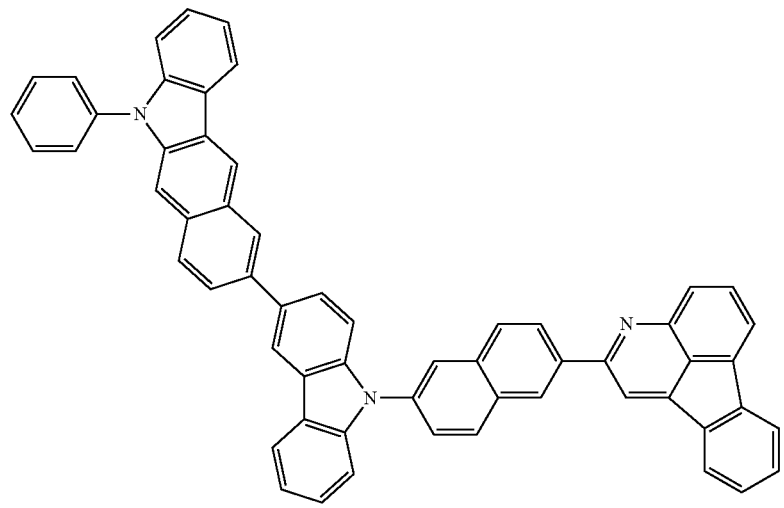
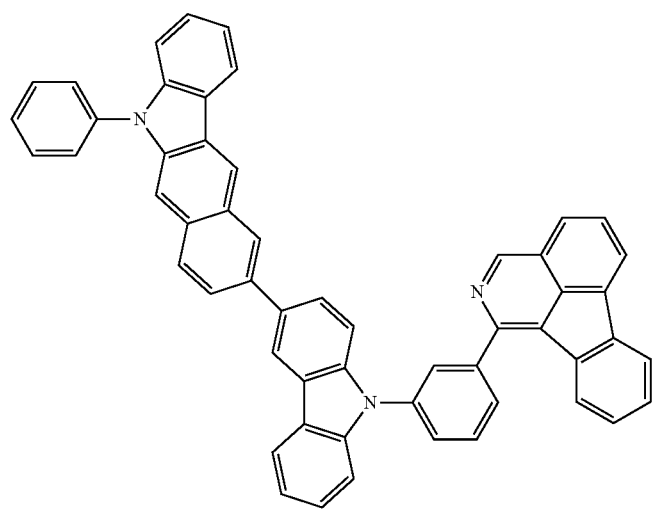
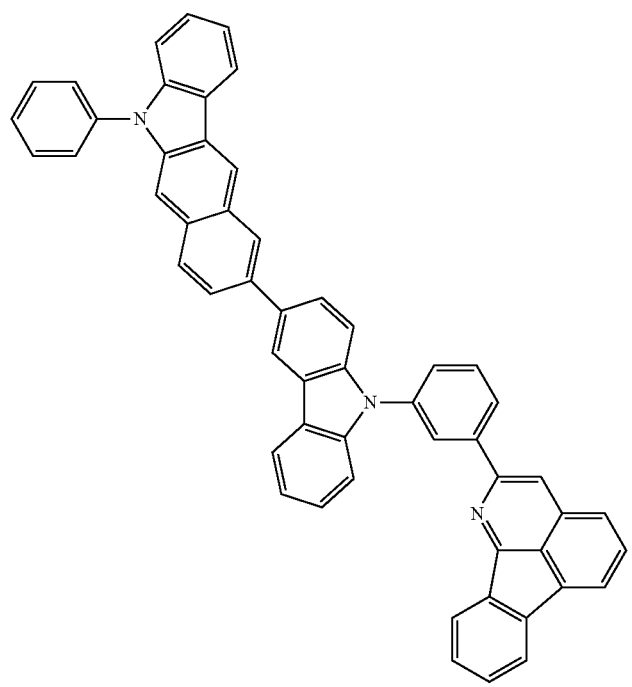

[Chem. 125]
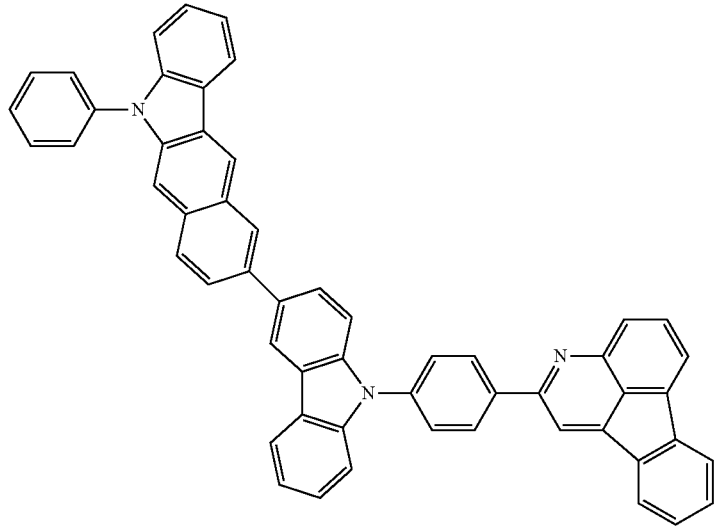
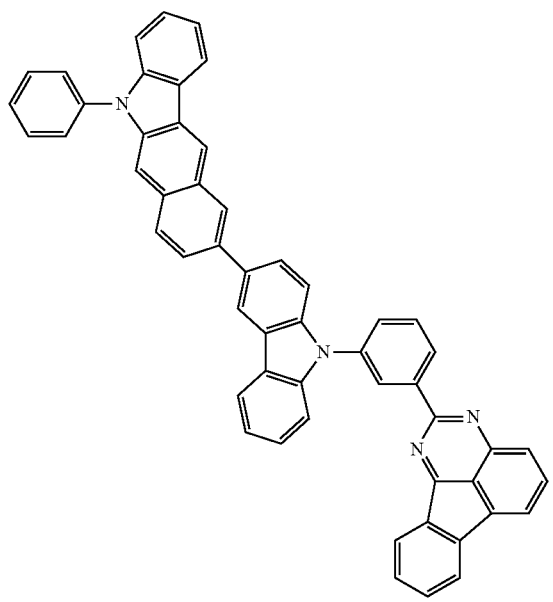
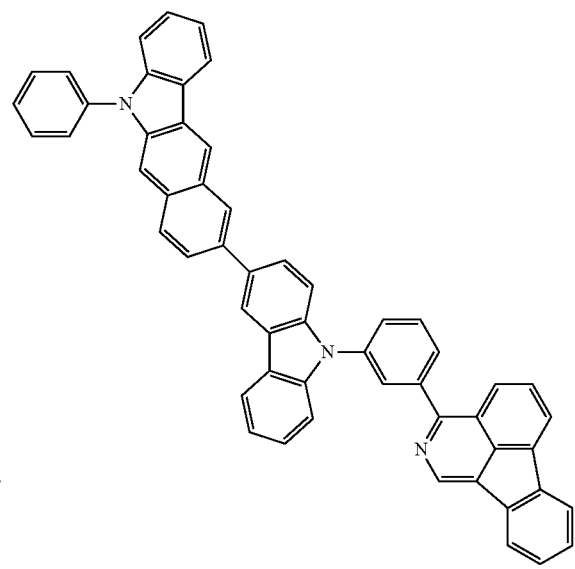
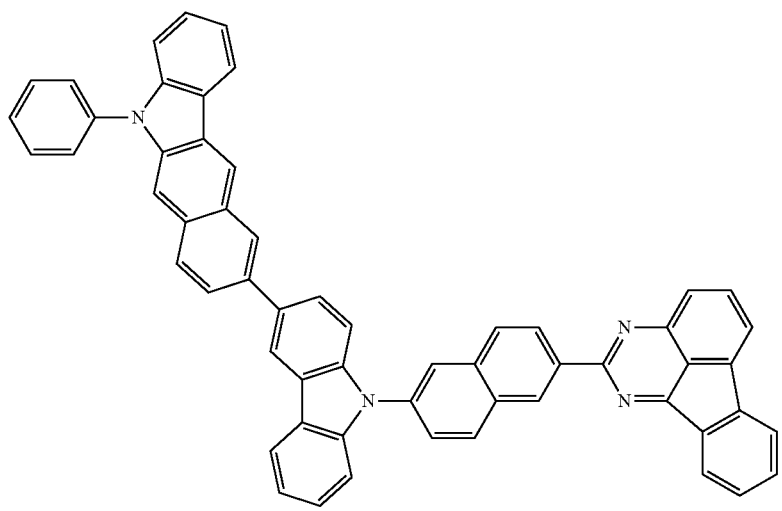

465
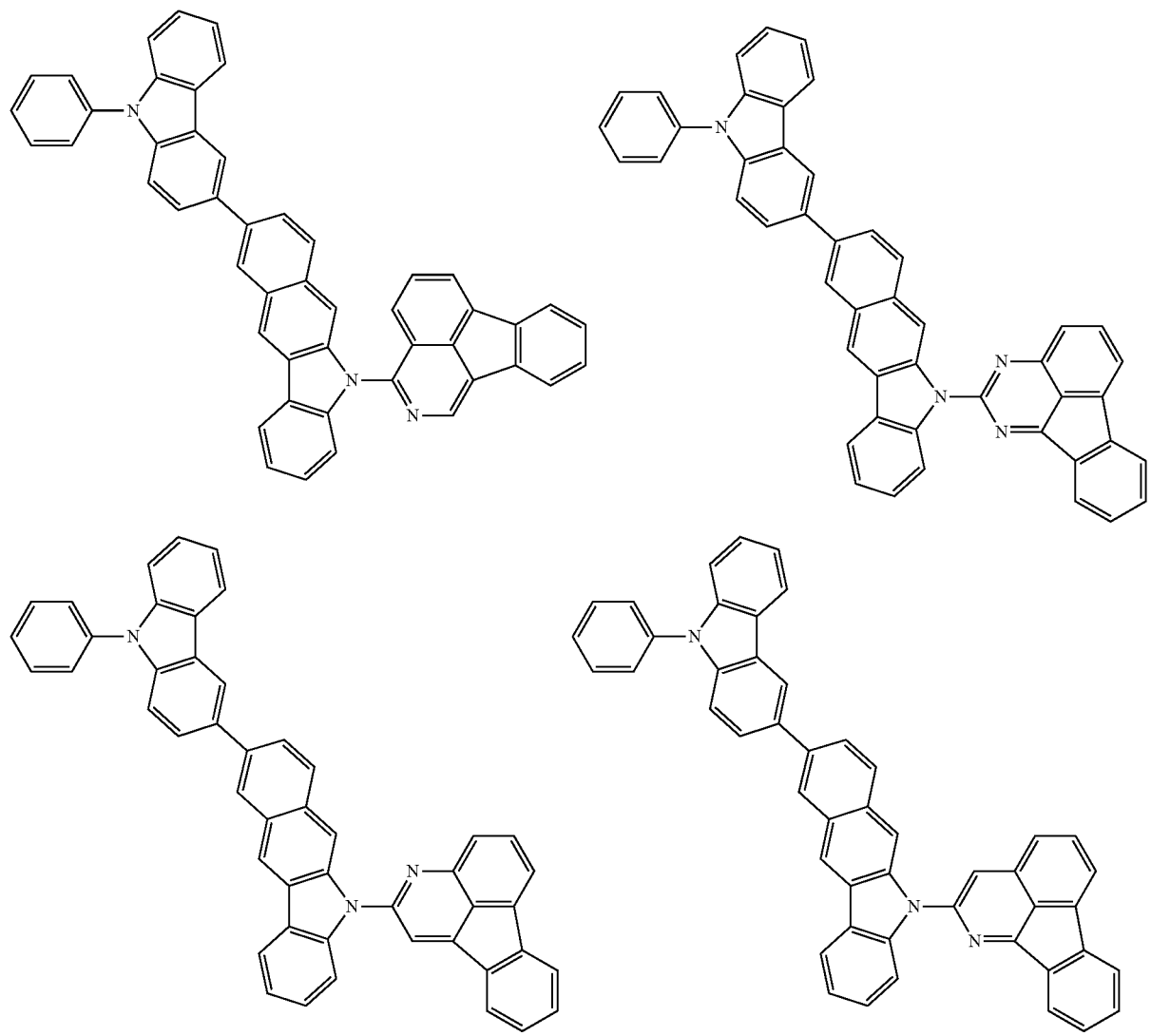
466
[Chem. 126]
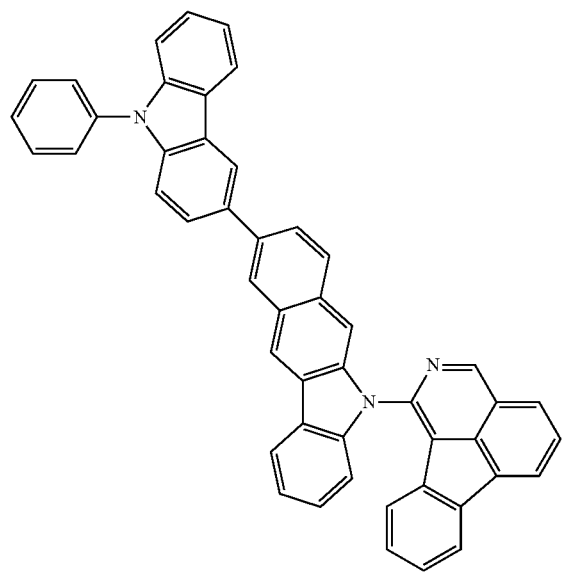

-continued
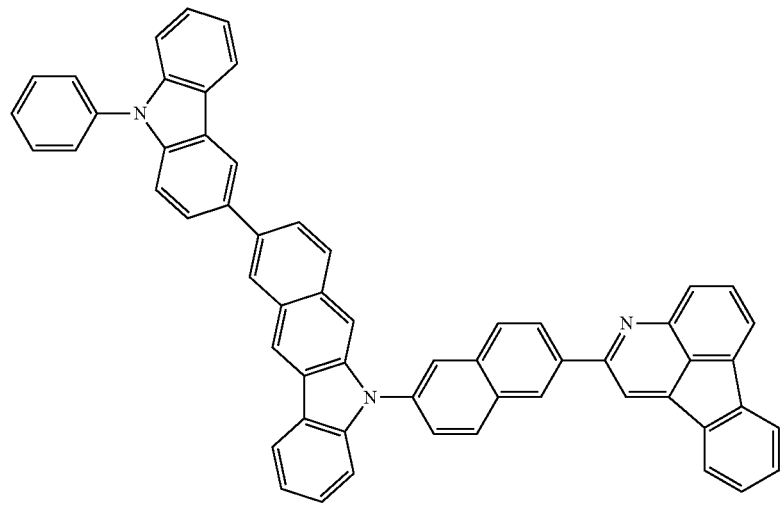
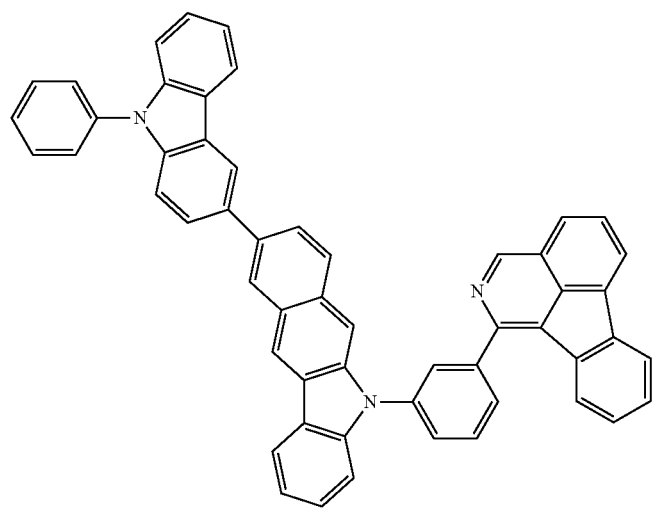
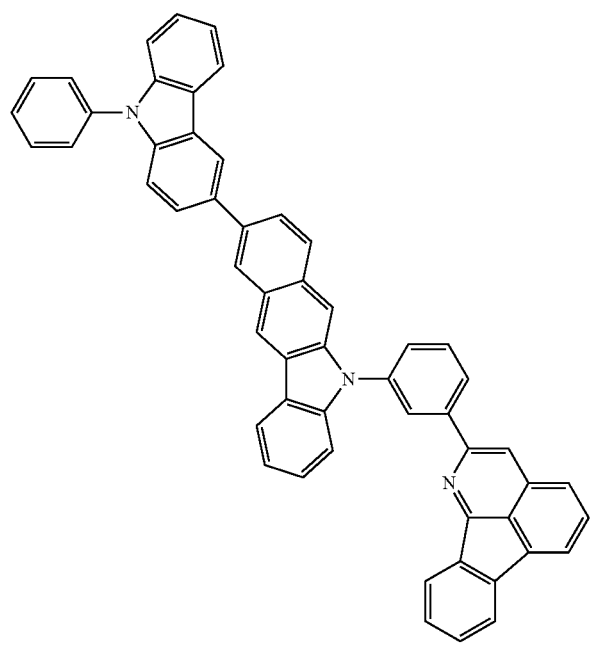

-continued
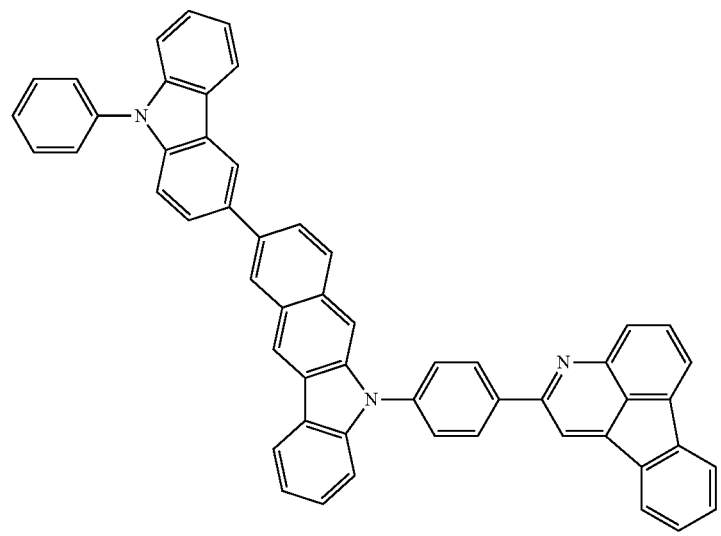
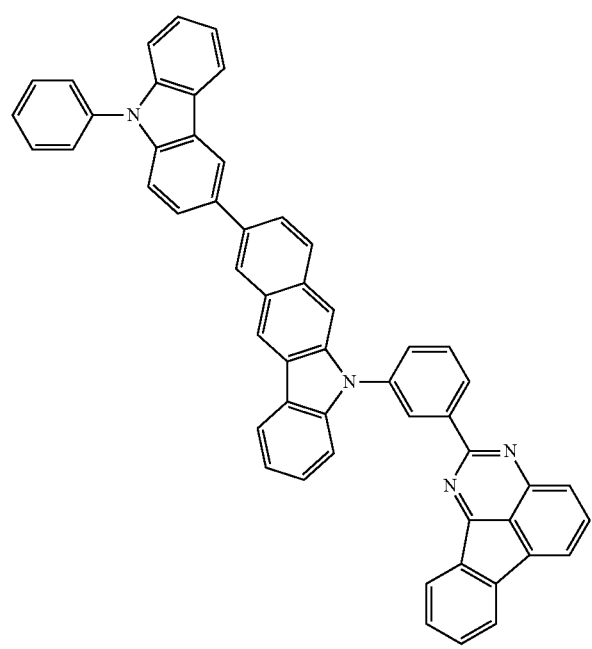

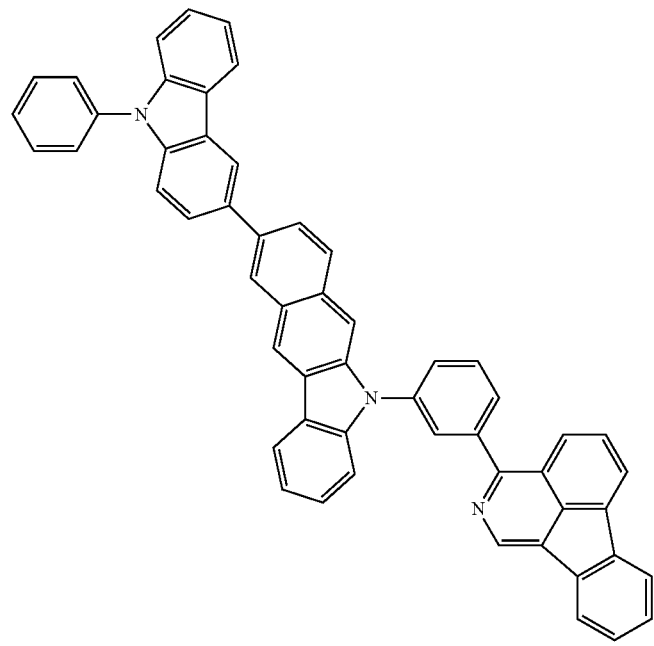
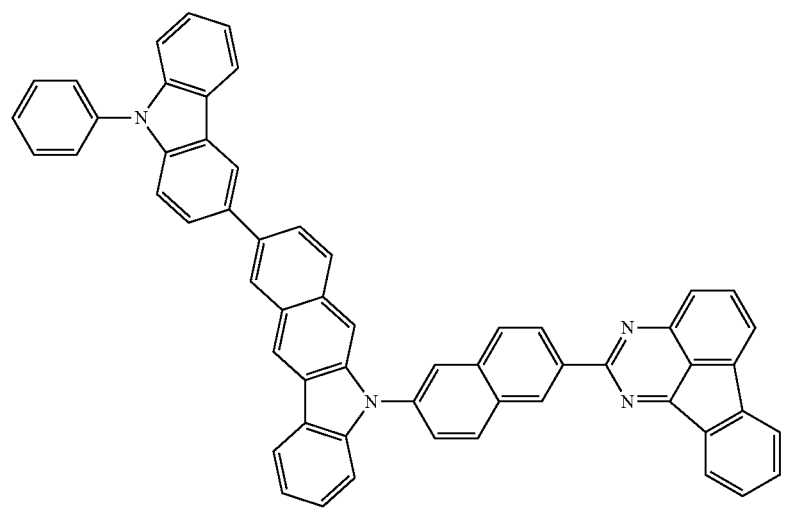
[Chem. 127]
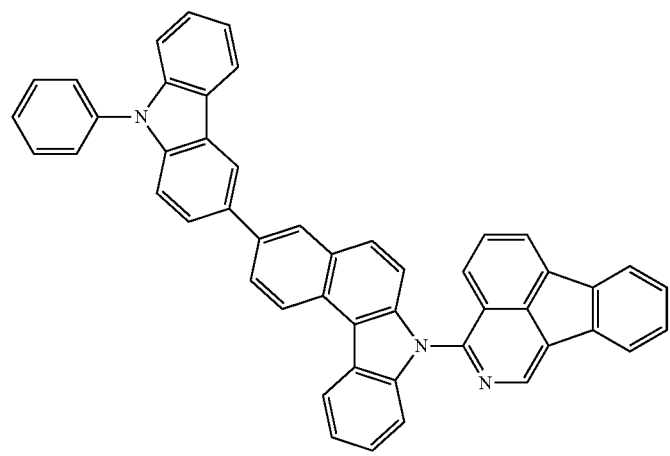

-continued
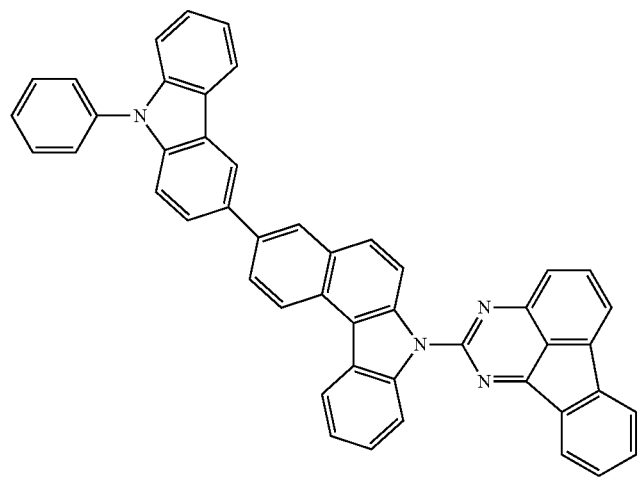
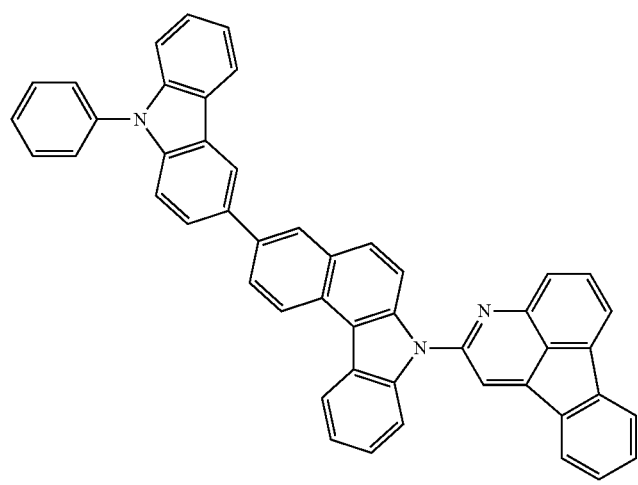
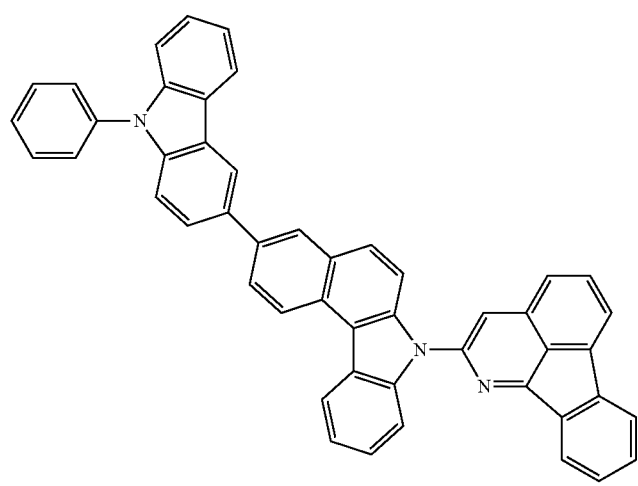

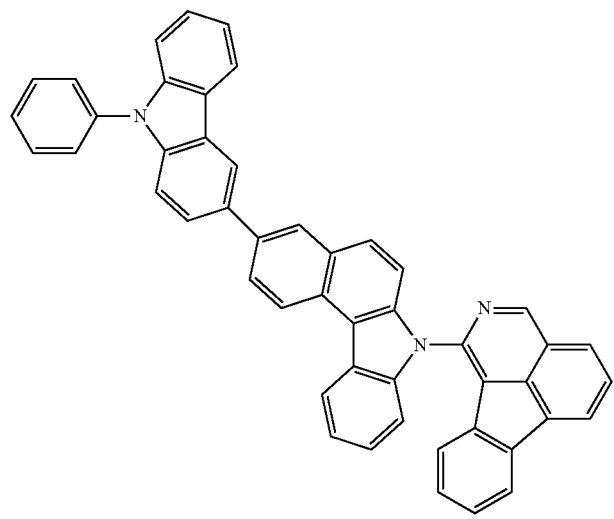
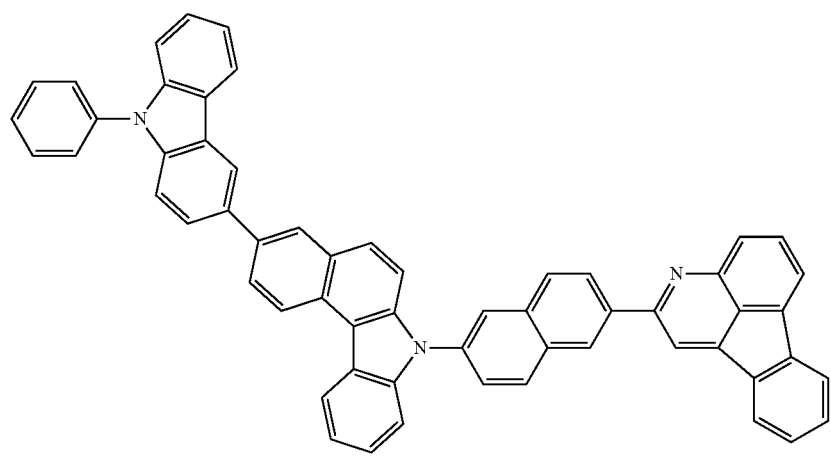
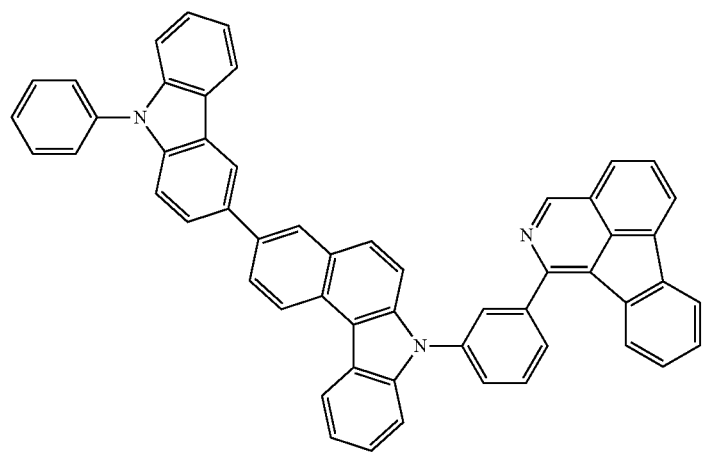

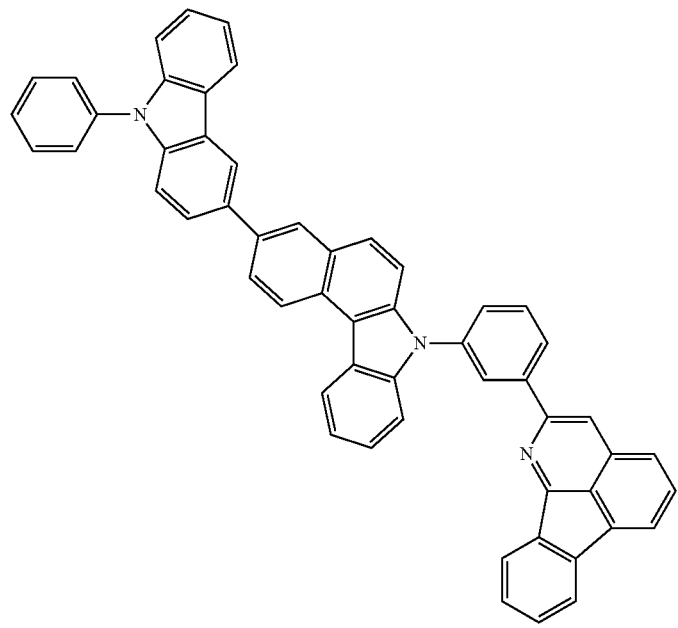
[Chem. 128]
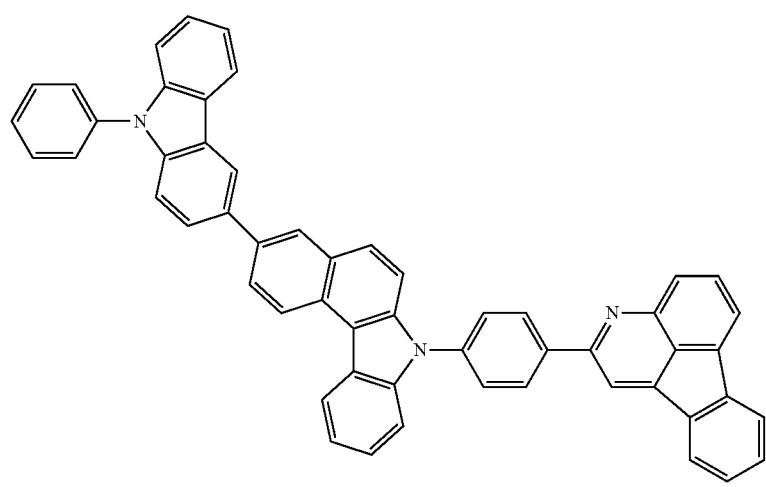

-continued
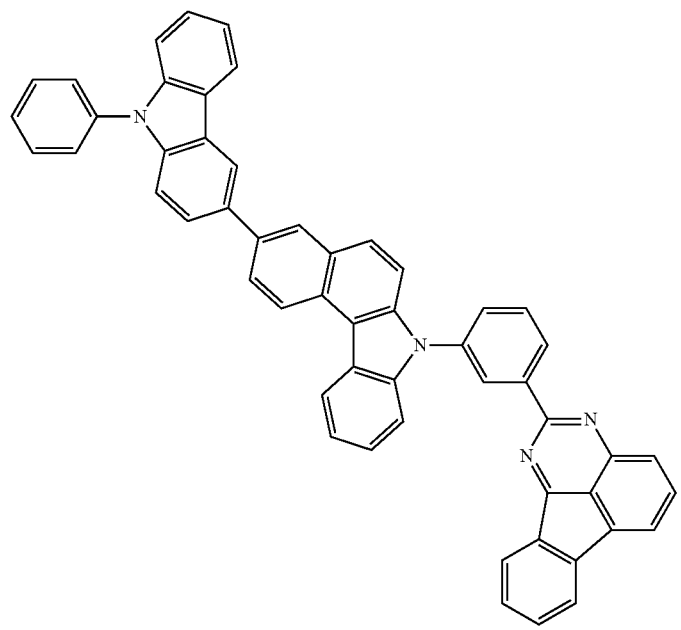
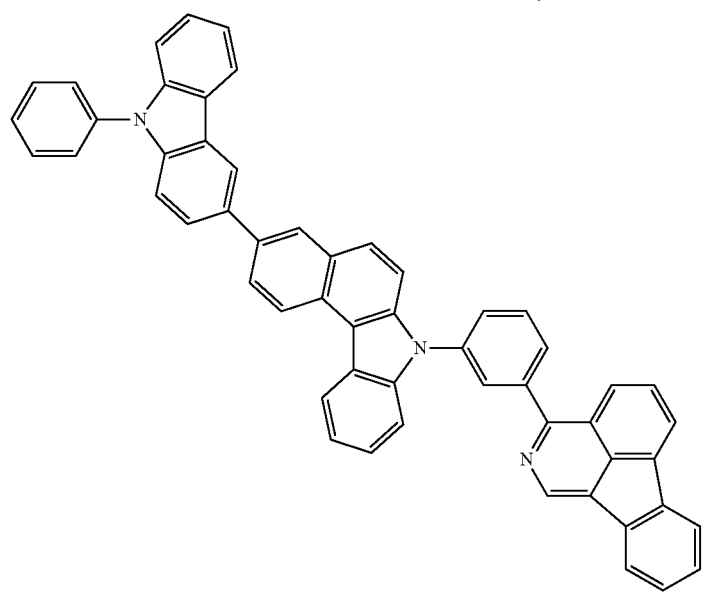
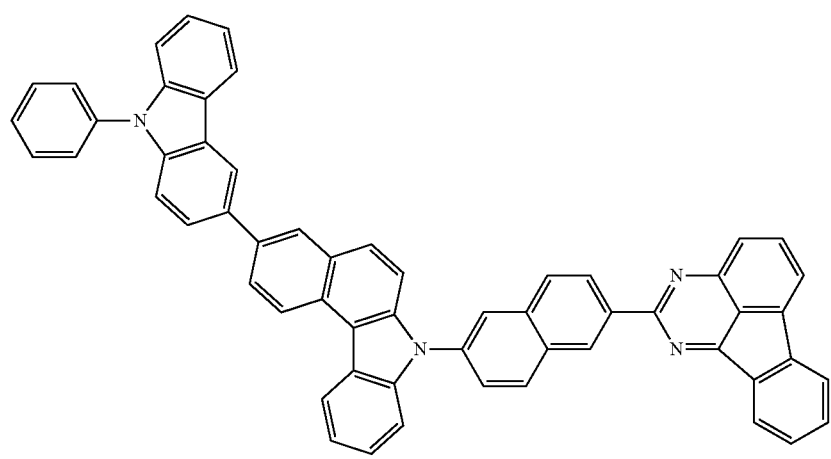

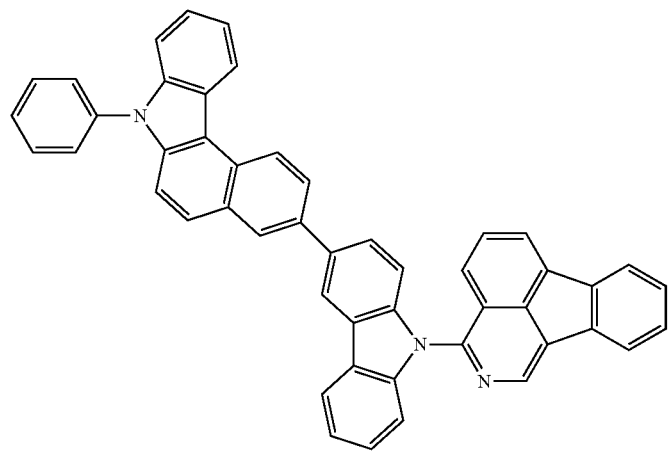
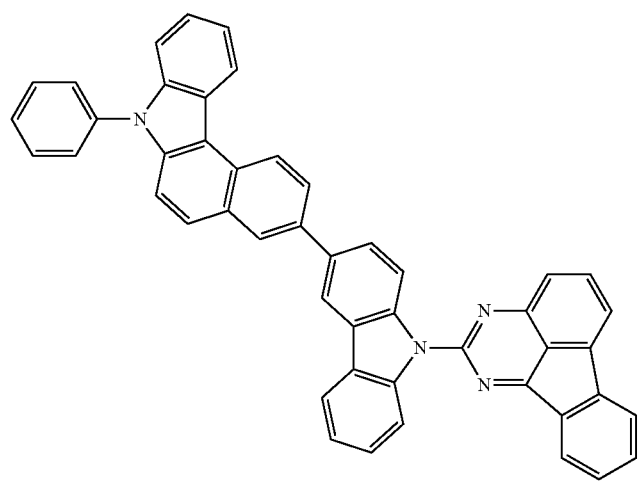
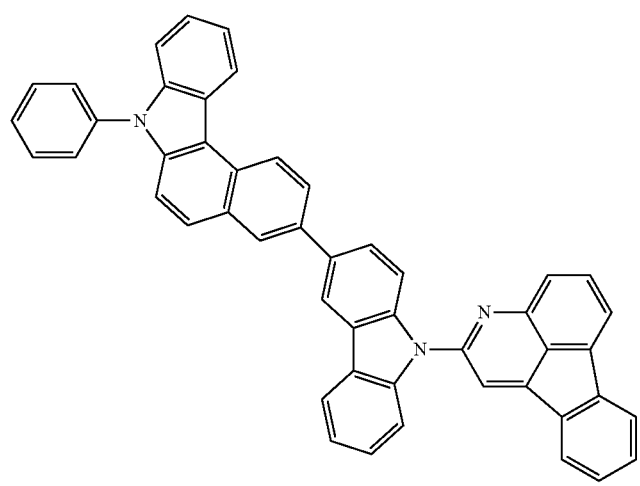

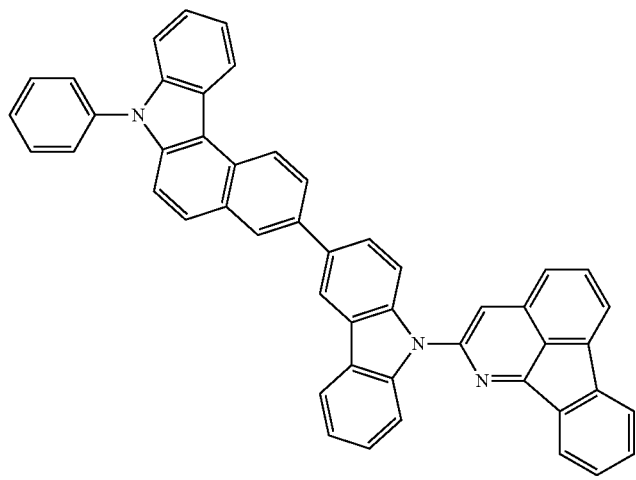
[Chem. 129]
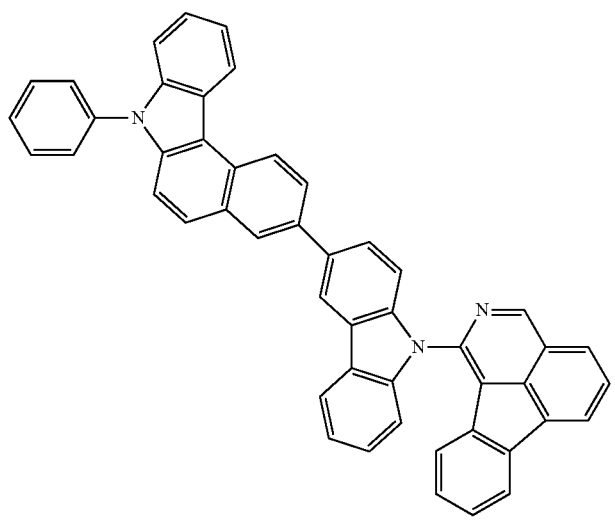
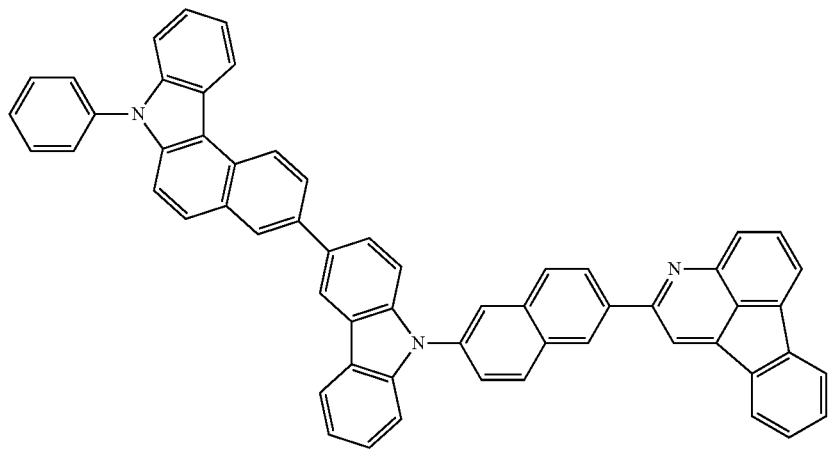

-continued
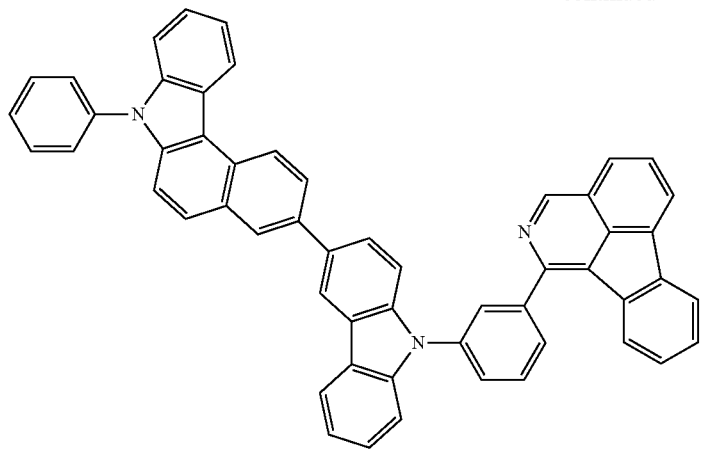
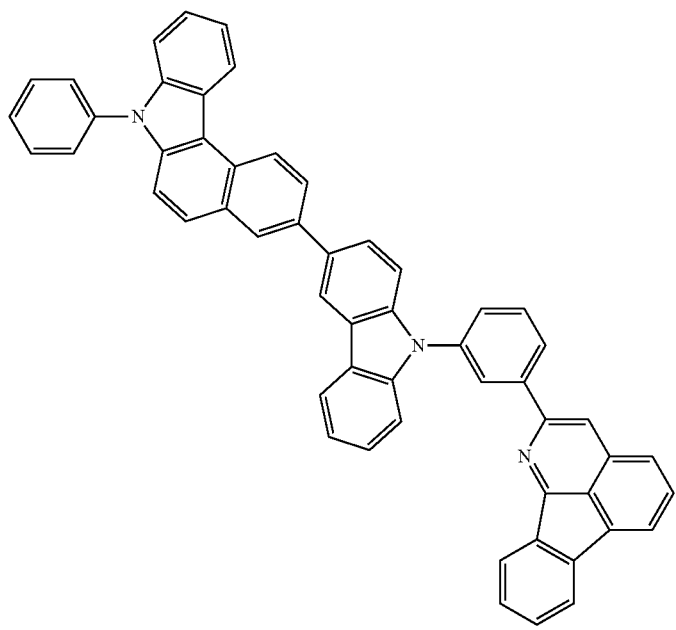
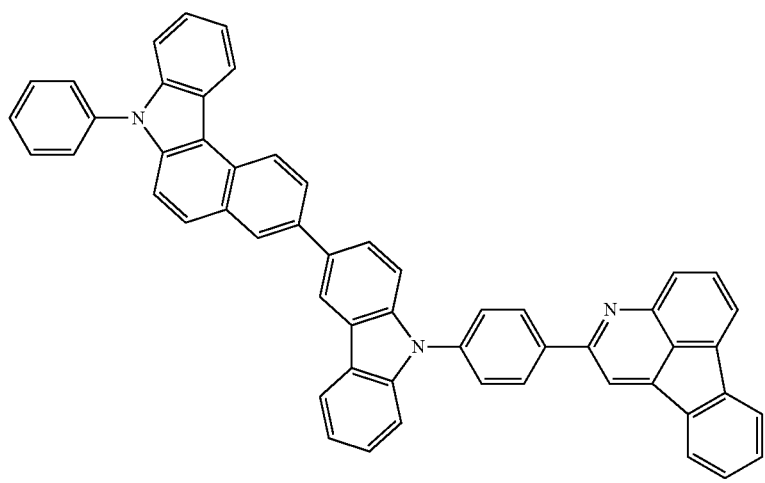

-continued
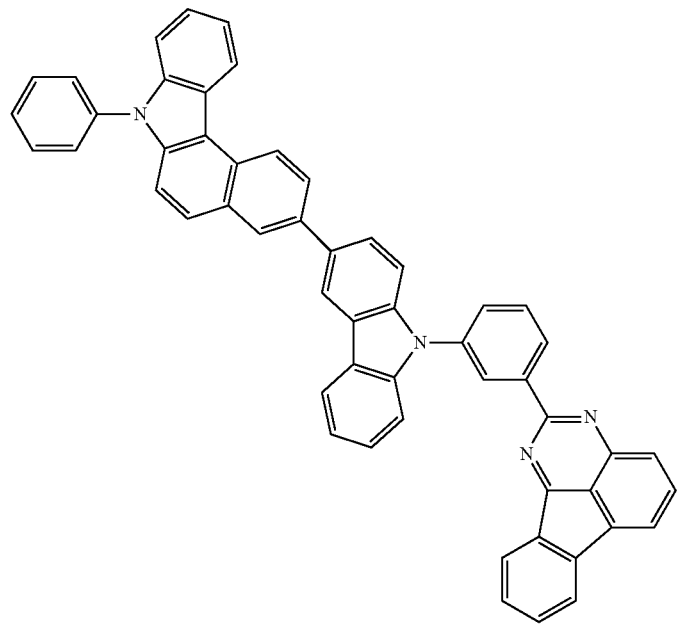
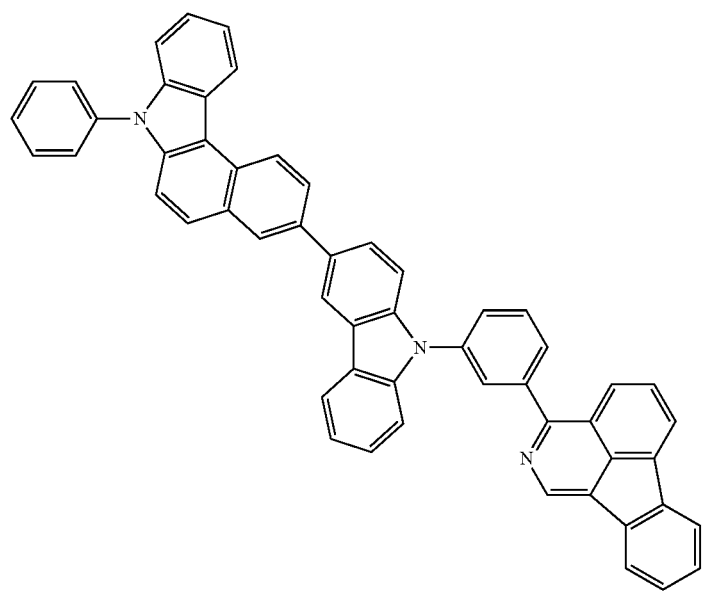
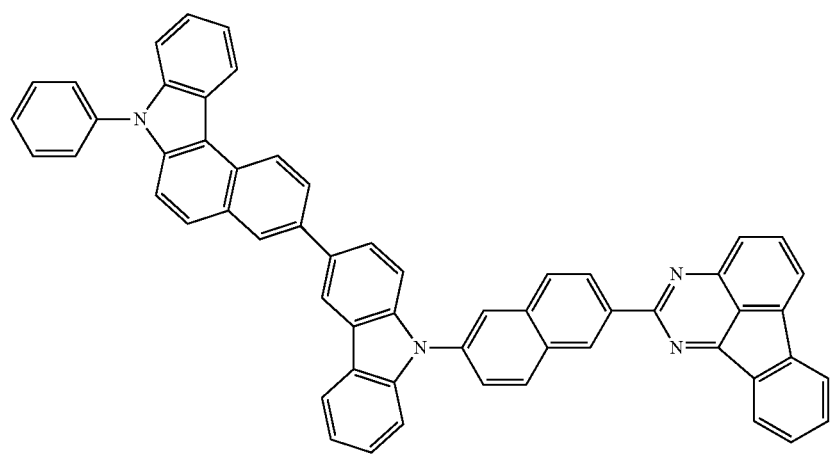

[Chem. 130]
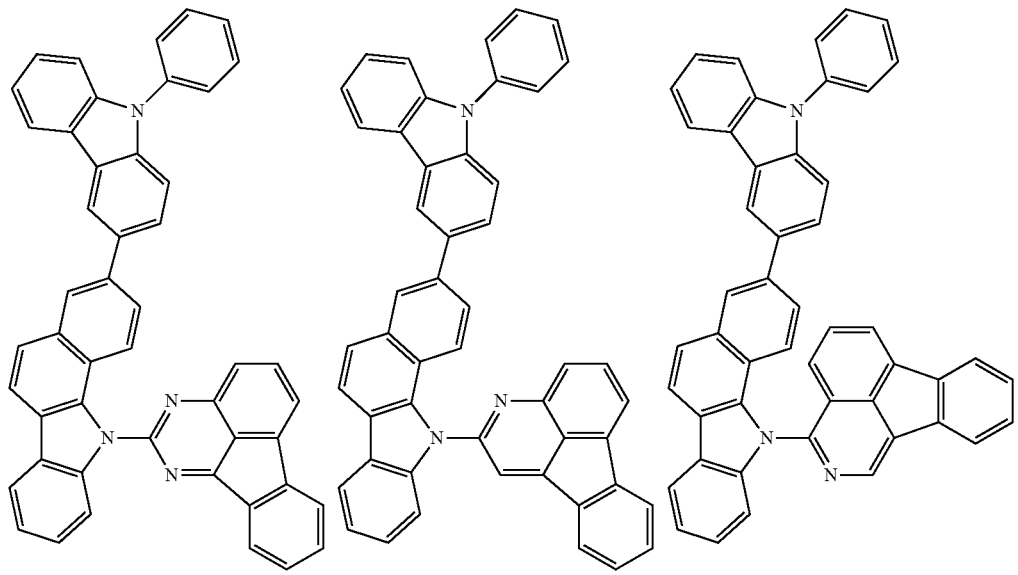
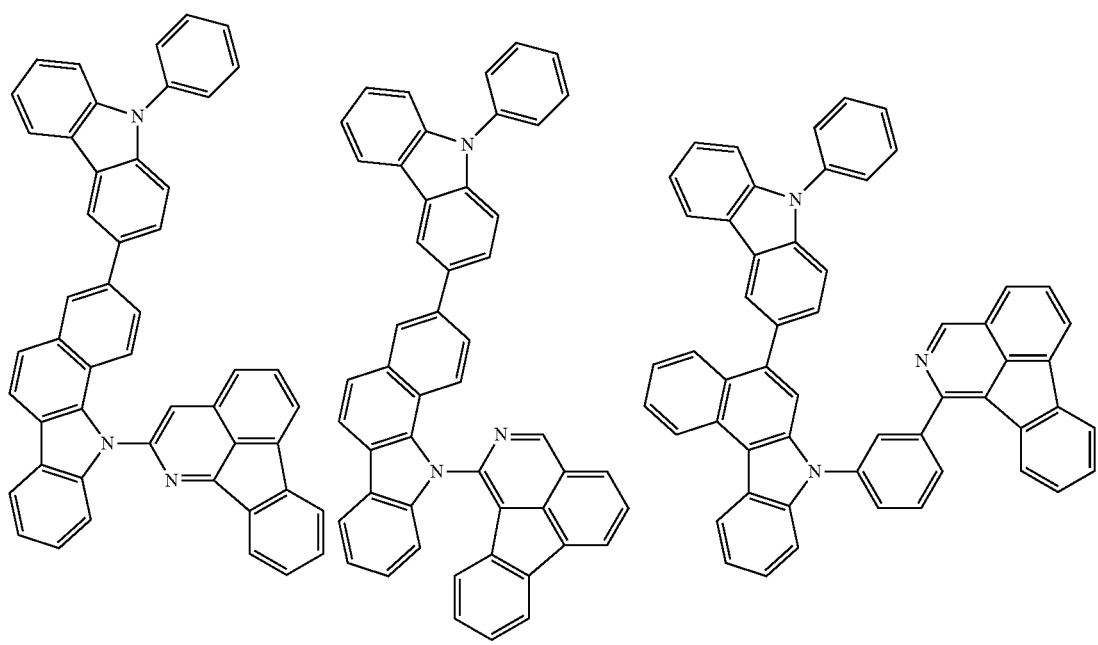

-continued
491 492
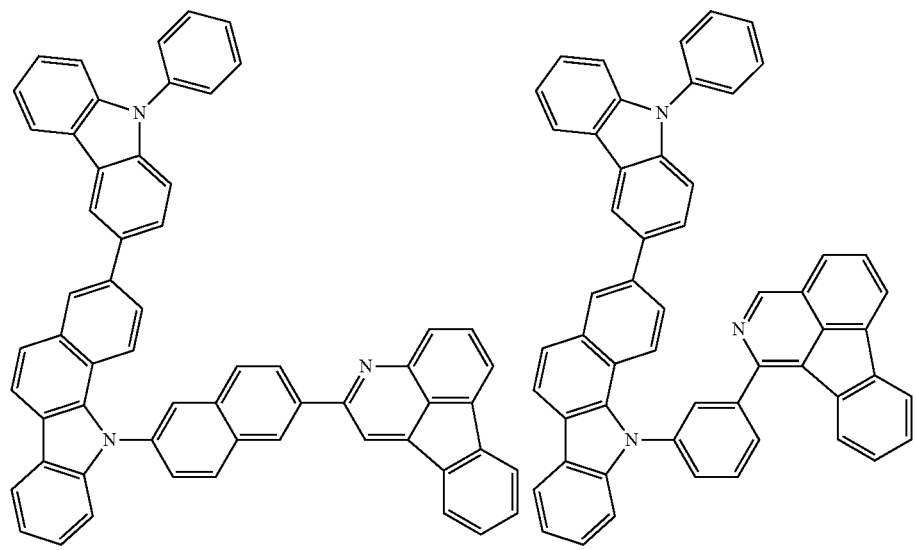
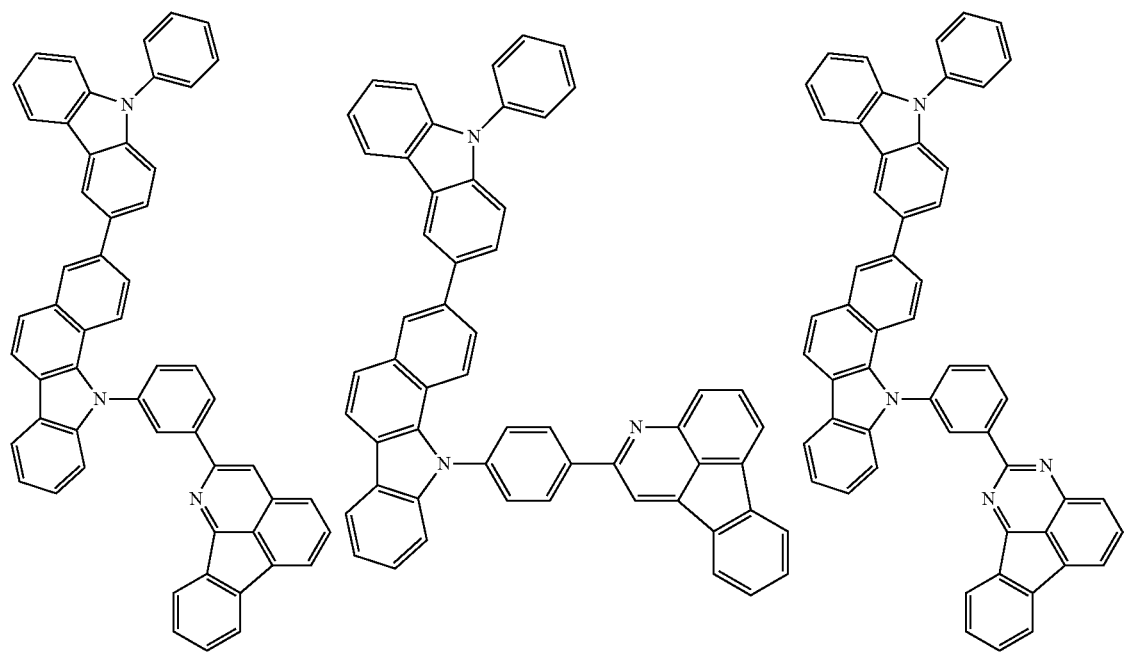

493
494
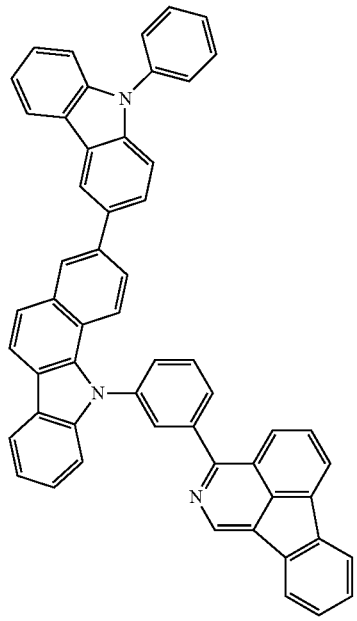
[Chem. 131]
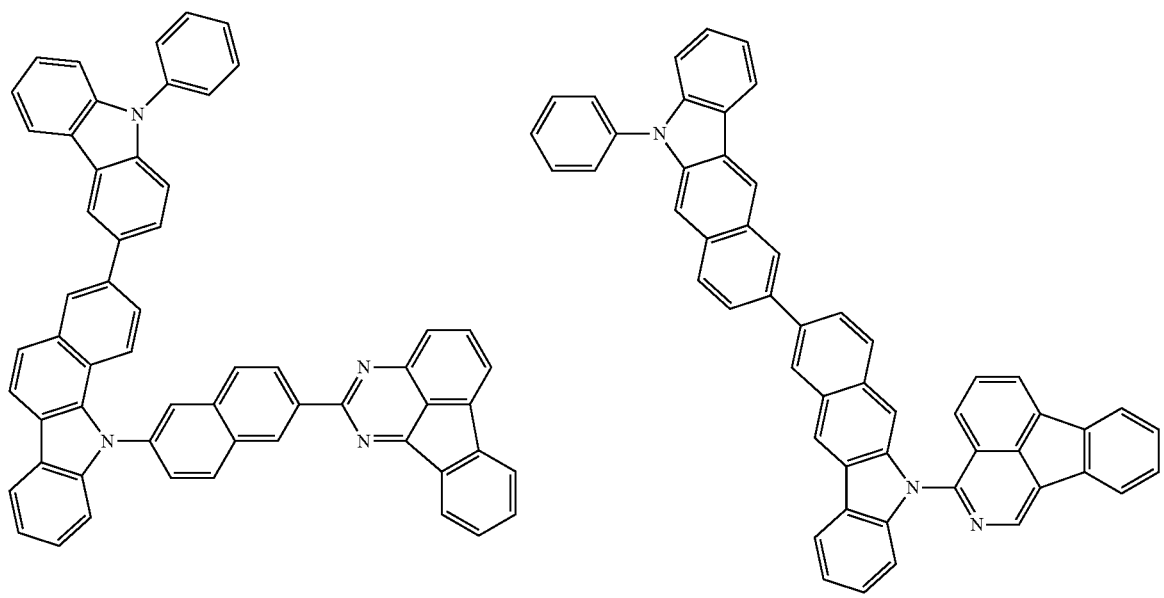

-continued
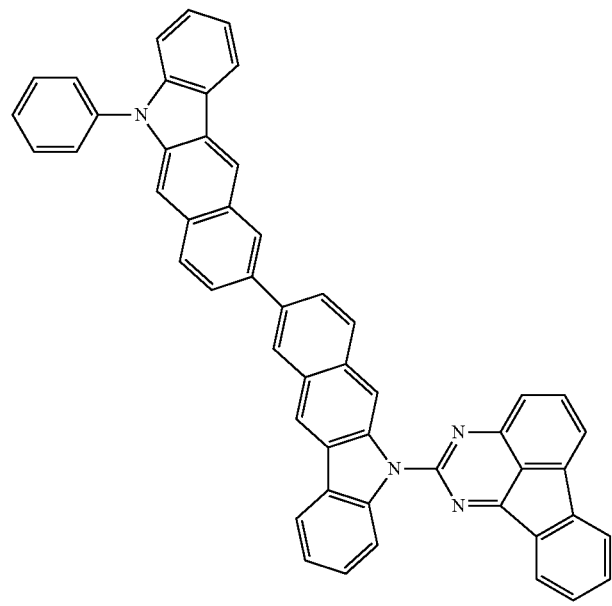
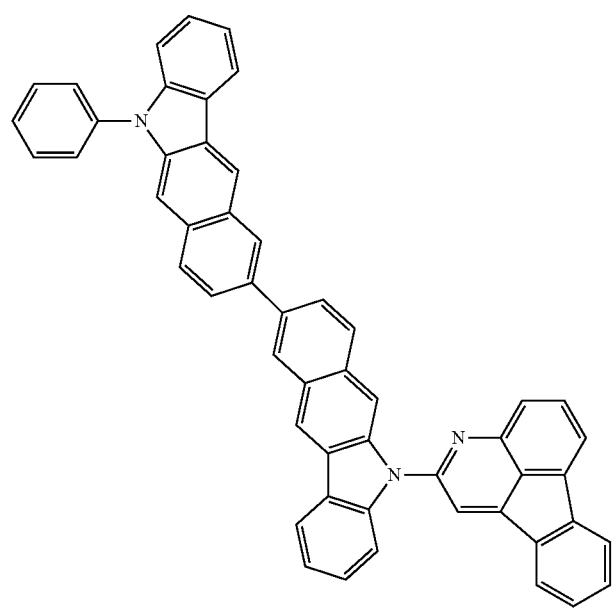

-continued
| 497 | 498 |
|---|---|
| 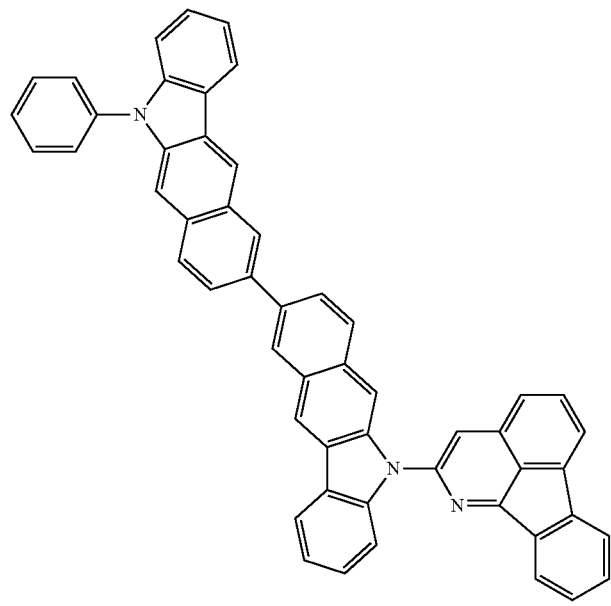 | 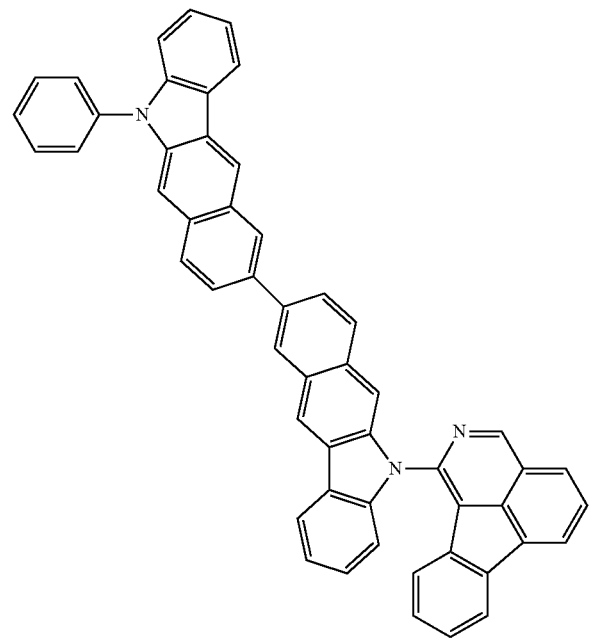 |
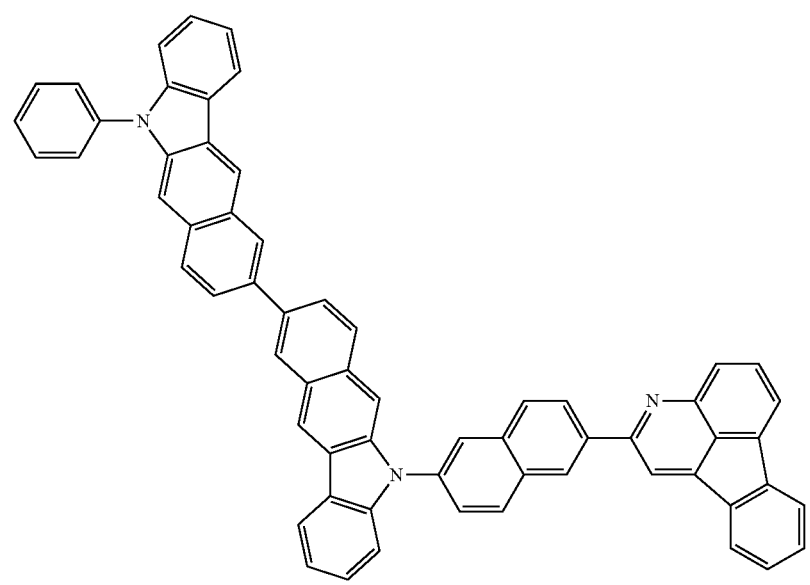

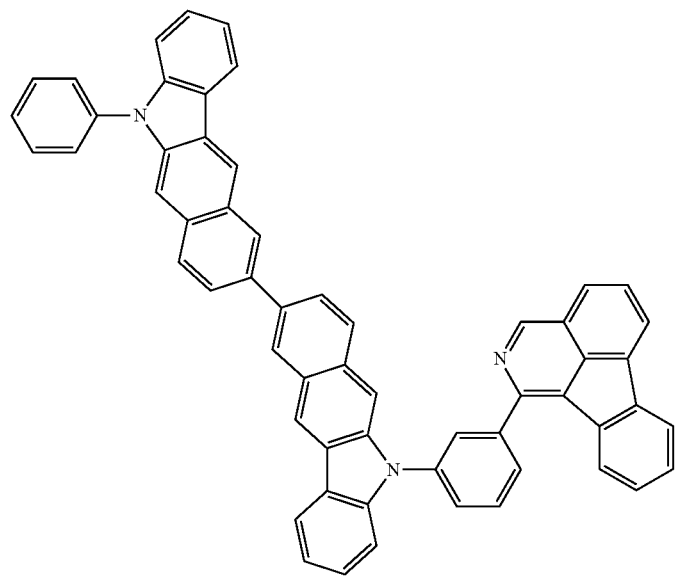
[Chem. 132]
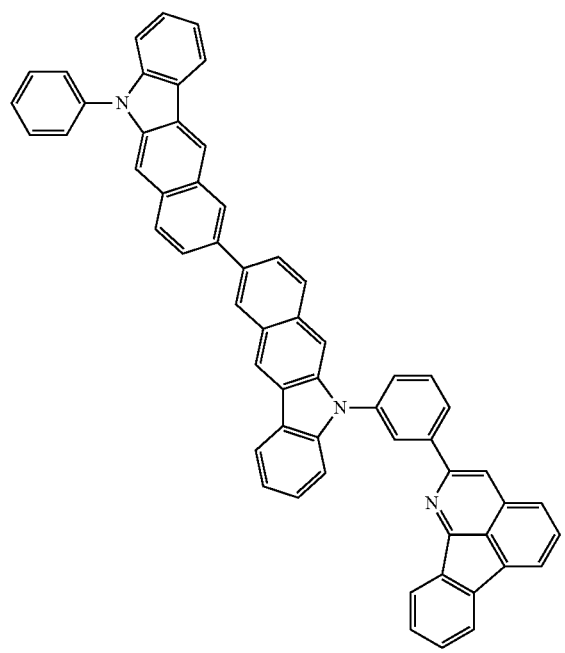

-continued
501
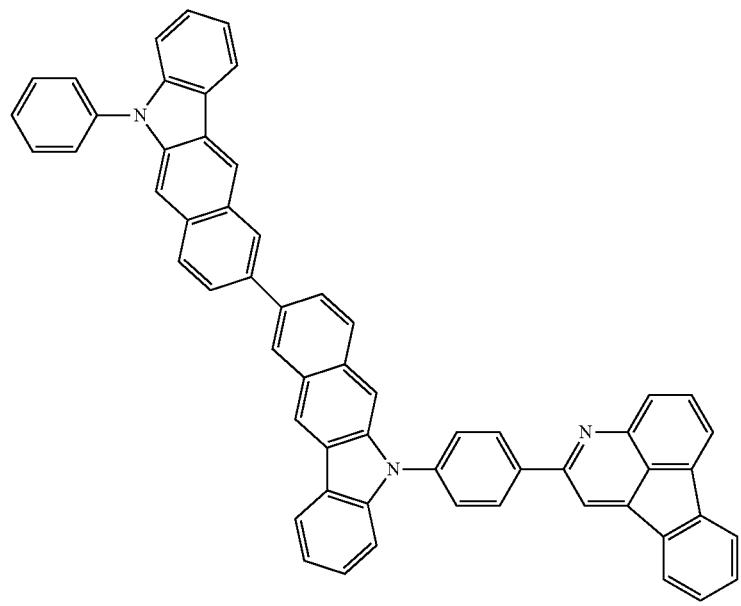
502
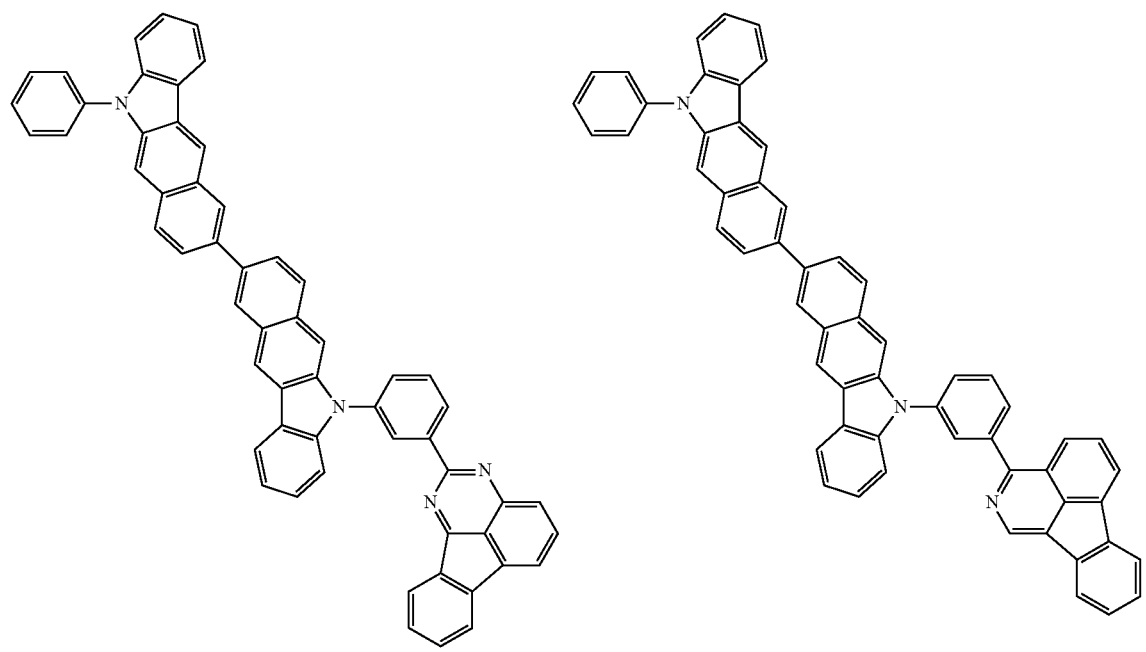

503 504
-continued
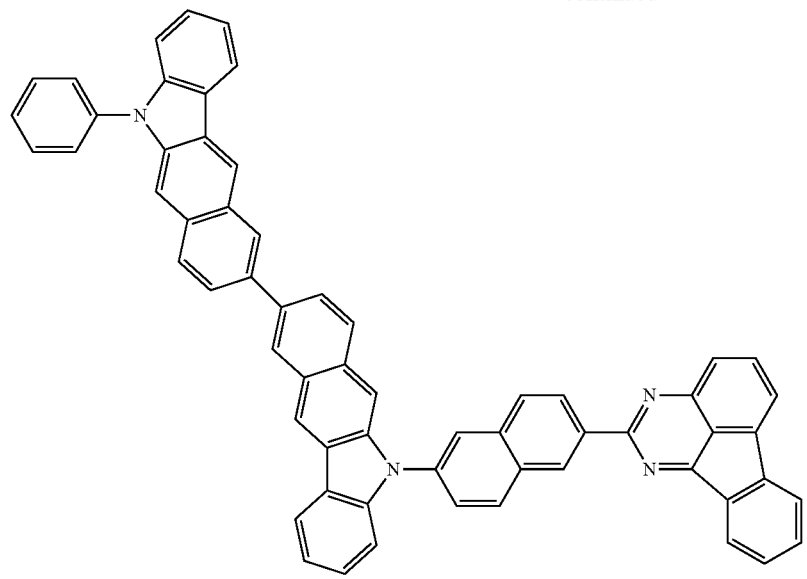
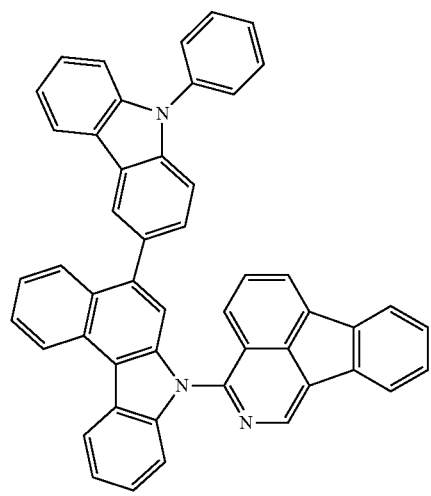
[Chem. 133]
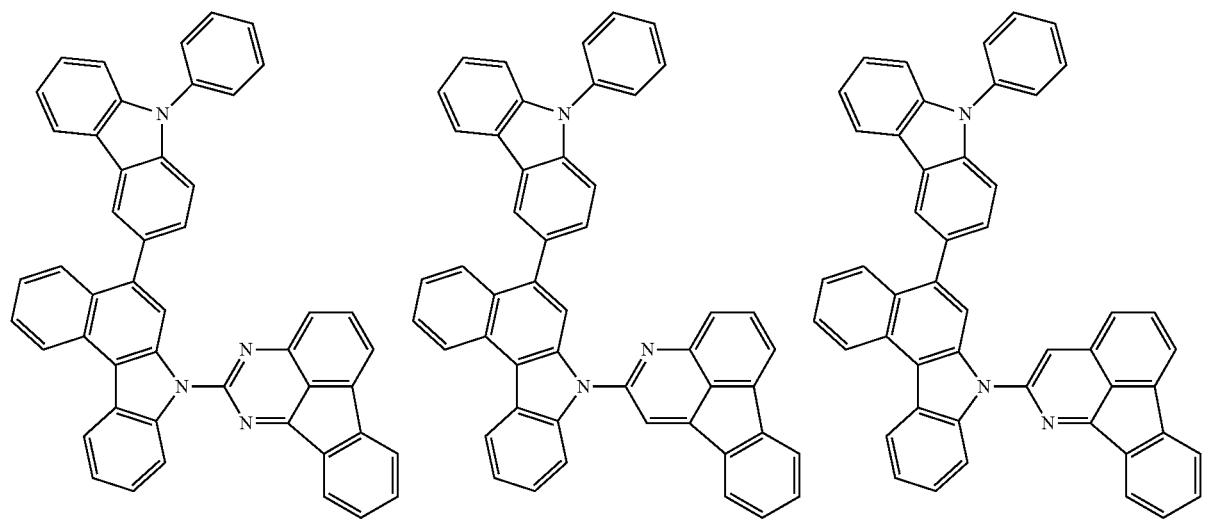

-continued
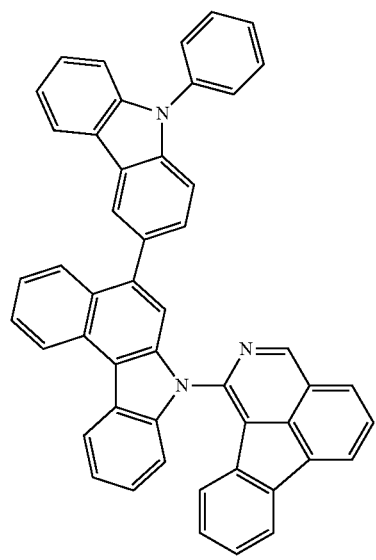
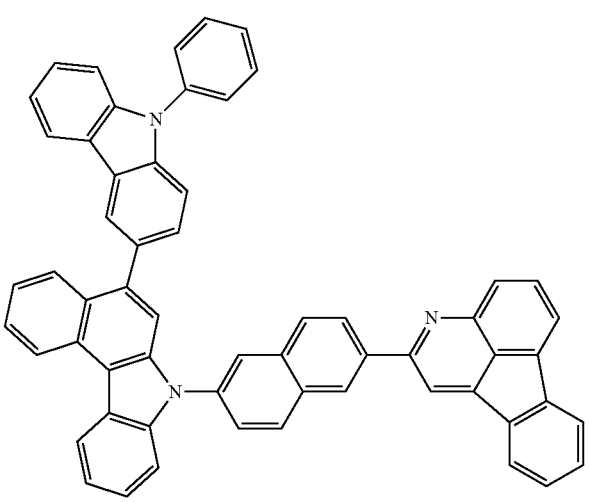
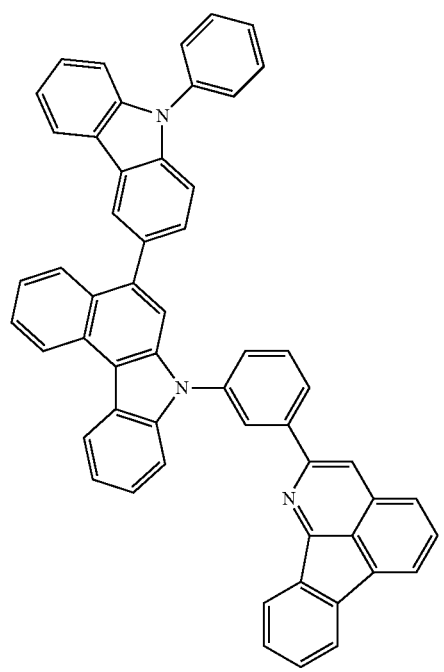
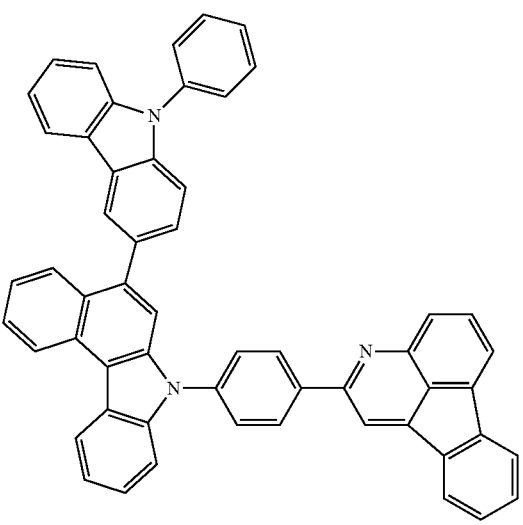

-continued
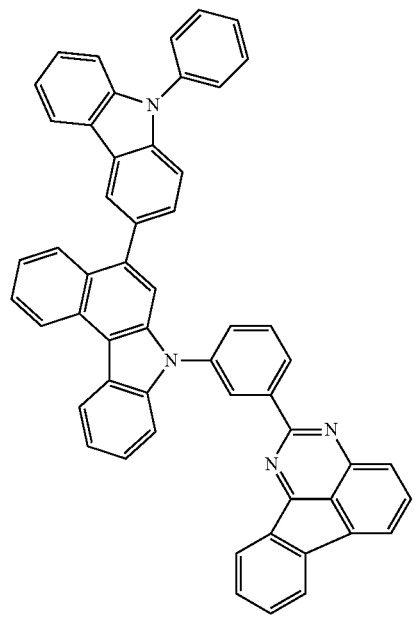
507
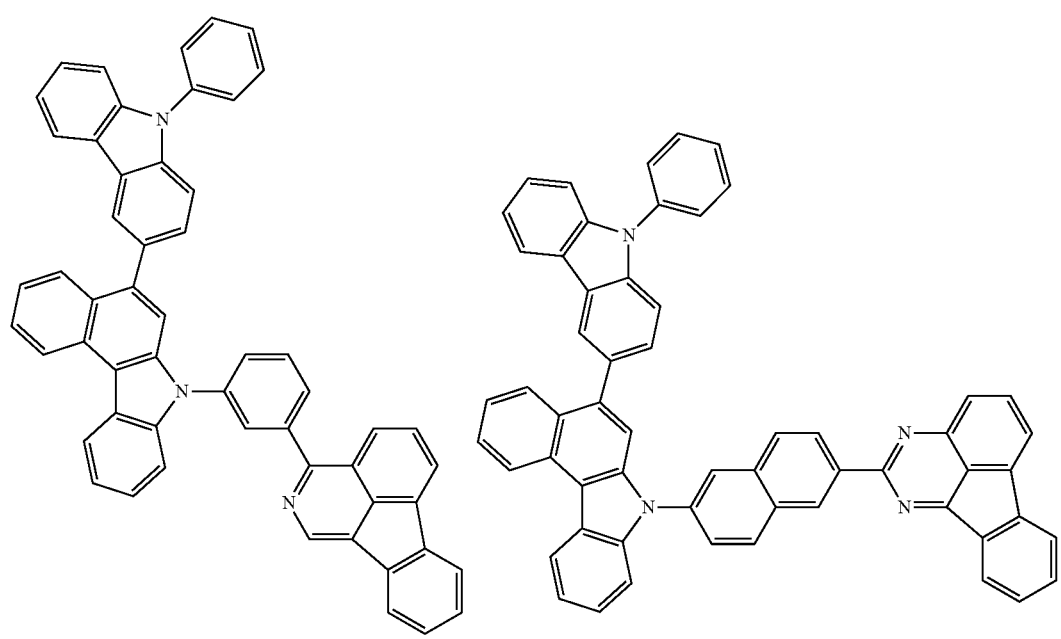
508

[Chem. 134]
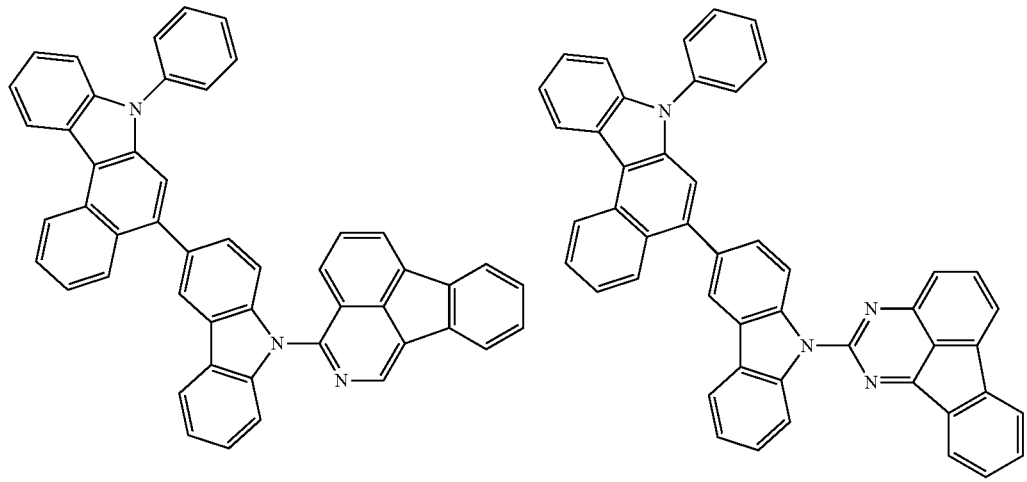
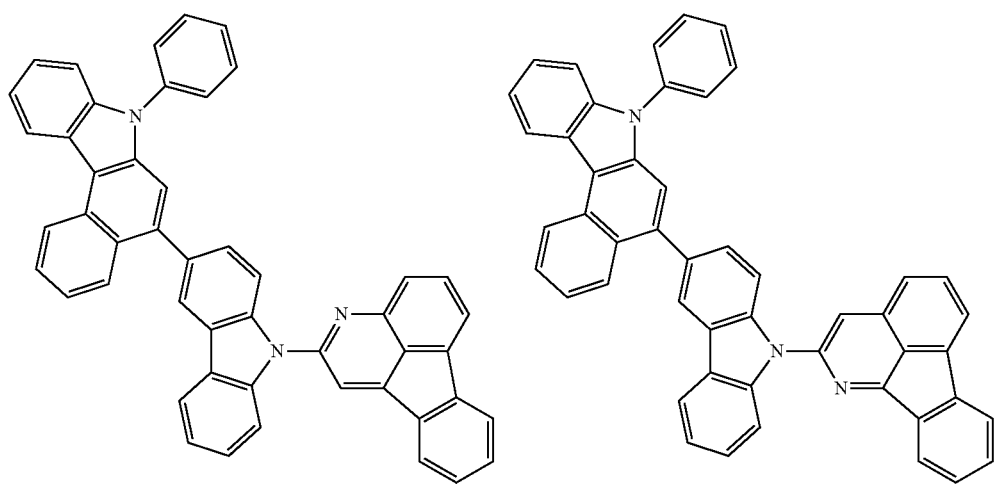
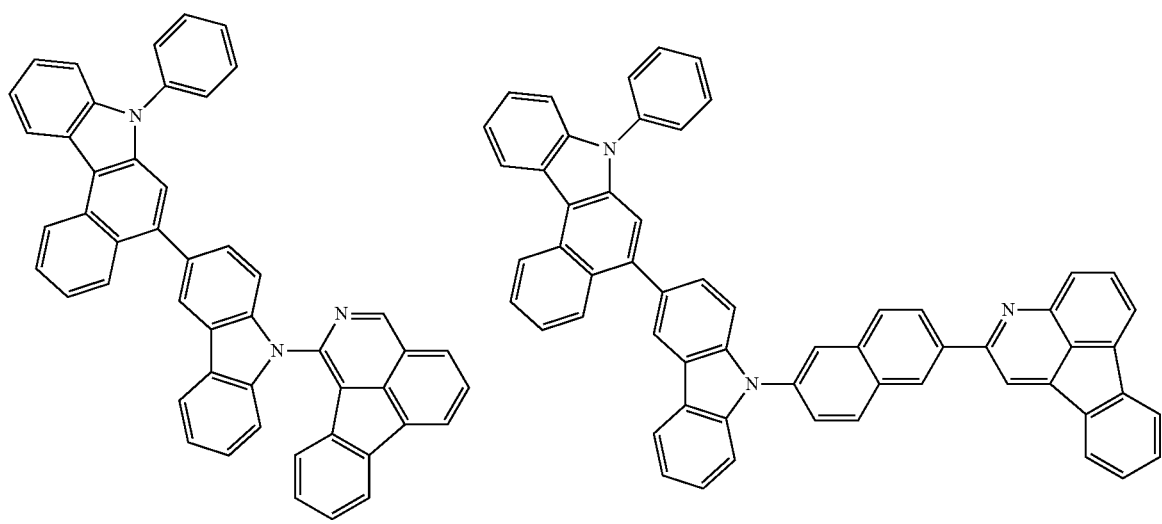

511
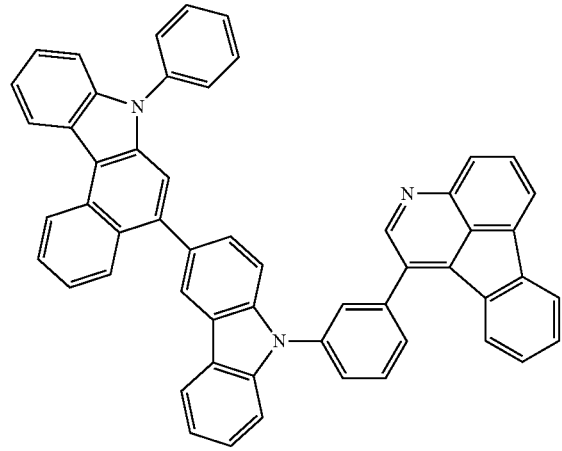
512
-continued
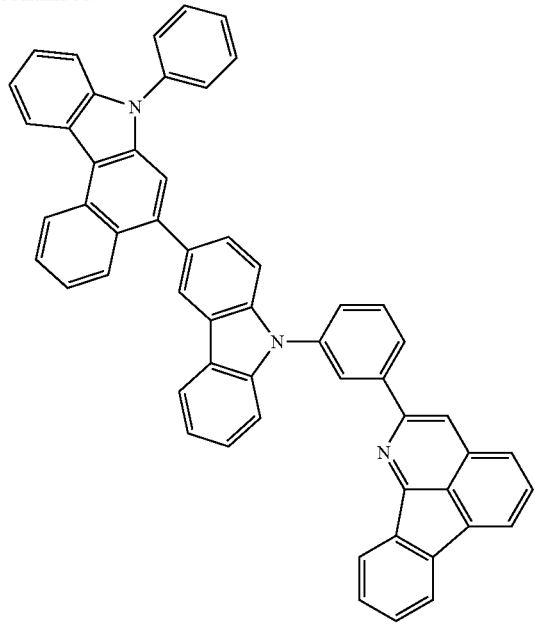
[Chem. 135]
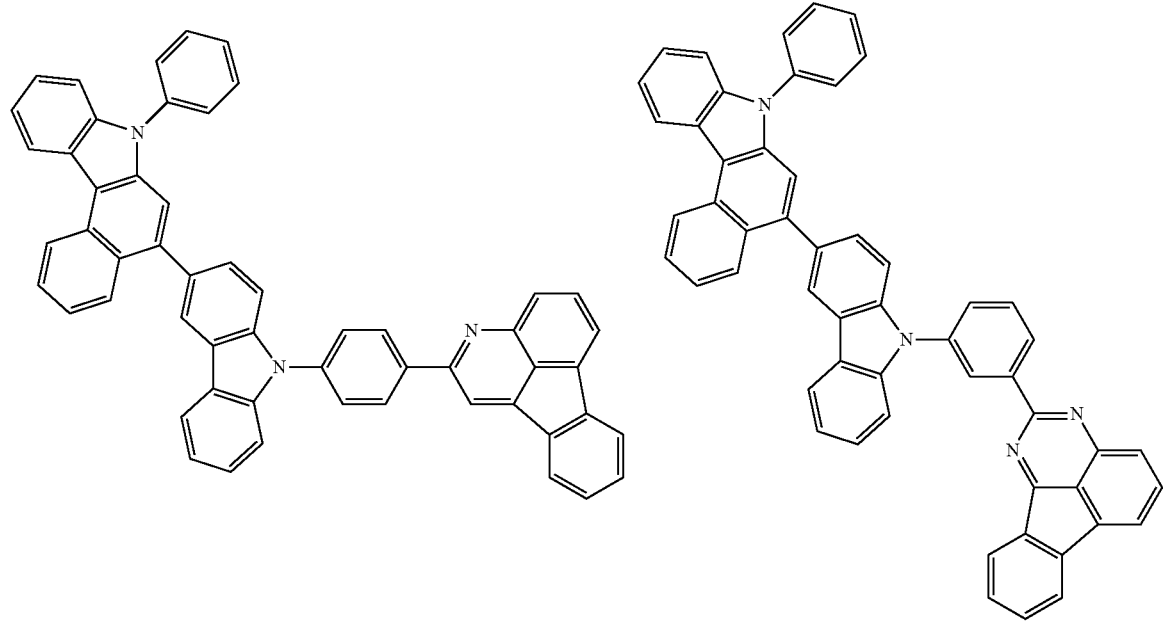

513 514
-continued
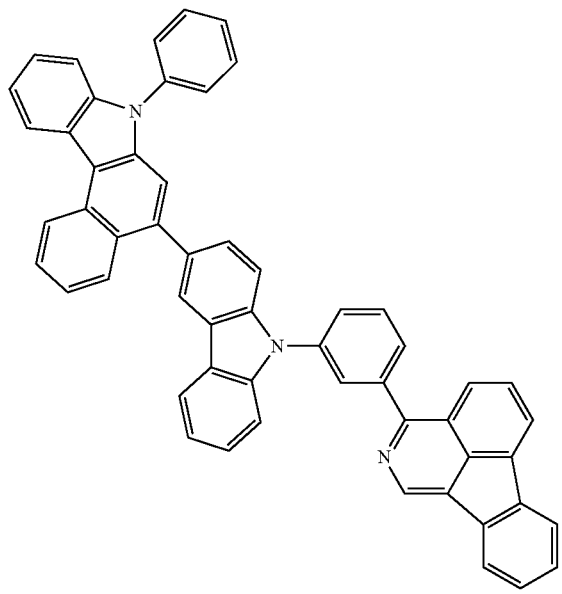
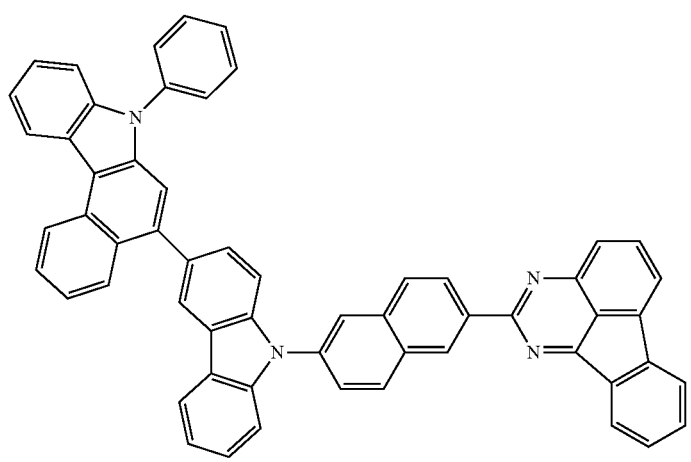
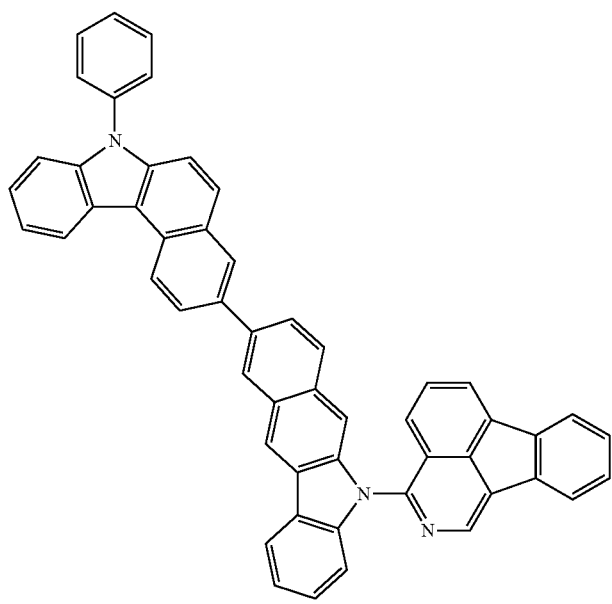
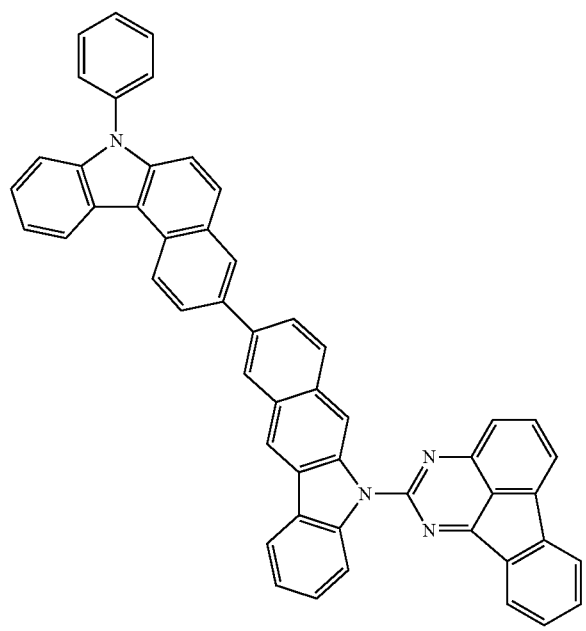

515
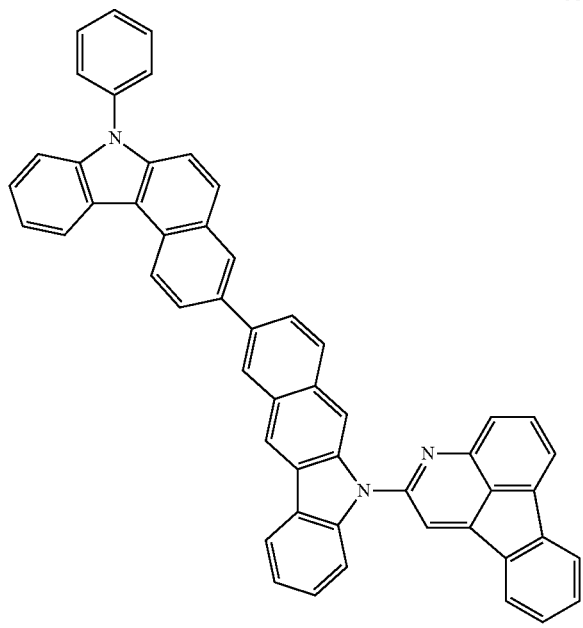
-continued
516
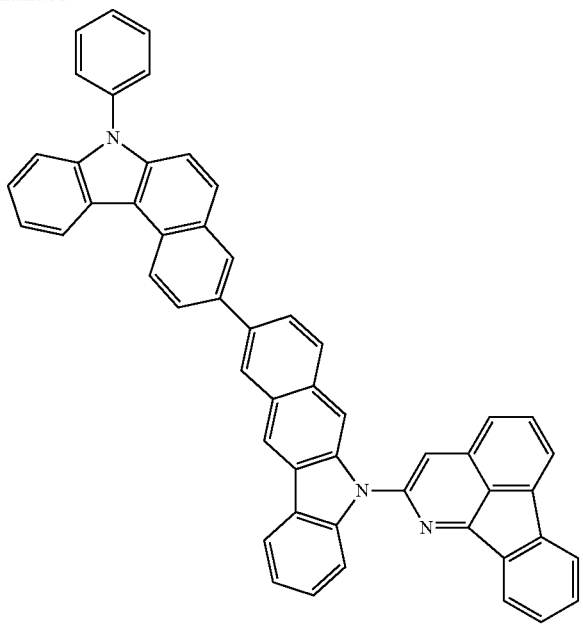
[Chem. 136]
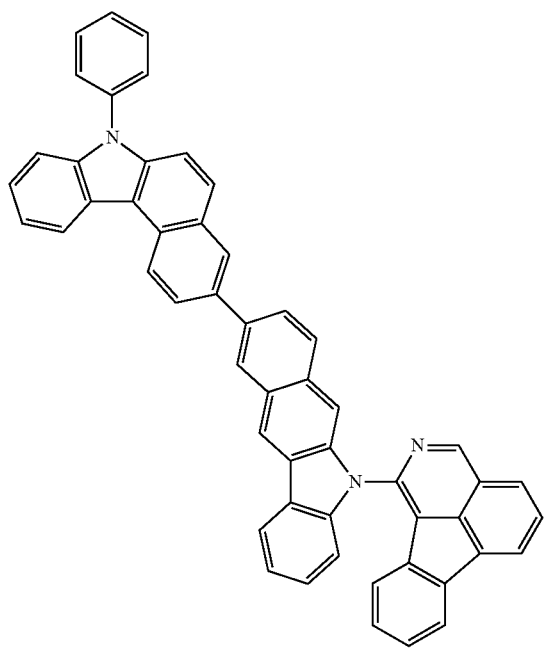

517 518
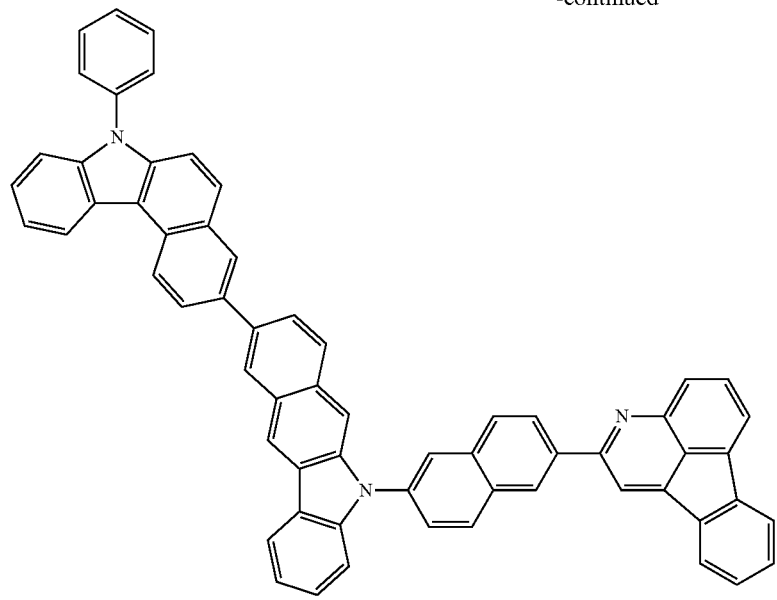
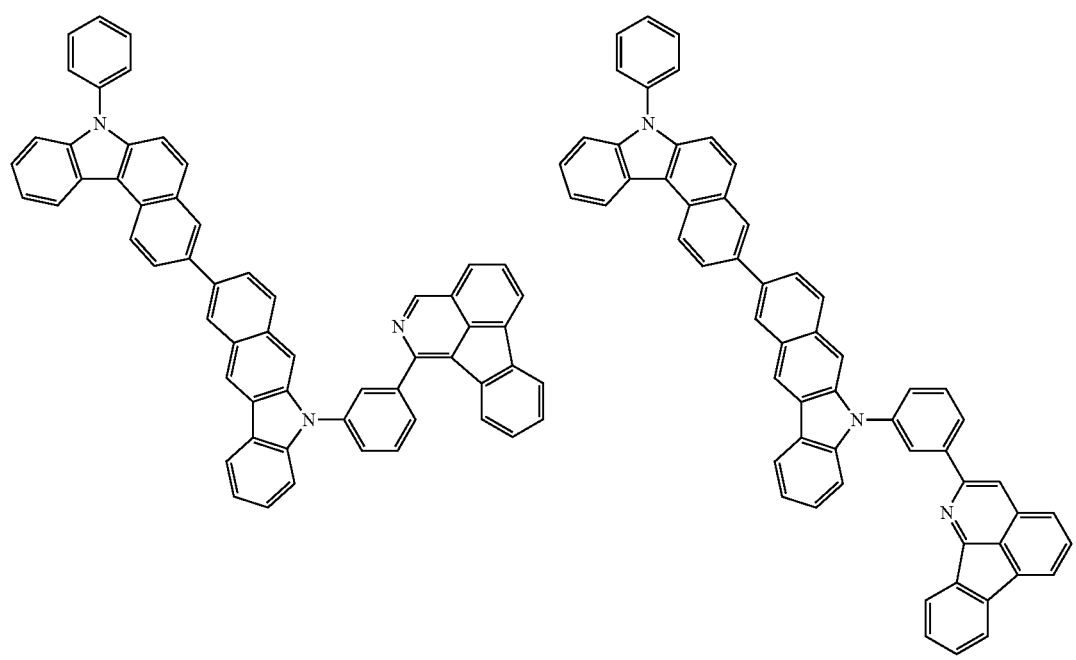

-continued
519
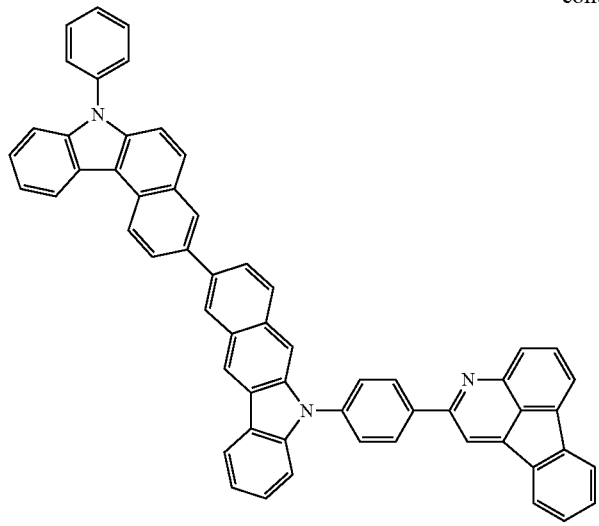
520
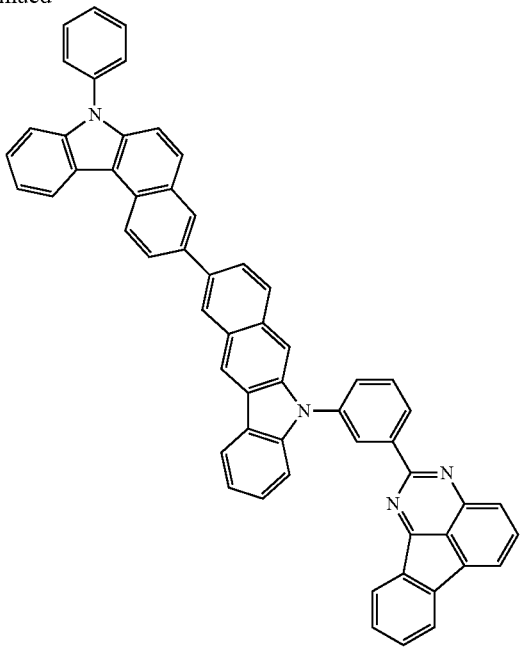
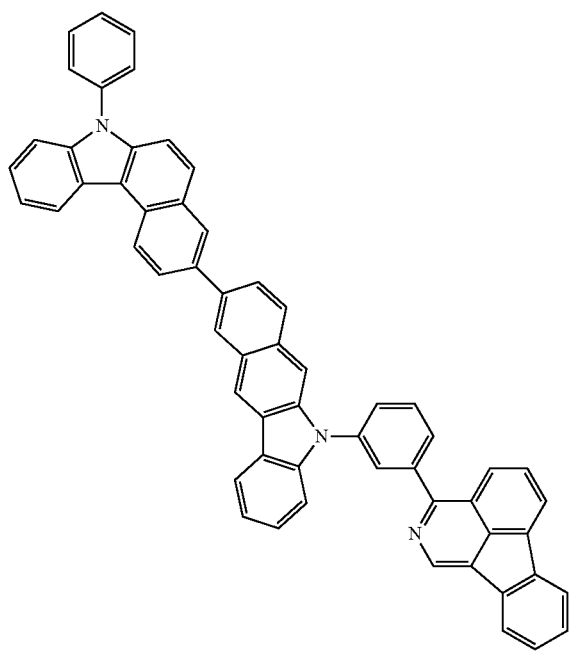

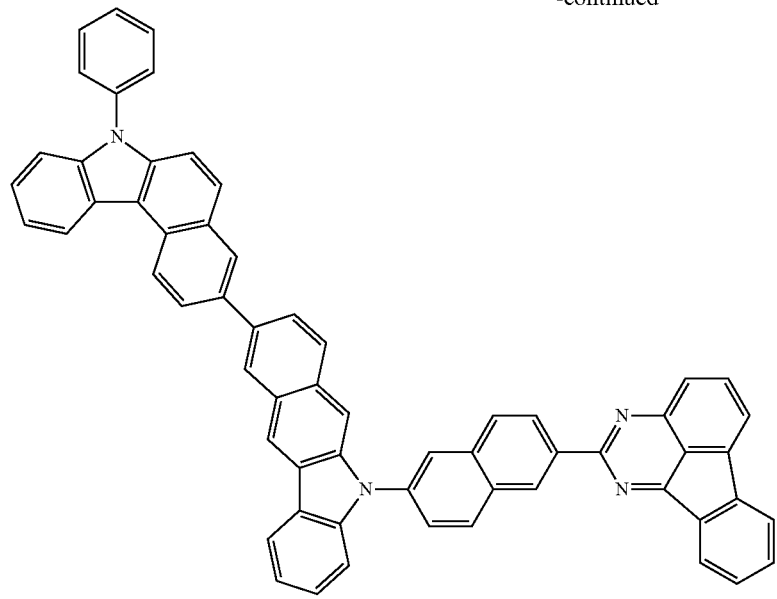
[Chem. 137]
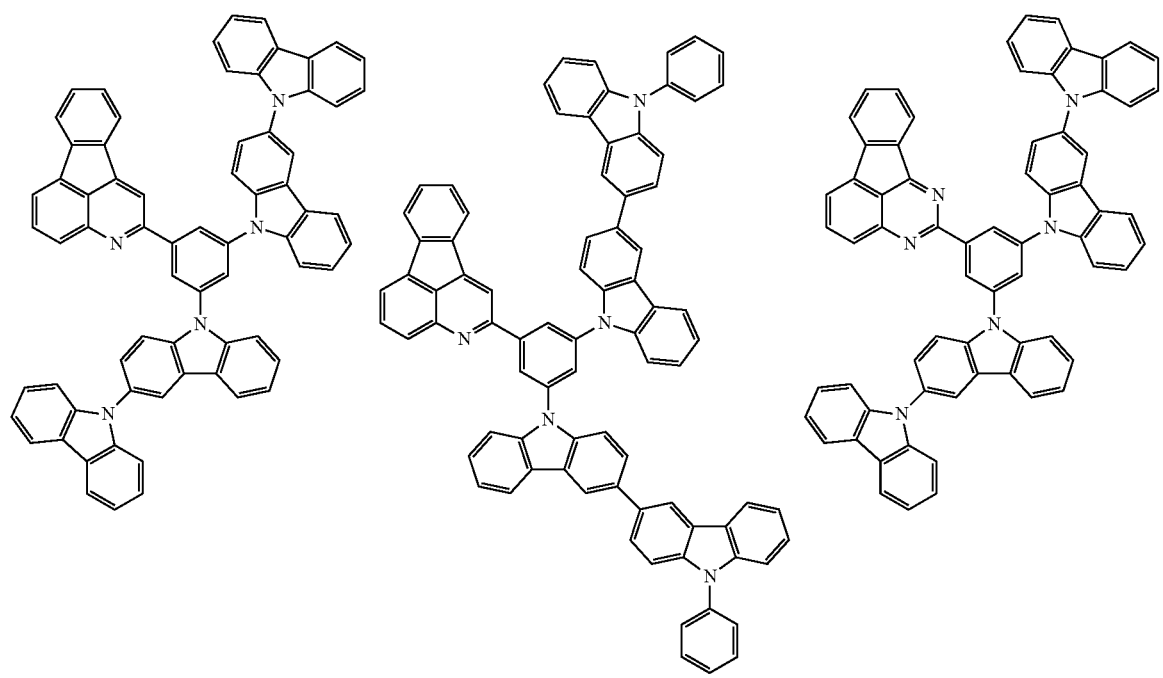

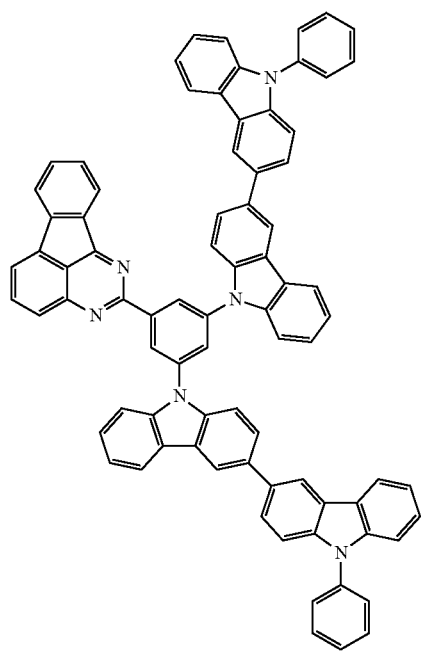
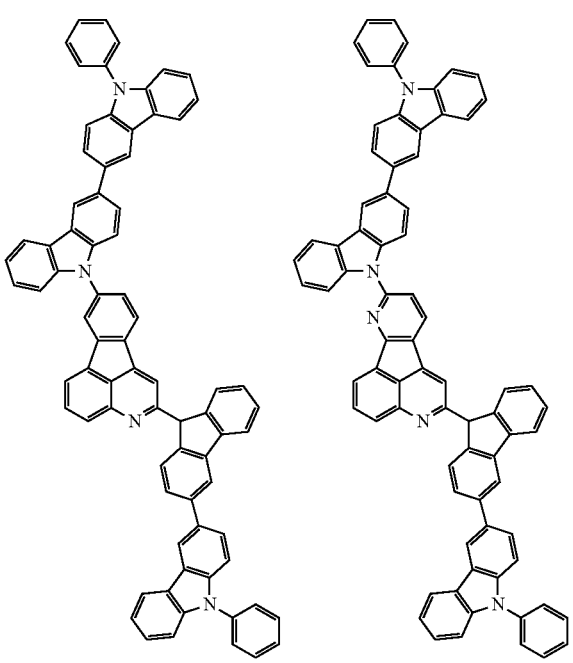

-continued

[Organic Electroluminescence Device (Organic EL Device)]

Next, an organic EL device of an aspect of the present invention is described.

The organic EL device of an aspect of the present invention is an organic electroluminescence device including a cathode, an anode and an organic thin-film layer formed of one layer or plural layers sandwiched between the cathode and the anode, wherein the organic thin-film layer contains a light emitting layer and at least one layer of the organic thin-film layer contains the above-described compound of the present invention [a compound represented by the above-described formula (1) and the above-described each compound of a subordinate concept included in the former, or a compound represented by the above-described formula (13) and the above-described each compound of a subordinate concept included in the former].

Examples of the organic thin-film layer containing the above-described compound of the present invention include, though not limited thereto, an anode-side organic thin-film layer (hole transporting layer, hole injection layer, etc.) to be arranged between an anode and a light emitting layer, a cathode-side organic thin-film layer (electron transporting layer, electron injection layer, etc.) to be arranged between a cathode and a light emitting layer, a space layer, a blocking layer, etc. The compound (1) may be contained in any of the above-described layers, and for example, the compound can be used as a host material or a dopant material in the light emitting layer of a fluorescent light emitting unit, a host material in the light emitting layer of a phosphorescent light emitting unit, a hole transporting layer material, an electron transporting layer material or the like in a light emitting unit, etc. In particular, it is preferable that the above-described compound of the present invention is contained in a light emitting layer, and in the case, the compound of the present invention can function as a host material.

In an aspect of the present invention, the organic EL device may be a fluorescent or phosphorescent light emission-type monochromatic light emitting device or may be a fluorescent/phosphorescent hybrid-type white light emitting device, or may also be a simple-type device having a single light emitting unit or a tandem-type device having plural light emitting units. Above all, the device is preferably a phosphorescent light emission-type one. Here, the "light emitting unit" is the smallest unit which includes one or more organic layers, where one of the layers is a light emitting layer, and which can emit light through the recombination of the injected holes and electrons.

Thus, a representative device structure of the simple-type organic EL device is the following device structure.

(1) Anode/light emitting unit/cathode

The light emitting unit may be a laminate having phosphorescent light emitting layers and fluorescent light emitting layers, and in this case, the light emitting unit may have spacer layers between the light emitting layers to prevent excitons produced in the phosphorescent light emitting layers from diffusing in the fluorescent light emitting layers. Representative layer structures of the light emitting unit are shown below.

(a) Hole transporting layer/light emitting layer (/electron transporting layer)

(b) Hole transporting layer/first phosphorescent light emitting layer/second phosphorescent light emitting layer (/electron transporting layer)

(c) Hole transporting layer/phosphorescent light emitting layer/spacer layer/fluorescent light emitting layer (/electron transporting layer)

(d) Hole transporting layer/first phosphorescent light emitting layer/second phosphorescent light emitting layer/spacer layer/fluorescent light emitting layer (/electron transporting layer)

(e) Hole transporting layer/first phosphorescent light emitting layer/spacer layer/second phosphorescent light emitting layer/spacer layer/fluorescent light emitting layer (/electron transporting layer)

(f) Hole transporting layer/phosphorescent light emitting layer/spacer layer/first fluorescent light emitting layer/second fluorescent light emitting layer (/electron transporting layer)

(g) Hole transporting layer/electron blocking layer/light emitting layer (/electron transporting layer)

(h) Hole transporting layer/light emitting layer/hole blocking layer (/electron transporting layer)

(i) Hole transporting layer/fluorescent light emitting layer/triplet blocking layer (/electron transporting layer)

The phosphorescent or fluorescent light emitting layers may emit light of colors which are different from each other. A specific layer structure is, in the laminated light emitting unit (d), hole transporting layer/first phosphorescent light emitting layer (which emits red light)/second phosphorescent light emitting layer (which emits green light)/spacer layer/fluorescent light emitting layer (which emits blue light)/electron transporting layer or the like.

An electron blocking layer may be suitably provided between a light emitting layer and the hole transporting layer or the spacer layer. Also, a hole blocking layer may be suitably provided between a light emitting layer and the electron transporting layer. When an electron blocking layer or a hole blocking layer is provided, it is possible to trap electrons or holes in the light emitting layer, increase the probability of charge recombination in the light emitting layer and extend the lifetime.

A representative device structure of the tandem-type organic EL device is the following device structure.

(2) Anode/first light emitting unit/intermediate layer/second light emitting unit/cathode As the first light emitting unit and the second light emitting unit, for example, light emitting units which are similar to the light emitting unit described above can be each independently selected.

The intermediate layer is also generally called an intermediate electrode, an intermediate conductive layer, a charge generating layer, an electron withdrawing layer, a connection layer or an intermediate insulating layer, and a known material composition which supplies electrons to the first light emitting unit and holes to the second light emitting unit can be used.

The rough structure of an example of the organic EL device is shown in 1 FIGURE. The organic EL device 1 has a substrate 2, an anode 3, a cathode 4 and a light emitting unit 10 provided between the anode 3 and the cathode 4. The light emitting unit 10 includes a light emitting layer 5 including at least one phosphorescent light emitting layer containing a phosphorescent host material and a phosphorescent dopant (phosphorescent materials). A hole injection/transporting layer (anode-side organic thin-film layer) 6 or the like may be formed between the light emitting layer 5 and the anode 3, and an electron injection/transporting layer (cathode-side organic thin-film layer) 7 or the like may be formed between the light emitting layer 5 and the cathode 4. Also, an electron blocking layer (not shown) may be provided on the anode 3 side of the light emitting layer 5, and a hole blocking layer (not shown) may be provided on the cathode 4 side of the light emitting layer 5. The electron blocking layer and the hole blocking layer can trap electrons and holes in the light emitting layer 5 and increase the probability of the exciton generation in the light emitting layer 5.

In the present invention, a host combined with a fluorescent dopant (fluorescent light emitting material) is called a fluorescent host, and a host combined with a phosphorescent dopant is called a phosphorescent host. The fluorescent host and the phosphorescent host are not distinguished from each other only by the molecular structures. That is, the phosphorescent host means a material constituting a phosphorescent light emitting layer containing a phosphorescent dopant, but it is not meant that the phosphorescent host cannot be used as a material constituting a fluorescent light emitting layer. The same applies to the fluorescent host.

(Substrate)

The substrate is used as a support of the light emitting device. As the substrate, for example, glass, quartz, a plastic and the like can be used. Also, a flexible substrate may be used. A flexible substrate is a substrate which can be folded (flexible) and is, for example, a plastic substrate of polycarbonate or polyvinyl chloride or the like.

(Anode)

For the anode formed on the substrate, a metal, an alloy and an electroconductive compound which have high work functions (specifically, 4.0 eV or more) as well as a mixture thereof and the like are preferably used. Specific examples include indium tin oxide (ITO), indium tin oxide containing silicon or silicon oxide, indium zinc oxide, tungsten oxide, indium oxide containing zinc oxide, graphene and the like. Moreover, gold (Au), platinum (Pt), a nitride of a metal material (for example, titanium nitride) and the like are also included.

(Cathode)

For the cathode, a metal, an alloy and an electroconductive compound which have low work functions (specifically, 3.8 eV or less) as well as a mixture thereof and the like are preferably used. Specific examples of such a cathode material include group 1 or group 2 elements of the periodic table of the elements, namely alkali metals such as lithium (Li) and cesium (Cs), alkaline earth metals such as magnesium (Mg), rare-earth metals such as alloys containing the metals (for example, MgAg and AlLi), alloys containing the metals and the like.

(Guest Material of Light emitting Layer)

The light emitting layer is a layer containing a highly luminescent substance, and various materials can be used. For example, as highly luminescent substances, fluorescent compounds which emit fluorescent light and phosphorescent compounds which emit phosphorescent light can be used. A fluorescent compound is a compound which can emit light from the singlet excitation state, and a phosphorescent compound is a compound which can emit light from the triplet excitation state.

As blue fluorescent light emitting materials which can be used for the light emitting layer, pyrene derivatives, styrylamine derivatives, chrysene derivatives, fluoranthene derivatives, fluorene derivatives, diamine derivatives, triarylamine derivatives and the like can be used. Specifically, N,N'-bis [4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA) and the like are used.

As green fluorescent light emitting materials which can be used for the light emitting layer, aromatic amine derivatives and the like can be used. Specifically, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA) and the like are used.

As red fluorescent light emitting materials which can be used for the light emitting layer, tetracene derivatives, diamine derivatives and the like can be used. Specifically, N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD) and the like are used.

As blue phosphorescent light emitting materials which can be used for the light emitting layer, ortho-metallized complexes with a metal atom selected from iridium (Ir), osmium (Os) and platinum (Pt), that is, metal complexes such as iridium complexes, osmium complexes and platinum complexes are used. Specifically, bis[2-(4',6'-difluorophenyl)pyridinato-N,C2'] iridium(III) tetrakis(1-pyrazolyl)borate (abbreviation: FIr$_6$), bis[2-(4',6'-difluorophenyl)pyridinato-N,C2'] iridium(III) picolinate (abbreviation: FIrpic), bis[2-(3',5'bistrifluoromethylphenyl)pyridinato-N,C2'] iridium(III) picolinate (abbreviation: Ir(CF$_3$ppy)$_2$(pic)), bis[2-(4',6'-difluorophenyl)pyridinato-N,C2'] iridium(III) acetylacetonate (abbreviation: FIracac) and the like are used.

As green phosphorescent light emitting materials which can be used for the light emitting layer, iridium complexes and the like are used. Tris(2-phenylpyridinato-N,C2') iridium(III) (abbreviation: Ir(ppy)$_3$), bis(2-phenylpyridinato-N,C2') iridium(III) acetylacetonate (abbreviation: Ir(ppy)$_2$(acac)), bis(1,2-diphenyl-1H-benzimidazolato) iridium(III) acetylacetonate (abbreviation: Ir(pbi)$_2$(acac)), bis(benzo[h]quinolinato) iridium(III) acetylacetonate (abbreviation: Ir(bzq)$_2$(acac)) and the like are used.

As red phosphorescent light emitting materials which can be used for the light emitting layer, metal complexes such as iridium complexes, platinum complexes, terbium complexes and europium complexes are used. Specifically, organometallic complexes such as bis[2-(2'-benzo[4,5-α]thienyl)pyridinato-N,C3'] iridium(III) acetylacetonate (abbreviation: Ir(btp)$_2$(acac)), bis(1-phenylisoquinolinato-N,C2') iridium(III) acetylacetonate (abbreviation: Ir(piq)$_2$(acac)), (acetylacetonato)bis[2,3-bis(4-fluorophenyl)quinoxalinato] iridium(III) (abbreviation: Ir(Fdpq)$_2$(acac)) and 2,3,7,8,12,13,17,18-octaethyl-21H,23H-porphyrin platinum(II) (abbreviation: PtOEP) are used.

Also, rare-earth metal complexes such as tris(acetylacetonato)(monophenanthroline) terbium(III) (abbreviation: Tb(acac)$_3$(Phen)), tris (1,3-diphenyl-1,3-propanedionato)(monophenanthroline) europium(III) (abbreviation: Eu(DBM)$_3$(Phen)) and tris[1-(2-thenoyl)-3,3,3-trifluoroacetonato](monophenanthroline) europium(III) (abbreviation: Eu(TTA)$_3$(Phen)) can be used as phosphorescent compounds because light is emitted from rare-earth metal ions (electron transition between different multiplicities).

The phosphorescent light emitting material of an ortho-metallized complex with a metal atom selected from iridium (Ir), osmium (Os) and platinum (Pt) are preferably complexes represented by the following formula (V), (X), (Y) or (Z).

[Chem. 138]

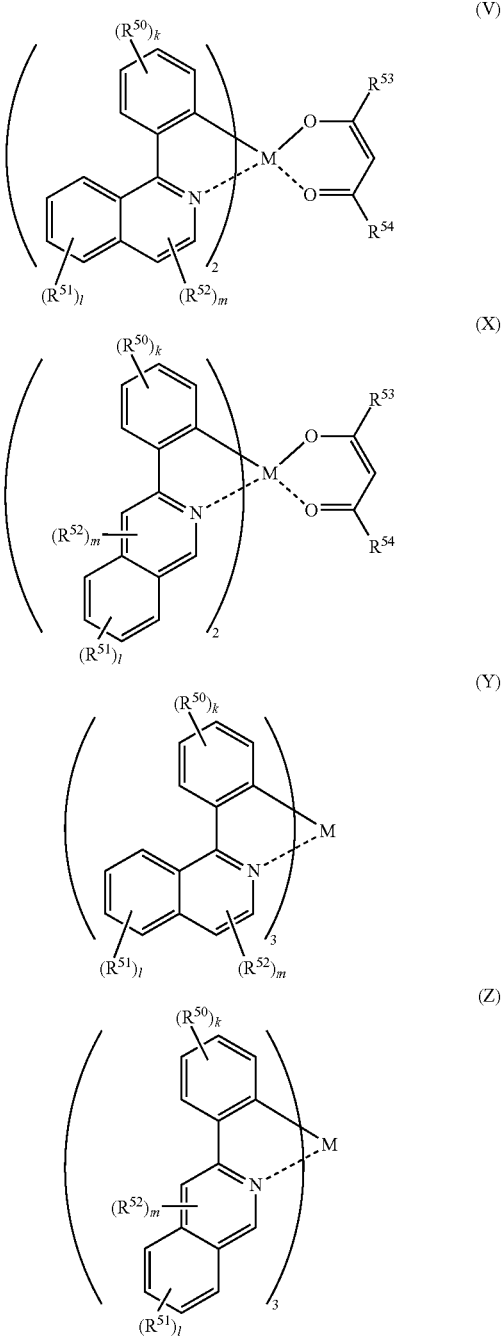

In the formula (V), (X), (Y) or (Z), $R^{50}$ to $R^{54}$ each represent a hydrogen atom or a substituent, k indicates an integer of 1 to 4, l indicates an integer of 1 to 4, m indicates an integer of 1 to 2. M is Ir, Os or Pt.

Examples of the substituent represented by $R^{50}$ to $R^{54}$ are the same ones as those described hereinabove for $R^1$ in the above-described formula (1).

Preferably, the formula (V) is represented by the following formula (V-1), and the formula (X) is preferably represented by the following formula (X-1) or (X-2). In the following formulae (V-1), (X-1) and (X-2), $R^{50}$, k and M are the same as the above-described $R^{50}$, k and M.

[Chem. 139]
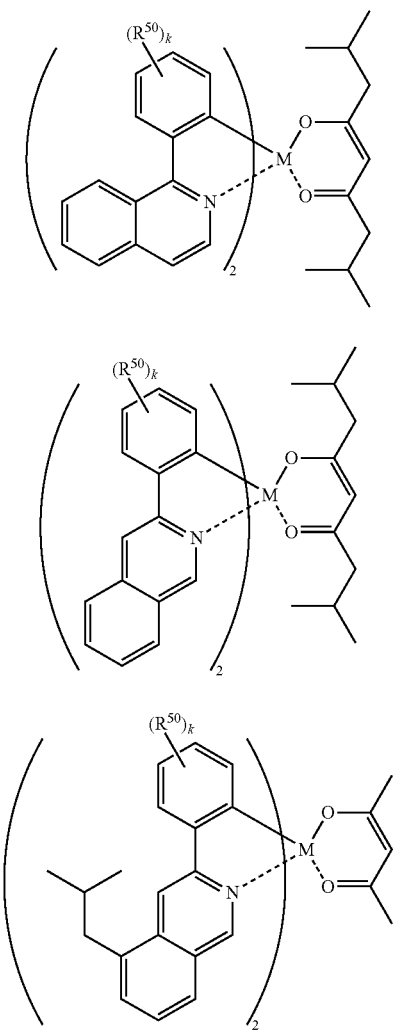
(V-1)
(X-1)
(X-2)
Preferred examples of the metal complexes are shown below, though not specifically limited thereto.
[Chem. 140]
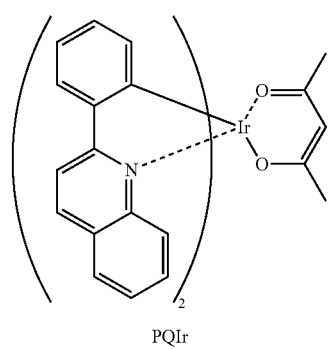
PQIr
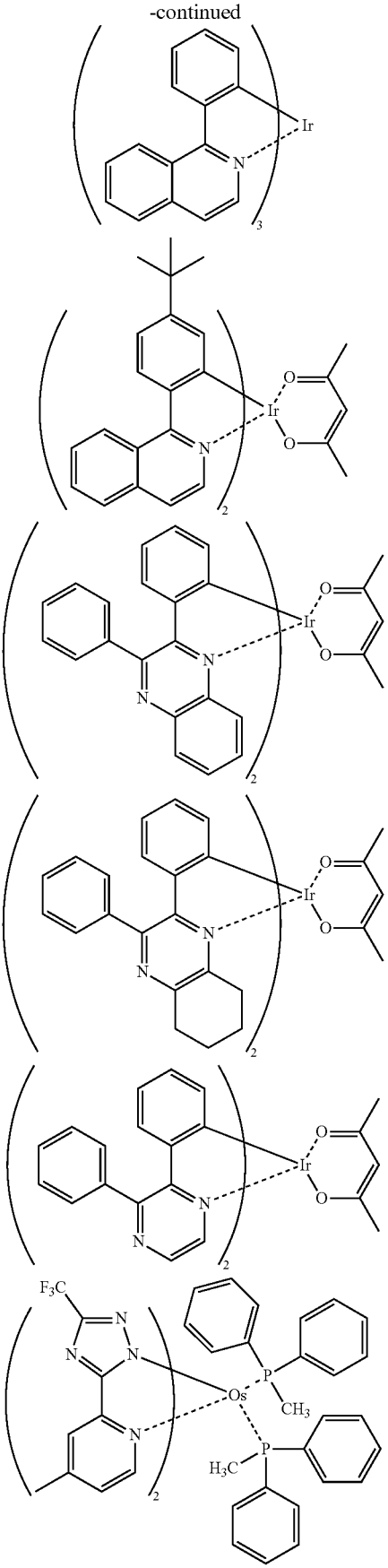

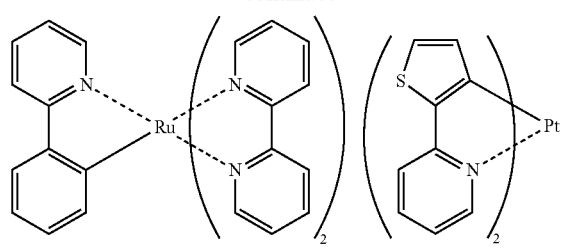
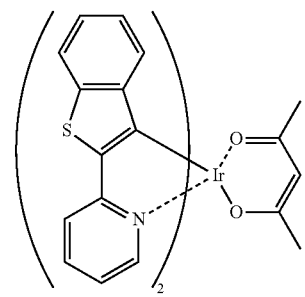
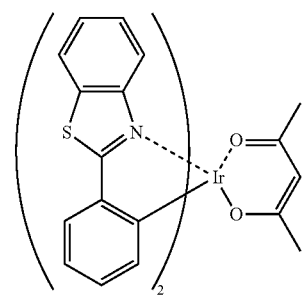
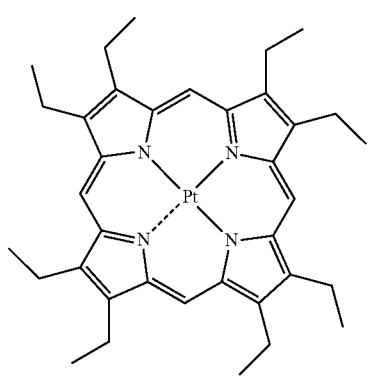
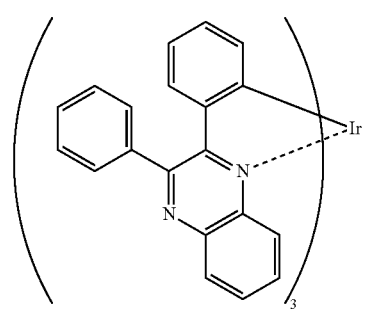
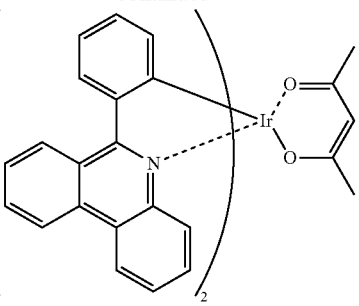
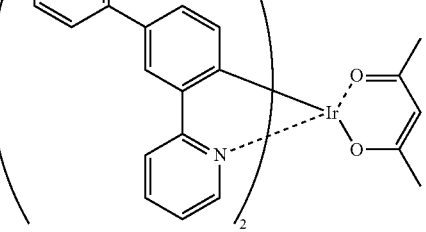
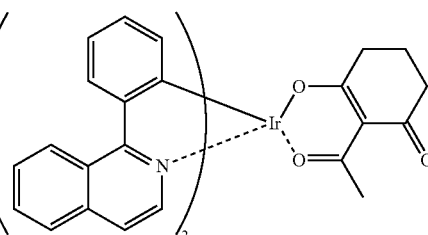
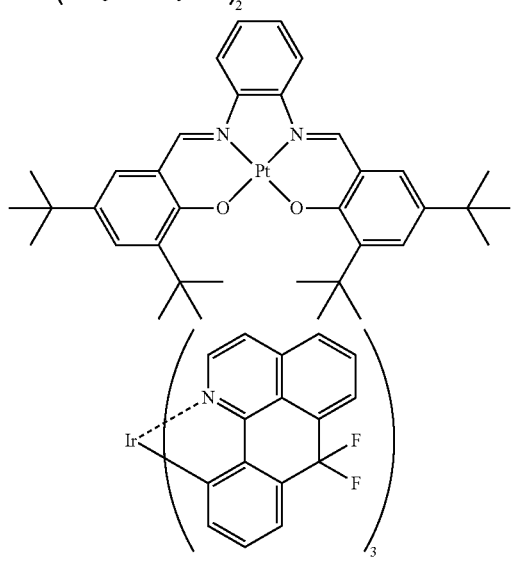
[Chem. 141]
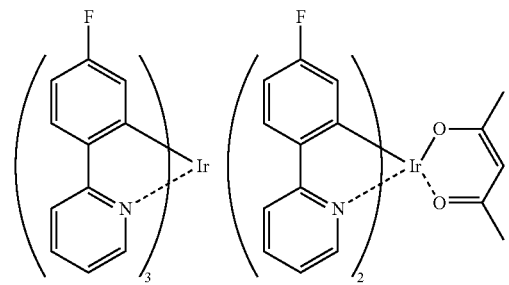

533
-continued
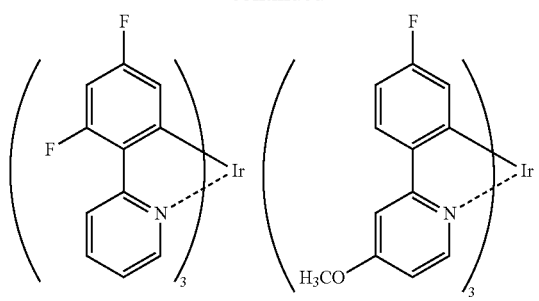
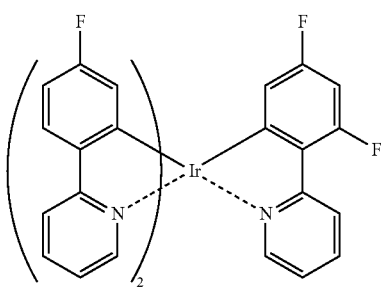
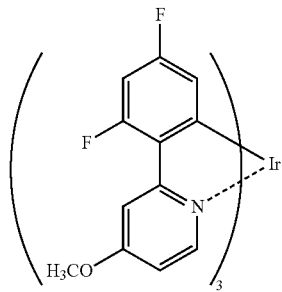
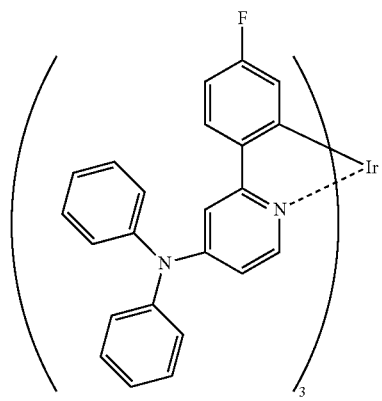
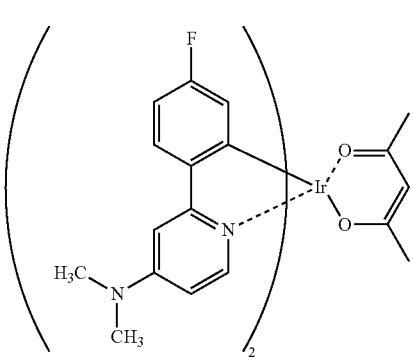
534
-continued
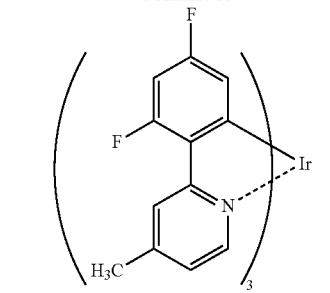
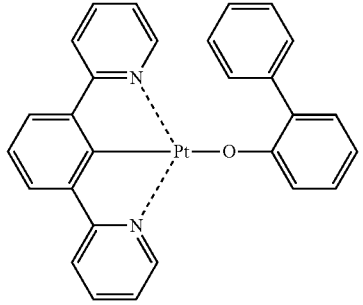
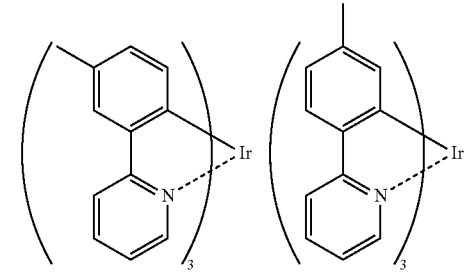
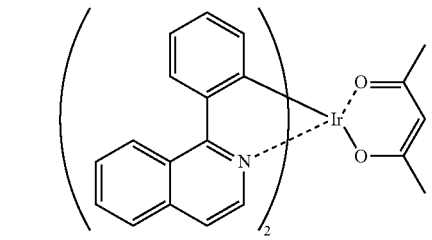
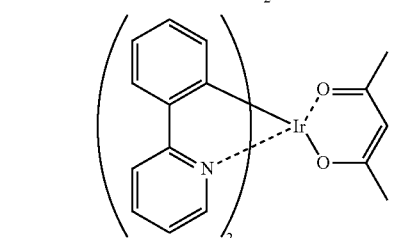
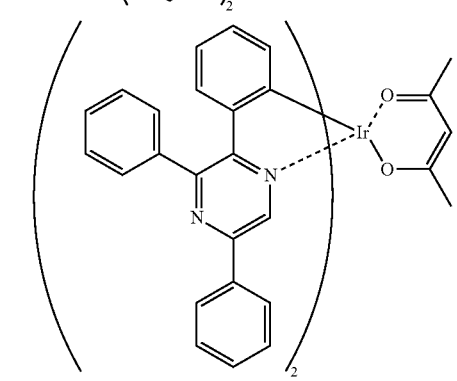

[Chem. 142]
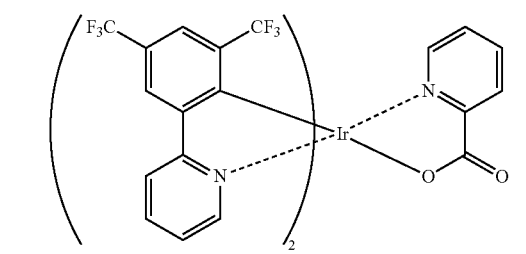
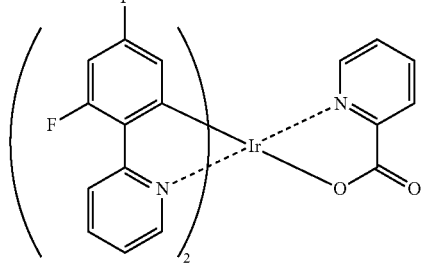
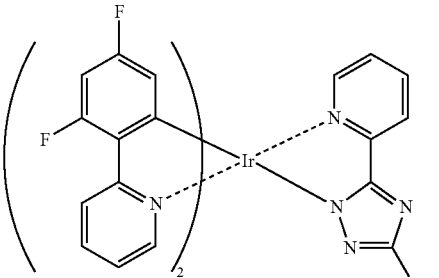
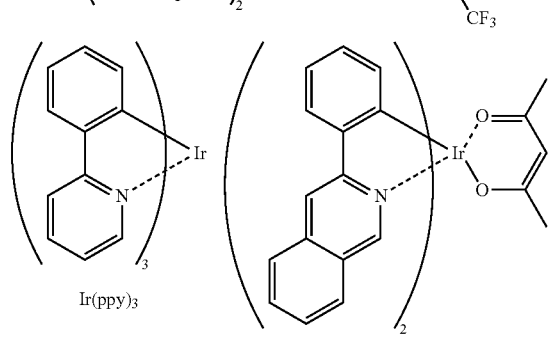
Ir(ppy)₃
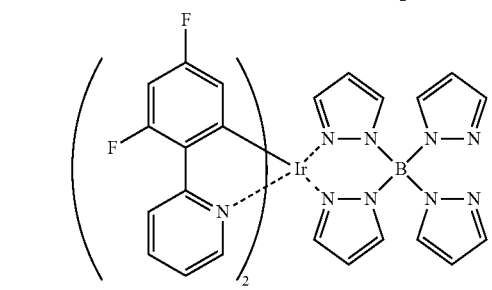
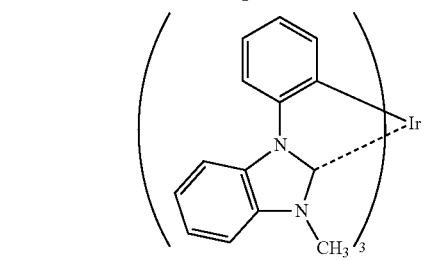
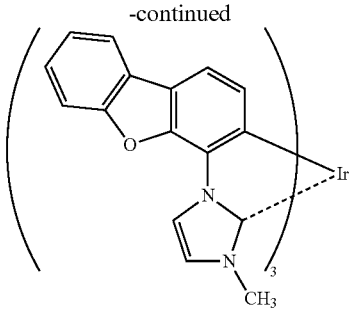
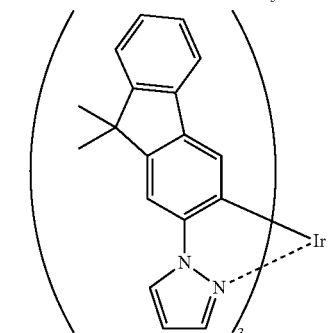
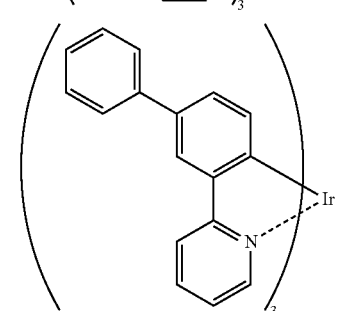
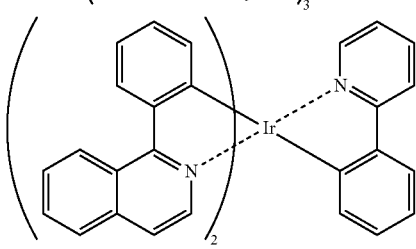
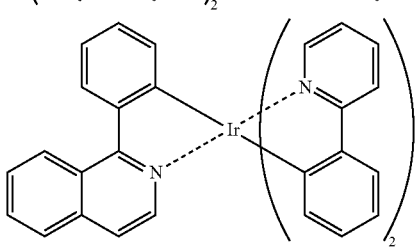
[Chem. 143]
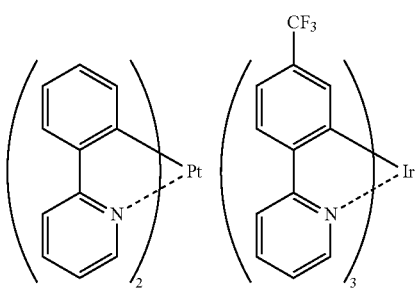

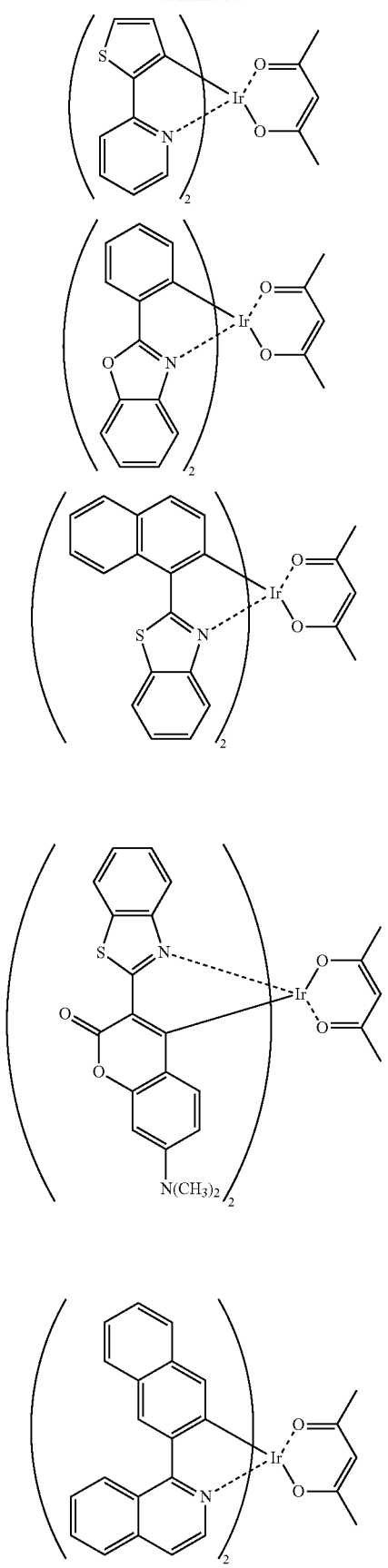

(Host Material of Light Emitting Layer)

The light emitting layer may have a composition in which any of the highly luminescent substances (guest materials) described above is dispersed in another substance (host material). Various substances can be used as the substance for dispersing a highly luminescent substance, and a substance which has a higher lowest unoccupied molecular orbital level (LUMO level) and a lower highest occupied molecular orbital level (HOMO level) than the highly luminescent substance is preferably used.

The substance for dispersing the highly luminescent substance (host material) is preferably the above-described compound of the present invention. In addition to the compound of the present invention, for example, 1) metal complexes such as aluminum complexes, beryllium complexes or zinc complexes, 2) heterocyclic compounds such as oxadiazole derivatives, benzimidazole derivatives or phenanthroline derivatives, 3) condensed aromatic compounds such as carbazole derivatives, anthracene derivatives, phenanthrene derivatives, pyrene derivatives or chrysene derivatives and 4) aromatic amine compounds such as triarylamine derivatives or condensed polycyclic aromatic amine derivatives can be used. More specifically, metal complexes such as tris(8-quinolinolato) aluminum(III) (abbreviation: Alq), tris(4-methyl-8-quinolinolato) aluminum(III) (abbreviation: Almq$_3$), bis(10-hydroxybenzo[h]quinolinato) beryllium(II) (abbreviation: BeBq$_2$), bis(2-methyl- 8-quinolinolato)(4-phenylphenolato) aluminum(III) (abbreviation: BAlq), bis(8-quinolinolato) zinc(II) (abbreviation: Znq), bis[2-(2-benzoxazolyl)phenolato] zinc(II) (abbreviation: ZnPBO) and bis[2-(2-benzothiazolyl)phenolato] zinc(II) (abbreviation: ZnBTZ), heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen) and bathocuproine (abbreviation: BCP), condensed aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB$_3$), 9,10-diphenylanthracene (abbreviation: DPAnth) and 6,12-dimethoxy-5,11-diphenylchrysene, aromatic amine compounds such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi and BSPB and the like can be used. Two or more kinds of the substance for dispersing the highly luminescent substance (guest material) (host material) can be used.

(Electron Transporting Layer)

The electron transporting layer is a layer containing a substance having high electron transporting performance. In the electron transporting layer, 1) metal complexes such as aluminum complexes, beryllium complexes, zinc complexes, etc., 2) heteroaromatic compounds such as imidazole derivatives, benzimidazole derivatives, azine derivatives, carbazole derivatives, phenanthroline derivatives, etc., 3) polymer compounds can be used.

(Electron Injection Layer)

The electron injection layer is a layer containing a substance having high electron injection performance. In the electron injection layer, alkali metals, alkaline earth metals or compounds thereof, such as lithium (Li), lithium fluoride (LiF), cesium fluoride (CsF), calcium fluoride (CaF$_2$), lithium oxide (LiOx) and the like can be used.

In the case where aluminum is used as the cathode, organic metal complexes such as 8-quinolinolato-lithium (abbreviation: Liq), Alq, tris(4-methyl-8-quinolinolato) aluminum (abbreviation; Almq$_3$), bis(10-hydroxybenzo[h]quinolinato)beryllium (abbreviation: BeBq$_2$), BAlq, Znq, ZnPBO, ZnBTZ and the like can also be used from the viewpoint of increasing the electron injecting performance.

(Hole Injection Layer)

The hole injection layer is a layer containing a substance having high hole injection performance. As the substance having high hole injection performance, molybdenum oxides, titanium oxides, vanadium oxides, rhenium oxides, ruthenium oxides, chromium oxides, zirconium oxides, hafnium oxides, tantalum oxides, silver oxides, tungsten oxides, manganese oxides, aromatic amine compounds, high-molecular compounds (oligomers, dendrimers, polymers, etc.) and the like are usable.

(Hole Transporting Layer)

The hole transporting layer is a layer containing a substance having high hole transporting performance. For the hole transporting layer, aromatic amine compounds, carbazole derivatives, anthracene derivatives and others can be used. Polymer compounds such as poly(N-vinylcarbazole) (abbreviation: PVK), poly(4-vinyltriphenylamine) (abbreviation: PVTPA) and others are also usable. However, any other substances than these, which realize higher performance of hole transportation than electron transportation, may also be used. The layer that contains a substance having high hole transporting performance is not limited to a single layer but, in addition thereto, may include a configuration of two or more layers formed of the above-described substance as laminated.

The hole transporting layer is positioned as a first charge transporting layer between an anode and a light emitting layer, and the first charge transporting layer may contain a compound represented by the formula (1) or the formula (13). Alternatively, the layer may be positioned as a second charge transporting layer between a cathode and a light emitting layer, and the second charge transporting layer may contain a compound represented by the formula (1) or the formula (13).

In an aspect of the present invention, each layer of the organic EL device can be formed according to a known vacuum evaporation method, spin coating method or the like. For example, the layers may be formed according to a known method of a vacuum evaporation method, a molecular beam epitaxy method (MBE method), or any other coating method using a solution of the compound to form the layer, such as a dipping method, a spin coating method, a casting method, a bar coating method, a roll coating method, etc.

The thickness of each organic layer of the organic EL device of an aspect of the present invention is not specifically limited but, in general, when the thickness is too small, there may often occur defects such as pin holes and the like, but on the contrary, when the thickness is too large, the device would require high voltage application and therefore the efficiency thereof would worsen. Therefore, in general, the thickness is preferably within a range of a few nm to 1 μm. As a method for forming a layer (especially a light emitting layer) that contains the compound of an aspect of the present invention, for example, there is mentioned a method of forming a film from a solution containing the compound and optionally other materials such as dopant, etc.

In the case where an organic EL device material containing a compound of the formula (13) is used as the organic EL device material of an aspect of the present invention, it is preferable that a solution containing the compound is used for film formation.

As a film formation method, any known coating method may be used effectively. For example, there are mentioned a spin coating method, a casting method, a microgravure coating method, a gravure coating method, a bar coating method, a roll coating method, a slit coating method, a wire bar coating method, a dip coating method, a spray coating method, a screen printing method, a flexographic printing method, an offset printing method, an inkjet coating method, a nozzle printing method, etc. For pattern formation, a screen printing method, a flexographic printing method, an offset printing method or an inkjet printing method is preferred. Film formation according to these methods may be carried out under the condition well known to those skilled in the art.

After film formation, the film may be dried in vacuum by heating (upper limit 250° C.) to remove the solvent, and polymerization reaction by light or by high-temperature heating at higher than 250° C. is unnecessary. Accordingly, it is possible to prevent the device performance from degrading by light or by high-temperature heating at higher than 250° C.

The solution for film formation may contain at least one kind of compound of an aspect of the present invention, and may optionally contain any other additives such as a hole transporting material, an electron transporting material, a light emitting material, an acceptor material, a solvent, a stabilizer, etc.

The solution for film formation may contain an additive for regulating viscosity and/or surface tension, for example, a thickener (high-molecular-weight compound, etc.), a viscosity depressant (low-molecular-weight compound, etc.), a surfactant, etc. In addition, for improving storage stability, the solution may contain an antioxidant not having any negative influence on the performance of organic EL devices, such as a phenolic antioxidant, a phosphorus-containing antioxidant, etc.

The content of the compound of an aspect of the present invention in the above-described solution for film formation is preferably 0.1 to 15% by mass relative to the total amount of the solution for film formation, more preferably 0.5 to 10% by mass.

The high-molecular-weight compound that can be used as a thickener includes insulating resins such as polystyrene, polycarbonate, polyarylate, polyester, polyamide, polyurethane, polysulfone, polymethyl methacrylate, polymethyl acrylate, cellulose, etc., and copolymers thereof, photoconductive resins such as poly-N-vinylcarbazole, polysilane, etc., and electroconductive resins such as polythiophene, polypyrrole, etc.

Examples of the solvent for the solution for film formation include chlorine-containing solvents such as chloroform, methylene chloride, 1,2-dichloroethane, 1,1,2-trichloroethane, chlorobenzene, o-dichlorobenzene, etc.; ether solvents such as tetrahydrofuran, dioxane, dioxolan, anisole, etc.; aromatic hydrocarbon solvents such as toluene, xylene, etc.; aliphatic hydrocarbon solvents such as cyclohexane, methylcyclohexane, n-pentane, n-hexane, n-heptane, n-octane, n-nonane, n-decane, etc.; ketone solvents such as acetone, methyl ethyl ketone, cyclohexanone, benzophenone, acetophenone, etc.; ester solvents such as ethyl acetate, butyl acetate, ethyl cellosolve acetate, methyl benzoate, phenyl acetate, etc.; polyalcohols and their derivatives such as ethylene glycol, ethylene glycol monobutyl ether, ethylene glycol monoethyl ether, ethylene glycol monomethyl ether, dimethoxyethane, propylene glycol, diethoxymethane, triethylene glycol monomethyl ether, glycerin, 1,2-hexanediol, etc.; alcohol solvents such as methanol, ethanol, propanol, isopropanol, cyclohexanol, etc.; sulfoxide solvents such as dimethyl sulfoxide, etc.; amide solvents such as N-methyl-2-pyrrolidone, N,N-dimethylformamide, etc. One alone or two or more kinds of these solvents may be used either singly or as combined.

Among these solvents, from the viewpoint of solubility, uniformity in film formation and viscosity characteristics, aromatic hydrocarbon solvents, ether solvents, aliphatic hydrocarbon solvents, ester solvents and ketone solvents are preferred, and toluene, xylene, ethylbenzene, diethylbenzene, trimethylbenzene, n-propylbenzene, isopropylbenzene, n-butylbenzene, isobutylbenzene, 5-butylbenzene, n-hexylbenzene, cyclohexylbenzene, 1-methylnaphthalene, tetralin, 1,3-dioxane, 1,4-dioxane, 1,3-dioxolan, anisole, ethoxybenzene, cyclohexane, bicyclohexyl, cyclohexenylcyclohexanone, n-heptylcyclohexane, n-hexylcyclohexane, decalin, methyl benzoate, cyclohexanone, 2-propylcyclohexanone, 2-heptanone, 3-heptanone, 4-heptanone, 2-octanone, 2-nonanone, 2-decanone, dicyclohexyl ketone, acetophenone and benzophenone are more preferred.

The organic electroluminescence device of an aspect of the present invention can be used for electronic equipments such as display parts including an organic EL panel module and the like; display devices of a television, a mobile phone, a personal computer and the like; and light emitting devices including a light, a vehicle light and the like.

EXAMPLES

Next, the present invention is explained more concretely by Examples, but the present invention is not limited thereto at all.

For synthesis of the compound of an aspect of the present invention, first, intermediates (A) and (B) were synthesized. The synthesis methods for the intermediates (A) and (B) are as follows.

<Synthesis of Intermediate (A)>
[Synthesis of Intermediate (1)]

In an argon atmosphere, 9.5 g of 4-bromoquinoline, 9.2 g of 2-bromophenylboronic acid, 1.0 g of tetrakis(triphenyl phosphine)palladium, 50 mL of an aqueous 2 mol sodium carbonate solution and 200 mL of DME were put into a flask, and heated under reflux with stirring for 4 hours.

After cooled to room temperature, the reaction solution was extracted with ethyl acetate. The resultant organic layer was concentrated to give 15.4 g of an intermediate (1). The intermediate (1) was subjected to the next reaction without being purified.

As a result of mass spectrometry, m/e=283 relative to the molecular weight 283 of the intermediate (1).

[Chem. 144]

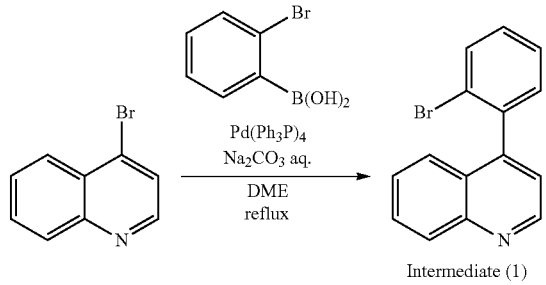

Intermediate (1)

[Synthesis of Intermediate (2)]

In an argon atmosphere, 15.4 g of the intermediate (1), 3.2 g of bis(triphenyl phosphine)palladium(II) dichloride, 9.8 mL of diazabicycloundecene and 230 mL of DMF were put into a flask, and heated with stirring at 150° C. for 60 hours. After cooled to room temperature, the reaction solution was extracted with ethyl acetate and toluene. The resultant organic layer was dried and concentrated, and the resultant residue was purified through column chromatography to give 9.2 g of an intermediate (2). Yield 99% (2 steps).

As a result of mass spectrometry, m/e=203 relative to the molecular weight 203 of the intermediate (2).

[Chem. 145]

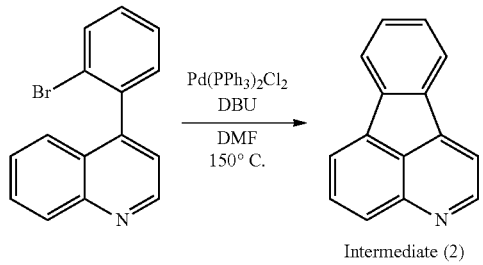

Intermediate (2)

[Synthesis of Intermediate (A)] 1.0 g of the intermediate (2), 3.26 g of metachloroperbenzoic acid (mCPBA), and 50 mL of dichloromethane were put into a flask at 0° C., and stirred at room temperature for 30 hours. The reaction solution was extracted with dichloromethane, and the resultant organic layer was dried and concentrated to give a brown oily N-oxide form. 5.0 mL of phosphorus oxychloride was added to 1.55 g of the N-oxide, and heated with stirring at 130° C. for 3 hours. The reaction solution was extracted with dichloromethane, the organic layer was dried and concentrated, and the resultant residue was purified through column chromatography to give 767 mg of an intermediate (A). Yield 66% (2 steps).

As a result of mass spectrometry, m/e=237 relative to the molecular weight 237 of the intermediate (A).

[Chem. 146]

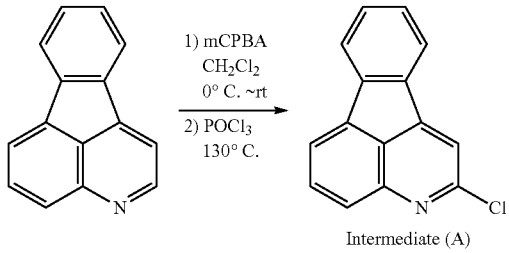

Intermediate (A)

<Synthesis of Intermediate (B)>
[Synthesis of Intermediate (3)]

In an argon atmosphere, 258 g of acenaphthene and 3.5 L of acetic acid were put into a flask at room temperature, and at 40° C., 498 g of sodium dichromate dehydrate was, as divided into three portions, added thereto. The reaction liquid was stirred at the same temperature for 1 hour, and after left cooled, 20 L of water with ice was poured into the reaction liquid, and the resultant precipitate was taken out through filtration. The precipitated crystal was dissolved in a mixed solvent of chloroform and heptane while hot, and purified through silica gel chromatography to give 55.1 g of an intermediate (3). Yield 19%.

As a result of mass spectrometry, m/e=168 relative to the molecular weight 168 of the intermediate (3).

[Chem. 147]

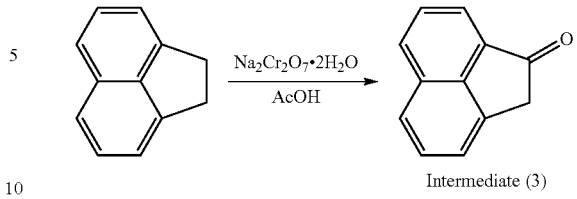

Intermediate (3)

[Synthesis of Intermediate (4)]

In an argon atmosphere, 52.1 g of the intermediate (3), 5.28 g of copper(II) chloride dehydrate, 900 mL of 1-butanol and 34.1 g of propargylamine were put into a flask, and heated with stirring at 112° C. for 29 hours. At 105° C., 0.25 g of copper(II) chloride dehydrate was added and again stirred at 112° C. for 18 hours, and further, 0.25 g of copper(II) chloride dehydrate was added at 105° C., and stirred at 112° C. for 18 hours. After left cooled to room temperature, the reaction solution was filtered under normal pressure, and the mother liquid was concentrated to dryness. The resultant crude product was dissolved under heat in toluene and chloroform, and purified through column chromatography to give 18.3 g of an intermediate (4). Yield 29%.

As a result of mass spectrometry, m/e=203 relative to the molecular weight 203 of the intermediate (4).

[Chem. 148]

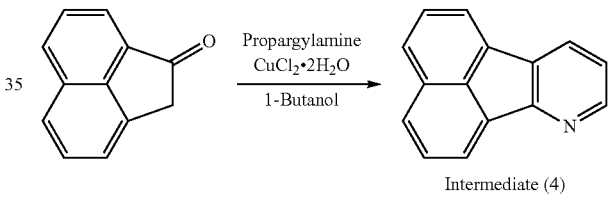

Intermediate (4)

[Synthesis of Intermediate (5)]

In an argon atmosphere, 18.3 g of the intermediate (4), and 360 mL of chloroform were put into a flask, and at 5° C. or lower, 53.9 g of 72 mass % mCPBA was gradually added thereto. While heated up to room temperature, the reaction solution was stirred overnight, and then the reaction liquid was poured into 400 mL of saturated sodium bicarbonate water cooled with ice, and stirred for 30 minutes. The organic layer was washed with saturated sodium bicarbonate water, water and saturated saline water, then dewatered with anhydrous sodium sulfate, and concentrated and recrystallized to give an intermediate (5). As it was, the intermediate (5) was directly subjected to the next reaction.

[Chem. 149]

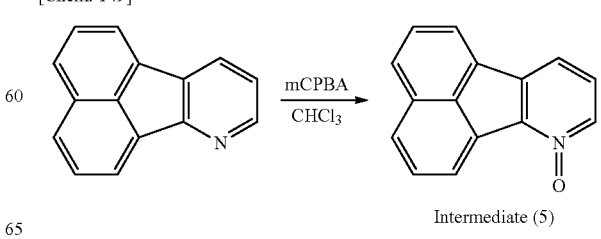

Intermediate (5)

[Synthesis of Intermediate (B)]

In an argon atmosphere, 12.5 g of the intermediate (5), and 130 mL of phosphoryl chloride were put into a flask, and stirred at 100° C. for 4 hours. The reaction liquid was concentrated, the residue was dissolved in 200 mL of chloroform, and then the reaction liquid was poured into 1.5 L of saturated sodium bicarbonate water cooled with ice, and stirred for 1 hour. The organic layer was washed with water and saturated saline water, and concentrated to dryness to give a crude product. The crude product was dissolved in chloroform, and purified through silica gel chromatography to give 4.0 g of an intermediate (B). Yield 19% (2 steps).

As a result of mass spectrometry, m/e=237 relative to the molecular weight 237 of the intermediate (B).

[Chem. 150]

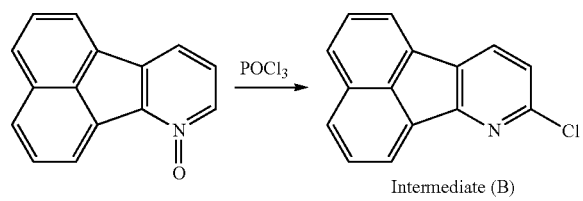

Intermediate (B)

Synthesis Examples

[Synthesis of Compound 1]

In an argon atmosphere, 344 mg of the following starting compound (1), 200 mg of the intermediate (A), 15 mg of tris(dibenzylideneacetone)dipalladium(0), 19 mg of tri-t-butylphosphonium tetrafluoroborate, 113 mg of sodium t-butoxide and 4 mL of toluene were put into a flask, and heated under reflux for 5 hours. After cooled to room temperature, the reaction solution was extracted with toluene, and the organic layer was dried and concentrated. The resultant residue was purified through column chromatography to give a compound 1 (294 mg, yield 37%).

As a result of mass spectrometry, m/e=609 relative to the molecular weight 609 of the compound 1.

[Chem. 151]

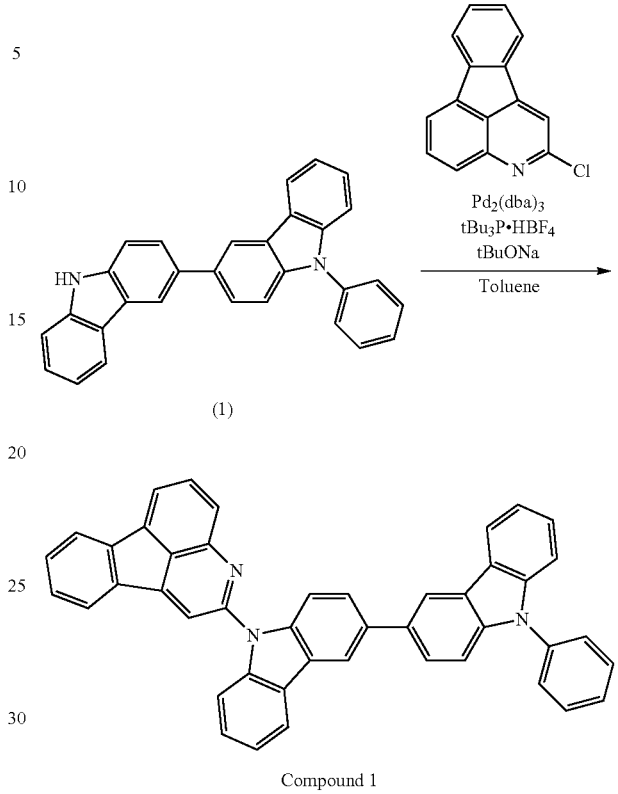

Compound 1

[Synthesis of Compound 2]

A compound 2 was synthesized according to the same method except for using the following starting compound (2) that had been synthesized in a known method in place of the starting compound (1) in synthesis of the compound 1.

As a result of mass spectrometry, m/e=685 relative to the molecular weight 685 of the compound 2.

[Chem. 152]

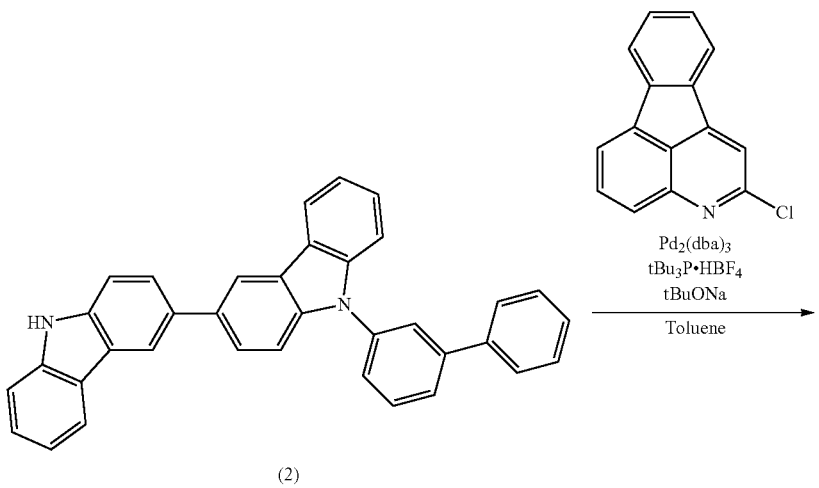

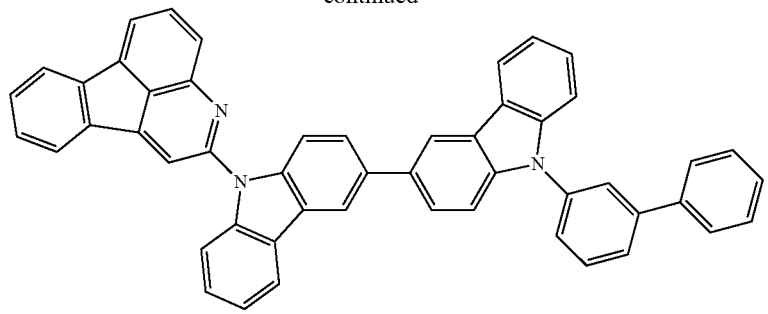
Compound 2
[Synthesis of Compound 3]
A compound 3 was synthesized according to the same method except for using the following starting compound (3) that had been synthesized in a known method in place of the starting compound (1) in synthesis of the compound 1.
As a result of mass spectrometry, m/e=685 relative to the molecular weight 685 of the compound 3.
[Chem. 153]
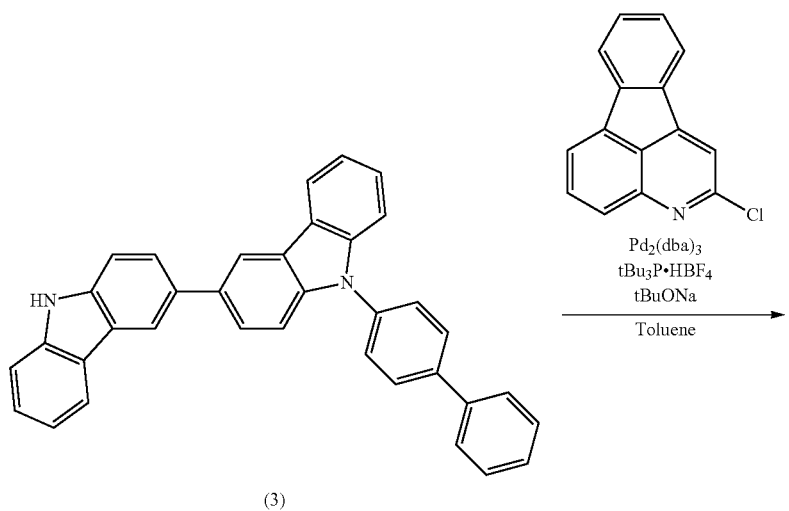
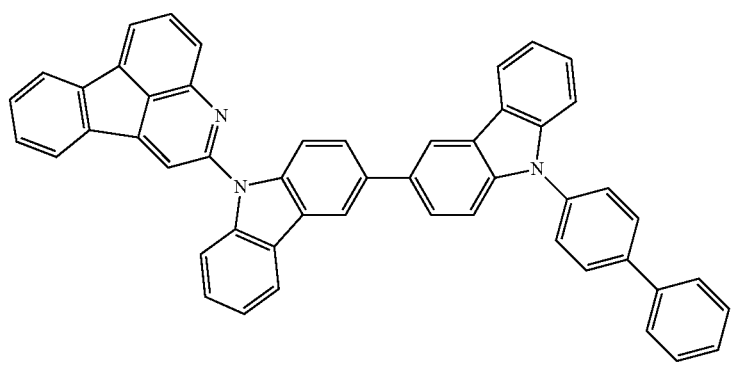
Compound 3

[Synthesis of Compound 4]

A compound 4 was synthesized according to the same method except for using the following starting compound (4) that had been synthesized in a known method in place of the starting compound (1) in synthesis of the compound 1.

As a result of mass spectrometry, m/e=685 relative to the molecular weight 685 of the compound 4.

[Chem. 154]

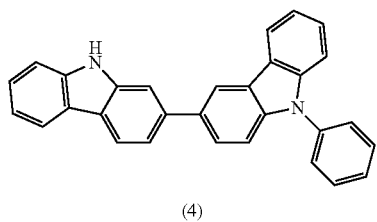

(4)

[Chem. 155]

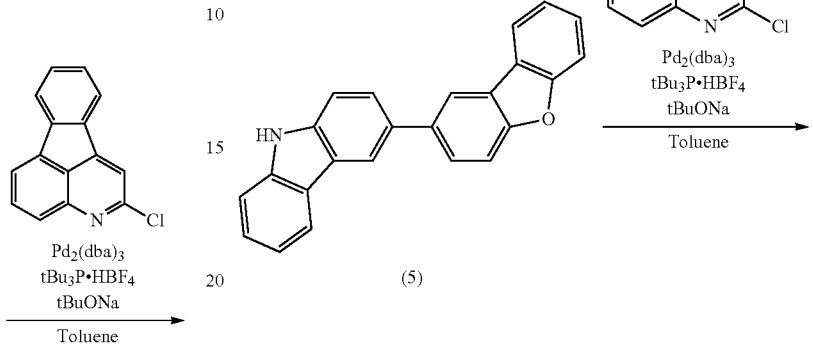

(5)

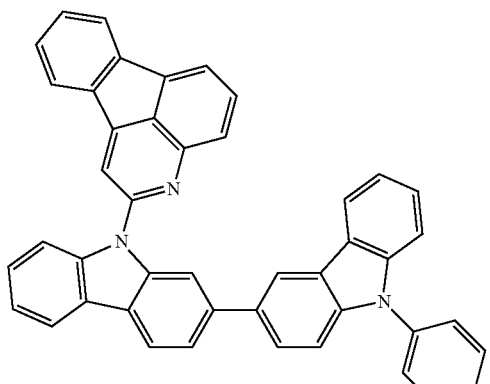

Compound 4

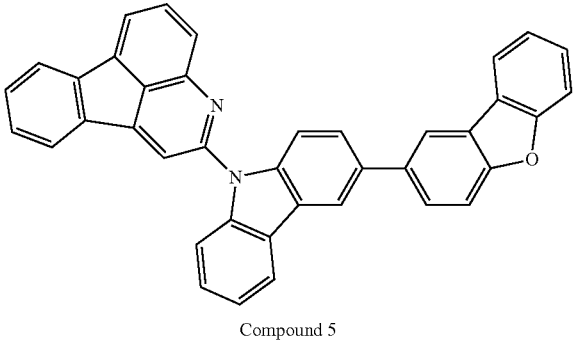

Compound 5

[Synthesis of Compound 5]

A compound 5 was synthesized according to the same method except for using the following starting compound (5) that had been synthesized in a known method in place of the starting compound (1) in synthesis of the compound 1.

As a result of mass spectrometry, m/e=534 relative to the molecular weight 534 of the compound 5.

[Synthesis of Compound 6]

A compound 6 was synthesized according to the same method except for using the following starting compound (6) that had been synthesized in a known method in place of the starting compound (1) in synthesis of the compound 1.

As a result of mass spectrometry, m/e=659 relative to the molecular weight 659 of the compound 6.

[Chem. 156]

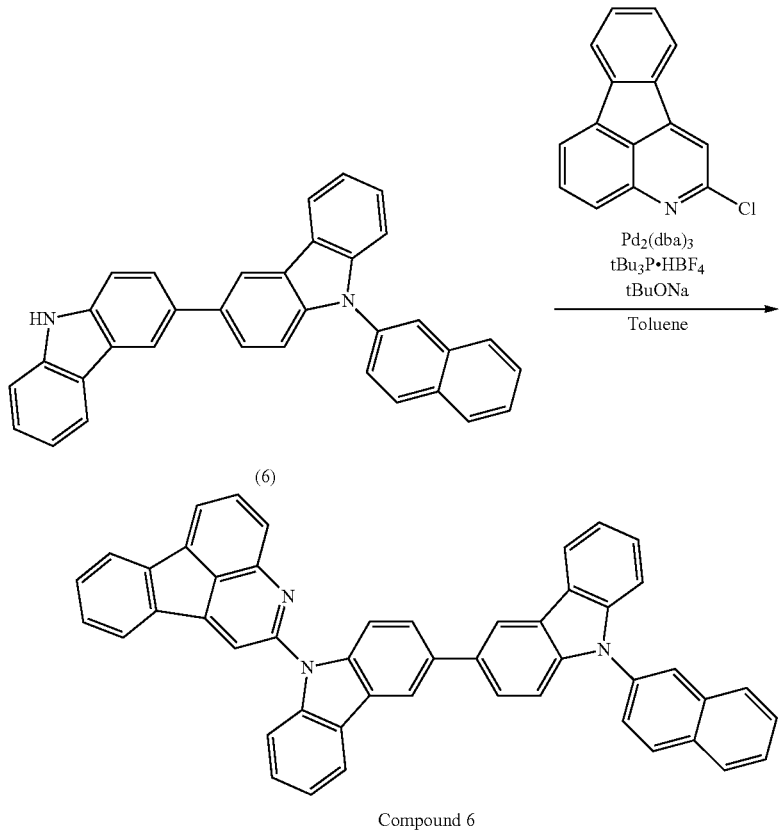

Compound 6

[Synthesis of Compound 7]

A compound 7 was synthesized according to the same method except for using the following starting compound (7) that had been synthesized in a known method in place of the starting compound (1) in synthesis of the compound 1.

As a result of mass spectrometry, m/e=659 relative to the molecular weight 659 of the compound 7.

[Chem. 157]

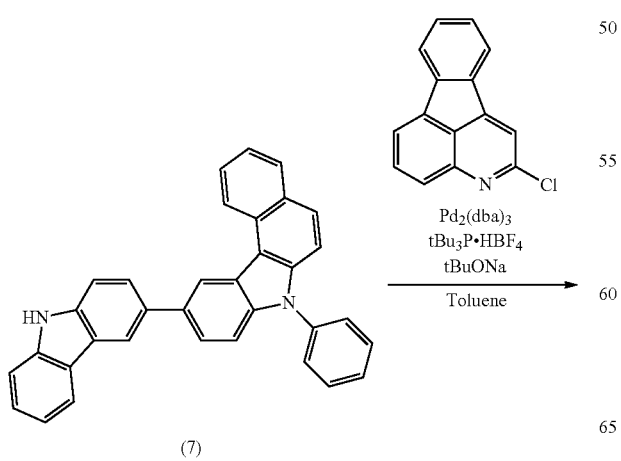

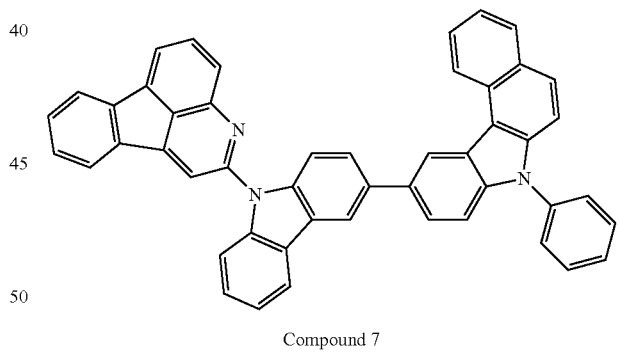

Compound 7

[Synthesis of Compound 8]

A compound 8 was synthesized according to the same method except for using the following starting compound (8) that had been synthesized in a known method in place of the starting compound (1) in synthesis of the compound 1.

As a result of mass spectrometry, m/e=659 relative to the molecular weight 659 of the compound 8.

[Chem. 158]

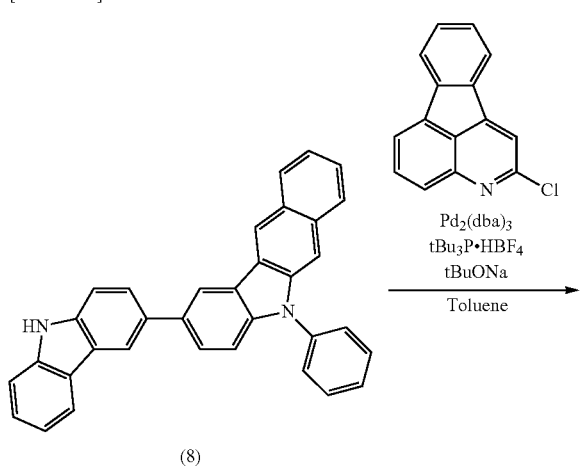

(8)

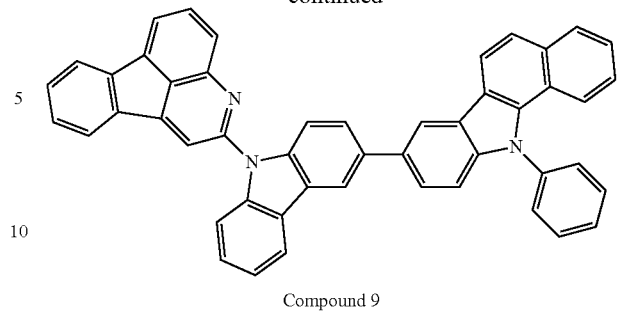

Compound 9

[Synthesis of Compound 10]

A compound 10 was synthesized according to the same method except for using the following starting compound (10) that had been synthesized in a known method in place of the starting compound (1) in synthesis of the compound 1.

As a result of mass spectrometry, m/e=659 relative to the molecular weight 659 of the compound 10.

[Chem. 160]

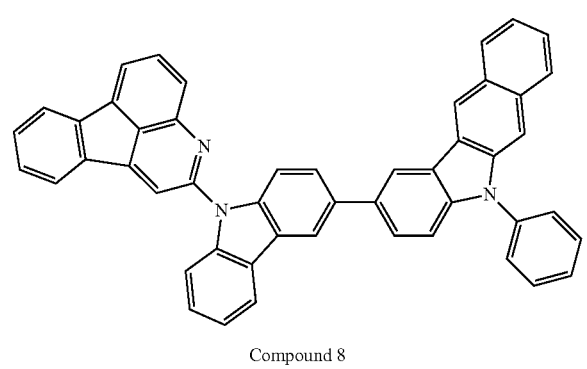

Compound 8

[Synthesis of Compound 9]

A compound 9 was synthesized according to the same method except for using the following starting compound (9) that had been synthesized in a known method in place of the starting compound (1) in synthesis of the compound 1.

As a result of mass spectrometry, m/e=659 relative to the molecular weight 659 of the compound 9.

[Chem. 159]

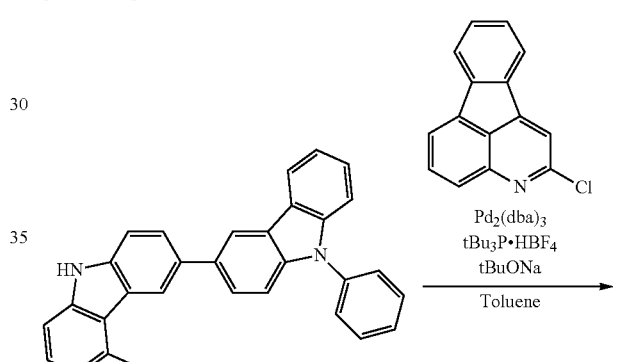

(10)

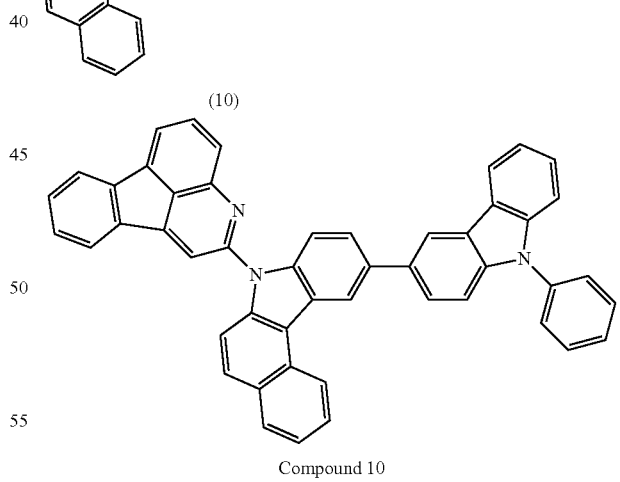

Compound 10

[Synthesis of Compound 11]

A compound 11 was synthesized according to the same method except for using the following starting compound (11) that had been synthesized in a known method in place of the starting compound (1) in synthesis of the compound 1.

As a result of mass spectrometry, m/e=659 relative to the molecular weight 659 of the compound 11.

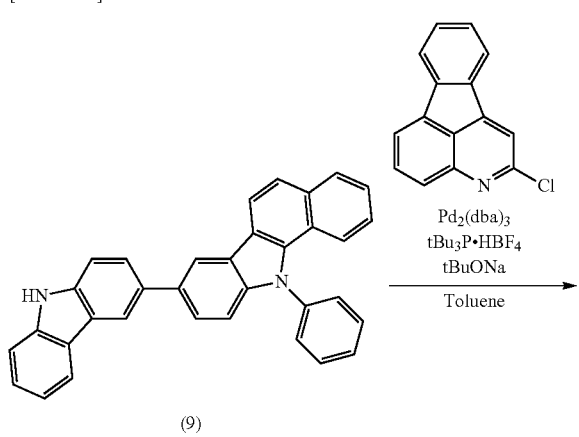

(9)

[Chem. 161]
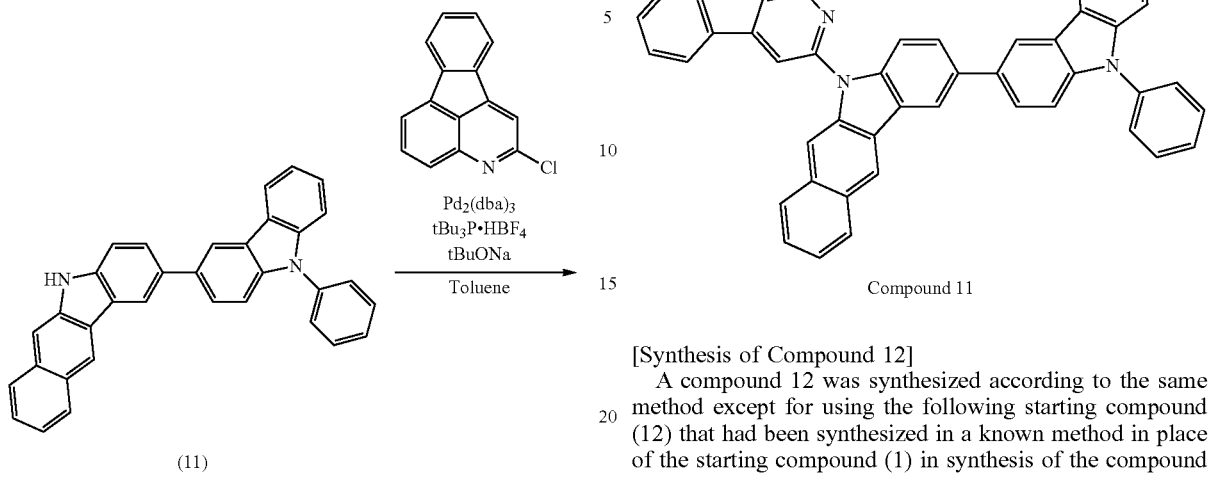
[Synthesis of Compound 12]
A compound 12 was synthesized according to the same method except for using the following starting compound (12) that had been synthesized in a known method in place of the starting compound (1) in synthesis of the compound 1.
As a result of mass spectrometry, m/e=659 relative to the molecular weight 659 of the compound 12.
[Chem. 162]
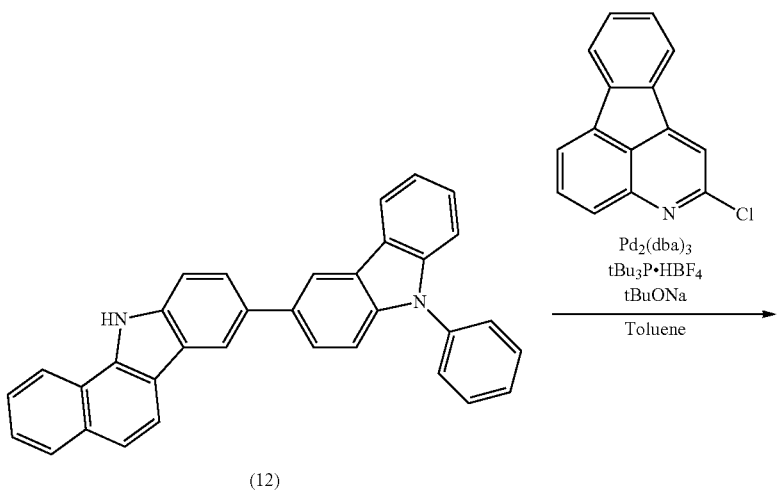
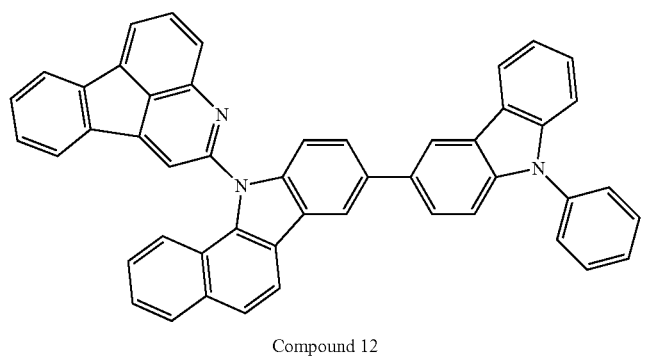
Compound 12

[Synthesis of Compound 13]

A compound 13 was synthesized according to the same method except for using the intermediate (B) in place of the intermediate (A) in synthesis of the compound 1.

As a result of mass spectrometry, m/e=609 relative to the molecular weight 609 of the compound 13.

[Chem. 163]

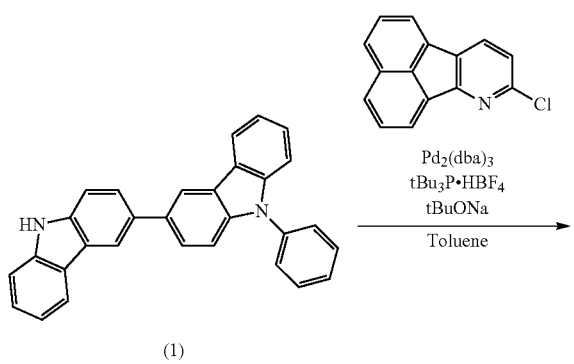

(1)

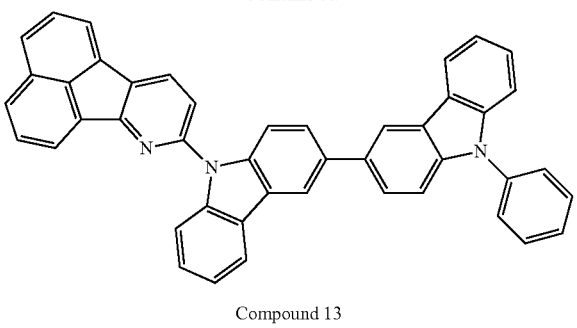

Compound 13

[Synthesis of Compound 14]

A compound 14 was synthesized according to the same method except for using the following starting compound (2) that had been synthesized in a known method in place of the starting compound (1) in synthesis of the compound 13.

As a result of mass spectrometry, m/e=685 relative to the molecular weight 685 of the compound 14.

[Chem. 164]

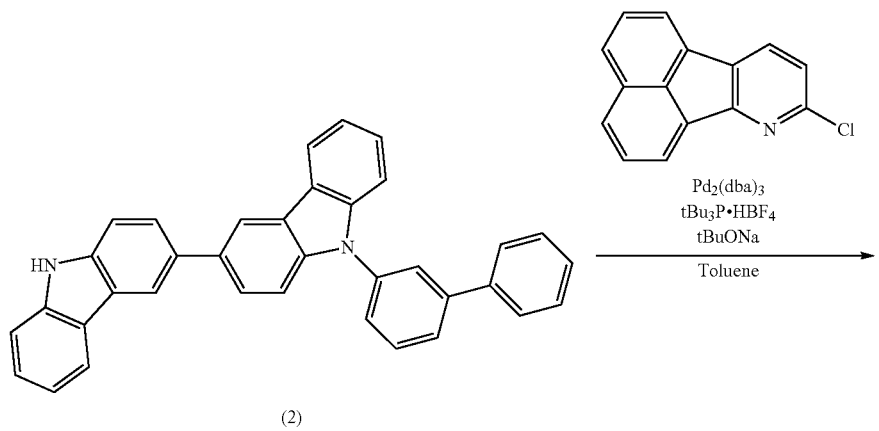

(2)

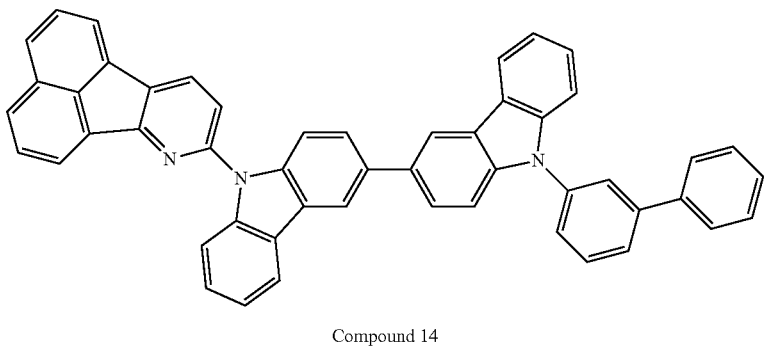

Compound 14

[Synthesis of Compound 15]

A compound 15 was synthesized according to the same method except for using the following starting compound (5) that had been synthesized in a known method in place of the starting compound (1) in synthesis of the compound 13.

As a result of mass spectrometry, m/e=534 relative to the molecular weight 534 of the compound 15.

[Chem. 165]

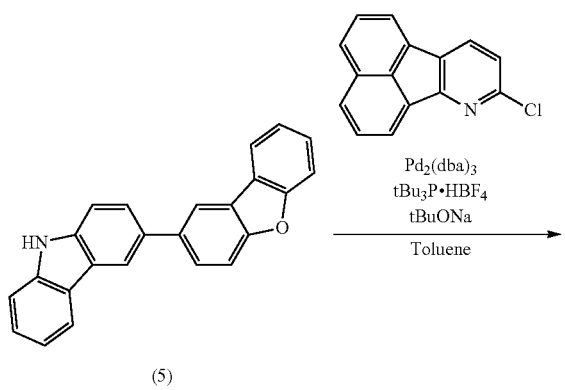

(5)

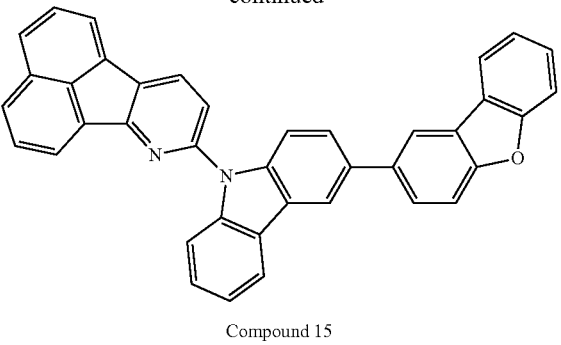

Compound 15

[Synthesis of Compound 16]

A compound 16 was synthesized according to the same method except for using the following starting compound (6) that had been synthesized in a known method in place of the starting compound (1) in synthesis of the compound 13.

As a result of mass spectrometry, m/e=659 relative to the molecular weight 659 of the compound 16.

[Chem. 166]

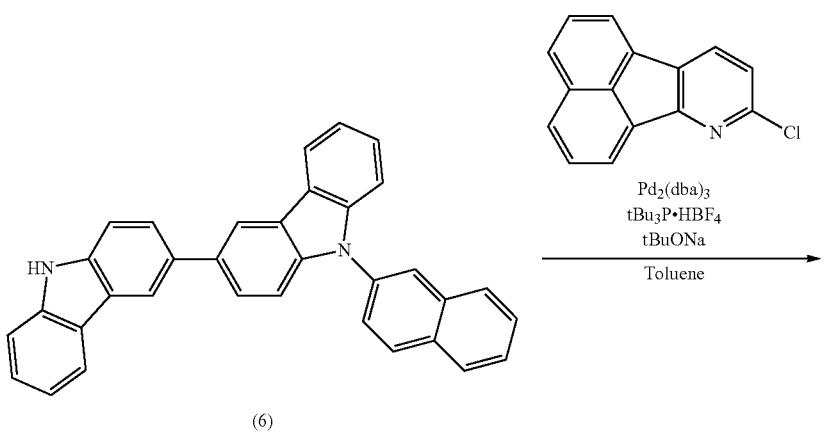

(6)

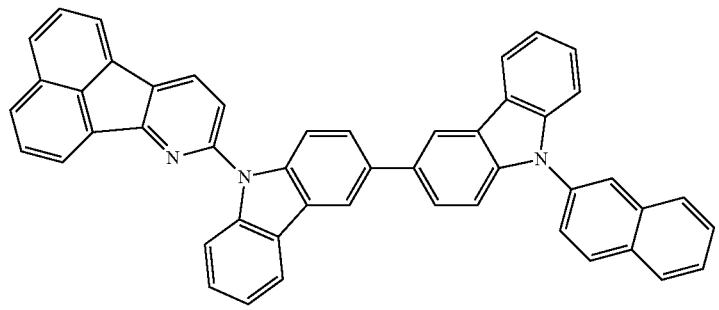

Compound 16

[Synthesis of Compound 17]

A compound 17 was synthesized according to the same method except for using the following starting compound (7) that had been synthesized in a known method in place of the starting compound (1) in synthesis of the compound 13.

As a result of mass spectrometry, m/e=659 relative to the molecular weight 659 of the compound 17.

[Chem. 167]

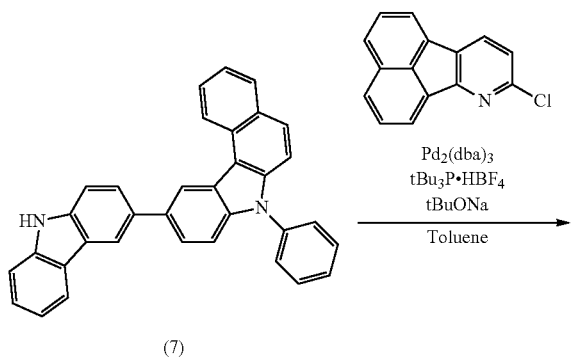

(7)

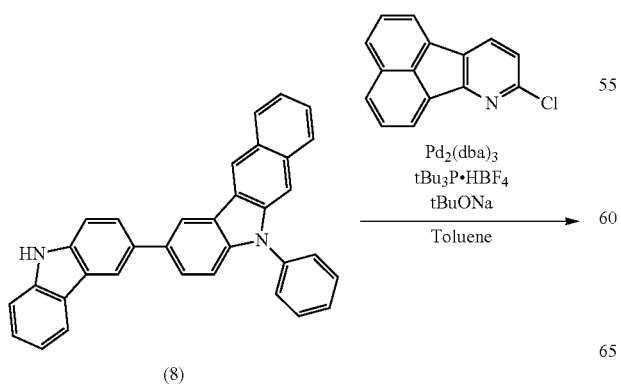

Compound 17

[Synthesis of Compound 18]

A compound 18 was synthesized according to the same method except for using the following starting compound (8) that had been synthesized in a known method in place of the starting compound (1) in synthesis of the compound 13.

As a result of mass spectrometry, m/e=659 relative to the molecular weight 659 of the compound 18.

[Chem. 168]

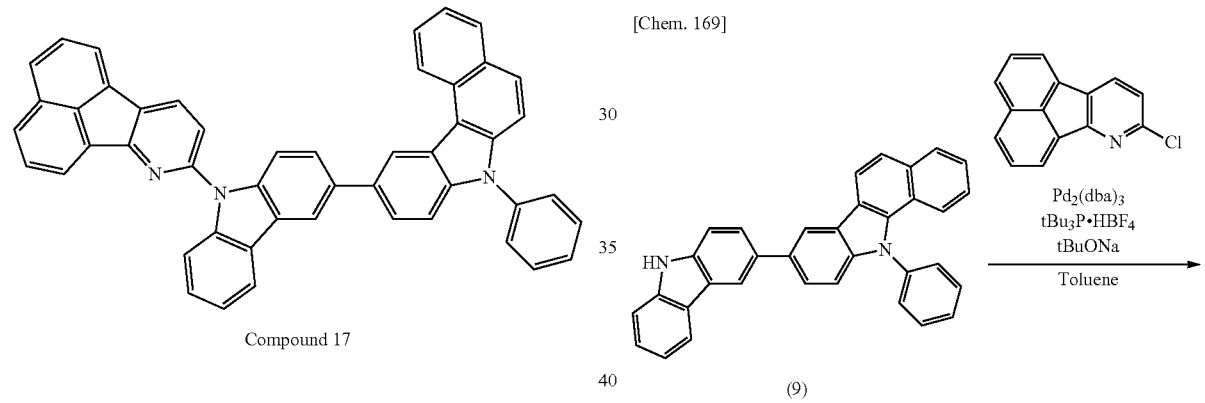

(8)

Compound 18

[Synthesis of Compound 19]

A compound 19 was synthesized according to the same method except for using the following starting compound (9) that had been synthesized in a known method in place of the starting compound (1) in synthesis of the compound 13.

As a result of mass spectrometry, m/e=659 relative to the molecular weight 659 of the compound 19.

[Chem. 169]

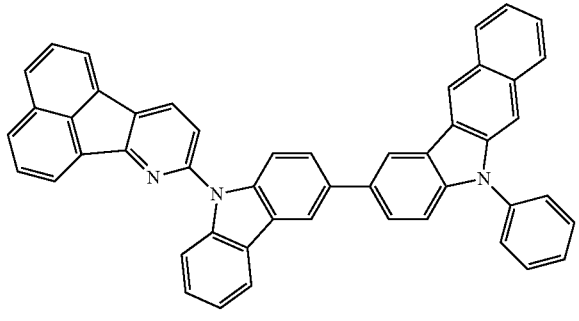

(9)

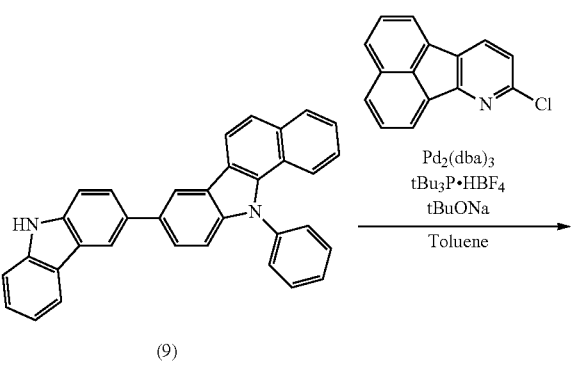

Compound 19

[Synthesis of Compound 20]

A compound 20 was synthesized according to the same method except for using the following starting compound (10) that had been synthesized in a known method in place of the starting compound (1) in synthesis of the compound 13.

As a result of mass spectrometry, m/e=659 relative to the molecular weight 659 of the compound 20.

[Chem. 170]

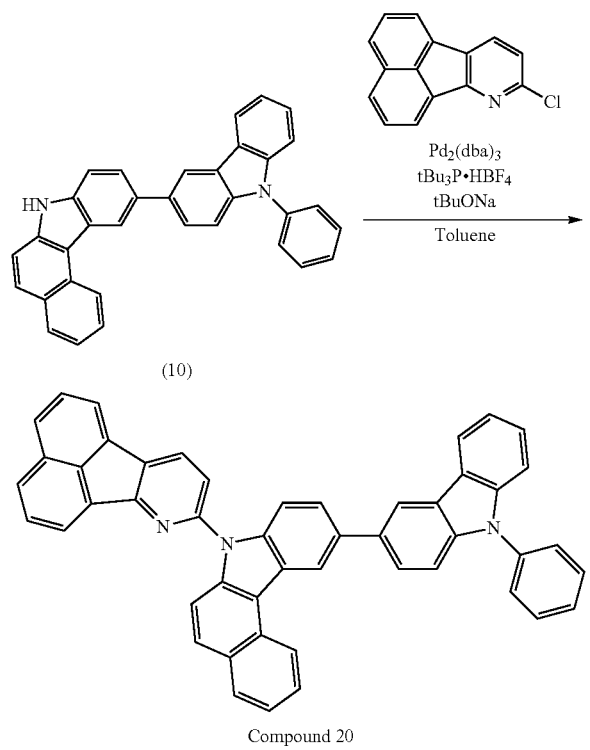

(10)

Compound 20

[Chem. 171]

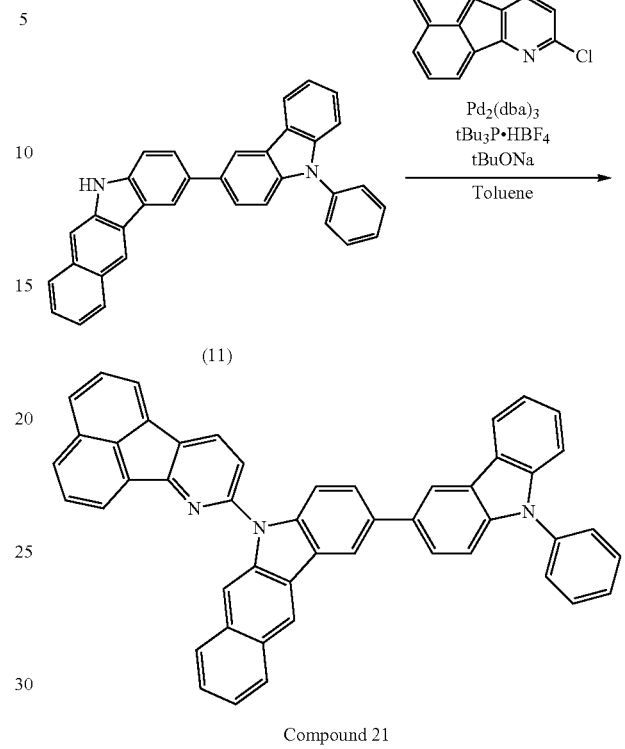

(11)

Compound 21

[Synthesis of Compound 21]

A compound 21 was synthesized according to the same method except for using the following starting compound (11) that had been synthesized in a known method in place of the starting compound (1) in synthesis of the compound 13.

As a result of mass spectrometry, m/e=659 relative to the molecular weight 659 of the compound 21.

[Synthesis of Compound 22]

A compound 22 was synthesized according to the same method except for using the following starting compound (12) that had been synthesized in a known method in place of the starting compound (1) in synthesis of the compound 13.

As a result of mass spectrometry, m/e=659 relative to the molecular weight 659 of the compound 22.

[Chem. 172]

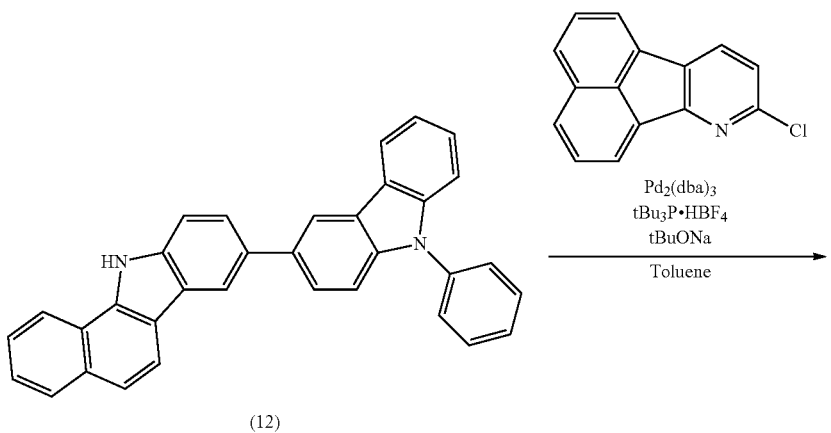

(12)

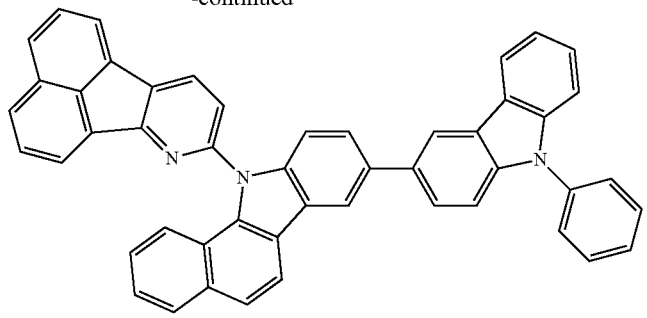

Compound 22

[Synthesis of Compound 23]

A compound 23 was synthesized according to the same method except for using the following starting compound (13) that had been synthesized in a known method in place of the starting compound (1) in synthesis of the compound 13.

As a result of mass spectrometry, m/e=584 relative to the molecular weight 584 of the compound 23.

[Chem. 173]

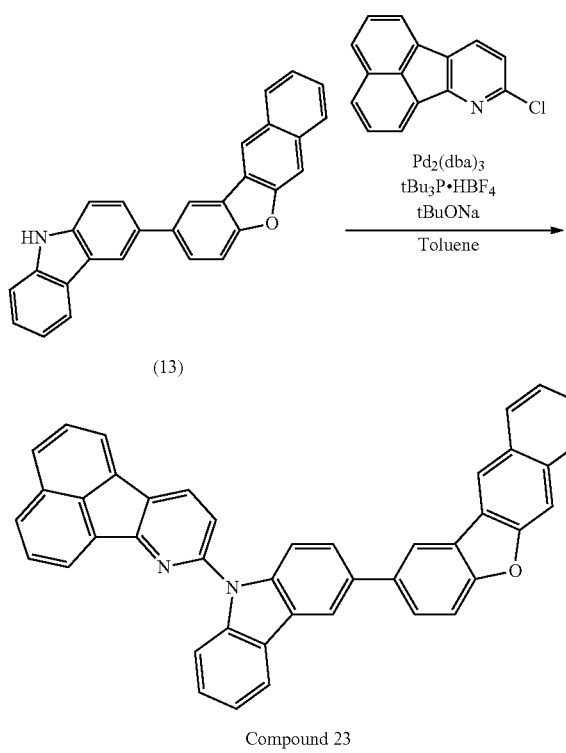

Compound 23

[Synthesis of Compound 24]

A compound 24 was synthesized according to the same method except for using the following starting compound (14) that had been synthesized in a known method in place of the starting compound (1) in synthesis of the compound 13.

As a result of mass spectrometry, m/e=584 relative to the molecular weight 584 of the compound 24.

[Chem. 174]

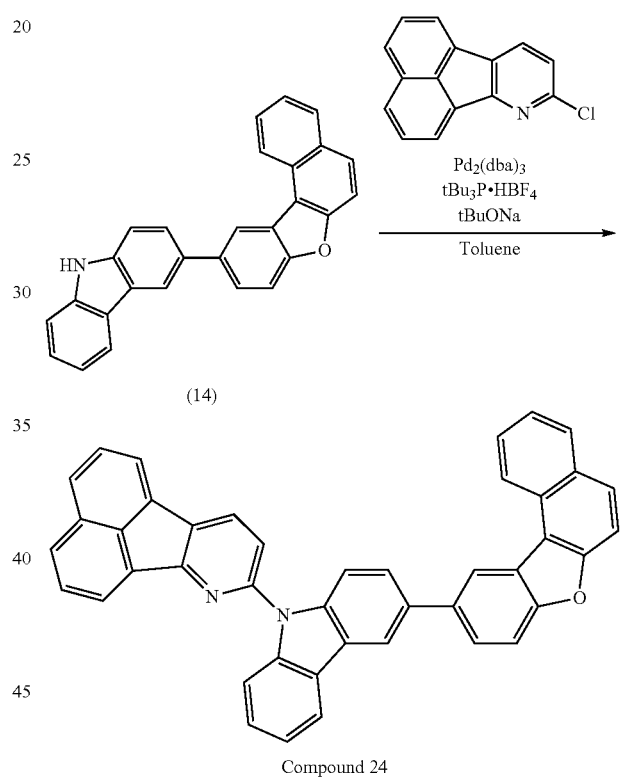

Compound 24

Example 1

Production and Evaluation of Organic EL Device

A glass substrate with an ITO transparent electrode of 25 mm×75 mm×1.1 mm (thickness) (manufactured by GEO-MATEC Co., Ltd.) was subjected to ultrasonic cleaning in isopropyl alcohol for five minutes and then to UV ozone cleaning for 30 minutes. The thickness of the ITO transparent electrode was 130 nm.

The glass substrate with the transparent electrode line after cleaning was attached to a substrate holder of a vacuum evaporator, and the acceptor material (HA) below was first deposited on the surface with the transparent electrode line to cover the transparent electrode, and an acceptor film having a thickness of 5 nm was thus formed. On the acceptor layer, the following aromatic amine compound HT was deposited to form a hole transporting layer having a thickness of 210 nm.

Next, on the hole transporting layer, the compound 1 (host material) obtained in Synthesis Example 1 and the following compound RD-1 (dopant material) were co-deposited to form a co-deposited film having a thickness of 40 nm. The concentration of the compound RD-1 was 2.0% by mass. The co-deposited film functions as a light emitting layer.

With that, on the light emitting layer, the following compound ET (50% by mass) and an electron donating dopant Liq (50% by mass) were deposited in a mode of binary deposition to form an ET film having a thickness of 30 nm, thereby forming an electron transporting layer.

Next, on the ET film, Liq was deposited at a film-forming rate of 0.1 angstrom/min to form a Liq film having a thickness of 1 nm, thereby forming an electron injecting electrode (cathode).

With that, a metal Al was deposited on the Liq film to form a metal Al film having a thickness of 80 nm, thereby forming a metal Al cathode. Thus, an organic EL device was prepared.

(Evaluation of Organic EL Device)

The produced organic EL device was operated on direct current for light emission, and the driving voltage (V) at a current density of 1 mA/cm$^2$ and 10 mA/cm$^2$ was measured. In addition the electron affinity was calculated. The results are shown in Table 1.

[Chem. 175]

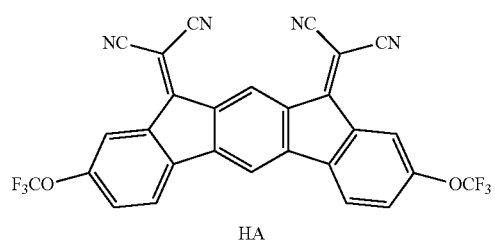

HA

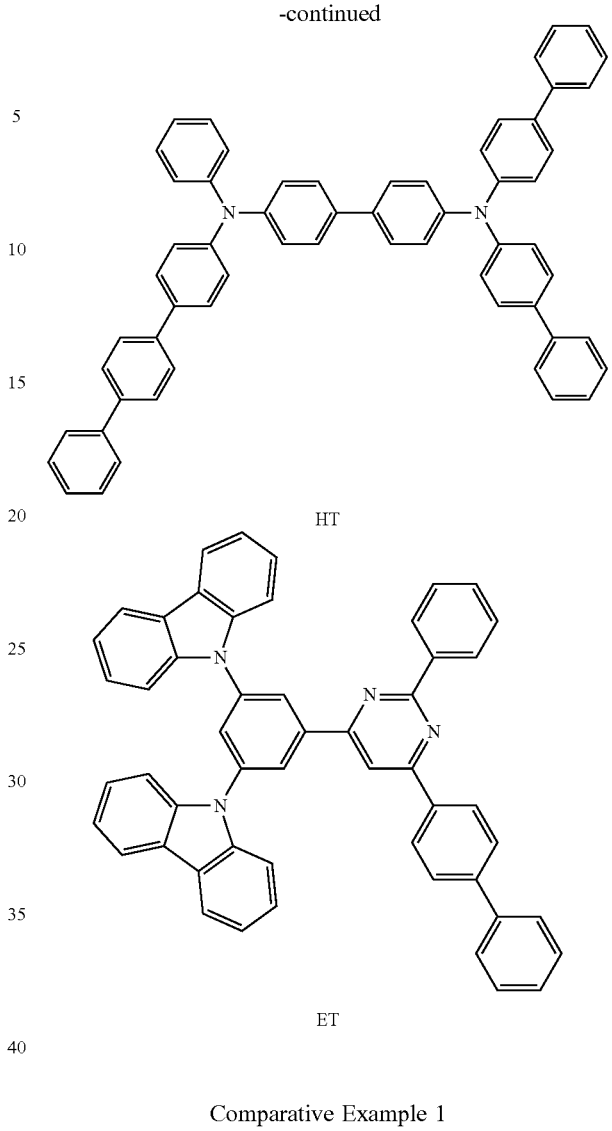

HT

ET

Comparative Example 1

An organic EL device was produced and evaluated in the same manner as in Example 1 except that the light emitting layer was formed using the comparative compound 1 in place of the compound 1 in Example 1.

The measured result of the driving voltage and the calculated value of the electron affinity are shown in Table 1.

[Chem. 176]

Comparative Compound 1

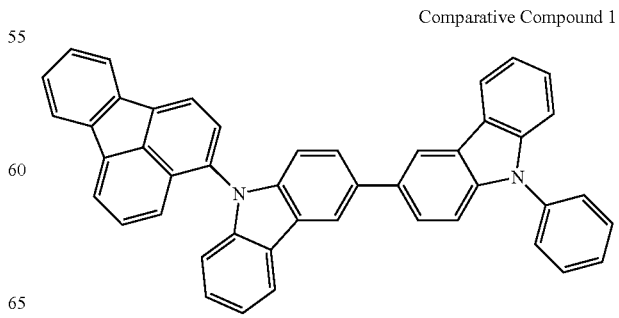

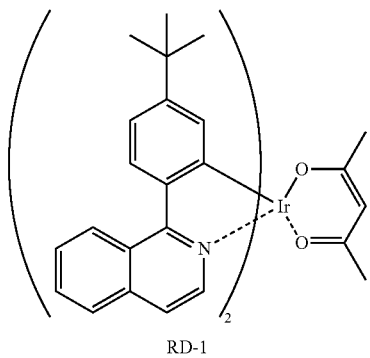

RD-1

TABLE 1

| | | Driving Voltage (V) | | Electron |
| | Host Material | 1 mA/cm² | 10 mA/cm² | Affinity [eV] |
|---|---|---|---|---|
| Example 1 | Compound 1 | 2.90 | 4.31 | 3.11 |
| Comparative Example 1 | Comparative Compound 1 | 3.18 | 4.70 | 2.99 |

Example 2

An organic EL device was produced and evaluated in the same manner as in Example 1 except that the light emitting layer was formed using the compound 13 in place of the compound 1 in Example 1, and the driving voltage thereof was evaluated.

The measured result of the driving voltage is shown in Table 2.

TABLE 2

| | | Driving Voltage (V) | |
| | Host Material | 1 mA/cm² | 10 mA/cm² |
|---|---|---|---|
| Example 2 | Compound 13 | 2.49 | 3.85 |

By using a compound having an azafluoranthene skeleton that is an aspect of the present invention, carrier injection performance, especially electron injection performance is improved. It is presumed that, by introducing a nitrogen atom onto a fluoranthene skeleton, the nitrogen-containing conjugated system of the azafluoranthene skeleton could expand and therefore could have an increased affinity as compared with the fluoranthene skeleton. As a result, in Example 1 of the organic EL device using the compound, low-voltage driving can be attained in a low-current density region of 1 mA/cm² to a high-current density region of 10 mA/cm², as compared with the case of Comparative Example 1.

Also in Example 2, low-voltage driving can be attained in a low-current density region of 1 mA/cm² to a high-current density region of 10 mA/cm².

REFERENCE SIGNS LIST

1: Organic electroluminescence device
2: Substrate
3: Anode
4: Cathode
5: Light emitting layer
6: Anode-side organic thin-film layer
7: Cathode-side organic thin-film layer
10: Light emitting unit

The invention claimed is:
1. A compound represented by the following formula (1):

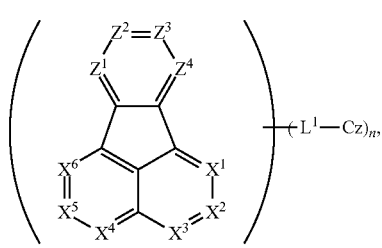

(1)

wherein any "n" number of $X^1$ to $X^6$ and $Z^1$ to $Z^4$ each represent a carbon atom bonding to $L^1$; and when $X^1$ to $X^6$ and $Z^1$ to $Z^4$ do not represent a carbon atom bonding to $L^1$, $X^1$ to $X^6$ and $Z^1$ to $Z^4$ each independently represent $CR^1$ or a nitrogen atom, with the proviso that only one selected from the group consisting of $X^1$ to $X^6$ and $Z^1$ to $Z^4$ is a nitrogen atom, n indicates an integer of 1 to 3, $R^1$ each independently represent a hydrogen atom or a substituent, $L^1$ represents a single bond, a substituted or unsubstituted arylene group having 6 to 50 ring carbon atoms, or a substituted or unsubstituted heteroarylene group having 5 to 50 ring atoms, and Cz is represented by the following formula (7):

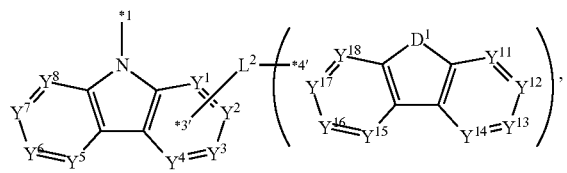

(7)

wherein $Y^1$ to $Y^8$ each independently represent $CR^9$ or a nitrogen atom, $Y^{11}$ to $Y^{18}$ each independently represent $CR^{10}$ or a nitrogen atom, $R^9$ each independently represent a hydrogen atom, a substituent or a single bond bonding to *2', $R^{10}$ each independently represent a hydrogen atom, a substituent or a single bond bonding to *4', $D^1$ represents an oxygen atom, a sulfur atom, or $NR^8$, $L^2$ represents a single bond, a substituted or unsubstituted arylene group having 6 to 50 ring carbon atoms, or a substituted or unsubstituted heteroarylene group having 5 to 50 ring atoms,

*1 represents a bonding position to $L^1$,

*2' bonds to the carbon atom that any one of $R^9$ represents,

*3' bonds to any one of plural $R^9$'s, and

*4' bonds to any one of plural $R^{16}$'s.

2. The compound according to claim 1, which is represented by the following formula (3):

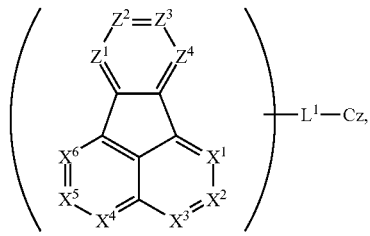

(3)

wherein $X^1$ to $X^6$, $Z^1$ to $Z^4$, $L^1$ and Cz are the same as defined above.

3. The compound according to claim 1, wherein the bonding position of the condensed ring represented by the following formula (F) in the formula (1) to the above $L^1$ is a bonding position shown by any one selected from the group consisting of the following formulae (NL1) to (NL4):

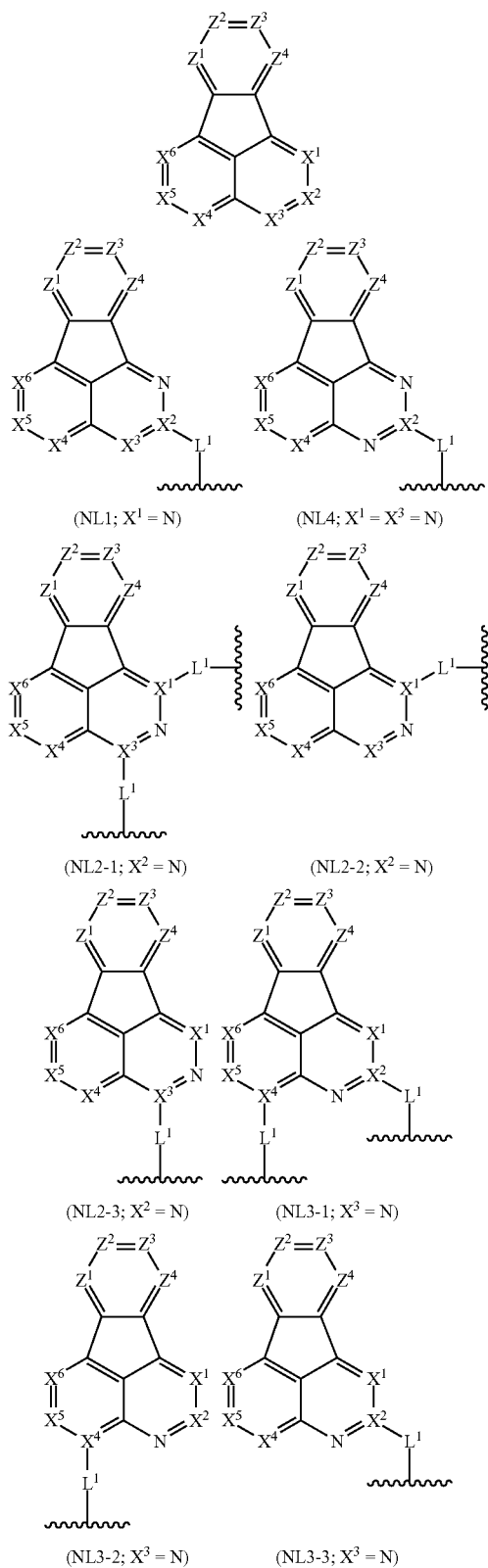

wherein $X^1$ to $X^6$, $Z^1$ to $Z^4$ and $L^1$ in the formulae (NL1) to (NL4) are the same as $X^1$ to $X^6$, $Z^1$ to $Z^4$ and $L^1$ in the formula (1), and the undulating line connecting to $L^1$ means that Cz in the formula (1) bonds to $L^1$.

4. The compound according to claim 1, which is represented by the following formula (4):

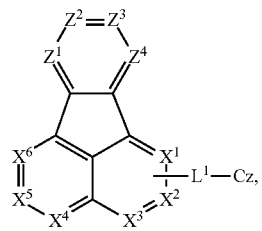

(4)

wherein $L^1$ and Cz are the same as defined above,
$Z^1$ to $Z^4$ each independently represent $CR^1$ or a nitrogen atom,
any one of $X^1$ to $X^3$ represents a carbon atom bonding to $L^1$; and the other $X^1$-$X^3$, and $X^4$-$X^6$ each independently represent $CR^1$ or a nitrogen atom, provided that one from $Z^1$ to $Z^4$ and $X^1$ to $X^6$ is a nitrogen atom, and $R^1$ is the same as defined above.

5. The compound according to claim 1, wherein Cz is represented by the following formula (8):

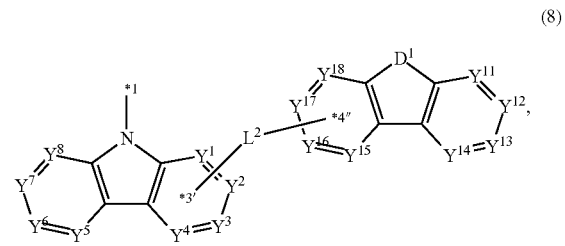

(8)

wherein *1, *3', $Y^1$ to $Y^8$, $Y^{11}$ to $Y^{18}$, $L^2$, and $D^1$ are the same as defined above,
*4" bonds to the carbon atom that any one of $Y^{15}$ to $Y^{18}$ represents; and the other $Y^{15}$ to $Y^{18}$ each independently represent $CR^{10}$ or a nitrogen atom, and $R^{10}$ is the same as defined above.

6. The compound according to claim 1, which is represented by the following formula (11):

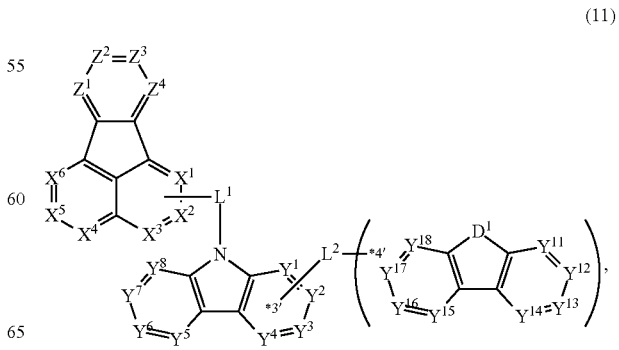

(11)

wherein $X^1$ to $X^6$, $Z^1$ to $Z^4$, $L^1$, $Y^1$ to $Y^8$, *3', $L^2$, *4', $Y^{11}$ to $Y^{18}$, and $D^1$ are the same as defined above.

7. The compound according to claim 1, which is represented by the following formula (12):

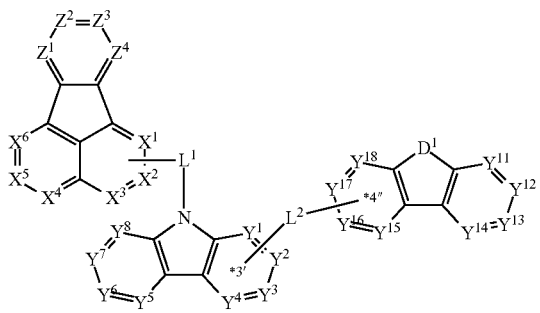

(12)

wherein $X^1$ to $X^6$, $Z^1$ to $Z^4$, $L^1$, $Y^1$ to $Y^8$, *3', $L^2$, *4", $Y^{11}$ to $Y^{18}$, and $D^1$ are the same as defined above.

8. The compound according to claim 1, wherein $L^1$ bonds to the carbon atom adjacent to any one of $X^1$ to $X^6$ that represents a nitrogen atom.

9. The compound according to claim 1, wherein $X^3$ is a nitrogen atom.

10. The compound according to claim 1, wherein $L^1$ bonds to the carbon atom that $X^2$ represents.

11. The compound according to claim 1, wherein $D^1$ is $NR^8$.

12. The compound according to claim 1, wherein $L^2$ bonds to the two carbon atoms that $Y^2$ and $Y^{13}$ represent, the two carbon atoms that $Y^3$ and $Y^{12}$ represent, or the two carbon atoms that $Y^3$ and $Y^{13}$ represent.

13. The compound according to claim 1, wherein $L^1$ represents a single bond, or a substituted or unsubstituted arylene group having 6 to 50 ring carbon atoms.

14. The compound according to claim 1, wherein $L^2$ represents a single bond, or a substituted or unsubstituted arylene group having 6 to 50 ring carbon atoms.

15. The compound according to claim 1, wherein the substituent is a group selected from the group consisting of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a substituted or unsubstituted aralkyl group having 7 to 61 carbon atoms, an amino group, a monosubstituted or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted cycloalkoxy group having 3 to 50 ring carbon atoms, a substituted or unsubstituted aryloxy group having 6 to 60 ring carbon atoms, a substituted or unsubstituted alkylthio group having 1 to 50 carbon atoms, a substituted or unsubstituted arylthio group having 6 to 60 ring carbon atoms, a monosubstituted, disubstituted or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 60 ring carbon atoms, a di-substituted phosphoryl group having substituents selected from a substituted or unsubstituted alkyl group having 1 to 50 carbon atoms and a substituted or unsubstituted aryl group having 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxy group, an alkyl-substituted or aryl-substituted carbonyl group, a carboxyl group, a vinyl group, a (meth)acryloyl group, an epoxy group, and an oxetanyl group.

16. The compound according to claim 1, wherein the substituent is a group selected from the group consisting of a substituted or unsubstituted methyl group, a substituted or unsubstituted ethyl group, a substituted or unsubstituted n-propyl group, a substituted or unsubstituted isopropyl group, a substituted or unsubstituted n-butyl group, a substituted or unsubstituted isobutyl group, a substituted or unsubstituted s-butyl group, a substituted or unsubstituted t-butyl group, a substituted or unsubstituted pentyl group (including isomers), a substituted or unsubstituted hexyl group (including isomers), a substituted or unsubstituted heptyl group (including isomers), a substituted or unsubstituted octyl group (including isomers), a substituted or unsubstituted nonyl group (including isomers), a substituted or unsubstituted decyl group (including isomers), a substituted or unsubstituted undecyl group (including isomers), a substituted or unsubstituted dodecyl group (including isomers), a substituted or unsubstituted tridecyl group (including isomers), a substituted or unsubstituted tetradecyl group, a substituted or unsubstituted octadecyl group, a substituted or unsubstituted cyclopentyl group, a substituted or unsubstituted cyclohexyl group, a substituted or unsubstituted phenyl group, a substituted or unsubstituted naphthyl group, a substituted or unsubstituted biphenylyl group, a substituted or unsubstituted terphenylyl group, a substituted or unsubstituted phenanthryl group, a substituted or unsubstituted benzophenanthryl group, a substituted or unsubstituted fluorenyl group, a substituted or unsubstituted 9,9'-spirobifluorenyl group, a substituted or unsubstituted benzofluorenyl group, a substituted or unsubstituted dibenzofluorenyl group, a substituted or unsubstituted chrysenyl group, a substituted or unsubstituted benzochrysenyl group, a substituted or unsubstituted s-indanyl group, a substituted or unsubstituted as-indanyl group, a substituted or unsubstituted triphenylenyl group, a substituted or unsubstituted benzotriphenylenyl group, a substituted or unsubstituted anthryl group, a substituted or unsubstituted 9,9-dimethylfluorenyl group, a substituted or unsubstituted 9,9-diphenylfluorenyl group, a substituted or unsubstituted pyridyl group, a substituted or unsubstituted pyridazinyl group, a substituted or unsubstituted pyrimidinyl group, a substituted or unsubstituted pyrazinyl group, a substituted or unsubstituted triazinyl group, a substituted or unsubstituted imidazolyl group, a substituted or unsubstituted indolyl group, a substituted or unsubstituted isoindolyl group, a substituted or unsubstituted benzofuranyl group, a substituted or unsubstituted isobenzofuranyl group, a substituted or unsubstituted benzothiophenyl group, a substituted or unsubstituted isobenzothiophenyl group, a substituted or unsubstituted indolidinyl group, a substituted or unsubstituted quinolidinyl group, a substituted or unsubstituted quinolyl group, a substituted or unsubstituted isoquinolyl group, a substituted or unsubstituted quinazolinyl group, a substituted or unsubstituted quinoxalinyl group, a substituted or unsubstituted benzimidazolyl group, a substituted or unsubstituted benzoxazolyl group, a substituted or unsubstituted benzothiazolyl group, a substituted or unsubstituted benzisoxazolyl group, a substituted or unsubstituted benzisothiazolyl group, a substituted or unsubstituted dibenzofuranyl group, a substituted or unsubstituted dibenzothiophenyl group, a substituted or unsubstituted carbazolyl group, a substituted or unsubstituted bicarbazolyl group, a substituted or unsubstituted phenanthridinyl group, a substituted or unsubstituted acridinyl group, a substituted or unsubstituted phenanthrolinyl group, a substituted or unsubstituted azatriphenylenyl group, a substituted or unsubstituted diazatriphenylenyl group, a substituted or unsubstituted xanthenyl group, a substituted or unsubstituted azacarbazolyl group, a substituted or unsubstituted azadibenzofuranyl group, and a substituted or unsubstituted azadibenzothiophenyl group.

17. The compound according to claim 1, wherein the substituent is a group selected from the group consisting of a substituted or unsubstituted methyl group, a substituted or unsubstituted ethyl group, a substituted or unsubstituted n-propyl group, a substituted or unsubstituted isopropyl group, a substituted or unsubstituted n-butyl group, a substituted or unsubstituted isobutyl group, a substituted or unsubstituted s-butyl group, a substituted or unsubstituted t-butyl group, a substituted or unsubstituted pentyl group (including isomers), a substituted or unsubstituted hexyl group (including isomers), a substituted or unsubstituted heptyl group (including isomers), a substituted or unsubstituted octyl group (including isomers), a substituted or unsubstituted phenyl group, a substituted or unsubstituted biphenylyl group, a substituted or unsubstituted terphenylyl group, a substituted or unsubstituted naphthyl group, a substituted or unsubstituted phenanthryl group, a substituted or unsubstituted fluorenyl group, a substituted or unsubstituted 9,9'-spirobifluorenyl group, a substituted or unsubstituted chrysenyl group, a substituted or unsubstituted triphenylenyl group, a substituted or unsubstituted 9,9-dimethylfluorenyl group, a substituted or unsubstituted 9,9-diphenylfluorenyl group, a substituted or unsubstituted pyridyl group, a substituted or unsubstituted pyrimidinyl group, a substituted or unsubstituted triazinyl group, a substituted or unsubstituted benzofuranyl group, a substituted or unsubstituted isobenzofuranyl group, a substituted or unsubstituted quinolyl group, a substituted or unsubstituted isoquinolyl group, a substituted or unsubstituted quinazolyl group, a substituted or unsubstituted benzothiophenyl group, a substituted or unsubstituted isobenzothiophenyl group, a substituted or unsubstituted indolidinyl group, a substituted or unsubstituted dibenzofuranyl group, a substituted or unsubstituted dibenzothiophenyl group, a substituted or unsubstituted carbazolyl group, a substituted or unsubstituted bicarbazolyl group, a substituted or unsubstituted azatriphenylenyl group, a substituted or unsubstituted diazatriphenylenyl group, a substituted or unsubstituted xanthenyl group, a substituted or unsubstituted azacarbazolyl group, a substituted or unsubstituted azadibenzofuranyl group, and a substituted or unsubstituted azadibenzothiophenyl group.

18. A material for organic electroluminescence devices, comprising the compound of claim 1.

19. A material for organic electroluminescence devices, comprising a compound of the following formula (13):

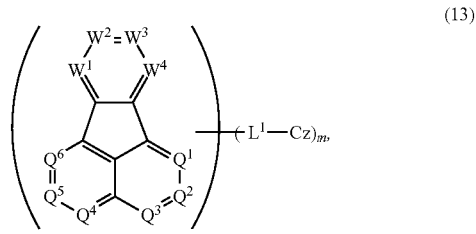

(13)

wherein any "m" number of $Q^1$ to $Q^6$ and $W^1$ to $W^4$ each represent a carbon atom bonding to $L^1$; and when $Q^1$ to $Q^6$ and $W^1$ to $W^4$ do not represent a carbon atom bonding to $L^1$, $W^2$ and $W^3$ each independently represent $CR^{11}$; $W^1$ and $W^4$ each independently represent $CR^{11}$ or a nitrogen atom; and $Q^1$ to $Q^6$ each independently represent $CR^{11}$ or a nitrogen atom, with the proviso that at least one of $W^1$ and $W^4$ is a nitrogen atom, m indicates an integer of 1 to 3, $R^{11}$ each independently represent a hydrogen atom or a substituent, $L^1$ represents a single bond, a substituted or unsubstituted arylene group having 6 to 50 ring carbon atoms, or a substituted or unsubstituted heteroarylene group having 5 to 50 ring atoms, Cz is represented by the following formula (7):

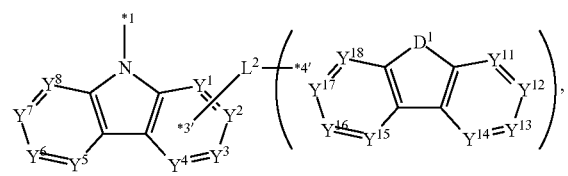

(7)

wherein $Y^1$ to $Y^8$ each independently represent $CR^9$ or a nitrogen atom, $Y^{11}$ to $Y^{18}$ each independently represent $CR^{10}$ or a nitrogen atom, $R^9$ each independently represent a hydrogen atom, a substituent or a single bond bonding to *2', $R^{10}$ each independently represent a hydrogen atom, a substituent or a single bond bonding to *4', D' represents an oxygen atom, a sulfur atom, or $NR^8$, $L^2$ represents a single bond, a substituted or unsubstituted arylene group having 6 to 50 ring carbon atoms, or a substituted or unsubstituted heteroarylene group having 5 to 50 ring atoms,

*1 represents a bonding position to $L^1$,

*2' bonds to the carbon atom that any one of $R^9$ represents,

*3' bonds to any one of plural $R^9$'s, and

*4' bonds to any one of plural $R^{10}$'s.

20. The material for organic electroluminescence devices according to claim 19, wherein Cz is represented by the following formula (8):

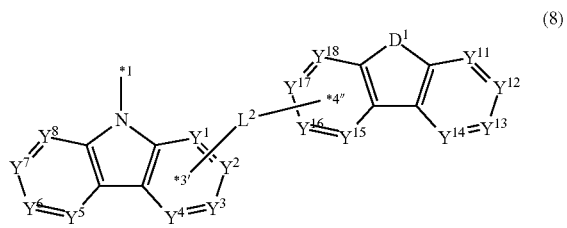

(8)

wherein *1, *3', $Y^1$ to $Y^8$, $Y^{11}$ to $Y^{18}$, $L^2$, and $D^1$ are the same as defined above,

*4" bonds to the carbon atom that any one of $Y^{15}$ to $Y^{18}$ represents; and the other $Y^{15}$ to $Y^{18}$ each independently represent $CR^{10}$ or a nitrogen atom, and $R^{10}$ is the same as defined above.

21. The material for organic electroluminescence devices according to claim 19, wherein $W^1$ is a nitrogen atom.

22. The material for organic electroluminescence devices according to claim 19, wherein $L^1$ bonds to any one to three carbon atoms that $Q^1$ to $Q^6$ and $W^2$ to $W^4$ represent.

23. The material for organic electroluminescence devices according to claim 19, wherein the substituent is a group selected from the group consisting of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a substituted or unsubstituted aralkyl group having 7 to 61 carbon atoms, an amino group, a monosubstituted or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted cycloalkoxy group having 3 to 50 ring carbon atoms, a substituted or unsubstituted aryloxy group having 6 to 60 ring carbon atoms, a substituted or unsubstituted alkylthio group having 1 to 50 carbon atoms, a substituted or unsubstituted arylthio group having 6 to 60 ring carbon atoms, a monosubstituted, disubstituted or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 60 ring carbon atoms, a di-substituted phosphoryl group having substituents selected from a substituted or unsubstituted alkyl group having 1 to 50 carbon atoms and a substituted or unsubstituted aryl group having 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxy group, an alkyl-substituted or aryl-substituted carbonyl group, a carboxyl group, a vinyl group, a (meth)acryloyl group, an epoxy group, and an oxetanyl group.

24. The material for organic electroluminescence devices according to claim 19, wherein the substituent is a group selected from the group consisting of a substituted or unsubstituted methyl group, a substituted or unsubstituted ethyl group, a substituted or unsubstituted n-propyl group, a substituted or unsubstituted isopropyl group, a substituted or unsubstituted n-butyl group, a substituted or unsubstituted isobutyl group, a substituted or unsubstituted s-butyl group, a substituted or unsubstituted t-butyl group, a substituted or unsubstituted pentyl group (including isomers), a substituted or unsubstituted hexyl group (including isomers), a substituted or unsubstituted heptyl group (including isomers), a substituted or unsubstituted octyl group (including isomers), a substituted or unsubstituted nonyl group (including isomers), a substituted or unsubstituted decyl group (including isomers), a substituted or unsubstituted undecyl group (including isomers), a substituted or unsubstituted dodecyl group (including isomers), a substituted or unsubstituted tridecyl group, a substituted or unsubstituted tetradecyl group, a substituted or unsubstituted octadecyl group, a substituted or unsubstituted cyclopentyl group, a substituted or unsubstituted cyclohexyl group, a substituted or unsubstituted phenyl group, a substituted or unsubstituted naphthyl group, a substituted or unsubstituted biphenylyl group, a substituted or unsubstituted terphenylyl group, a substituted or unsubstituted phenanthryl group, a substituted or unsubstituted benzophenanthryl group, a substituted or unsubstituted fluorenyl group, a substituted or unsubstituted 9,9'-spirobifluorenyl group, a substituted or unsubstituted benzofluorenyl group, a substituted or unsubstituted dibenzofluorenyl group, a substituted or unsubstituted chrysenyl group, a substituted or unsubstituted benzochrysenyl group, a substituted or unsubstituted s-indanyl group, a substituted or unsubstituted as-indanyl group, a substituted or unsubstituted triphenylenyl group, a substituted or unsubstituted benzotriphenylenyl group, a substituted or unsubstituted anthryl group, a substituted or unsubstituted 9,9-dimethyifluorenyl group, a substituted or unsubstituted 9,9-diphenylfluorenyl group, a substituted or unsubstituted pyridyl group, a substituted or unsubstituted pyridazinyl group, a substituted or unsubstituted pyrimidinyl group, a substituted or unsubstituted pyrazinyl group, a substituted or unsubstituted triazinyl group, a substituted or unsubstituted imidazolyl group, a substituted or unsubstituted indolyl group, a substituted or unsubstituted isoindolyl group, a substituted or unsubstituted benzofuranyl group, a substituted or unsubstituted isobenzofuranyl group, a substituted or unsubstituted benzothiophenyl group, a substituted or unsubstituted isobenzothiophenyl group, a substituted or unsubstituted indolidinyl group, a substituted or unsubstituted quinolidinyl group, a substituted or unsubstituted quinolyl group, a substituted or unsubstituted isoquinolyl group, a substituted or unsubstituted quinazolinyl group, a substituted or unsubstituted quinoxalinyl group, a substituted or unsubstituted benzimidazolyl group, a substituted or unsubstituted benzoxazolyl group, a substituted or unsubstituted benzothiazolyl group, a substituted or unsubstituted benzisoxazolyl group, a substituted or unsubstituted benzisothiazolyl group, a substituted or unsubstituted dibenzofuranyl group, a substituted or unsubstituted carbazolyl group, a substituted or unsubstituted bicarbazolyl group, a substituted or unsubstituted phenanthridinyl group, a substituted or unsubstituted acridinyl group, a substituted or unsubstituted phenanthrolinyl group, a substituted or unsubstituted azatriphenylenyl group, a substituted or unsubstituted diazatriphenylenyl group, a substituted or unsubstituted xanthenyl group, a substituted or unsubstituted azacarbazolyl group, a substituted or unsubstituted azadibenzofuranyl group, and a substituted or unsubstituted azadibenzothiophenyl group.

25. The material for organic electroluminescence devices according to claim 19, wherein the substituent is a group selected from the group consisting of a substituted or unsubstituted methyl group, a substituted or unsubstituted ethyl group, a substituted or unsubstituted n-propyl group, a substituted or unsubstituted isopropyl group, a substituted or unsubstituted n-butyl group, a substituted or unsubstituted isobutyl group, a substituted or unsubstituted s-butyl group, a substituted or unsubstituted t-butyl group, a substituted or unsubstituted pentyl group (including isomers), a substituted or unsubstituted hexyl group (including isomers), a substituted or unsubstituted heptyl group (including isomers), a substituted or unsubstituted octyl group (including isomers),
  a substituted or unsubstituted phenyl group, a substituted or unsubstituted biphenylyl group, a substituted or unsubstituted terphenylyl group, a substituted or unsubstituted naphthyl group, a substituted or unsubstituted phenanthryl group, a substituted or unsubstituted fluorenyl group, a substituted or unsubstituted 9,9'-spirobifluorenyl group, a substituted or unsubstituted chrysenyl group, a substituted or unsubstituted triphenylenyl group, a substituted or unsubstituted 9,9-dimethylfluorenyl group, a substituted or unsubstituted 9,9-diphenylfluorenyl group,
  a substituted or unsubstituted pyridyl group, a substituted or unsubstituted pyrimidinyl group, a substituted or unsubstituted triazinyl group, a substituted or unsubstituted benzofuranyl group, a substituted or unsubstituted isobenzofuranyl group, a substituted or unsubstituted quinolyl group, a substituted or unsubstituted isoquinolyl group, a substituted or unsubstituted quinazolyl group, a substituted or unsubstituted benzothiophenyl group, a substituted or unsubstituted isobenzothiophenyl group, a substituted or unsubstituted indolidinyl group, a substituted or unsubstituted dibenzofuranyl group, a substituted or unsubstituted dibenzothiophenyl group, a substituted or unsubstituted carbazolyl group, a substituted or unsubstituted bicarbazolyl group, a substituted or unsubstituted azatriphenylenyl group, a substituted or unsubstituted diazatriphenylenyl group, a substituted or unsubstituted xanthenyl group, a substituted or unsubstituted azacarbazolyl group, a substituted or unsubstituted azadibenzofuranyl group, and a substituted or unsubstituted azadibenzothiophenyl group.

26. An organic electroluminescence device comprising a cathode, an anode and an organic thin film layer formed of one layer or plural layers sandwiched between the cathode and the anode, wherein the organic thin film layer contains a light emitting layer and at least one layer of the organic thin film layer contains the compound according to claim 1.

27. An organic electroluminescence device comprising a cathode, an anode and an organic thin film layer formed of one layer or plural layers sandwiched between the cathode and the anode, wherein the organic thin film layer contains a light emitting layer and at least one layer of the organic thin film layer contains the material for organic electroluminescence devices according to claim 19.

28. The organic electroluminescence device according to claim 26, wherein the light emitting layer comprises the above-described compound.

29. The organic electroluminescence device according to claim 26, further comprising a first charge transporting layer between the anode and the light emitting layer, wherein the first charge transporting layer comprises the above-described compound.

30. The organic electroluminescence device according to claim 26, further comprising a second charge transporting layer between the cathode and the light emitting layer, wherein the second charge transporting layer comprises the above-described compound.

31. The organic electroluminescence device according to claim 26, wherein the light emitting layer comprises a phosphorescent light emitting material.

32. The organic electroluminescence device according to claim 26, wherein the light emitting layer comprises a fluorescent light emitting material.

33. The organic electroluminescence device according to claim 31, wherein the phosphorescent light emitting material is an ortho-metalated complex with a metal atom selected from iridium (Ir), osmium (Os) and platinum (Pt).

34. The organic electroluminescence device according to claim 33, wherein the phosphorescent light emitting material is a complex represented by the following formula (V), (X), (Y) or (Z):

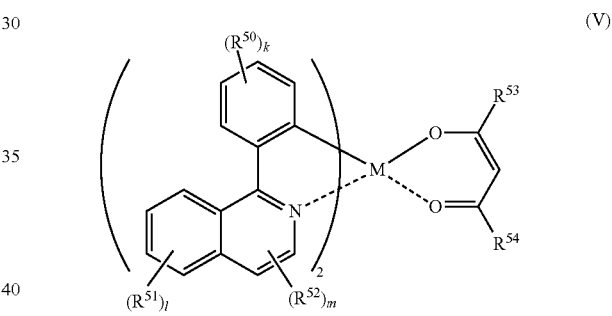

(V)

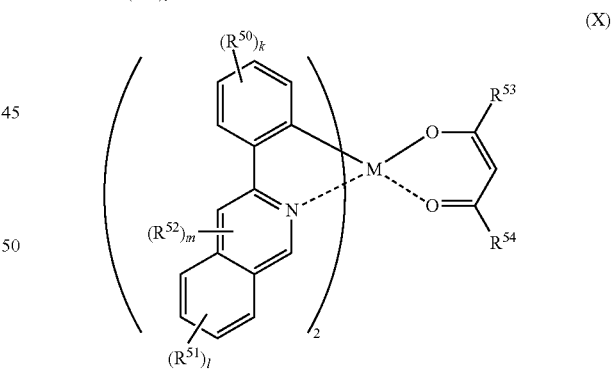

(X)

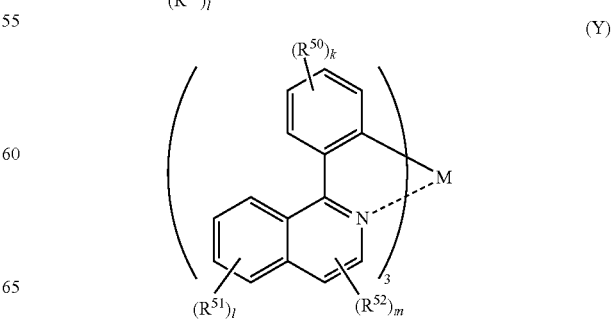

(Y)

-continued
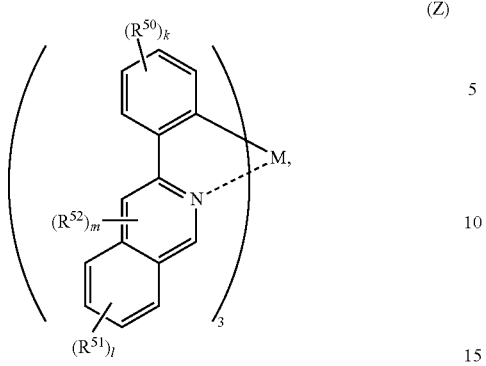
(Z)
wherein $R^{50}$ to $R^{54}$ each represents a hydrogen atom or a substituent,
k indicates an integer of 1 to 4,
l indicates an integer of 1 to 4, m indicates an integer of 1 or 2, and
M represents Ir, Os or Pt.
35. An electronic equipment comprising the organic electroluminescence device of claim 26.
* * * * *

UNITED STATES PATENT AND TRADEMARK OFFICE
CERTIFICATE OF CORRECTION

PATENT NO. : 10,629,821 B2
APPLICATION NO. : 15/502398
DATED : April 21, 2020
INVENTOR(S) : Tasuku Haketa et al.

It is certified that error appears in the above-identified patent and that said Letters Patent is hereby corrected as shown below:

In the Claims

Column 569, Line 56, Claim 1, " 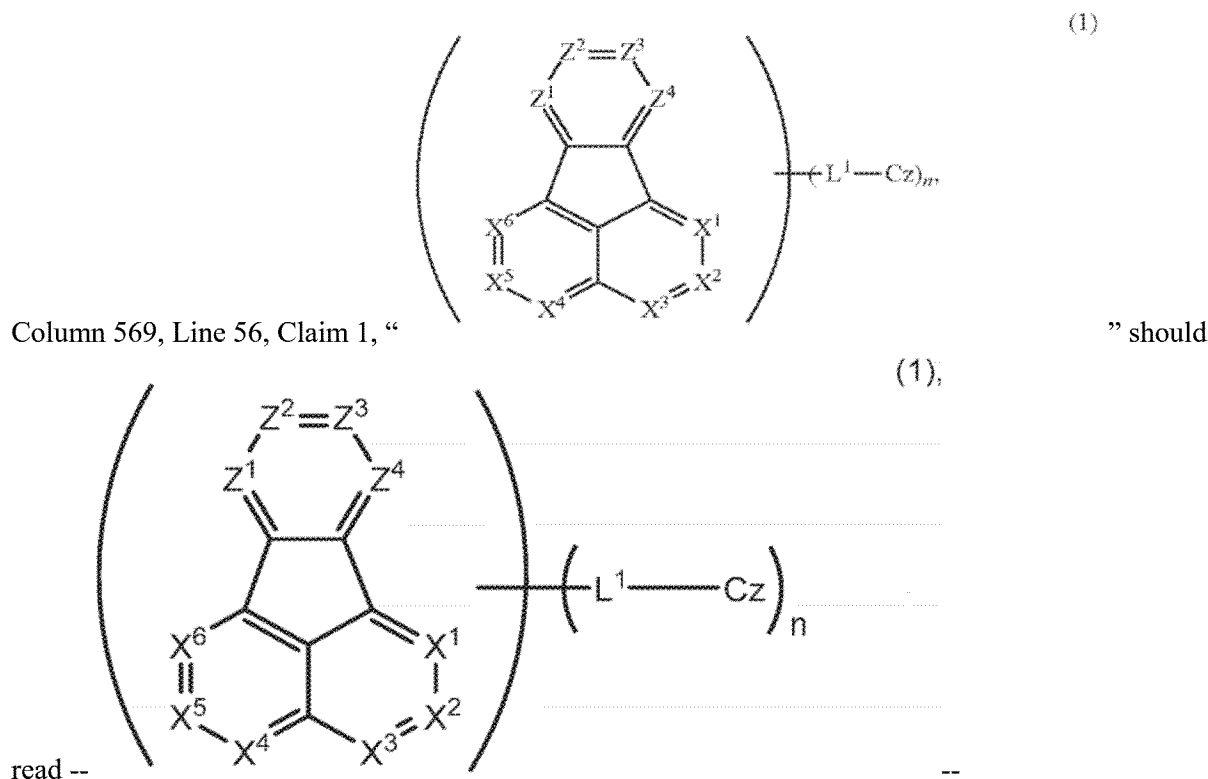 " should read -- --

Signed and Sealed this
Sixth Day of October, 2020

Andrei Iancu
*Director of the United States Patent and Trademark Office*

CERTIFICATE OF CORRECTION (continued)
U.S. Pat. No. 10,629,821 B2

Column 570, Line 20, Claim 1,

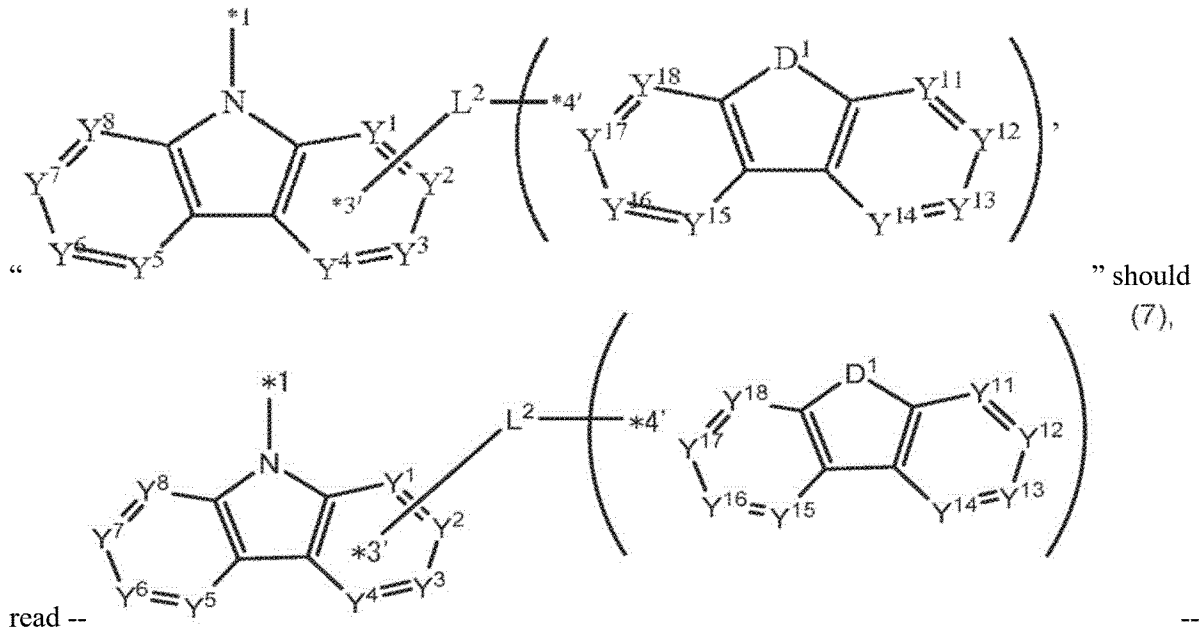

" should read --

Column 570, Line 47, Claim 1, "plural $R^{16'}$s." should read -- plural $R^{10'}$s. --

Column 570, Line 51, Claim 2,

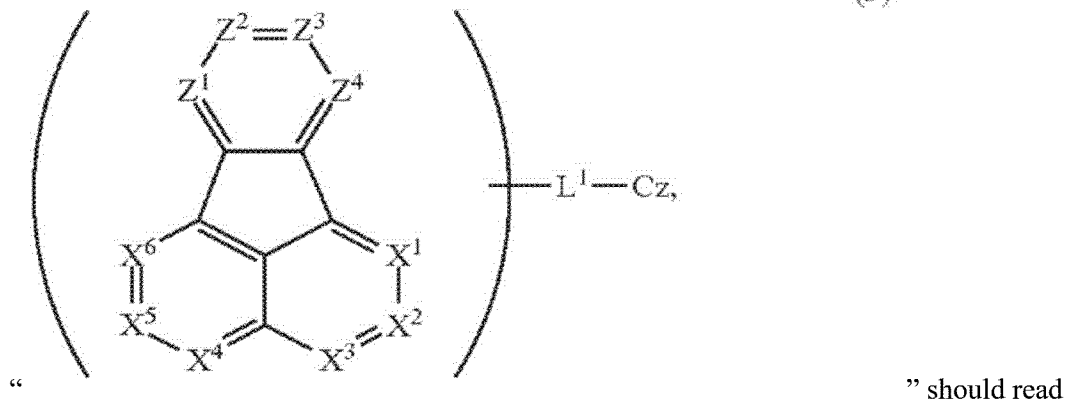

" should read

CERTIFICATE OF CORRECTION (continued)
U.S. Pat. No. 10,629,821 B2

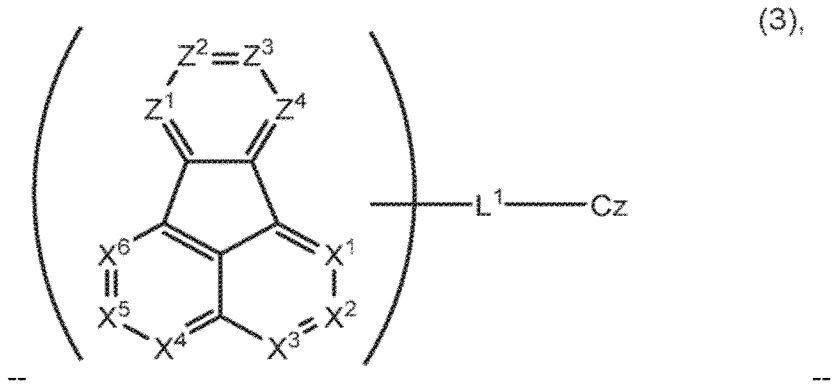

Column 572, Claim 4, Line 10, " 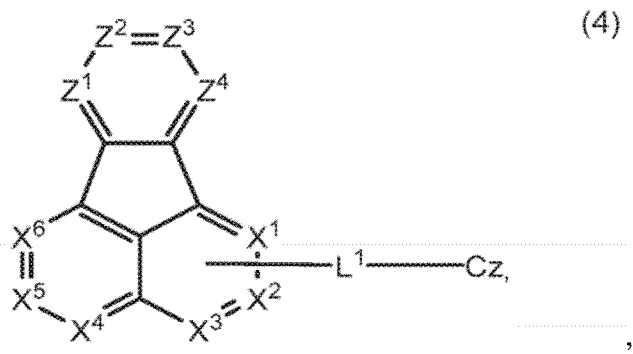 " should read

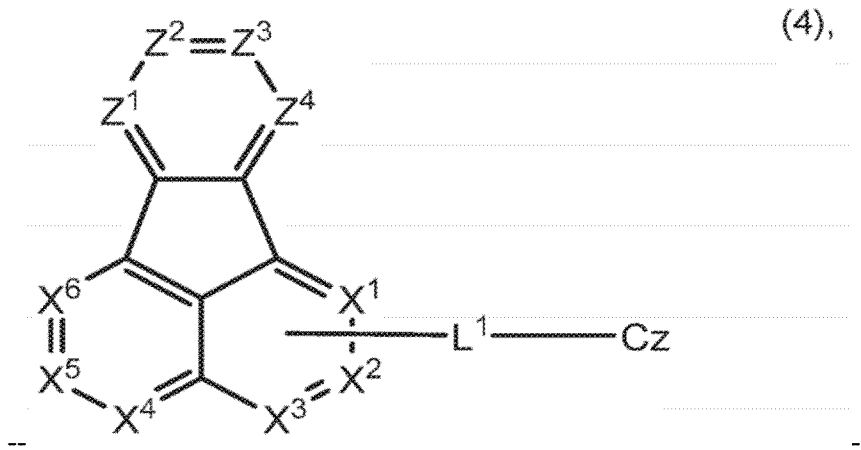

CERTIFICATE OF CORRECTION (continued)
U.S. Pat. No. 10,629,821 B2

Column 572, Line 32, Claim 5,

" 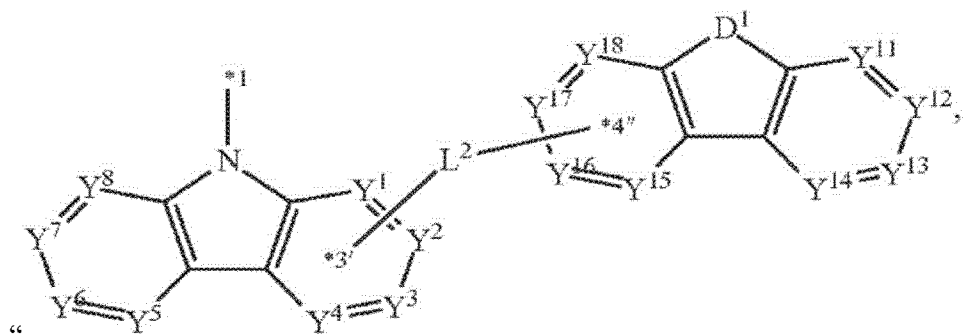 " should read

-- 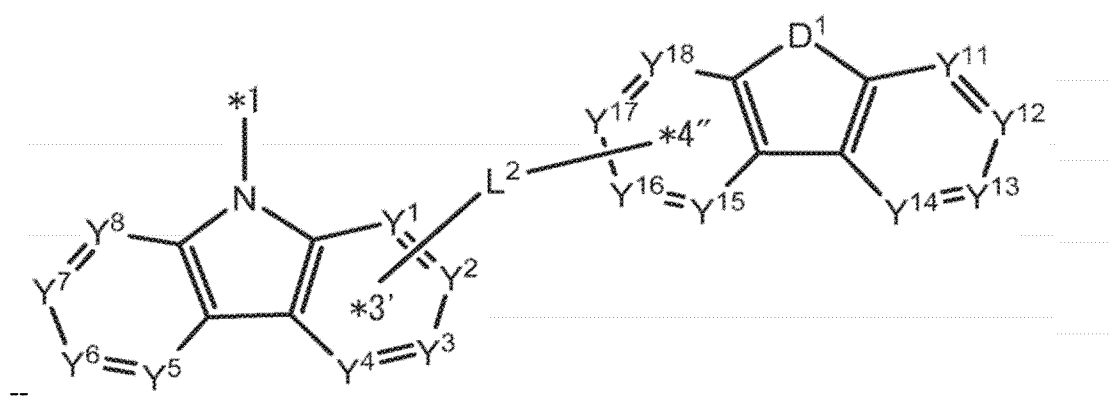 --

Column 572, Line 52, Claim 6,

" 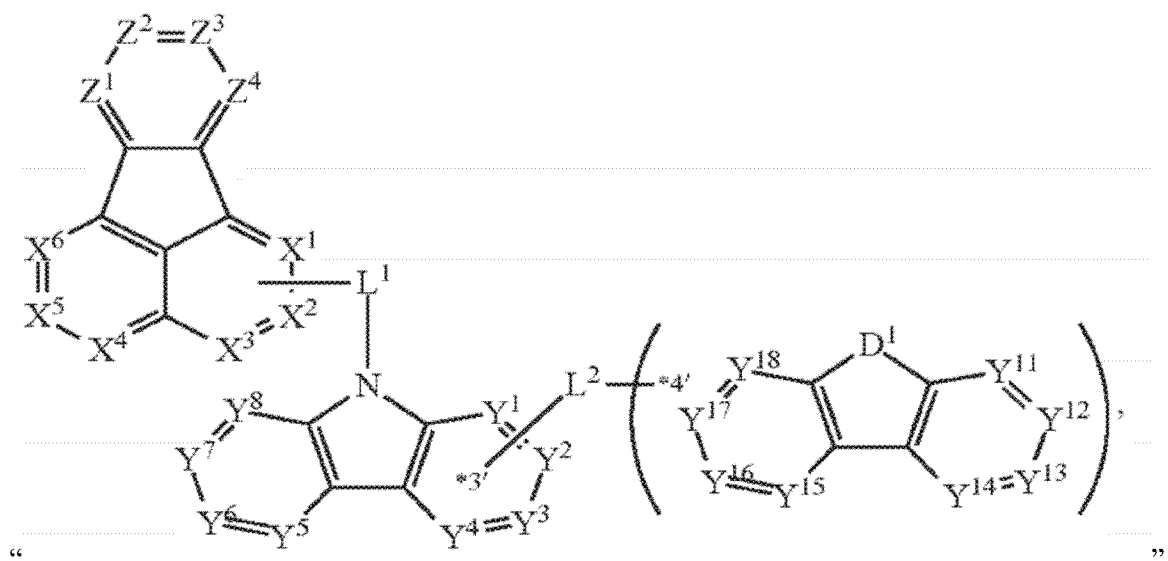"

should read

CERTIFICATE OF CORRECTION (continued)
U.S. Pat. No. 10,629,821 B2

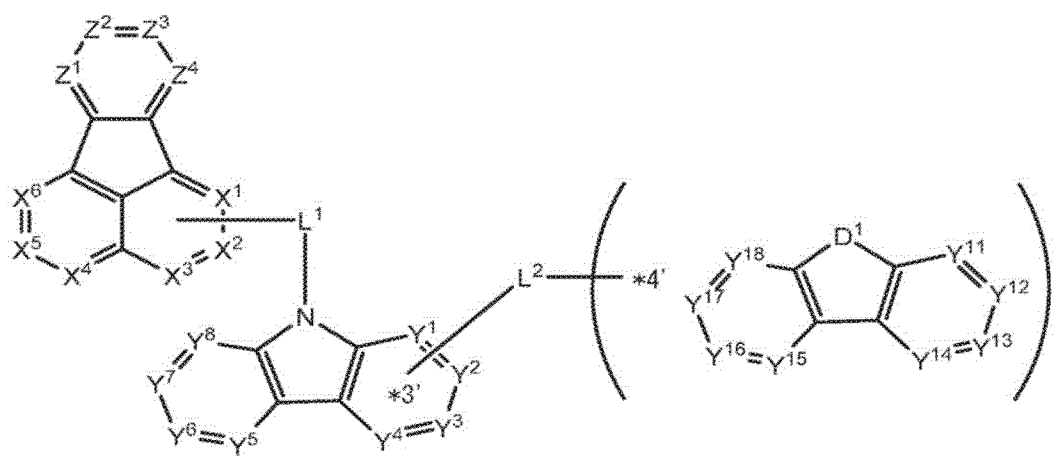

Column 576, Line 10, Claim 19,

"  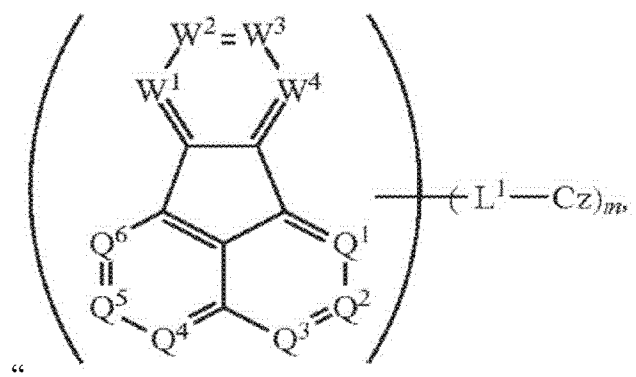  " should read

--  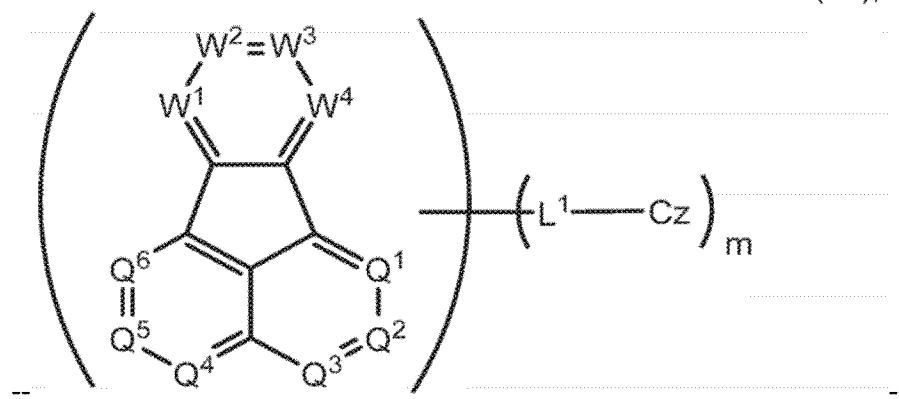  --

CERTIFICATE OF CORRECTION (continued)
U.S. Pat. No. 10,629,821 B2

Column 576, Line 40, Claim 19,

"
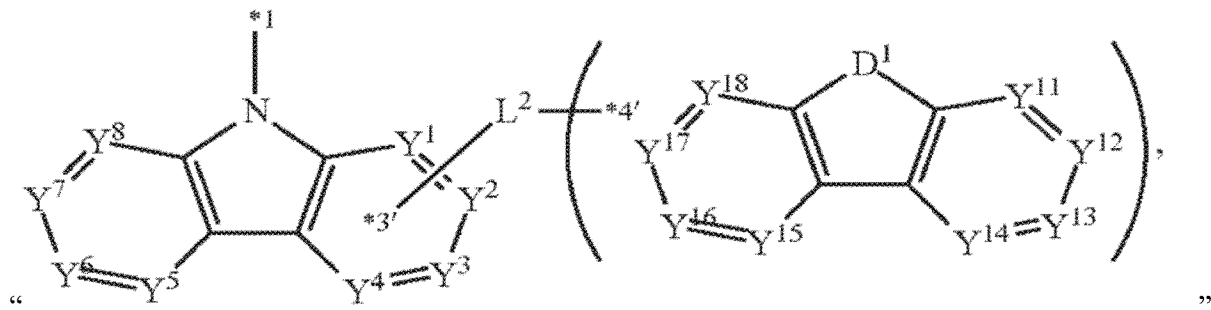
(7)

"

should read

--
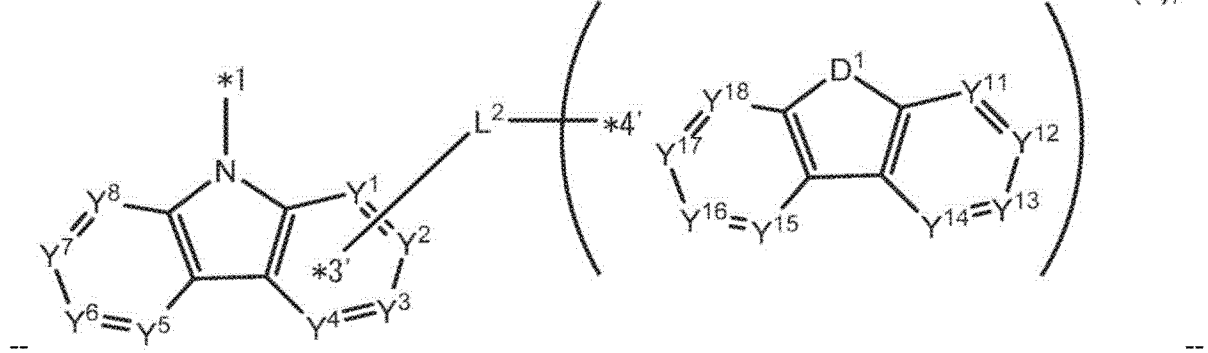
(7),

--

Column 578, Line 41, Claim 24, "9,9-dimethyifluorenyl group," should read -- 9,9-dimethylfluorenyl group, --

CERTIFICATE OF CORRECTION (continued)
U.S. Pat. No. 10,629,821 B2

Column 581, Line 1, Claim 34,

" 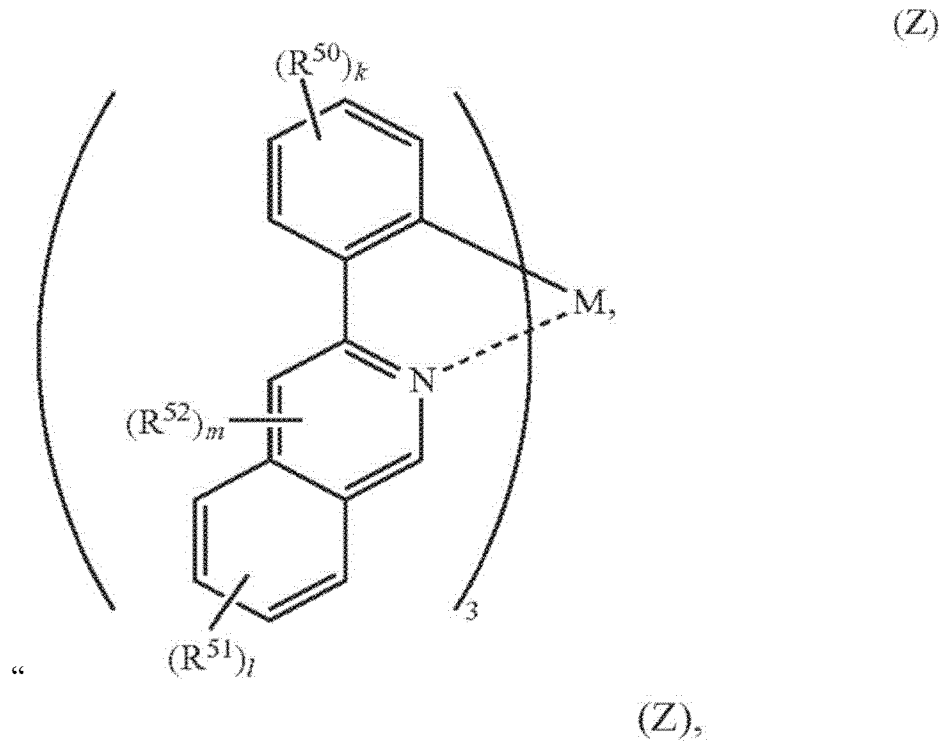 " should read

-- 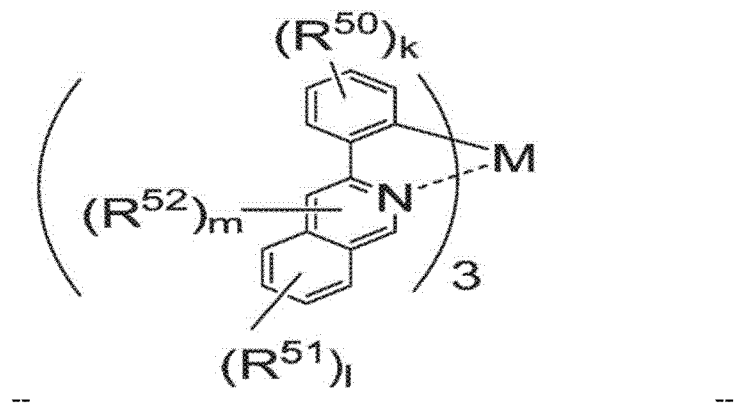 --